(12) United States Patent
Patman et al.

(10) Patent No.: US 12,297,190 B2
(45) Date of Patent: May 13, 2025

(54) MODULATORS OF STING (STIMULATOR OF INTERFERON GENES)

(71) Applicant: PFIZER INC., New York, NY (US)

(72) Inventors: Ryan Patman, San Diego, CA (US); Martin James Wythes, Solana Beach, CA (US); Eugene Yuanjin Rui, San Diego, CA (US); Indrawan James McAlpine, San Diego, CA (US); Andrew Fensome, Harvard, MA (US); Mehran Jalaie, San Diego, CA (US); Ketan S. Gajiwala, San Diego, CA (US); Chan Woo Huh, East Lyme, CT (US); Tuan Phong Tran, Ledyard, CT (US); Lei Zhang, Auburndale, MA (US); Dahui Zhou, Groton, CT (US); Ethan Lawrence Fisher, Chester, CT (US)

(73) Assignee: Pfizer Inc., New York, NY (US)

( * ) Notice: Subject to any disclaimer, the term of this patent is extended or adjusted under 35 U.S.C. 154(b) by 880 days.

(21) Appl. No.: 17/029,557

(22) Filed: Sep. 23, 2020

(65) Prior Publication Data
US 2021/0087180 A1    Mar. 25, 2021

Related U.S. Application Data

(60) Provisional application No. 63/069,831, filed on Aug. 25, 2020, provisional application No. 63/021,216, (Continued)

(51) Int. Cl.
| | | |
|---|---|---|
| *C07D 403/14* | (2006.01) | |
| *A61K 31/4196* | (2006.01) | |
| *A61K 31/424* | (2006.01) | |
| *A61K 31/427* | (2006.01) | |
| *A61K 31/437* | (2006.01) | |
| *A61K 31/454* | (2006.01) | |
| *A61K 31/5377* | (2006.01) | |
| *A61K 31/5386* | (2006.01) | |
| *A61K 38/21* | (2006.01) | |
| *A61K 39/395* | (2006.01) | |
| *C07D 401/14* | (2006.01) | |
| *C07D 413/14* | (2006.01) | |
| *C07D 417/14* | (2006.01) | |
| *C07D 471/04* | (2006.01) | |
| *C07D 487/06* | (2006.01) | |
| *C07D 491/08* | (2006.01) | |

(Continued)

(52) U.S. Cl.
CPC ........ *C07D 403/14* (2013.01); *A61K 31/4196* (2013.01); *A61K 31/424* (2013.01); *A61K 31/427* (2013.01); *A61K 31/437* (2013.01); *A61K 31/454* (2013.01); *A61K 31/5377* (2013.01); *A61K 31/5386* (2013.01); *A61K 38/21* (2013.01); *A61K 39/3955* (2013.01); *A61K 39/39558* (2013.01); *C07D 401/14* (2013.01); *C07D 413/14* (2013.01); *C07D 417/14* (2013.01); *C07D 471/04* (2013.01); *C07D 487/06* (2013.01); *C07D 491/08* (2013.01); *C07D 491/107* (2013.01); *C07D 498/04* (2013.01); *C07D 498/08* (2013.01)

(58) Field of Classification Search
CPC .. C07D 403/14; C07D 401/14; C07D 413/14; C07D 417/14; C07D 471/04; C07D 487/06; C07D 491/08; C07D 491/107; C07D 498/04; C07D 498/08; A61K 39/3955; A61K 39/39558; A61K 38/21; A61K 31/424; A61K 31/427; A61K 31/437; A61K 31/454; A61K 31/5386; A61K 31/5377

See application file for complete search history.

(56) References Cited

U.S. PATENT DOCUMENTS

| | | |
|---|---|---|
| 8,337,850 B2 | 12/2012 | Ahrens et al. |
| 10,155,037 B2 | 12/2018 | Abdiche et al. |

(Continued)

FOREIGN PATENT DOCUMENTS

| | | |
|---|---|---|
| WO | 91/11172 A1 | 8/1991 |
| WO | 94/02518 A1 | 2/1994 |

(Continued)

OTHER PUBLICATIONS

Zhang, X. et al., Cyclic GMP-AMP containing mixed phosphodiester linkages is an endogenous high-affinity ligand for STING, 2013, Molecular Cell, vol. 51, No. 2, 226-235 (Year: 2013).*

(Continued)

*Primary Examiner* — Jennifer A Berrios
*Assistant Examiner* — Richard Grant Peckham
(74) *Attorney, Agent, or Firm* — Alexey Kuznetsov

(57) ABSTRACT

Compounds of the general formula (I):

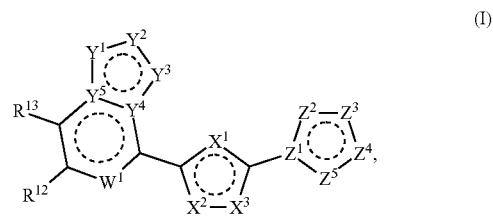

or a pharmaceutically acceptable salt thereof, processes for the preparation of these compounds, compositions containing these compounds, and the uses of these compounds.

28 Claims, No Drawings

Related U.S. Application Data filed on May 7, 2020, provisional application No. 62/905,532, filed on Sep. 25, 2019.

(51) Int. Cl.
    *C07D 491/107*      (2006.01)
    *C07D 498/04*      (2006.01)
    *C07D 498/08*      (2006.01)

(56) References Cited

U.S. PATENT DOCUMENTS

| | | | |
|---|---|---|---|
| 10,538,542 B2 * | 1/2020 | Wythes | C07F 9/65744 |
| 2013/0078240 A1 | 3/2013 | Ahrens et al. | |
| 2019/0284216 A1 | 9/2019 | Wythes et al. | |
| 2020/0040009 A1 | 2/2020 | Wu et al. | |

FOREIGN PATENT DOCUMENTS

| | | |
|---|---|---|
| WO | 98/55148 A1 | 12/1998 |
| WO | 2010/132999 A1 | 11/2010 |
| WO | 2016/092419 A1 | 6/2016 |
| WO | 2017/130076 A1 | 8/2017 |
| WO | 2017175156 A1 | 10/2017 |
| WO | 2018/234808 A1 | 12/2018 |
| WO | 2020/181050 A1 | 9/2020 |
| WO | 2020/232375 A1 | 11/2020 |

OTHER PUBLICATIONS

Barber (Nature Reviews Immunology. 2015. vol. 15. p. 760-770) (Year: 2015).*
He (Cancer Letters 402 (2017) 203-212) (Year: 2017).*
Khoo (EMBO reports 19: e46935 | 2018. p. 1-10) (Year: 2018).*
Berger, Gilles et al., "Pharmacological Modulation of the STING Pathway for Cancer Immunotherapy", Trends in Molecular Medicine, 2019, 25(5), 412-427.
Lian, Yiqian et al., "STING Activation and its Application in Immuno-Oncology", Current Topics in Medicinal Chemistry. 2019, 19(24), 2205-2227.
International Search Report of the International Searching Authority, PCT/IB2020/058854.
Written Opinion of the International Searching Authority, PCT/IB2020/058854.
Chin, E., et al., "Antitumor activity of a systemic STING-activating non-nucleotide cGAMP mimetic," Science, 2020, 993-999, vol. 369, No. 6506.
Chmielewski, S., et al., "Development of selective small molecule STING agonists suitable for systemic administration," American Association for Cancer Research, Virtual Annual Meeting II, Jun. 22-24, 2020, Abstract No. 5845, Poster No. 4532A.
Pan, B., et al., "An orally available non-nucleotide STING agonist with antitumor activity," Science, 2020, Article eaba6098, vol. 369, No. 6506.
Ramanjulu, J., et al., "Design of amidobenzimidazole STING receptor agonists with systemic activity", Nature, 2018, 439-454, vol. 564, No. 7736.
Viller, N., et al., "TTI-10001, A Next Generation Small Molecule STING Agonist, Demonstrates Potent Anti-Tumor Activity in Mice Following Intravenous or Oral Administration," Society for Immunotherapy of Cancer, Nov. 6-10, 2019, National Harbor, MD, Poster No. 668.
Wang, Z., et al., "Preclinical Characterization of a Novel Non-Cyclic Dinucleotide Small Molecule STING Agonist with Potent Anti-Tumor Activity in Mice," , American Association for Cancer Research, 2019 Annual Meeting, Mar. 29-Apr. 3, 2019, Atlanta, GA, Abstract No. 3854.
Bala et al., "PLGA Nanoparticles in Drug Delivery: The State of the Art", Critical Reviews in Therapeutic Drug Carrier Systems, 2004, 21(5), 387-422.
Barber, Glen N., "STING: infection, inflammation and cancer", Nature Reviews Immunology, 2015, 15, 760-770.
Bundesmann, et al., "Amidation of esters assisted by Mg(OCH3)2 or CaCl2", Tetrahedron Letters, 2010, 51, 3879-3882.
Burdette, "STING and the innate immune response to nucleic acids in the cystol", Nature Immunology, 2013, 14(1), 19-26.
Chen, "Activation of STAT6 by STING Is Critical for Antiviral Innate Immunity", Cell, 2011, 147, 436-446.
Cheng, "Relationship Between the Inhibition Constant (k1) and the Concentration of Inhibitor Which Causes 50 Per Cent Inhibition (I50) of an Enzymatic Reaction*", Biochemical Pharmacology, 1973, 22, 3099-3108.
Cheuk, "Role of 4-1BB:4-1BB ligand in cancer immunotherapy", Cancer Gene Therapy, 2004, 11, 215-226.
Dong, "B7-H1, a third member of the B7 family, co-stimulates T-cell proliferation and interleukin-10 secretion", Nature Medicine, 1999, 5(12), 1365-1369.
Freeman, "Engagement of the PD-1 Immunoinhibitory Receptor by a Novel B7 Family Member Leads to Negative Regulation of Lymphocyte Activation", Journal Experimental Medicine, 2000, 192(7), 1027-1034.
Haleblian, John K., "Characterization of Habits and Crystalline Modification of Solids and Their Pharmaceutical Applications", 1975, 64(8), 1269-1288.
Higuchi T., et al., Pro-drugs as Novel Delivery Systems, vol. 14, ACS Symposium Series.
Hughes, "Nanostructure-mediated drug delivery", Nanomedicine: Nanotechnology, Biology, and Medicine, 2005, 1, 22-30.
Iwai, "Involvement of PD-L1 on tumor cells in the escape from host immune system and tumor immunotherapy by PD-L1 blockade", PNAS, 2002, 99(19), 12293-12297.
Joo et al., "C-H Bonds as Ubiquitous Functionality: Preparation of Multiple Regioisomers of Arylated 1,2,4-Triazoles via C-H Arylation", The Journal of Organic Chemistry, 2013, 78, 738-743.
Libanova, "Cyclic di-nucleotides: new era for small molecules as adjuvants", Microbial Biotechnology, 2012, 5(2), 168-176.
Liu, "Systematic identification of type I and type II interferon-induced antiviral factors", PNAS, 2012, 109(11), 4239-4244.
McCune, "Active Specific Immunotherapy With Tumor Cells and Corynebcterium Parvum a Phase I Study", 1979, 43, 1619-1623.
Stocks et al., "Efficient and Regiospecific One-Pot Synthesis of Substituted 1,2,4-Triazoles", Organic Letters, 2004, 6(17), 2969-2971.
Bundgaard, H., Design Prodrugs, 1985, (Elsevier).
Remington's Pharmaceutical Sciences, 19th Edition (Mack Publishing Company, 1995).
Protective Groups in Organic Synthesis, A. Wiley-Interscience Publication, 1981.
Protecting Groups, 10 Georg Thieme Verlag, 1994.
Roche, E B, Bioreversible Carriers in Drug Design, Pergamon Press, 1987 (American Pharmaceutical Association).
Eliel, EL, Stereochemistry of Organic Compounds, 1994 (Wiley, New York).
Stahl & Wermuth, Handbook of Pharmaceutical Salts: Properties, Selection and Use, 2002, (Wiley-VCH, Weinheim, Germany).
Corrales, et al., "Direct Activation of STING in the Tumor Microenvironment Leads to Potent and Systemic Tumor Regression and Immunity", Cell Reports, 2015, pp. 1018-1030, 11.
Fuertes, et al., "Host type I IFN signals are required for antitumor CD8+ T cell responses through CD8alpha+ dendritic cells", The Journal of Experimental Medicine, 2011, pp. 2005-2016, 208(10).
Harding, et al., "Mitotic progression following DNA damage enables pattern recognition within micronuclei", Nature, 2017, pp. 466-480, 548.
Sivick, et al., "Magnitude of Therapeutics STING Activation Determines CD8+ T Cell-Mediated Anti-tumor Immunity", Cell Reports, 2018, pp. 3074-3085, 25.
Sivick, et al., "Magnitude of Therapeutics STING Activation Determines CD8+ T Cell-Mediated Anti-tumor Immunity", Cell Reports Correction, 2018, pp. 3074-3085, e1-e5, 25.
Vanpouille-Box, "DNA exonuclease Trex1 regulates radiotherapy-induced tumor immunogenicity", Nature Communications, 2017, pp. 1-15.

(56) References Cited

OTHER PUBLICATIONS

Woo, et al., "STING-Dependent Cytosolic DNA Sensing Mediates Innate Immune Recognition of Immunogenic Tumors", Immunity, 2014, pp. 830-842, 41.
Baird et al., "Evaluation of Explant Responses to STING Ligands: Personalized Immunosurgical Therapy for Head and Neck Squamous Cell Carcinoma", Cancer Res. 2018, 78(21), 6308-6319.
Sato et al., "STING Signaling and Skin Cancers", Cancers 2021, 13(22), 5603.

* cited by examiner

MODULATORS OF STING (STIMULATOR OF INTERFERON GENES)

CROSS-REFERENCE TO RELATED APPLICATIONS

This application claims the benefit of priority to U.S. provisional patent application Ser. No. 62/905,532, filed on Sep. 25, 2019; to U.S. provisional patent application Ser. No. 63/021,216, filed on May 7, 2020; and to U.S. provisional patent application Ser. No. 63/069,831, filed on Aug. 25, 2020, each of which is incorporated by reference herein in its entirety.

FIELD OF THE INVENTION

This invention relates to additional novel activators of STING (Stimulator of Interferon Genes) useful in the treatment of diseases and conditions such as inflammatory diseases, allergic and autoimmune diseases, infectious diseases, and abnormal cell growth, such as cancer, in mammals and as vaccine adjuvants. This invention also relates to a method of using such compounds in the treatment of abnormal cell growth in mammals, especially humans, and to pharmaceutical compositions of such compounds.

BACKGROUND OF THE INVENTION

The innate immune system is the first line of defense which is initiated by pattern recognition receptors (PRRs) upon detection of ligands from pathogens as well as damage associated molecular patterns. A growing number of these receptors have been identified, which include sensors of double stranded DNA and unique nucleic acids called cyclic dinucleotides (CDNs). Activation of PRRs leads to up regulation of genes involved in the inflammatory response, including type 1 interferons (IFNs and INFs), proinflammatory cytokines and chemokines which suppress pathogen replication and facilitate adaptive immunity.

The adaptor protein STING, also know as TMEM 173, has been identified as a central signalling molecule in the innate immune sensing pathway in response to cytosolic nucleic acids. Activation of STING results in up-regulation of IRF3 and NFκB pathways leading to induction of interferon beta (INF-β) and other cytokines. STING is critical for responses to cytosolic DNA from pathogens or of host origin, and in response to CDNs, sometime referred to second messengers. G. N. Barber, "Sting: infection, inflammation and cancer," *Nat. Rev. Immun.*, 2015, 15, pp 760.

CDNs were first identified as bacterial messengers responsible for controlling numerous responses in prokaryotic cells. Bacterial CDNs, such as c-di-GMP are symmetrical molecules characterized by two 3',5' phosphodiester linkages. Direct activation of STING by bacterial CDNs has recently been confirmed through X-ray crystallography (Burdette D. L. and Vance R. E., *Nature Immunology*, 2013: 14 19-26). Bacterial CDNs have consequently attracted interest as potential vaccine adjuvants (Libanova R. et al, *Microbial Biotechnology* 2012: 5, 168-176). More recently, the response to cytosolic DNA has been shown to involve generation of endogenous CDNs by an enzyme called cyclic guanine adenine synthase (cGAS), producing a novel mammalian CDN signalling molecule identified as cyclic guanine adenine monophosphate (cGAMP), which binds to and activates STING. Interaction of cGAMP with STING has also been demonstrated by X-ray crystallography. Unlike bacterial CDNs, cGAMP is an unsymmetrical molecule characterised by its mixed 2',5' and 3',5' phosphodiester linkages. Like bacterial CDNs, cGAMP activates STING leading to induction of type 1 interferons (type 1 INFs). The role of type 1 INFs in response to invading pathogens is well established. Recombinant interferon alpha (IFNα) was the first approved biological therapeutic and has become an important therapy in viral infections and in cancer. INFs are also known to be potent modulators of the immune response, acting on cells of the immune system.

In contrast to the synthetic campaigns used to prepare CDNs, the compounds exemplified vide infra are, in a general sense, more accessible synthetically. Additionally, compounds of this type engender a significant improvement in cell permeability when compared to the CDN class of STING activators.

Given its role in regulating various biological processes, STING continues to be an attractive target for modulation with small molecules. Nevertheless, to date, few effective STING activators have been developed or have entered the clinic. There remains a need to identify further compounds which bind to STING. There remains a need to identify further compounds which activate STING. Further there remains a need for compounds which bind to and/or activate STING and which may be useful as therapeutic agents.

SUMMARY OF THE INVENTION

Administration of a small molecule compound which could stimulate the innate immune response, including the activation of type 1 INF and other cytokines, could become an important strategy for the treatment and prevention of human diseases including viral infections and cancer. This type of immunomodulatory strategy has the potential to identify compounds which may be useful to treat diseases and conditions such as inflammatory diseases, allergic and autoimmune diseases, infectious diseases, and abnormal cell growth, such as cancer, in mammals and as vaccine adjuvants.

Certain compounds of the invention have been shown to bind to STING, to activate STING and/or to induce type 1 INF and/or other cytokines and/or co-stimulatory factors on incubation with human dendritic cells (DCs) and/or peripheral blood mononucleocytes (PBMCs). Compounds which induce human INFs may be useful in the treatment of various disorders, for example the treatment of allergic diseases and other inflammatory conditions. Certain compounds of the invention may bind to STING but act as antagonists and these could be useful in the treatment of various autoimmune diseases.

It is envisioned that targeting STING with activating or inhibiting agents may be a promising approach for treating diseases and conditions in which modulation of the type1 INF pathway is beneficial, including inflammatory diseases, allergic and autoimmune diseases, infectious diseases, cancer and as vaccine adjuvants.

Each of the embodiments of the small molecule compounds of the present invention described below can be combined with any other embodiment of the compounds of the present invention described herein not inconsistent with the embodiment with which it is combined.

Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of formula (I):

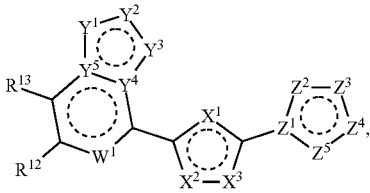

or a pharmaceutically acceptable salt thereof, wherein each

in a ring independently represents two conjugated double bonds in a five-membered heteroaromatic ring and three conjugated double bonds in a six-membered aromatic or heteroaromatic ring;

$W^1$ is selected from $CR^{11}$ and N;
$X^1$ is selected from $CR^1$, $C(R^1)_2$, N, $NR^1$, O and S;
$X^2$ is selected from $CR^2$, $C(R^2)_2$, N, $NR^2$, O and S;
$X^3$ is selected from $CR^3$, $C(R^3)_2$, N, $NR^3$, O and S;
where two or three of $X^1$, $X^2$ and $X^3$ are independently selected from N, $NR^1$, $NR^2$, $NR^3$, O and S; and
where at least one of $X^1$, $X^2$ and $X^3$ is selected from N, $NR^1$, $NR^2$ and $NR^3$;
$Y^1$ is selected from N, $NR^4$, O, S, $CR^4$ and $C(R^4)_2$;
$Y^2$ is selected from N, $NR^5$, O, S, $CR^5$ and $C(R^5)_2$;
$Y^3$ is selected from N, $NR^6$, O, S, $CR^6$ and $C(R^6)_2$;
$Y^4$ is selected from C and N;
$Y^5$ is selected from C and N;
where at least one and not more than two of $Y^1$, $Y^2$ and $Y^3$ are independently selected from N, $NR^4$, $NR^5$ and $NR^6$;
where when if one of $Y^4$ or $Y^5$ is N, the other one of $Y^4$ or $Y^5$ is C;
$Z^1$ is selected from C and N;
$Z^2$ is selected from N, $NR^8$ and $CR^8$;
$Z^3$ is selected from N, $NR^9$ and $CR^9$;
$Z^4$ is selected from N, $NR^{10}$ and $CR^{10}$;
$Z^5$ is selected from N, $NR^7$ and $CR^7$;
where two or three of $Z^1$, $Z^2$, $Z^3$, $Z^4$ and $Z^5$ are independently selected from N, $NR^7$, $NR^8$, $NR^9$, and $NR^{10}$;
each $R^1$ is independently selected from the group consisting of H, $C_1$-$C_8$ alkyl, $C_1$-$C_8$ alkylene-NRR and $C_1$-$C_8$ alkylene-C(O)OR;
each $R^2$ is independently selected from the group consisting of H, $C_1$-$C_8$ alkyl, $C_1$-$C_8$ alkylene-NRR, $C_1$-$C_8$ alkylene-C(O)OR, $C_1$-$C_8$ alkylene-OR and $C_1$-$C_8$ alkylene-O—P(O)(OH)$_2$;
each $R^3$ is independently selected from the group consisting of H, $C_1$-$C_8$ alkyl, $C_1$-$C_8$ alkylene-NRR, $C_1$-$C_8$ alkylene-C(O)OR and $C_1$-$C_8$ alkylene-O—P(O)(OH)$_2$;
each $R^4$ is independently selected from the group consisting of H, —OR, —NRR, $C_1$-$C_8$ alkyl optionally substituted with one or two —OR, $C_1$-$C_8$ alkylene-NRR, —C(O)OR, $C_1$-$C_8$ alkylene-C(O)OR, 3-10 membered heterocyle, $C_1$-$C_8$ alkylene-3-10 member heterocycle optionally substituted with one 3-10 member heterocycle, ($C_3$-$C_{10}$)-cycloalkyl, and $C_1$-$C_8$ alkylene-($C_3$-$C_{10}$)-cycloalkyl;
each $R^5$ is independently selected from the group consisting of H, OR, $C_1$-$C_8$ alkyl, —NRR, $C_1$-$C_8$ alkylene-NRR, —C(O)OR, $C_1$-$C_8$ alkylene-C(O)OR, 3-10 membered heterocycle, $C_1$-$C_8$ alkylene-3-10 member heterocycle optionally substituted with one 3-10 member heterocycle, and $C_1$-$C_8$ alkylene-OR;
each $R^6$ is H;
$R^7$ is selected from the group consisting of H, halo, hydroxy or $NH_2$;
$R^8$ is selected from the group consisting of H, $C_1$-$C_8$ alkyl optionally substituted with one or two —NRR or —OR, $C_1$-$C_8$ alkylene-C(O)OR and $C_1$-$C_8$ alkylene-$SO_2R$;
$R^9$ is H;
$R^{10}$ is selected from the group consisting of H, $C_1$-$C_8$ alkyl optionally substituted with one or two —OR, and halo;
$R^{11}$ is selected from the group consisting of H, $C_1$-$C_8$ alkyl, —OR and halo;
$R^{12}$ is —C(O)N(R)$_2$ or —C(O)NHR;
$R^{13}$ is H;
each R is independently selected from the group consisting of H or $C_1$-$C_8$ alkyl, or $C_1$—C haloalkyl, or two R join to form, together with the atom or atoms to which they are bound, a —($C_3$-$C_{10}$) cycloalkyl or 3-10 member heterocycle, where said 3-10 member heterocycle contains one, two or three atoms selected from N, O and S; and
where, when two R join to form, together with the atom or atoms to which they are bound, a —($C_3$-$C_{10}$) cycloalkyl or 3-10 member heterocycle, said —($C_3$-$C_{10}$) cycloalkyl or 3-10 member heterocycle is optionally substituted with one or more substituents each independently selected from $C_1$-$C_8$ alkyl, hydroxy, $C_1$-$C_8$ alkoxy, —($C_3$-$C_{10}$) cycloalkyl, 3-10 member heterocycle, halo and cyano.

The invention includes embodiments wherein there is provided a compound of formula

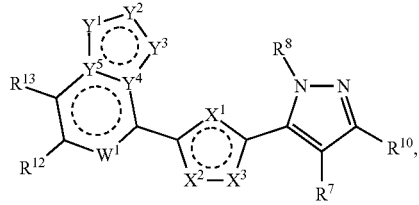

or a pharmaceutically acceptable salt thereof, wherein each

in a ring independently represents two conjugated double bonds in a five-membered heteroaromatic ring and three conjugated double bonds in a six-membered aromatic or heteroaromatic ring; and
wherein $W^1$; $X^1$; $X^2$; $X^3$; $Y^1$; $Y^2$; $Y^3$; $Y^4$; $Y^5$; $R^1$; $R^2$; $R^3$; $R^4$; $R^5$; $R^6$; $R^7$; $R^8$; $R^{10}$; $R^{11}$; $R^{12}$; $R^{13}$; and R are defined as for formula (I).

The invention includes embodiments wherein there is provided a compound of formula (III):

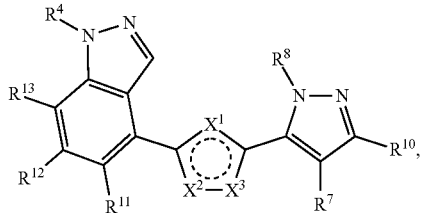
(III)

or a pharmaceutically acceptable salt thereof, wherein each

in a ring independently represents two conjugated double bonds in a five-membered heteroaromatic ring and three conjugated double bonds in a six-membered aromatic or heteroaromatic ring; and
wherein $X^1$; $X^2$; $X^3$; $R^1$; $R^2$; $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (IIIA):

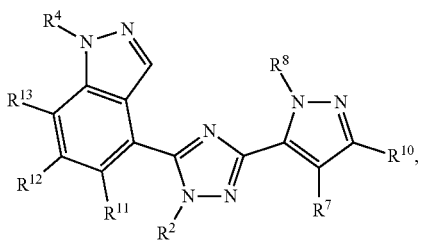
(IIIA)

or a pharmaceutically acceptable salt thereof, wherein $R^2$; $R^4$; $R^7$; $R^8$; $R^{10}$; $R^{11}$; $R^{12}$; $R^{13}$; and R are defined as for formula (I).

The invention includes embodiments wherein there is provided a compound of formula (IIIB):

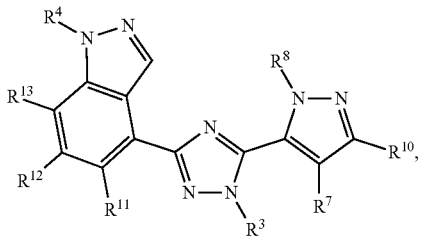
(IIIB)

or a pharmaceutically acceptable salt thereof, wherein $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (IIIc):

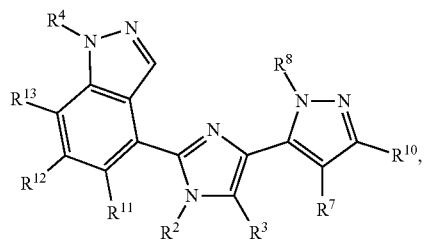
(IIIC)

or a pharmaceutically acceptable salt thereof, wherein $R^2$; $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (IIID):

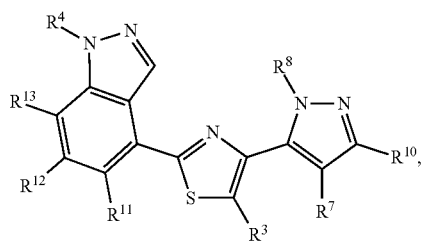
(IIID)

or a pharmaceutically acceptable salt thereof, wherein $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (IV):

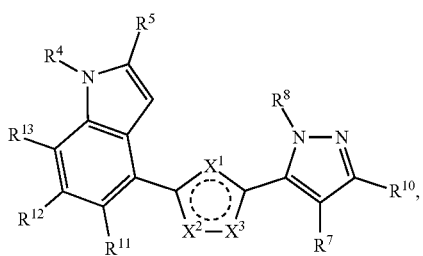
(IV)

or a pharmaceutically acceptable salt thereof, wherein each

in a ring independently represents two conjugated double bonds in a five-membered heteroaromatic ring and three conjugated double bonds in a six-membered aromatic or heteroaromatic ring; and wherein $X^1$; $X^2$; $X^3$; $R^1$; $R^2$; $R^3$; $R^4$; $R^5$; $R^7$; $R^8$; $R^{10}$; $R^{11}$; $R^{12}$; $R^{13}$; and R are defined as for formula (I).

The invention includes embodiments wherein there is provided a compound of formula (IVA):

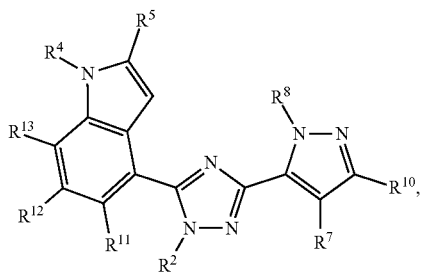

(IVA)

or a pharmaceutically acceptable salt thereof, wherein $R^2$; $R^4$; $R^5$; $R^7$; $R^8$; $R^{10}$; $R^{11}$; $R^{12}$; $R^{13}$; and R are defined as for formula (I).

The invention includes embodiments wherein there is provided a compound of formula (IVB):

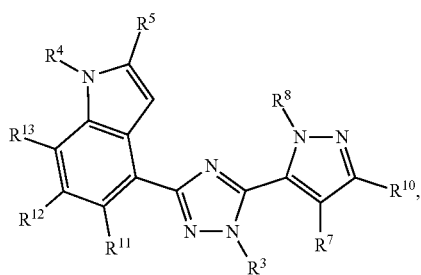

(IVB)

or a pharmaceutically acceptable salt thereof, wherein $R^3$; $R^4$; $R^5$; $R^7$; $R^8$; $R^{10}$; $R^{11}$; $R^{12}$; $R^{13}$; and R are defined as for formula (I).

The invention includes embodiments wherein there is provided a compound of formula (V):

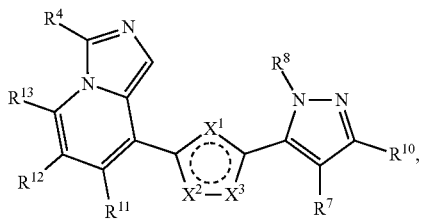

(V)

or a pharmaceutically acceptable salt thereof, wherein each

in a ring independently represents two conjugated double bonds in a five-membered heteroaromatic ring and three conjugated double bonds in a six-membered aromatic or heteroaromatic ring; and wherein $X^1$; $X^2$; $X^3$; $R^1$; $R^2$; $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (VA):

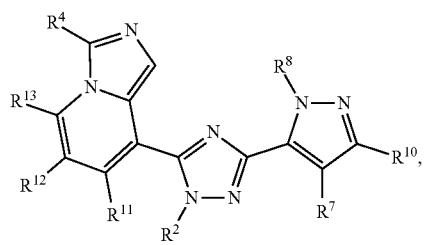

(VA)

or a pharmaceutically acceptable salt thereof, wherein $R^2$; $R^4$; $R^7$; $R^8$; $R^{10}$; $R^{11}$; $R^{12}$; $R^{13}$; and R are defined as for formula (I).

The invention includes embodiments wherein there is provided a compound of formula (VB):

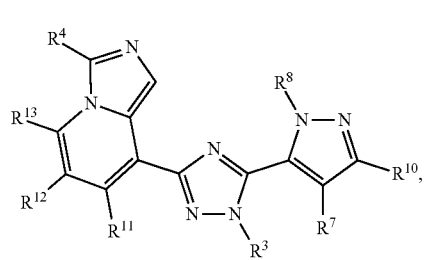

(VB)

or a pharmaceutically acceptable salt thereof, wherein $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (VI):

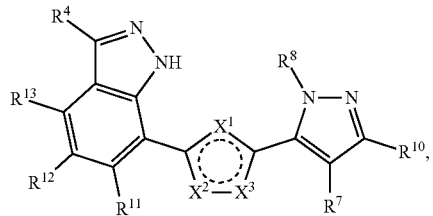

(VI)

or a pharmaceutically acceptable salt thereof, wherein each

in a ring independently represents two conjugated double bonds in a five-membered heteroaromatic ring and three conjugated double bonds in a six-membered aromatic or heteroaromatic ring; and wherein $X^1$; $X^2$; $X^3$; $R^1$; $R^2$; $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (VIA):

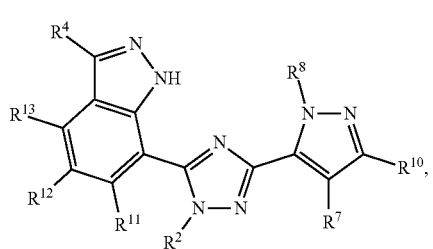

(VIA)

or a pharmaceutically acceptable salt thereof, wherein $R^2$; $R^4$; $R^7$; $R^8$; $R^{10}$; $R^1$; $R^{12}$; $R^{13}$ and R are defined as for formula (I).

The invention includes embodiments wherein there is provided a compound of formula (VIB):

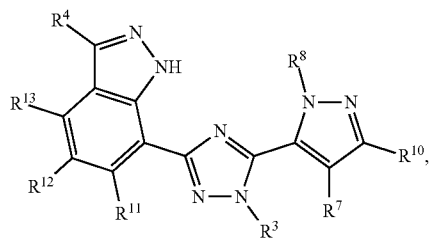

(VIB)

or a pharmaceutically acceptable salt thereof, wherein $R^3$; $R^4$; $R^7$; $R^8$; $R^{10}$; $R^{11}$; $R^{12}$; $R^{13}$; and R are defined as for formula (I).

The invention includes embodiments wherein there is provided a compound of formula (VII):

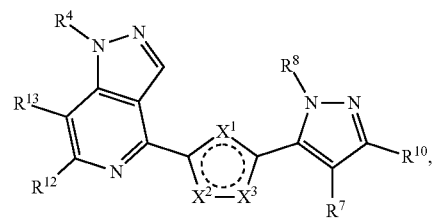

(VII)

or a pharmaceutically acceptable salt thereof, wherein each

in a ring independently represents two conjugated double bonds in a five-membered heteroaromatic ring and three conjugated double bonds in a six-membered aromatic or heteroaromatic ring; and wherein $X^1$; $X^2$; $X^3$; $R^1$; $R^2$; $R^3$; $R^4$; $R^7$; $R^8$; $R^{10}$; $R^{12}$; $R^{13}$; and R are defined as for formula (I).

The invention includes embodiments wherein there is provided a compound of formula (VIIA):

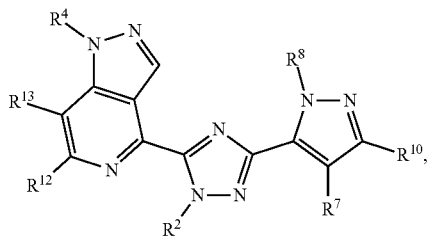

(VIIA)

or a pharmaceutically acceptable salt thereof, wherein $R^2$; $R^4$; $R^7$; $R^8$; $R^{10}$; $R^{12}$; $R^{13}$; and R are defined as for formula (I).

The invention includes embodiments wherein there is provided a compound of formula (VIIB):

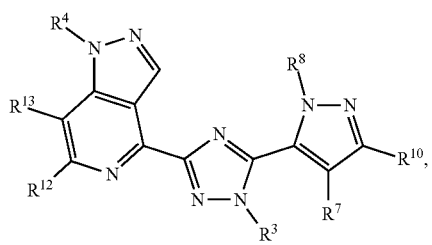

(VIIB)

or a pharmaceutically acceptable salt thereof, wherein $R^3$; $R^4$; $R^7$; $R^8$; $R^{10}$; $R^{12}$; $R^{13}$; and R are defined as for formula (I).

The invention includes embodiments wherein there is provided a compound of formula (VIIC):

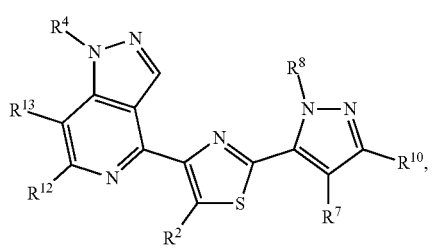

(VIIC)

or a pharmaceutically acceptable salt thereof, wherein $R^2$; $R^4$; $R^7$; $R^8$; $R^{10}$; $R^{12}$; $R^{13}$; and R are defined as for formula (I).

The invention includes embodiments wherein there is provided a compound of formula (VIID):

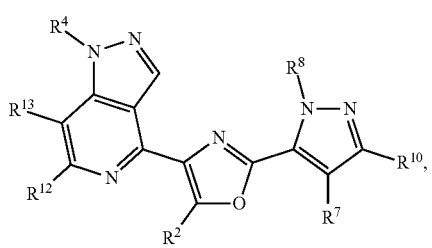

(VIID)

or a pharmaceutically acceptable salt thereof, wherein $R^2$; $R^4$; $R^7$; $R^8$; $R^{10}$; $R^{12}$; $R^{13}$; and R are defined as for formula (I).

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^1$ is independently H.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^2$ is independently selected from the group consisting of H; $C_1$-$C_8$ alkyl, for example $CH_3$; and C1-C alkylene-NRR. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^2$ is independently $C_1$-$C_8$ alkylene-NRR and where R is selected from the group consisting of H and $C_1$-$C_8$ alkyl, for example $CH_3$, to form, for example, $CH_2NH_2$, $CH(NH_2)CH_3$, and $CH_2NH(CH_3)$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^2$ is independently selected from the group consisting of H, $CH_3$, $CH_2NH_2$, $CH(NH_2)CH_3$ and $CH_2NH(CH_3)$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^2$ is independently $CH_2NH_2$.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^3$ is independently selected from the group consisting of H; and $C_1$-$C_8$ alkylene-O—P(O)(OH)$_2$, for example $CH_2OPO(OH)_2$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^3$ is independently selected from the group consisting of H and $CH_2OPO(OH)_2$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^3$ is independently H.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently selected from the group consisting of $C_1$-$C_8$ alkyl, for example $CH_3$, $CH_2CH_3$ or $CH_2CH(CH_3)_2$, which $C_1$-$C_8$ alkyl is optionally substituted with one or two —OR; $C_1$-$C_8$ alkylene-NRR, for example $(CH_2)_2NRR$, $(CH_2)_3$—NRR, and $CH(CH_3)CH_2$—NRR; $C_1$-$C_8$ alkylene-C(O)OR, for example $CH_2C(O)OR$; and $C_1$-$C_8$ alkylene-3-10 member heterocycle, for example $CH_2$-3-10 member heterocycle. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkyl, optionally substituted with one or two —OR. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-NRR, for example $(CH_2)_2NRR$, wherein R is selected from $C_1$-$C_8$ alkyl and $C_1$-$C_8$ haloalkyl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-NRR, wherein two R join to form, together with the atom to which they are bound, a 3-10 member heterocycle, which 3-10 member heterocycle is morpholinyl to form, for example, $(CH_2)_2$—(N-morpholinyl), $(CH_2)_3$—(N-morpholinyl) and $CH(CH_3)CH_2$—(N-morpholinyl), and which morpholinyl ring may be optionally further substituted with one or two $C_1$-$C_8$ alkyl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-NRR, for example $(CH_2)_2NRR$, wherein two R join to form, together with the atom to which they are bound, a 3-10 member heterocycle, which 3-10 member heterocycle is 8-oxa-3-azabicyclo[3.2.1]octan-3-yl to form, for example, $(CH_2)_2$—(N-8-oxa-3-azabicyclo[3.2.1]octan-3-yl). In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-NRR, for example $(CH_2)_2NRR$, wherein two R join to form, together with the atom to which they are bound, a 3-10 member heterocycle, which 3-10 member heterocycle is piperidinyl to form, for example, $(CH_2)_2$—(N-piperidinyl), and which piperdinyl ring may be optionally further substituted with one or two substituents selected from the group consisting of cyano and halo. In one embodiment of compounds of the invention, including those of, formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-3-10 member heterocycle, for example $CH_2$-3-10 member heterocycle, which 3-10 member heterocycle is azetidinyl to form, for example, $CH_2$-azetidinyl, which azetidinyl may be optionally further substituted with 3-10 membered heterocycle, for example, tetrahydropyranyl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIII), or a pharmaceutically acceptable salt thereof, each $R^4$ is independently $C_1$-$C_8$ alkylene-C(O)OR, for example $CH_2C(O)OR$, wherein R is H to form, for example, $CH_2C(O)OH$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^4$ is independently selected from the group consisting of $CH_3$, $CH_2CH_3$, $(CH_2)_3OH$, $CH_2CH(CH_2OH)_2$, $(CH_2)_2N(CH_3)CH_2CF_3$, $(CH_2)_2$—(N-morpholinyl), $(CH_2)_3$—(N-morpholinyl), $CH(CH_3)CH_2$—(N-morpholinyl), $(CH_2)_2$—(N-2,6-dimethyl morpholinyl), $(CH_2)_2$—(N-2,5-dimethyl-morpholinyl), $(CH_2)_2$—(N-8-oxa-3-azabicyclo[3.2.1]octan-3-yl), $(CH_2)_2$—(N-4-cyano piperidinyl), $(CH_2)_2$—(N-4,4-difluoro-piperidinyl), $(CH_2)_2$—(N-2-fluoro azetidinyl), $CH_2$-(2-azetidinyl-N-tetrahydropyranyl) and $CH_2C(O)OH$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^4$ is independently $CH_3$.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently selected from the group consisting of H; $C_1$-$C_8$ alkyl, for example $CH_3$ or $CH_2CH_3$; $C_1$-$C_8$ alkylene-NRR, for example $(CH_2)_2NRR$ and $(CH_2)_3$—NRR; and $C_1$-$C_8$ alkylene-3-10 member heterocycle, for example $CH_2$-3-10 membered heterocycle. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently $C_1$-$C_8$ alkyl, for example $CH_3$ or $CH_2CH_3$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently $C_1$-$C_8$ alkylene-NRR, for example $(CH_2)_2NRR$, wherein R is selected from C1-C alkyl and $C_1$-$C_8$ haloalkyl to form, for example $(CH_2)_2N(CH_3)(CH_2CF_3)$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently $C_1$-$C_8$ alkylene-NRR, wherein two R join to form, together with the atom to which they are bound, a 3-10 member heterocycle, which 3-10 member heterocycle is morpholinyl to form, for example, $(CH_2)_2$—(N-morpholinyl) and $(CH_2)$—(N-morpholinyl), and which morpholinyl ring may be optionally further substituted with one or two $C_1$-$C_8$ alkyl, for example $CH_3$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently $C_1$-$C_8$ alkylene-3-10 member heterocycle, for example $CH_2$-3-10 member heterocycle, which 3-10 member heterocycle is azetidinyl to form, for example, $CH_2$-azetidinyl, which azetidinyl may be optionally further substituted with 3-10 membered heterocycle, for example, tetrahydropyranyl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each $R^5$ is independently selected from the group consisting of H, $CH_3$, $CH_2CH_3$, $(CH_2)_2N(CH_3)(CH_2CF_3)$, $(CH_2)_2$—(N-morpholinyl), $(CH_2)$—(N-morpholinyl), $(CH_2)_2$—(N-2,6-dimethyl morpholinyl) and $CH_2$-(2-azetidinyl-N-tetrahydropyranyl).

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^7$ is halo, for example fluoro or chloro. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^7$ is selected from the group consisting of H, fluoro, chloro, hydroxy and $NH_2$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^7$ is hydroxy.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^8$ is $C_1$-$C_8$ alkyl, for example $CH_3$ or $CH_2CH_3$, optionally substituted with one or two-NRR or —OR. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^8$ is $C_1$-$C_8$ alkylene-C(O)OR. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^8$ is selected from the group consisting of $CH_3$, $CH_2CH_3$, $(CH_2)_3NH_2$, $(CH_2)_2OH$, $(CH_2)_3OH$ and $(CH_2)_2COOH$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^8$ is $CH_2CH_3$.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{10}$ is $C_1$-$C_8$ alkyl, for example $CH_3$, which $C_1$-$C_8$ alkyl is optionally substituted with one or two —OR. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{10}$ is selected from the group consisting of $CH_3$ and $CH_2OH$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{10}$ is $CH_3$.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{11}$ is selected from the group consisting of H and halo, for example fluoro. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{11}$ is selected from the group consisting of H and fluoro.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, $R^{12}$ is —CONH$_2$.

In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each R is independently selected from the group consisting of H, $C_1$-$C_8$ alkyl and $C_1$-$C_8$ haloalkyl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, two R join to form, together with the atom or atoms to which they are bound, a 3-10 member heterocycle, where said 3-10 member heterocycle contains one, two or three atoms selected from N, O and S, for example morpholinyl, piperidinyl, azetidinyl or N-8-oxa-3-azabicyclo[3.2.1]octan-3-yl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, two R join to form, together with the atom or atoms to which they are bound, a morpholinyl, which morpholinyl is optionally substituted with one or two $C_1$-$C_8$ alkyl, for example $CH_3$. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, two R join to form, together with the atom or atoms to which they are bound, a piperidinyl, which piperidinyl is optionally substituted with one or two substituents independently selected from cyano and halo, for example fluoro. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, two R join to form, together with the atom or atoms to which they are bound, an azetidinyl, which azetidinyl is optionally substituted with one substituent selected from halo, for example fluoro. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, two R join to form, together with the atom or atoms to which they are bound, a N-8-oxa-3-azabicyclo[3.2.1]octan-3-yl. In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each R is independently selected from the group consisting of H, $CH_3$, $CH_2FCF_3$, In one embodiment of compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, each R is independently H.

The invention also includes embodiments wherein there is provided a compound of formula (IA):

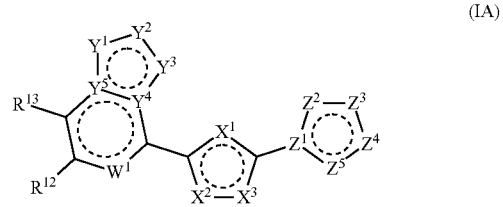

(IA)

or a pharmaceutically acceptable salt thereof, wherein each

in a ring independently represents two conjugated double bonds in a five-membered heteroaromatic ring and three conjugated double bonds in a six-membered aromatic or heteroaromatic ring;

$W^1$ is selected from $CR^{11}$ and N;
$X^1$ is selected from $CR^1$, $C(R^1)_2$, N, $NR^1$, O and S;
$X^2$ is selected from $CR^2$, $C(R^2)_2$, N, $NR^2$, O and S;
$X^3$ is selected from $CR^3$, $C(R^3)_2$, N, $NR^3$, O and S;
where two or three of $X^1$, $X^2$, and $X^3$ are independently selected from $NR^1$, $NR^2$, $NR^3$, O and S; and
where at least one of $X^1$, $X^2$ and $X^3$ is selected from $NR^1$, $NR^2$ and $NR^3$;
$Y^1$ is selected from N, $NR^4$, O, S, $CR^4$ and $C(R^4)_2$;
$Y^2$ is selected from N, $NR^5$, O, S, $CR^5$ and $C(R^5)_2$;
$Y^3$ is selected from N, $NR^6$, O, S, $CR^6$ and $C(R^6)_2$;
$Y^4$ is selected from C and N;
$Y^5$ is selected from C and N;
where only one, or only two, of $Y^1$, $Y^2$ and $Y^3$ are independently selected from N, $NR^4$, $NR^5$ and $NR^6$;
where when one of $Y^4$ and $Y^5$ is N, the other one of $Y^4$ and $Y^5$ is C;
$Z^1$ is selected from C and N;
$Z^2$ is selected from N, $NR^8$ and $CR^8$;
$Z^3$ is selected from N, $NR^9$ and $CR^9$;
$Z^4$ is selected from N, $NR^{10}$ and $CR^{10}$;
$Z^5$ is selected from N, $NR^7$ and $CR^7$;
where two or three of $Z^1$, $Z^2$, $Z^3$, $Z^4$ and $Z^5$ are independently selected from N, $NR^7$, $NR^8$, $NR^9$, and $NR^{10}$;
$R^1$ is selected from H, $C_1$-$C_8$ alkyl, $C_1$-$C_8$ alkylene-NRR and $C_1$-$C_8$ alkylene-C(O)OR;
$R^2$ is selected from H, $C_1$-$C_8$ alkyl, $C_1$-$C_8$ alkylene-NRR, $C_1$-$C_8$ alkylene-C(O)OR, $C_1$-$C_8$ alkylene-OR and $C_1$-$C_8$ alkylene-O—P(O)(OH)$_2$;

$R^3$ is selected from H, $C_1$-$C_8$ alkyl, $C_1$-$C_8$ alkylene-NRR, $C_1$-$C_8$ alkylene-C(O)OR and $C_1$—C alkylene-O—P(O)(OH)$_2$;

$R^4$ is selected from H, OR, $C_1$-$C_8$ alkyl optionally substituted with one or two —OR, $C_0$-$C_8$ alkylene-NRR, $C_0$-$C_8$ alkylene-C(O)OR, $C_0$-$C_8$ alkylene-3-10 member heterocycle, and $C_0$-$C_8$ alkylene-($C_3$-$C_{10}$)-cycloalkyl;

$R^5$ is selected from H, OR, $C_1$-$C_8$ alkyl, $C_0$-$C_8$ alkylene-NRR, $C_0$-$C_8$ alkylene-C(O)OR, $C_0$-$C_8$ alkylene-3-10 member heterocycle and $C_0$-$C_8$ alkylene-OR;

$R^6$ is H;

$R^7$ is H or halo;

$R^8$ is selected from H, $C_1$-$C_8$ alkyl optionally substituted with one or two —OR, $C_1$-$C_8$ alkylene-C(O)OR and $C_1$-$C_8$ alkylene-SO$_2$R;

$R^9$ is H;

$R^{10}$ is selected from H, $C_1$-$C_8$ alkyl optionally substituted with one or two —OR, and halo;

$R^{11}$ is selected from H, $C_1$-$C_8$ alkyl, —OR and halo;

$R^{12}$ is —C(O)N(R)$_2$ or —C(O)NHR;

$R^{13}$ is H;

each R is independently H or $C_1$-$C_8$ alkyl, or two R join to form, together with the atom or atoms to which they are bound, a —($C_3$-$C_{10}$) cycloalkyl or 3-10 member heterocycle, where said 3-10 member heterocycle contains one, two or three atoms selected from N, O and S; and where —($C_3$-$C_{10}$) cycloalkyl or 3-10 member heterocycle is optionally substituted with one or more substituents each independently selected from $C_1$-$C_8$ alkyl, hydroxy, $C_1$-$C_8$ alkoxy, —($C_3$-$C_{10}$) cycloalkyl, 3-10 member heterocycle, halo and cyano.

The invention also includes embodiments of formula IA wherein there are provided compounds or salts of formula IA where no more than two of $Y^1$, $Y^2$, $Y^3$, $Y^4$ and $Y^5$ are independently selected from N, NR$^4$, NR$^5$ and NR$^6$.

The invention also includes embodiments of formula IA wherein there are provided compounds or salts of formula IA where at least one of $Y^1$, $Y^2$ and $Y^3$ is C, for example wherein at least one of $Y^1$, $Y^2$ and $Y^3$ are selected from CR$^4$, C(R$^4$)$_2$, CR$^5$, C(R$^5$)$_2$, CR$^6$ and C(R$^6$)$_2$.

The invention also includes embodiments of formula IA wherein there are provided compounds or salts of formula IA where at least one of $Y^4$ and $Y^5$ is C.

The invention also includes embodiments of formula IA wherein there are provided compounds or salts of formula IA where $Y^1$—R$^4$ is not C—OH, for example wherein when $Y^1$ is selected from CR$^4$ or C(R$^4$)$_2$ then R$^4$ is not OH.

The invention also includes embodiments of formula IA wherein there are provided compounds or salts of formula IA where $Y^1$—R$^4$ is not C—OH if $Y^2$ is N or NR$^5$, for example wherein when $Y^2$ is selected from N or NR$^5$ and $Y^1$ is selected from CR$^4$ or C(R$^4$)$_2$, then R$^4$ is not OH. The invention also includes embodiments of formula IA wherein there are provided compounds or salts of formula IA where $Y^2$—R$^5$ is not C—OH, for example wherein when $Y^2$ is selected from CR$^5$ or C(R$^5$)$_2$ then R$^5$ is not OH.

The invention also includes embodiments of formula IA wherein there are provided compounds or salts of formula IA where $Y^2$—R$^2$ is not C—OH if $Y^1$ is N or NR$^4$, or if $Y^3$ is N or NR$^6$, for example wherein when $Y^1$ is selected from N or NR$^4$ and $Y^2$ is selected from CR$^5$ or C(R$^5$)$_2$, then R$^5$ is not OH or for example wherein when $Y^3$ is selected from N or NR$^6$ and $Y^2$ is selected from CR$^5$ or C(R$^5$)$_2$, then R$^5$ is not OH. The invention further includes embodiments of formula IA wherein there are provided compounds or salts of formula IA, where: $X^1$ is selected from N and NR$^1$; $X^2$ is selected from N, NR$^2$ and S; $X^3$ is selected from CR$^3$, NR$^3$ and S; $Y^1$ is selected from N and NR$^4$; $Y^2$ is selected from N and NR$^5$; $Y^3$ is selected from NR$^6$ and CR$^6$; $Y^4$ is selected from C; $Z^1$ is selected from C; $Z^2$ is selected from NR$^8$; $Z^3$ is selected from N; $Z^4$ is selected from CR$^{10}$; $Z^5$ is selected from CR$^7$; R$^2$ is selected from H, $C_1$-$C_8$ alkyl, $C_1$-$C_8$ alkylene-NRR and $C_1$-$C_8$ alkylene-O—P(O)(OH)$_2$; R$^3$ is selected from H; R$^4$ is selected from H, $C_1$-$C_8$ alkyl and $C_0$-$C_8$ alkylene-NRR; R$^5$ is selected from H and $C_1$-$C_8$ alkyl; R$^{10}$ is selected from H and $C_1$-$C_8$ alkyl; and R$^{11}$ is selected from H and halo.

The invention includes embodiments wherein there is provided a compound of formula (IB):

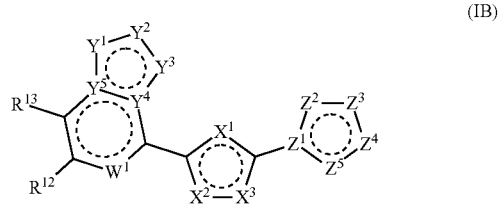

or a pharmaceutically acceptable salt thereof, wherein each

in a ring independently represents two conjugated double bonds in a five-membered heteroaromatic ring and three conjugated double bonds in a six-membered aromatic or heteroaromatic ring;

$W^1$ is selected from CR$^{11}$ and N;

$X^1$ is selected from CR$^1$, C(R$^1$)$_2$, N, NR$^1$, O and S;

$X^2$ is selected from CR$^2$, C(R$^2$)$_2$, N, NR$^2$, O and S;

$X^3$ is selected from CR$^3$, C(R$^3$)$_2$, N, NR$^3$, O and S;

where two or three of $X^1$, $X^2$, and $X^3$ are independently selected from NR$^1$, NR$^2$, NR$^3$, O and S; and where at least one of $X^1$, $X^2$ and $X^3$ is selected from NR$^1$, NR$^2$ and NR$^3$;

$Y^1$ is selected from N, NR$^4$, O, S, CR$^4$ and C(R$^4$)$_2$;

$Y^2$ is selected from N, NR$^5$, O, S, CR$^5$ and C(R$^5$)$_2$;

$Y^3$ is selected from N, NR$^6$, O, S, CR$^6$ and C(R$^6$)$_2$;

$Y^4$ is selected from C and N;

$Y^5$ is selected from C and N;

where only one, or only two, of $Y^1$, $Y^2$ and $Y^3$ are independently selected from N, NR$^4$, NR$^5$ and NR$^6$;

where when one of $Y^4$ and $Y^5$ is N, the other one of $Y^4$ and $Y^5$ is C;

$Z^1$ is selected from C and N;

$Z^2$ is selected from N, NR$^8$ and CR$^8$;

$Z^3$ is selected from N, NR$^9$ and CR$^9$;

$Z^4$ is selected from N, NR$^{10}$ and CR$^{10}$;

$Z^5$ is selected from N, NR$^7$ and CR$^7$;

where two or three of $Z^1$, $Z^2$, $Z^3$, $Z^4$ and $Z^5$ are independently selected from N, NR$^7$, NR$^8$, NR$^9$, and NR$^{10}$;

R$^1$ is selected from H, $C_1$-$C_8$ alkyl, $C_1$-$C_8$ alkylene-NRR and $C_1$-$C_8$ alkylene-C(O)OR;

R$^2$ is selected from H, $C_1$-$C_8$ alkyl, $C_1$-$C_8$ alkylene-NRR, $C_1$-$C_8$ alkylene-C(O)OR, $C_1$-$C_8$ alkylene-OR and $C_1$-$C_8$ alkylene-O—P(O)(OH)$_2$;

R³ is selected from H, $C_1$-$C_8$ alkyl, $C_1$-$C_8$ alkylene-NRR, $C_1$-$C_8$ alkylene-C(O)OR and $C_1$-$C_8$ alkylene-O—P(O)(OH)$_2$;

R⁴ is selected from H, OR, $C_1$-$C_8$ alkyl, $C_0$-$C_8$ alkylene-NRR, $C_0$-$C_8$ alkylene-C(O)OR, $C_0$-$C_8$ alkylene-3-10 member heterocycle, $C_0$-$C_8$ alkylene-($C_3$-$C_{10}$) cycloalkyl and $C_0$-$C_8$ alkylene-OR;

R⁵ is selected from H, OR, $C_1$-$C_8$ alkyl, $C_0$-$C_8$ alkylene-NRR, $C_0$-$C_8$ alkylene-C(O)OR, $C_0$-$C_8$ alkylene-3-10 member heterocycle and $C_0$-$C_8$ alkylene-OR;

R⁶ is H;

R⁷ is H or halo;

R⁸ is selected from H, $C_1$-$C_8$ alkyl optionally substituted with one or two —OR, $C_1$-$C_8$ alkylene-C(O)OR and $C_1$-$C_8$ alkylene-SO$_2$R;

R⁹ is H;

R¹⁰ is selected from H, $C_1$-$C_8$ alkyl and halo;

R¹¹ is selected from H, $C_1$-$C_8$ alkyl, —OR and halo;

R¹² is —C(O)N(R)$_2$ or —C(O)NHR;

R¹³ is H;

each R is independently H or $C_1$-$C_8$ alkyl, or two R join to form, together with the atom or atoms to which they are bound, a —($C_3$-$C_{10}$) cycloalkyl or 3-10 member heterocycle, where said 3-10 member heterocycle contains one, two or three atoms selected from N, O and S, and where said —($C_3$-$C_{10}$) cycloalkyl or 3-10 member heterocycle is optionally substituted with one or more substituents each independently selected from $C_1$-$C_8$ alkyl, hydroxy, $C_1$-$C_8$ alkoxy, —($C_3$-$C_{10}$) cycloalkyl, 3-10 member heterocycle, halo and cyano.

The invention also includes embodiments of formula IB wherein there are provided compounds or salts of formula IB where no more than two of Y¹, Y², Y³, Y⁴ and Y⁵ are independently selected from N, NR⁴, NR⁵ and NR⁶.

The invention also includes embodiments of formula IB wherein there are provided compounds or salts of formula IB where at least one of Y¹, Y² and Y³ is C, for example wherein at least one of Y¹, Y² and Y³ are selected from CR⁴, C(R⁴)$_2$, CR⁵, C(R⁵)$_2$, CR⁶ and C(R⁶)$_2$.

The invention also includes embodiments of formula IB wherein there are provided compounds or salts of formula IB where at least one of Y⁴ and Y⁵ is C.

The invention also includes embodiments of formula IB wherein there are provided compounds or salts of formula IB where Y¹—R⁴ is not C—OH, for example wherein when Y¹ is selected from CR⁴ or C(R⁴)$_2$ then R⁴ is not OH.

The invention also includes embodiments of formula IB wherein there are provided compounds or salts of formula IB where Y¹—R⁴ is not C—OH if Y² is N or NR⁵, for example wherein when Y² is selected from N or NR⁵ and Y¹ is selected from CR⁴ or C(R⁴)$_2$, then R⁴ is not OH.

The invention also includes embodiments of formula IB wherein there are provided compounds or salts of formula IB where Y²—R⁵ is not C—OH, for example wherein when Y² is selected from CR⁵ or C(R⁵)$_2$ then R⁵ is not OH.

The invention also includes embodiments of formula IB wherein there are provided compounds or salts of formula IB where Y²—R⁵ is not C—OH if Y¹ is N or NR⁴, or if Y³ is N or NR⁶, for example wherein when Y¹ is selected from N or NR⁴ and Y² is selected from CR⁵ or C(R⁵)$_2$, then R⁵ is not OH or for example wherein when Y³ is selected from N or NR⁶ and Y² is selected from CR⁵ or C(R⁵)$_2$, then R⁵ is not OH.

The invention further includes embodiments of formula IB wherein there are provided compounds or salts of formula IB, where: X¹ is selected from N and NR¹; X² is selected from N, NR² and S; X³ is selected from CR³, NR³ and S; Y¹ is selected from N and NR⁴; Y² is selected from N and NR⁵; Y³ is selected from NR⁶ and CR⁶; Y⁴ is selected from C; Z¹ is selected from C; Z² is selected from NR⁸; Z³ is selected from N; Z⁴ is selected from CR¹⁰; Z⁵ is selected from CR⁷; R² is selected from H, $C_1$-$C_8$ alkyl, $C_1$-$C_8$ alkylene-NRR and $C_1$-$C_8$ alkylene-O—P(O)(OH)$_2$; R³ is selected from H; R⁴ is selected from H, $C_1$-$C_8$ alkyl and $C_0$-$C_8$ alkylene-NRR; R⁵ is selected from H and $C_1$-$C_8$ alkyl; R¹⁰ is selected from H and $C_1$-$C_8$ alkyl; and R¹¹ is selected from H and halo.

Further embodiments of the invention include a compound selected from:

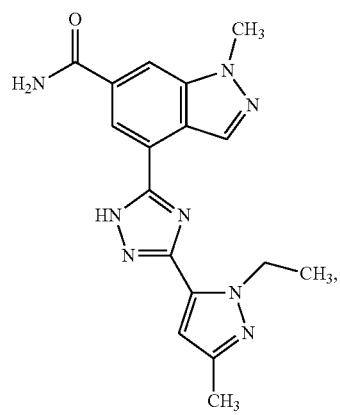

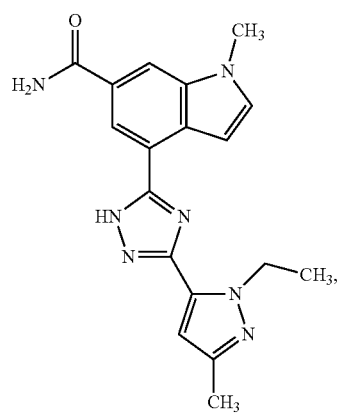

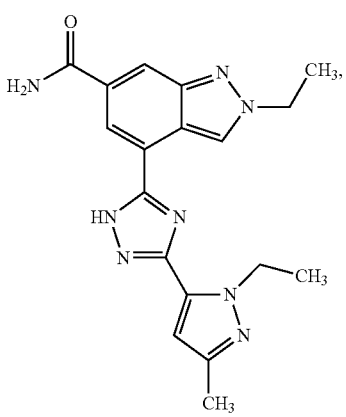

-continued
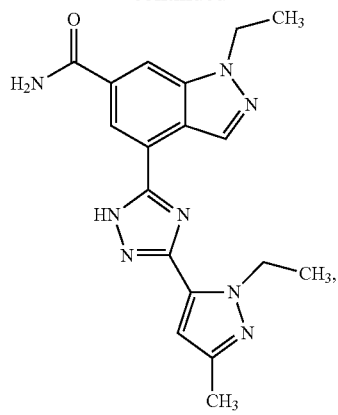
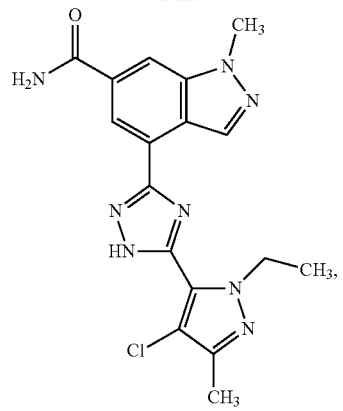
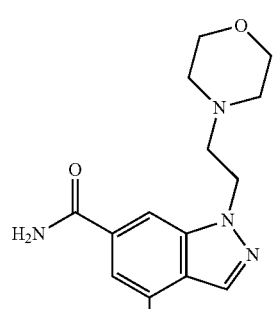
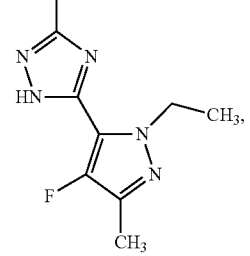
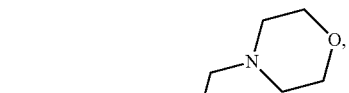
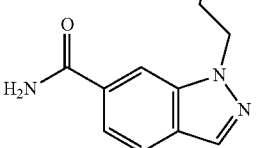
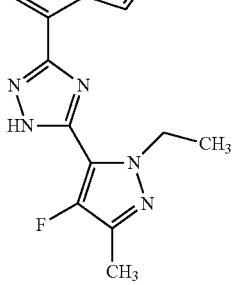

23
-continued
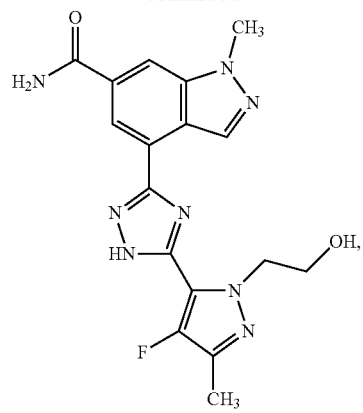
24
-continued
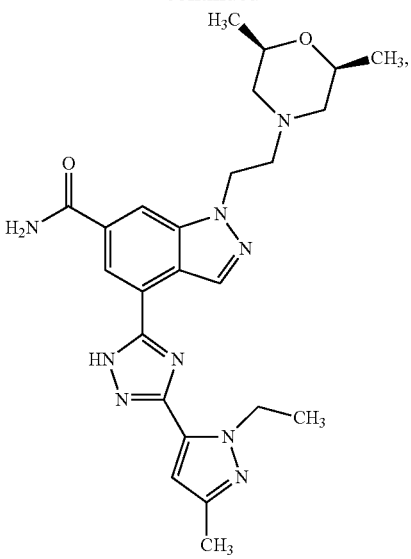
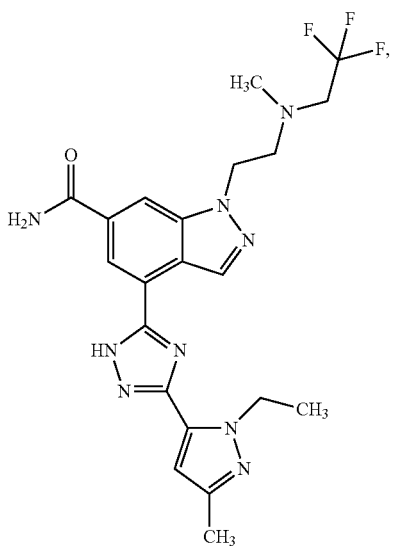

25
-continued
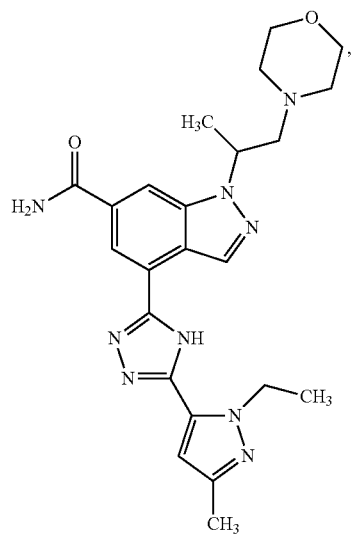
26
-continued
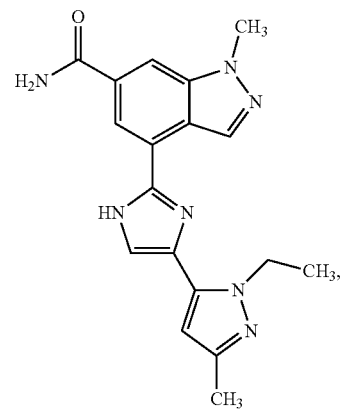
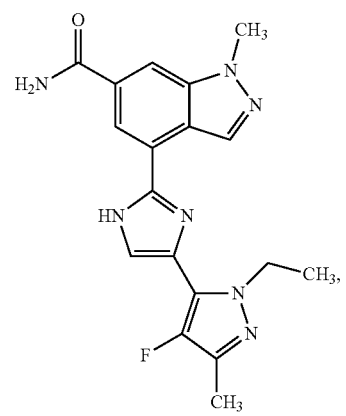
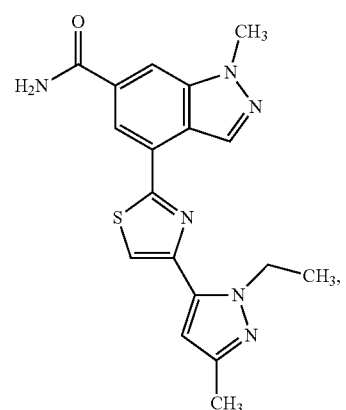
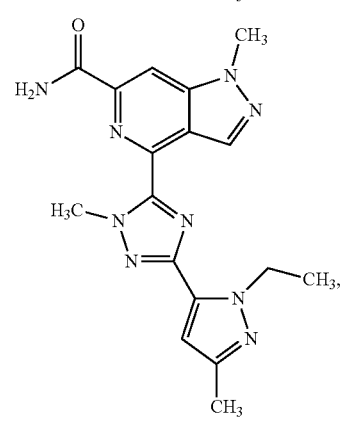

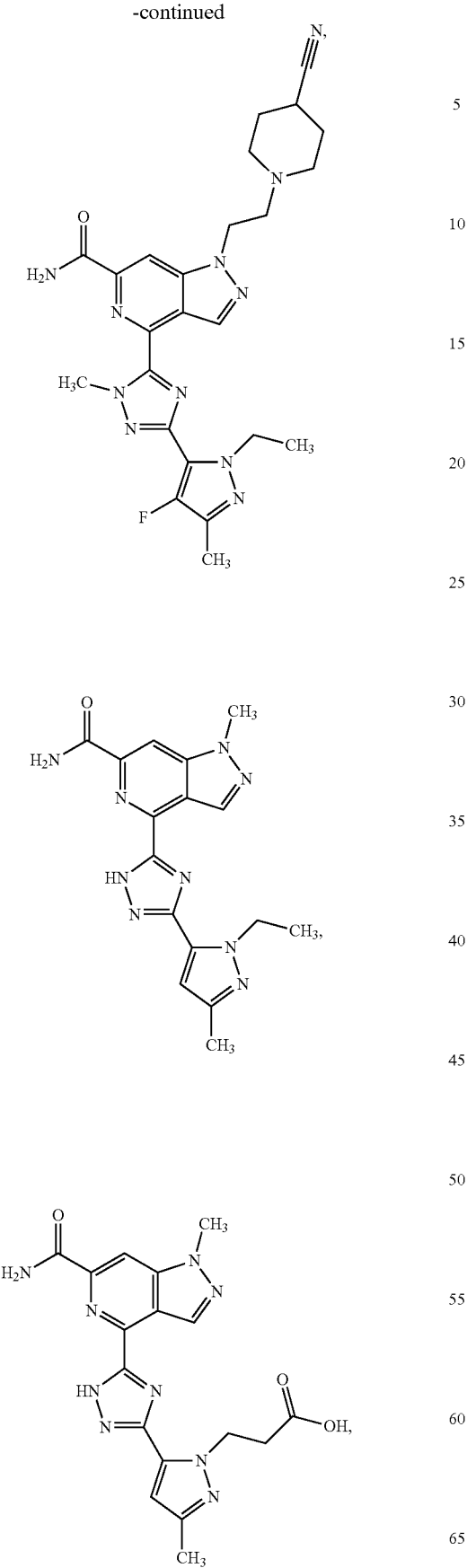
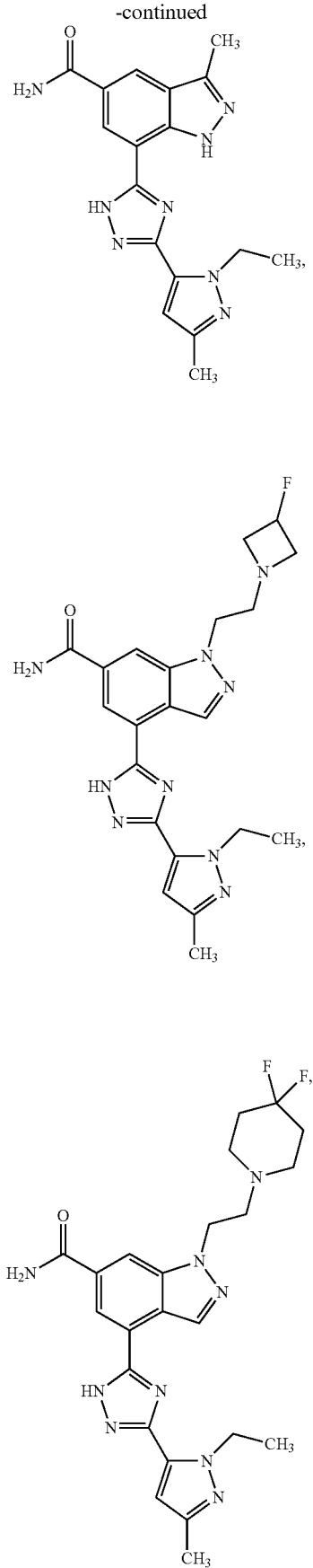

29
-continued
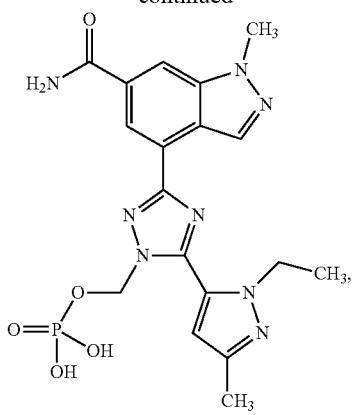
30
-continued
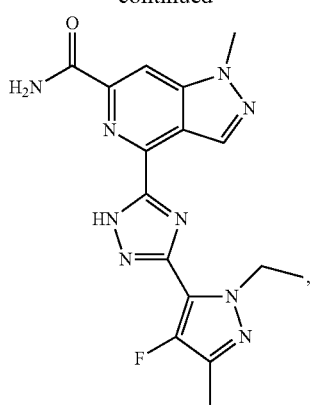
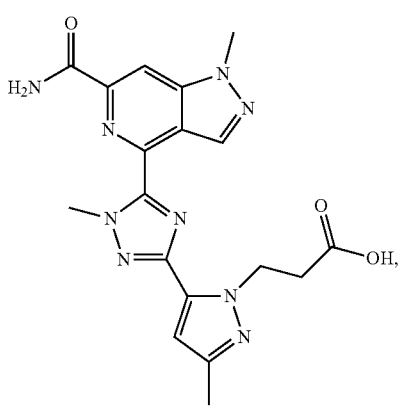
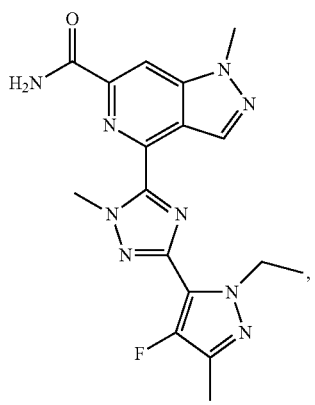 [SMILES: CCn1nc(C)c(F)c1-c1nc(-c2nc(C(N)=O)cc3c2cnn3C)n(C)n1]

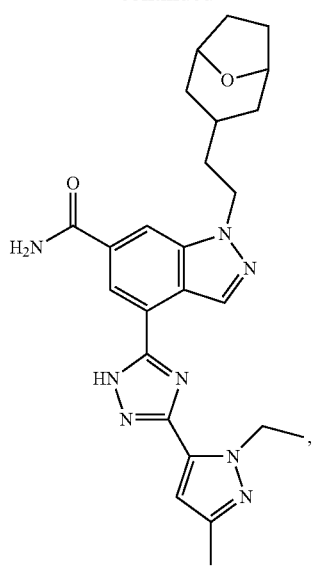
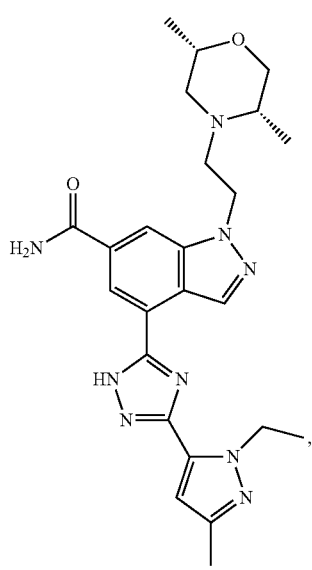
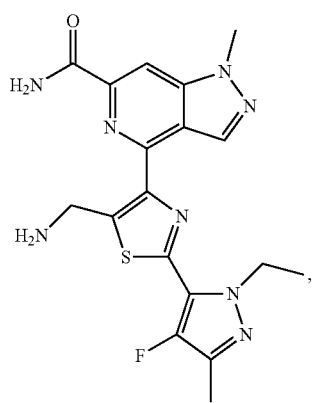
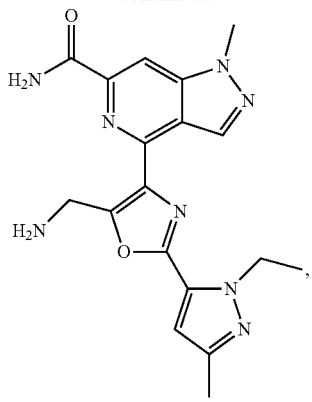
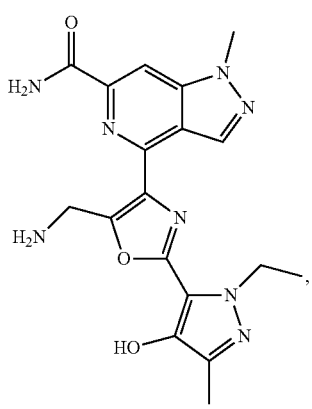
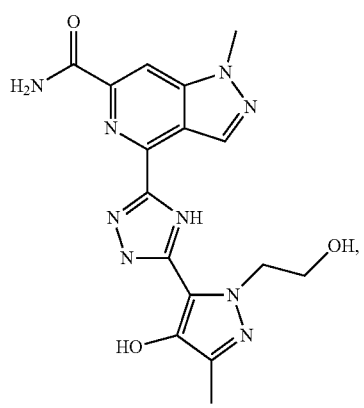
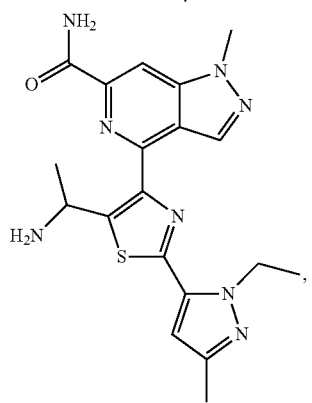

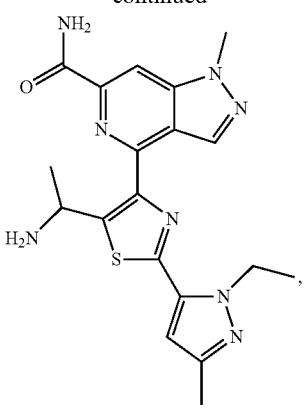
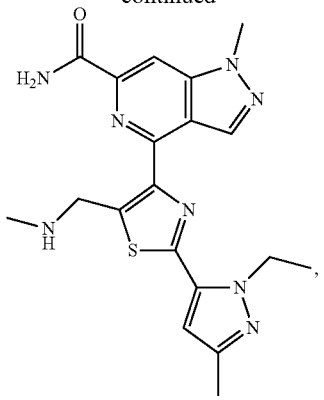
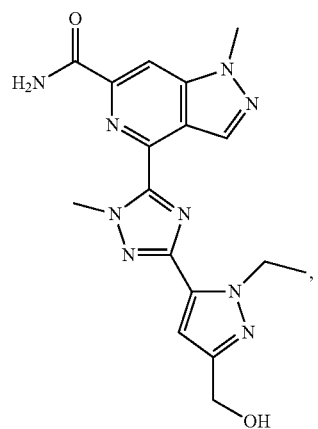
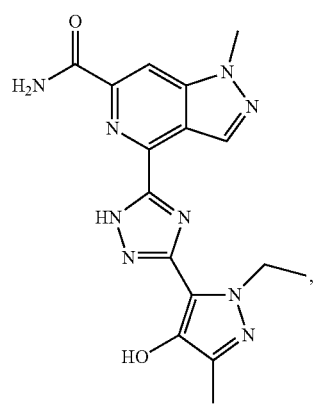
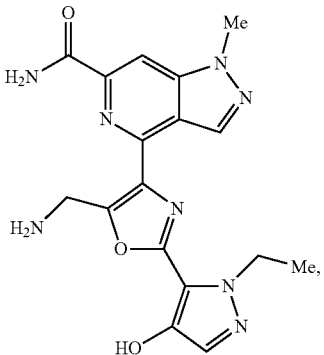

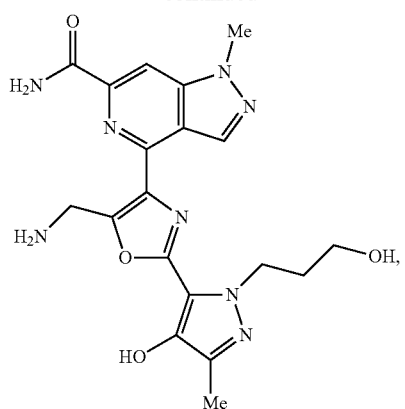
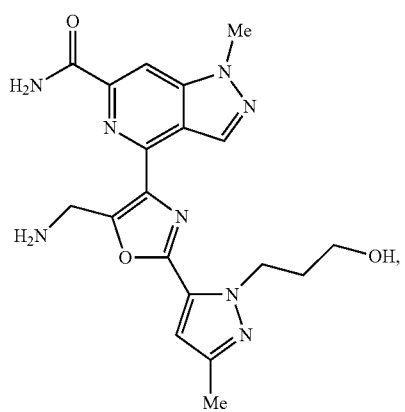
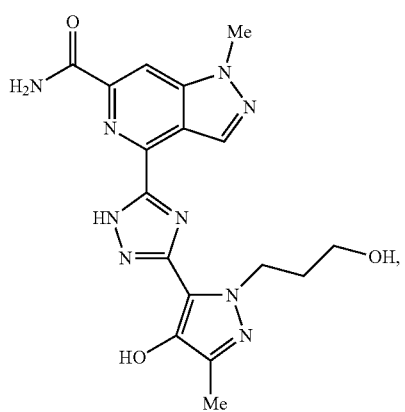
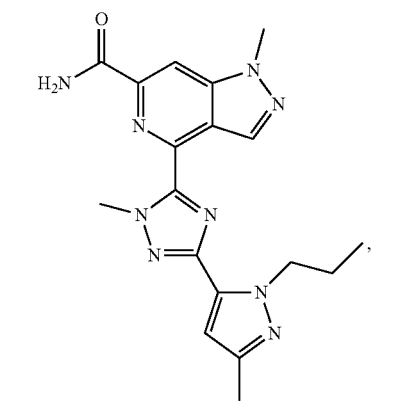
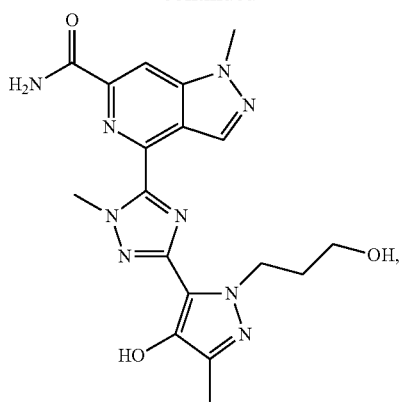
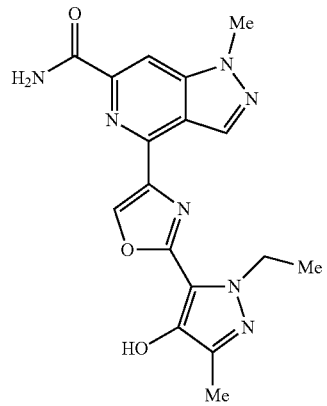
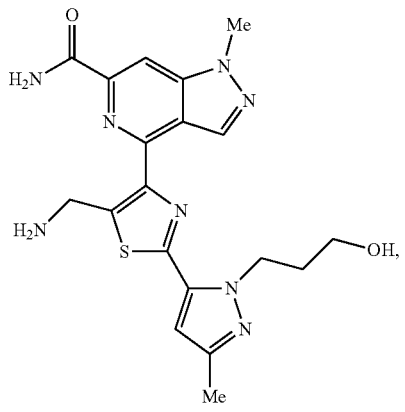
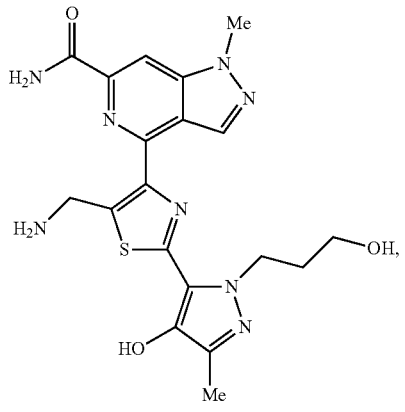

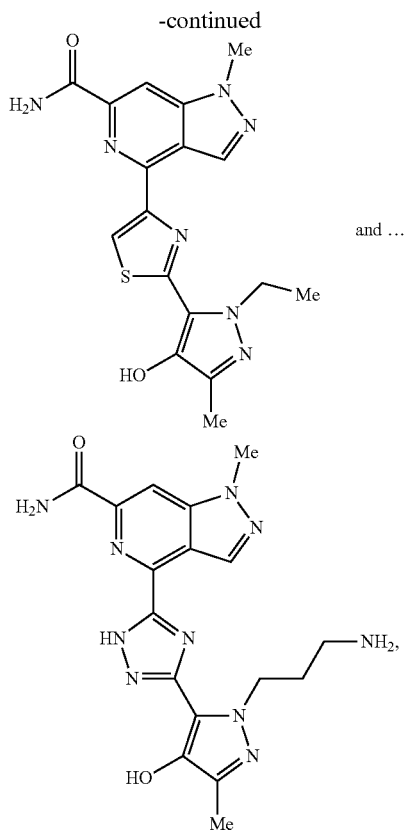

or a pharmaceutically acceptable salt thereof.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, bind to STING. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING when compared to the native ligand. In one embodiment, the compounds of the invention, including those of formulae (I), (IA), (IB), (II), (I), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM, which in vitro $K_i$ is determined by a radioligand binding assay, such as the Scintiallation Proximity Assay. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM, which in vitro $K_i$ is determined by a Scintiallation Proximity Assay, which assay comprises the steps of:

(i) immobilizing 100 nM STING protein on a suitable carrier, for example 20 µg streptavidin polyvinyl toluene (SA-PVT) beads, in a suitable buffer, which buffer optionally comprises 150 mM NaCl, 25 mM Hepes (pH 7.5), 0.1 mM EDTA, 1 mM DTT, 0.005% (v/v) Tween-20, and 1% (v/v) DMSO;

(ii) adding a compound of the invention, or a pharmaceutically acceptable salt thereof, in a three-fold dilution series from a 100 µM starting concentration and allowing it to come to equilibrium at room temperature, for example for 20 mins;

(iii) adding $^3$H-cGAMP at 100 nM concentration;

(iv) normalising to a positive control compound that completely blocks $^3$H-cGAMP binding and a negative control DMSO; and (v) determining the $K_i$ for competitive binding from the $IC_{50}$ using the Cheng-Prusoff equation;

wherein said STING protein is a STING construct comprised of residues 155-341 with both N- and C-terminal truncations wherein the N-terminal transmembrane domains have been removed (1-154), as well as the C-terminal tail (342-379) and which has been enzymatically highly specifically N-terminal biotinylated, for example with the E. coli biotin ligase (BirA), with the inclusion of a high-affinity biotinylation peptide, for example AviTag™.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate the STING pathway, including STING pathway members such as IRF3. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, stimulate the innate immune response. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, induce type 1 IFN, for example IFNβ. In one embodiment, the compounds of the invention, or pharmaceutically acceptable salts thereof, induce cytokines other than type 1 IFN. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate co-stimulatory factors. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, induce type 1 IFN and other cytokines and activate co-stimulatory factors.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 100 µM or less, preferably about 50 µM or less, more preferably about µM or less and most preferably about 10 µM or less, which in vitro $EC_{50}$ is determined by an assay which monitors phosphorylation of IRF3, such as a THP-1 cell ELISA assay. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 100 µM or less, preferably about 50 µM or less, more preferably about 20 µM or less and most preferably about 10 µM or less, which in vitro $EC_{50}$ is determined by monitoring phosphorylation of IRF3 using a THP-1 cell ELISA assay, which assay comprises the steps of:
(i) growing THP-1 cells in RPMI media plus 2 mM L-glutamine, 10% fetal bovine serum, and 0.5% Pen-Strep and incubating, for example overnight at 37° C., 5% $CO_2$;
(ii) adding a compound of the invention, or a pharmaceutically acceptable salt thereof, which compound, or salt thereof, has been diluted in RPMI media, and incubating, for example for 3 hours;
(iii) lysing the cells in RIPA buffer, transferring an aliquot of the lysate to plates coated with mouse anti-human IRF-3 capture antibody and incubating, for example at 4° C. for 16 hours;
(iv) adding rabbit anti-phospho-IRF3 detection antibody and further incubating, for example for 1.5 hours;
(v) adding an HRP-linked secondary antibody and further incubating, for example 30 minutes;
(vi) generating a luminescent signal with a luminescent reagent; and
(vii) normalizing the signal to "% effect" with a positive control STING agonist known to maximize the phosphorylated IRF3 signal and a negative control DMSO.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 100 µM or less, preferably about 50 µM or less, more preferably about 20 µM or less and most preferably about 10 µM or less, which in vitro $EC_{50}$ is determined by an assay which monitors interferon-β induction, such as a THP-1 SG reporter cell line assay. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 100 µM or less, preferably about 50 µM or less, more preferably about 20 µM or less and most preferably about 10 µM or less, which in vitro $EC_{50}$ is determined by monitoring interferon-β induction using a THP-1 SG reporter cell line assay, which assay comprises the steps of:
(i) growing THP-1 ISG cells in RPMI media plus 2 mM L-glutamine, 10% fetal bovine serum, and 0.5% Pen-Strep in the presence of hygromycin B and zeocin;
(ii) adding a compound of the invention, or a pharmaceutically acceptable salt thereof, which compound, or salt thereof, has been diluted in RPMI media, and incubating, for example for 24 hours;
(iii) adding a luminescent reagent to an aliquot of supernatant of centrifuged cells; and
(iv) measuring the luminescent signal and normalizing it to "% effect" with a positive control STING agonist known to maximize the luciferase signal and a negative control DMSO.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 15 µM or less, preferably about 1 µM or less, more preferably about 0.5 µM or less and most preferably about 0.1 µM or less, which in vitro $EC_{50}$ is determined by an assay which monitors interferon-β induction in peripheral blood mononuclear cells (PBMCs), such as a HTRF IFNβ assay. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 15 µM or less, preferably about 1 µM or less, more preferably about 0.5 µM or less and most preferably about 0.1 µM or less, which in vitro $EC_{50}$ is determined by monitoring interferon-β induction in PBMCs using a HTRF IFNβ assay, which assay which comprises:
(i) seeding PBMCs in RPMI media and incubating, for example at 37° C. overnight;
(ii) adding a compound of the invention, or a pharmaceutically acceptable salt thereof, which compound, or salt thereof, has been diluted in RPMI media and incubating, for example for an additional 4 hours;
(iii) collecting the media following centrifugation, for example at 1500×g for 5 mins; (iv) mixing an aliquot of the media with an anti-body reaction reagent from the HTRF IFNβ assay and combining with the associated assay antibodies, for example at a 2:1 ratio;
(v) measuring the FRET signal, for example using a BMG Pherastar microplate reader (ratio 665 nm/620 nm); and
(vi) normalizing the signal to "% effect" with a positive control STING agonist known to maximize the luciferase signal and a negative control DMSO;
wherein the PBMCs were isolated from a leukopak preparation of fresh human whole blood using equal volumes of phosphate buffered saline and 2% fetal bovine serum, a density gradient medium, for example Lymphoprep™, and centrifugation; and
wherein the PBMCs were from a single human donor verified to be wild-type for STING.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 5 µM or less, preferably about 1 µM or less, more preferably about 0.5 µM or less and most preferably about 0.1 µM or less, which in vitro $EC_{50}$ is determined by an assay which monitors phosphorylation of IRF3 in peripheral blood mononuclear cells (PBMCs), such as a phospho-IRF3 assay. In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, activate STING with an in vitro $EC_{50}$ of about 5 µM or less, preferably about 1 µM or less, more preferably about 0.5 µM or less and most preferably about 0.1 µM or less which in vitro $EC_{50}$ is determined by monitoring phosphorylation of IRF3 in peripheral blood mononuclear cells (PBMCs) using a phospho-IRF3 assay, which assay comprises:

(i) seeding PBMCs in RPMI media and incubating, for example at 37° C. overnight under 5% $CO_2$;
(ii) adding a compound of the invention, or a pharmaceutically acceptable salt thereof, which compound, or salt thereof, has been diluted in RPMI media and incubating, for example for an additional 4 hours;
(iii) lysing the cells in RIPA buffer, transferring an aliquot of the lysate to plates coated with mouse anti-human IRF-3 capture antibody and incubating, for example at 4° C. for 16 hours;
(iv) adding rabbit anti-phospho-IRF3 detection antibody and further incubating, for example for 1.5 hours;
(v) adding an HRP-linked secondary antibody and further incubating, for example 30 minutes;
(viii) generating a luminescent signal with a luminescent reagent; and
(vii) normalizing the signal to "% effect" with a positive control STING agonist known to maximize the luciferase signal and a negative control DMSO;
wherein the PBMCs were isolated from a leukopak preparation of fresh human whole blood using equal volumes of phosphate buffered saline and 2% fetal bovine serum, a density gradient medium, for example Lymphoprep™, and centrifugation; and
wherein the PBMCs were from a single human donor verified to be wild-type for STING.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM and activate STING with an in vitro $EC_{50}$ of about 100 µM or less, preferably about 50 µM or less, more preferably about 20 µM or less and most preferably about 10 µM or less, which in vitro $EC_{50}$ is determined by an assay which monitors phosphorylation of IRF3.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM and activate STING with an in vitro $EC_{50}$ of about 100 µM or less, preferably about 50 µM or less, more preferably about 20 µM or less and most preferably about 10 µM or less, which in vitro $EC_{50}$ is determined by an assay which monitors interferon-β induction.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM and activate STING with an in vitro $EC_{50}$ of about 15 µM or less, preferably about 1 µM or less, more preferably about 0.5 µM or less and most preferably about 0.1 µM or less, which in vitro $EC_{50}$ is determined by an assay which monitors interferon-β induction in peripheral blood mononuclear cells.

In one embodiment, the compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or pharmaceutically acceptable salts thereof, competitively bind to STING with an in vitro $K_i$ of less than 0.750 µM, preferably less than about 0.500 µM, more preferably less than about 0.250 µM, and even more preferably less than about 0.100 µM and activate STING with an in vitro $EC_{50}$ of about 5 µM or less, preferably about 1 µM or less, more preferably about 0.5 µM or less and most preferably about 0.1 µM or less, which in vitro $EC_{50}$ is determined by an assay which monitors phosphorylation of IRF3 in peripheral blood mononuclear cells.

Further embodiments of the invention include a pharmaceutical composition comprising a compound or salt as described herein, or a pharmaceutically acceptable salt thereof, and a pharmaceutically acceptable carrier. Optionally, such compositions may comprise a compound or salt as described herein which is a component of an antibody-drug conjugate; and/or may comprise a compound as described herein which is a component of a particle-based delivery system.

Also embodied in the invention is a method of treating abnormal cell growth in a mammal, the method comprising administering to the mammal a therapeutically effective amount of a compound or salt as described herein. This method may optionally employ a compound or salt as described herein as a component of an antibody-drug conjugate, or as a component of a particle-based delivery system. In such embodiments the abnormal cell growth may be cancer. If the abnormal cell growth is cancer, the cancer to be treated may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In one embodiment, the cancer is cancer of the bladder. In one embodiment, the cancer of the bladder is urothelial carcinoma. In one embodiment, the cancer of the bladder is non-muscle invasive bladder cancer (NMIBC). In one embodiment the cancer of the bladder cancer of the bladder is muscle invasive bladder cancer (MIBC). In one embodiment, the cancer of the bladder is non-metastatic urothelial carcinoma. In one embodiment, the cancer of the bladder is metastatic urothelial carcinoma. In one embodiment, the cancer of the bladder is non-urothelial carcinoma. In one embodiment the mammal is a human.

Also embodied in the invention is a method of treating inflammatory diseases, allergic diseases, autoimmune diseases and infectious diseases in a mammal, the method comprising administering to the mammal a therapeutically effective amount of a compound or salt as described herein. This method may optionally employ a compound or salt as described herein as a component of an antibody-drug conjugate, or as a component of a particle-based delivery system. One embodiment of the invention is a method of treating inflammatory diseases in a mammal. One embodiment of the invention is a method of treating allergic diseases. One embodiment of the invention is a method of treating autoimmune disease. One embodiment of the invention is a method of treating infectious diseases. In one embodiment, the mammal is a human.

Also embodied in the invention is the use of a compound or salt as described herein for the preparation of a medicament useful in the treatment of abnormal cell growth in a mammal. In such embodiments the abnormal cell growth may be cancer. If the abnormal cell growth is cancer, the cancer to be treated may be lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma. In one embodiment, the cancer is cancer of the bladder. In one embodiment, the cancer of the bladder is urothelial carcinoma. In one embodiment, the cancer of the bladder is non-muscle invasive bladder cancer (NMIBC). In one embodiment the cancer of the bladder cancer of the bladder is muscle invasive bladder cancer (MIBC). In one embodiment, the cancer of the bladder is non-metastatic urothelial carcinoma. In one embodiment, the cancer of the bladder is metastatic urothelial carcinoma. In one embodiment, the cancer of the bladder is non-urothelial carcinoma. In one embodiment the mammal is a human.

Further still, embodiments of the invention include those where there is provided a method of upregulating the activity of STING in a mammal, comprising the step of administering to said mammal an effective amount of a compound or salt as described herein; and/or a method of increasing interferon-beta levels in a mammal, comprising the step of administering to said mammal an effective amount of a compound or salt as described herein. In one embodiment the mammal is a human.

Yet further embodiments of the invention include those where there is provided a method of activating STING in a mammal, comprising the step of administering to said mammal an effective amount of a compound or salt described herein. Also provides is a method of stimulating the innate immune response in a mammal, comprising the step of administering to said mammal an effective amount of a compound or salt described herein. In one embodiment the mammal is a human.

Definitions

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("($C_1$-$C_{20}$)alkyl"), preferably 1 to 12 carbon atoms ("($C_1$-$C_{12}$)alkyl"), more preferably 1 to 8 carbon atoms ("($C_1$-$C_8$)alkyl"), or 1 to 6 carbon atoms ("($C_1$-$C_6$)alkyl"), or 1 to 4 carbon atoms ("($C_1$-$C_4$)alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, 0-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl", for instance ($C_1$-$C_8$)haloalkyl, refers to an alkyl having one or more, preferably 1, 2, 3, 4, 5, or 6, halo substituents. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —$NR^xR^y$ group, wherein $R^x$ and $R^y$ are both hydrogen, ie —$NH_2$.

"Cyano" refers to a —C≡N group. Cyano may be expressed as CN.

The term "cycloalkyl", as used herein, refers to a non-aromatic, monocyclic, fused or bridged bicyclic or tricyclic carbocyclic ring group containing, in certain embodiments, from three to ten carbon atoms. As used herein, a cycloalkyl group may optionally contain one or two double bonds. The term "cycloalkyl" also includes spirocyclic carbocyclic groups, including multi-ring systems joined by a single atom. The terms "$C_3$-$C_{10}$ cycloalkyl", "$C_3$-$C_7$ cycloalkyl", "$C_3$-$C_6$ cycloalkyl", "$C_3$-$C_5$ cycloalkyl", "$C_3$-$C_4$ cycloalkyl", and "$C_5$-$C_7$ cycloalkyl" contain from three to ten, from three to seven, from three to six, from three to five, from three to four, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, octahydropentalenyl, octahydro-1H-indenyl, bicyclo[2.2.1]heptanyl, bicyclo[3.2.1]octanyl, bicyclo[5.2.0]nonanyl, adamantanyl, cyclohexadienyl, adamantanyl, cycloheptanyl, cycloheptatrienyl, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro and amino.

"Halogen" or the prefix "halo" refers to fluoro, chloro, bromo and iodo. Preferably halogen or halo refers to fluoro or chloro.

"Heteroatom" refers to an atom selected from the group consisting of O, N, Si, S and P, and wherein the nitrogen and sulfur atoms may optionally be oxidized.

The term "heterocycle", as used herein, refers to a non-aromatic, monocyclic, fused or bridged bicyclic or tricyclic, or spirocyclic ring group containing, in certain embodiments, a total of three to ten ring atoms, three to seven ring atoms, or four to six ring atoms, in which one, one to two, one to three, or one to four ring atoms are heteroatoms. Said heteroatoms are independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycle ring may also be substituted by an oxo (=O) group at any available carbon atom. The rings may also have one or more double bonds. Furthermore, such groups may be bonded to the remainder of the compounds of embodiments disclosed herein through either a carbon atom or a heteroatom, if possible. Examples of heterocycle groups include, but are not limited to:

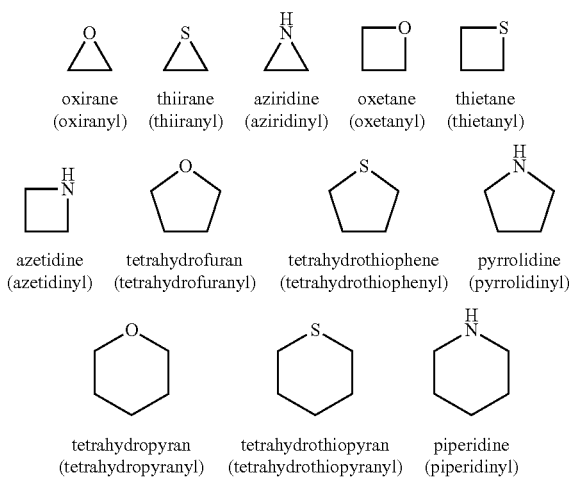

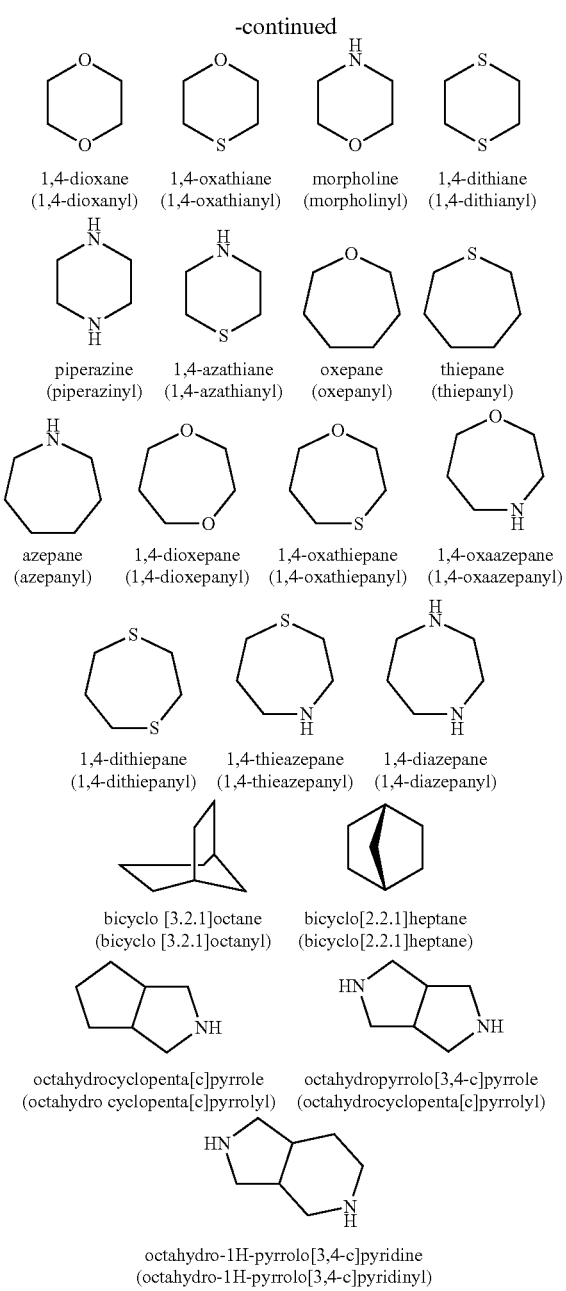

The heterocycle group is optionally substituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro and amino.

"Hydroxy" or "hydroxyl" refers to an —OH group.

"Aryl" or "aromatic" refer to an optionally substituted monocyclic, biaryl or fused bicyclic or polycyclic ring system, having the well known characteristics of aromaticity, wherein at least one ring contains a completely conjugated pi-electron system. Typically aryl groups contain 6 to 20 carbon atoms ("$C_6$-$C_{20}$ aryl") as ring members, preferably 6 to 14 carbon atoms ("$C_6$-$C_{14}$ aryl") or more preferably 6 to 12 carbon atoms ("$C_6$-$C_{12}$ aryl"). Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a C atom of the aromatic portion or a C or N atom of the non-aromatic portion of the ring system. Examples, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein.

Similarly, "heteroaryl" or "heteroaromatic" refer to monocyclic, heterobiaryl or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthyridine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl and pyridazinyl rings. The heteroaryl group may be unsubstituted or substituted as further described herein.

Illustrative examples of monocyclic heteroaryl groups include, but are not limited to:

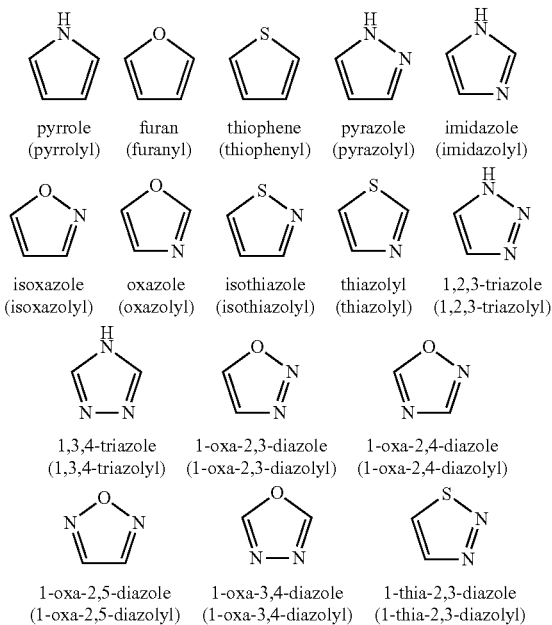

-continued

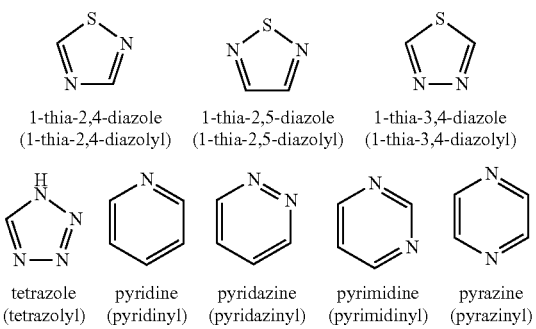

Illustrative examples of fused ring heteroaryl groups include, but are not limited to:

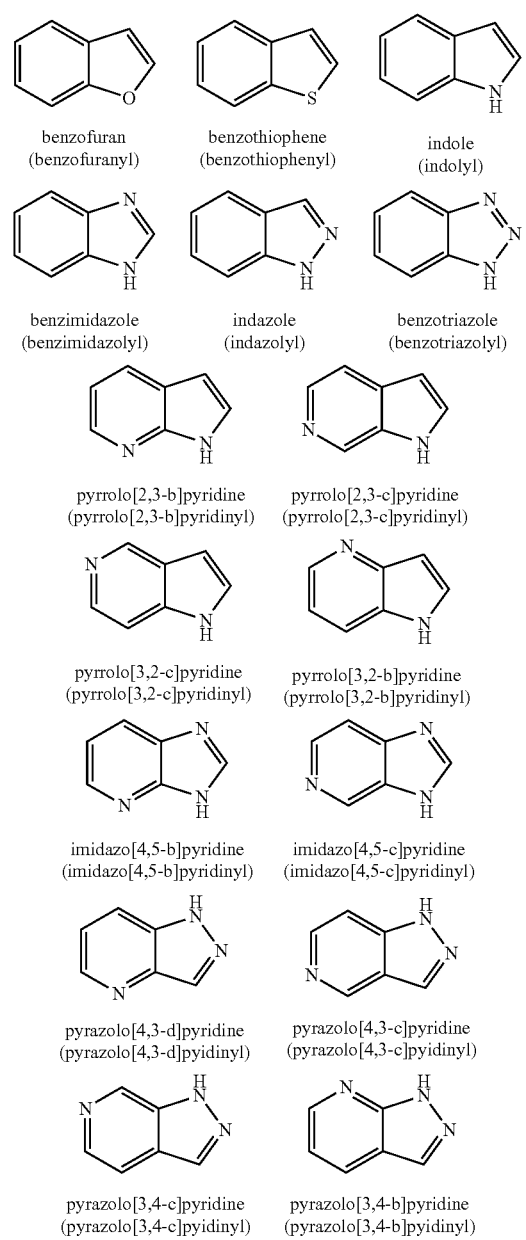

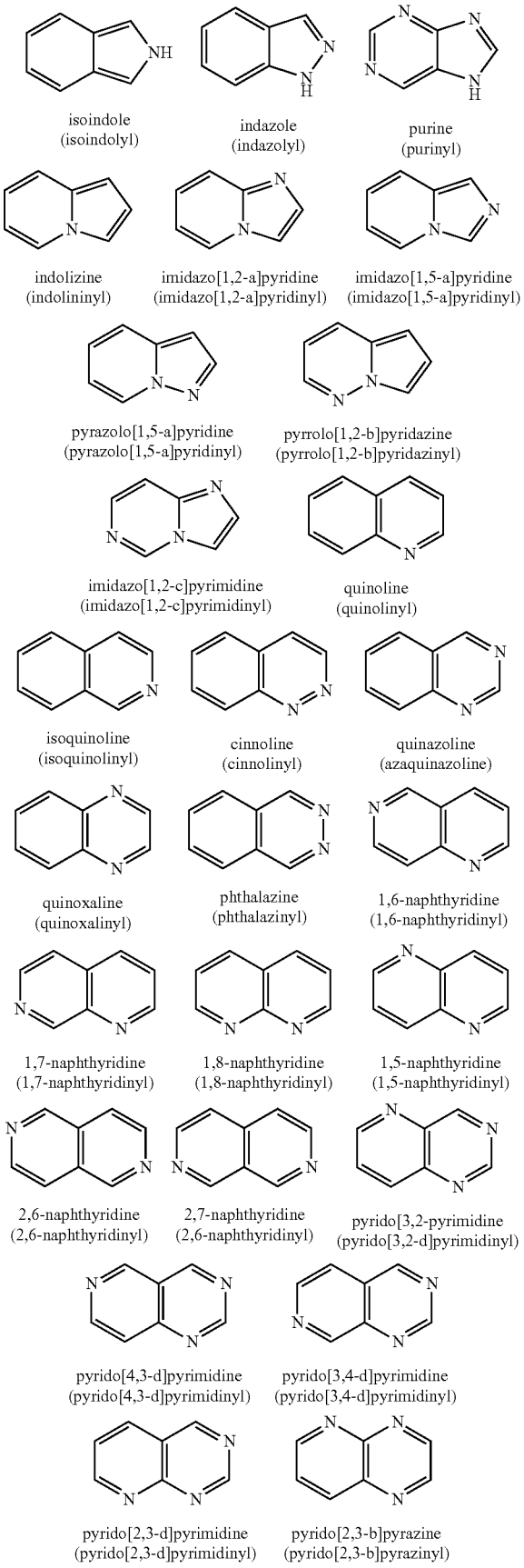
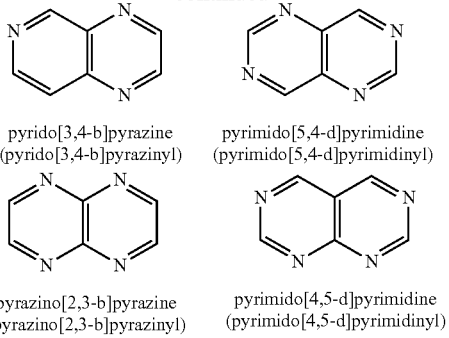

Aryl and heteroaryl moieties described herein as optionally substituted by may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably 1-2 optional substituents. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro and amino.

"In vitro" refers to procedures performed in an artificial environment such as, e.g., without limitation, in a test tube or culture medium.

"In vivo" refers to procedures performed within a living organism such as, without limitation, a mouse, rat, rabbit and/or human.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukaryotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, trialkylammonium and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Treat", "treating" and "treatment" refer to a method of alleviating or abrogating a cellular disorder and/or its attendant symptoms. With regard particularly to cancer, these terms simply mean that the life expectancy of an individual affected with a cancer will be increased or that one or more of the symptoms of the disease will be reduced.

The stimulator of interferon genes (STING) protein functions as both a cytosolic DNA sensor and an adaptor protein in Type 1 interferon signaling. The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammalia species of native sequence STING, e.g. human, monkey, and mouse.

As used herein, the term "STING activator" or "STING agonist" refers to a compound which, upon binding, (1) stimulates or activates STING and inducing downstream signal transduction characterized by activation of the molecules associated with STING function; (2) enhances, increases, promotes, induces, or prolongs an activity, function, or presence of STING, or (3) enhances, increases, promotes, or induces the expression of STING. Such actions include, but are not limited to, direct phosphorylation of STING, IRF3 and/or NF-κB and could also include STAT6. STING pathway activation results in, for example, increased production of type 1 interferons (mainly IFN-α and IFN-β) and expression of interferon-stimulated genes (Chen H, et al.

"Activation of STAT6 by STING is Critical for Antiviral Innate Immunity". Cell, 2011, vol 14: 433-446; and Liu S-Y., et al. "Systematic identification of type I and type II interferon-induced antiviral factors". Proc. Natl. Acad. Sci. 2012: vol 109 4239-4244).

As used herein, the term "STING-modulated" refers to a condition affected by STING directly or via the STING pathway, including, but not limited to, inflammatory diseases, allergic and autoimmune diseases, infectious diseases, cancer and as vaccine adjuvants.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including tautomers, polymorphs, stereoisomers, and isotopically labeled versions thereof.

Pharmaceutically acceptable salts include acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds.

Derivatives of compounds of the invention which may have little or no pharmacological activity themselves but can, when administered to a patient, be converted into the inventive compounds, for example, by hydrolytic cleavage. Such derivatives are referred to as 'pro-drugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as pro-moieties' as described, for example, in "Design of Prodrugs" by H Bundgaard (Elsevier, 1985), the disclosure of which is incorporated herein by reference in its entirety.

Some examples of prodrugs in accordance with the invention include:
(i) where the compound contains a carboxylic acid functionality —(COOH), an ester thereof, for example, replacement of the hydrogen with ($C_1$-$C_8$)alkyl;
(ii) where the compound contains an alcohol functionality (—OH), an ether thereof, for example, replacement of the hydrogen with ($C_1$-$C_6$)alkanoyloxymethyl; and
(iii) where the compound contains a primary or secondary amino functionality (—$NH_2$ or —NHR where R≠H), an amide thereof, for example, replacement of one or both hydrogens with ($C_1$-$C_{10}$)alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon and/or phosphorous atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention.

The choice of excipient will to a large extent depend on factors such as the particular mode of administration, the effect of the excipient on solubility and stability, and the nature of the dosage form.

The compositions described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the compositions are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

In some aspects of the invention, the methods described herein further include a step of treating a subject with an additional form of therapy. In some aspects, the additional form of therapy is an additional anti-cancer therapy including, but not limited to, chemotherapy, radiation, surgery, hormone therapy, and/or additional immunotherapy.

The disclosed STING modulatory compounds may be administered as an initial treatment, or for treatment of cancers that are unresponsive to conventional therapies. In addition, the disclosed STING modulatory compounds may be used in combination with other therapies (e.g., surgical excision, radiation, additional anti-cancer drugs etc.) to thereby elicit additive or potentiated therapeutic effects and/or reduce cytotoxicity of some anti-cancer agents. The STING modulatory compounds of the invention may be co-administered or co-formulated with additional agents, or formulated for consecutive administration with additional agents in any order.

The STING modulatory compounds of the invention may be used in combination with other therapeutic agents including, but not limited to, therapeutic antibodies, ADCs, immunomodulating agents, cytotoxic agents, and cytostatic agents. A cytotoxic effect refers to the depletion, elimination and/or the killing of a target cells (i.e., tumor cells). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious. The compounds of the invention, and one or more other therapeutic agents may be administered as part of the same or separate dosage forms, via the same or different routes of administration and on the same or different administration schedules according to standard pharmaceutical practice known to the person of ordinary skill in the art.

In one embodiment the other therapeutic agent is an interferon. The term "interferon" or "IFN" or "INF", each of which may be used interchangeably, refers to any member of the family of highly homologous species-species proteins that inhibit viral replication and cellular proliferation and modulate immune response. For example, human interferons are groups into three classes: Type I, which includes interferon-alpha, interferon-beta, and interferon-omega; Type II which includes interferon-gamma, and Type III which includes interferon-lambda. Recombinant forms of interferons that have been developed an are commercially available are encompasses by the term "interferon" as used herein. Subtypes of interferons, such as chemically modified or mutated interferons, are also encompassed by the term "interferon" as used herein. Chemically modified interferons may include pegylated interferons and glycosylated interferons. Examples of interferons also included, but are not limited to, interferon-alpha-2a, interferon-alpha-2b, interferon-alpha-n1, interferon-beta-1a, interferon-beta-1b, interferon-lamda-1, interferon-lambda-2, and interferon-lambda-3. Examples of pegylated interferons include pegylated interferon-alpha-2a and pegylated interferon-alpha-2b.

In one embodiment the other therapeutic agent is a CTLA-4 pathway antagonist. In one embodiment, the other therapeutic agent is an anti-4-1BB antibody.

The term "4-1BB antibody" as used herein means an antibody, as defined herein, capable of binding to human 4-1BB receptor (also referred to herein as an "anti-4-1BB antibody"). The terms "4-1BB" and "4-1BB receptor" are used interchangeably in the present application and refer to any form of 4-1BB receptor, as well as variants, isoforms, and species homologs thereof that retain at least a part of the activity of 4-1BB receptor. Accordingly, a binding molecule, as defined and disclosed herein, may also bind 4-1BB from species other than human. In other cases, a binding molecule may be completely specific for the human 4-1BB and may not exhibit species or other types of cross-reactivity. Unless indicated differently, such as by specific reference to human 4-1BB, 4-1BB includes all mammalian species of native sequence 4-1BB, e.g., human, canine, feline, equine and bovine. One exemplary human 4-1BB is a 255 amino acid protein (Accession No. NM_001561; NP_001552). 4-1BB comprises a signal sequence (amino acid residues 1-17), followed by an extracellular domain (169 amino acids), a transmembrane region (27 amino acids), and an intracellular domain (42 amino acids) (Cheuk A T C et al. 2004 Cancer Gene Therapy 11: 215-226). The receptor is expressed on the cell surface in monomer and dimer forms and likely trimerizes with 4-1BB ligand to signal. "4-1BB agonist" as used herein means, any chemical compound or biological molecule, as defined herein, which upon binding to 4-1BB, (1) stimulates or activates 4-1BB, (2) enhances, increases, promotes, induces, or prolongs an activity, function, or presence of 4-1BB, or (3) enhances, increases, promotes, or induces the expression of 4-1BB. 4-1BB agonists useful in the any of the treatment method, medicaments and uses of the present invention include a monoclonal antibody (mAb), or antigen binding fragment thereof, which specifically binds to 4-1BB. Alternative names or synonyms for 4-1BB include CD137 and TNFRSF9. In any of the treatment method, medicaments and uses of the present invention in which a human individual is being treated, the 4-1BB agonists increase a 4-1BB-mediated response. In some embodiments of the treatment method, medicaments and uses of the present invention, 4-1BB agonists markedly enhance cytotoxic T-cell responses, resulting in anti-tumor activity in several models. Human 4-1BB comprises a signal sequence (amino acid residues 1-17), followed by an extracellular domain (169 amino acids), a transmembrane region (27 amino acids), and an intracellular domain (42 amino acids) (Cheuk A T C et al. 2004 Cancer Gene Therapy 11: 215-226). The receptor is expressed on the cell surface in monomer and dimer forms and likely trimerizes with 4-1BB ligand to signal. Examples of mAbs that bind to human 4-1BB, and useful in the treatment method, medicaments and uses of the present invention, are described in U.S. Pat. No. 8,337,850 and US20130078240. In some embodiments, the anti-4-1BB antibody has a VH as shown in SEQ ID NO: 17 and a VL as shown in SEQ ID NO: 18 of WO2017/130076.

In one embodiment the other therapeutic agent is a PD-1 pathway antagonist. In one embodiment, the other therapeutic agent is an anti-PD-1 antibody. In one embodiment, the other therapeutic agent is an anti-PD-L1 antibody.

The programmed death 1 (PD-1) receptor and PD-1 ligands 1 and 2 (PD-L1 and PD-L2, respectively) play integral roles in immune regulation. Expressed on activated T cells, PD-1 is activated by PD-L1 (also known as B7-H1) and PD-L2 expressed by stromal cells, tumor cells, or both, initiating T-cell death and localized immune suppression (Dong et al., Nat Med 1999; 5:1365-69; Freeman et al. J Exp Med 2000; 192:1027-34), potentially providing an immune-tolerant environment for tumor development and growth. Conversely, inhibition of this interaction can enhance local T-cell responses and mediate antitumor activity in nonclinical animal models (Iwai Y, et al. Proc Natl Acad Sci USA 2002; 99:12293-97). Examples of anti-PD-1 antibodies that are useful in the treatment method, medicaments and uses of the present invention include BCD-100, camrelizumab, cemiplimab, genolimzumab (CBT-501), MEDI0680, nivolumab, pembrolizumab, RN888 (see WO2016/092419), sintilimab, spartalizumab, STI-A1110, tislelizumab, and TSR-042. In some embodiments, the anti-PD-1 antibody has a VH as shown in SEQ ID NO: 4 and a VL as shown in SEQ ID NO: 8 of U.S. Ser. No. 10/155,037. Examples of anti-PD-L1 antibodies that are useful in the treatment method, medicaments and uses of the present invention include atezolizumab, durvalumab, BMS-936559 (MDX-1105), and LY3300054.

For combination therapies, the STING modulatory compounds are administered within any time frame suitable for performance of the intended therapy. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s).

The disclosed combination therapies may elicit a synergistic therapeutic effect, i.e., an effect greater than the sum of their individual effects or therapeutic outcomes. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

The compositions may be administered before, after, and/or together with an additional therapeutic or prophylactic composition or modality. These include, without limitation, B7 costimulatory molecule, interleukin-2, interferon-7, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminium hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and in addition retinoic acid-inducible gene I (RIG-1) agonists such as poly 1:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

In one embodiment, compounds of the invention, including those of formulae (I), (IA), (IB), (II), (III), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, may be administered orally.

The compounds of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intravesical (e.g., bladder), subcutaneous and intratumoral. Suitable devices for parenteral administration include needle (including micro needle) injectors, needle-free injectors and infusion techniques. In one embodiment compounds of the invention, including those of formulae (I), (IA), (IB), (II), (I), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, are administered intravenously. In one embodiment, compounds of the invention, including those of formulae (I), (IA), (IB), (II), (I), (IIIA), (IIIB), (IIIC), (IIID), (IV), (IVA), (IVB), (V), (VA), (VB), (VI), (VIA), (VIB), (VII), (VIIA), (VIIB), (VIIC) or (VIID), or a pharmaceutically acceptable salt thereof, are administered intravesically.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PLGA microspheres.

Nanoparticles also represent drug delivery systems suitable for most administration routes. Over the years, a variety of natural and synthetic polymers have been explored for the preparation of nanoparticles, of which Poly(lactic acid) (PLA), Poly(glycolic acid) (PGA), and their copolymers (PLGA) have been extensively investigated because of their biocompatibility and biodegradability. Nanoparticles and other nanocarriers act as potential carries for several classes of drugs such as anticancer agents, antihypertensive agents, immunomodulators, and hormones; and macromolecules such as nucleic acids, proteins, peptides, and antibodies. See, e.g., Crit. Rev. Ther. Drug Carrier Syst. 21:387-422, 2004; Nanomedicine: Nanotechnology, Biology and Medicine 1:22-30, 2005.

The compositions of the present invention may comprise, or be administered together with, one or more additional pharmaceutically active components such as adjuvants, lipids, interbilayer crosslinked multilamellar vesicles, biodegradeable poly(D, L-lactic-co-glycolic acid) [PLGA]-based or poly anhydride-based nanoparticles or microparticles, and nanoporous particle-supported lipid bilayers such as liposomes, CTLA-4 and PD-1 pathway Antagonists, PD-1 pathway blocking agents, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), pathogen associated molecular patterns ("PAMPs"), chemotherapeutic agents, and the like.

The compounds and compositions of the present invention may be administered as a component of an antibody-drug conjugate or other targeted delivery modality.

Topical Administration

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage: The amount of the active compound administered will be dependent on the subject being treated, the severity of the disorder or condition, the rate of administration, the disposition of the compound and the discretion of the prescribing physician. One possible dosage is in the range of about 0.001 to about 100 mg per kg body weight, administered daily, every other day, every third day, every fourth day, every fifth day, every sixth day, weekly, every other week, every three weeks, monthly, or on other dosing schedules. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts: Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

General Methods
Synthetic Experimental Procedures:

Experiments were generally carried out under inert atmosphere (nitrogen or argon), particularly in cases where oxygen- or moisture-sensitive reagents or intermediates were employed. Commercial solvents and reagents were generally used without further purification and dried over molecular sieves (generally Sure-Sea™ products from the Aldrich Chemical Company, Milwaukee, Wisconsin). Mass spectrometry data is reported from either liquid chromatography-mass spectrometry (LC-MS), atmospheric pressure chemical ionization (APCI), electrospray ionization (ESI) or liquid chromatography-Time of Flight (LC-TOF) methods. Chemical shifts for nuclear magnetic resonance (NMR) data are expressed in parts per million (ppm) referenced to residual peaks from the deuterated solvents employed.

For syntheses referencing procedures in other Examples or Methods, reaction Protocol (length of reaction and temperature) may vary. In general, reactions were followed by thin layer chromatography, LC-MS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/freeze-drying. Intermediate and final compounds were stored at (0° C.) or room temperature in closed vials or flasks under nitrogen. Compound names were generated with Chemdraw or ACD Labs software.

Abbreviations for solvents and/or reagents are based on American Chemical Society guidelines and are highlighted below:

Ac=Acetyl; AcOH=Acetic acid; Ad=Adamantyl; $B_2Pin_2$=Bis(pinacolato)diboron; Bn=Benzyl; Boc=N-tert-butoxycarbonyl; CataCXium A=Di-(1-adamantyl)-n-butylphosphine; CDI=N,N'-Carbonyldiimidazole; $CF_3$=Trfluoromethyl; CMBP=(Cyanomethylene)tributylphosphorane=(Tributylphosphoranylidene)acetonitrile=Tsunoda Reagent; CO=carbon monoxide; 18-crown-6=1,4,7,10,13,16-Hexaoxacyclooctadecane; DCC=1,3-Dicyclohexylcarbodiimide; DCE=Dichloroethane; DCM=Dichloromethane; Dess-Martin periodinane=DMP=1,1,1-Tris(acetyloxy)-1,1-dihydro-1,2-benziodoxol-3-(1H)-one; DIAD=Diisopropyl azodicarboxylate; DIPEA=N,N-Diisopropylethylamine; DIBAL=Diisobutylaluminum hydride; DMA=Dimethylacetamide; DMAP=4-Dimethylaminopyridine; DMB=2,4-Dimethoxybenzyl; DME=Dimethoxyethane; DMF=N,N-Dimethylformamide; DMF-DMA=N,N-Dimethylformamide dimethyl acetal; DMSO=Dimethyl sulfoxide; dppf=1,1'-Ferrocenediyl-bis(diphenylphosphine); dtbpf=1,1'-Bis(di-tert-butylphosphino)ferrocene; EDCl=1-Ethyl-3-(3-dimethylaminopropyl)carbodiimide; Et=Ethyl; EtOAc=Ethyl acetate; h=hour; HATU=o-(7-azabenzotriazol-1-yl)-N,N,N',N'tetramethyluronium hexafluorophosphate; HBTU=N,N,N',N'Tetramethyl-O-(1H-benzotriazol-1-yl)uronium hexafluorophosphate; HFIP=1,1,1,3,3,3-Hexafluoro-2-propanol; HOAc=Acetic acid; HOAt=1-Hydroxy-7-azabenzotriazole; HOBt=1-Hydroxybenzotriazole hydrate; HPLC=High-performance Liquid Chromatography; Lawesson Reagent=2,4-Bis(4-methoxyphenyl)-2,4-dithioxo-1,3,2,4-dithiadiphosphetane; LC=Liquid Chromatography; LCMS=Liquid Chromatography Mass Spectrometry; LDA=Lithium diisopropylamide; LAH=$LiAlH_4$=Lithium aluminum hydride; mCPBA=3-Chloroperbenzoic acid; Me=Methyl; MEK=Methyl Ethyl Ketone=2-Butanone; MeOH=Methanol; MeCN=Acetonitrile; Ms=Methansulfonyl; MSA or MsOH=Methanesulfonic acid; MTBE=Methyl tert-butyl ether; NaHMDS=Sodium bis(trimethylsilyl)amide; Boc=tert-butoxy carbonyl; n-Bu=n-Butyl; n-BuLi=n-Butyllithium; n-BuOH=1-Butanol; NBS=N-Bromosuccinimide; NCS=N-Chlorosuccinimide; NMI=N-methylimidazole; NMM=N-methyl morpholine; NMO=N-methyl morpholine N-oxide; NMP=1-Methyl-2-pyrrolidinone; $P(fur)_3$=Tri(2-furyl)phosphine; $Pd(OAc)_2$=Palladium (II) acetate; Pd-G3=Third generation (G3) Buchwald palladacycle precatalyst; Pd-G4=fourth generation (G4) Buchwald palladacycle precatalyst; PE=Pet. Ether=Petroleum Ether; $Pd(dppf)Cl_2$=[1,1'-Bis(diphenylphosphino)ferrocene]-dichloropalladium (II); Ph=Phenyl; PhMe=Toluene; PivOH=Pivalic acid; PivCl=Pivaloyl chloride; PMB=p-Methoxybenzyl; PPTS=Pyridinium p-Toluenesulfonate; p-TsOH=p-Toluenesulfonic acid; PyBOP=Benzotriazole-1-yl-oxy-tris-pyrrolidino-phosphonium hexafluorophosphate; rt=room temperature; Selectfluor=1-Chloromethyl-4-fluoro-1,4-diazoniabicyclo[2.2.2]octane bis(tetrafluoroborate); SFC=Super critical fluid chromatography; T3P=2,4,6-Tripropyl-1,3,5,2,4,6-trioxatriphosphorinane-2,4,6-trioxide; TEAB=Tetraethylammonium Bromide; TBAI=Tetrabutylammonium Iodide; t-Amyl alcohol=2-Methyl-2-butanol; t-Bu=tert-Butyl; TBS=tert-Butyldimethylsilyl; TBSCl=tert-Butyldimethylsilyl Chloride; TCFH=Chloro-N,N,N',N'-tetramethylformamidinium hexafluorophosphate; TEA=Triethylamine; Tf=Trifluoromethanesulfonate; TFA=Trifluoroacetic acid; TFE=2,2,2-Trifluoroethanol; THF=Tetrahydrofuran; THP=Tetrahydropyranyl; TMP=2,2,6,6-Tetramethylpiperidinyl; TMS=Trimethylsilyl; TPTU=O-(2-Oxo-1(2H)pyridyl)-N,N,N,'N'-tetramethyluronium tetrafluoroborate; Tr=Triphenylmethyl; XPhos-Pd-G2=Chloro(2-dicyclohexylphosphino-2',4',6'-triisopropyl-1,1'-biphenyl)[2-(2'-amino-1,1'-biphenyl)]palladium(II); Xantphos=4,5-Bis(diphenylphosphino)-9,9-dimethylxanthene.

General Schemes

General Scheme I

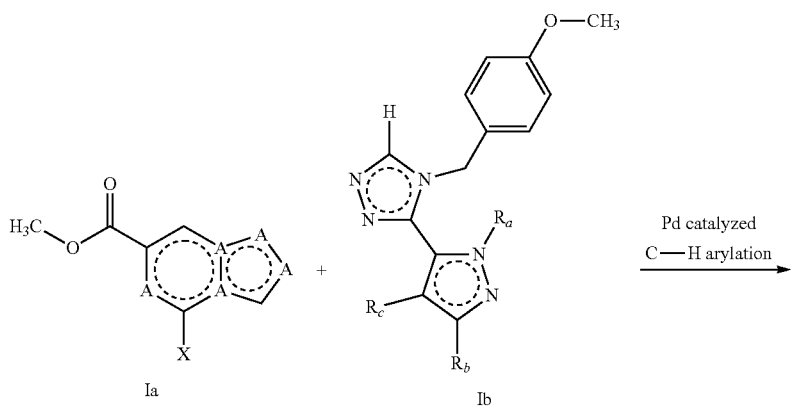

X = F, Cl, Br, or I

A = C, C—R, N, N—R

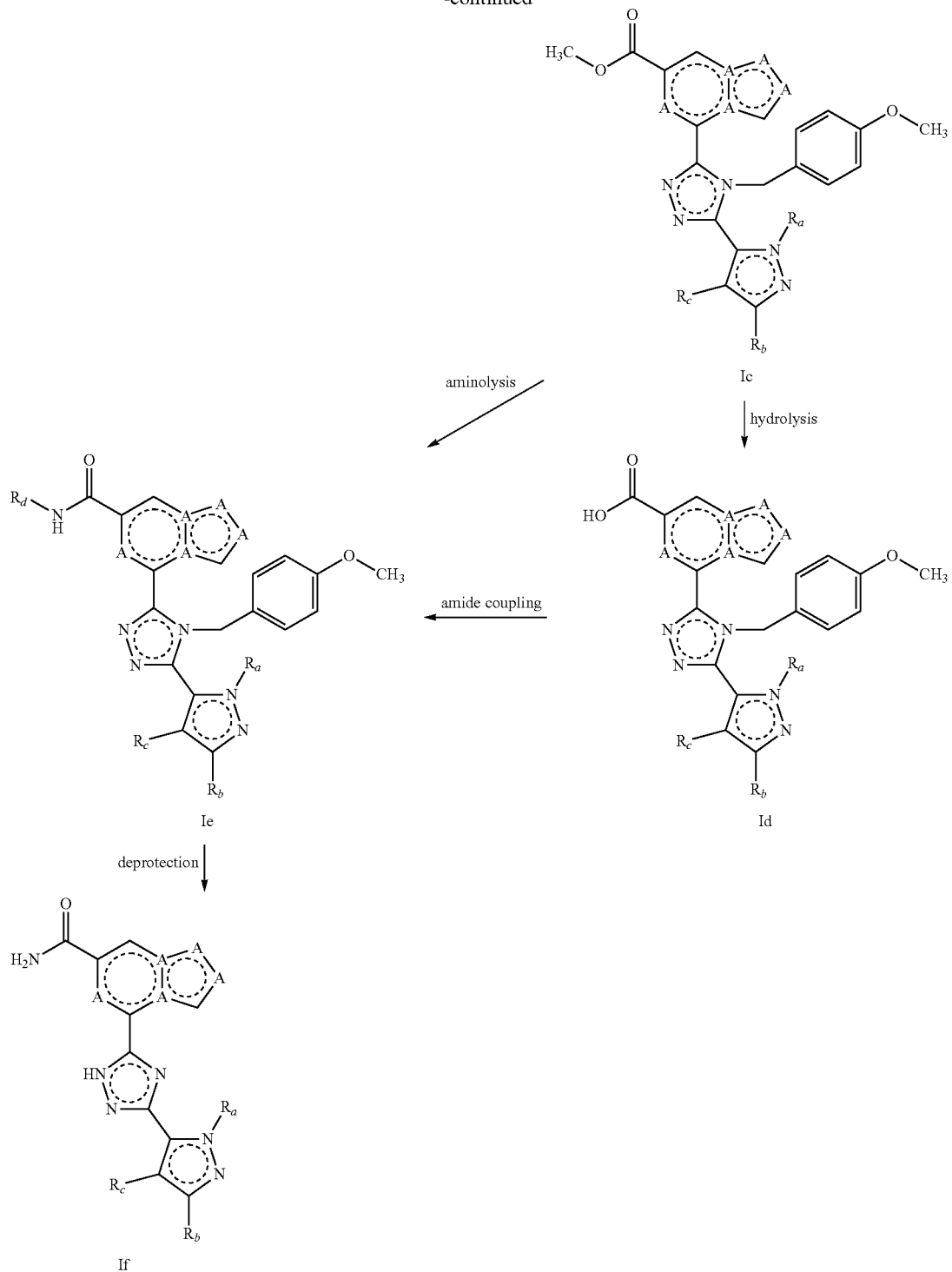

As exemplified in General Scheme I, a compound of type Ia can be cross-coupled to a compound of type Ib, prepared by treating an appropriate acyl hydrazide with DMF-DMA and p-methoxybenzyl amine under acidic conditions (Org. Lett. 2004, 6, 2969-2971), via C—H activation (J. Org. Chem. 2013, 78, 738-743) in the presence of a suitable catalyst system (such as Pd(dppf)Cl$_2$ or Pd(OAc)$_2$+cat-aCXium A) with a suitable base (such as CsOPiv, CsOAc, K$_2$CO$_3$+PivOH, TMPMgCl·LiCl, or TMPZnCl·LiCl) in an appropriate solvent (such as PhMe, Dioxane, MeCN, TFE, t-Amyl alcohol or similar solvent) at temperatures ranging from rt to 150° C. to provide compounds such as Ic. A compound such as Ic can by hydrolyzed under alkaline conditions using an appropriate base (MOH where M=Li, Na, K, or Cs) in a suitable solvent (such as THF, MeOH, water or similar solvent) to provide compounds such as Id. A compound such as Id can be treated with an appropriate amine or salt thereof (such as NH$_4$Cl or DMBNH$_2$) under amide coupling conditions employing a suitable activating reagent (such as HATU, TPTU, EDCl+HOAt, PyBOP, TCFH, T3P or a similar reagent) with a suitable base (such as TEA, DIPEA, NMI, Pyridine, or DMAP) in an appropriate solvent (such DMF, MeCN, or similar solvent) to provide compounds such as Ie. Alternatively, direct aminolysis of compounds such as Ic using an appropriate amine (such as $NH_3$ or $DMBNH_2$) in a suitable solvent (such as MeOH, n-BuOH, t-AmyOH or similar solvent) and in some cases with a Lewis acid (Tet. Lett. 2010, 51, 3879-3882) (such as $CaCl_2$, $CeCl_3$, $Mg(OMe)_2$, or $MgCl_2$) under elevated temperatures typically ranging from 50-120° C. can also deliver compounds such as Ie. Compounds such as Ie can contain acid labile protecting groups which can be removed at this stage using conditions (such as TFA/DCM or MsOH/HFIP) known in the art (*Protective Groups in Organic Synthesis*, A. Wiley-Interscience Publication, 1981 or Protecting Groups, 10 Georg Thieme Verlag, 1994) to afford compounds such as If or a tautomer thereof. Compounds at every step may be purified by standard techniques, such as column chromatography, crystallization, or reverse phase SFC or HPLC. If necessary, separation of regioisomers or stereoisomers of any product in the synthetic sequence can be carried out under standard methods known in the art such as chiral SFC or HPLC to afford single regio- or stereoisomers. Variables such as X, A, and $R_a$-$R_d$ are as defined and/or depicted in the analogous positions within the formulae and compounds of the embodiments, schemes, examples, and claims disclosed herein.

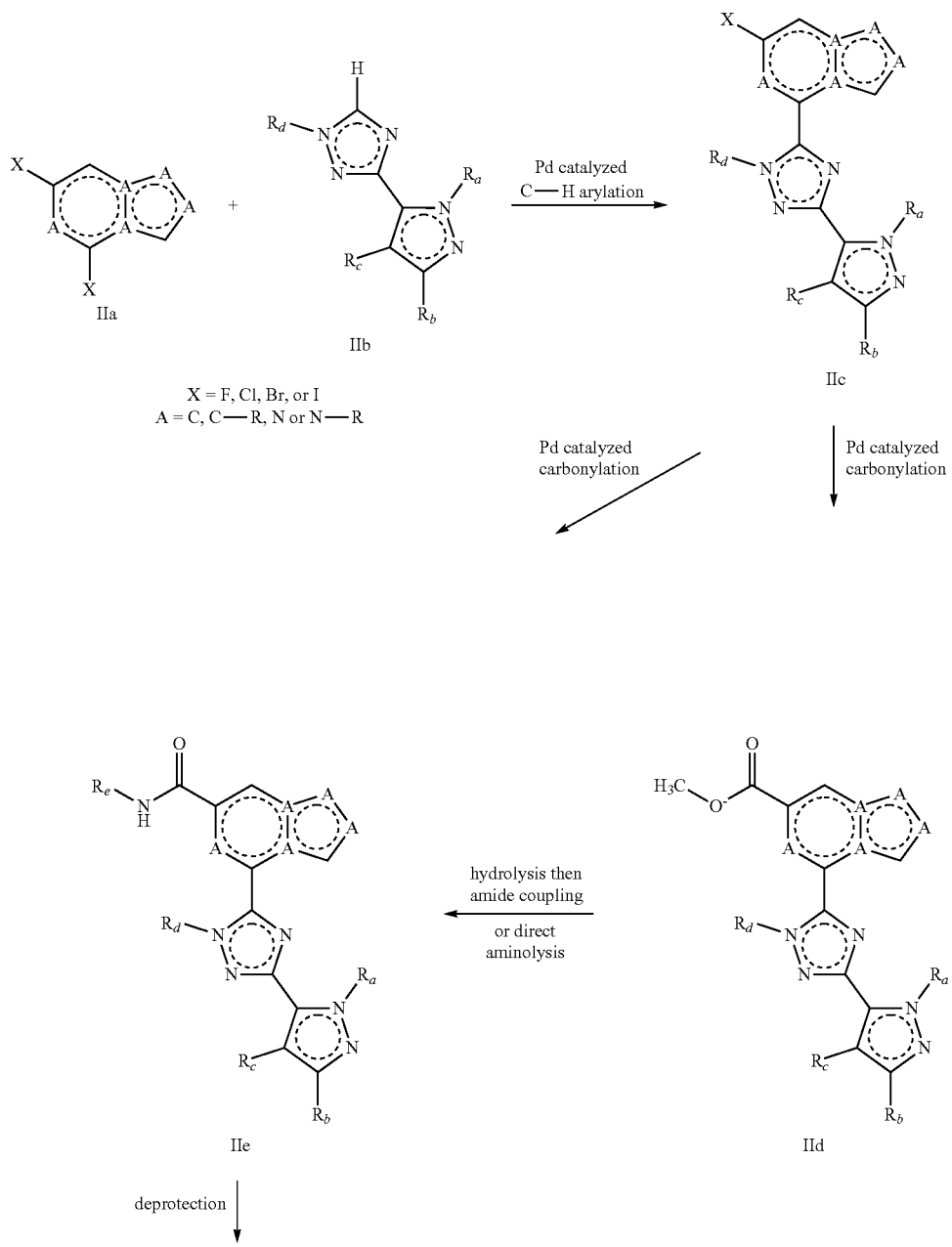

General Scheme II

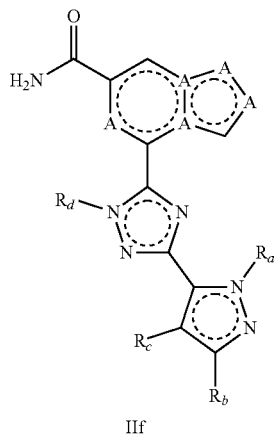

IIf

As exemplified in General Scheme II, a compound of type IIa can be cross-coupled to a compound of type IIb via C—H activation (J. Org. Chem. 2013, 78, 738-743) in the presence of a suitable catalyst system (such as Pd(dppf)Cl$_2$ or Pd(OAc)$_2$+cataCXium A) with a suitable base (such as CsOPiv, CsOAc, K$_2$CO$_3$+PivOH, TMPMgCl·LiCl, or TMPZnCl·LiCl) in an appropriate solvent (such as PhMe, Dioxane, MeCN, TFE, t-Amyl alcohol or similar solvent) at temperatures ranging from rt to 150° C. to provide compounds such as IIc. A compound such as IIc can by carbonylated with carbon monoxide or other suitable carbon monoxide precursor (such as N-formyl saccharin, Mo(CO)$_6$, Ph$_2$MeSiCO$_2$H or a similar reagent) in the presence of an suitable catalyst system (such as Pd(dppf)Cl$_2$, G3-Pd-Xanthphos, G4-Pd-Xanthphos or similar catalyst) with a suitable base (such as TEA or DIPEA) in MeOH solvent to provide compounds such as IId. Compounds such as IId can be hydrolyzed under alkaline conditions using an appropriate base (MOH where M=Li, Na, K, or Cs) in a suitable solvent (such as THF, MeOH, water or similar solvent) followed by treatment with an appropriate amine or salt thereof (such as NH$_4$Cl or DMBNH$_2$) under amide coupling conditions employing a suitable activating reagent (such as HATU, TPTU, EDCl+HOAt, PyBOP, TCFH, T3P or a similar reagent) with a suitable base (such as TEA, DIPEA, NMI, Pyridine, or DMAP) in an appropriate solvent (such DMF, MeCN, or similar solvent) to provide compounds such as IIe. Alternatively, compounds such as IId can undergo direct aminolysis using an appropriate amine (such as NH$_3$ or DMBNH$_2$) in a suitable solvent (such as MeOH, n-BuOH, t-AmylOH or similar solvent) and in some cases with a Lewis acid (Tet. Lett. 2010, 51, 3879-3882) (such as CaCl$_2$, CeCl$_3$, Mg(OMe)$_2$, or MgCl$_2$) under elevated temperatures typically ranging from 50-120° C. to deliver compounds such as IIe. Additionally, palladium catalysed carbonylation of compounds such as IIc using an appropriate amine (such as NH$_3$ or DMBNH$_2$) in a suitable solvent (such as DMF, DMA, MeOH, n-BuOH, t-AmylOH or similar solvent) under elevated temperatures typically ranging from 50-120° C. also delivers compounds such as IIe. Compounds such as IIe can contain acid labile protecting groups which can be removed at this stage using conditions (such as TFA/DCM or MsOH/HFIP) known in the art (*Protective Groups in Organic Synthesis*, A. Wiley-Interscience Publication, 1981 or Protecting Groups, 10 Georg Thieme Verlag, 1994) to afford compounds such as IIf or a tautomer thereof. Compounds at every step may be purified by standard techniques, such as column chromatography, crystallization, or reverse phase SFC or HPLC. If necessary, separation of regioisomers or stereoisomers of any product in the synthetic sequence can be carried out under standard methods known in the art such as chiral SFC or HPLC to afford single regio- or stereoisomers. Variables such as X, A, and R$_a$-R$_e$ are as defined and/or depicted in the analogous positions within the formulae and compounds of the embodiments, schemes, examples, and claims disclosed herein.

Preparation of Tail Group (TG) Intermediates

Preparation of 3-(1-ethyl-3-methyl-1H-pyrazol-5-yl)-4-[(4-methoxyphenyl)methyl]-4H-1,2,4-triazole (Int-TG-01) According to Scheme TG-1

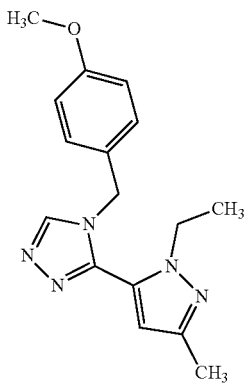 [SMILES: CCn1nc(C)cc1-c1nncn1Cc1ccc(OC)cc1]

Scheme TG-1

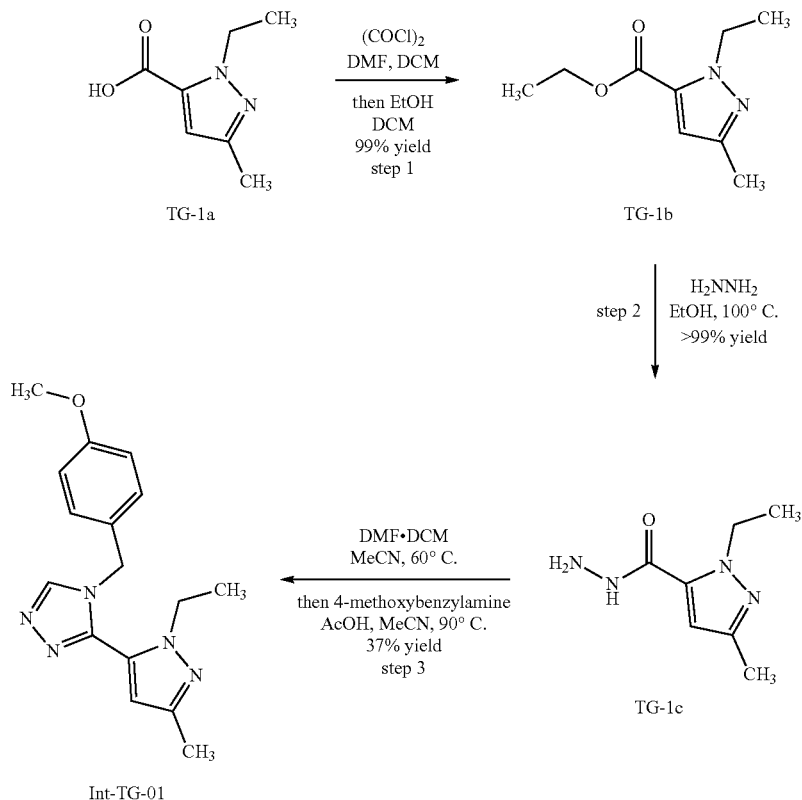

Step 1: Synthesis of ethyl 1-ethyl-3-methyl-1H-pyrazole-5-carboxylate (TG-1b)

To a suspension of 1-ethyl-3-methyl-1H-pyrazole-5-carboxylic acid (TG-1a) (32.6 g, 212 mmol) in anhydrous DCM (620 mL) and DMF (0.18 mL) was added oxalyl chloride (80.5 g, 634 mmol) drop-wise, maintaining the reaction temperature at 16-21° C. (internal temperature). The resultant mixture was stirred at room temperature for 1 h to provide a clear reaction solution. TLC analysis (1:20 MeOH/DCM) of a reaction aliquot quenched with MeOH showed complete consumption of the starting material. The mixture was concentrated to dryness. The residue was co-evaporated from DCM (2×200 mL). The residue was taken up in anhydrous DCM (465 mL) and EtOH (155 mL) was added. The mixture was stirred for 30 min. TLC analysis (1:20 MeOH/DCM) showed consumption of the starting material. The solvent was removed under reduced pressure. The residue was adjusted to pH ~7-8 by addition of saturated aqueous $NaHCO_3$. The mixture was extracted with EtOAc (2×300 mL). The combined organic phases were dried over anhydrous $Na_2SO_4$, filtered, and concentrated to provide ethyl 1-ethyl-3-methyl-1H-pyrazole-5-carboxylate (TG-1b) (38.2 g, 99% yield) as a pale-yellow oil. $^1$H NMR (400 MHz, $CDCl_3$) δ 6.58 (s, 1H), 4.51 (q, J=7.2 Hz, 2H), 4.30 (q, J=7.1 Hz, 2H), 2.25 (s, 3H), 1.39 (t, J=7.2 Hz, 3H), 1.35 (t, J=7.2 Hz, 3H).

Step 2: Synthesis of 1-ethyl-3-methyl-1H-pyrazole-5-carbohydrazide (TG-1c)

To a solution of ethyl 1-ethyl-3-methyl-1H-pyrazole-5-carboxylate (TG-1b) (38.2 g, 209 mmol) in EtOH (500 mL) was added hydrazine monohydrate (107 g, 2.09 mol). The mixture was stirred at 100° C. for 16 h. LCMS analysis showed consumption of the starting material with formation of the desired product mass. The mixture was concentrated to dryness. The residue was co-evaporated with EtOH (3×200 mL) and toluene (2×300 mL) to provide 1-ethyl-3-methyl-1H-pyrazole-5-carbohydrazide (TG-1c) (35.1 g, >99% yield) as a white solid. $^1$H NMR (400 MHz, DMSO-$d_6$) δ 9.70 (br s, 1H), 6.58 (s, 1H), 4.52 (br s, 2H), 4.45 (q, J=7.1 Hz, 2H), 2.19 (s, 3H), 1.31 (t, J=7.1 Hz, 3H); m/z (ESI+) for ($C_7H_{12}N_4O$), 168.9 $(M+H)^+$.

Step 3: Synthesis of 3-(1-ethyl-3-methyl-1H-pyrazol-5-yl)-4-[(4-methoxyphenyl)methyl]-4H-1,2,4-triazole (Int-TG-01)

To a suspension of 1-ethyl-3-methyl-1H-pyrazole-5-carbohydrazide (TG-1c) (28.5 g, 170 mmol) in MeCN (152 mL) was added N,N-dimethyldimethoxymethylamine (DMF·DMA) (20.8 g, 174 mmol). The mixture was stirred at 60° C. (internal temperature) for 40 min. LCMS analysis showed consumption of the starting material. The reaction was cooled to 22° C. (internal temperature) and a solution of 4-methoxybenzylamine (21.8 g, 159 mmol) in MeCN (66 mL) was added. Acetic acid (218 mL) was added drop-wise, maintaining the reaction temperature at −24-30° C. (internal temperature). The reaction was stirred at 90° C. (internal temperature) for 4 h. LCMS analysis showed consumption of the intermediate with formation of the desired product mass. The reaction was cooled to room temperature and combined with a parallel reaction run in identical fashion with 5.0 g of 1-ethyl-3-methyl-1H-pyrazole-5-carbohydrazide (TG-1c). The mixture was concentrated to dryness. The residue was diluted with H₂O (200 mL) and basified with saturated aqueous Na₂CO₃ to pH ~7-8. The mixture was extracted with EtOAc (2×300 mL). The combined organic layers were dried over Na₂SO₄, filtered, and concentrated. The residue was purified by flash chromatography in three parallel batches (330 g SiO₂, 0-1% MeOH/DCM). The mixed fractions were repurified by flash chromatography (120 g SiO₂, 0-1% MeOH/DCM). The product containing-fractions were combined to provide 3-(1-ethyl-3-methyl-1H-pyrazol-5-yl)-4-[(4-methoxyphenyl)methyl]-4H-1,2,4-triazole (Int-TG-01) (22.0 g, 37% yield) as an off-white solid. $^1$H NMR (400 MHz, CDCl₃) δ 8.21 (s, 1H), 7.00 (d, J=8.6 Hz, 2H), 6.90 (d, J=8.6 Hz, 2H), 6.19 (s, 1H), 5.14 (s, 2H), 4.32 (q, J=7.2 Hz, 2H), 3.82 (s, 3H), 2.33 (s, 3H), 1.38 (t, J=7.2 Hz, 3H); m/z (ESI+) for ($C_{16}H_{19}N_5O$), 298.1 (M+H)⁺.

Preparation of 3-(1-ethyl-4-fluoro-3-methyl-1H-pyrazol-5-yl)-4-[(4-methoxyphenyl)methyl]-4H-1,2,4-triazole (Int-TG-02) According to Scheme TG-2

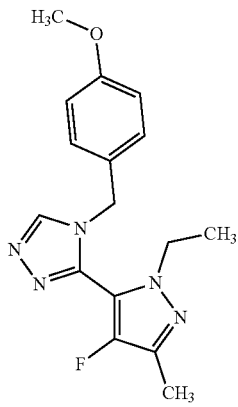 [SMILES: CCn1nc(C)c(Cl)c1-c1nncn1Cc1ccc(OC)cc1]

Scheme TG-2

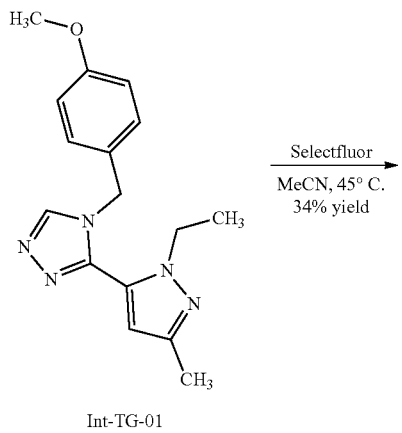

Int-TG-01

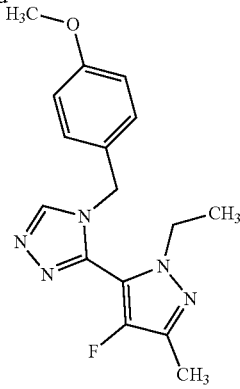

Int-TG-02

To a solution of 3-(1-ethyl-3-methyl-1H-pyrazol-5-yl)-4-[(4-methoxyphenyl)methyl]-4H-1,2,4-triazole (Int-TG-01) (15.0 g, 50.5 mmol) in MeCN (250 mL) was added Selectfluor (44.7 g, 126 mmol) portion-wise. The mixture was stirred at 45° C. for 16 h. LCMS analysis showed formation of the desired product mass with some remaining starting material. The yellow suspension was cooled to room temperature and filtered. The filtrate was concentrated to dryness. The residue was slurried with EtOAc (27° C., 10 min) and filtered. The filtrate was concentrated to dryness. The material was dissolved in DCM (200 mL) and stirred with saturated aqueous Na₂CO₃ (80 mL) at room temperature for 10 min. The mixture was separated. The aqueous layer was extracted with DCM (2×100 mL). The combined organic layers were dried over anhydrous Na₂SO₄, filtered, and concentrated. The crude material was purified by preparative HPLC with a YMC Triart C-18 column (250×50 mm, 7 μm particle size), which was eluted with 20-50% MeCN/H₂O (+0.04% NH₄OH, +10 mM NH₄HCO₃) with a flow rate of 120 mL/min to provide 3-(1-ethyl-4-fluoro-3-methyl-1H-pyrazol-5-yl)-4-[(4-methoxyphenyl)methyl]-4H-1,2,4-triazole (Int-TG-02) (5.41 g, 34% yield) as a yellow gum. $^1$H NMR (400 MHz, CDCl₃) δ 8.18 (s, 1H), 6.99 (d, J=8.6 Hz, 2H), 6.82 (d, J=8.6 Hz, 2H), 5.06 (s, 2H), 4.10 (q, J=7.2 Hz, 2H), 3.76 (s, 3H), 2.28 (s, 3H), 1.21 (t, J=7.2 Hz, 3H); $^{19}$F NMR (377 MHz, CDCl₃) δ −133.00; m/z (ESI+) for ($C_{16}H_{18}FN_5O$), 316.0 (M+H)⁺.

Preparation of 3-(4-chloro-1-ethyl-3-methyl-1H-pyrazol-5-yl)-4-[(4-methoxyphenyl)methyl]-4H-1,2,4-triazole (Int-TG-03) According to Scheme TG-3

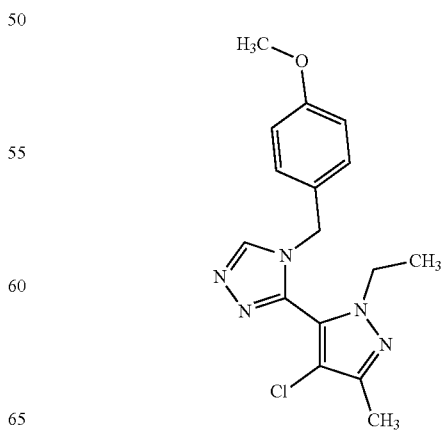

Scheme TG-3

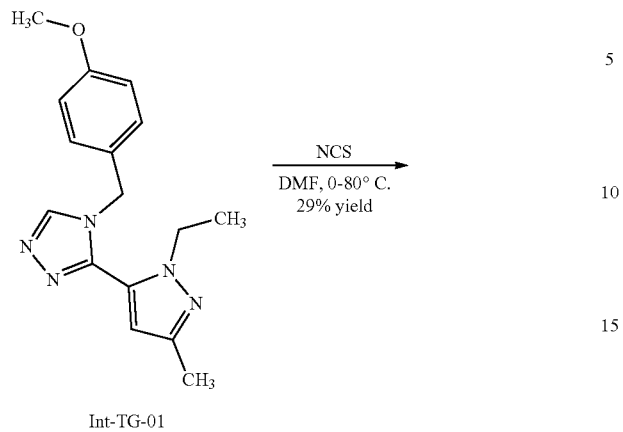

To a stirred solution of 3-(1-ethyl-3-methyl-1H-pyrazol-5-yl)-4-[(4-methoxyphenyl)methyl]-4H-1,2,4-triazole (Int-TG-01) (1.02 g, 3.43 mmol) in anhydrous DMF (3.0 mL) at 0° C. was added N-chlorosuccinimide (609 mg, 4.56 mmol) portion-wise. The mixture was stirred at 25° C. for 2 h. LCMS analysis showed formation of the desired product mass with remaining starting material. The mixture was stirred at 80° C. for 2 h. LCMS analysis showed consumption of the starting material. The reaction was cooled to room temperature, diluted with H$_2$O (20 mL), and extracted with EtOAc (2×20 mL). The combined organic layers were washed with brine (3×15 mL), dried over anhydrous Na$_2$SO$_4$, filtered, and concentrated. The residue was purified by flash chromatography (40 g SiO$_2$, 0-5% MeOH/EtOAc). The product-containing fractions were repurified by flash chromatography (40 g SiO$_2$, 0-3% MeOH/EtOAc) to provide 3-(4-chloro-1-ethyl-3-methyl-1H-pyrazol-5-yl)-4-[(4-methoxyphenyl)methyl]-4H-1,2,4-triazole (Int-TG-03) (330 mg, 29% yield) as a yellow gum. $^1$H NMR (400 MHz, CDCl$_3$) δ 8.26 (s, 1H), 6.94 (d, J=8.7 Hz, 2H), 6.82 (d, J=8.7 Hz, 2H), 5.06 (s, 2H), 3.92 (q, J=7.3 Hz, 2H), 3.77 (s, 3H), 2.32 (s, 3H), 1.19 (t, J=7.2 Hz, 3H); m/z (ESI+) for (C$_{16}$H$_{18}$ClN$_5$O), 331.8 (M+H)$^+$.

Preparation of 3-(1-ethyl-3-methyl-1H-pyrazol-5-yl)-1-methyl-1H-1,2,4-triazole (Int-TG-04) According to Scheme TG-4

Scheme TG-4

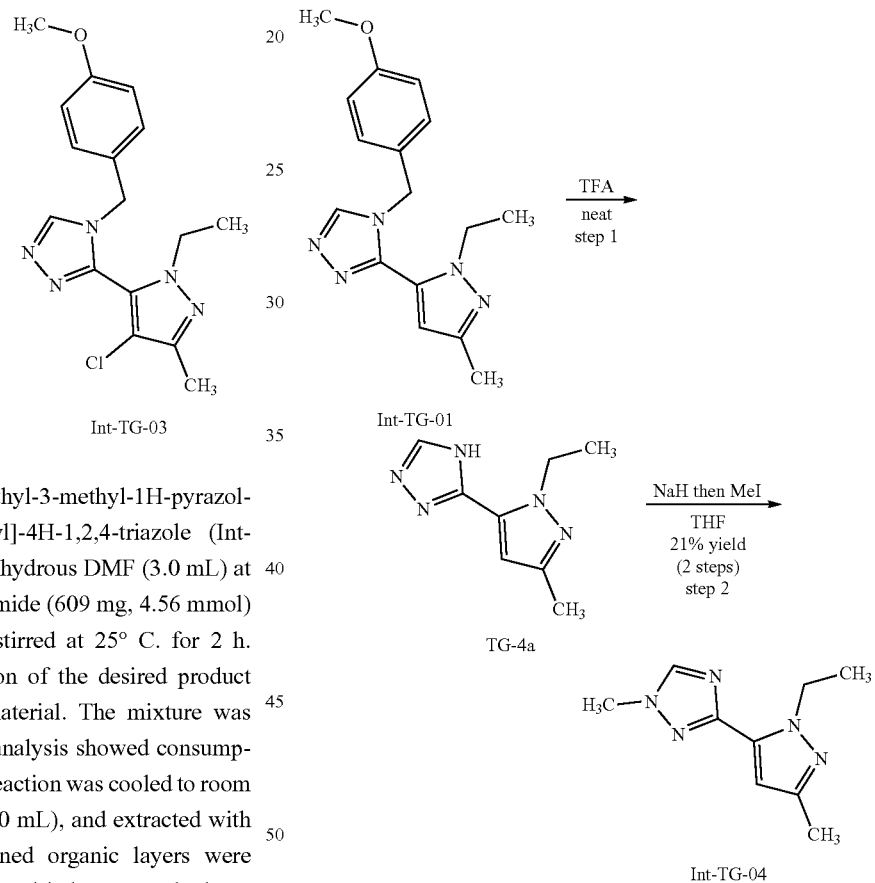

Step 1: Synthesis of 3-(1-ethyl-3-methyl-1H-pyrazol-5-yl)-4H-1,2,4-triazole acetic acid salt (TG-4a)

A solution of 3-(1-ethyl-3-methyl-1H-pyrazol-5-yl)-4-[(4-methoxyphenyl)methyl]-4H-1,2,4-triazole (Int-TG-01) (505 mg, 1.70 mmol) in TFA (4.5 mL) was stirred at 25° C. for 3 h. LCMS analysis showed consumption of the starting material with formation of the desired product mass. The reaction was concentrated to dryness. The crude residue was co-evaporated from DCM (5×10 mL). The material was taken up in a solution of NH$_3$ (7 N in MeOH, 10 ml) and concentrated to dryness to provide 3-(1-ethyl-3-methyl-1H-pyrazol-5-yl)-4H-1,2,4-triazole acetic acid salt (TG-4a) (301 mg, >99% yield), which was taken on without purification. m/z (ESI+) for (CH$_{11}$N5), 177.8 (M+H)$^+$.

Step 2: Synthesis of 3-(1-ethyl-3-methyl-1H-pyrazol-5-yl)-1-methyl-1H-1,2,4-triazole (Int-TG-04)

To a solution of 3-(1-ethyl-3-methyl-1H-pyrazol-5-yl)-4H-1,2,4-triazole acetic acid salt (TG-4a) (301 mg, 1.70 mmol) in THF (3.0 mL) and DMF (3.0 ML) was added NaH (60% dispersion in mineral oil, 89.6 mg, 2.2 mmol). The mixture was stirred for 20 min to provide a light-yellow suspension. Iodomethane (128 µL, 2.06 mmol) was added. The mixture was stirred at 25° C. for 1.5 h. LCMS analysis showed consumption of the starting material with formation of the desired product mass. The reaction was quenched by addition of H$_2$O (0.04 mL) and filtered through celite. The filtrate was diluted with H$_2$O and the mixture was re-filtered through celite. The filtrate was extracted with EtOAc (4×10 mL). The combined organic layers were dried over MgSO$_4$, filtered, and concentrated. NMR analysis indicated a 2.5:1 mixture of regioisomers. The residue was purified by preparative TLC (1:20 MeOH/DCM) to provide 3-(1-ethyl-3-methyl-1H-pyrazol-5-yl)-1-methyl-1H-1,2,4-triazole (55.6 mg, 21% yield) as a pale-yellow oil as the major and second-eluting regioisomer. $^1$H NMR (400 MHz, DMSO-d$_6$) δ 8.15 (s, 1H), 6.67 (s, 1H), 4.36 (q, J=7.1 Hz, 2H), 3.98 (s, 3H), 2.29 (s, 3H), 1.34 (t, J=7.2 Hz, 3H); m/z (ESI+) for (C$_9$H$_{13}$N$_5$), 191.8 (M+H)$^+$.

Intermediate Int-TG-05 was prepared according to the methods used for the synthesis of 3-(1-ethyl-3-methyl-1H-pyrazol-5-yl)-1-methyl-1H-1,2,4-triazole (Int-TG-04), with non-critical changes or substitutions to the exemplified procedures that one skilled in the art would be able to realize.

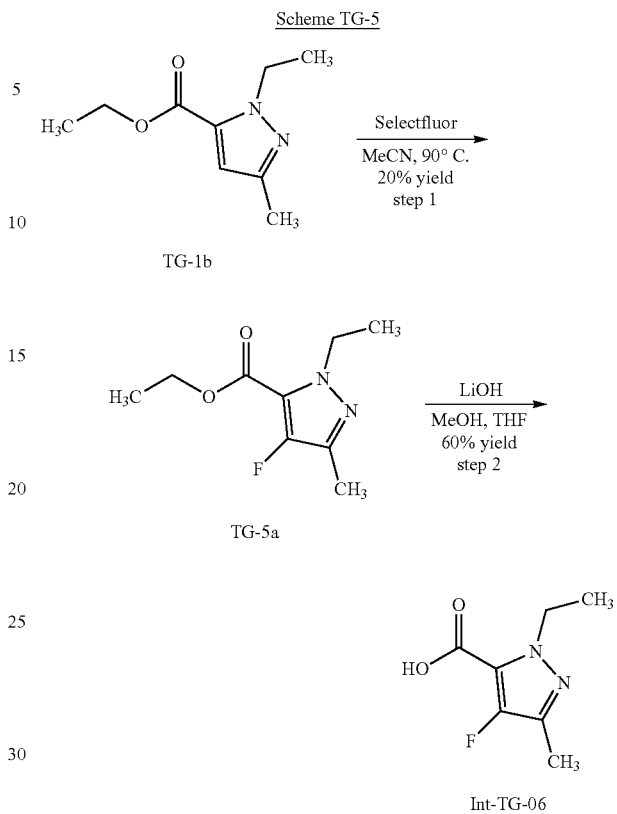

Scheme TG-5

| Compound Number | Structure/IUPAC Name | Analytical Data |
|---|---|---|
| Int-TG-05 | 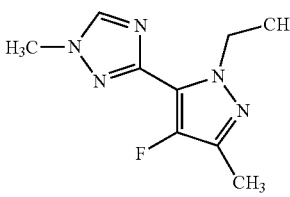<br>3-(1-ethyl-4-fluoro-3-methyl-1H-pyrazol-5-yl)-1-methyl-1H-1,2,4-triazole | $^1$H NMR (400 MHz, CDCl$_3$) δ 8.11 (s, 1H), 4.50 (q, J = 7.1 Hz, 2H), 4.00 (s, 3H), 2.27 (d, J = 0.8 Hz, 3H), 1.38 (t, J = 7.2 Hz, 3H). |

Preparation of 1-ethyl-4-fluoro-3-methyl-1H-pyrazole-5-carboxylic acid (Int-TG-06) According to Scheme TG-5

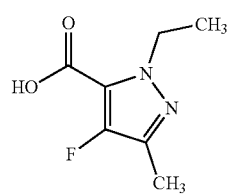

Step 1: Synthesis of ethyl 1-ethyl-4-fluoro-3-methyl-1H-pyrazole-5-carboxylate (TG-5a)

To a suspension of ethyl 1-ethyl-3-methyl-1H-pyrazole-5-carboxylate (TG-1b) (1.16 g, 6.36 mmol) in MeCN (15 mL) was added Selectfluor (6.77 g, 19.1 mmol). The mixture was stirred at 90° C. for 14 h. LCMS analysis showed formation of the desired mass with some remaining starting material. The mixture was filtered, and the filtrate was concentrated to dryness. The residue was purified by flash chromatography (0-5% EtOAc/petroleum ether) to provide ethyl 1-ethyl-4-fluoro-3-methyl-1H-pyrazole-5-carboxylate (TG-5a) (250 mg, 20% yield) as a colorless oil. $^1$H NMR (400 MHz, CDCl$_3$) δ 4.44 (q, J=7.2 Hz, 2H), 4.37 (q, J=7.1 Hz, 2H), 2.23 (s, 3H), 1.44-1.34 (m, 6H); m/z (ESI+) for (C$_9$H$_{13}$FN$_2$O$_2$), 200.8 (M+H)$^+$.

Step 2: Synthesis of 1-ethyl-4-fluoro-3-methyl-1H-pyrazole-5-carboxylic acid (Int-TG-06)

To a solution of ethyl 1-ethyl-4-fluoro-3-methyl-1H-pyrazole-5-carboxylate (TG-5a) (198 mg, 0.989 mmol) in MeOH/THF (1:5,1.2 mL) was added a solution of aqueous LiOH (1.0 N, 0.95 mL, 0.95 mmol). The mixture was stirred at 25° C. for 16 h. LCMS analysis showed consumption of the starting material. The reaction was combined with a parallel reaction run in identical fashion with 92 mg of ethyl 1-ethyl-4-fluoro-3-methyl-1H-pyrazole-5-carboxylate. The mixture was acidified with 1 N HCl to pH-3 and extracted with EtOAc (3×10 mL). The combined organic layers were dried over $Na_2SO_4$, filtered, and concentrated to provide 1-ethyl-4-fluoro-3-methyl-1H-pyrazole-5-carboxylic acid (Int-TG-06) (129 mg, 60% yield) as a white solid. $^1$H NMR (400 MHz, $CD_3OD$) δ 4.40 (q, J=7.4 Hz, 2H), 2.16 (d, J=0.8 Hz, 3H), 1.31 (t, J=7.1 Hz, 3H); m/z (ESI+) for ($C_7H_9FN_2O_2$), 172.7 (M+H)$^+$.

Preparation of 2-bromo-1-(1-ethyl-3-methyl-1H-pyrazol-5-yl)ethan-1-one (Int-TG-07) According to Scheme TG-6

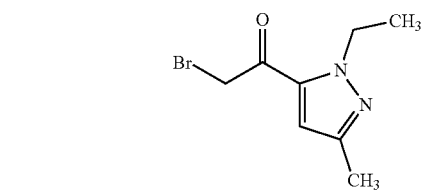

Scheme TG-6

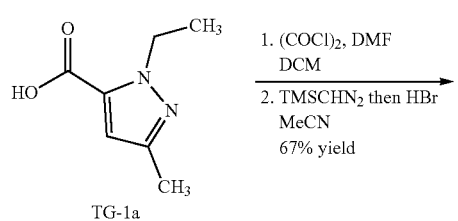

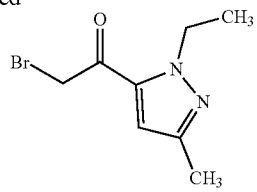

Int-TG-07

To a solution of 1-ethyl-3-methyl-1H-pyrazole-5-carboxylic acid (TG-1a, 300 mg, 1.95 mmol) in DCM (6.0 mL) was added DMF (2.0 μL) and $COCl_2$ (272 mg, 2.14 mmol). Gas evolution was observed. The mixture was stirred for 1 h at 12° C. and then concentrated to dryness. The residue was co-evaporated from DCM (2×5 mL). The crude material was dissolved in MeCN (8.0 mL) and $TMSCHN_2$ (2.14 mL, 489 mg, 4.28 mmol, 2M solution in n-hexane) was added. The reaction was stirred at room temperature for 2 hours. LCMS analysis showed that starting material remained. An additional aliquot of $TMSCHN_2$ (1.07 mL, 244 mg, 2.14 mmol, 2M solution in n-hexane) was added and the reaction stirred at rt for 1 h. At this stage, HBr (704 μL, 1.05 g, 4.28 mmol) was added drop-wise. Gas evolution was observed. The mixture was stirred at 12° C. for 16 h to provide a yellow suspension. LCMS analysis showed consumption of the starting material formation of the desired mass. The mixture was diluted with EtOAc (10 mL) and washed with $H_2O$. The organic layer was dried over $Na_2SO_4$, filtered, and concentrated. The residue was purified by flash chromatography (20 g $SiO_2$, 90-100% EtOAc/petroleum ether) to provide 2-bromo-1-(1-ethyl-3-methyl-1H-pyrazol-5-yl)ethan-1-one (Int-TG-07) (301 mg, 67% yield). $^1$H NMR (400 MHz, $CDCl_3$) δ 6.67 (d, J=0.7 Hz, 1H), 4.51 (q, J=7.2 Hz, 2H), 4.28 (s, 2H), 2.31 (d, J=0.5 Hz, 3H), 1.38 (t, J=7.2 Hz, 3H); m/z (ESI+) for ($CH_{11}BrN_2O$), 232.6 (M+H)$^+$.

Intermediate Int-TG-08 in the below table was prepared according to the methods used for the synthesis of 2-bromo-1-(1-ethyl-3-methyl-1H-pyrazol-5-yl)ethan-1-one (Int-TG-07), with non-critical changes or substitutions to the exemplified procedures that one skilled in the art would be able to realize.

| Compound Number | Structure/IUPAC Name | Analytical Data |
| --- | --- | --- |
| Int-TG-08 | ![structure] 2-bromo-1-(1-ethyl-4-fluoro-3-methyl-1H-pyrazol-5-yl)ethan-1-one | $^1$H NMR (400 MHz, $CDCl_3$) δ 4.51-4.41 (m, 2H), 4.39-4.25 (m, 2H), 2.29 (dt, J = 1.7, 0.8 Hz, 3H), 1.38 (t, J = 7.2 Hz, 3H); m/z (ESI+) for ($C_8H_{10}BrFN_2O$), 248.9 (M + H)$^+$. |

Preparation of ethyl 2-(methoxyimino)-4-oxopentanoate (Int-TG-09) According to Scheme TG-7

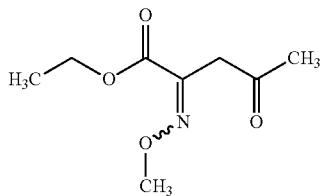

To a solution of ethyl 2,4-dioxopentanoate (TG-7a) (15.0 g, 94.9 mmol) in EtOH (150 mL) and H₂O (75 mL) was added a solution of O-methylhydroxylamine hydrochloride (7.92 g, 94.8 mmol) in H₂O (75 mL). The mixture was stirred at 25° C. for 2 h. TLC analysis (1:3 EtOAc/petroleum ether) indicated complete consumption of the starting material. The reaction was concentrated to dryness to provide ethyl 2-(methoxyimino)-4-oxopentanoate (Int-TG-09) (15.8 g, 89% yield) as a yellow oil, which was taken on without further purification. ¹H NMR (400 MHz, CDCl₃) δ 4.32 (q, J=7.1 Hz, 2H), 4.05 (s, 3H), 3.70 (s, 2H), 2.20 (s, 3H), 1.34 (t, J=7.1 Hz, 3H).

Preparation of tert-butyl 3-(5-{4-[(4-methoxyphenyl)methyl]-4H-1,2,4-triazol-3-yl}-3-methyl-1H-pyrazol-1-yl)propanoate (Int-TG-10) According to Scheme TG-8

Scheme TG-7

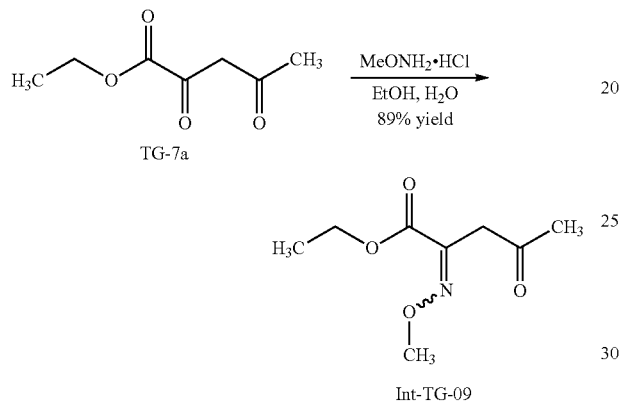

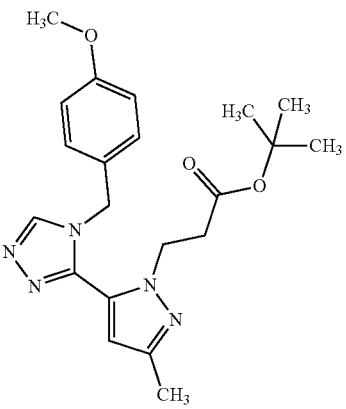 [SMILES: COc1ccc(Cn2cnnc2-c2cc(C)nn2CCC(=O)OC(C)(C)C)cc1]

Scheme TG-8

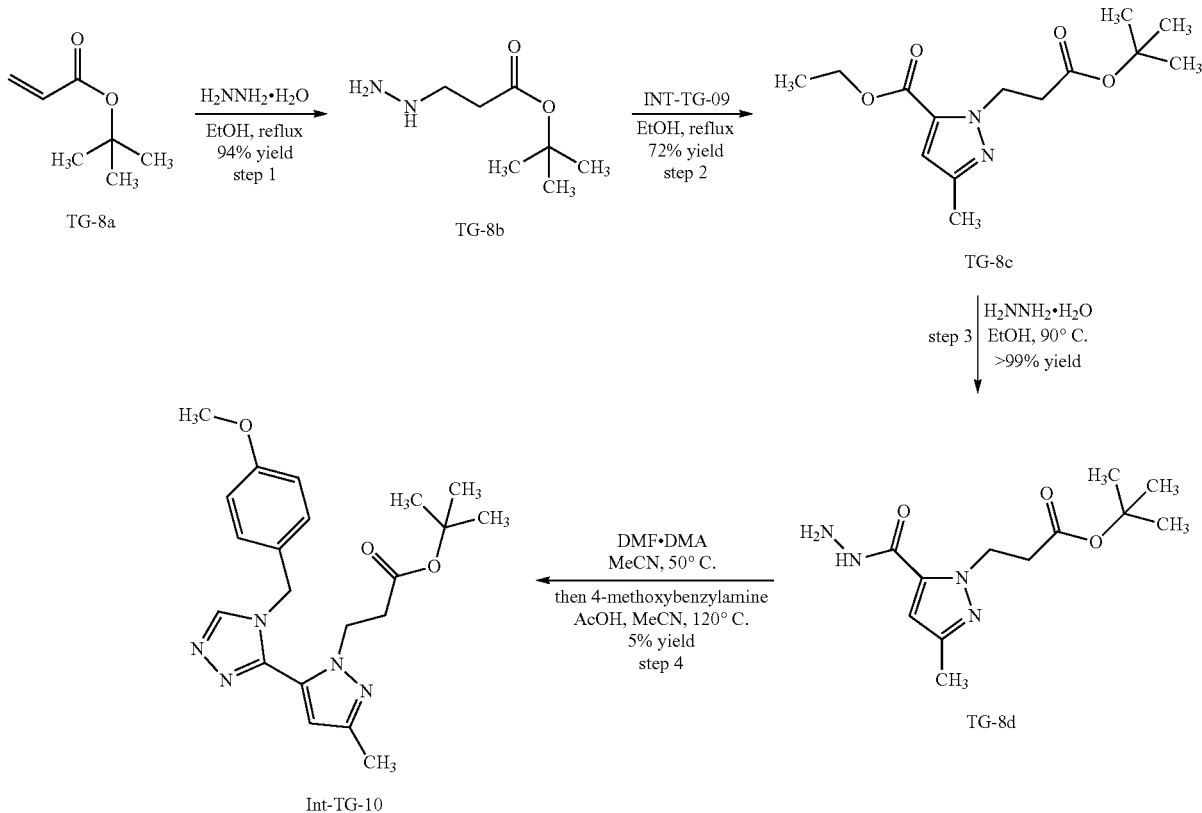

Step 1: Synthesis of tert-butyl 3-hydrazinylpropanoate (TG-8b)

A solution of hydrazine monohydrate (12.1 g, 236 mmol) in EtOH (150 mL) was heated to reflux and tert-butyl acrylate (15.0 g, 117 mmol) was added dropwise. The mixture was stirred at reflux for 10 min. TLC analysis (1:5 EtOAc/petroleum ether) showed consumption of the starting material. The reaction was concentrated to dryness to provide tert-butyl 3-hydrazinylpropanoate (TG-8b) (17.7 g, 94% yield) as a colorless oil. $^1$H NMR (400 MHz, CDCl$_3$) δ 3.11 (br s, 3H), 2.93 (t, J=6.5 Hz, 2H), 2.38 (t, J=6.4 Hz, 2H), 1.38 (s, 9H).

Step 2: Synthesis of ethyl 1-(3-tert-butoxy-3-oxopropyl)-3-methyl-1H-pyrazole-5-carboxylate (TG-8c)

A solution of ethyl 2-(methoxyimino)-4-oxopentanoate (Int-TG-09) (13.8 g, 73.7 mmol) and tert-butyl 3-hydrazinylpropanoate (TG-8b) (17.7 g, 110 mmol) in EtOH (200 mL) was stirred at reflux for 4 h. TLC analysis showed consumption of the starting material. The mixture was concentrated to dryness. The residue was purified by flash chromatography (330 g SiO$_2$, 0-25% EtOAc/petroleum ether) to provide ethyl 1-(3-tert-butoxy-3-oxopropyl)-3-methyl-1H-pyrazole-5-carboxylate (TG-8c) (14.9 g, 72% yield) as a colorless oil. $^1$H NMR (400 MHz, CDCl$_3$) δ 6.59 (s, 1H), 4.73 (t, J=7.4 Hz, 2H), 4.32 (q, J=7.2 Hz, 2H), 2.76 (t, J=7.4 Hz, 2H), 2.25 (s, 3H), 1.41 (s, 9H), 1.36 (t, J=7.1 Hz, 3H); m/z (ESI+) for (C$_{14}$H$_{22}$N$_2$O$_4$), 283.2 (M+H)$^+$.

Step 3: Synthesis of tert-butyl 3-[5-(hydrazinecarbonyl)-3-methyl-1H-pyrazol-1-yl]propanoate (TG-8d)

To a solution of ethyl 1-(3-tert-butoxy-3-oxopropyl)-3-methyl-1H-pyrazole-5-carboxylate (TG-8c) (14.9 g, 52.8 mmol) in EtOH (150 mL) was added hydrazine monohydrate (27.0 g, 528 mmol). The mixture was stirred at 90° C. for 16 h. LCMS analysis showed consumption of the starting material with formation of the desired product mass. The reaction was concentrated to dryness to provide tert-butyl 3-[5-(hydrazinecarbonyl)-3-methyl-1H-pyrazol-1-yl]propanoate (TG-8d) (14.2 g, >99% yield) as a colorless oil, which was taken on without further purification. $^1$H NMR (400 MHz, DMSO-d$_6$) δ 9.75 (br s, 1H), 6.61 (s, 1H), 4.64 (t, J=7.1 Hz, 2H), 4.51 (br s, 2H), 2.71 (t, J=7.1 Hz, 2H), 2.17 (s, 3H), 1.40 (s, 9H); m/z (ESI+) for (C$_{12}$H$_{20}$N$_4$O$_3$), 212.9 (M-tBu+H)$^+$.

Step 4: Synthesis of tert-butyl 3-(5-{4-[(4-methoxyphenyl)methyl]-4H-1,2,4-triazol-3-yl}-3-methyl-1H-pyrazol-1-yl)propanoate (Int-TG-10)

To a solution of tert-butyl 3-[5-(hydrazinecarbonyl)-3-methyl-1H-pyrazol-1-yl]propanoate (TG-8d) (14.2 g, 52.8 mmol) in MeCN (90 mL) was added N,N-dimethyldimethoxymethylamine (DMF·DMA) (6.59 g, 55.3 mmol). The mixture was stirred at 50° C. for 40 min. LCMS analysis showed consumption of the starting material. A solution of 4-methoxybenzylamine (6.90 g, 50.3 mmol) in MeCN (10 mL) and acetic acid (100 mL) were added sequentially. The mixture was stirred at 120° C. for 3 h. LCMS analysis showed formation of the desired product mass. The reaction was cooled to room temperature and concentrated to dryness. The residue was dissolved in H$_2$O (250 mL) and extracted with EtOAc (250 mL). The organic layer was dried over Na$_2$SO$_4$, filtered, and concentrated. The residue was purified by flash chromatography (220 g SiO$_2$, 0-5% MeOH/DCM) to provide tert-butyl 3-(5-{4-[(4-methoxyphenyl)methyl]-4H-1,2,4-triazol-3-yl}-3-methyl-1H-pyrazol-1-yl)propanoate (Int-TG-10) (1.08 g, 5% yield) as a yellow oil. $^1$H NMR (400 MHz, CDCl$_3$) δ 8.14 (s, 1H), 7.06 (d, J=8.7 Hz, 2H), 6.90 (d, J=8.6 Hz, 2H), 6.13 (s, 1H), 5.10 (s, 2H), 4.51 (t, J=7.1 Hz, 2H), 3.81 (s, 3H), 2.79 (t, J=7.1 Hz, 2H), 2.28 (s, 3H), 1.39 (s, 9H); m/z (ESI+) for (C$_{21}$H$_{27}$N$_5$O$_3$), 398.3 (M+H)$^+$.

Preparation of 3-(4-fluoro-5-{4-[(4-methoxyphenyl)methyl]-4H-1,2,4-triazol-3-yl}-3-methyl-1H-pyrazol-1-yl)propyl acetate (Int-TG-11) According to Scheme TG-9

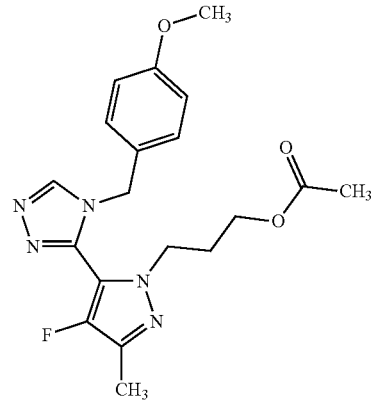 [SMILES: COc1ccc(Cn2cnnc2-c2c(F)c(C)nn2CCCOC(C)=O)cc1]

Scheme TG-9

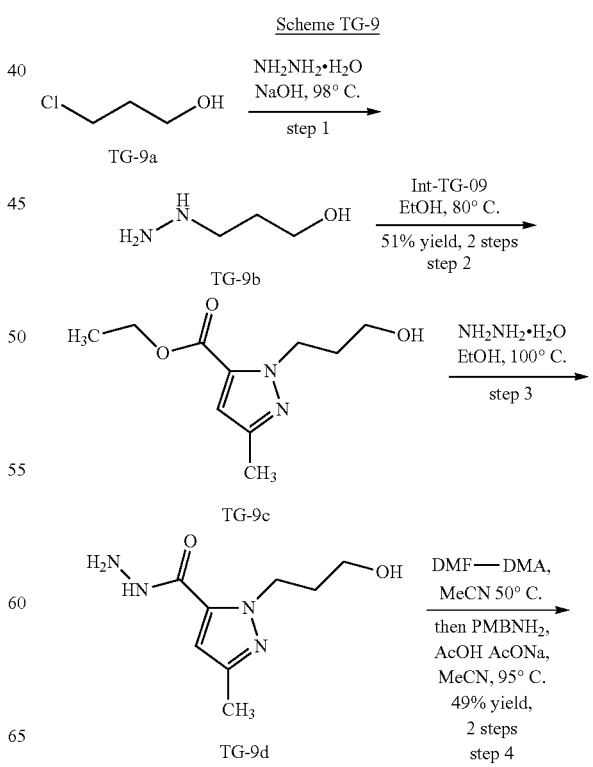

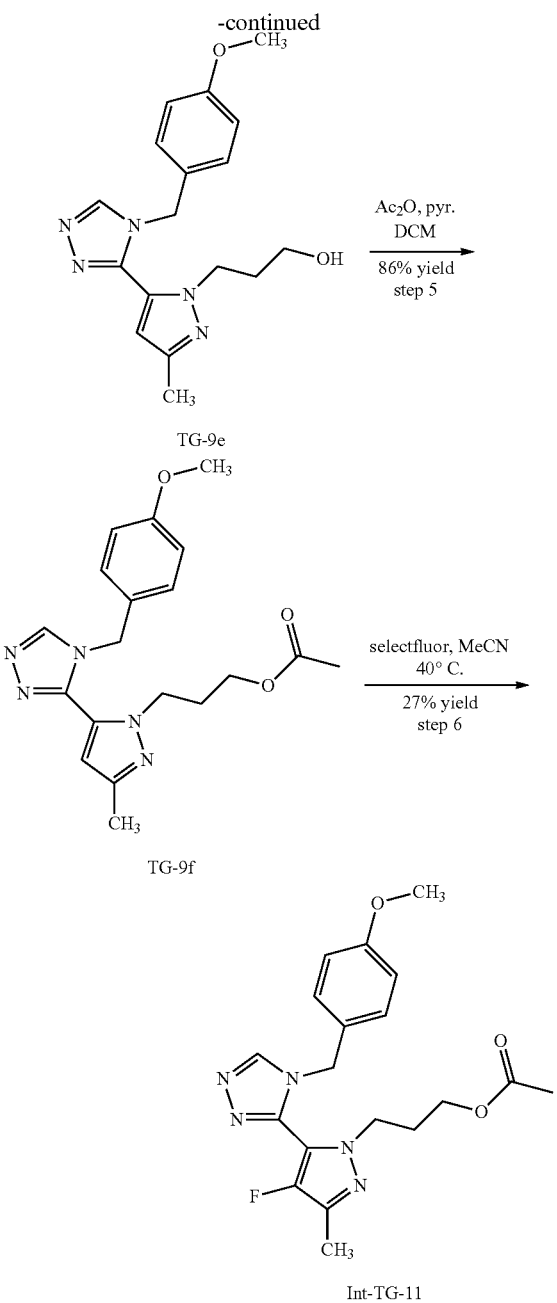

TG-9e

TG-9f

Int-TG-11

Step 1: Synthesis of 3-hydrazinylpropan-1-ol (TG-9b)

To a solution of NaOH (6.35 g, 159 mmol) in N$_2$H4-H$_2$O (46.7 g, 793 mmol) was added 3-chloropropan-1-ol TG-9a (15.0 g 158.66 mmol) dropwise at 98° C. under N$_2$. The mixture was stirred at 98° C. for 1 h. TLC (PE/EA=1:1, KMnO4) analysis showed consumption of TG-9a. The mixture was concentrated, filtered, and washed with EtOH. The filtrate was concentrated to give a colorless oil. The oil was further concentrated under high vacuum to give a white gum (24 g). The white gum was triturated with DCM/MeOH (100 mL), filtered and concentrated to give 3-hydrazinylpropan-1-ol (TG-9b) (15 g, >99% yield) as a colorless gum which was used in the next step without further purification. $^1$H NMR (400 MHz, DMSO-d6) δ 4.49-4.23 (m, 4H), 3.45-3.42 (m, 2H), 2.74-2.63 (m, 2H), 1.59-1.50 (m, 2H).

Step 2: Synthesis of ethyl 1-(3-hydroxypropyl)-3-methyl-1H-pyrazole-5-carboxylate (TG-9c)

To a solution of ethyl 2-(methoxyimino)-4-oxopentanoate (Int-TG-09) (2.30 g, 12.29 mmol) in 3-hydrazinylpropan-1-ol (TG-9b) (1.33 g, 14.7 mmol) was added EtOH (13 mL). The mixture was stirred at 80° C. for 2 h. TLC (PE/EA=1:1, UV) analysis showed consumption of starting material. The mixture was combined with a smaller batch, performed in parallel, and was concentrated under vacuum followed by flash chromatography (EtOAc in petroleum ether from 0% to 50%) to afford the title compound ethyl 1-(3-hydroxypropyl)-3-methyl-1H-pyrazole-5-carboxylate (TG-9c) (1.64 g, 51% yield) as a yellow oil. m/z (ESI+) for (C$_{10}$H$_{16}$N$_2$O$_3$), 213.1 (M+H)$^+$.

Step 3: Synthesis of 1-(3-hydroxypropyl)-3-methyl-1H-pyrazole-5-carbohydrazide (TG-9d)

To a solution of 1-(3-hydroxypropyl)-3-methyl-1H-pyrazole-5-carboxylate (TG-9c) (1.44 g, 6.785 mmol) in EtOH (7 mL) was added N$_2$H4-H$_2$O (1.20 g, 20.4 mmol). The mixture was stirred at 100° C. for 16 h. LCMS analysis showed consumption of starting material. The mixture was concentrated under vacuum to afford the title compound 1-(3-hydroxypropyl)-3-methyl-1H-pyrazole-5-carbohydrazide (TG-9d) (1.34 g, >99% yield) as a white solid which was used in the next step without further purification. m/z (ESI+) for (C$_8$H$_{14}$N$_4$O$_2$), 199.1 (M+H)$^+$.

Step 4: Synthesis of 3-(5-{4-[(4-methoxyphenyl)methyl]-4H-1,2,4-triazol-3-yl}-3-methyl-1H-pyrazol-1-yl)propan-1-ol (TG-9e)

To a solution of 1-(3-hydroxypropyl)-3-methyl-1H-pyrazole-5-carbohydrazide (TG-9d) (1.245 g, 6.281 mmol) in MeCN (30 mL) was added DMF-DMA (816 mg, 6.85 mmol) at rt. After the addition, the reaction mixture was stirred at 50° C. for 40 min. LC-MS analysis showed consumption of starting material. At this stage, 4-Methoxybenzylamine (2.58 g, 18.8 mmol), followed by AcOH (10 mL) and AcONa (1.55 g, 18.8 mmol) were added to the reaction mixture. The reaction was stirred at 95° C. for another 16 h. The solution was concentrated under vacuum. The crude residue was neutralized with sat. NaHCO$_3$, extracted with EtOAc (2×10 mL). The combined organic extracts were dried (Na$_2$SO$_4$), filtered, and concentrated under vacuum. The crude residue was purified by flash chromatography (4 g SiO$_2$, MeOH in DCM, 0% to 10%) to afford the title compound 3-(5-{4-[(4-methoxyphenyl)methyl]-4H-1,2,4-triazol-3-yl}-3-methyl-1H-pyrazol-1-yl)propan-1-ol (TG-9e) (1.02 g, 49% yield) as a yellow gum. $^1$H NMR (400 MHz, DMSO-d6) δ 8.77 (s, 1H), 7.03-6.97 (m, 2H), 6.92-6.86 (m, 2H), 6.39 (s, 1H), 5.23 (s, 2H), 4.60 (t, J=5.4 Hz, 1H), 4.17-4.08 (m, 2H), 3.72 (s, 3H), 3.28-3.23 (m, 2H), 2.21 (s, 3H), 1.72 (quin, J=6.6 Hz, 2H); m/z (ESI+) for (C$_{17}$H$_{21}$N$_5$O$_2$), 328.1 (M+H)$^+$.

Step 5: Synthesis of 3-(5-{4-[(4-methoxyphenyl)methyl]-4H-1,2,4-triazol-3-yl}-3-methyl-1H-pyrazol-1-yl)propyl acetate (TG-9f)

To a solution of 3-(5-{4-[(4-methoxyphenyl)methyl]-4H-1,2,4-triazol-3-yl}-3-methyl-1H-pyrazol-1-yl)propan-1-ol (TG-9e) (1.02 g, 3.116 mmol) in DCM (10 mL) was added pyridine (1.48 g, 18.7 mmol) and acetic anhydride (1.27 g, 12.5 mmol) at rt. The reaction was stirred at rt for 16 h. LCMS analysis showed almost complete consumption of starting material. The solution was diluted with water (15 mL) and extracted with DCM (2×20 mL). The combined organic extracts were purified by flash chromatography (MeOH in DCM from 0% to 10%) to afford the title compound 3-(5-{4-[(4-methoxyphenyl)methyl]-4H-1,2,4-triazol-3-yl}-3-methyl-1H-pyrazol-1-yl)propyl acetate (TG-9f) (1.00 g, 86% yield) as a yellow oil. m/z (ESI+) for ($C_{18}H_{23}N_5O_3$), 370.2 (M+H)+.

Step 6: Synthesis of 3-(4-fluoro-5-{4-[(4-methoxyphenyl)methyl]-4H-1,2,4-triazol-3-yl}-3-methyl-1H-pyrazol-1-yl)propyl acetate (Int-TG-11)

To a solution of 3-(5-{4-[(4-methoxyphenyl)methyl]-4H-1,2,4-triazol-3-yl}-3-methyl-1H-pyrazol-1-yl)propyl acetate (TG-9f) (500 mg, 1.35 mmol) in MeCN (5 mL) was added Selectfluor (959 mg, 2.71 mmol). The resulting mixture was heated to 40° C. and stirred for 14 h. LCMS analysis showed significant starting material remained. The reaction was quenched at this stage with water and extracted with EtOAc (3×10 mL). The combined organic extracts were dried ($Na_2SO_4$), filtered, and concentrated under vacuum. The crude residue was purified by flash chromatography (MeOH in DCM from 0% to 6%) to afford the title compound (146 mg, 27% yield) as a yellow gum. $^1$H NMR (400 MHz, CHLOROFORM-d) δ 8.13 (s, 1H), 7.07 (d, J=8.5 Hz, 2H), 6.90-6.84 (m, 2H), 5.08 (s, 2H), 4.32-4.23 (m, 2H), 3.90 (d, J=6.8 Hz, 2H), 3.80 (s, 3H), 2.30 (s, 3H), 2.02-1.99 (m, 1H), 2.01-1.95 (m, 5H); m/z (ESI+) for ($C_{19}H_{22}FN_5O_3$), 388.2 (M+H)+.

Preparation of 3-[4-(benzyloxy)-1-ethyl-3-methyl-1H-pyrazol-5-yl]-1-methyl-1H-1,2,4-triazole (Int-TG-12) According to Scheme TG-10

Scheme TG-10

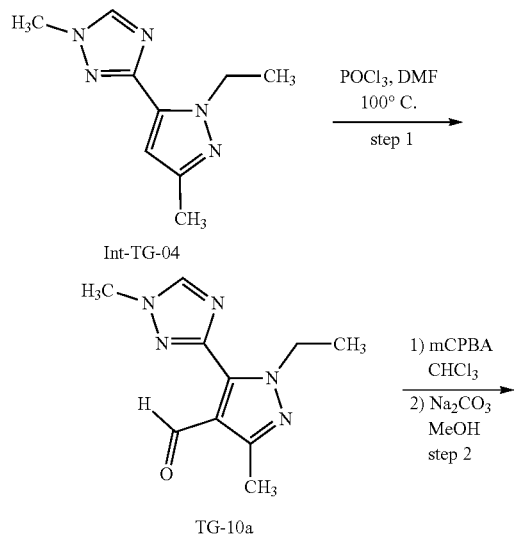

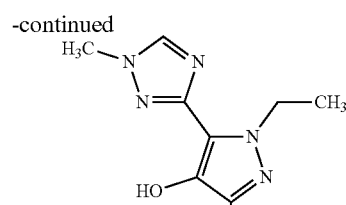

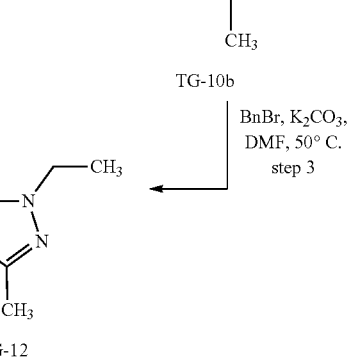

Step 1: Synthesis of 1-ethyl-3-methyl-5-(1-methyl-1H-1,2,4-triazol-3-yl)-1H-pyrazole-4-carbaldehyde (TG-10a)

A flask containing DMF (9.11 mL, 118 mmol) was cooled to 0° C. in an ice bath followed by the dropwise addition of phosphorus (V) oxychloride (0.877 mL, 9.41 mmol). The reaction was allowed to warm to rt over 15 min and stirred for an additional 45 min. At this stage, 3-(1-ethyl-3-methyl-1H-pyrazol-5-yl)-1-methyl-1H-1,2,4-triazole (Int-TG-04) (300 mg, 1.57 mmol) was added as a solution in DMF (2.25 mL). The reaction was heated at 100° C. for 40 min. LCMS analysis showed complete consumption of starting material. The solution was poured into ice and extracted with 3 portions DCM. The combined organic extracts were concentrated in vacuo. The crude product was purified by flash chromatography (12 g $SiO_2$, Isco, 0-100% EtOAc in Hept.) to afford the title compound 1-ethyl-3-methyl-5-(1-methyl-1H-1,2,4-triazol-3-yl)-1H-pyrazole-4-carbaldehyde (TG-10a) (57 mg, 90% yield) as a white solid. 1H NMR (400 MHz, DMSO-d6) δ=10.27 (s, 1H), 8.78 (s, 1H), 4.49 (q, J=7.3 Hz, 2H), 4.00 (s, 3H), 2.39 (s, 3H), 1.36 (t, J=7.2 Hz, 3H).

Step 2: Synthesis of 1-ethyl-3-methyl-5-(1-methyl-1H-1,2,4-triazol-3-yl)-1H-pyrazol-4-ol (TG-10b)

To a solution of 1-ethyl-3-methyl-5-(1-methyl-1H-1,2,4-triazol-3-yl)-1H-pyrazole-4-carbaldehyde (TG-10a) (274 mg, 1.30 mmol) in CHCl$_3$ (2 mL) was added mCPBA (678 mg, 2.75 mmol). The reaction was stirred at rt for 6.5 h. The solution was concentrated in vacuo. The crude material was dissolved in MeOH (8 mL) and Na$_2$CO$_3$ (437 mg, 4.13 mmol) was added as a solution in H$_2$O (2 mL). The reaction was stirred at rt for 2 h. The solution was transferred to a separatory funnel and extracted with 3 portions DCM. The combined organic extracts were concentrated in vacuo. The crude residue was purified by flash chromatography (40 g SiO$_2$, Isco, 0-100% EtOAc in Hept.) to afford the title compound 1-ethyl-3-methyl-5-(1-methyl-1H-1,2,4-triazol-3-yl)-1H-pyrazol-4-ol (TG-10b) (150 mg, 56% yield) as a white solid. $^1$H NMR (400 MHz, DMSO-d6) δ=8.65 (s, 1H), 7.95 (s, 1H), 4.32 (q, J=7.2 Hz, 2H), 3.94 (s, 3H), 2.08 (s, 3H), 1.25 (t, J=7.2 Hz, 3H); m/z (ESI+) for ($C_9H_{13}N_5O$), 208.5 (M+H)+ observed.

Step 3: Synthesis of 3-[4-(benzyloxy)-1-ethyl-3-methyl-1H-pyrazol-5-yl]-1-methyl-1H-1,2,4-triazole (Int-TG-12)

To a cold solution of 1-ethyl-3-methyl-5-(1-methyl-1H-1,2,4-triazol-3-yl)-1H-pyrazol-4-ol (TG-10b) (150 mg, 0.724 mmol) and $K_2CO_3$ (400 mg, 2.90 mmol) in DMF (1.5 mL) was added benzyl bromide (248 mg, 1.45 mmol, 172 µL) as a solution in DMF (0.5 mL) in a dropwise fashion. The reaction was stirred at 0-10° C. for 2 h and 50° C. overnight. The solution was diluted with $H_2O$ (20 mL) and extracted with 3 portions DCM. The combined organic extracts were concentrated in vacuo. The crude residue was purified by flash chromatography (12 g $SiO_2$, Isco, 0-100% EtOAc in Hept.) to afford the title compound 3-[4-(benzyloxy)-1-ethyl-3-methyl-1H-pyrazol-5-yl]-1-methyl-1H-1,2,4-triazole (Int-TG-12) (187 mg, 87% yield). $^1$H NMR (400 MHz, DMSO-d6) δ=8.65 (s, 1H), 7.47-7.40 (m, 2H), 7.39-7.27 (m, 3H), 4.93 (s, 2H), 4.33 (q, J=7.3 Hz, 2H), 3.97 (s, 3H), 2.01 (s, 3H), 1.26 (t, J=7.0 Hz, 3H).

Preparation of 1-ethyl-3-methyl-1H-pyrazole-5-carbothioamide (Int-TG-13) According to Scheme TG-11

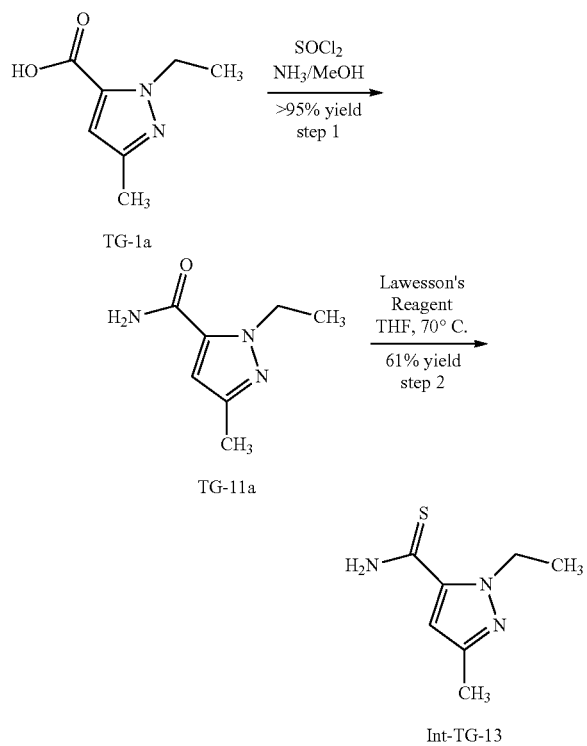

Step 1: Synthesis of 1-ethyl-3-methyl-1H-pyrazole-5-carboxamide (TG-11a)

To a flask containing 1-ethyl-3-methyl-1H-pyrazole-5-carboxylic acid (TG-1a) (258 mg, 1.69 mmol) was added $SOCl_2$ (1 mL). The reaction was heated at 65° C. for 2.5 h. The solution was concentrated in vacuo and the residue azeotroped with PhMe (3 mL). The crude residue was dissolved into dioxane (2 mL) and cooled in an ice bath to 0° C. To the solution was added sat. $NH_3$ as a solution in MeOH (2.41 mL, 7M). The reaction was stirred at rt for 1 h resulting in precipitation of a white solid. The solids were collected by filtration, washed with EtOAc, and dried under high vacuum overnight to afford the title compound 1-ethyl-3-methyl-1H-pyrazole-5-carboxamide (TG-11a) (300 mg, >95% yield) as a white solid. $^1$H NMR (400 MHz, DMSO-d6) δ=7.80 (br s, 1H), 7.39 (br s, 1H), 6.60 (s, 1H), 4.42 (q, J=7.3 Hz, 2H), 2.15 (s, 3H), 1.26 (t, J=7.0 Hz, 3H).

Step 2: Synthesis of 1-ethyl-3-methyl-1H-pyrazole-5-carbothioamide (Int-TG-13)

To a solution of 1-ethyl-3-methyl-1H-pyrazole-5-carboxamide (TG-11a) (30.0 mg, 0.20 mmol) in THF was added Lawesson's reagent (79.2 mg, 0.196 mmol). The reaction was stirred at 70° C. for 4 h. The reaction was quenched with $H_2O$ (10 mL) and transferred to a separatory funnel with EtOAc. The phases were separated and the aqeuous phase was extracted with 3 portions EtOAc. The combined organic extracts were dried ($Na_2SO_4$), filtered, and concentrated in vacuo. The crude residue was purified via flash chromatography (12 g $SiO_2$, Isco, 0-100% EtOAc in Hept.) to afford the title compound 1-ethyl-3-methyl-1H-pyrazole-5-carbothioamide (Int-TG-13) (20 mg, 61% yield) as a yellow solid. 1H NMR (400 MHz, DMSO-d6) δ=9.86 (br s, 1H), 9.40 (br s, 1H), 6.30 (s, 1H), 4.48 (q, J=7.0 Hz, 2H), 2.14 (s, 3H), 1.28 (t, J=7.2 Hz, 3H).

Preparation of methyl-2-(1-ethyl-3-methyl-1H-pyrazol-5-yl)-1,3-oxazole-5-carboxylate (Int-TG-14) According to Scheme TG-12

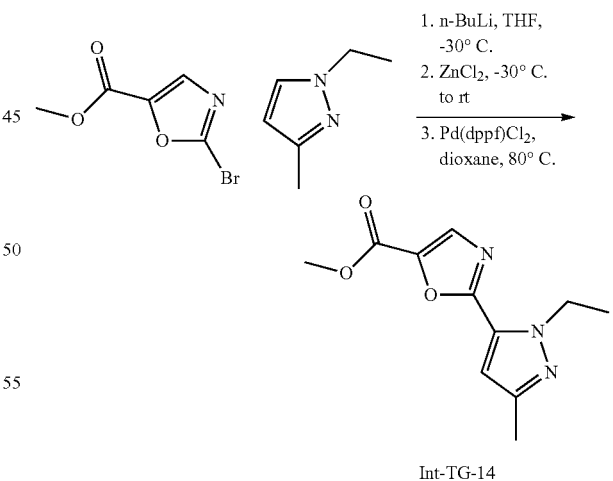

To a solution of 1-ethyl-3-methyl-1h-pyrazole (300.0 mg, 2.72 mmol) in THF (12 mL) was added n-BuLi (436 mg, 6.81 mmol, 2.72 mL, 2.5 M) dropwise at −30° C., the reaction was stirred for 10 min at −30° C. Then zinc chloride (928 mg, 6.81 mmol, 3.58 mL, 1.9 M) was introduced at −30° C., stirred at −30° C. for 30 min, then warmed up to rt and stirred for 1 h. The zincate solution (c=0.148 M) was used in the next step. A vial was charged with methyl 2-bromo-1,3-oxazole-5-carboxylate (250 mg, 1.21 mmol) and Pd(dppf)Cl$_2$ (178 mg, 0.243 mmol) in dioxane (5 mL), degassed for 5 min. Zincate solution (12.3 mL, 1.82 mmol, 0.148 M) was introduced at rt, and heated at 80° C. and monitored by LCMS. The reaction was filtered through a pad of celite and concentrated in vacuo. The crude product was purified by ISCO (silica, 40 g, 0-40% EtOAc in Heptane) to afford methyl 2-(1-ethyl-3-methyl-1H-pyrazol-5-yl)-1,3-oxazole-5-carboxylate (Int-TG-14) (62 mg, 22% yield) as a light-orange color solid. $^1$H NMR (400 MHz, DMSO-d$_6$) δ=8.20 (s, 1H), 6.79 (s, 1H), 4.57 (q, J=7.2 Hz, 2H), 3.33 (s, 3H), 2.24 (s, 3H), 1.36 (t, J=7.0 Hz, 3H). m/z (ESI+) for (C$_{11}$H$_{13}$N$_3$O$_3$), 236.2 (M+H)$^+$ observed.

Preparation of ethyl 2-[4-(benzyloxy)-1-ethyl-3-methyl-1H-pyrazol-5-yl]-1,3-oxazole-5-carboxylate (Int-TG-15) According to Scheme TG-13

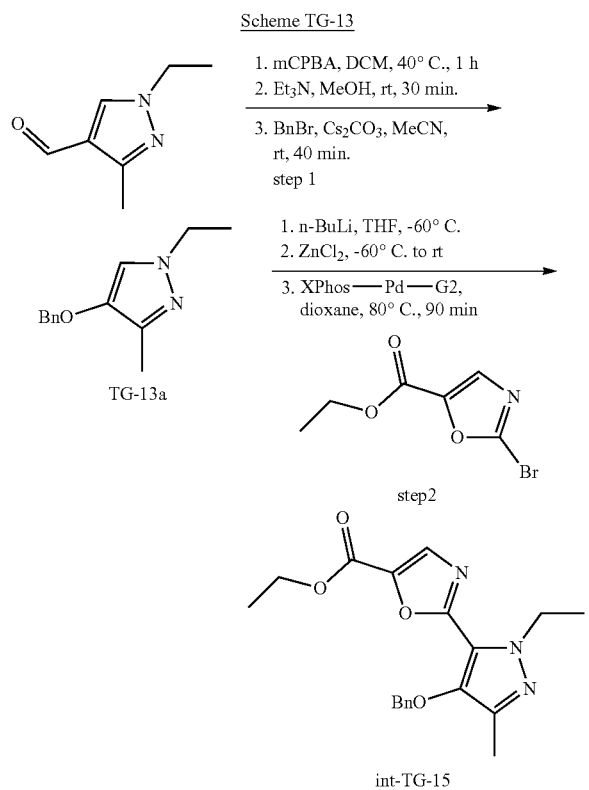

Step 1: Synthesis of 4-(benzyloxy)-1-ethyl-3-methyl-1H-pyrazole (TG-13a)

To a 100 mL flask containing 1-ethyl-3-methyl-1H-pyrazole-4-carbaldehyde (1.0 g, 7.24 mmol) was added DCM and m-chloroperoxybenzoic acid (mCPBA) (3.24 g, 77% purity, 14.5 mmol). The solution was heated at 40° C. for 1 h. The reaction was cooled to room temperature, diluted with DCM, washed with mixture of sat Na$_2$SO$_3$ and sat Na$_2$CO$_3$× 2, then brine, dried over Na$_2$SO$_4$, filtered and concentrated to afford 1 g of crude 1-ethyl-3-methyl-1H-pyrazol-4-yl formate which was used without further purification. To a 100 mL flask containing 1-ethyl-3-methyl-1H-pyrazol-4-yl formate (1 g, 6.49 mmol) was added MeOH and Et$_3$N (0.9 mL, 6.48 mmol). The solution was stirred at rt for 30 min. The solution was concentrated in vacuo to yield crude 1-ethyl-3-methyl-1H-pyrazol-4-ol as a pink oil which was used without further purification. To a 100 mL flask containing 1-ethyl-3-methyl-1H-pyrazol-4-ol (848 mg, 6.48 mmol) in CH$_3$CN (32.4 mL) was added Cs$_2$CO$_3$ (4.23 g, 13 mmol) and benzyl bromide (1.16 mL, 9.73 mmol). The solution was stirred at rt for 40 min. The reaction was filtered through celite with EtOAc, then concentrated. The crude product was adsorbed onto celite, purified via ISCO (0-35% EtOAc in heptane) to afford 4-(benzyloxy)-1-ethyl-3-methyl-1H-pyrazole (TG-13a) (1.1 g, 78% yield) as colorless oil. $^1$H NMR (400 MHz, DMSO-d$_6$) δ=7.55-7.26 (m, 5H), 4.87 (s, 2H), 3.92 (q, J=7.4 Hz, 2H), 2.03 (s, 3H), 1.29 (t, J=7.2 Hz, 3H). m/z (ESI+) for (C$_{13}$H$_{16}$N$_2$O), 217.2 (M+H)$^+$ observed.

Step 2: Synthesis of ethyl 2-[4-(benzyloxy)-1-ethyl-3-methyl-1H-pyrazol-5-yl]-1,3-oxazole-5-carboxylate (Int-TG-15)

To a solution of 4-(benzyloxy)-1-ethyl-3-methyl-1H-pyrazole (TG-13a) (308.0 mg, 1.42 mmol) in THF (9.0 mL) was added n-BuLi (0.490 mL, 1.22 mmol, 2.5 M) dropwise at −63° C., the reaction was stirred for 10 min at −63 to −60° C. Then ZnCl$_2$ (0.645 mL, 1.22 mmol, 1.9 M) was introduced at −60° C., stirred at −60 to −55° C. for 30 min, then warmed up to rt and stirred for 1 h. The zincate solution (c=0.13 M) was used in the next step. A vial was charged with ethyl 2-bromooxazole-5-carboxylate (200 mg, 0.909 mmol) and XPhos-Pd-G2 (64.4 mg, 0.0818 mmol) in dioxane (10 mL) was degassed for 5 min. The solution of zincate (10.5 mL, 1.36 mmol, 0.13M) was introduced at rt and the reaction heated at 80° C. for 90 min. The reaction mixture was reverse quenched into ice water containing 1.25 mL 1M HCl. The mixture was extracted with EtOAc×3. The combined organic extracts were concentrated in vacuo. The crude product was purified by ISCO (silica, 24 g, 0-30% EtOAc in Heptane) to afford ethyl 2-[4-(benzyloxy)-1-ethyl-3-methyl-1H-pyrazol-5-yl]-1,3-oxazole-5-carboxylate (Int-TG-15) (141 mg, 58% yield) as a clear oil $^1$H NMR (400 MHz, DMSO-d$_6$) δ=8.20 (s, 1H), 7.50 (dd, J=1.8, 7.6 Hz, 2H), 7.36 (d, J=7.0 Hz, 3H), 4.99 (s, 2H), 4.54-4.44 (m, 2H), 4.38 (q, J=7.0 Hz, 2H), 2.12 (s, 3H), 1.32 (t, J=7.2 Hz, 6H). m/z (ESI+) for (C$_{19}$H$_{21}$N$_3$O$_4$), 356.3 (M+H)$^+$ observed.

Preparation of 2-[4-(benzyloxy)-5-bromo-3-methyl-1H-pyrazol-1-yl]ethyl acetate (Int-TG-16) According to Scheme TG-14

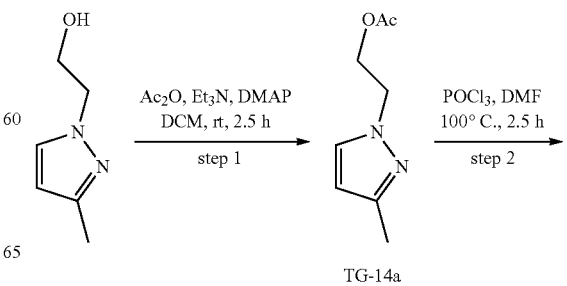

-continued

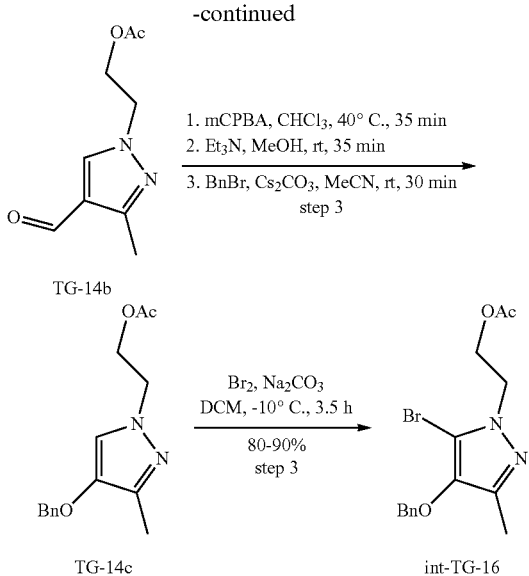

Step 1: Synthesis of 2-(3-methyl-1H-pyrazol-1-yl) ethyl acetate (TG-14a)

To a 50 mL flask was added 2-(3-methyl-1h-pyrazol-1-yl)ethan-1-ol (239 mg, 1.47 mmol), acetyl acetate (180 mg, 1.76 mmol, 167 µL), triethylamine (446 mg, 4.41 mmol, 0.615 mL) and DMAP (35.9 mg, 0.294 mmol) in DCM (20.0 mL) at rt for 2.5 h. The reaction mixture stayed as a suspension. The solid was filtered out, the filtrate was diluted with DCM and washed with water, dried over $Na_2SO_4$, and concentrated in vacuo. The crude material was purified by ISCO (silica, 12 g 0-40% EtOAc in petroleum ether) to afford 2-(3-methyl-1H-pyrazol-1-yl)ethyl acetate (TG-14a) (278, 86% yield) as a clear oil. 1H NMR (400 MHz, DMSO-d6) δ ppm 7.59 (d, J=1.95 Hz, 1H), 6.00 (d, J=1.95 Hz, 1H), 4.28-4.33 (m, 2H), 4.21-4.27 (m, 2H), 2.15 (s, 3H), 1.98 (s, 3H).

Step 2: Synthesis of 2-(4-formyl-3-methyl-1H-pyrazol-1-yl)ethyl acetate (TG-14b)

To a mixture of 2-(3-methyl-1H-pyrazol-1-yl)ethyl acetate (TG-14a) (254 mg, 1.51 mmol) in DMF (993 mg, 13.6 mmol, 1.05 mL) was added phosphorus oxychloride (695 mg, 4.53 mmol, 0.422 mL) at rt, exothermic reaction, after 2 min, the reaction was heated at 100° C. for 2.5 h. The reaction was cooled to rt, diluted with DCM and poured into ice, stirring for 5 min, the aqueous layer was carefully neutralized with sat. $Na_2CO_3$ to pH 8. The reaction products were extracted with DCM×3. The organic layer was washed with water×1 and concentrated in vacuo. The crude mixture was purified by ISCO (silica, 12 g, 0-100% EtOAc in petroleum ether) to afford 348 mg of 2-(4-formyl-3-methyl-1H-pyrazol-1-yl)ethyl acetate (TG-14b) as a light yellow oil. $^1$H NMR (400 MHz, DMSO-$d_6$) δ=9.82 (s, 1H), 8.40 (s, 1H), 4.48-4.22 (m, 4H), 2.36 (s, 3H), 1.98 (s, 3H).

Step 3: Synthesis of 2-[4-(benzyloxy)-3-methyl-1H-pyrazol-1-yl]ethyl acetate (TG-14c)

To a 25 mL flask containing 2-(4-formyl-3-methyl-1H-pyrazol-1-yl)ethyl acetate (TG-14b) (220 mg, 1.31 mmol) was added chloroform and m-CPBA (526 mg, 77% purity, 2.35 mmol). The reaction was heated at 40° C. for 35 min. The reaction was cooled to room temperature, diluted with dichloromethane, washed with mix of sat $Na_2SO_3$ and sat $Na_2CO_3$×1, adjusted pH=8, extracted with DCM×3, then the organic layer was washed with water, dried over $Na_2SO_4$, filtered and concentrated in vacuo to afford crude 2-[4-(formyloxy)-3-methyl-1H-pyrazol-1-yl]ethyl acetate which was used in next step without purification. To a 50 mL flask containing 2-[4-(formyloxy)-3-methyl-1H-pyrazol-1-yl] ethyl acetate (260 mg, 1.23 mmol) was added MeOH and triethylamine (161 mg, 1.59 mmol, 0.222 mL). The solution was stirred at rt for 35 min. The solution was concentrated in vacuo to yield 2-(4-hydroxy-3-methyl-1H-pyrazol-1-yl)-ethyl acetate as a yellow oil, which was directly used in the next step. To a 50 mL flask containing 2-(4-hydroxy-3-methyl-1H-pyrazol-1-yl)ethyl acetate (226 mg, 1.23 mmol) was added MeCN (8 mL), cesium carbonate (480 mg, 1.47 mmol), and benzyl bromide (0.219 mL, 1.84 mmol) at rt. The reaction was stirred at rt for 30 min. The reaction was filtered through celite, the solids washed with EtOAc, and the filtrate concentrated in vacuo. The crude product was adsorbed onto silica, purified via ISCO (12 g, 0-50% EtOAc in heptane) to afford the title compound (205 mg, 58% over 3 steps) 2-[4-(benzyloxy)-3-methyl-1H-pyrazol-1-yl]ethyl acetate (TG-14c) as a clear oil. $^1$H NMR (400 MHz, DMSO-$d_6$) δ=7.50-7.24 (m, 6H), 4.88 (s, 2H), 4.28-4.23 (m, 2H), 4.14 (d, J=5.5 Hz, 2H), 2.04 (s, 3H), 1.97 (s, 3H).

Step 4: Synthesis of 2-[4-(benzyloxy)-5-bromo-3-methyl-1H-pyrazol-1-yl]ethyl acetate (Int-TG-16)

To a stirred solution of 2-[4-(benzyloxy)-3-methyl-1H-pyrazol-1-yl]ethyl acetate (TG-14c) (156.0 mg, 0.569 mmol) and sodium carbonate (181 mg, 1.71 mmol) in dichloromethane (2.0 mL) at −9° C. was added bromine (273 mg, 1.71 mmol, 87.4 uL). The reaction was stirred at −10° C. for 3.5 h. The reaction was quenched by addition of sat $Na_2S_2O_3$ at 0° C., extracted with DCM×2, removed solvent in vacuo. The crude product was purified by ISCO (silica, 12 g, 0-70% EtOAc in Hept) to afford the title compound (180 mg, 90%) 2-[4-(benzyloxy)-5-bromo-3-methyl-1H-pyrazol-1-yl]ethyl acetate (Int-TG-16) as a clear oil. $^1$H NMR (400 MHz, DMSO-d6) δ ppm 7.31-7.45 (m, 5H), 4.90 (s, 2H), 4.29 (t, J=4.88 Hz, 2H), 4.22 (t, J=4.88 Hz, 2H), 2.00 (s, 3H), 1.97 (s, 3H). m/z (ESI+) for ($C_{15}H_{17}BrN_2O$), 355.3 (M+H)$^+$ observed.

Preparation of 3-[1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-17) According to Scheme TG-15

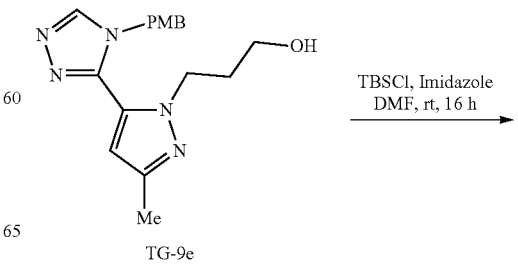

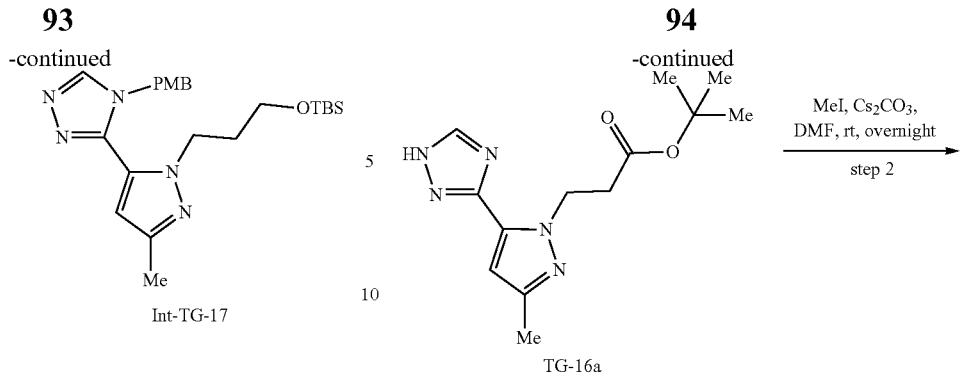

Int-TG-17

Step 1: Synthesis of 3-[1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-17)

To a solution of 3-(5-{4-[(4-methoxyphenyl)methyl]-4H-1,2,4-triazol-3-yl}-3-methyl-1H-pyrazol-1-yl)propan-1-ol (TG-9e) (600.0 mg, 1.44 mmol) in DMF (6.0 mL) was added imidazole (490 mg, 7.20 mmol) and TBSCl (651 mg, 4.32 mmol). The resulting light-yellow reaction solution was stirred at 25° C. for 16 h. The reaction was quenched with H$_2$O (20 mL) to give a light brown solution which was extracted with EtOAc (50 mL*3). The combined organic extracts were washed with brine (50 mL), dried (anhydrous Na$_2$SO$_4$), filtered and concentrated to give a light yellow oil. The crude residue was further purified by combi flash (MeOH in DCM from 0 to 10% on 12 g silica gel) to give the title compound 3-[1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-17) (550 mg, 86.5%) as a light yellow oil. m/z (ESI+) for (C$_{23}$H$_{36}$N$_5$O$_2$Si), 442.3 (M+H)$^+$ observed.

Preparation of tert-butyl-3-[3-methyl-5-(1-methyl-1H-1,2,4-triazol-3-yl)-1H-pyrazol-1-yl]-propanoate (Int-TG-18) According to Scheme TG-16

Scheme TG-16

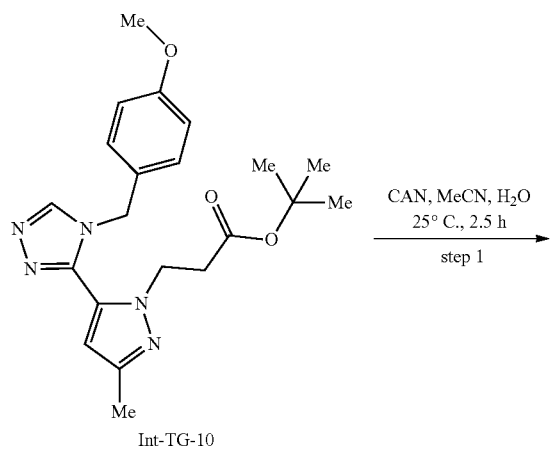

TG-16a

Int-TG-18

Step 1: Synthesis of tert-butyl-3-[3-methyl-5-(1H-1,2,4-triazol-3-yl)-1H-pyrazol-1-yl]-propanoate (TG-16a)

To a solution of tert-butyl 3-(5-{4-[(4-methoxyphenyl)methyl]-4H-1,2,4-triazol-3-yl}-3-methyl-1H-pyrazol-1-yl)propanoate (Int-TG-10) (448.2 mg, 1.128 mmol) in MeCN (10 mL) was added ceric ammonium nitrate (CAN) (1830 mg, 3.34 mmol) in H$_2$O (3 mL). The resulting mixture was stirred at 25° C. for 2.5 hours. This reaction was a yellow solution. The reaction was quenched with water (40 mL) and transferred to a separatory funnel. The solution was extracted with EtOAc (50 mL*3). The combined organic extracts were dried (Na$_2$SO$_4$) and concentrated under vacuum. The crude residue was combined with the crude residue of a batch prepared under similar conditions. The combined batches were purified via Prep-TLC (DCM:MeOH=10:1) to afford the title compound tert-butyl-3-[3-methyl-5-(1H-1,2,4-triazol-3-yl)-1H-pyrazol-1-yl]-propanoate (TG-16a) (263 mg, 54%) as a yellow solid. m/z (ESI+) for (C$_{13}$H$_{20}$N$_5$O$_2$), 278.1 (M+H)$^+$ observed.

Step 2: Synthesis of tert-butyl-3-[3-methyl-5-(1-methyl-1H-1,2,4-triazol-3-yl)-1H-pyrazol-1-yl]-propanoate (Int-TG-18)

To a solution of tert-butyl-3-[3-methyl-5-(1H-1,2,4-triazol-3-yl)-1H-pyrazol-1-yl]-propanoate (TG-16a) (263 mg, 0.95 mmol) and Cs$_2$CO$_3$ (775 mg, 2.38 mmol, 2.4 eq) in DMF (5.0 mL, 0.2 M) was added MeI (1.0 mmol, 63 µL, 1.05 eq). The resulting mixture was stirred at 25° C. for 20 hours, during which time it became a yellow suspension. LCMS analysis showed the starting material was consumed, and TLC (petroleum ether:EtOAc=1:1, UV) showed three new spots. The reaction was then quenched with water and extracted with three portions (5 mL each) EtOAc.

The combined organic extracts were concentrated under vacuum. The crude residue was purified by Prep-TLC (petroleum ether:EtOAc, 2:1.5) to afford the title compound tert-butyl-3-[3-methyl-5-(1-methyl-1H-1,2,4-triazol-3-yl)-1H-pyrazol-1-yl]-propanoate (Int-TG-18) (170 mg, 61%) as colorless gum. ¹H NMR (400 MHz, Chloroform-d) δ 8.04 (s, 1H), 6.55 (s, 1H), 4.84-4.78 (m, 2H), 3.96 (s, 3H), 2.86-2.74 (m, 2H), 2.28 (s, 3H), 1.57 (s, 9H). m/z (ESI+) for ($C_{14}H_{22}N5O_2$), 292.0 (M+H)+ observed.

Preparation of Ethyl 2-(1-ethyl-3-methyl-1H-pyrazol-5-yl)-1,3-thiazole-5-carboxylate (Int-TG-19) According to Scheme TG-17

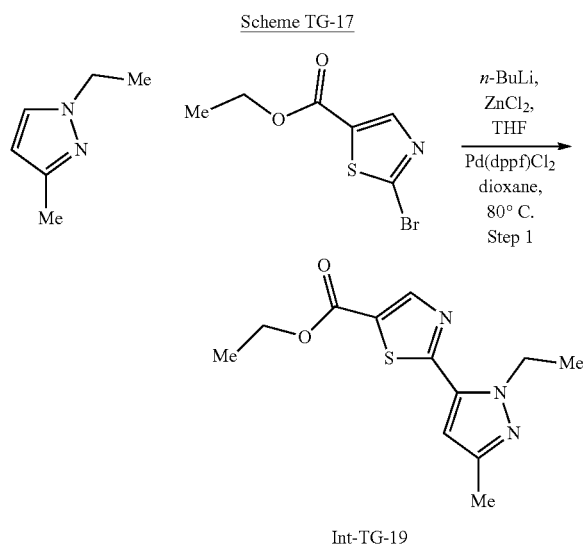

Scheme TG-17

Step 1: Synthesis of Ethyl 2-(1-ethyl-3-methyl-1H-pyrazol-5-yl)-1,3-thiazole-5-carboxylate (Int-TG-19)

To a dried 200 mL flask under inert atmosphere of nitrogen gas was added 1-ethyl-3-methylpyrazole (1 g, 9.1 mmol, 1.8 eq) and THF (45 mL, 0.2 M). This mixture was cooled to −30 C, then n-BuLi (2.5 M in hexanes, 4 mL, 10 mmol, 2.2 eq) was added, giving a yellow solution, along with a small amount of precipitate. After 20 min, an aliquot was removed and quenched with CD₃OD. GCMS analysis of this aliquot showed only 30% deuteration, so to the reaction mixture was added an additional 1 mL n-BuLi. After another 45 min, GCMS analysis in the previously described manner showed full lithiation. At this stage, ZnCl₂ (1.9 M in THF, 7 mL, 13.2 mmol, 2.8 eq) was added to the reaction mixture, maintaining a temperature of −30 C. After addition was complete, the flask was removed from the cooling bath and allowed to warm to room temperature over 1 hr. The flask was then charged with freshly-degassed dioxane (22.7 mL), which yielded formation of additional precipitate, followed by the ethyl 2-bromo-1,3-thiazole-5-carboxylate (1.19 g, 5.05 mmol, 1 eq) and Pd(dppf)Cl₂ (555 mg, 0.15 eq). After addition of all reagents, the reaction mixture was heated to 80° C. After 1 hr, LCMS analysis showed the presence of product mass, so the flask was cooled to room temperature, then quenched with sat. aqueous NH₄Cl. The biphasic solution was concentrated under vacuum to remove volatile organics and the remaining aqueous layer was transferred to a separatory funnel. The solution was extracted with two portions EtOAc. The combined organic extracts were washed with one portion brine, dried (Na₂SO₄), filtered, and concentrated under vacuum. The crude residue was adsorbed onto Celite and subjected to purification by column chromatography (ISCO automated column, 0-100% EtOAc/heptane; 0-5% MeOH/DCM). TLC analysis revealed that two compounds had eluted, the first of which proved to be the product of nBuLi coupling to the thiazole (Rf=0.5, 4:1 heptane/EtOAc, UV active) and the second of which was identified as the product (Rf=0.4, 4:1 heptane/EtOAc). The fractions containing pure product as determined by TLC were collected to afford the title ethyl 2-(1-ethyl-3-methyl-1H-pyrazol-5-yl)-1,3-thiazole-5-carboxylate (Int-TG-19) (660 mg, 23%) as a red oil. ¹H NMR (400 MHz, Chloroform-d) δ 8.38 (s, 1H), 6.50 (s, 1H), 4.63 (q, J=7.2 Hz, 2H), 4.39 (q, J=7.1 Hz, 2H), 2.30 (s, 3H), 1.43 (t, J=7.2 Hz, 3H), 1.40 (t, J=7.2 Hz, 3H).

Preparation of 3-{3-[(benzyloxy)methyl]-1-ethyl-1H-pyrazol-5-yl}-1-methyl-1H-1,2,4-triazole (Int-TG-20) According to Scheme TG-18

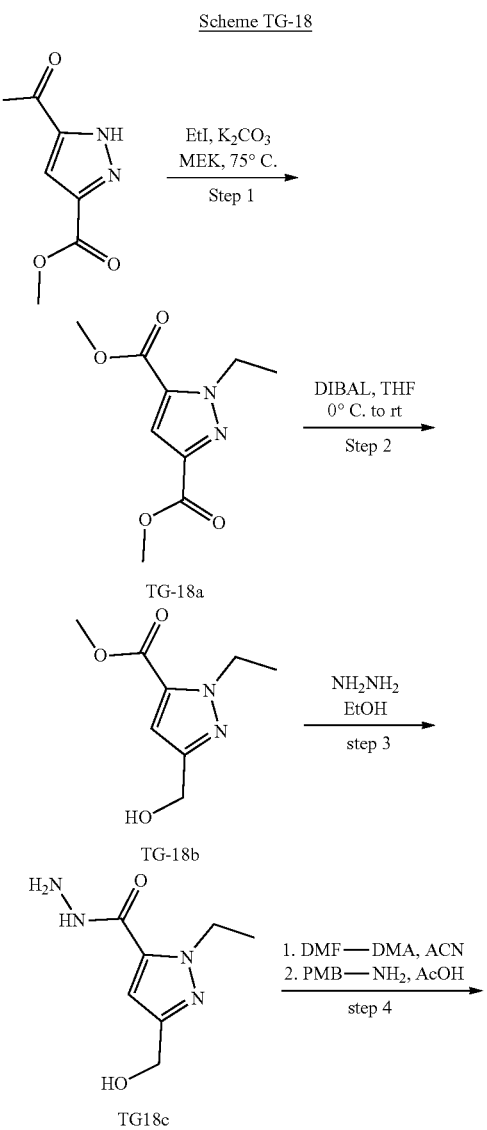

Scheme TG-18

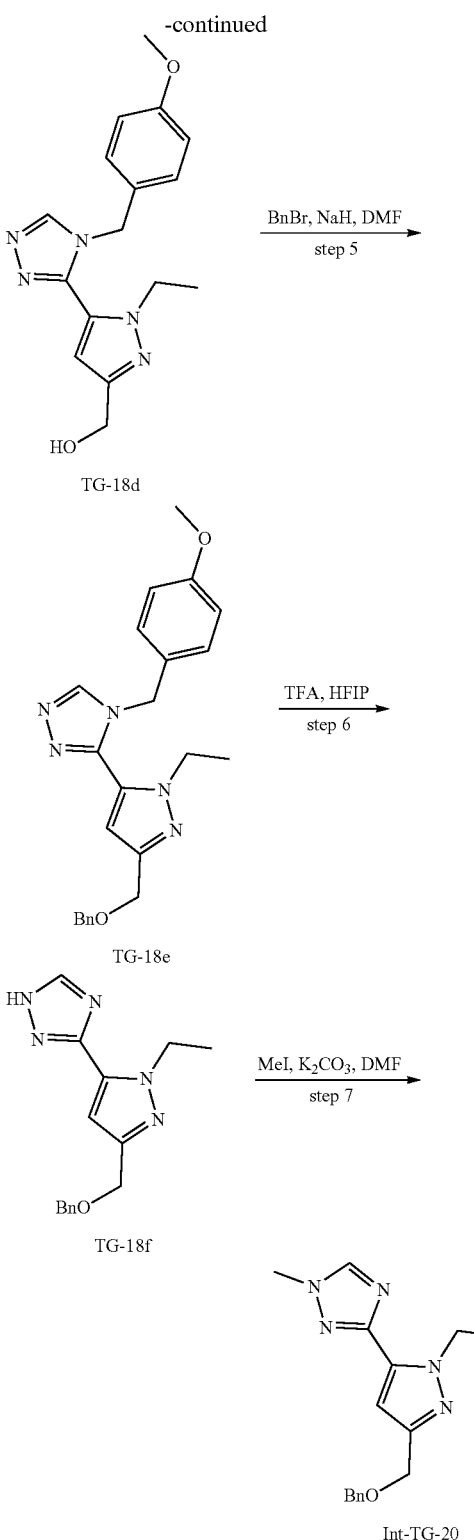

mL, 20 mL). After heating at 75° C. for 1 hour, the reaction was cooled then diluted with ethyl acetate.

The organics were washed with water and brine, dried ($Na_2SO_4$), filtered, and concentrated under vacuum. The crude residue was purified via flash chromatography (80 g $SiO_2$, Isco, 0-50% EtOAc/heptanes) to afford the title compound dimethyl 1-ethyl-1H-pyrazole-3,5-dicarboxylate (TG-18a) (3.4 g, 98%) as a clear gum that solidified overnight. LCMS [M+H]=213 observed; $^1$H NMR (400 MHz, DMSO-d6) δ ppm 7.26 (s, 1H) 4.57 (q, J=7.17 Hz, 2H) 3.86 (s, 3H) 3.82 (s, 3H) 1.37 (t, J=7.21 Hz, 3H).

Step 2: Synthesis of methyl 1-ethyl-3-(hydroxymethyl)-1H-pyrazole-5-carboxylate (TG-18b)

To a cooled (ice bath) solution of dimethyl 1-ethyl-1H-pyrazole-3,5-dicarboxylate (TG-18a) (3.7 g, 17 mmol) was added diisobutylaluminum hydride (DIBAL) (1 M in DCM, 38 mL, 38 mmol) drop wise via syringe pump over 30 min. The reaction was warmed to room temperature and quenched after 1 hour with saturated sodium potassium tartrate. The solution was transferred to a separatory funnel and the phases separated. The aqueous phase was extracted with ethyl acetate. The combined organic extracts were washed with brine, dried ($Na_2SO_4$), filtered, and concentrated under vacuum. The crude residue was purified via flash chromatography (80 g $SiO_2$, Isco, 0-60% EtOAc/heptanes) to afford the title compound methyl 1-ethyl-3-(hydroxymethyl)-1H-pyrazole-5-carboxylate (TG-18b) (2.7 g, 85%) as a clear gum that solidified overnight. LCMS [M+H]=185 observed; $^1$H NMR (400 MHz, DMSO-d6) δ ppm 6.77 (s, 1H) 5.10 (t, J=5.81 Hz, 1H) 4.45 (q, J=7.17 Hz, 2H) 4.41 (d, J=5.75 Hz, 2H) 3.83 (s, 3H) 1.32 (t, J=7.21 Hz, 3H).

Step 3: Synthesis of 1-ethyl-3-(hydroxymethyl)-1H-pyrazole-5-carbohydrazide (TG-18c)

To a solution of methyl 1-ethyl-3-(hydroxymethyl)-1H-pyrazole-5-carboxylate (TG-18b) (2.7 g, 15 mmol) in ethanol (50 mL) was added hydrazine hydrate (7.2 mL, 150 mmol). The reaction was heated at 80° C. for 2 hours then cooled to room temperature. The solution was concentrated under vacuum to afford the title compound 1-ethyl-3-(hydroxymethyl)-1H-pyrazole-5-carbohydrazide (TG-18c) (2.7 g, >95%) as a white solid which was used in the next step without further purification. $^1$H NMR (400 MHz, DMSO-d6) δ ppm 9.71 (br s, 1H) 6.72 (s, 1H) 5.06 (t, J=5.69 Hz, 1H) 4.45 (q, J=7.05 Hz, 4H) 4.39 (d, J=5.62 Hz, 2H) 1.29 (t, J=7.09 Hz, 3H).

Step 4: Synthesis of (1-ethyl-5-{4-[(4-methoxyphenyl)methyl]-4H-1,2,4-triazol-3-yl}-1H-pyrazol-3-yl)methanol (TG-18d)

To a mixture 1-ethyl-3-(hydroxymethyl)-1H-pyrazole-5-carbohydrazide (TG-18c) (2.7 g, 15 mmol) in acetonitrile (50 mL) was added N,N-dimethylformamide dimethylacetal (DMF-DMA) (2.2 mL, 16 mmol). The reaction was heated at 50° C. resulting in a yellow solution. After 30 min, 4-methoxybenzylamine (PMB-$NH_2$) (1.5 mL, 16 mmol) was added followed by acetic acid (50 mL). The reaction was heated at 120° C. (MeCN evaporated) for 1.5 hours then cooled. The solution was concentrated and purified via flash chromatography (80 g $SiO_2$, Isco, 0-10% MeOH/DCM) to afford the title compound (1-ethyl-5-{4-[(4-methoxyphenyl)methyl]-4H-1,2,4-triazol-3-yl}-1H-pyrazol-3-yl)methanol Step 1: Synthesis of dimethyl 1-ethyl-1H-pyrazole-3,5-dicarboxylate (TG-18a)

To a mixture of dimethyl 1H-pyrazole-3,5-dicarboxylate (3.0 g, 16 mmol) and potassium carbonate (4.5 g, 33 mmol) in butan-2-one (MEK) (75 mL) was added ethyl iodide (1.6

(TG-18d) (880 mg, 19%) as a gum. LCMS [M+H]=185 observed; ¹H NMR (400 MHz, DMSO-d6) δ ppm 8.79 (s, 1H) 6.94-7.01 (m, 2H) 6.85-6.90 (m, 2H) 6.56 (s, 1H) 5.23 (s, 2H) 5.03-5.14 (m, 1H) 4.44 (s, 2H) 4.11 (q, J=7.17 Hz, 2H) 3.71 (s, 3H) 1.14 (t, J=7.15 Hz, 3H).

Step 5: Synthesis of 3-{3-[(benzyloxy)methyl]-1-ethyl-1H-pyrazol-5-yl}-4-[(4-methoxyphenyl)methyl]-4H-1,2,4-triazole (TG-18e)

To a solution of (1-ethyl-5-{4-[(4-methoxyphenyl)methyl]-4H-1,2,4-triazol-3-yl}-1H-pyrazol-3-yl)methanol (TG-18d) (805 mg, 2.6 mmol) in N,N-dimethylformamide (17 mL) was added sodium hydride (60% dispersion in mineral oil, 308 mg, 7.7 mmol). After 10 min., benzyl bromide (915 μL, 7.7 mmol) was added. After 2 hours, the reaction was quenched with water and concentrated under vacuum. The residue was dissolved in ethyl acetate and transferred to a separatory funnel. The organic phase was washed with 1 portion water, 1 portion brine, dried (Na₂SO₄), filtered, and concentrated under vacuum to afford the title compound 3-{3-[(benzyloxy)methyl]-1-ethyl-1H-pyrazol-5-yl}-4-[(4-methoxyphenyl)methyl]-4H-1,2,4-triazole (TG-18e) which was used in the next step without further purification. LCMS [M+H]=404 observed.

Step 6: Synthesis of 3-{3-[(benzyloxy)methyl]-1-ethyl-1H-pyrazol-5-yl}-1H-1,2,4-triazole (TG-18f)

To a solution of 3-{3-[(benzyloxy)methyl]-1-ethyl-1H-pyrazol-5-yl}-4-[(4-methoxyphenyl)methyl]-4H-1,2,4-triazole (TG-18e) (crude from previous step) in hexafluoroisopropanol (17 mL) was added trifluoroacetic acid (1.9 mL, 25 mmol). The resulting orange solution was heated at 50° C. for 3 hrs then cooled gradually to rt. The solution was concentrated under vacuum and the crude residue purified via flash chromatography (24 g SiO₂, Isco, 0-10% MeOH/DCM) to afford the title compound 3-{3-[(benzyloxy)methyl]-1-ethyl-1H-pyrazol-5-yl}-1H-1,2,4-triazole (TG-18f) (0.880 g) as an amber gum contaminated with minor impurities. LCMS [M+H]=284 observed; ¹H NMR (400 MHz, DMSO-d6) δ ppm 8.58 (br s, 1H) 7.33-7.38 (m, 5H) 6.74 (s, 1H) 4.55-4.62 (m, 2H) 4.53 (s, 2H) 4.49 (s, 2H) 1.34 (t, J=7.15 Hz, 3H).

Step 7: Synthesis of 3-{3-[(benzyloxy)methyl]-1-ethyl-1H-pyrazol-5-yl}-1-methyl-1H-1,2,4-triazole (Int-TG-20)

To a mixture of 3-{3-[(benzyloxy)methyl]-1-ethyl-1H-pyrazol-5-yl}-1H-1,2,4-triazole (TG-18f) (702 mg, 2.5 mmol) and potassium carbonate (1.0 g, 7.4 mmol) in DMF (17 mL) was added methyl iodide (460 μL, 7.4 mmol). After 1 hour the reaction was concentrated under vacuum. The residue was slurried in dichloromethane and filtered through celite. The filtrate was concentrated and purified via flash chromatography (24 g SiO₂, Isco, 0-10% MeOH/DCM) to afford the title compound 3-{3-[(benzyloxy)methyl]-1-ethyl-1H-pyrazol-5-yl}-1-methyl-1H-1,2,4-triazole (Int-TG-20) (314 mg, 43%). LCMS [M+H]=298 observed; ¹H NMR (400 MHz, DMSO-d6) δ ppm 8.60 (s, 1H) 7.33-7.37 (m, 4H) 7.25-7.31 (m, 1H) 6.67 (s, 1H) 4.53-4.59 (m, 2H) 4.53 (s, 2H) 4.48 (s, 2H) 3.94 (s, 3H) 1.34 (t, J=7.15 Hz, 3H).

Preparation of 3-[4-(benzyloxy)-1-ethyl-3-methyl-1H-pyrazol-5-yl]-4-[(4-methoxyphenyl)methyl]-4H-1,2,4-triazole (Int-TG-21) According to Scheme TG-19

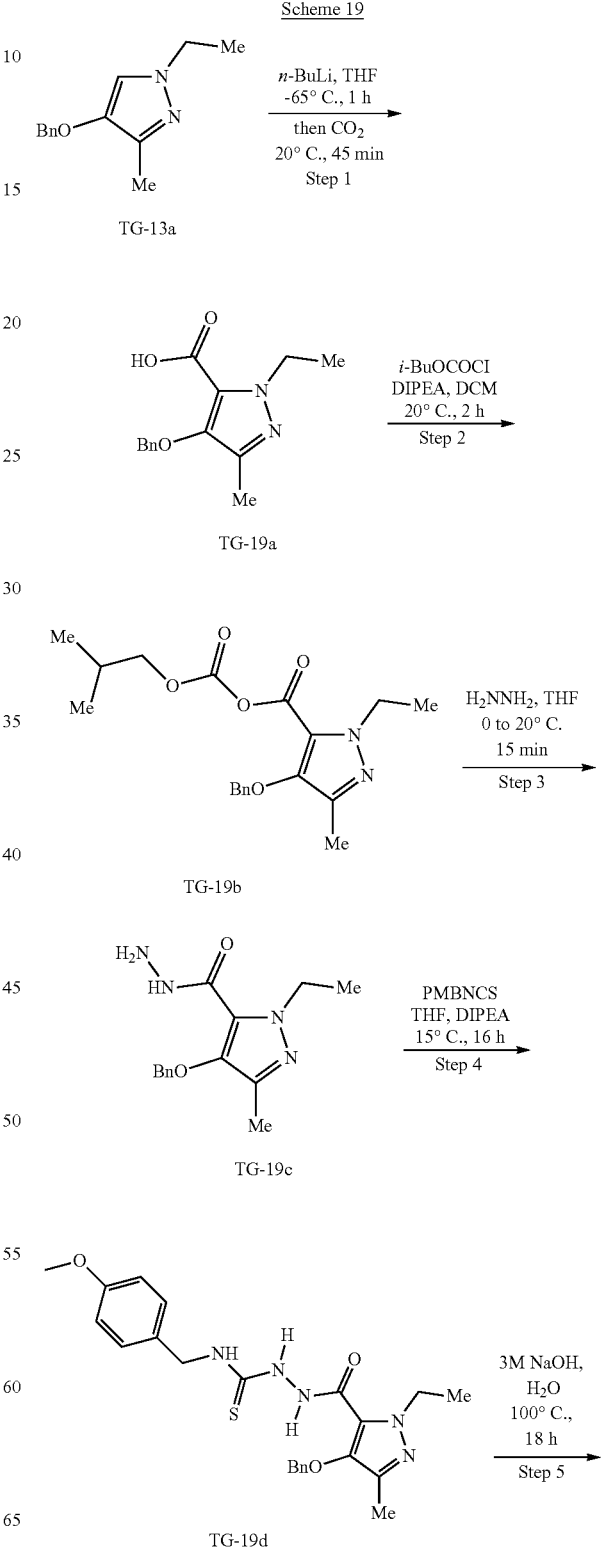

Scheme 19

-continued

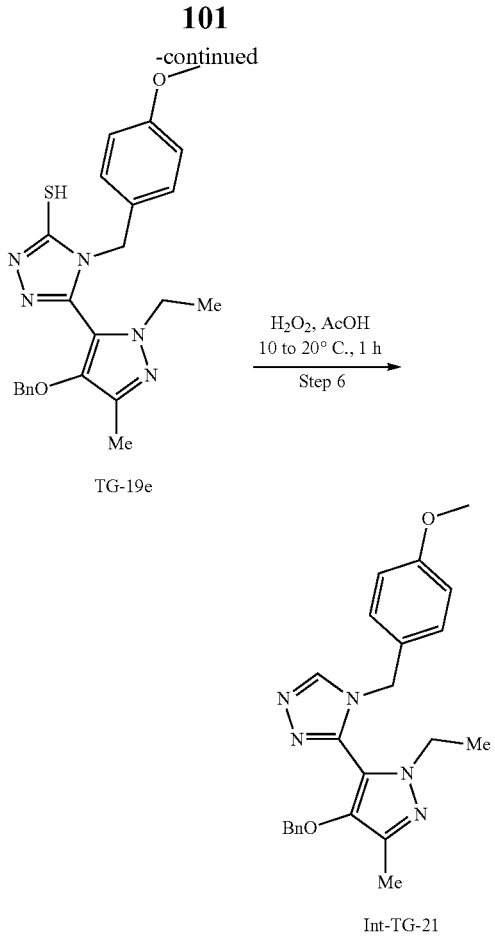

TG-19e

↓ H₂O₂, AcOH
10 to 20° C., 1 h
Step 6

Int-TG-21

Step 1: Synthesis of 4-(benzyloxy)-1-ethyl-3-methyl-1H-pyrazole-5-carboxylic acid (TG-19a)

A light yellow solution of 4-(benzyloxy)-1-ethyl-3-methyl-1H-pyrazole (TG-13a) (2600 mg, 12.02 mmol) in anhydrous THF (39 mL) was cooled with dry ice bath, then n-BuLi (7.26 mL, 18.2 mmol) was added at −65° C. at a rate to maintain an internal temperature >−60° C. After addition was completed, the resulting yellow solution was stirred at −65° C. for 1 h. A yellow green suspension was formed. An aliquot of the mixture was quenched with MeOH-d4, NMR analysis confirmed successful lithiation had taken place. Then excess solid carbon dioxide (dry ice) was added in one portion. The mixture was stirred at −65° C. for 15 min, then removed from the cooling bath and allowed to warm gradually to rt with stirring over 45 minutes. The solution was acidified with conc. HCl to pH ~1 and concentrated under vacuum to remove THF. The residue was azeotroped with toluene (100 mL*2) and dried to afford the title compound 4-(benzyloxy)-1-ethyl-3-methyl-1H-pyrazole-5-carboxylic acid (TG-19a) (4700 mg) as an off-white solid which was used in the next step without further purification. ¹H NMR (400 MHz, DMSO-d₆) δ=13.23 (br s, 1H), 7.66-6.98 (m, 5H), 4.91 (s, 2H), 4.34 (q, J=7.1 Hz, 2H), 1.96 (s, 3H), 1.25 (t, J=7.1 Hz, 3H).

Step 2: Synthesis of 4-(benzyloxy)-1-ethyl-3-methyl-1H-pyrazole-5-carbonyl 2-methylpropyl carbonate (TG-19b)

To a white suspension of 4-(benzyloxy)-1-ethyl-3-methyl-1H-pyrazole-5-carboxylic acid (TG-19a) (4700 mg, 18.06 mmol) in DCM (90 mL) was added DIPEA (9.44 mL, 54.2 mmol) and i-BuOCOCl (4.68 mL, 36.1 mmol). The resulting mixture was stirred at room temperature (20° C.) for 2 h. LCMS analysis showed consumption of starting material and formation of a new peak with the desired product mass. The yellow solution was concentrated under vacuum to afford the title compound 4-(benzyloxy)-1-ethyl-3-methyl-1H-pyrazole-5-carbonyl 2-methylpropyl carbonate (TG-19b) (12.5 g) as a yellow solid which was used in the next step without further purification. m/z (ESI+) for ($C_{19}H_{25}N_2O_5$), 361.1 (M+H)⁺ observed.

Step 3: Synthesis of 4-(benzyloxy)-1-ethyl-3-methyl-1H-pyrazole-5-carbohydrazide (TG-19c)

To a colorless solution of hydrazine hydrate (3.45 mL, 69.4 mmol) in THF (30 mL) was added a suspension of 4-(benzyloxy)-1-ethyl-3-methyl-1H-pyrazole-5-carbonyl 2-methylpropyl carbonate (TG-19b) (12.5 g, 45.60 mmol) in THF (60 mL) drop-wise at 0° C. After addition, the ice-water bath was removed and the mixture allowed to warm gradually to rt (20° C.) with stirring for an additional 15 min. TLC (Petroleum ether:EtOAc=2:1, UV and I2) showed consumption of starting material and formation of a new product. The yellow suspension was concentrated under vacuum. The residue was dissolved in water (50 mL) and transferred to a separatory funnel. The aqueous phase was extracted with EtOAc (50 mL×2). The combined organic extracts were washed with sat. NH₄Cl (20 mL×3), sat. NaHCO₃ (20 mL×3), dried (Na₂SO₄), filtered, and concentrated under vacuum. The crude material (4.2 g) and the crude material from a parallel batch (9.3 g) were combined at this stage. The combined batches were purified via flash column chromatography (80 g SiO₂, 15% EtOAc/Petroleum ether to 100% EtOAc/Petroleum ether). Product containing fractions were collected and concentrated under vacuum to afford the title compound 4-(benzyloxy)-1-ethyl-3-methyl-1H-pyrazole-5-carbohydrazide (TG-19c) (7.2 g) as a yellow oil containing impurities. The material obtained was used in the next step without further purification. m/z (ESI+) for ($C_{14}H_{19}N_4O_2$), 275.0 (M+H)⁺ observed.

Step 4: Synthesis of 2-[4-(benzyloxy)-1-ethyl-3-methyl-1H-pyrazole-5-carbonyl]-N-[(4-methoxyphenyl)methyl]hydrazine-1-carbothioamide (TG-19d)

To a yellow solution of 4-(benzyloxy)-1-ethyl-3-methyl-1H-pyrazole-5-carbohydrazide (TG-19c) (6.1 g 22.24 mmol) in anhydrous THF (44 mL) was added DIPEA (5750 mg, 44.5 mmol), followed by the addition of 1-(isothiocyanatomethyl)-4-methoxybenzene (PMBNCS) (5.98 g, 33.4 mmol) in anhydrous THF (11 mL) drop-wise. The yellow solution was stirred at room temperature (15° C.) for 16 h. LCMS analysis showed consumption of the starting material and formation of a new peak with the desired product mass. This batch was combined with a smaller parallel batch for further processing. The combined batches were concentrated under vacuum, transferred to a separatory funnel with EtOAc, and diluted with water (100 mL). The phases were separated and the aqeuous phase was extracted with EtOAc (100 mL×5). The combined organic extracts were washed with NH₄Cl (50 mL×3), dried (Na₂SO4), filtered, and concentrated under vacuum. The crude residue was triturated with EtOAc (150 mL) for 30 min and filtered to afford the title compound 2-[4-(benzyloxy)-1-ethyl-3-methyl-1H-pyrazole-5-carbonyl]-N-[(4-methoxyphenyl)methyl]hydrazine-1-carbothioamide (TG-19d) (6.0 g) as a white solid.

m/z (ESI+) for (C$_{23}$H$_{28}$N$_5$O$_3$S), 454.1 (M+H)$^+$ observed; $^1$H NMR (400 MHz, DMSO-d$_6$) δ=9.46 (br s, 2H), 8.52 (br s, 1H), 7.52-7.32 (m, 5H), 7.24 (br d, J=8.1 Hz, 2H), 6.85 (br d, J=8.1 Hz, 2H), 5.03 (br s, 2H), 4.64 (br d, J=5.0 Hz, 2H), 4.42-4.15 (m, 2H), 3.72 (s, 3H), 2.11 (s, 3H), 1.26 (br t, J=7.0 Hz, 3H).

Step 5: Synthesis of 5-[4-(benzyloxy)-1-ethyl-3-methyl-1H-pyrazol-5-yl]-4-[(4-methoxyphenyl)methyl]-4H-1,2,4-triazole-3-thiol (TG-19e)

To a suspension of 2-[4-(benzyloxy)-1-ethyl-3-methyl-1H-pyrazole-5-carbonyl]-N-[(4-methoxyphenyl)methyl]hydrazine-1-carbothioamide (TG-19d) (6.0 g, 13.23 mmol) in H$_2$O (26.4 mL) was added NaOH (13.2 mL, 39.7 mmol, 3M in H$_2$O). The reaction was heated at 100° C. with stirring for 18 h. LCMS analysis showed consumption of starting material and formation of a new peak with the desired product mass. The solution was neutralized with 1N HCl and transferred to a separatory funnel with EtOAc. The phases were separated, and the aqueous phase was extracted with EtOAc (50 mL*3). The combined organic extracts were dried (Na$_2$SO$_4$), filtered, and concentrated under vacuum to afford the title compound 5-[4-(benzyloxy)-1-ethyl-3-methyl-1H-pyrazol-5-yl]-4-[(4-methoxyphenyl)methyl]-4H-1,2,4-triazole-3-thiol (TG-19e) (5.74 g) as a white solid which was used in the next step without further purification. $^1$H NMR (400 MHz, CHLOROFORM-d) δ=11.66 (br s, 1H), 7.38-7.29 (m, 3H), 7.20 (br d, J=1.7 Hz, 2H), 6.99 (d, J=8.7 Hz, 2H), 6.69 (d, J=8.7 Hz, 2H), 5.27 (s, 2H), 4.81 (s, 2H), 3.71 (s, 3H), 3.70-3.62 (m, 2H), 2.27 (s, 3H), 0.88 (t, J=7.2 Hz, 3H).

Step 6: Synthesis of 3-[4-(benzyloxy)-1-ethyl-3-methyl-1H-pyrazol-5-yl]-4-[(4-methoxyphenyl)methyl]-4H-1,2,4-triazole (Int-TG-21)

To a yellow solution of 5-[4-(benzyloxy)-1-ethyl-3-methyl-1H-pyrazol-5-yl]-4-[(4-methoxyphenyl)methyl]-4H-1,2,4-triazole-3-thiol (TG-19e) (5.74 g, 13.18 mmol) in AcOH (26.4 mL) was added H$_2$O$_2$ (52.8 mL, 520 mmol) drop-wise at 10° C. Reaction was observed to be exothermic thus the reaction flask was transferred to an ice-water bath immediately prior to completion of the addition. After addition was complete, the mixture was warmed gradually to rt (20° C.) and stirred for an additional 1 h. LCMS analysis showed consumption of the starting material and formation of a new peak with the desired product mass. The solution was diluted with water (200 mL) and transferred to a separatory funnel with EtOAc. The phases were separated, and the aqueous phase was extracted with EtOAc (100 mL×4). The combined organic extracts were washed with sat. Na$_2$CO$_3$ (100 mL×4), sat. Na$_2$SO (100 mL×3), dried (Na$_2$SO$_4$), filtered, and concentrated under vacuum. The crude residue was purified via flash column chromatography (120 g SiO$_2$, 1.5% MeOH/EtOAc to 7.5% MeOH/EtOAc) to afford the title compound 3-[4-(benzyloxy)-1-ethyl-3-methyl-1H-pyrazol-5-yl]-4-[(4-methoxyphenyl)methyl]-4H-1,2,4-triazole (Int-TG-21) (4.1 g, 77%) as a white solid. m/z (ESI+) for (C$_{23}$H$_{25}$N$_5$O$_2$), 404.3 (M+H)$^+$ observed; $^1$H NMR (400 MHz, CHLOROFORM-d) δ=8.12 (s, 1H), 7.38-7.29 (m, 3H), 7.20 (dd, J=2.9, 6.4 Hz, 2H), 6.89 (d, J=8.7 Hz, 2H), 6.76 (d, J=8.7 Hz, 2H), 5.01 (s, 2H), 4.76 (s, 2H), 4.04 (q, J=7.2 Hz, 2H), 3.76 (s, 3H), 2.24 (s, 3H), 1.16 (t, J=7.2 Hz, 3H).

Preparation of 3-[3-methyl-5-(1-methyl-1H-1,2,4-triazol-3-yl)-1H-pyrazol-1-yl]propyl acetate (Int-TG-22) According to Scheme TG-20

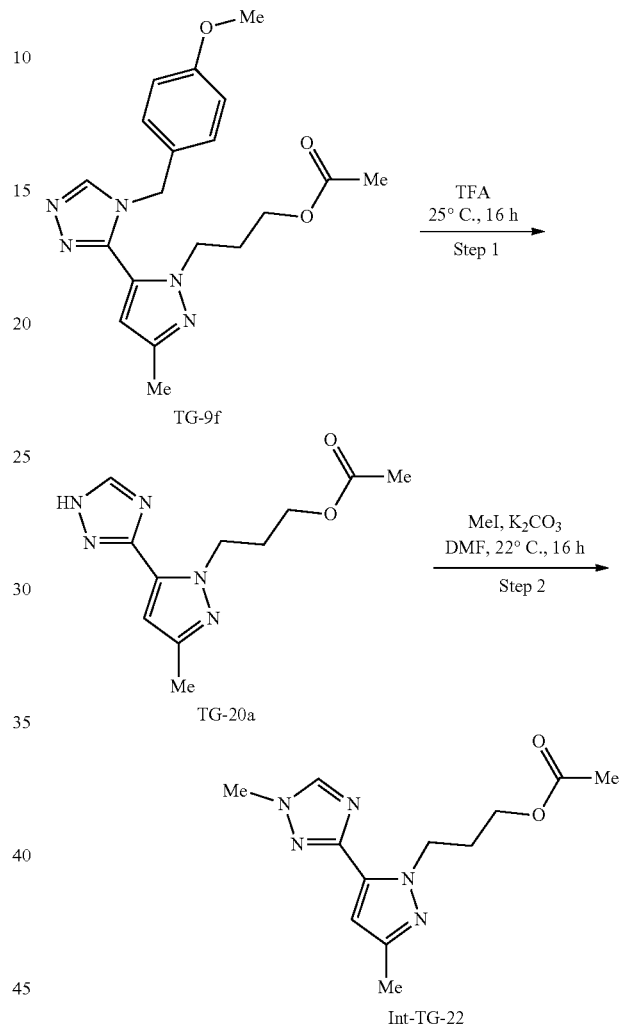

Step 1: Synthesis of 3-[3-methyl-5-(1H-1,2,4-triazol-3-yl)-1H-pyrazol-1-yl]propyl acetate (TG-20a)

To a round bottom flask containing 3-(5-{4-[(4-methoxyphenyl)methyl]-4H-1,2,4-triazol-3-yl}-3-methyl-1H-pyrazol-1-yl)propyl acetate (1.0 g, 2.7 mmol) was added TFA (10 mL, 0.3 M) at room temperature. The reaction was stirred at rt for 16 h at which point it the reaction solution had turned from clear to red. TLC analysis (DCM/MeOH=10/1, UV visualization) showed the starting material had been consumed. The reaction mixture was concentrated in vacuo to afford the product as a red gum. This crude product was diluted with MeOH (10 mL) and stirred at room temperature for 30 min. The mixture was then filtered and the filtrate subsequently concentrated under vacuum to afford the title compound 3-[3-methyl-5-(1H-1,2,4-triazol-3-yl)-1H-pyrazol-1-yl]propyl acetate (TG-20a) (1.057 g, >99%) as a yellow oil. $^1$H NMR (400 MHz, DMSO-d$_6$) δ 8.57 (s, 1H), 6.52 (s, 1H), 4.60 (t, J=6.8 Hz, 2H), 3.94 (t, J=6.3 Hz, 2H), 2.18 (s, 3H), 2.06 (p, J=6.6 Hz, 2H), 1.93 (s, 3H).

Step 2: Synthesis of 3-[3-methyl-5-(1-methyl-1H-1,2,4-triazol-3-yl)-1H-pyrazol-1-yl]propyl acetate (Int-TG-22)

To a solution of 3-[3-methyl-5-(1H-1,2,4-triazol-3-yl)-1H-pyrazol-1-yl]propyl acetate (TG-20a) (757 mg, 1.94 mmol) in DMF (8 mL) was added K$_2$CO$_3$ (803 mg, 5.81 mmol) at room temperature (20° C.). After the addition, the reaction mixture was cooled to 0° C. and a solution of MeI (358 mg, 2.52 mmol) in DMF (2 mL) was added slowly over 2 minutes. Then, the reaction mixture was stirred at 22° C. for 16 hrs. A pale-yellow suspension was formed. LCMS analysis showed the starting material was consumed completely and the desired product was formed. The reaction mixture was diluted with water (5 mL) and extracted with 2 10 mL portions of EtOAc/Pet. Ether (V/V=2/1). The combined organic extracts were dried (Na$_2$SO$_4$), filtered, and concentrated in vacuo. The crude residue was purified by flash column chromatography (25 g SiO$_2$, Isco, 0-3% MeOH/EtOAc) to afford the title compound 3-[3-methyl-5-(1-methyl-1H-1,2,4-triazol-3-yl)-1H-pyrazol-1-yl]propyl acetate (Int-TG-22) (341.8 mg, 67%) as yellow oil containing a minor amount of residual DMF. $^1$H NMR (400 MHz, CHLOROFORM-d) δ=8.05 (s, 1H), 6.57 (s, 1H), 4.67 (t, J=7.2 Hz, 2H), 4.11 (t, J=6.4 Hz, 2H), 3.97 (s, 3H), 2.29 (s, 3H), 2.20 (quin, J=6.7 Hz, 2H), 2.01 (s, 3H).

Preparation of 5-bromo-1-ethyl-4-[(4-methoxyphenyl)methoxy]-3-methyl-1H-pyrazole (Int-TG-23) According to Scheme TG-21

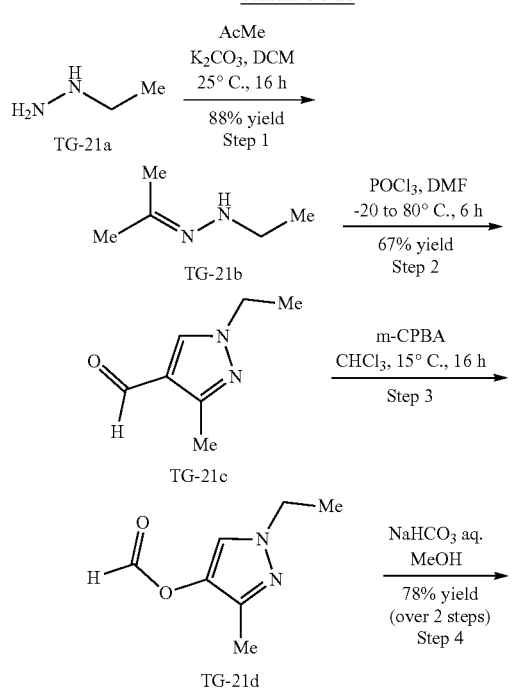

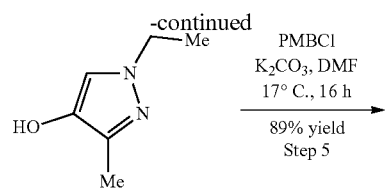

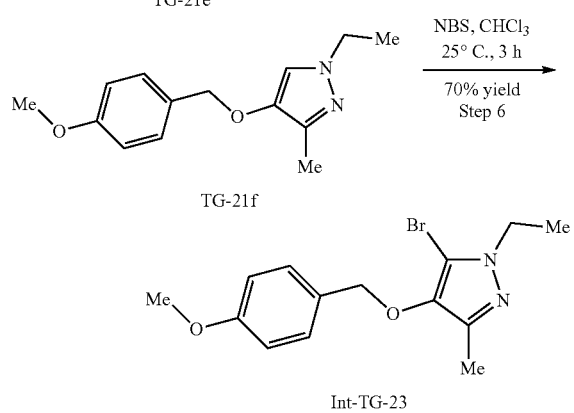

Step 1: Synthesis of 1-ethyl-2-(propan-2-ylidene)hydrazine (TG-21b)

To the mixture of ethylhydrazine hydrochloride salt (TG-21a) (200 g, 1.50 mol) in DCM (3 L) was added acetone (127.12 mL, 1.73 mol) and K$_2$CO$_3$ (519.51 g, 3.76 mol) at 25° C., and the reaction mixture was stirred for 16 hrs. LCMS analysis showed the reaction was complete. The reaction mixture was filtered and the filter cake was washed with DCM (500 mL×3), the filtrate was concentrated in vacuo to afford the title compound 1-ethyl-2-(propan-2-ylidene)hydrazine (TG-21b) (280 g, 2.66 mol, 88% yield) as a colorless oil. $^1$H NMR (400 MHz, CHLOROFORM-d) δ=4.26 (br s, 1H), 3.11 (q, J=7.1 Hz, 2H), 1.85 (s, 3H), 1.67 (s, 3H), 1.08 (t, J=7.2 Hz, 3H).

Step 2: Synthesis of 1-ethyl-3-methyl-1H-pyrazole-4-carbaldehyde (TG-21c)

POCl$_3$ (317.52 mL, 3.42 mol) was added dropwise to DMF (800 mL) at 0° C. and stirred for 1 h. The mixture was cooled to −20° C., and a solution of 1-ethyl-2-(propan-2-ylidene)-hydrazine (TG-21b) (140 g, 1.40 mol) in DMF (400 mL) was added dropwise at −20° C. The mixture was stirred at −20° C. for 3 h at which point the ice bath was removed and the reaction allowed to gradually warm to 25° C. Next, the mixture was stirred at 80° C. for 2 h. LCMS analysis showed the reaction was complete. The reaction mixture was cooled to ambient temperature and poured into ice (3 kg) slowly. The mixture was made alkaline with 30% NaOH aq. (pH=9-10) followed by extraction with DCM (2 L×3). The combined organic extracts were dried (Na$_2$SO$_4$), filtered, and concentrated under vacuum. The crude residue was purified by flash column chromatography (SiO$_2$, 0-50% EtOAc/Pet. ether) to afford the title compound 1-ethyl-3-methyl-1H-pyrazole-4-carbaldehyde (TG-21c) (130 g, 940.89 mmol, 67% yield) as a yellow oil. $^1$H NMR (400 MHz, DMSO-d$_6$) δ=9.79 (s, 1H), 8.34 (s, 1H), 4.10 (q, J=7.3 Hz, 2H), 2.34 (s, 3H), 1.36 (t, J=7.3 Hz, 3H).

Step 3: Synthesis of 1-ethyl-3-methyl-1H-pyrazol-4-yl formate (TG-21d)

The reaction was carried out in 3 parallel batches. To a mixture of 1-ethyl-3-methyl-1H-pyrazole-4-carbaldehyde (TG-21c) (50 g, 361.88 mmol) in CHCl₃ (1 L) was added mCPBA (94.04 g, 463.21 mmol) in portions for 30 mins at 15° C. The reaction mixture was stirred for 16 h at 15° C. The reaction mixture was filtered and the filter cake washed with DCM (200 mL×2). To the filtrate was added $K_2CO_3$ (250.07 g, 1.81 mol) at 15° C. and the mixture was stirred for 1 h. LCMS analysis indicated the starting material was consumed and the desired product had formed. The reaction mixture was filtered and the filter cake was washed DCM (200 mL×2). The filtrate was concentrated under vacuum to provide a crude residue which was purified by flash column chromatography ($SiO_2$, 0-10% EtOAc/Pet. ether) to afford the title compound 1-ethyl-3-methyl-1H-pyrazol-4-yl formate (TG-21d) (~140 g) as black oil. This material was used in the next step without further purification. LCMS [M+H]= 155 observed.

Step 4: Synthesis of 1-ethyl-3-methyl-1H-pyrazol-4-ol (TG-21e)

To the mixture of 1-ethyl-3-methyl-1H-pyrazol-4-yl formate (TG-21d) (140 g, crude product) in MeOH (50 mL) was added $NaHCO_3$ aq. (150 mL) at 10° C. and the mixture was stirred for 1 h at 10° C. TLC (Pet. ether:EtOAc=1:1, UV visualization, starting material: Rf=0.55) indicated the starting material was consumed. The mixture was filtered and the filter cake was washed with MeOH (50 mL×3). The filtrate was concentrated under vacuum to provide a crude residue which was purified by flash column chromatography ($SiO_2$, 30-85% EtOAc/Pet. ether) to afford the title compound 1-ethyl-3-methyl-1H-pyrazol-4-ol (TG-21e) (90 g, 713.40 mmol, 78% yield) as a white solid. m/z (ESI+) for ($C_6H_{11}N_2O$), 127.0 (M+H)⁺ observed.

Step 5: Synthesis of 1-ethyl-4-[(4-methoxyphenyl)methoxy]-3-methyl-1H-pyrazole (TG-21f)

In a reaction vessel, PMBCl (12.9 mL, 95.1 mmol) was added dropwise to a light brown suspension of 1-ethyl-3-methyl-1H-pyrazol-4-ol (TG-21e) (10.0 g 79.3 mmol) and $K_2CO_3$ (16.4 g, 119 mmol) in DMF (130 mL) at 17° C. The reaction mixture was stirred at 17° C. for 16 h. LCMS analysis showed near consumption of starting material and formation of a new peak with the desired product mass. The reaction mixture was diluted with water (200 mL) and extracted with EtOAc/Pet. Ether (V/V=2/1, 300 mL×2). The combined organic extracts were washed with brine (100 mL), dried ($Na_2SO_4$), filtered, and concentrated in vacuo. The crude residue was purified by flash column chromatography (120 g $SiO_2$, Isco, 0-25% EtOAc/Pet. Ether) to afford the title compound 1-ethyl-4-[(4-methoxyphenyl)methoxy]-3-methyl-1H-pyrazole (TG-21f) (17.5 g, 89%) as yellow oil. ¹H NMR (400 MHz, CHLOROFORM-d) δ=7.39-7.28 (m, 2H), 6.96 (s, 1H), 6.94-6.87 (m, 2H), 4.81 (s, 2H), 3.99 (q, J=7.3 Hz, 2H), 3.83 (s, 3H), 2.19 (s, 3H), 1.41 (t, J=7.3 Hz, 3H). m/z (ESI+) for ($C_{14}H_{19}N_2O_2$), 247.0 (M+H)⁺ observed.

Step 6: Synthesis of 5-bromo-1-ethyl-4-[(4-methoxyphenyl)methoxy]-3-methyl-1H-pyrazole (Int-TG-23)

To a yellow solution of 1-ethyl-4-[(4-methoxyphenyl)methoxy]-3-methyl-1H-pyrazole (TG-21f) (18.1 g, 73.6 mmol) in CHCl₃ (500 mL) was added NBS (15.7 g, 88.4 mmol). The reaction was stirred at 25° C. for 3 h. TLC (50% EtOAc/Pet. Ether, visualized by UV) showed the starting material was consumed and a new product had been formed. The reaction mixture was combined with the crude reaction mixtures from 2 smaller batches. The combined solution was diluted with water (100 mL) and extracted with DCM (200 mL*2). The combined organic extracts were washed with brine (100 mL), dried ($Na_2SO_4$), filtered, and concentrated in vacuo. The crude residue was purified via flash column chromatography (120 g $SiO_2$, Isco, 13-25% EtOAc/Pet. Ether) to afford the title compound 5-bromo-1-ethyl-4-[(4-methoxyphenyl)methoxy]-3-methyl-1H-pyrazole (Int-TG-23) (17.43 g, 70%) as a yellow oil. ¹H NMR (400 MHz, CHLOROFORM-d) δ=7.31 (d, J=8.5 Hz, 2H), 6.89 (d, J=8.5 Hz, 2H), 4.85 (s, 2H), 4.08 (q, J=7.2 Hz, 2H), 3.82 (s, 3H), 2.07 (s, 3H), 1.37 (t, J=7.3 Hz, 3H).

Preparation of 3-methyl-1-{3-[(oxan-2-yl)oxy]propyl}-1H-pyrazole (Int-TG-24) According to Scheme TG-22

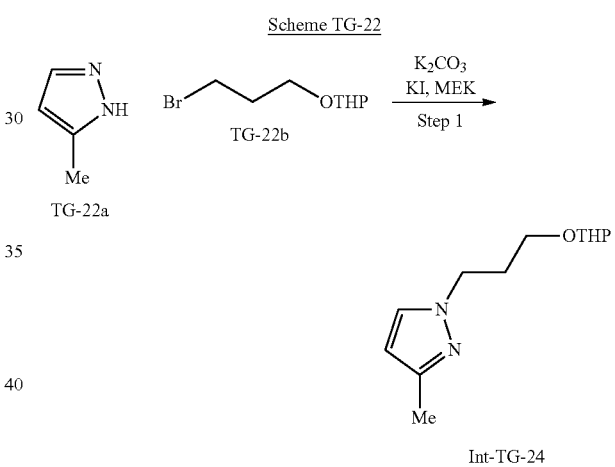

Step 1: Synthesis of 3-methyl-1-{3-[(oxan-2-yl)oxy]propyl}-1H-pyrazole (Int-TG-24)

In a sealed tube a mixture of 5-methyl-1H-pyrazole (TG-22a) (980 μL, 12 mmol), 2-(3-bromopropoxy)tetrahydro-2H-pyran (TG-22b) (4.1 mL, 24 mmol), potassium carbonate (3.4 g, 24 mmol) and potassium iodide (4.0 g, 24 mmol) in 2-butanone (MEK) (49 mL) was heated at 70° C. overnight. The reaction was cooled to room temperature and the solids were filtered out. The filtrate was concentrated and purified via flash chromatography (80 g $SiO_2$, Isco, 0-50% EtOAc/heptanes) to afford the title compound (Int-TG-24) (704 mg, 26%) as an oil, 3:1 mixture of regioisomers. LCMS [M+H]+=225 observed; ¹H NMR (400 MHz, DMSO-d₆) δ ppm (major regioisomer) 7.53 (d, J=2.08 Hz, 1H) 5.97 (dd, J=2.08, 0.37 Hz, 1H) 4.50-4.52 (m, 1H) 4.06 (t, J=6.91 Hz, 2H) 3.72 (ddd, J=11.07, 7.82, 3.12 Hz, 1H) 3.55-3.62 (m, 1H) 3.37-3.44 (m, 1H) 3.24-3.29 (m, 1H) 2.14 (s, 3H) 1.93-2.01 (m, 2H) 1.66-1.77 (m, 1H) 1.57-1.66 (m, 1H) 1.40-1.52 (m, 4H).

Preparation of 5-bromo-1-ethyl-4-[(4-methoxyphenyl)methoxy]-1H-pyrazole (Int-TG-25) According to Scheme TG-23

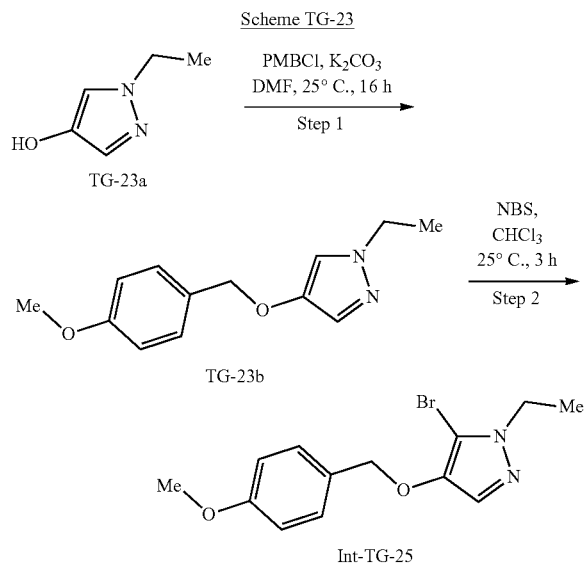

Step 1: Synthesis of 1-ethyl-4-[(4-methoxyphenyl)methoxy]-1H-pyrazole (TG-23b)

To a solution of 1-ethyl-1H-pyrazol-4-ol (TG-23a) (300 mg, 2.68 mmol) in anhydrous DMF (4.5 mL) was added $K_2CO_3$ (407 mg, 2.94 mmol) and PMBCl (461 mg, 2.94 mmol). The resulting light red reaction suspension was stirred at 25° C. for 16 h. TLC (Petroleum ether:EtOAc=2:1, UV) analysis showed the starting material had been consumed. The resulting white suspension was diluted with water (20 mL) and extracted with EtOAc (3×30 mL). The organic phase was washed with brine (3×30 mL), dried over anhydrous $Na_2SO_4$, filtered, and concentrated to dryness. The crude residue was purified by flash column chromatography (12 g $SiO_2$, Combi-flash, EtOAc/Petroleum ether=12.5% to 75%) to afford the title compound 1-ethyl-4-[(4-methoxyphenyl)methoxy]-1H-pyrazole (TG-23b) (520 mg, 83%) as a colorless oil. $^1H$ NMR (400 MHz, CHLOROFORM-d) δ=7.33 (d, J=8.5 Hz, 2H), 7.25 (s, 1H), 7.08 (s, 1H), 6.95-6.88 (m, 2H), 4.86 (s, 2H), 4.07 (q, J=7.3 Hz, 2H), 3.82 (s, 3H), 1.65 (s, 1H), 1.44 (t, J=7.4 Hz, 3H).

Step 2: Synthesis of 5-bromo-1-ethyl-4-[(4-methoxyphenyl)methoxy]-1H-pyrazole (Int-TG-25)

To a colorless solution of 1-ethyl-4-[(4-methoxyphenyl)methoxy]-1H-pyrazole (TG-23b) (520 mg, 2.24 mmol) in $CHCl_3$ (16 mL) was added NBS (598 mg, 3.36 mmol) in portions at room temperature (25° C.). The resulting light red mixture was stirred at the temperature for 3 h. LCMS analysis showed the reaction was completed. The resulting mixture was diluted with water (10 mL). The phases were separated and the aqueous layer was extracted with DCM (2×20 mL). The combined organic extracts were dried over anhydrous $Na_2SO_4$, filtered and concentrated to dryness. The crude residue was purified by flash column chromatography (40 g $SiO_2$, Combi-flash, EtOAc/Petroleum ether=5% to 30%) to afford the title compound 5-bromo-1-ethyl-4-[(4-methoxyphenyl)methoxy]-1H-pyrazole (Int-TG-25) (410 mg, 58.9%) as a white solid. $^1H$ NMR (400 MHz, CHLOROFORM-d) δ=7.34 (d, J=8.5 Hz, 2H), 7.24 (s, 1H), 6.95-6.86 (m, 2H), 4.93 (s, 2H), 4.14 (q, J=7.3 Hz, 2H), 3.82 (s, 3H), 1.40 (t, J=7.3 Hz, 3H). m/z (ESI+) for ($C_{13}H_{16}BrN_2O_2$), 311.8 (M+H)$^+$ observed.

Preparation of 3-[4-(benzyloxy)-1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-26) According to Scheme TG-24

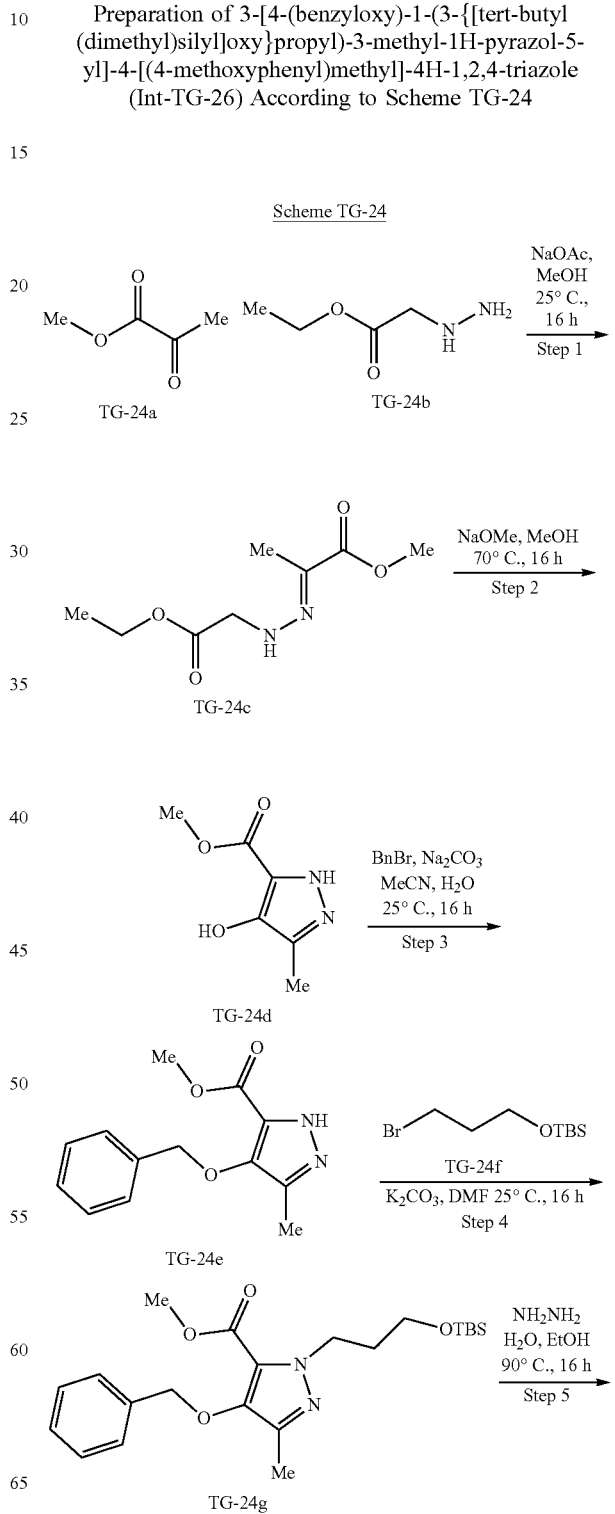

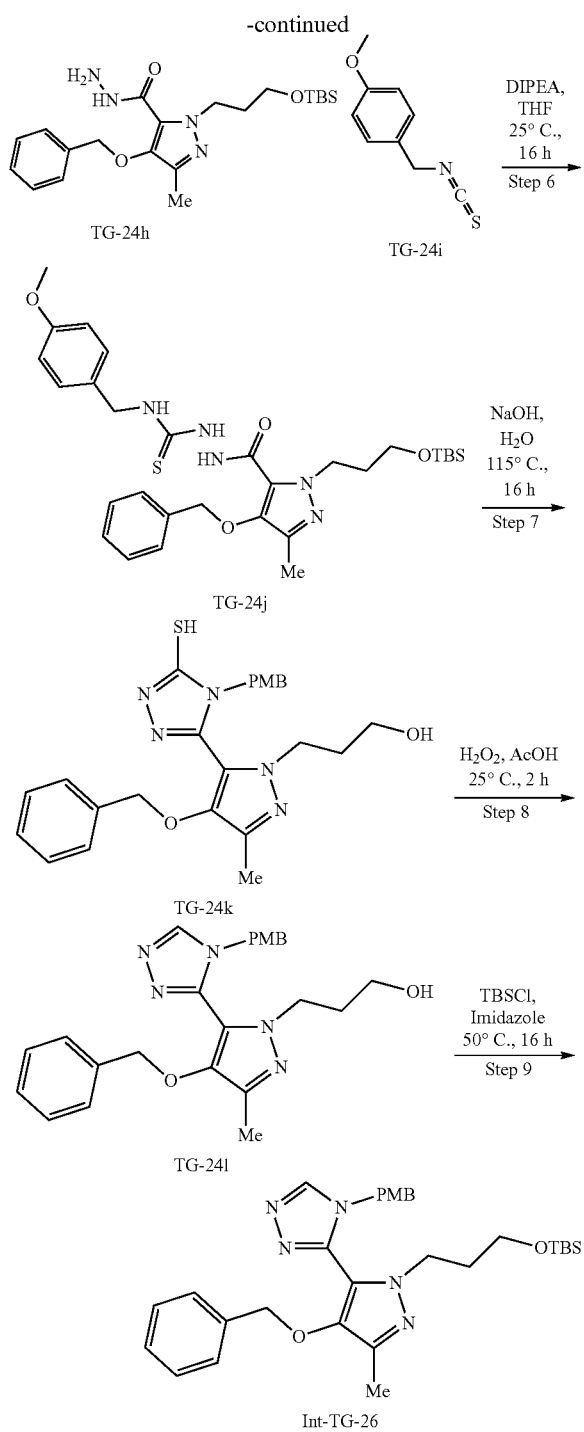

Step 1: Synthesis of methyl (2E)-2-[2-(2-ethoxy-2-oxoethyl)hydrazinylidene]propanoate (TG-24c)

To a solution of methyl pyruvate (4000 mg, 39.18 mmol) in MeOH (100 mL) was added sodium acetate (3210 mg, 39.18 mmol) and ethyl hydrazinylacetate (6060 mg, 39.2 mmol). The resulting light-yellow reaction solution was stirred at 25° C. for 16 h. LCMS analysis showed consumption of starting material and new a peak with the desired product mass. The reaction was quenched with H$_2$O (100 mL) which was added to the light-yellow solution. The solution was extracted with EtOAc (3×50 mL). The combined organic extracts were washed with brine (200 mL), dried by anhydrous Na$_2$SO$_4$, filtered and concentrated to afford the title compound methyl (2E)-2-[2-(2-ethoxy-2-oxoethyl)hydrazinylidene]propanoate (TG-24c) (7000 mg, 88%) as a light yellow solid. $^1$H NMR (400 MHz, CHLOROFORM-d) δ=5.97 (br s, 1H), 4.28-4.16 (m, 4H), 3.82 (s, 3H), 2.02 (s, 3H), 1.28 (t, J=7.2 Hz, 3H). m/z (ESI+) for (C$_8$H$_{15}$N$_2$O$_4$), 202.9 (M+H)$^+$ observed.

Step 2: Synthesis of methyl 4-hydroxy-3-methyl-1H-pyrazole-5-carboxylate (TG-24d)

To a solution of methyl (2E)-2-[2-(2-ethoxy-2-oxoethyl)hydrazinylidene]propanoate (TG-24c) (5200 mg, 25.72 mmol) in MeOH (50.0 mL) was added NaOAc (4170 mg, 77.1 mmol, 5M, 15.4 mL). The resulting pale-yellow reaction solution was stirred at 70° C. for 16 h. LCMS analysis showed consumption of starting material and a new peak with the desired product mass. The reaction was quenched with 5% HCl at 0° C., extracted with EtOAc (3×100 mL). The combined organic extracts were washed with brine (150 mL), dried by anhydrous Na$_2$SO$_4$, filtered and concentrated to give a yellow solid. The crude residue was purified by flash column chromatography (40 g SiO$_2$, combi flash, EtOAc in Petroleum ether from 0 to 50%) to afford the title compound methyl 4-hydroxy-3-methyl-1H-pyrazole-5-carboxylate (TG-24d) (2900 mg, 72%) as alight yellow solid. $^1$H NMR (400 MHz, DMSO-d$_6$) δ=12.76 (br s, 1H), 8.40 (br s, 1H), 3.76 (s, 3H), 2.08 (s, 3H). m/z (ESI+) for (C$_6$H$_9$N$_2$O$_3$), 156.8 (M+H)$^+$ observed.

Step 3: Synthesis of methyl 4-(benzyloxy)-3-methyl-1H-pyrazole-5-carboxylate (TG-24e)

To a solution of methyl 4-hydroxy-3-methyl-1H-pyrazole-5-carboxylate (TG-24d) (2700 mg, 17.29 mmol) in MeCN (30.0 mL) and water (30.0 mL) was added benzyl bromide (3250 mg, 19.0 mmol) and Na$_2$CO$_3$ (2200 mg, 20.8 mmol). The resulting yellow suspension was stirred at 25° C. for 16 h. The reaction was quenched with water (120 mL) which was added to the light brown reaction solution. The aqueous phase was then extracted with EtOAc (3×100 mL). The combined organic extracts were dried over Na$_2$SO$_4$, filtered, and concentrated under vacuum. The crude residue was purified via flash column chromatography (40 g SiO$_2$, CombiFlash, EtOAc in petroleum ether) to afford the title compound methyl 4-(benzyloxy)-3-methyl-1H-pyrazole-5-carboxylate (TG-24e) (3640 mg, 85%) as a light yellow oil. $^1$H NMR (400 MHz, CHLOROFORM-d) 5=10.59 (br s, 1H), 7.48-7.30 (m, 5H), 5.14-5.01 (m, 2H), 4.00-3.89 (m, 3H), 2.08 (s, 3H). m/z (ESI+) for (C$_{13}$H$_{15}$N2O), 246.9 (M+H)$^+$ observed.

Step 4: Synthesis of methyl 4-(benzyloxy)-1-(3-{[tert-butyl(dimethyl)silyl]oxy}propyl)-3-methyl-1H-pyrazole-5-carboxylate (TG-24g)

To a solution of methyl 4-(benzyloxy)-3-methyl-1H-pyrazole-5-carboxylate (TG-24e) (3640 mg, 14.78 mmol) and potassium carbonate (4090 mg, 29.6 mmol) in DMF (40.0 mL) was added (3-bromopropoxy)-tert-butyldimethylsilane (TG-24f) (4490 mg, 17.7 mmol). The resulting yellow suspension was stirred at 25° C. for 16 h. The reaction was quenched with water (150 mL) which was added to the yellow reaction suspension. The aqueous phase was extracted with EtOAc (4×100 mL). The combined organic extracts were washed with brine (2×150 mL), dried over anhydrous sodium sulfate, filtered, and concentrated in vacuo. The crude residue was purified via flash column chromatography (80 g SiO$_2$, CombiFlash, EtOAc in petroleum ether from 0 to 25%) to afford the title compound methyl 4-(benzyloxy)-1-(3-{[tert-butyl(dimethyl)silyl]oxy}propyl)-3-methyl-1H-pyrazole-5-carboxylate (TG-24g) (3500 mg, 56%) as a light yellow oil. $^1$H NMR (400 MHz, CHLOROFORM-d) δ=7.46-7.30 (m, 5H), 4.94 (s, 2H), 4.54-4.44 (m, 2H), 3.88 (s, 3H), 3.64 (t, J=6.2 Hz, 2H), 2.09 (s, 3H), 2.05-1.95 (m, 2H), 0.96-0.86 (m, 9H), 0.09-0.01 (m, 6H). m/z (ESI+) for (C$_{22}$H$_{35}$N$_2$O$_4$Si), 419.2 (M+H)$^+$ observed.

Step 5: Synthesis of 4-(benzyloxy)-1-(3-{[tert-butyl(dimethyl)silyl]oxy}propyl)-3-methyl-1H-pyrazole-5-carbohydrazide (TG-24h)

To a solution of methyl 4-(benzyloxy)-1-(3-{[tert-butyl(dimethyl)silyl]oxy}propyl)-3-methyl-1H-pyrazole-5-carboxylate (TG-24g) (3500 mg, 8.361 mmol) in EtOH (40.0 mL) was added hydrazine monohydrate (4270 mg, 83.6 mmol). The resulting light yellow reaction solution was stirred at 90° C. for 16 h. The light yellow reaction solution was concentrated in vacuo to afford the title compound 4-(benzyloxy)-1-(3-{[tert-butyl(dimethyl)silyl]oxy}propyl)-3-methyl-1H-pyrazole-5-carbohydrazide (TG-24h) (3500 mg, 100%) as a light yellow oil. $^1$H NMR (400 MHz, CHLOROFORM-d) δ=8.13 (br s, 1H), 7.48-7.31 (m, 5H), 4.97 (s, 2H), 4.54 (t, J=7.2 Hz, 2H), 3.83 (br s, 2H), 3.64 (t, J=6.3 Hz, 2H), 2.25 (s, 3H), 2.00 (quin, J=6.8 Hz, 2H), 0.89 (s, 9H), 0.04 (s, 6H).

Step 6: Synthesis of 2-[4-(benzyloxy)-1-(3-{[tert-butyl(dimethyl)silyl]oxy}propyl)-3-methyl-1H-pyrazole-5-carbonyl]-N-[(4-methoxyphenyl)methyl]hydrazine-1-carbothioamide (TG-24j)

To a solution of 4-(benzyloxy)-1-(3-{[tert-butyl(dimethyl)silyl]oxy}propyl)-3-methyl-1H-pyrazole-5-carbohydrazide (TG-24h) (3500 mg, 8.361 mmol) in THF (40.0 mL) was added DIEPA (1620 mg, 12.5 mmol) and 1-(isothiocyanatomethyl)-4-methoxybenzene (TG-24i) (2100 mg, 11.7 mmol). The resulting light yellow reaction solution was stirred at 25° C. for 16 h. The yellow solution was concentrated to afford the title compound 2-[4-(benzyloxy)-1-(3-{[tert-butyl(dimethyl)silyl]oxy}propyl)-3-methyl-1H-pyrazole-5-carbonyl]-N-[(4-methoxyphenyl)methyl]hydrazine-1-carbothioamide (TG-24j) (5000 mg). The crude material was used in the next step without further purification. m/z (ESI+) for (C$_{30}$H$_{44}$N$_5$O$_4$SSi), 598.1 (M+H)$^+$ observed.

Step 7: Synthesis of 3-[4-(benzyloxy)-5-{4-[(4-methoxyphenyl)methyl]-5-sulfanyl-4H-1,2,4-triazol-3-yl}-3-methyl-1H-pyrazol-1-yl]propan-1-ol (TG-24k)

To a solution of crude 2-[4-(benzyloxy)-1-(3-{[tert-butyl(dimethyl)silyl]oxy}propyl)-3-methyl-1H-pyrazole-5-carbonyl]-N-[(4-methoxyphenyl)methyl]hydrazine-1-carbothioamide (TG-24j) (5000 mg, 8.363 mmol) in water (65 mL) was added NaOH (1050 mg, 26.25 mmol). The resulting yellow reaction solution was stirred at 115° C. (oil bath) for 16 hours. To the reaction was added DCM (100 mL) and the solution acidified to pH ~6 with 1 M HCl and the phases separated. The aqueous phase was extracted with DCM (1×50 mL). The combined organic extracts were dried over Na$_2$SO$_4$, filtered, and the filtrate concentrated under vacuum. The crude residue was purified via flash column chromatography (80 g SiO$_2$, CombiFlash, DCM:MeOH=100% to 95%) to afford the title compound 3-[4-(benzyloxy)-5-{4-[(4-methoxyphenyl)methyl]-5-sulfanyl-4H-1,2,4-triazol-3-yl}-3-methyl-1H-pyrazol-1-yl]propan-1-ol (TG-24k) (2900 mg, 74%) as light yellow oil. $^1$H NMR (400 MHz, CHLOROFORM-d) δ=12.18 (br s, 1H), 7.35-7.27 (m, 3H), 7.18-7.11 (m, 2H), 6.96 (d, J=8.8 Hz, 2H), 6.68 (d, J=8.8 Hz, 2H), 5.31 (s, 2H), 4.83 (s, 2H), 3.87-3.77 (m, 1H), 3.76-3.69 (m, 5H), 3.39-3.27 (m, 2H), 2.27 (s, 3H), 1.77 (td, J=5.7, 11.4 Hz, 2H).

Step 8: Synthesis of 3-[4-(benzyloxy)-5-{4-[(4-methoxyphenyl)methyl]-4H-1,2,4-triazo-3-yl}-3-methyl-1H-pyrazol-1-yl]propan-1-ol (TG-24l)

To a solution of 3-[4-(benzyloxy)-5-{4-[(4-methoxyphenyl)methyl]-5-sulfanyl-4H-1,2,4-triazol-3-yl}-3-methyl-1H-pyrazol-1-yl]propan-1-ol (TG-24k) (2.9 g, 6.2 mmol) in acetic acid (12 mL). The reaction was cooled in an ice water bath followed by the slow addition of H$_2$O$_2$ (24 mL). The ice bath was removed and the resulting light-yellow reaction solution was stirred at 25° C. for 2 h. The reaction was quenched with ice-water (100 mL) and Na$_2$SO$_3$. The solution was transferred to separatory funnel and the phases separated. The aqueous phase was extracted with EtOAc (3×50 mL). The combined organic extracts were washed with brine (50 mL), dried with anhydrous Na$_2$SO$_4$, filtered and concentrated under vacuum. The crude residue was purified via flash column chromatography (80 g SiO$_2$, CombiFlash, EtOAc:MeOH=100% to 95%) to afford the title compound 3-[4-(benzyloxy)-5-{4-[(4-methoxyphenyl)methyl]-4H-1,2,4-triazol-3-yl}-3-methyl-1H-pyrazol-1-yl]propan-1-ol (TG-24l) (2160 mg, 80%) as a light yellow gum. $^1$H NMR (400 MHz, CHLOROFORM-d) δ=8.03 (s, 1H), 7.37-7.28 (m, 3H), 7.13 (d, J=6.6 Hz, 2H), 6.92 (d, J=8.6 Hz, 2H), 6.80 (d, J=8.6 Hz, 2H), 5.06 (s, 2H), 4.78 (s, 2H), 4.09-4.00 (m, 2H), 3.78 (s, 3H), 3.48-3.39 (m, 2H), 2.25 (s, 3H), 2.00 (td, J=5.4, 10.6 Hz, 2H). m/z (ESI+) for (C$_{24}$H$_{28}$N$_5$O$_3$), 434.3 (M+H)$^+$ observed.

Step 9: Synthesis of 3-[4-(benzyloxy)-1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-26)

To a solution of 3-[4-(benzyloxy)-5-{4-[(4-methoxyphenyl)methyl]-4H-1,2,4-triazo-3-yl}-3-methyl-1H-pyrazol-1-yl]propan-1-ol (TG-24l) (499 mg, 1.15 mmol) in DMF (12 mL) was added imidazole (414 mg, 6.08 mmol) and TBSCl (520 mg, 3.45 mmol). The resulting light-yellow reaction solution was stirred at 50° C. (oil bath) for 16 hours. The reaction was quenched with water and extracted with EtOAc (3×30 mL). The combined organic extracts were washed with NaCl aq. and concentrated in vacuo. The crude residue was purified via flash column chromatography (20 g SiO$_2$, CombiFlash, DCM:MeOH=100% to 95%) to afford the title compound 3-[4-(benzyloxy)-1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-26) (526.5 mg, 83%) as colorless gum. $^1$H NMR (400 MHz, CHLOROFORM-d) δ=8.08 (s, 1H), 7.35-7.29 (m, 3H), 7.19 (dd, J=2.9, 6.7 Hz, 2H), 6.91 (d, J=8.8 Hz, 2H), 6.82-6.71 (m, 2H), 4.99 (s, 2H), 4.75 (s, 2H), 4.15-4.04 (m, 2H), 3.77 (s, 3H), 3.50 (t, J=6.1 Hz, 2H), 2.22 (s, 3H), 1.84-1.70 (m, 2H), 0.85 (s, 10H), 0.04--0.04 (m, 6H). m/z (ESI+) for (C$_{30}$H$_{42}$N$_5$O$_3$Si), 548.4 (M+H)$^+$ observed.

Preparation of 3-[4-(benzyloxy)-3-methyl-5-(1-methyl-1H-1,2,4-triazo-3-yl)-1H-pyrazol-1-yl]propyl acetate (Int-TG-27) According to Scheme TG-25

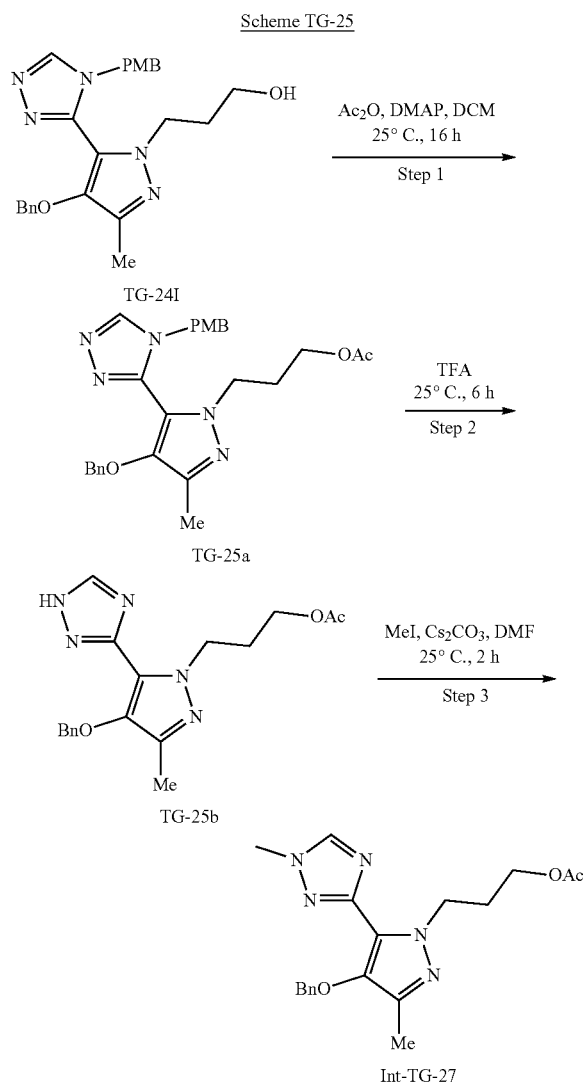

Step 1: Synthesis of 3-[4-(benzyloxy)-5-{4-[(4-methoxyphenyl)methyl]-4H-1,2,4-triazol-3-yl}-3-methyl-1H-pyrazol-1-yl]propyl acetate (TG-25a)

Ac$_2$O (0.22 mL, 2.3 mmol) was added to a solution of 3-[4-(benzyloxy)-5-{4-[(4-methoxyphenyl)methyl]-4H-1,2,4-triazol-3-yl}-3-methyl-1H-pyrazol-1-yl]propan-1-ol (TG-24I) (498.9 mg, 1.151 mmol) and DMAP (141.5 mg, 1.158 mmol) in DCM (5.0 mL). The resulting colorless solution was stirred at 25° C. for 16 h. The reaction was quenched with water (10 mL) and extracted with DCM (10 mL). The organic extract was washed with brine (25 mL), dried over MgSO$_4$, filtered and concentrated under vacuum to afford the title compound 3-[4-(benzyloxy)-5-{4-[(4-methoxyphenyl)methyl]-4H-1,2,4-triazol-3-yl}-3-methyl-1H-pyrazol-1-yl]propyl acetate (TG-25a) (535.9 mg, 97% yield) as a colorless oil which was used in the next step without further purification. $^1$H NMR (400 MHz, CHLOROFORM-d) δ=8.09 (s, 1H), 7.38-7.31 (m, 3H), 7.25-7.16 (m, 2H), 6.99-6.89 (m, 2H), 6.83-6.75 (m, 2H), 5.04 (s, 2H), 4.78 (s, 2H), 4.16 (t, J=6.9 Hz, 2H), 3.88 (t, J=6.1 Hz, 2H), 3.79 (s, 3H), 2.24 (s, 3H), 2.00 (s, 3H), 1.90 (quin, J=6.5 Hz, 2H). m/z (ESI+) for (C$_{26}$H$_{30}$N$_5$O$_4$), 476.2 (M+H)$^+$ observed.

Step 2: Synthesis of 3-[4-(benzyloxy)-3-methyl-5-(1H-1,2,4-triazol-3-yl)-1H-pyrazol-1-yl]propyl acetate (TG-25b)

A colorless solution of 3-[4-(benzyloxy)-5-{4-[(4-methoxyphenyl)methyl]-4H-1,2,4-triazol-3-yl}-3-methyl-1H-pyrazol-1-yl]propyl acetate (TG-25a) (535.9 mg, 1.127 mmol) in TFA (3.0 mL) was stirred at 25° C. for 3 h. The reaction was concentrated under vacuum followed by azeotropic removal of residual TFA with DCM (3×5 mL) to afford the title compound 3-[4-(benzyloxy)-3-methyl-5-(1H-1,2,4-triazol-3-yl)-1H-pyrazol-1-yl]propyl acetate (TG-25b) (729.5 mg) as pink gum which was used in the next step without further purification. m/z (ESI+) for (C$_{18}$H$_{21}$N$_5$O$_3$), 356.0 (M+H)$^+$ observed.

Step 3: Synthesis of 3-[4-(benzyloxy)-3-methyl-5-(1-methyl-1H-1,2,4-triazol-3-yl)-1H-pyrazol-1-yl]propyl acetate (Int-TG-27)

MeI (192 mg, 84.2 uL, 1.35 mmol) was added to a white suspension of 3-[4-(benzyloxy)-3-methyl-5-(1H-1,2,4-triazol-3-yl)-1H-pyrazol-1-yl]propyl acetate (TG-25b) (729.5 mg, 1.13 mmol) and Cs$_2$CO$_3$ (1100 mg, 3.38 mmol) in DMF (6.0 mL). The resulting off-white slurry was stirred at 25° C. for 2 hours. The reaction was diluted with water (30 mL) and EtOAc (25 mL) and transferred to a separatory funnel. The phases were separated and the aqueous phase was extracted with EtOAc (3×25 mL). The combined organic extracts were dried over Na$_2$SO$_4$, filtered, and concentrated under vacuum. The crude residue was purified via flash column chromatography (12 g SiO$_2$, Isco, EtOAc/Pet. Ether: 0 to 66%) to afford the title compound 3-[4-(benzyloxy)-3-methyl-5-(1-methyl-1H-1,2,4-triazol-3-yl)-1H-pyrazol-1-yl]propyl acetate (Int-TG-27) (233.6 mg, 56% yield) as a white solid. $^1$H NMR (400 MHz, CHLOROFORM-d) δ=8.10 (s, 1H), 7.46-7.40 (m, 2H), 7.38-7.29 (m, 3H), 4.99 (s, 2H), 4.55 (t, J=7.1 Hz, 2H), 4.08 (t, J=6.4 Hz, 2H), 3.99 (s, 3H), 2.20-2.11 (m, 2H), 2.09 (s, 3H), 2.02 (s, 3H). m/z (ESI+) for (C$_9$H$_{24}$N$_5$O$_3$), 370.0 (M+H)$^+$ observed.

Preparation of 4-(benzyloxy)-1-[3-(benzyloxy)propyl]-3-methyl-1H-pyrazole (Int-TG-28) According to Scheme TG-26

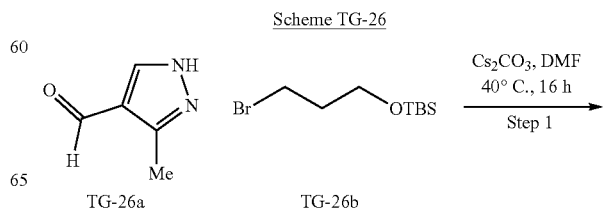

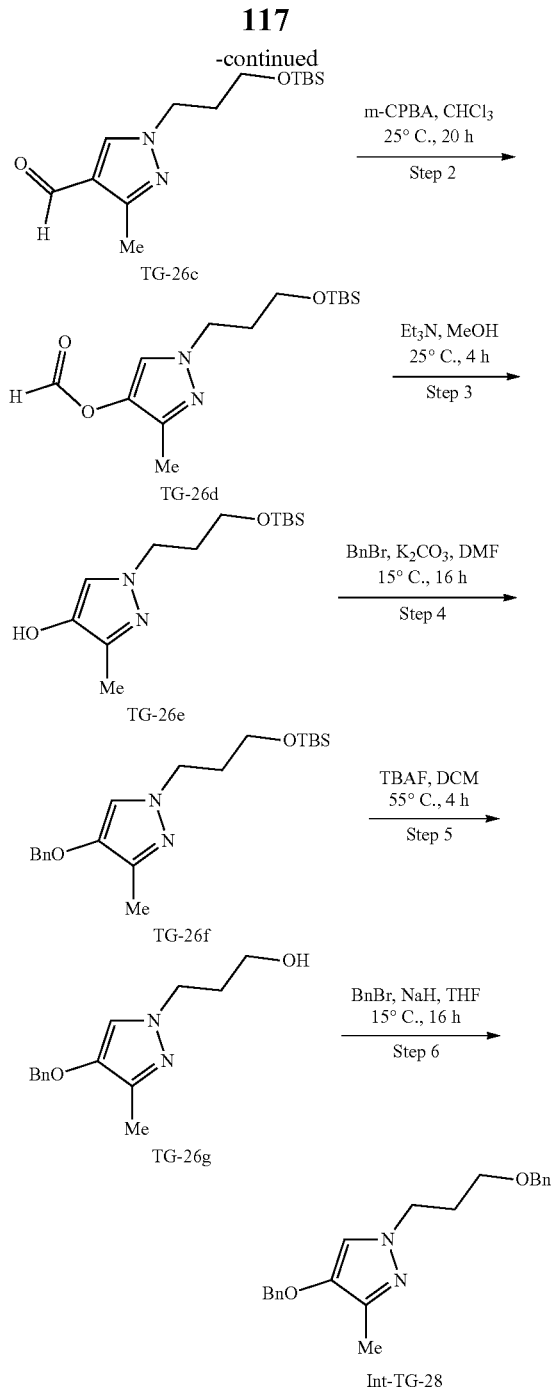

Step 1: Synthesis of 1-(3-{[tert-butyl(dimethyl)silyl]oxy}propyl)-3-methyl-1H-pyrazole-4-carbaldehyde (TG-26c)

To a solution of 3-methyl-1H-pyrazole-4-carbaldehyde (TG-26a) (6800 mg, 61.75 mmol) in DMF (100 mL) was added $Cs_2CO_3$ (22100 mg, 67.9 mmol). After stirring for 10 min, (3-bromopropoxy)-tert-butyldimethylsilane (TG-26b) (16400 mg, 64.8 mmol) was added. The resulting yellow suspension was stirred at 40° C. for 16 h. This reaction was filtered and diluted with EtOAc (250 mL). The organic solution was washed with water (350 mL). The organic phase was concentrated in vacuo and the crude residue was purified by flash column chromatography (120 g $SiO_2$, Combi-flash, 100% Pet. Ether to 15% EtOAc/Pet. Ether) to afford the title compound 1-(3-{[tert-butyl(dimethyl)silyl]oxy}propyl)-3-methyl-1H-pyrazole-4-carbaldehyde (TG-26c) (16405 mg, 94.1%, ~1.5:1 mixture of regioisomers favoring TG-26c) as light yellow oil. $^1$H NMR (400 MHz, CHLOROFORM-d) δ=9.88 (s, 1H), 7.89 (s, 1H, minor regioisomer), 7.83 (s, 1H, major regioisomer), 4.20 (q, J=6.8 Hz, 2H), 3.58 (dt, J=1.9, 5.7 Hz, 2H), 2.58 (s, 3H, minor regioisomer), 2.49 (s, 3H, major regioisomer), 2.11-2.00 (m, 2H), 0.95-0.88 (m, 9H), 0.09-0.03 (m, 6H).

Step 2: Synthesis of 1-(3-{[tert-butyl(dimethyl)silyl]oxy}propyl)-3-methyl-1H-pyrazol-4-yl formate (TG-26d)

To a solution of 1-(3-{[tert-butyl(dimethyl)silyl]oxy}propyl)-3-methyl-1H-pyrazole-4-carbaldehyde (TG-26c) (12.2 g, 43.2 mmol) in $CHCl_3$ (150 mL) was added m-CPBA (14.9 g, 86.4 mmol). The resulting white reaction suspension was stirred at 25° C. (oil bath) for 18 hours. TLC analysis showed that the starting material had been consumed. This solution containing the title compound 1-(3-{[tert-butyl(dimethyl)silyl]oxy}propyl)-3-methyl-1H-pyrazol-4-yl formate (TG-26d) was used in the next step without further purification. m/z (ESI+) for ($C_{14}H_{27}N_2O_3Si$), 299.0 $(M+H)^+$ observed.

Step 3: Synthesis of 1-(3-{[tert-butyl(dimethyl)silyl]oxy}propyl)-3-methyl-1H-pyrazol-4-ol (TG-26e)

To a solution of 1-(3-{[tert-butyl(dimethyl)silyl]oxy}propyl)-3-methyl-1H-pyrazol-4-yl formate (TG-26d) (12900 mg, 43.223 mmol in 150 mL of $CHCl_3$), diluted with MeOH (100 mL), was added $Et_3N$ (38 mL, 300 mmol) at a rate such that the internal temperature did not exceed 25° C. The resulting light yellow reaction solution was stirred at 25° C. (oil bath) for 4 hours. The reaction was quenched with water (350 mL) and transferred to a separatory funnel. The aqueous mixture was extracted with DCM (100 mL) and the phases separated. The combined organic extracts were dried over $Na_2SO_4$, filtered, and concentrated under vacuum. The crude residue was combined with another crude batch of the same material and purified via flash column chromatography ($SiO_2$, 100% Pet. Ether to 20% EtOAc/Pet. Ether) to afford the title compound 1-(3-{[tert-butyl(dimethyl)silyl]oxy}propyl)-3-methyl-1H-pyrazol-4-ol (TG-26e) (5410 mg, 42%, single regioisomer) as a yellow solid. $^1$H NMR (400 MHz, CHLOROFORM-d) δ=7.03 (s, 1H), 4.23 (br s, 1H), 4.04 (t, J=6.9 Hz, 2H), 3.58 (t, J=5.9 Hz, 2H), 2.19 (s, 3H), 1.98 (quin, J=6.4 Hz, 2H), 0.90 (s, 9H), 0.05 (s, 6H). m/z (ESI+) for ($C_{13}H_{27}N_2O_2Si$), 271.0 $(M+H)^+$ observed.

Step 4: Synthesis of 4-(benzyloxy)-1-(3-{[tert-butyl(dimethyl)silyl]oxy}propyl)-3-methyl-1H-pyrazole (TG-26f)

To a solution of 1-(3-{[tert-butyl(dimethyl)silyl]oxy}propyl)-3-methyl-1H-pyrazol-4-ol (TG-26e) (7400 mg, 27.36 mmol) in DMF (120 mL) was added $K_2CO_3$ (5810 mg, 42.0 mmol) and benzyl bromide (4 mL, 6000 mg, 30 mmol). The resulting yellow suspension was stirred at 15° C. for 16 hours. The reaction was quenched with water (250 mL) and extracted with EtOAc (2×250 mL). The organic phase was washed with brine and concentrated in vacuo. The crude residue was purified via flash column chromatography (80 g SiO$_2$, Combi-Flash, 100% Pet. Ether to 15% EtOAc/Pet.) to afford the title compound 4-(benzyloxy)-1-(3-{[tert-butyl(dimethyl)silyl]oxy}propyl)-3-methyl-1H-pyrazole (TG-26f) (9370 mg, 80%) as yellow oil. $^1$H NMR (400 MHz, CHLOROFORM-d) δ=7.45-7.29 (m, 5H), 6.96 (s, 1H), 4.88 (s, 2H), 4.04 (t, J=6.8 Hz, 2H), 3.56 (t, J=5.9 Hz, 2H), 2.20 (s, 3H), 1.98 (quin, J=6.4 Hz, 2H), 0.90 (s, 9H), 0.04 (s, 6H). m/z (ESI+) for (C$_{20}$H$_{33}$N$_2$O$_2$Si), 261.4 (M+H)$^+$ observed.

Step 5: Synthesis of 3-[4-(benzyloxy)-3-methyl-1H-pyrazol-1-yl]propan-1-ol (TG-26g)

To a solution of 4-(benzyloxy)-1-(3-{[tert-butyl(dimethyl)silyl]oxy}propyl)-3-methyl-1H-pyrazole (TG-26f) (1500 mg, 4.160 mmol) in THF (15 mL) was added TBAF (1000 mg, 4 mmol, 1 M THF 4.2 mL). The resulting yellow solution was stirred at 25° C. for 4 hours. TLC analysis showed the starting material had been consumed. This reaction solution was concentrated in vacuo. The crude residue was purified via flash column chromatography (20 g SiO$_2$, Combi-Flash, EtOAc:DCM=10:1/MeOH=100% to 95%) to afford the title compound 3-[4-(benzyloxy)-3-methyl-1H-pyrazol-1-yl]propan-1-ol (TG-26g) (1010 mg, 98%) as a colorless oil. $^1$H NMR (400 MHz, CHLOROFORM-d) δ=7.46-7.30 (m, 5H), 6.96 (s, 1H), 4.89 (s, 2H), 4.10 (t, J=6.3 Hz, 2H), 3.60 (q, J=5.6 Hz, 2H), 2.88 (t, J=5.8 Hz, 1H), 2.19 (s, 3H), 1.97 (quin, J=5.9 Hz, 2H).

Step 6: Synthesis of 4-(benzyloxy)-1-[3-(benzyloxy)propyl]-3-methyl-1H-pyrazole (Int-TG-28)

To a solution of 3-[4-(benzyloxy)-3-methyl-1H-pyrazol-1-yl]propan-1-ol (TG-26g) (1010 mg, 4.101 mmol) in anhydrous THF (10 mL) was added NaH (197 mg, 4.92 mmol) at ice water bath. The resulting mixture was stirred for 15 min, then the solution of benzyl bromide (536 µL, 771 mg, 4.51 mmol) in anhydrous THF (5 mL) was added drop-wise. Upon complete addition, the ice bath was removed and the reaction allowed to warm gradually to room temperature and stirred for 16 h. The reaction was quenched with water and extracted with EtOAc (3×30 mL). The combined organic extracts were concentrated in vacuo. The crude residue was purified via flash column chromatography (20 g SiO$_2$, Combi-Flash, 100% Pet Ether to 80% EtOAc/Pet. Ether) to afford the title compound 4-(benzyloxy)-1-[3-(benzyloxy)propyl]-3-methyl-1H-pyrazole (Int-TG-28) (1210 mg, 87%) as a colorless gum. $^1$H NMR (400 MHz, CHLOROFORM-d) δ=7.47-7.28 (m, 10H), 6.88 (s, 1H), 4.85 (s, 2H), 4.45 (s, 2H), 4.06 (t, J=6.7 Hz, 2H), 3.40 (t, J=5.8 Hz, 2H), 2.20 (s, 3H), 2.07 (quin, J=6.3 Hz, 2H). m/z (ESI+) for (C$_{21}$H$_{25}$N$_2$O$_2$), 337.2 (M+H)$^+$ observed.

Preparation of 4-(benzyloxy)-1-[3-(benzyloxy)propyl]-5-bromo-3-methyl-1H-pyrazole (Int-TG-29) According to Scheme TG-27

Scheme TG-27

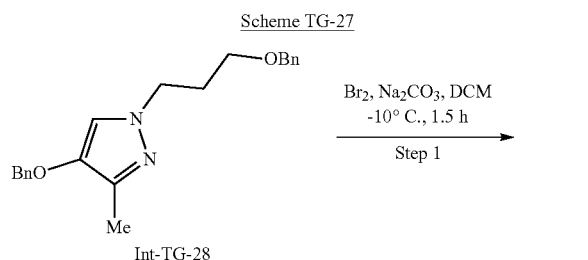

Step 1: Synthesis of 4-(benzyloxy)-1-[3-(benzyloxy)propyl]-5-bromo-3-methyl-1H-pyrazole (Int-TG-29)

To a stirred solution of 4-(benzyloxy)-1-[3-(benzyloxy)propyl]-3-methyl-1H-pyrazole (Int-TG-28) (350 mg 1.04 mmol) in DCM (15 mL) cooled in an ice bath to −10° C. was added Na$_2$CO$_3$ (386 mg, 3.64 mmol) followed by addition of Br$_2$ (600 µL, 250 mg, 1.56 mmol). The resulting mixture was stirred between −10° C.−−20° C. for 1.5 hours. This reaction was quenched with sat. Na$_2$S2O$_3$ aq. and extracted with DCM (2×45 mL). The combined organic extracts were concentrated in vacuo. The crude residue was purified via flash column chromatography (40 g SiO$_2$, CombiFlash, 100% Pet. Ether to 20% EtOAc/Pet. Ether) to afford the title compound 4-(benzyloxy)-1-[3-(benzyloxy)propyl]-5-bromo-3-methyl-1H-pyrazole (Int-TG-29) (384 mg, 88%) as light yellow oil. $^1$H NMR (400 MHz, CHLOROFORM-d) δ=7.45-7.28 (m, 9H), 4.92 (s, 2H), 4.50 (s, 2H), 4.17 (t, J=6.9 Hz, 2H), 3.45 (t, J=6.0 Hz, 2H), 2.15-2.06 (m, 5H). m/z (ESI+) for (C$_{21}$H$_{24}$BrN$_2$O$_2$), 415.1 (M+H)$^+$ observed.

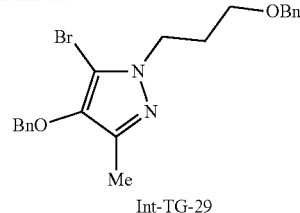

Preparation of 1-[3-(benzyloxy)propyl]-5-bromo-3-methyl-1H-pyrazole (Int-TG-30) According to Scheme TG-28

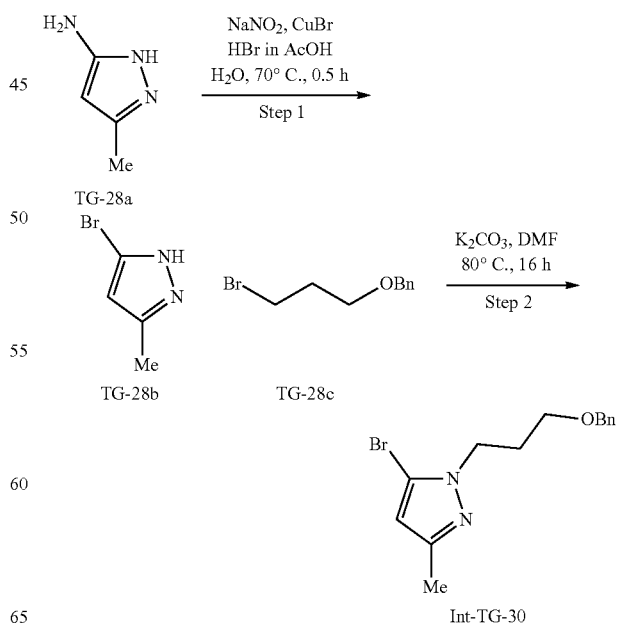

Step 1: Synthesis of 5-bromo-3-methyl-1H-pyrazole (TG-28b)

3-methyl-1H-pyrazol-5-amine (TG-28a) (10 g, 100 mmol) in HBr·AcOH (150 mL) was added CuBr (14.8 g, 103 mmol). The dark solution was heated to 70° C. NaNO$_2$ (7.81 g 113 mmol) in H$_2$O (40.0 mL) was added to the solution slowly using a constant pressure addition funnel. After the addition was complete, the reaction was stirred at 70° C. for another 30 minutes. The reaction was removed from heating and allowed to cool to rt. The reaction was diluted with 100 mL THF and quenched with 100 mL water. The solution was transferred to a separatory funnel and extracted with EtOAc. The organic extract was washed with Na$_2$S2O$_3$, dried over Na$_2$SO$_4$ and concentrated in vacuo. The crude residue was diluted with water and extracted with DCM. The organic extract was dried over Na$_2$SO$_4$ and concentrated in vacuo to afford the title compound 5-bromo-3-methyl-1H-pyrazole (TG-28b) (1900 mg, 11%) as brown oil which was used in the next step without further purification. m/z (ESI+) for (C$_4$H$_6$BrN$_2$), 161.8 (M+H)$^+$ observed.

Step 2: Synthesis of 1-[3-(benzyloxy)propyl]-5-bromo-3-methyl-1H-pyrazole (Int-TG-30)

To a pale yellow solution of [(3-bromopropoxy)methyl]benzene (TG-28c) (1500 mg, 4.7 mmol) in DMF (45 mL) was added 5-bromo-3-methyl-1H-pyrazole (TG-28b) (470 mg, 2.05 mmol) and K$_2$CO$_3$ (3100 mg, 22.4 mmol) at room temperature. After the addition, the reaction mixture was then stirred at 80° C. for 16 hours. The reaction solution was combined with another crude batch of the same material and quenched with water. The solution was transferred to a separatory funnel and extracted with EtOAc (3×100 mL). The combined organic extracts were concentrated in vacuo. The crude residue was purified via flash chromatography (80 g SiO$_2$, Combi-Flash, 100% Pet. Ether to 20% EtOAc/Pet. Ether) to afford the title compound (Int-TG-30) (1800 mg) as a mixture of regioisomers. This material was further purified via Prep-HPLC (Boston Prime C18 150×25 mm×5 um column, water/MeCN with 0.05% NH$_4$OH, 30 mL/min flowrate, 25 injections). Product containing fractions were collected and lyophilized to afford the title compound 1-[3-(benzyloxy)propyl]-5-bromo-3-methyl-1H-pyrazole (Int-TG-30) (399 mg, 20%, minor regioisomer) as a colorless oil. $^1$H NMR (400 MHz, CHLOROFORM-d) δ=7.40-7.28 (m, 4H), 6.05 (s, 1H), 4.51 (s, 2H), 4.23 (t, J=7.0 Hz, 2H), 3.48 (t, J=6.0 Hz, 2H), 2.25 (s, 3H), 2.13 (quin, J=6.5 Hz, 2H).

Preparation of tert-butyl {3-[4-(benzyloxy)-5-bromo-3-methyl-1H-pyrazol-1-yl]propyl}carbamate (Int-TG-31) According to Scheme 29

Scheme 29

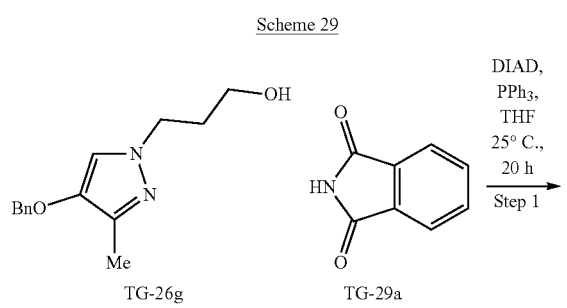

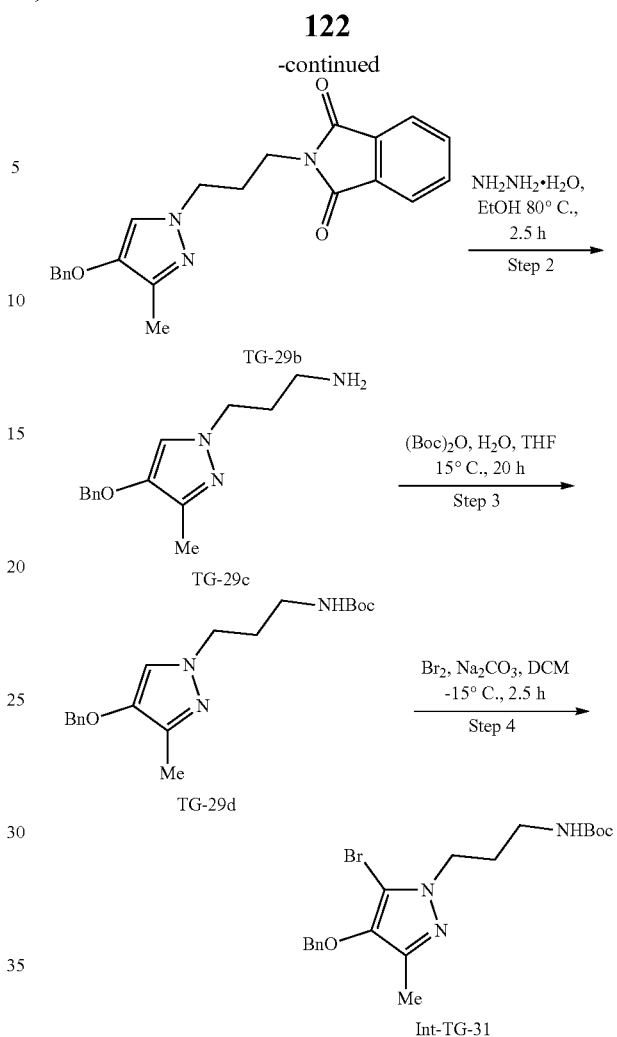

Step 1: Synthesis of 2-{3-[4-(benzyloxy)-3-methyl-1H-pyrazol-1-yl]propyl}-1H-isoindole-1,3(2H)-dione (TG-29b)

A solution of 3-[4-(benzyloxy)-3-methyl-1H-pyrazol-1-yl]propan-1-ol (TG-26g) (255 mg, 1.04 mmol) and DIAD (230 mg, 1.14 mmol) in THF (3.5 mL) was slowly added via cannula to a solution of phthalimide (TG-29a) (168 mg, 1.14 mmol) and PPh$_3$ (285 mg, 1.09 mmol) in THF (3 mL). The flask and cannula were rinsed and transferred to the reaction mixture with an additional portion of dry THF to ensure complete addition. The reaction was stirred at 25° C. for 20 hours. The reaction was concentrated in vacuo to give crude compound. The crude residue was purified via flash column chromatography (25 g SiO$_2$, Combiflash, 100% Pet. Ether to 30% EtOAc/Pet. Ether) to afford the title compound 2-{3-[4-(benzyloxy)-3-methyl-1H-pyrazol-1-yl]propyl}-1H-isoindole-1,3(2H)-dione (TG-29b) (330 mg, 84%) as a yellow gum. $^1$H NMR (400 MHz, CHLOROFORM-d) δ=7.91-7.80 (m, 2H), 7.73 (dd, J=3.1, 5.4 Hz, 2H), 7.48-7.29 (m, 5H), 7.09 (s, 1H), 4.88 (s, 2H), 4.00 (t, J=6.8 Hz, 2H), 3.72 (t, J=6.6 Hz, 2H), 2.21 (quin, J=6.7 Hz, 2H), 2.12 (s, 3H). m/z (ESI+) for (C$_{22}$H$_{22}$N$_3$O$_3$), 376.1 (M+H)$^+$ observed.

Step 2: Synthesis of 3-[4-(benzyloxy)-3-methyl-1H-pyrazol-1-yl]propan-1-amine (TG-29c)

To a mixture of 2-{3-[4-(benzyloxy)-3-methyl-1H-pyrazol-1-yl]propyl}-1H-isoindole-1,3(2H)-dione (TG-29b)

(330 mg, 0.879 mmol) in EtOH (5 mL) was added hydrazine hydrate (426 μL, 440 mg, 8.79 mmol). The reaction mixture was stirred at 80° C. for 2.5 hours. The reaction was cooled in an ice-water bath and the precipitates filtered off. The filtrate was concentrated under vacuum to afford the title compound 3-[4-(benzyloxy)-3-methyl-1H-pyrazol-1-yl]propan-1-amine (TG-29c) (210 mg, 97%) as yellow gum. This material was used in the next step without further purification. m/z (ESI+) for ($C_{14}H_{20}N_3O$), 246.1 $(M+H)^+$ observed.

Step 3: Synthesis of tert-butyl {3-[4-(benzyloxy)-3-methyl-1H-pyrazol-1-yl]propyl}carbamate (TG-29d)

To a solution of 3-[4-(benzyloxy)-3-methyl-1H-pyrazol-1-yl]propan-1-amine (TG-29c) (210 mg, 0.856 mmol) in THF (6.0 mL) and $H_2O$ (2 mL) was added $(Boc)_2O$ (280 mg, 1.28 mmol). The reaction mixture was stirred at 15° C. for 20 hours. The reaction was diluted with water and extracted with EtOAc (2×20 mL). The combined organic extracts were dried over $Na_2SO_4$ and concentrated in vacuo. The crude residue was purified via flash column chromatography (10 g $SiO_2$, Combi-Flash, 100% Pet. Ether to 40% EtOAc/Pet. Ether) to afford the title compound tert-butyl {3-[4-(benzyloxy)-3-methyl-1H-pyrazol-1-yl]propyl}carbamate (TG-29d) (220 mg, 74%) as colorless gum. $^1$H NMR (400 MHz, CHLOROFORM-d) δ=7.46-7.30 (m, 5H), 6.96 (s, 1H), 4.89 (s, 2H), 4.76 (br s, 1H), 3.99 (t, J=6.7 Hz, 2H), 3.08 (q, J=5.9 Hz, 2H), 2.20 (s, 3H), 1.94 (quin, J=6.6 Hz, 2H), 1.45 (s, 9H). m/z (ESI+) for ($C_9H_{28}N_3O_3$), 346.1 $(M+H)^+$ observed.

Step 4: Synthesis of tert-butyl {3-[4-(benzyloxy)-5-bromo-3-methyl-1H-pyrazol-1-yl]propyl}carbamate (Int-TG-31)

A stirred solution of tert-butyl {3-[4-(benzyloxy)-3-methyl-1H-pyrazol-1-yl]propyl}carbamate (TG-29d) (220.0 mg, 0.637 mmol) in DCM (15.0 mL) was cooled in an ice bath to −20° C. To the solution was added $Na_2CO_3$ (236 mg, 2.23 mmol) followed by addition of $Br_2$ (68 μL, 1.3 mmol). The resulting mixture was stirred at −15° C. for 2.5 hours. The reaction was quenched with sat. $Na_2S_2O_3$ at a rate which maintained an internal temperature below 10° C. The solution was transferred to a separatory funnel and extracted with DCM (2×45 mL). The combined organic extracts were concentrated in vacuo. The crude residue was purified via flash column chromatography (10 g $SiO_2$, Combi-Flash, 100% Pet. Ether to 50% EtOAc/Pet. Ether) to afford the title compound tert-butyl {3-[4-(benzyloxy)-5-bromo-3-methyl-1H-pyrazol-1-yl]propyl}carbamate (Int-TG-31) (262.5 mg, 97%) as colorless oil. $^1$H NMR (400 MHz, CHLOROFORM-d) δ=7.46-7.31 (m, 5H), 4.93 (s, 2H), 4.80 (br s, 1H), 4.10 (t, J=6.7 Hz, 2H), 3.14-2.98 (m, 2H), 2.08 (s, 3H), 1.95 (quin, J=6.5 Hz, 2H), 1.45 (s, 9H).

Preparation of Head Group (HG) Intermediates:

Preparation of methyl 4-bromo-1-methyl-1H-indazole-6-carboxylate (Int-HG-01) according to Scheme HG-1

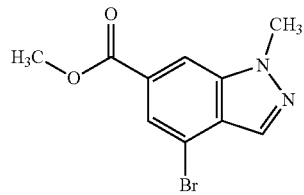

Preparation of methyl 4-bromo-2-methyl-2H-indazole-6-carboxylate (Int-HG-02) according to Scheme HG-1

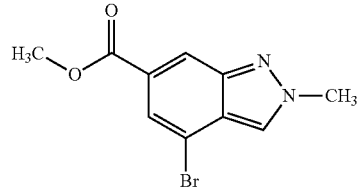

Scheme HG-1

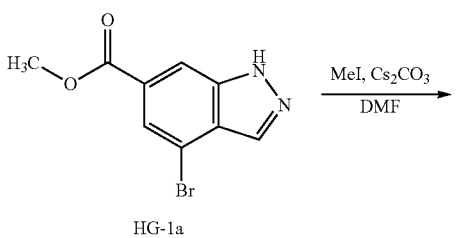

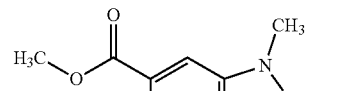

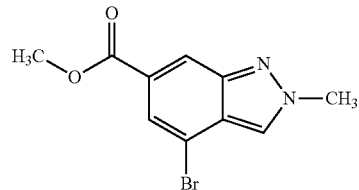

To a mixture of methyl 4-bromo-1H-indazole-6-carboxylate (HG-1a) (2.00 g, 7.84 mmol) and $Cs_2CO_3$ (5.11 g, 15.7 mmol) in DMF (20.0 mL) was added iodomethane (1.42 g, 10.0 mmol). The mixture was stirred at 16° C. for 16 h, providing a brown suspension. LCMS analysis showed consumption of the starting material with formation of the product mass. The mixture was filtered. The filtrate was diluted with saturated aqueous NH₄Cl (30 mL). The mixture was extracted with EtOAc (2×30 mL). The combined organic layers were washed with brine, dried over anhydrous Na₂SO₄, filtered, and concentrated. The residue was purified by flash chromatography (20 g SiO₂, 0-100% EtOAc/petroleum ether) to provide methyl 4-bromo-1-methyl-1H-indazole-6-carboxylate (Int-HG-01) (1.36 g, 64% yield) as a pale-yellow solid as the first-eluting regioisomer. $^1$H NMR (400 MHz, CDCl₃) δ 8.12 (s, 1H), 8.03 (d, J=1.1 Hz, 1H), 7.97 (d, J=1.1 Hz, 1H), 4.14 (s, 3H), 3.98 (s, 3H). Methyl 4-bromo-2-methyl-2H-indazole-6-carboxylate (Int-HG-02) (751 mg, 36% yield) was obtained as the second-eluting regioisomer as a yellow solid. $^1$H NMR (400 MHz, CDCl₃) δ 8.42 (t, J=1.0 Hz, 1H), 7.96 (s, 1H), 7.89 (d, J=1.1 Hz, 1H), 4.27 (s, 3H), 3.95 (s, 3H).

Intermediates Int-HG-03, Int-HG-04 and Int-HG-05 were prepared according to the methods used for the synthesis of methyl 4-bromo-1-methyl-1H-indazole-6-carboxylate (Int-HG-01) and methyl 4-bromo-2-methyl-2H-indazole-6-carboxylate (Int-HG-02), with non-critical changes or substitutions to the exemplified procedures that one skilled in the art would be able to realize. If necessary, separation of regioisomeric mixtures was carried out under standard methods known in the art.

| Compound Number | Structure/IUPAC Name | Analytical Data |
|---|---|---|
| Int-HG-03 | 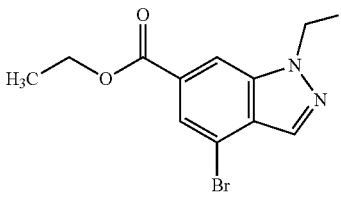<br>ethyl 4-bromo-1-ethyl-1H-indazole-6-carboxylate | $^1$H NMR (400 MHz, CDCl₃) δ 8.12 (t, J = 1.0 Hz, 1H), 8.04 (d, J = 1.0 Hz, 1H), 7.96 (d, J = 1.1 Hz, 1H), 4.52-4.45 (m, 2H), 4.47-4.39 (m, 2H), 1.54 (t, J = 7.3 Hz, 3H), 1.44 (t, J = 7.1 Hz, 3H); m/z (ESI+) for (C₁₂H₁₃BrN₂O₂), 298.8 (M + H)⁺. |
| Int-HG-04 | 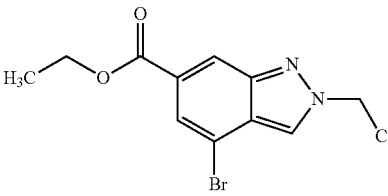<br>ethyl 4-bromo-2-ethyl-2H-indazole-6-carboxylate | $^1$H NMR (400 MHz, CDCl₃) δ 8.45 (t, J = 1.1 Hz, 1H), 7.99 (s, 1H), 7.88 (d, J = 1.1 Hz, 1H), 4.52 (q, J = 7.3 Hz, 2H), 4.41 (q, J = 7.1 Hz, 2H), 1.67 (t, J = 7.3 Hz, 3H), 1.42 (t, J = 7.1 Hz, 3H); m/z (ESI+) for (C₁₂H₁₃BrN₂O₂), 296.8 (M + H)⁺. |
| Int-HG-05 | 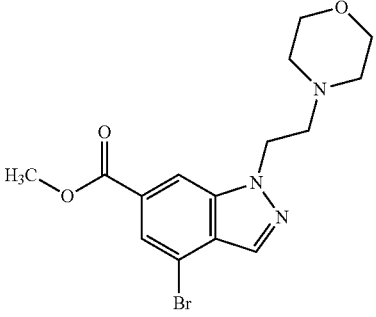 [SMILES: COC(=O)c1cc(Br)c2cnn(CCN3CCOCC3)c2c1]<br>methyl 4-bromo-1-[2-(morpholin-4-yl)ethyl]-1H-indazole-6-carboxylate | $^1$H NMR (400 MHz, CDCl₃) δ 8.21 (s, 1H), 8.07 (d, J = 1.0 Hz, 1H), 7.99 (d, J = 1.1 Hz, 1H), 4.57 (t, J = 6.5 Hz, 2H), 4.01 (s, 3H), 3.80-3.55 (m, 4H), 2.90 (t, J = 6.3 Hz, 2H), 2.65-2.28 (m, 4H); m/z (ESI+) for (C₁₅H₁₈BrN₃O₃), 367.7 (M + H)⁺. |

Preparation of methyl 4-bromo-1-[3-(morpholin-4-yl)propyl]-1H-indazole-6-carboxylate (Int-HG-06) According to Scheme HG-2

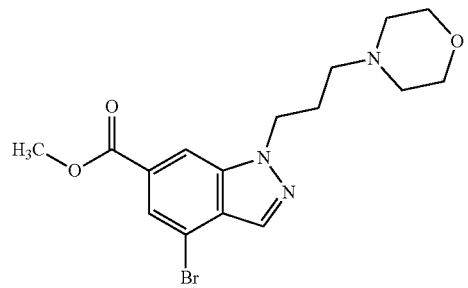 [SMILES: COC(=O)c1cc(Br)c2cnn(CCCN3CCOCC3)c2c1]

Scheme HG-2

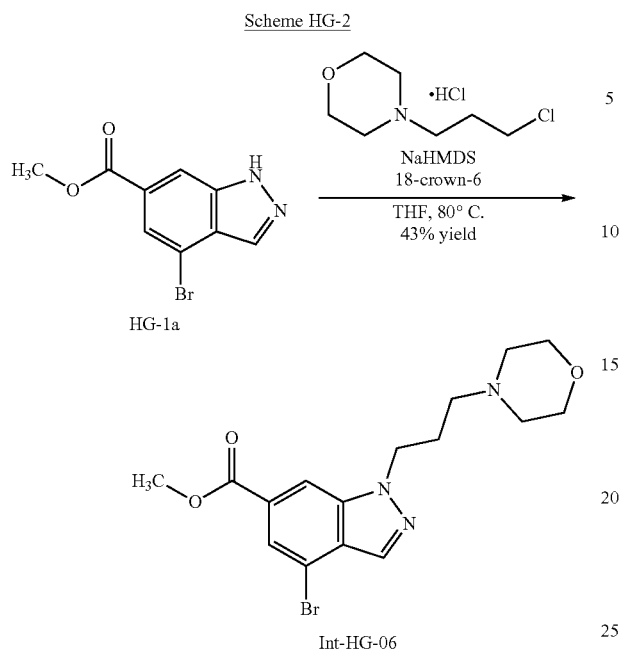

Scheme HG-3

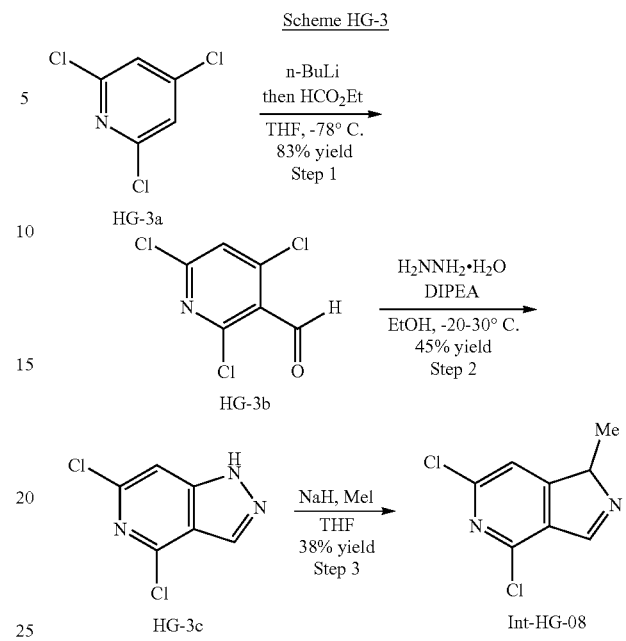

To a solution of methyl 4-bromo-1H-indazole-6-carboxylate (HG-1a) (502 mg, 1.97 mmol) in THF (10 mL) were added 4-(3-chloropropyl)morpholine hydrogen chloride (409 mg, 2.5 mmol), 18-crown-6 (51.8 mg, 0.196 mmol), and a solution of NaHMDS (1.0 M in THF, 2.2 mL, 2.2 mmol). The mixture was stirred at reflux for 16 h. LCMS analysis showed consumption of the starting material with formation of the desired product mass. The reaction was concentrated to dryness. The residue was purified by flash chromatography (SiO$_2$, 80% EtOAc/petroleum ether then 10% MeOH/EtOAc) to provide methyl 4-bromo-1-[3-(morpholin-4-yl)propyl]-1H-indazole-6-carboxylate (327 mg, 43% yield) as a yellow oil. $^1$H NMR (400 MHz, CDCl$_3$) δ 8.22 (d, J=1.2 Hz, 1H), 8.05 (d, J=1.0 Hz, 1H), 7.95 (d, J=1.2 Hz, 1H), 4.53 (t, J=6.4 Hz, 2H), 3.97 (s, 3H), 3.71 (t, J=4.6 Hz, 4H), 2.35 (t, J=4.7 Hz, 4H), 2.23 (t, J=6.6 Hz, 2H), 2.11 (p, J=6.4 Hz, 2H); m/z (ESI+) for (C$_{16}$H$_{20}$BrN$_3$O$_3$), 383.9 (M+H)$^+$.

Preparation of methyl 4,6-dichloro-1-methyl-1H-pyrazolo[4,3-c]pyridine (Int-HG-08) According to Scheme HG-3

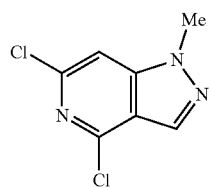 [SMILES: Cn1ncc2c(Cl)nc(Cl)cc21]

Step 1: Synthesis of 2,4,6-trichloropyridine-3-carbaldehyde (HG-3b)

A solution of 2,4,6-trichloropyridine (HG-3a) (9.00 g, 49.3 mmol) in anhydrous THF was cooled to −68° C. (internal temperature) under an atmosphere of N$_2$ and n-BuLi (2.5 M in hexane, 20.7 mL, 51.8 mmol) was added dropwise, maintaining the reaction temperature below −63° C. (internal temperature). The mixture was stirred at −68° C. (internal temperature) for 30 min. Ethyl formate (4.75 g, 64.1 mmol) was added dropwise, maintaining the reaction temperature below −63° C. (internal temperature). The mixture was stirred at −68° C. (internal temperature) for 1 h. TLC analysis showed consumption of the starting material. The mixture was poured into a 1:1 mixture of ice and saturated aqueous NH$_4$Cl (100 mL). The mixture was stirred for 10 min and then extracted with EtOAc (2×200 mL). The combined organic layers were washed with brine (2×100 mL), dried over anhydrous Na$_2$SO$_4$, filtered, and concentrated to dryness. The residue was purified by flash chromatography (80 g SiO$_2$, 0-5% EtOAc/petroleum ether). The mixed fractions were repurified by flash chromatography (20 g SiO$_2$, 0-5% EtOAc/petroleum ether). The product batches were combined to provide 2,4,6-trichloropyridine-3-carbaldehyde (HG-3b) (8.62 g, 83% yield) as a white solid. $^1$H NMR (400 MHz, CDCl$_3$) δ 10.42 (s, 1H), 7.46 (s, 1H).

Step 2: Synthesis of 4,6-dichloro-1H-pyrazolo[4,3-c]pyridine (HG-3c)

A solution of 2,4,6-trichloropyridine-3-carbaldehyde (HG-3b) (4.00 g, 19.0 mmol) and DIPEA (7.62 g, 58.9 mmol) in EtOH (100 mL) was cooled to −20° C. under an atmosphere of N$_2$ and hydrazine monohydrate (3.81 g, 76.0 mmol) was added dropwise. The mixture was stirred at −20° C. for 24 h and then 30° C. for 16 h. LCMS analysis showed formation of the desired product mass. The solution was concentrated to dryness. The resultant solids were slurried with 1:2 EtOAc/petroleum ether (300 mL) for 30 min. The solids were collected by filtration. The filter cake was purified by flash chromatography (40 g SiO$_2$, 8-50% EtOAc/petroleum ether) to provide 4,6-dichloro-1H-pyrazolo[4,3-c]pyridine (HG-3c) (1.6 g, 45% yield) as a white solid. $^1$H NMR (400 MHz, DMSO-d$_6$) δ 14.06 (br s, 1H), 8.41 (s, 1H), 7.78 (d, J=1.0 Hz, 1H).

Step 3: Synthesis of 4,6-dichloro-1-methyl-1H-pyrazolo[4,3-c]pyridine (Int-HG-08)

To a solution of 4,6-dichloro-1H-pyrazolo[4,3-c]pyridine (HG-3c) (1.25 g, 6.65 mmol) in anhydrous THF at 0° C. was added NaH (60% dispersion in mineral oil, 500 mg, 12.5 mmol). The mixture was stirred at 0° C. for 10 min and then iodomethane (1.89 g, 13.3 mmol) was added dropwise at the same temperature. The mixture was stirred for 1 h at 0° C. and then 16 h at 25° C. TLC analysis (2:1 EtOAc/petroleum ether) showed complete consumption of the starting material. The reaction was quenched by addition of saturated aqueous NH$_4$Cl (20 mL) and then concentrated to remove the THF. The aqueous mixture was extracted with EtOAc (3×20 mL). The combined organic layers were dried over Na$_2$SO$_4$, filtered, and concentrated to dryness. The residue was purified by flash chromatography (40 g SiO$_2$, 5-30% EtOAc/petroleum ether) to provide 4,6-dichloro-1-methyl-1H-pyrazolo[4,3-c]pyridine (Int-HG-08) (510 mg, 38% yield) as an off-white solid. $^1$H NMR (400 MHz, DMSO-d$_6$) δ 8.42 (d, J=1.0 Hz, 1H), 8.05 (d, J=0.9 Hz, 1H), 4.12 (s, 3H).

Preparation of 1-[2-(4,6-dichloro-1H-pyrazolo[4,3-c]pyridin-1-yl)ethyl]piperidine-4-carbonitrile (Int-HG-09) According to Scheme HG-4

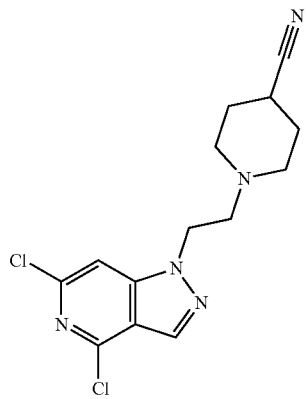 [SMILES: N#CC1CCN(CCn2ncc3c(Cl)nc(Cl)cc32)CC1]

Scheme HG-4

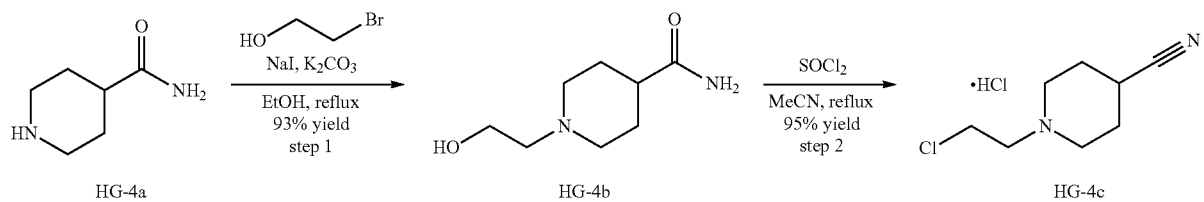

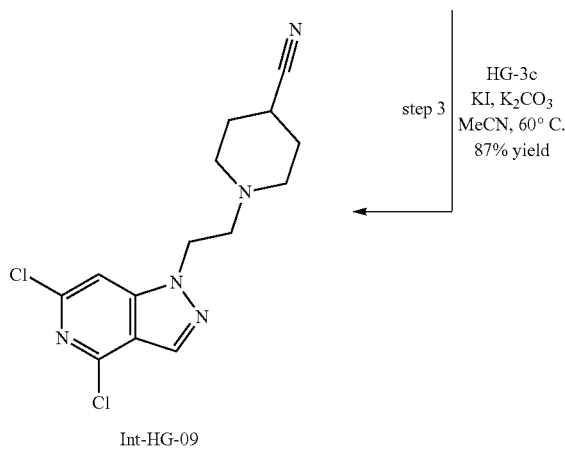

Int-HG-09

Step 1: Synthesis of 1-(2-hydroxyethyl)piperidine-4-carboxamide (HG-4b)

To a solution of piperidine-4-carboxamide (HG-4a) (1.00 g, 7.80 mmol) in EtOH (15.0 mL) were added 2-bromoethanol (1.17 g, 9.36 mmol), $K_2CO_3$ (2.32 g, 16.8 mmol), and NaI (117 mg, 0.780 mmol) successively. The mixture was stirred at reflux for 20 h. TLC analysis (1:15 MeOH/DCM) showed consumption of the starting material. The mixture was filtered through celite and the filtrate was concentrated to dryness to provide 1-(2-hydroxyethyl)piperidine-4-carboxamide (HG-4b) (1.25 g, 93% yield), which was taken on without further purification. $^1$H NMR (400 MHz, DMSO-$d_6$) δ 7.24 (br s, 1H), 6.74 (br s, 1H), 4.82-4.28 (m, 1H), 3.51 (t, J=6.4 Hz, 2H), 2.89 (d, J=11.7 Hz, 2H), 2.38 (t, J=6.4 Hz, 2H), 2.05 (tt, J=11.6, 4.0 Hz, 1H), 1.94 (td, J=11.7, 2.6 Hz, 2H), 1.71-1.62 (m, 2H), 1.62-1.50 (m, 2H).

Step 2: Synthesis of 1-(2-chloroethyl)piperidine-4-carbonitrile hydrochloride (HG-4c)

To a suspension of 1-(2-hydroxyethyl)piperidine-4-carboxamide (HG-4b) (1.25 g, 7.26 mmol) in MeCN (15.0 mL) was added $SOCl_2$ (4.32 g, 36.3 mmol), maintaining the reaction temperature below 5° C. (internal temperature). The mixture was stirred at reflux for 4 h and then concentrated to dryness to provide 1-(2-chloroethyl)piperidine-4-carbonitrile hydrochloride (HG-4c) (1.45 g, 95% yield) as a brown solid, which was taken on without further purification. $^1$H NMR (400 MHz, DMSO-$d_6$) δ 11.51 (br s, 1H), 4.10 (q, J=6.8 Hz, 2H), 3.70-3.35 (m, 4H), 3.21-2.92 (m, 3H), 2.38-1.98 (m, 4H).

Step 3: Synthesis of 1-[2-(4,6-dichloro-1H-pyrazolo[4,3-c]pyridin-1-yl)ethyl]piperidine-4-carbonitrile (Int-HG-09)

To a solution of 4,6-dichloro-1H-pyrazolo[4,3-c]pyridine (HG-3c) (500 mg, 2.66 mmol) and 1-(2-chloroethyl)piperidine-4-carbonitrile hydrochloride (HG-4c) (834 mg, 3.99 mmol) in MeCN (10.0 mL) were added $K_2CO_3$ (1.10 g, 7.98 mmol) and KI (44.1 mg, 0.266 mmol). The mixture was stirred at 60° C. for 16 h. TLC analysis (1:1 EtOAc/petroleum ether) showed consumption of the starting material. The mixture was filtered through celite and the filtrate was concentrated to dryness. The residue was purified by flash chromatography (12 g $SiO_2$, 0-50% EtOAc/petroleum ether) to provide 1-[2-(4,6-dichloro-1H-pyrazolo[4,3-c]pyridin-1-yl)ethyl]piperidine-4-carbonitrile (Int-HG-09) (750 mg, 87% yield) as a brown oil. $^1$H NMR (400 MHz, CDCl$_3$) δ 8.11 (d, J=0.9 Hz, 1H), 7.29 (d, J=1.0 Hz, 1H), 4.40 (t, J=6.3 Hz, 2H), 2.85 (t, J=6.3 Hz, 2H), 2.73-2.54 (m, 3H), 2.45-2.27 (m, 2H), 1.90-1.68 (m, 4H).

Preparation of 5-bromo-3-methyl-1H-indazole-7-carbonitrile (Int-HG-10) According to Scheme HG-5

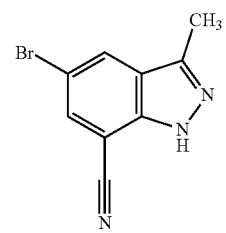

Scheme HG-5

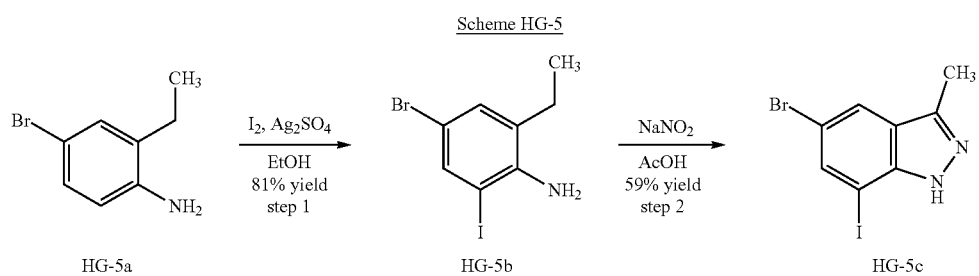

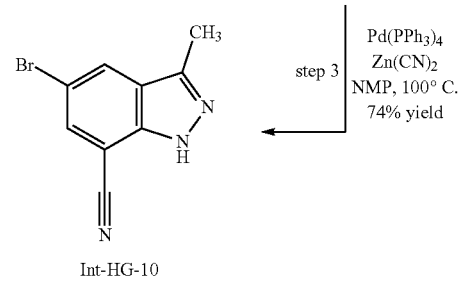

Int-HG-10

Step 1: Synthesis of 4-bromo-2-ethyl-6-iodoaniline (HG-5b)

To a solution of 4-bromo-2-ethylaniline (HG-5a) (1.00 g, 5.00 mmol) in EtOH (20.0 mL) were added 12 (1.27 g, 5.00 mmol) and $Ag_2SO_4$ (1.56 g, 5.00 mmol). The mixture was stirred at room temperature for 3 h. TLC analysis (1:3 EtOAc/petroleum ether) showed consumption of the starting material. The mixture was filtered and the filtrate was concentrated to dryness. The residue was dissolved in EtOAc (100 mL) and washed with saturated aqueous $Na_2S_2O_3$ (100 mL).

The organic layer was dried over $Na_2SO_4$, filtered, and concentrated. The residue was purified by flash chromatography (20 g $SiO_2$, 0-5% EtOAc/petroleum ether) to provide 4-bromo-2-ethyl-6-iodoaniline (HG-5b) (1.32 g, 81% yield) as a dark red oil. $^1$H NMR (400 MHz, $CDCl_3$) δ 7.63 (d, J=2.3 Hz, 1H), 7.14 (d, J=2.2 Hz, 1H), 4.12 (br s, 2H), 2.51 (q, J=7.5 Hz, 2H), 1.24 (t, J=7.5 Hz, 3H).

Step 2: Synthesis of 5-bromo-7-iodo-3-methyl-1H-indazole (HG-5c)

To a solution of 4-bromo-2-ethyl-6-iodoaniline (HG-5b) (1.32 g, 4.05 mmol) in HOAc (20.0 mL) was added $NaNO_2$ (279 mg, 4.05 mmol) at room temperature. The mixture was stirred at room temperature for 16 h. TLC analysis (1:10 EtOAc/petroleum ether) showed consumption of the starting material with formation of the desired product mass. The mixture was concentrated to dryness. The residue was purified by flash chromatography (20 g $SiO_2$, 0-50% EtOAc/petroleum ether) to provide 5-bromo-7-iodo-3-methyl-1H-indazole (HG-5c) (810 mg, 59% yield) as a pink solid. $^1$H NMR (400 MHz, $CDCl_3$) δ 9.86 (s, 1H), 7.85 (d, J=1.5 Hz, 1H), 7.82 (d, J=1.6 Hz, 1H), 2.57 (s, 3H); m/z (ESI+) for ($C_3H_6BrIN_2$), 338.8 (M+H)$^+$.

Step 3: Synthesis of 5-bromo-3-methyl-1H-indazole-7-carbonitrile (Int-HG-10)

To a solution of 5-bromo-7-iodo-3-methyl-1H-indazole (HG-5c) (500 mg, 1.48 mmol) in NMP (5.0 mL) under an atmosphere of $N_2$ were added $Zn(CN)_2$ (105 mg, 0.890 mmol) and $Pd(PPh_3)_4$ (171 mg, 0.148 mmol). The mixture was stirred at 100° C. for 4 h. TLC analysis (1:1 EtOAc/petroleum ether) showed consumption of the starting material. The mixture was diluted with EtOAc (50 mL) and washed with saturated aqueous $NH_4Cl$ (3×50 mL). The combined organic layers were dried over $Na_2SO_4$, filtered, and concentrated. The residue was purified by flash chromatography (4 g $SiO_2$, 0-25% EtOAc/petroleum ether) to provide 5-bromo-3-methyl-1H-indazole-7-carbonitrile (Int-HG-10) (260 mg, 74% yield) as a light yellow solid. $^1$H NMR (400 MHz, $CDCl_3$) δ 8.07 (d, J=1.6 Hz, 1H), 7.81 (d, J=1.7 Hz, 1H), 2.60 (s, 3H).

Preparation of 4-bromo-N-[(2,4-dimethoxyphenyl)methyl]-5-fluoro-1-methyl-1H-indazole-6-carboxamide (Int-HG-11) According to Scheme HG-6

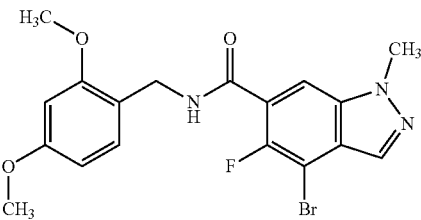 [SMILES: COc1ccc(CNC(=O)c2cc3c(cnn3C)c(Br)c2F)c(OC)c1]

Scheme HG-6

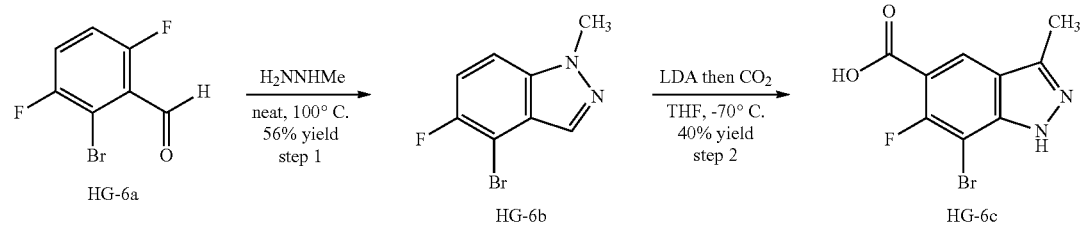

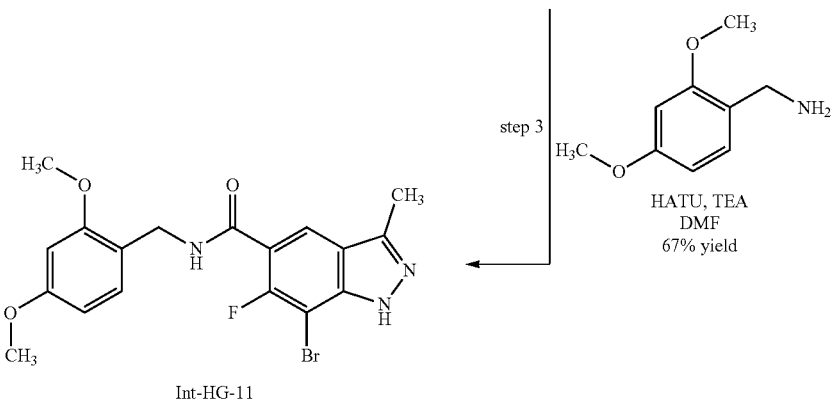

Int-HG-11

Step 1: Synthesis of 4-bromo-5-fluoro-1-methyl-1H-indazole (HG-6b)

A mixture of 2-bromo-3,6-difluorobenzaldehyde (HG-6a) (900 mg, 4.18 mmol) and methylhydrazine (1.35 g, 29.3 mmol) was stirred at 100° C. for 24 h. LCMS analysis showed consumption of the starting material with formation of the desired product mass. The mixture was concentrated. The residue was diluted with $H_2O$ and extracted with EtOAc. The combined organic layers were dried over $Na_2SO_4$, filtered, and concentrated. The residue was purified by flash chromatography (24 g $SiO_2$, 20% EtOAc/heptane) to provide 4-bromo-5-fluoro-1-methyl-1H-indazole (HG-6b) (532 mg, 56% yield) as a white solid. $^1H$ NMR (400 MHz, $CDCl_3$) δ 7.99 (d, J=0.61 Hz, 1H), 7.28-7.33 (m, 1H), 7.18-7.24 (m, 1H), 4.09 (s, 3H); $^{19}F$ NMR (376 MHz, $CDCl_3$) δ −120.6 (br s, 1F); m/z (ESI+) for ($C_8H_6BrFN_2$), 229.0 (M+H)$^+$.

Step 2: Synthesis of 4-bromo-5-fluoro-1-methyl-1H-indazole-6-carboxylic acid (HG-6c)

A solution of 4-bromo-5-fluoro-1-methyl-1H-indazole (HG-6b) (100 mg, 0.437 mmol) in THF (4.37 mL) at was cooled to −70° C. under an atmosphere of $N_2$. A solution of LDA (1.0 M in THF, 0.611 mL, 0.611 mmol) was added dropwise. The mixture was stirred for 1 h maintaining the reaction temperature below −60° C. to provide an orange reaction mixture. $CO_2$ (g) was bubbled through the reaction for 10 min to provide a clear reaction solution. The mixture was warmed to room temperature, diluted with $H_2O$, and basified with saturated aqueous $NaHCO_3$ (5 mL). The mixture was washed with heptane (2×). The aqueous layer was acidified to pH ~2 with 1 N HCl and then extracted with EtOAc (3×). The combined organic extracts were dried over $Na_2SO_4$, filtered, and concentrated to provide 4-bromo-5-fluoro-1-methyl-1H-indazole-6-carboxylic acid (HG-6c) (48 mg, 40% yield) as a yellow solid. $^1H$ NMR (400 MHz, $CDCl_3$) δ 13.57 (br s, 1H), 8.25 (dd, J=5.32, 0.79 Hz, 1H), 8.13 (d, J=0.86 Hz, 1H), 4.14 (s, 3H); $^{19}F$ NMR (376 MHz, $CDCl_3$) δ −119.85 (s, 1F); m/z (ESI+) for ($C_9H_6BrFN_2O_2$), 273.0 (M+H)$^+$.

Step 3: Synthesis of 4-bromo-N-[(2,4-dimethoxyphenyl)methyl]-5-fluoro-1-methyl-1H-indazole-6-carboxamide (Int-HG-11)

To a solution of 4-bromo-5-fluoro-1-methyl-1H-indazole-6-carboxylic acid (HG-6c) (47 mg, 0.170 mmol) in DMF (1.72 mL) were added 1-(2,4-dimethoxyphenyl)methanamine (34.5 mg, 0.207 mmol), TEA (34.8 mg, 0.344 mmol), and HATU (98.2 mg, 0.258 mmol). The mixture was stirred at room temperature for 5 min. LCMS analysis showed consumption of the starting material with formation of the desired product mass. The reaction was concentrated to dryness. The residue was dissolved in $H_2O$ and extracted with EtOAc (3×). The combined organic layers were dried over $Na_2SO_4$, filtered, and concentrated. The residue was purified by flash chromatography (4 g $SiO_2$, 60% EtOAc/heptane) to provide 4-bromo-N-[(2,4-dimethoxyphenyl)methyl]-5-fluoro-1-methyl-1H-indazole-6-carboxamide (Int-HG-11) (49 mg, 67% yield) as a white solid. $^1H$ NMR (400 MHz, $CDCl_3$) δ 8.21 (dd, J=5.38, 0.86 Hz, 1H), 8.00 (d, J=0.86 Hz, 1H), 7.33-7.46 (m, 1H), 6.51 (d, J=2.32 Hz, 1H), 6.47 (dd, J=8.19, 2.32 Hz, 1H), 4.61-4.67 (m, 2H), 4.12 (s, 3H), 3.90 (s, 3H), 3.82 (s, 3H); $^{19}F$ NMR (376 MHz, $CDCl_3$) δ −121.51 (s, 1F); m/z (ESI+) for ($C_{18}H_{17}BrFN_3O_3$), 422.0 (M+H)$^+$.

Preparation of methyl 8-bromo-3-methylimidazo[1,5-a]pyridine-6-carboxylate (Int-HG-12) According to Scheme HG-7

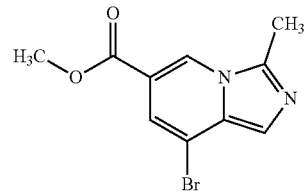

Scheme HG-7

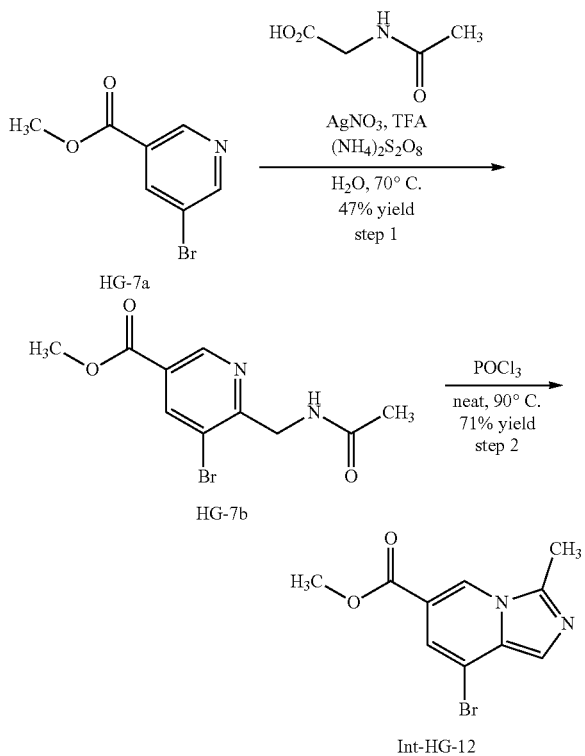

Step 1: Synthesis of methyl 6-(acetamidomethyl)-5-bromopyridine-3-carboxylate (HG-7b)

A round bottom flask was charged with methyl 5-bromopyridine-3-carboxylate (HG-7a) (1.00 g, 4.63 mmol), N-acetylglycine (916 mg, 7.82 mmol), and $AgNO_3$ (78.6 mg, 0.463 mmol). The flask was purged with Ar and then $H_2O$ (8.25 mL) and TFA (106 mg, 0.926 mmol) were added. The mixture was heated to 70° C. and a solution of $(NH_4)_2S_2O_8$ (1.90 g, 8.33 mmol) in $H_2O$ (2.75 ml) was added dropwise over 30 min. The reaction was stirred at 70° C. for 30 min. LCMS analysis showed consumption of the starting material with formation of the desired product mass. The mixture was cooled to room temperature and extracted with EtOAc. The aqueous layer was basified to pH ~9 by addition of NH₄OH and then extracted with EtOAc. The combined organic extracts were washed with aqueous NaHCO₃ (1 M, 10 mL), dried over MgSO₄, filtered, and concentrated to dryness. The residue was purified by flash chromatography (40 g SiO₂, 100% heptane then 100% EtOAc then 10% MeOH/EtOAc) to provide methyl 6-(acetamidomethyl)-5-bromopyridine-3-carboxylate (HG-7b) (619 mg, 47% yield) as a white solid. $^1$H NMR (400 MHz, CDCl₃) δ 9.07 (d, J=1.7 Hz, 1H), 8.46 (d, J=1.8 Hz, 1H), 7.08 (br s, 1H), 4.68 (d, J=4.3 Hz, 2H), 3.98 (s, 3H), 2.14 (s, 3H).

Step 2: Synthesis of methyl 8-bromo-3-methylimidazo[1,5-a]pyridine-6-carboxylate (Int-HG-12)

A mixture of methyl 6-(acetamidomethyl)-5-bromopyridine-3-carboxylate (HG-7b) (300 mg, 1.04 mmol) and POCl₃ (7.05 g, 46.0 mmol) was stirred at 90° C. After 1 h, LCMS analysis showed consumption of the starting material with formation of the desired product mass. The mixture was diluted with H₂O, basified with aqueous K₂CO₃ (1 M, 50 mL), and extracted with DCM (3×). The combined organic layers were dried over MgSO₄, filtered, and concentrated. The residue was purified by flash chromatography (12 g SiO₂, 100% heptane then 10% MeOH/EtOAc) to provide methyl 8-bromo-3-methylimidazo[1,5-a]pyridine-6-carboxylate (Int-HG-12) (200 mg, 71% yield) as a yellow solid. $^1$H NMR (400 MHz, CDCl₃) δ 8.76 (br s, 1H), 7.82 (s, 1H), 7.77 (br s, 1H), 4.02 (s, 3H), 3.13 (br s, 3H).

Preparation of 6-bromo-1-methyl-1H-indazole-4-carboxylic acid (Int-HG-13) According to Scheme HG-8

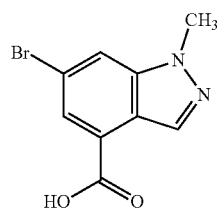

Scheme HG-8

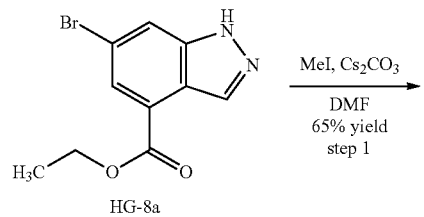

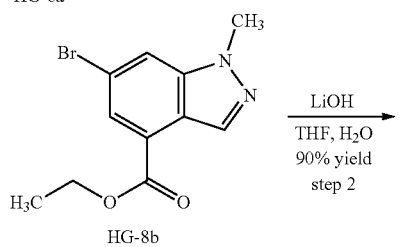

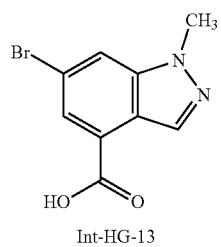

Int-HG-13

Step 1: Synthesis of ethyl 6-bromo-1-methyl-1H-indazole-4-carboxylate (HG-8b)

To a solution of ethyl 6-bromo-1H-indazole-4-carboxylate (HG-8a) (1.05 g, 4.12 mmol) and Cs₂CO₃ (2.68 g, 8.23 mmol) in DMF (20.0 mL) was added iodomethane (744 mg, 5.24 mmol). The mixture was stirred at room temperature for 3 h. TLC analysis (1:4 EtOAc/petroleum ether) showed consumption of the starting material. The reaction was quenched with H₂O (30 mL) and extracted with EtOAc (2×50 mL). The combined organic layers were dried over Na₂SO₄, filtered, and concentrated. The residue was purified by flash chromatography (12 g Si₂, 0-50% EtOAc/petroleum ether) to provide ethyl 6-bromo-1-methyl-1H-indazole-4-carboxylate (HG-8b) (680 mg, 65% yield) as a pink solid. $^1$H NMR (400 MHz, CDCl₃) δ 8.43 (s, 1H), 8.01 (d, J=1.2 Hz, 1H), 7.78 (d, J=1.1 Hz, 1H), 4.08 (s, 3H), 4.02 (s, 3H).

Step 2: Synthesis of 6-bromo-1-methyl-1H-indazole-4-carboxylic acid (Int-HG-13)

To a solution of 6-bromo-1-methyl-1H-indazole-4-carboxylate (HG-8b) (680 mg, 2.53 mmol) in THF (10.0 mL) was added LiOH·H₂O (848 mg, 20.2 mmol) and H₂O (4.0 mL). The reaction was stirred at room temperature for 16 h. TLC analysis (1:4 EtOAc/petroleum ether) showed consumption of the starting material. The mixture was concentrated to dryness. The residue was acidified with 1 N HCl to pH ~3. The mixture was extracted with EtOAc (3×25 mL). The combined organic layers were dried over Na₂SO₄, filtered, and concentrated to provide 6-bromo-1-methyl-1H-indazole-4-carboxylic acid (Int-HG-13) (580 mg, 90% yield) as a pale-yellow solid. $^1$H NMR (400 MHz, CD₃OD) δ 8.39 (s, 1H), 8.07 (s, 1H), 7.94 (d, J=1.6 Hz, 1H), 4.08 (s, 3H).

Preparation of 6-bromo-1-methyl-1H-indazole-4-carbothioamide (Int-HG-14) According to Scheme HG-9

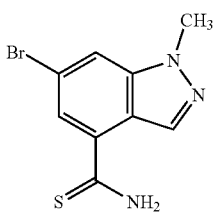

139

Scheme HG-9

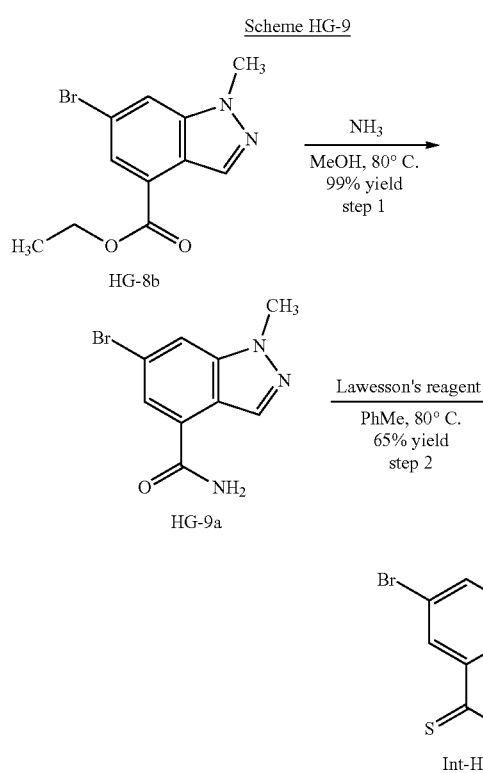

140

Preparation of methyl 4-bromo-1-(triphenylmethyl)-1H-indazole-6-carboxylate (Int-HG-15) According to Scheme HG-10

Scheme HG-10

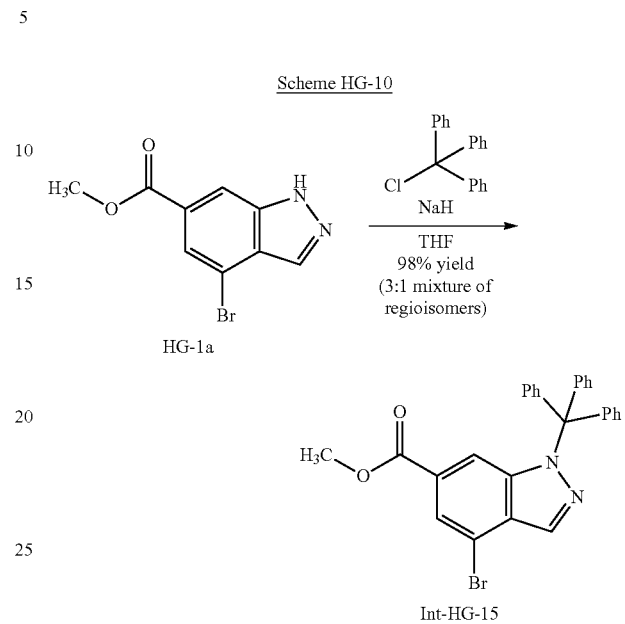

Step 1: Synthesis of 6-bromo-1-methyl-1H-indazole-4-carboxamide (HG-9a)

A suspension of ethyl 6-bromo-1-methyl-1H-indazole-4-carboxylate (HG-8b) (148 mg, 0.550 mmol) in methanolic NH$_3$ (7 N in MeOH, 2.5 mL) was stirred at 80° C. for 36 h. LCMS analysis showed consumption of the starting material. The mixture was concentrated to dryness to provide 6-bromo-1-methyl-1H-indazole-4-carboxamide (HG-9a) (138 mg, 99% yield) as a white solid. $^1$H NMR (400 MHz, DMSO-d$_6$) δ 8.40 (d, J=1.0 Hz, 1H), 8.23 (s, 1H), 8.18 (br s, 1H), 7.82 (d, J=1.5 Hz, 1H), 7.64 (br s, 1H), 4.11 (s, 3H); m/z (ESI+) for (C$_9$H$_8$BrN$_3$O), 253.7 (M+H)$^+$.

Step 2: Synthesis of 6-bromo-1-methyl-1H-indazole-4-carbothioamide (Int-HG-14)

To a suspension of 6-bromo-1-methyl-1H-indazole-4-carboxamide (HG-9a) (135 mg, 0.531 mmol) in anhydrous PhMe (3.0 mL) was added Lawesson's reagent (215 mg, 0.531 mmol). The mixture was stirred at 80° C. for 2 h. LCMS analysis showed consumption of the starting material. The mixture was diluted with H$_2$O (5 mL) and extracted with EtOAc (5×15 mL). The combined organic layers were washed with saturated aqueous NaHCO$_3$ (2×5 mL), dried over Na$_2$SO$_4$, filtered, and concentrated. The residue was triturated with DCM to provide 6-bromo-1-methyl-1H-indazole-4-carbothioamide (Int-HG-14) (93.5 mg, 65% yield) as a yellow solid. $^1$H NMR (400 MHz, DMSO-d$_6$) δ 10.20 (br s, 1H), 9.73 (br s, 1H), 8.33 (d, J=1.0 Hz, 1H), 8.18 (t, J=1.2 Hz, 1H), 7.51 (d, J=1.5 Hz, 1H), 4.11 (s, 3H); m/z (ESI+) for (C$_9$H$_8$BrN$_3$O), 269.6 (M+H)$^+$.

A solution of methyl 4-bromo-1H-indazole-6-carboxylate (HG-1a) (10.0 g, 39.2 mmol) in THF (200 mL) was cooled to 0° C. and NaH (60% dispersion in mineral oil, 1.88 g, 47.0 mmol) was added. The mixture was stirred at 15° C. and then triphenylmethyl chloride (13.1 g, 47.0 mmol) was added. The reaction was stirred at 15° C. for 2 h. TLC analysis showed consumption of the starting material. The mixture was diluted with H$_2$O (200 mL) and extracted with EtOAc (2×200 mL). The combined organics were washed with brine (100 mL), dried over anhydrous Na$_2$SO$_4$, filtered, and concentrated. The residue was purified by flash chromatography (120 g SiO$_2$, 0-15% EtOAc/petroleum ether) to provide methyl 4-bromo-1-(triphenylmethyl)-1H-indazole-6-carboxylate (Int-HG-15) (19.1 g, 98% yield) as a 3:1 mixture of N-1 and N-2 regioisomers, which was taken on without further purification. $^1$H NMR (400 MHz, CDCl$_3$) δ 8.67-8.12 (m, 1H), 8.06-7.80 (m, 1H), 7.51-7.03 (m, 16H), 4.21-3.45 (m, 3H).

Preparation of methyl 2-bromo-3-(6-chloro-1-methyl-1H-pyrazolo[4,3-c]pyridin-4-yl)-3-oxopropanoate (Int-HG-16) According to Scheme HG-11

Scheme HG-11

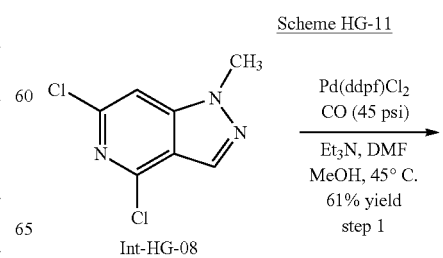

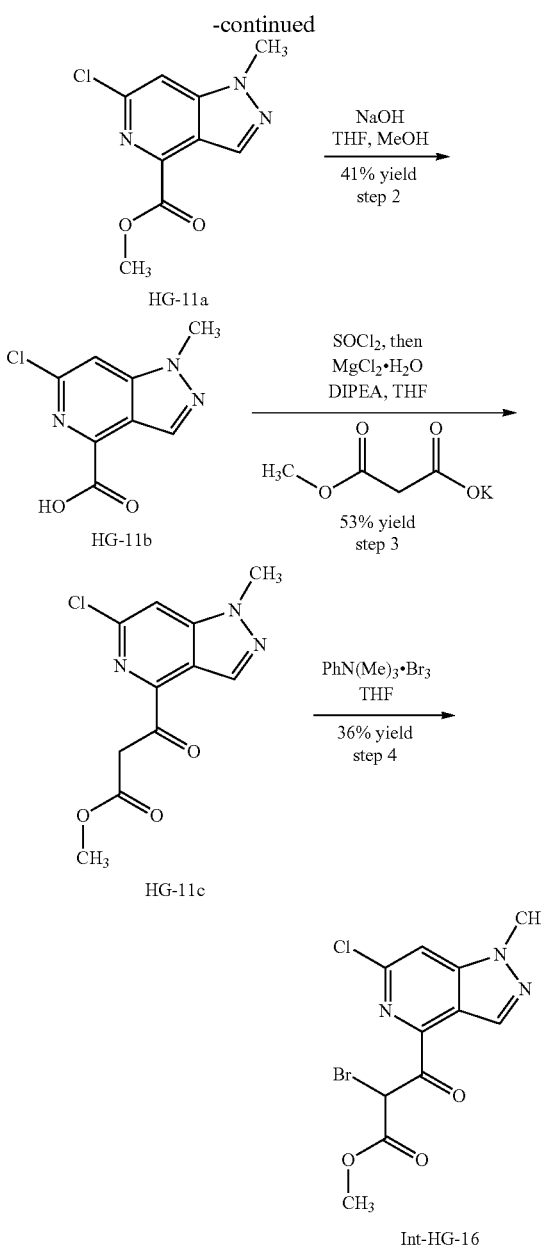

Step 1: Synthesis of methyl 6-chloro-1-methyl-1H-pyrazolo[4,3-c]pyridine-4-carboxylate (HG-11a)

To a solution of 4,6-dichloro-1-methyl-1H-pyrazolo[4,3-c]pyridine (Int-HG-08) (50.0 mg, 0.25 mmol) in MeOH (20 mL) was added Pd(dppf)Cl$_2$ (36.2 mg, 0.0495 mmol) and TEA (0.103 mL, 0.742 mmol). The reaction mixture was heated at 45° C. under CO gas (45 psi) for 6 h. The reaction mixture was allowed to cool gradually to rt followed by filtration through a pad of celite. The filtrate was concentrated in vacuo. The crude residue was purified by flash chromatography (12 g SiO$_2$, 0-30% EtOAc in Hept.) to afford the title compound methyl 6-chloro-1-methyl-1H-pyrazolo[4,3-c]pyridine-4-carboxylate (HG-11a) (34 mg, 61% yield) as a white solid. $^1$H NMR (400 MHz, DMSO-d6) δ=8.55 (s, 1H), 8.22 (s, 1H), 4.11 (s, 3H), 3.99 (s, 3H).

Step 2: Synthesis of 6-chloro-1-methyl-1H-pyrazolo[4,3-c]pyridine-4-carboxylic acid (HG-11b)

To a suspension of methyl 6-chloro-1-methyl-1H-pyrazolo[4,3-c]pyridine-4-carboxylate (HG-11a) (345 mg, 1.53 mmol) in THF (4 mL) and MeOH (4 mL) was added 1M NaOH (3.32 mL). The reaction was stirred at rt for 1.5 h. The solution was concentrated to afford a white solid which was further dried under high vacuum. The solid was dissolved in 1N HCl (2 mL) and further diluted with H$_2$O. Upon stirring, solid precipitate formed which was collected by filtration. The filtered solids were then dried under high vacuum to afford the title compound 6-chloro-1-methyl-1H-pyrazolo[4,3-c]pyridine-4-carboxylic acid (HG-11b) (132 mg, 41% yield) as a light yellow solid. $^1$H NMR (400 MHz, DMSO-d6) δ=13.88 (br s, 1H), 8.50 (d, J=0.8 Hz, 1H), 8.18 (d, J=0.8 Hz, 1H), 4.10 (s, 3H).

Step 3: Synthesis of methyl 3-(6-chloro-1-methyl-1H-pyrazolo[4,3-c]pyridin-4-yl)-3-oxopropanoate (HG-11c)

A flask (flask A) was charged with methyl potassium malonate (104 mg, 0.665 mmol), magnesium chloride hydrate (54.9 mg, 0.576 mmol) and DIPEA (0.193 mL, 1.11 mmol) in THF (5 mL). The reaction stirred at rt for 2 h.

In a separate flask (flask B) was added 6-chloro-1-methyl-1H-pyrazolo[4,3-c]pyridine-4-carboxylic acid (HG-11b) (100 mg, 0.443 mmol) and thionyl chloride (3.0 mL). The reaction was heated at 65° C. for 2 h. The solution was concentrated to remove excess thionyl chloride. The residue was cooled to 0° C. in an ice bath. At this stage, the mixture from flask A was added to flask B and the mixture stirred at 0° C. for 2 min. The reaction was then heated at to 70° C. for 2 h. The solution was removed from heating and allowed to cool to rt. To the solution was added 1N HCl and the mixture transferred to a separatory funnel. The solution was extracted with 3 portions DCM and the combined extracts were concentrated in vacuo. The crude residue was purified via flash chromatography (24 g SiO$_2$, Isco, 0-100% EtOAc) to afford the title compound methyl 3-(6-chloro-1-methyl-1H-pyrazolo[4,3-c]pyridin-4-yl)-3-oxopropanoate (HG-11c) (120 mg, 53% yield) as a white solid. $^1$H NMR (400 MHz, DMSO-d6) δ=8.61 (s, 1H), 8.29 (s, 1H), 4.25 (s, 2H), 4.12 (s, 3H), 3.65 (s, 3H).

Step 4: Synthesis of methyl 2-bromo-3-(6-chloro-1-methyl-1H-pyrazolo[4,3-c]pyridin-4-yl)-3-oxopropanoate (Int-HG-16)

To a solution of methyl 3-(6-chloro-1-methyl-1H-pyrazolo[4,3-c]pyridin-4-yl)-3-oxopropanoate (HG-11c) (118 mg, 0.441 mmol) in THF was added trimethylphenylammonium tribromide (182 mg, 0.485 mmol). The reaction was stirred at rt overnight during which precipitation occurred. The solids were filtered and the filtrate transferred to a separatory funnel with DCM followed by dilution with 10% Na$_2$S2. The phases were separated and the aqeuous phase was extracted with 3 portions DCM. The combined organic extracts were concentrated in vacuo. The crude residue was purified via flash chromatography (24 g SiO$_2$, Isco, 0-30% EtOAc in DCM) to afford the desired product with significant impurities. The material was resubmitted to purification by flash chromatography (24 g SiO$_2$, Isco, 100% DCM to 50% EtOAc in DCM) to afford the title compound methyl 2-bromo-3-(6-chloro-1-methyl-1H-pyrazolo[4,3-c]pyridin-4-yl)-3-oxopropanoate (Int-HG-16) (55 mg, 36% yield) as a clear oil. $^1$H NMR (400 MHz, DMSO-d6) δ=8.65 (d, J=0.8 Hz, 1H), 8.33 (d, J=1.2 Hz, 1H), 6.44 (s, 1H), 4.13 (s, 3H), 3.73 (s, 3H); m/z (APCI+) for ($C_{11}H_9BrN_3O_3$), 346.0 (M+H)$^+$ observed.

Preparation of methyl 2-bromo-3-(6-chloro-1-methyl-1H-pyrazolo[4,3-c]pyridin-4-yl)-3-oxopropanoate (Int-HG-17) According to Scheme HG-12 product (Rf=0.29). The reaction was then transferred to 100 mL beaker, rinsing the reaction vial with DCM, and sat. aqueous sodium bicarbonate was added dropwise with magnetic stirring until effervescence ceased. After this, the contents of this beaker were transferred to a separatory funnel, where the organic layer was separated. Subsequently, the aqueous layer was extracted with 4×100 mL 3:1 DCM/iPrOH and 2×150 mL DCM. The combined organics were

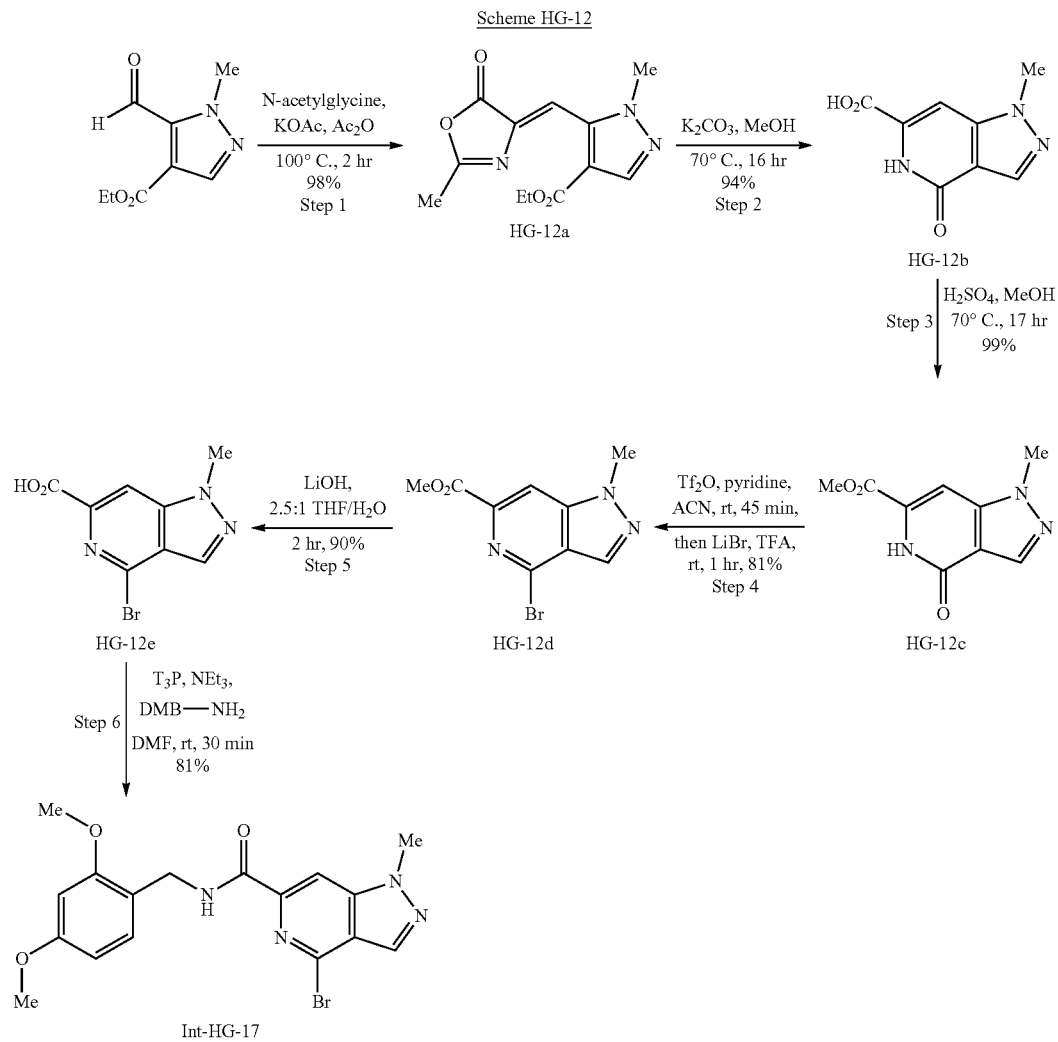

Step 1: Synthesis of ethyl 1-methyl-5-{[(4Z)-2-methyl-5-oxo-1,3-oxazol-4-ylidene]methyl}pyrazole-4-carboxylate (HG-12a)

To a solution of ethyl 5-formyl-1-methyl-1H-pyrazole-4-carboxylate (10.7 g, 58.6 mmol) and N-acetylglycine (10.3 g, 88.0 mmol, 1.5 eq) in acetic anhydride (15 mL, 4 M) at room temperature was added potassium acetate (9.09 g, 88.0 mmol, 1.5 eq), and to this slurry was added an additional 5 mL Ac$_2$O to re-induce stirring. This was then topped with a Findenser and heated to 100° C. During heating, the white, turbid suspension became a clear yellow solution, and after 10 minutes, had become a brown solution. After 1 hr, the reaction was cooled to room temperature. TLC analysis (2:1 heptane/EtOAc, KMnO4 stain) showed consumption of starting material (Rf=0.61) concomitant with formation of dried over MgSO$_4$, filtered, and solvent removed under reduced pressure. The resultant dark brown residue was dissolved in about 5 mL DCM. To this was added MTBE dropwise (about 5 mL), and this mixture was subsequently poured into a flask containing 200 mL heptane. Upon sonication, a yellow solid precipitated from solution and was filtered off under reduced pressure. The mother liquor was then left to stand at 0° C. for 2 h, whereupon another crop of product crashed out and was again filtered under reduced pressure. These two batches were combined to give the title compound ethyl 1-methyl-5-{[(4Z)-2-methyl-5-oxo-1,3-oxazol-4-ylidene]methyl}pyrazole-4-carboxylate (HG-12a) as an amorphous, light yellow solid (15.2 g, 98%). $^1$H NMR (400 MHz, Chloroform-d) δ 7.93 (s, 1H), 7.53 (s, 1H), 4.29 (q, J=7.1 Hz, 2H), 3.98 (s, 3H), 1.34 (t, J=7.1 Hz, 3H).

Step 2: Synthesis of 1-methyl-4-oxo-4,5-dihydro-1H-pyrazolo[4,3-c]pyridine-6-carboxylic acid (HG-12b)

To ethyl 1-methyl-5-{[(4Z)-2-methyl-5-oxo-1,3-oxazol-4-ylidene]methyl}pyrazole-4-carboxylate (HG-12a) (15.2 g, 57.8 mmol) in methanol (57.8 mL, 1 M) was added potassium carbonate (16.8 g, 116 mmol, 2 eq) and the vessel was subsequently capped and heated to 70° C. After stirring for 16 h, the previously deep brown turbid solution had lightened to a tan-brown. Based on LCMS, all the starting material was consumed, so the cooled mixture was filtered under reduced pressure and filter cake of washed with MeOH and MTBE. Addition of MTBE to the resultant filtrate led to precipitation of additional solid which was refiltered using the same apparatus. The solid filter cake was then suspended in $H_2O$ and conc. HCl was added to acidify to pH 1. A tan solid precipitated which was filtered off under reduced pressure, after which the filtrate was diluted with 1:1 MeOH/MTBE and filtered again under reduced pressure. These two batches were combined to afford the title compound 1-methyl-4-oxo-4,5-dihydro-1H-pyrazolo[4,3-c]pyridine-6-carboxylic acid (HG-12b) as a tan, amorphous solid (10.46 g, 94% yield). $^1$H NMR (400 MHz, DMSO-d6) δ 10.56 (s, 1H), 8.11 (d, J=0.9 Hz, 1H), 7.40 (d, J=0.9 Hz, 1H), 4.03 (s, 3H).

Step 3: Synthesis of methyl 1-methyl-4-oxo-4,5-dihydro-1H-pyrazolo[4,3-c]pyridine-6-carboxylate (HG-12c)

To 1-methyl-4-oxo-4,5-dihydro-1H-pyrazolo[4,3-c]pyridine-6-carboxylic acid (HG-12b) (10.46 g, 54.17 mmol) in methanol (40 mL, 1.4 M) was added conc. sulfuric acid (90 mmol, 5 mL, 2 eq) dropwise. This led to exotherm on the addition of each drop. The resultant yellow slurry was heated to 70° C. After 17 h, the reaction was cooled to room temperature, at which point starting material appeared to have been consumed and a white, microcrystalline solid began to precipitate from the solution. The reaction mixture was filtered under reduced pressure and the filter cake washed with water. This first batch was collected, after which the filtrate was diluted with 5 mL ACN, 5 mL MTBE and 10 mL EtOH before allowing to sit at 0° C. After 2 h, the white microcrystals which precipitated from solution were collected via vacuum filtration and combined with the previous batch to afford the title compound methyl 1-methyl-4-oxo-4,5-dihydro-1H-pyrazolo[4,3-c]pyridine-6-carboxylate (HG-12c) as a white crystalline solid (11.1 g, 99.0%). $^1$H NMR (400 MHz, Methanol-d4) δ 8.20 (d, J=0.9 Hz, 1H), 7.56 (d, J=0.9 Hz, 1H), 4.12 (s, 3H), 4.04 (s, 3H).

Step 4: Synthesis of methyl 4-bromo-1-methyl-1H-pyrazolo[4,3-c]pyridine-6-carboxylate (HG-12d)

To methyl 1-methyl-4-oxo-4,5-dihydro-1H-pyrazolo[4,3-c]pyridine-6-carboxylate (HG-12c) (11.1 g) in acetonitrile (53.9 mL, 1.0 M) was added pyridine (6.51 mL, 80.8 mmol, 1.5 eq) in one portion, followed by triflic anhydride (13.6 mL, 80.8 mmol, 1.5 eq) portionwise in approximately 1 mL portions. After addition of 6 mL, the solution changed from yellow to red (though remaining turbid), and after addition of the remaining triflic anhydride, the reaction turned yellow again and began to clear. After 45 min, LCMS showed consumption of starting material along with clean formation of triflate. To the reaction mixture was then added lithium bromide (23.4 g, 269 mmol, 5 eq) and trifluoroacetic acid (5.23 mL, 59.3 mmol, 1.1 eq) to produce an orange suspension. After 1 hr from this point, LCM analysis showed disappearance of triflate and conversion to bromide. The reaction mixture was then poured slowly into an Erlenmeyer flask containing 200 mL sat. $NaHCO_3$ with magnetic stirring, and after cessation of the biphasic mixture was transferred to a separatory funnel containing 800 mL EtOAc, shaken, and aqueous layer discarded. The organic layer was then washed once with sodium thiosulfate to decolourize, and the two layers separated. The organics were dried over $MgSO_4$, filtered and solvent removed under reduced pressure. The resultant brown oil was dissolved in 10 mL DCM, and to this was added 10 mL MeCN and 10 mL acetone. This cloudy solution was left at 0° C. overnight, after which the product had precipitated and was collected via vacuum filtration to afford the title compound methyl 4-bromo-1-methyl-1H-pyrazolo[4,3-c]pyridine-6-carboxylate (HG-12d) as a tan solid (11.77 g, 81%). $^1$H NMR (400 MHz, Chloroform-d) δ 8.23 (1H, d, J=1 Hz), 8.14 (1H, d, J=1.0 Hz), 4.16 (3H, s), 4.05 (3H, s).

Step 5: Synthesis of 4-bromo-1-methyl-1H-pyrazolo[4,3-c]pyridine-6-carboxylic acid (HG-12e)

4-bromo-1-methyl-1H-pyrazolo[4,3-c]pyridine-6-carboxylate (HG-12d) (1333 mg, 4.935 mmol) was added to a flask containing 5 mL tetrahydrofuran and 2 mL $H_2O$. To this solution was added lithium hydroxide (177 mg, 7.40 mmol, 1.5 eq) at room temperature and allowed to stir. After 2 h, LCMS analysis showed consumption of starting material concomitant with product formation. The reaction mixture was acidified to pH 1 with conc. HCl, at which point it became cloudy. The resultant acidic suspension was left at 0° C. for 1 hr, after which the product was observed to have precipitated. This solid was collected using vacuum filtration to afford the title compound 4-bromo-1-methyl-1H-pyrazolo[4,3-c]pyridine-6-carboxylic acid (HG-12e) as a white semi-crystalline solid (1.15 g, 90%). $^1$H NMR (400 MHz, DMSO-d6) δ 13.43 (1H, br s), 8.49 (1H, d, J=0.8 Hz), 8.32 (1H, d, J=0.8 Hz), 4.18 (3H, s)

Step 6: Synthesis of 4-bromo-N-(2,4-dimethoxybenzyl)-1-methyl-1H-pyrazolo[4,3-c]pyridine-6-carboxamide (Int-HG-17)

To a suspension of 4-bromo-1-methyl-1H-pyrazolo[4,3-c]pyridine-6-carboxylic acid (HG-12e) (1.90 g, 9.79 mmol) in DMF (2 mL) was added first triethylamine (4.13 mL, 29.4 mmol), then dimethoxybenzylamine (1.64 g, 9.79 mmol), the latter of which led to a clear solution. To the solution was added $T_3P$ (8.60 mL, 50% in EtOAc, 14.7 mmol) after which the solution had turned yellow and warmed significantly. After 30 min, LCMS analysis of the turbid yellow suspension showed consumption of starting material and formation of product. This was diluted with 5 mL EtOAc with magnetic stirring, then filtered under reduced pressure. The solid was washed with EtOAc and dried to afford the title compound 4-bromo-N-(2,4-dimethoxybenzyl)-1-methyl-1H-pyrazolo[4,3-c]pyridine-6-carboxamide (Int-HG-17) as a white crystalline solid (3.18 g, 81%). $^1$H NMR (400 MHz, Chloroform-d) δ 8.53-8.38 (1H, m), 8.26 (1H, d, J=1 Hz), 8.09 (1H, d, J=1.0 Hz), 7.28 (1H, s), 6.50 (2H, dd, J=8.2, 2.4 Hz), 6.45 (2H, dd, J=8.2, 2.4 Hz), 4.63 (2H, d, J=6.1 Hz), 4.13 (3H, s), 3.90 (3H, s), 3.80 (3H, s).

Preparation of N-[(2,4-dimethoxyphenyl)methyl]-4-{4-[(4-methoxyphenyl)methyl]-4H-1,2,4-triazol-3-yl}-1-methyl-1H-pyrazolo[4,3-c]pyridine-6-carboxamide (Int-HG-18) According to Scheme HG-13

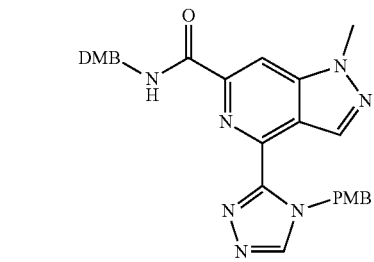

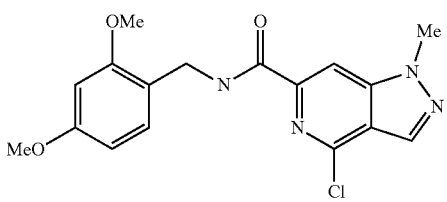 [SMILES: COc1ccc(CNC(=O)c2cc3c(cnn3C)c(Cl)n2)c(OC)c1]

Scheme HG-13

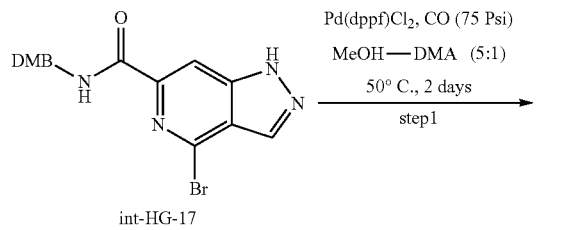

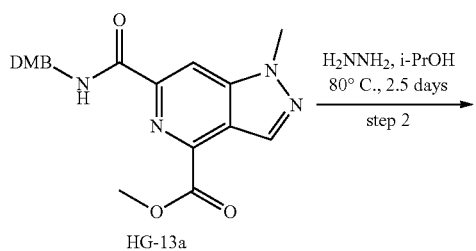

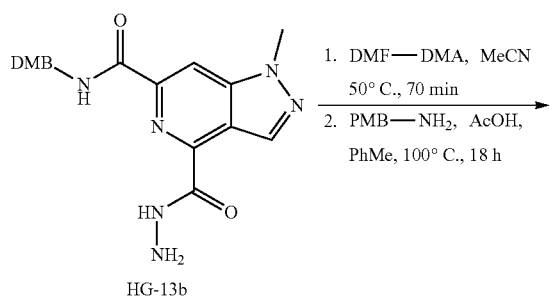

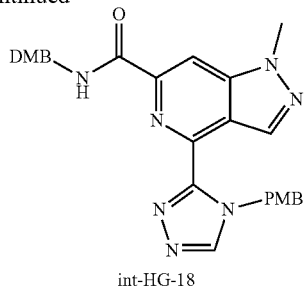

int-HG-18

Step 1: Synthesis of methyl 6-{[(2,4-dimethoxyphenyl)methyl]carbamoyl}-1-methyl-1H-pyrazolo[4,3-c]pyridine-4-carboxylate (HG-13a)

A suspension of 4-bromo-N-[(2,4-dimethoxyphenyl)methyl]-1H-pyrazolo[4,3-c]pyridine-6-carboxamide (Int-HG-17) (1.5 g, 3.7 mmol), Pd(dppf)Cl$_2$ (0.406 g, 0.555 mmol) and triethylamine (1.12 g, 11.1 mmol, 1.55 mL) in 20 mL MeOH and 5 mL DMA was carbonylated under 75 psi of CO for 2 days at 50° C. The reaction was removed from the heat and allowed to cool gradually to rt. The suspension was filtered through a pad of celite and the solids washed with DCM. The filtrate was concentrated and the crude residue was purified by ISCO (silica, 40 g, 0-60% Ethyl acetate in Heptane, then 10% DCM/10% MeOH in EtOAc) to afford the tile compound methyl 6-{[(2,4-dimethoxyphenyl)methyl]carbamoyl}-1-methyl-1H-pyrazolo[4,3-c]pyridine-4-carboxylate (HG-13a) (1074 mg, 77%) as a yellow solid. $^1$H NMR (400 MHz, DMSO-d6) δ ppm 8.84 (t, J=6.05 Hz, 1H), 8.61 (s, 2H), 7.16 (d, J=8.20 Hz, 1H), 6.62 (d, J=2.34 Hz, 1H), 6.49 (dd, J=8.59, 2.34 Hz, 1H), 4.51 (d, J=6.24 Hz, 2H), 4.22 (s, 3H), 4.03 (s, 3H), 3.88 (s, 3H), 3.75 (s, 3H). m/z (ESI+) for (C$_{19}$H$_{20}$N$_4$O$_5$), 385.2 (M+H)$^+$ observed.

Step 2: Synthesis of N-[(2,4-dimethoxyphenyl)methyl]-4-(hydrazinecarbonyl)-1-methyl-1H-pyrazolo[4,3-c]pyridine-6-carboxamide (HG-13b)

A suspension of methyl 6-{[(2,4-dimethoxyphenyl)methyl]carbamoyl}-1-methyl-1H-pyrazolo[4,3-c]pyridine-4-carboxylate (HG-13a) (286 mg, 0.744 mmol) and hydrazine, dihydrate (119 mg, 3.72 mmol, 117 μL) in 20 mL isopropanol was heated at 80° C. for 2.5 days. The solid was collected and washed with MeOH, dried to afford the title compound methyl 6-{[(2,4-dimethoxyphenyl)methyl]carbamoyl}-1-methyl-1H-pyrazolo[4,3-c]pyridine-4-carboxylate (HG-13b) (267 mg, 93% yield) as a grey solid. m/z (ESI+) for (C$_{18}$H$_{21}$N$_6$O$_4$), 383.2 (M+H)$^+$ observed.

Step 3: N-[(2,4-dimethoxyphenyl)methyl]-4-{4-[(4-methoxyphenyl)methyl]-4H-1,2,4-triazol-3-yl}-1-methyl-1H-pyrazolo[4,3-c]pyridine-6-carboxamide (Int-HG-18)

A suspension of methyl 6-{[(2,4-dimethoxyphenyl)methyl]carbamoyl}-1-methyl-1H-pyrazolo[4,3-c]pyridine-4-carboxylate (HG-13b) (267 mg, 0.695 mmol) and DMF-DMA (91.0 mg, 0.764 mmol, 0.102 mL) in 15 mL acetonitrile was heated at 50° C. for 70 min. The volatiles were removed, the crude product was triturated with toluenex3 to afford 325 mg of N-[(2,4-dimethoxyphenyl)

methyl]-4-{(2E)-2-[(dimethylamino)methylidene]hydrazinecarbonyl}-1-methyl-1H-pyrazolo[4,3-c]pyridine-6-carboxamide as a grey solid. To a suspension of N-[(2,4-dimethoxyphenyl)methyl]-4-{(2E)-2-[(dimethylamino)methylidene]hydrazinecarbonyl}-1-methyl-1H-pyrazolo[4,3-c]pyridine-6-carboxamide (283 mg, 0.644 mmol) in toluene, which was degassed for 5 min, was added p-methoxybenzylamine (PMB-NH$_2$) (0.168 mL, 1.29 mmol) and acetic acid (92.1 µL, 1.61 mmol). The reaction was heated at 99° C. overnight. The reaction mixture was filtered through a pad of celite and the filtrate concentrated in vacuo. The crude product was purified by ISCO (silica, 24 g, 0-100% EtOAc in Heptane then followed by 1:1:8=DCM:MeOH:EtOAc) to afford the title compound N-[(2,4-dimethoxyphenyl)methyl]-4-{4-[(4-methoxyphenyl)methyl]-4H-1,2,4-triazol-3-yl}-1-methyl-1H-pyrazolo[4,3-c]pyridine-6-carboxamide (Int-HG-18) (227 mg, 68% yield) as an off-white solid. $^1$H NMR (400 MHz, DMSO-d$_6$) δ ppm 8.90 (s, 1H), 8.71 (d, J=1.17 Hz, 1H) 8.37-8.47 (m, 2H), 6.94-7.03 (m, 3H), 6.68-6.76 (m, 2H), 6.55 (d, J=2.34 Hz, 1H), 6.40 (dd, J=8.20, 2.34 Hz, 1H), 5.90 (s, 2H), 4.42 (d, J=6.24 Hz, 2H), 4.20 (s, 3H), 3.80 (s, 3H), 3.73 (s, 3H), 3.60 (s, 3H). m/z (ESI+) for (C$_{27}$H$_{27}$N$_7$O$_4$), 514.4 (M−H).

Preparation of 4,6-dichloro-1-[(2,2-dimethyl-1,3-dioxan-5-yl)methyl]-1H-pyrazolo[4,3-c]pyridine (Int-HG-19) According to Scheme HG-14

Scheme HG-14

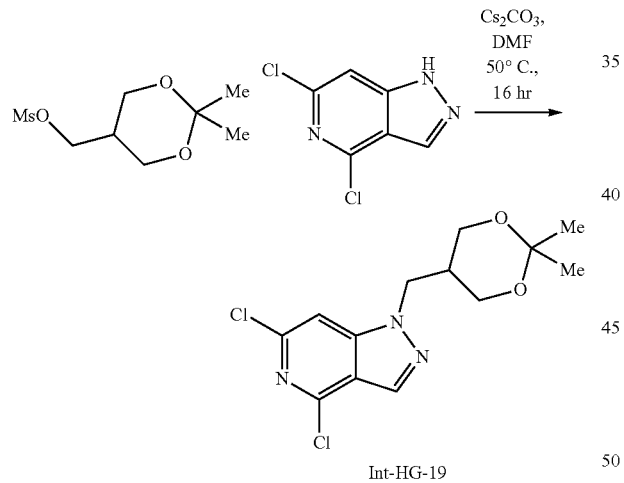

Int-HG-19

To a solution of 4,6-dichloro-1H-pyrazolo[4,3-c]pyridine (1.40 g, 7.45 mmol) in DMF (14 mL) was added (2,2-dimethyl-1,3-dioxan-5-yl)methyl methanesulfonate (1.75 g, 7.82 mmol, 1.05 eq) and Cs$_2$CO$_3$ (4.85 g, 14.9 mmol, 2 eq). The resulting yellow reaction solution was stirred at 50° C. for 16 hr. At this time, LCMS analysis showed that the starting material was consumed completely, and the desired product was detected. The mixture was then filtered and the filter cake washed with 50 mL EtOAc. The filtrate was washed twice with 50 mL brine, dried over anhydrous sodium sulfate, filtered, and concentrated in vacuo to give a yellow oil, which was purified by Prep-TLC (petroleum ether:EtOAc=2:1) to afford the title compound 4,6-dichloro-1-[(2,2-dimethyl-1,3-dioxan-5-yl)methyl]-1H-pyrazolo[4,3-c]pyridine (Int-HG-19) (650 mg, 27.6%) as a yellow oil. $^1$H NMR (400 MHz, Chloroform-d) δ 8.14 (d, J=1.0 Hz, 1H), 7.39 (d, J=1.0 Hz, 1H), 4.60 (d, J=7.8 Hz, 2H), 4.08 (dd, J=12.6, 3.0 Hz, 1H), 3.50 (ddd, J=11.3, 2.8, 1.5 Hz, 2H), 2.20 (tq, J=7.7, 2.9 Hz, 1H), 2.04 (s, 1H), 1.50 (s, 3H), 1.48 (s, 3H).

Preparation of 4-chloro-N-[(2,4-dimethoxyphenyl)methyl]-1-methyl-1H-pyrazolo[4,3-c]pyridine-6-carboxamide (Int-HG-20) According to Scheme HG-15

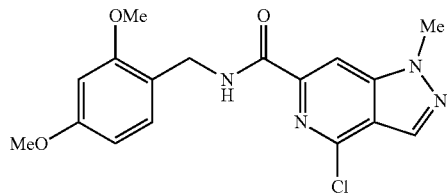 [SMILES: COc1ccc(CNC(=O)c2cc3c(cnn3C)c(Cl)n2)c(OC)c1]

Scheme HG-15

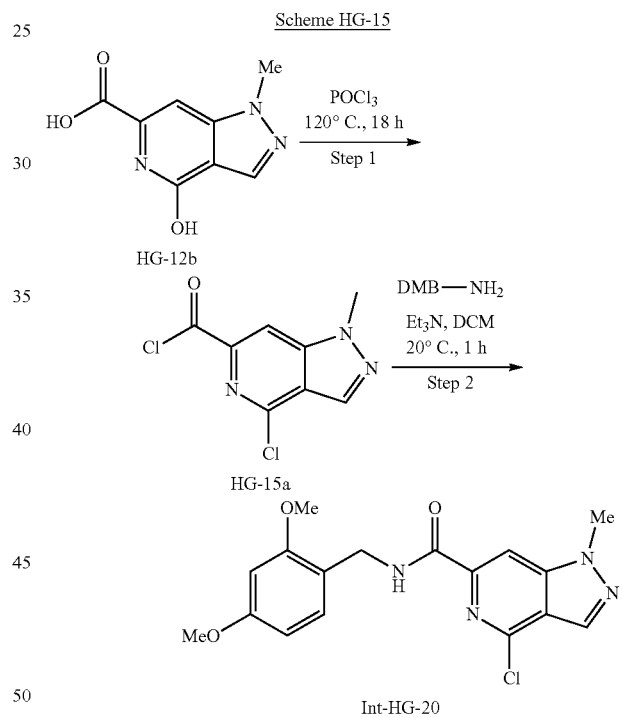

Int-HG-20

Step 1: Synthesis of 4-chloro-1-methyl-1H-pyrazolo[4,3-c]pyridine-6-carbonyl chloride (HG-15a)

To a yellow suspension of 4-hydroxy-1-methyl-1H-pyrazolo[4,3-c]pyridine-6-carboxylic acid (HG-12b) (1.25 g, 6.471 mmol) in anhydrous toluene (32 mL) was added POCl$_3$ (3.97 g, 25.9 mmol). The resulting mixture was heated at 100° C. and stirred for 41 h. The resulting yellow suspension was concentrated under vacuum to give a yellow solid (1.90 g). NMR analysis revealed significant starting material remained. The solid was re-dissolved in POCl$_3$ (5.0 mL) and heated to 120° C. The mixture was stirred for another 18 hours. The resulting brown mixture was concentrated under vacuum to afford the title compound 4-chloro- 1-methyl-1H-pyrazolo[4,3-c]pyridine-6-carbonyl chloride (HG-15a) as a dark brown gum which was used in the next step without further purification. m/z (ESI+) for ($C_9H_9ClN_3O_2$), 225.9 (M−HCl+MeOH)+ observed.

Step 2: Synthesis of 4-chloro-N-[(2,4-dimethoxyphenyl)methyl]-1-methyl-1H-pyrazolo[4,3-c]pyridine-6-carboxamide (Int-HG-20)

To a dark brown suspension of 4-chloro-1-methyl-1H-pyrazolo[4,3-c]pyridine-6-carbonyl chloride (HG-15a) (1.94 g, 3.23 mmol) in DCM (10 mL) was added triethylamine (1.96 g, 19.4 mmol). The resulting mixture was stirred at room temperature (20° C.) for 5 min, then 1-(2,4-dimethoxyphenyl)-methanamine (DMB-$NH_2$) (648 mg, 3.88 mmol) was added. The resulting mixture was stirred at temperature for 1 hr. The mixture was diluted with water (20 mL) and DCM (20 mL). The resulting suspension was filtered to remove solid precipitates. The phases were separated and the aqueous phase was extracted with DCM (15 mL×2). The combined organic extracts were dried ($Na_2SO_4$), filtered, and concentrated under vacuum. The crude residue was purified via column chromatography (35 g $SiO_2$, 12.5% EtOAc/petroleum ether to 75% EtOAc/petroleum ether) to afford the title compound 4-chloro-N-[(2,4-dimethoxyphenyl)methyl]-1-methyl-1H-pyrazolo[4,3-c]pyridine-6-carboxamide (Int-HG-20) (586 mg, 50%) as a light yellow solid. $^1$H NMR (400 MHz, CHLOROFORM-d) δ=8.42 (br t, J=5.3 Hz, 1H), 8.25 (d, J=1.0 Hz, 1H), 8.16 (d, J=0.9 Hz, 1H), 7.28 (d, J=8.1 Hz, 1H), 6.50 (d, J=2.4 Hz, 1H), 6.46 (dd, J=2.4, 8.3 Hz, 1H), 4.63 (d, J=6.0 Hz, 2H), 4.15 (s, 3H), 3.90 (s, 3H), 3.81 (s, 3H)

Preparation of ethyl 4-(6-{[(2,4-dimethoxyphenyl)methyl]carbamoyl}-1-methyl-1H-pyrazolo[4,3-c]pyridin-4-yl)-1,3-oxazole-5-carboxylate (Int-HG-21) According to Scheme HG-16

Scheme HG-16

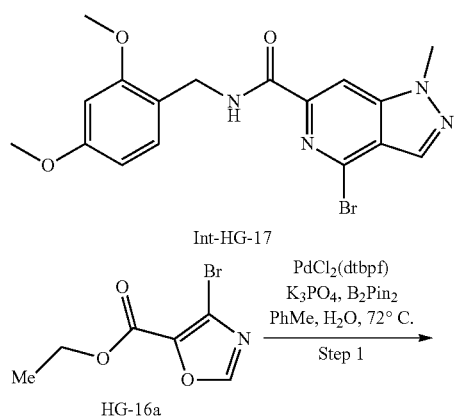

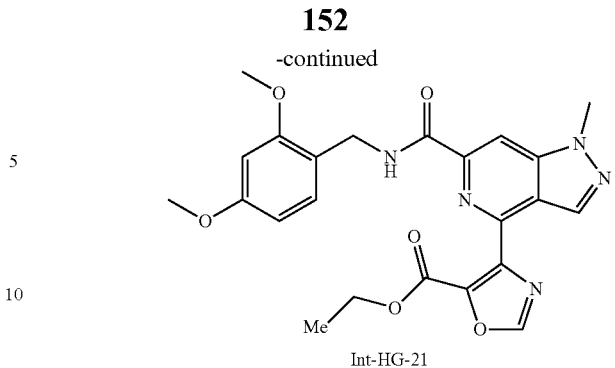

Step 1: Synthesis of ethyl 4-(6-{[(2,4-dimethoxyphenyl)methyl]carbamoyl}-1-methyl-1H-pyrazolo[4,3-c]pyridin-4-yl)-1,3-oxazole-5-carboxylate (Int-HG-21)

To a stirred mixture of compound 4-bromo-N-[(2,4-dimethoxyphenyl)methyl]-1-methyl-1H-pyrazolo[4,3-c]pyridine-6-carboxamide (Int-HG-17) (19 g, 46.89 mmol, 1 eq) in toluene (380 mL) and $H_2O$ (95 mL) was added compound ethyl 4-bromo-1,3-oxazole-5-carboxylate (HG-16a) (11.35 g, 51.57 mmol, 1.1 eq), $B_2Pin_2$ (23.81 g, 93.77 mmol, 2 eq) and $K_3PO_4$ (29.86 g, 140.66 mmol, 3 eq) at 20° C. The mixture was degassed and purged with $N_2$ three times. $PdCl_2$(dtbpf) (3.06 g, 4.69 mmol, 0.1 eq) was added at 20° C. The mixture was degassed and purged with $N_2$ an additional three times. The reaction mixture was heated to 72° C. (internal temperature) and stirred at 72° C. (internal temperature) for 4 hrs. LCMS analysis showed that starting material (Int-HG-17) was consumed and a new peak with the desired product mass was detected. The reaction mixture was removed from heating and allowed to cool to 20° C. The mixture was filtered through a pad of Celite. The organic layer of filtrate was separated. The filter cake was rinsed with DCM (300 mL×3). The combined organic phases were dried over $Na_2SO_4$, and filtered. The filtrate was concentrated under vacuum to give crude product. The crude product was purified by column chromatography on silica gel (eluted with THF in petroleum ether 0% 80%) to afford the title compound ethyl 4-(6-{[(2,4-dimethoxyphenyl)methyl]carbamoyl}-1-methyl-1H-pyrazolo[4,3-c]pyridin-4-yl)-1,3-oxazole-5-carboxylate (Int-HG-21) (8 g, 17.19 mmol 36% yield) as a brown solid. $^1$H NMR (400 MHz, CHLOROFORM-d) δ=9.01 (br t, J=5.4 Hz, 1H), 8.68 (d, J=0.9 Hz, 1H), 8.33 (d, J=0.9 Hz, 1H), 8.11 (s, 1H), 7.33 (d, J=8.3 Hz, 1H), 6.48 (d, J=2.3 Hz, 1H), 6.45 (dd, J=2.3, 8.4 Hz, 1H), 4.67 (d, J=5.9 Hz, 2H), 4.26-4.16 (m, 5H), 3.85 (s, 3H), 3.80 (s, 3H), 1.24 (t, J=7.2 Hz, 3H).

Preparation of methyl 4-bromo-1-methyl-1H-indole-6-carboxylate (Int-HG-07) According to Scheme HG-17

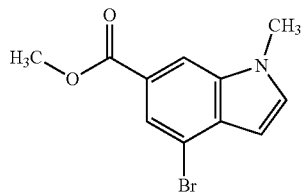

Scheme HG-17

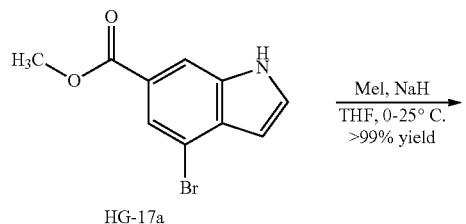

To a solution of methyl 4-bromo-1H-indole-6-carboxylate (HG-17a) (200 mg, 0.787 mmol) in anhydrous THF (2.0 mL) at 0° C. was added NaH (60% dispersion in mineral oil, 63 mg, 1.57 mmol) portion-wise. The mixture was stirred for 15 min and then iodomethane (223 mg, 1.57 mmol) was added. The mixture was stirred at 25° C. for 2 h. TLC analysis (1:5 EtOAc/petroleum ether) showed consumption of the starting material. The resultant suspension was quenched by addition of saturated aqueous NH$_4$Cl (2 mL) and diluted with H$_2$O (3 mL). The mixture was extracted with EtOAc (3×10 mL). The combined organic layers were dried over anhydrous Na$_2$SO$_4$, filtered, and concentrated to provide methyl 4-bromo-1-methyl-1H-indole-6-carboxylate (Int-HG-07) (217 mg, >99% yield), which was taken on without further purification. $^1$H NMR (400 MHz, CDCl$_3$) δ 8.05 (s, 1H), 7.98 (d, J=1.2 Hz, 1H), 7.28-7.21 (m, 1H), 6.57 (dd, J=3.1, 0.9 Hz, 1H), 3.95 (s, 3H), 3.87 (s, 3H).

PREPARATION OF EXAMPLES

Preparation of 4-[3-(1-ethyl-3-methyl-1H-pyrazol-5-yl)-1H-1,2,4-triazol-5-yl]-1-methyl-1H-indazole-6-carboxamide (Example A01) According to Scheme A

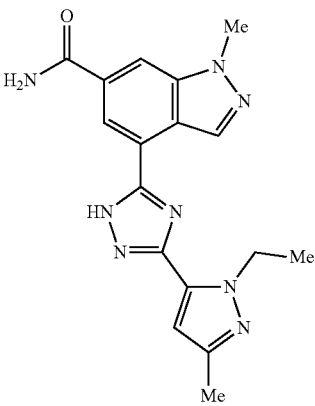 [SMILES: CCn1nc(C)cc1-c1n[nH]c(-c2cc(C(N)=O)cc3c2cnn3C)n1]

Scheme A

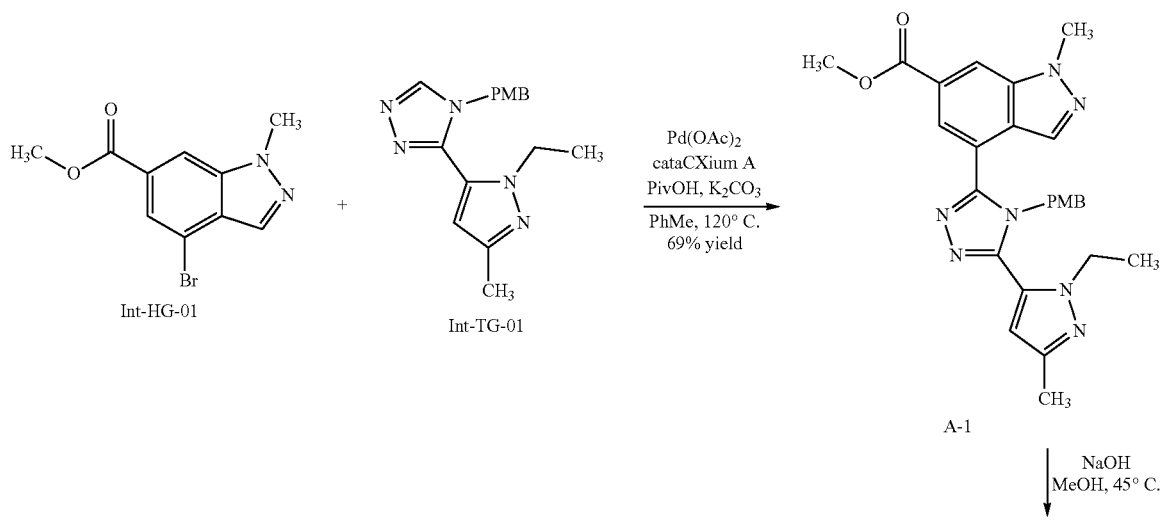

-continued

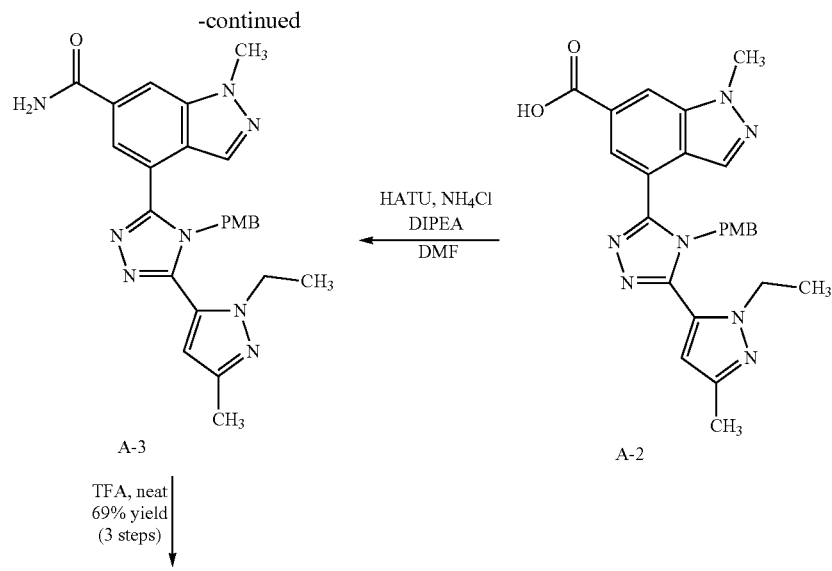

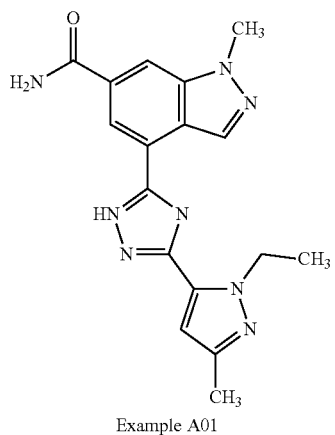

Example A01

Step 1: Synthesis of methyl 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylate (A-1)

To a suspension of 3-(1-ethyl-3-methyl-1H-pyrazol-5-yl)-4-[(4-methoxyphenyl)methyl]-4H-1,2,4-triazole (Int-TG-01) (1.40 g, 4.71 mmol) in PhMe (9.0 mL) was added $K_2CO_3$ (1.95 g, 14.1 mmol), $Pd(OAc)_2$ (106 mg, 0.471 mmol), methyl 4-bromo-1-methyl-1H-indazole-6-carboxylate (1.88 g, 6.98 mmol) (Int-HG-01), PivOH (144 mg, 1.41 mmol), and cataCXium A (338 mg, 0.942 mmol). The mixture was sparged with $N_2$ for 2 min and then stirred at 120° C. for 16 h. LCMS analysis showed consumption of the starting material with formation of the desired product mass. The mixture was filtered and the filtrate was concentrated to dryness. The residue was purified by flash chromatography (40 g $SiO_2$, 100% EtOAc) to provide methyl 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylate (A-1) (1.59 g, 65% yield) as a yellow solid. $^1H$ NMR (400 MHz, $CDCl_3$) δ 8.46 (d, J=1.0 Hz, 1H), 8.30 (s, 1H), 7.91 (d, J=1.1 Hz, 1H), 6.81 (d, J=8.9 Hz, 2H), 6.77 (d, J=8.9 Hz, 2H), 6.20 (s, 1H), 5.35 (s, 2H), 4.39 (q, J=7.2 Hz, 2H), 4.22 (s, 3H), 3.91 (s, 3H), 3.78 (s, 3H), 2.32 (s, 3H), 1.46 (t, J=7.2 Hz, 3H); m/z (ESI+) for ($C_{26}H_{27}N_7O_3$), 486.2 (M+H)⁺.

Step 2: Synthesis of 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylic acid (A-2)

To a suspension of methyl 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylate (A-1) (1.59 g, 3.27) in MeOH (30 mL) was added aqueous NaOH (2.0 N, 16.3 mL, 32.7 mmol). The mixture was stirred at 45° C. for 16 h. LCMS showed consumption of the starting material with formation of the desired product mass. The reaction was cooled room to temperature and acidified by addition of HCl (1.0 N) to pH ~3-4. The mixture was extracted with EtOAc (2×50 mL). The combined organic layers were dried over $Na_2SO_4$, filtered, and concentrated to provide 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylic acid (A-2) (1.57 g, >99% yield) as a yellow solid, which was taken on without further purification. $^1$H NMR (400 MHz, $CDCl_3$) δ 8.35 (s, 1H), 8.29 (s, 1H), 7.95 (s, 1H), 6.68 (d, J=8.7 Hz, 2H), 6.63 (d, J=8.7 Hz, 2H), 6.15 (s, 1H), 5.27 (s, 2H), 4.28 (q, J=7.2 Hz, 2H), 4.15 (s, 3H), 3.66 (s, 3H), 2.26 (s, 3H), 1.35 (t, J=7.1 Hz, 3H). m/z (ESI+) for ($C_{25}H_{25}N_7O_3$), 472.2 $(M+H)^+$.

Step 3: Synthesis of 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxamide (A-3)

A solution of 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylic acid (A-2) (1.57 g, 3.33 mmol) and HATU (4.42 g, 11.6 mmol) in DMF (30.0 mL) was stirred for 30 min. Solid $NH_4Cl$ (1.78 g, 33.3 mmol) and DIPEA (4.30 g, 33.3 mmol) were added. The mixture was stirred a further 16 h. LCMS analysis showed consumption of the starting material with formation of the desired product mass. The reaction was concentrated to dryness. The residue was diluted with $H_2O$ (100 mL) and extracted with EtOAc/ petroleum ether (2:1 v/v, 4×20 mL). The combined organic layers were dried over $Na_2SO_4$, filtered, and concentrated to provide 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxamide (A-3) (1.57 g, >99% yield) as a yellow gum, which was taken on without further purification. m/z (ESI+) for ($C_{25}H_{26}N_8O_2$), 471.2 $(M+H)^+$.

Step 4: Synthesis of 4-[3-(1-ethyl-3-methyl-1H-pyrazol-5-yl)-1H-1,2,4-triazol-5-yl]-1-methyl-1H-indazole-6-carboxamide (Example A01)

A solution of 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxamide (A-3) (1.57 g, 3.34 mmol) in TFA (30 mL) was stirred for 16 h. LCMS analysis showed consumption of the starting material with formation of the product mass. The reaction was concentrated to dryness. The residue was slurried with MeOH (50 mL) for 1 h. The solids were collected by filtration and dried under vacuum. The material was slurried with MeOH/DMF (20:1 v/v, 20 mL) for 1 h and the solids were collected by filtration. The filter-cake was slurried with MeOH/DMF (10:1 v/v, 20 ml) for 1 h and the solids were collected by filtration. The filter cake was washed with MeOH (1×10 mL) and then dried under vacuum to provide 4-[3-(1-ethyl-3-methyl-1H-pyrazol-5-yl)-1H-1,2,4-triazol-5-yl]-1-methyl-1H-indazole-6-carboxamide (Example A01) (801 mg, 69% yield over 3 steps) as a pale-yellow solid. $^1$H NMR (400 MHz, DMSO-$d_6$) δ 8.71 (s, 1H), 8.46-8.45 (m, 1H), 8.39 (s, 1H), 8.24 (br s, 1H), 7.63 (br s, 1H), 6.74 (s, 1H), 4.74 (q, J=7.1 Hz, 2H), 4.21 (s, 3H), 2.29 (s, 3H), 1.48 (t, J=7.1 Hz, 3H). m/z (ESI+) for ($C_{17}H_{18}N8O$), 351.1 $(M+H)^+$.

Example A02 was prepared according to the methods used for the synthesis of 4-[3-(1-ethyl-3-methyl-1H-pyrazol-5-yl)-1H-1,2,4-triazol-5-yl]-1-methyl-1H-indazole-6-carboxamide (Example A01) with non-critical changes or substitutions to the exemplified procedures that one skilled in the art would be able to realize.

| Compound Number | Structure/IUPAC Name | Analytical Data |
|---|---|---|
| A02 | 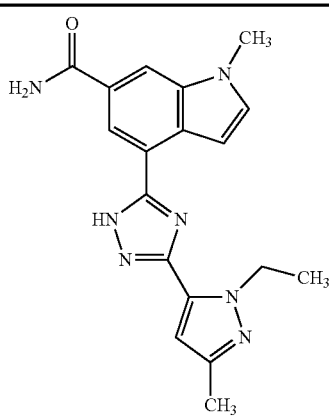<br>4-[3-(1-ethyl-3-methyl-1H-pyrazol-5-yl)-1H-1,2,4-triazol-5-yl]-1-methyl-1H-indole-6-carboxamide | $^1$H NMR (400 MHz, $CD_3OD$) δ 8.27 (s, 1H), 8.16 (s, 1H), 7.51 (d, J = 3.1 Hz, 1H), 7.24-7.07 (m, 1H), 6.67 (s, 1H), 4.74 (q, J = 7.2 Hz, 2H), 3.96 (s, 3H), 2.31 (s, 3H), 1.48 (t, J = 7.1 Hz, 3H); m/z (ESI+) for ($C_{18}H_{19}N_7O$), 350.1 $(M + H)^+$. |

Examples B01 and B02 were prepared according to the methods used for the synthesis of 4-[3-(1-ethyl-3-methyl-1H-pyrazol-5-yl)-1H-1,2,4-triazol-5-yl]-1-methyl-1H-indazole-6-carboxamide (Example A01) in high through-put fashion with non-critical changes or substitutions to the exemplified procedures that one skilled in the art would be able to realize.

| Compound Number | Structure/IUPAC Name | Analytical Data |
|---|---|---|
| B01 | 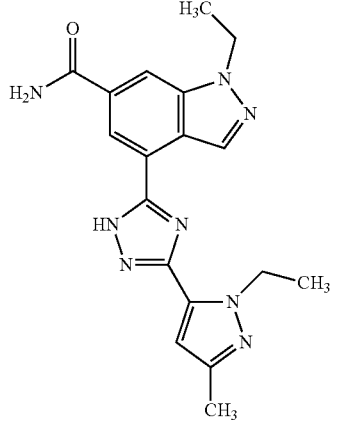 [SMILES: CCn1nc(C)cc1-c1n[nH]c(-c2cc(C(N)=O)cc3c2cnn3CC)n1]<br>1-ethyl-4-[3-(1-ethyl-3-methyl-1H-pyrazol-5-yl)-1H-1,2,4-triazol-5-yl]-1H-indazole-6-carboxamide | M/Z (ESI+) for ($C_{18}H_{20}N_8O$), 365 (M + H)$^+$. |
| B02 | 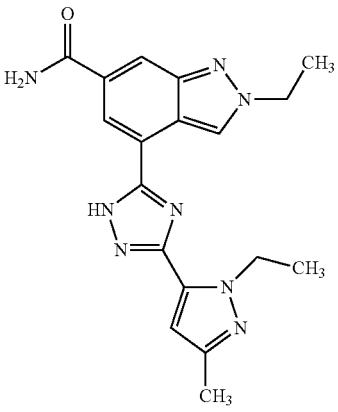 [SMILES: CCn1cc2c(-c3nc(-c4cc(C)nn4CC)n[nH]3)cc(C(N)=O)cc2n1]<br>2-ethyl-4-[3-(1-ethyl-3-methyl-1H-pyrazol-5-yl)-1H-1,2,4-triazol-5-yl]-2H-indazole-6-carboxamide | m/z (ESI+) for ($C_{18}H_{20}N_8O$), 365 (M + H)$^+$. |

Preparation of 4-[3-(1-ethyl-3-methyl-1H-pyrazol-5-yl)-1H-1,2,4-triazo-5-yl]-2-methyl-2H-indazole-6-carboxamide (Example C01) According to Scheme C

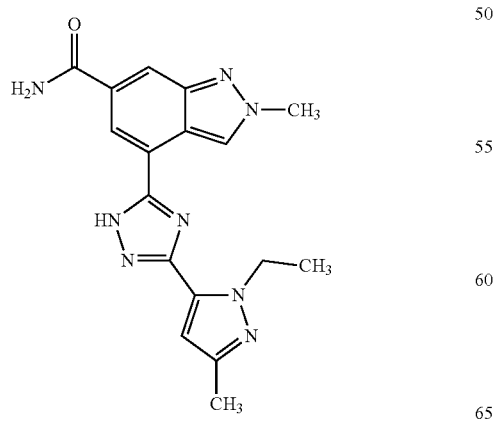

Scheme C

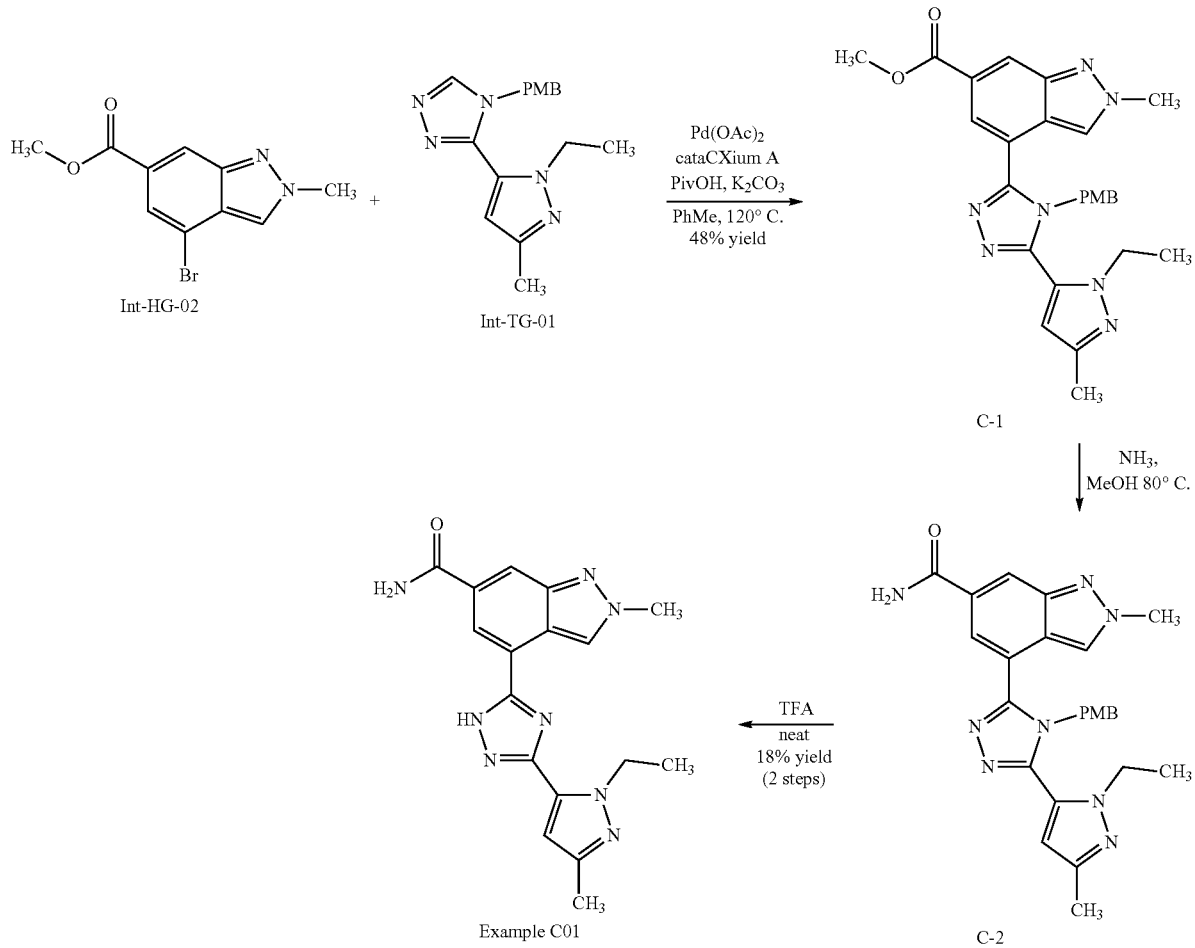

Step 1: Synthesis of methyl 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxylate (C-1)

To a suspension of 3-(1-ethyl-3-methyl-1H-pyrazol-5-yl)-4-[(4-methoxyphenyl)methyl]-4H-1,2,4-triazole (Int-HG-02) (133 mg, 0.446 mmol) in PhMe (2.0 mL) were added $K_2CO_3$ (185 mg, 1.34 mmol), $Pd(OAc)_2$ (23.0 mg, 0.100 mmol), methyl 4-bromo-2-methyl-2H-indazole-6-carboxylate (Int-TG-01) (180 mg, 0.669 mmol), PivOH (13.7 mg, 0.134 mmol), and cataCXium A (19.2 mg, 0.0535 mmol). The mixture was sparged with $N_2$ for 2 min and then stirred at 120° C. for 16 h. LCMS analysis showed consumption of the starting material with formation of the desired product mass. The reaction was combined with a parallel reaction run in identical fashion with 70 mg 3-(1-ethyl-3-methyl-1H-pyrazol-5-yl)-4-[(4-methoxyphenyl)methyl]-4H-1,2,4-triazole (Int-HG-02). The mixture was filtered and the filter cake was washed with MeOH (2×5 mL). The combined filtrate was concentrated to dryness. The residue was purified by flash chromatography (12 g $SiO_2$, 100% EtOAc) to provide methyl 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxylate (C-1) (160 mg, 48% yield) as a yellow oil. $^1$H NMR (400 MHz, $CDCl_3$) δ 8.59 (s, 1H), 8.56 (s, 1H), 7.83 (d, J=1.2 Hz, 1H), 6.91-6.73 (m, 4H), 6.15 (s, 1H), 5.41 (s, 2H), 4.39 (q, J=7.2 Hz, 2H), 4.29 (s, 3H), 3.85 (s, 3H), 3.78 (s, 3H), 2.29 (s, 3H), 1.45 (t, J=7.2 Hz, 3H); m/z (ESI+) for ($C_{26}H_{27}N_7O_3$), 486.2 (M+H)$^+$.

Step 2: Synthesis of 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxamide (C-2)

To methyl 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxylate (C-1) (160 mg, 0.330 mmol) was added a solution of $NH_3$ in MeOH (7 N, 5.0 mL, freshly prepared) and the mixture was stirred at 80° C. for 16 h. LCMS analysis showed ~50% consumption of the starting material. An additional aliquot of $NH_3$ in MeOH (7 N, 3.0 mL) was added. The mixture was stirred at 80° C. for 24 h and then concentrated to dryness. A solution of $NH_3$ in MeOH (7 N, 5.0 mL, freshly prepared) was added and the mixture was stirred at 80° C. for 48 h. The mixture was concentrated to dryness to provide 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxamide (C-2) (155 mg, >99% yield), which was taken on without further purification. m/z (ESI+) for ($C_{25}H_{26}N_8O_2$), 471.2 (M+H)$^+$.

Step 3: Synthesis of 4-[3-(1-ethyl-3-methyl-1H-pyrazol-5-yl)-1H-1,2,4-triazol-5-yl]-2-methyl-2H-indazole-6-carboxamide (Example C01)

A solution of 4-{5-(1-ethyl-3-methyl-1H-pyrazol-5-yl)-4-[(4-methoxyphenyl)methyl]-4H-1,2,4-triazol-3-yl}-2-methyl-2H-indazole-6-carboxamide (C-2) (155 mg, 0.329 mmol) in TFA (3.0 mL) was stirred at 25° C. for 16 h. LCMS analysis showed consumption of the starting material with formation of the desired product mass. The reaction was concentrated to dryness. The residue was diluted with H$_2$O (10 mL), neutralized by addition of aqueous NaOH (2 N), and then concentrated to dryness. The residue was purified by preparative HPLC with a Boston Prime C18 column (150×30 mm, 5 μm particle size), which was eluted with 15-40% MeCN/H$_2$O (+0.05% NH$_4$OH) with a flow rate of 25 mL/min to provide 4-[3-(1-ethyl-3-methyl-1H-pyrazol-5-yl)-1H-1,2,4-triazol-5-yl]-2-methyl-2H-indazole-6-carboxamide (Example C01) (20.6 mg, 18% yield) as a pale-yellow solid. $^1$H NMR (400 MHz, DMSO-d$_6$) δ 8.85 (s, 1H), 8.35 (d, J=1.3 Hz, 1H), 8.33 (s, 1H), 8.17 (br s, 1H), 7.47 (br s, 1H), 6.69 (s, 1H), 4.67 (q, J=7.1 Hz, 2H), 4.30 (s, 3H), 2.24 (s, 3H), 1.42 (t, J=7.1 Hz, 3H); m/z (ESI+) for (C$_{17}$H$_{18}$N$_8$O), 351.1 (M+H)$^+$.

Examples C02-C09 were prepared according to the methods used for the synthesis of 4-[3-(1-ethyl-3-methyl-1H-pyrazol-5-yl)-1H-1,2,4-triazol-5-yl]-2-methyl-2H-indazole-6-carboxamide (Example C01) with non-critical changes or substitutions to the exemplified procedures that one skilled in the art would be able to realize.

| Compound Number | Structure/IUPAC Name | Analytical Data |
| --- | --- | --- |
| C02 | 4-[5-(1-ethyl-4-fluoro-3-methyl-1H-pyrazol-5-yl)-1H-1,2,4-triazol-3-yl]-1-methyl-1H-indazole-6-carboxamide | $^1$H NMR (400 MHz, DMSO-d$_6$) δ 8.69 (s, 1H), 8.46 (br s, 1H), 8.43 (s, 1H), 8.24 (br s, 1H), 7.66 (br s, 1H), 4.60 (q, J = 7.1 Hz, 2H), 4.21 (s, 3H), 2.28 (s, 3H), 1.45 (t, J = 7.1 Hz, 3H); $^{19}$F NMR (376 MHz, DMSO-d$_6$) δ −172.50; m/z (ESI+) for (C$_{17}$H$_{17}$FN$_8$O), 369.3 (M + H)$^+$. |
| C03 | 3-{5-[5-(6-carbamoyl-1-methyl-1H-indazol-4-yl)-1H-1,2,4-triazol-3-yl]-3-methyl-1H-pyrazol-1-yl}propanoic acid | $^1$H NMR (400 MHz, DMSO-d$_6$) δ 8.68 (s, 1H), 8.41 (s, 1H), 8.34 (s, 1H), 8.19 (br s, 1H), 7.59 (br s, 1H), 6.71 (s, 1H), 4.88 (t, J = 7.2 Hz, 2H), 4.17 (s, 3H), 2.87 (t, J = 7.3 Hz, 2H), 2.24 (s, 3H); m/z (ESI+) for (C$_{18}$H$_{18}$N$_8$O$_3$), 395.1 (M + H)$^+$. |

| Compound Number | Structure/IUPAC Name | Analytical Data |
|---|---|---|
| C04 | 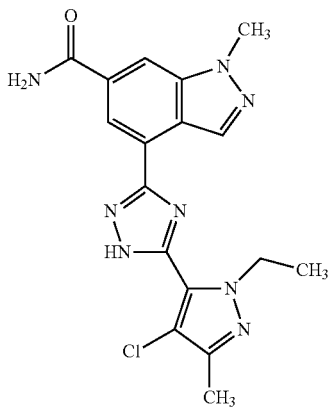 [SMILES: CCn1nc(C)c(Cl)c1-c1nc(-c2cc(C(N)=O)cc3c2cnn3C)n[nH]1]<br>4-[5-(4-chloro-1-ethyl-3-methyl-1H-pyrazol-5-yl)-1H-1,2,4-triazol-3-yl]-1-methyl-1H-indazole-6-carboxamide | $^1$H NMR (400 MHz, DMSO-$d_6$) δ 8.68 (s, 1H), 8.42 (s, 1H), 8.39 (s, 1H), 8.19 (br s, 1H), 7.63 (br s, 1H), 4.52 (q, J = 9.1, 8.3 Hz, 2H), 4.17 (s, 3H), 2.24 (s, 3H), 1.40 (t, J = 7.1 Hz, 3H); m/z (ESI+) for ($C_{17}H_{17}ClN_8O$), 385.2 (M + H)$^+$. |
| C05 | 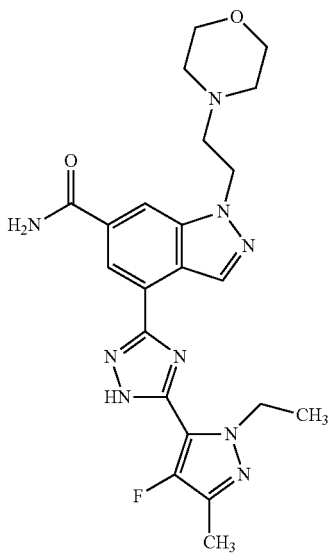 [SMILES: CCn1nc(C)c(F)c1-c1nc(-c2cc(C(N)=O)cc3c2cnn3CCN2CCOCC2)n[nH]1]<br>4-[5-(1-ethyl-4-fluoro-3-methyl-1H-pyrazol-5-yl)-1H-1,2,4-triazol-3-yl]-1-[2-(morpholin-4-yl)ethyl]-1H-indazole-6-carboxamide | $^1$H NMR (400 MHz, CD$_3$OD) δ 8.89 (s, 1H), 8.45 (s, 1H), 8.32 (s, 1H), 4.99 (t, J = 5.9 Hz, 2H), 4.66 (q, J = 7.2 Hz, 2H), 4.11-3.68 (m, 6H), 3.55-3.36 (m, 2H), 2.30 (s, 3H), 1.48 (t, J = 7.1 Hz, 3H) (2H obscured by solvent); $^{19}$F NMR (376 MHz, CD$_3$OD) δ −76.99; m/z (ESI+) for ($C_{22}H_{26}FN_9O_2$), 468.3 (M + H)$^+$. |

| Compound Number | Structure/IUPAC Name | Analytical Data |
|---|---|---|
| C06 | 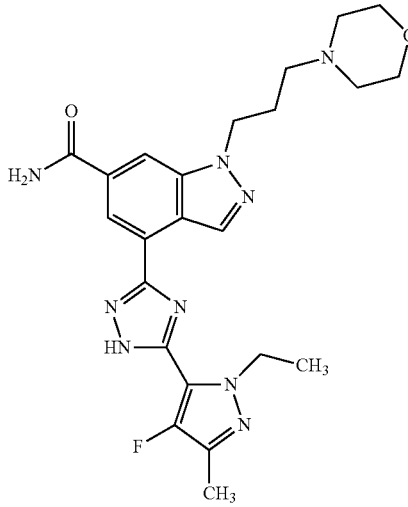<br>4-[5-(1-ethyl-4-fluoro-3-methyl-1H-pyrazol-5-yl)-1H-1,2,4-triazol-3-yl]-1-[3-(morpholin-4-yl)propyl]-1H-indazole-6-carboxamide | $^1$H NMR (400 MHz, DMSO-d$_6$) δ 15.01 (br s, 1H), 8.68 (d, J = 0.8 Hz, 1H), 8.42 (d, J = 1.2 Hz, 1H), 8.40 (d, J = 1.1 Hz, 1H), 8.21 (br s, 1H), 7.61 (br s, 1H), 4.70-4.35 (m, 4H), 3.52 (t, J = 4.6 Hz, 4H), 2.29-2.22 (m, 7H), 2.20 (t, J = 6.8 Hz, 2H), 2.06 (p, J = 6.3 Hz, 2H), 1.41 (t, J = 7.1 Hz, 3H); $^{19}$F NMR (377 MHz, DMSO-d$_6$) δ −172.49; m/z (ESI+) for (C$_{23}$H$_{28}$FN$_9$O$_2$), 482.3 (M + H)$^+$. |
| C07 | 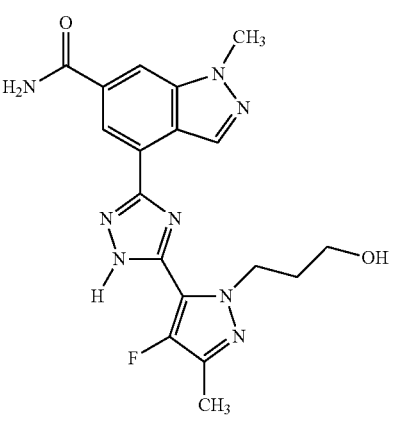 [SMILES: Cc1nn(CCCO)c(-c2nc(-c3cc(C(N)=O)cc4c3cnn4C)n[nH]2)c1F]<br>4-{5-[4-fluoro-1-(3-hydroxypropyl)-3-methyl-1H-pyrazol-5-yl]-1H-1,2,4-triazol-3-yl}-1-methyl-1H-indazole-6-carboxamide | $^1$H NMR (400 MHz, DMSO-d$_6$) δ 14.97 (br s, 1H), 8.59 (s, 1H), 8.32 (s, 1H), 8.29 (s, 1H), 8.07 (br s, 1H), 7.49 (br s, 1H), 4.51 (br t, J = 7.1 Hz, 2H), 4.08 (s, 3H), 3.36 (t, J = 6.3 Hz, 2H), 3.20 (br s, 1H), 2.15 (s, 3H), 1.88 (quin, J = 6.7 Hz, 2H); $^{19}$F NMR (377 MHz, DMSO-d$_6$) δ −172.57; m/z (ESI+) for (C$_{18}$H$_{19}$FN$_8$O$_2$), 399.1 (M + H)$^+$. |

| Compound Number | Structure/IUPAC Name | Analytical Data |
|---|---|---|
| C08 | 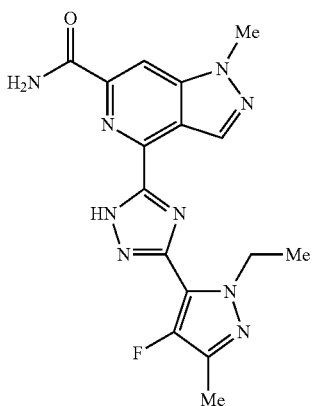 [SMILES: CCn1nc(C)c(F)c1-c1n[nH]c(-c2nc(C(N)=O)cc3c2cnn3C)n1]<br>4-[3-(1-ethyl-4-fluoro-3-methyl-1H-pyrazol-5-yl)-1H-1,2,4-triazol-5-yl]-1-methyl-1H-pyrazolo[4,3-c]pyridine-6-carboxamide | $^1$H NMR (400 MHz, DMSO-$d_6$) δ 8.84 (s, 1H), 8.75 (s, 1H), 8.48 (s, 1H), 7.89 (s, 1H), 4.57 (q, J = 7.1 Hz, 2H), 4.23 (s, 3H), 2.23 (s, 3H), 1.41 (t, J = 7.1 Hz, 3H). $^{19}$F NMR (376 MHz, DMSO-$d_6$) δ −172.23. m/z (ESI+) for ($C_{16}H_{17}FN_9O$), 370.1 (M + H)$^+$. |
| C09 | 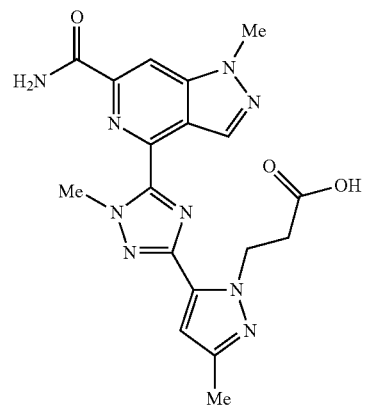 [SMILES: Cc1cc(-c2nc(-c3nc(C(N)=O)cc4c3cnn4C)n(C)n2)n(CCC(=O)O)n1]<br>3-{5-[5-(6-carbamoyl-1-methyl-1H-pyrazolo[4,3-c]pyridin-4-yl)-1-methyl-1H-1,2,4-triazol-3-yl]-3-methyl-1H-pyrazol-1-yl}propanoic acid | $^1$H NMR (400 MHz, DMSO-$d_6$) δ 12.38 (s, 1H), 8.77 (s, 1H), 8.51 (s, 1H), 8.00 (d, J = 43.5 Hz, 2H), 6.68 (s, 1H), 4.84 (t, J = 7.4 Hz, 2H), 4.45 (s, 3H), 4.22 (s, 3H), 2.86 (t, J = 7.4 Hz, 2H), 2.22 (s, 3H). m/z (ESI+) for ($C_{18}H_{20}N_9O_3$), 410.1 (M + H)$^+$. |

Preparation of 4-[3-(1-ethyl-3-methyl-1H-pyrazol-5-yl)-1H-1,2,4-triazol-5-yl]-1-[3-(morpholin-4-yl)propyl]-1H-indazole-6-carboxamide formic acid salt (Example D01) According to Scheme D

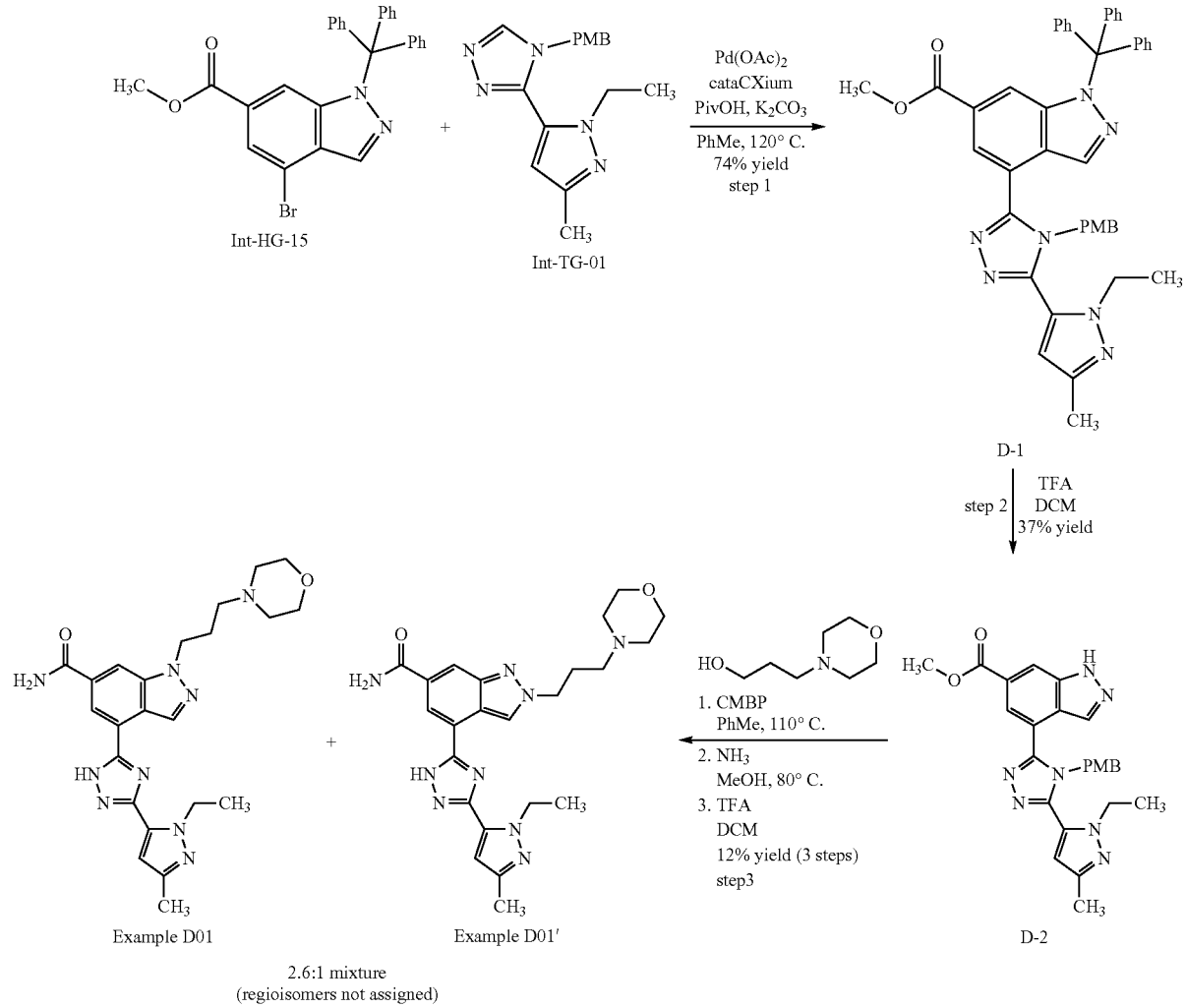

Step 1: Synthesis of methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (D-1)

To a 500 mL round-bottom flask equipped with a magnetic stir bar were sequentially added PivOH (1.03 g, 10.1 mmol), K₂CO₃ (13.9 g, 101 mmol), 3-(1-ethyl-3-methyl-1H-pyrazol-5-yl)-4-[(4-methoxyphenyl)methyl]-4H-1,2,4-triazole (Int-TG-01) (10.0 g, 33.6 mmol), methyl 4-bromo-1-(triphenylmethyl)-1H-indazole-6-carboxylate (Int-HG-15) (25.0 g, 50.3 mmol, 3:1 mixture of N-1 and N-2 regioisomers), and PhMe (100 mL). The flask was purged with N₂ and then Pd(OAc)₂ (755 mg, 3.36 mmol), and cataCXium A (2.41 mg, 6.73 mmol) were added. The mixture was stirred at 120° C. for 16 h. LCMS analysis showed consumption of the starting material with formation of the desired product mass. The mixture was filtered through celite and the filtrate was concentrated to dryness. The residue was purified by flash chromatography in two parallel batches (220 g SiO₂, 0-0.5% MeOH/DCM) to provide methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (D-1) (17.7 g, 74% yield, 3.5:1 mixture of N-1 and N-2 isomers). ¹H NMR (400 MHz, CDCl₃) δ 8.74-8.20 (m, 1H), 7.80 (dd, J=20.4, 1.2 Hz, 1H), 7.37-7.30 (m, 9H), 7.27-7.13 (m, 7H), 6.84-6.55 (m, 4H), 6.28-6.03 (m, 1H), 5.30 (d, J=18.3 Hz, 2H), 4.49-4.16 (m, 2H), 3.95-3.56 (m, 6H), 2.36-2.24 (m, 3H), 1.50-1.37 (m, 3H); m/z (ESI+) for (C₄₄H₃₉N₇O₃), 714.2 (M+H)⁺.

Step 2: Synthesis of methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (D-2)

To a solution of methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (D-1) (15.3 g, 21.4 mmol, 3.5:1 mixture of N-1 and N-2 isomers) in DCM (1.5 L) was added TFA (15.3 mL, 200 mmol). The reaction was stirred at ambient temperature for 1 h and then quenched by addition of saturated aqueous NaHCO₃ (1 L). The mixture was extracted with DCM (2×1 L). The combined organic layers were dried over Na$_2$SO$_4$, filtered, and concentrated to dryness. The residue was purified by flash chromatography (220 g SiO$_2$, 0-2% MeOH/DCM) to provide methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (D-2) (3.7 g, 37% yield) as a yellow solid. $^1$H NMR (400 MHz, CDCl$_3$) δ 11.03 (br s, 1H), 8.52 (d, J=1.1 Hz, 1H), 8.35 (d, J=1.2 Hz, 1H), 7.91 (d, J=1.1 Hz, 1H), 6.96-6.56 (m, 4H), 6.19 (s, 1H), 5.33 (s, 2H), 4.38 (q, J=7.2 Hz, 2H), 3.87 (s, 3H), 3.75 (s, 3H), 2.30 (s, 3H), 1.44 (t, J=7.2 Hz, 3H); m/z (ESI+) for (C$_{25}$H$_{25}$N$_7$O$_3$), 472.2 (M+H)$^+$.

Step 3: Synthesis of 4-[3-(1-ethyl-3-methyl-1H-pyrazol-5-yl)-1H-1,2,4-triazo-5-yl]-1-[3-(morpholin-4-yl)propyl]-1H-indazole-6-carboxamide formic acid salt (Example D01) and 4-[3-(1-ethyl-3-methyl-1H-pyrazol-5-yl)-1H-1,2,4-triazol-5-yl]-2-[3-(morpholin-4-yl)propyl]-2H-indazole-6-carboxamide formic acid salt (Example D01') Using a High Throughput Library Protocol To a vial was dispensed a solution of 3-(morpholin-4-yl)propan-1-ol (26.1 mg, 180 μmol) in PhMe (625 μL), a solution of methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (D-2) (70.7 mg, 180 μmol) in PhMe (750 μL), and a solution of cyanomethylenetributylphosphorane (CMBP) (36.2 mg, 180 μmol) in PhMe (750 μL). The vial was capped and the mixture was maintained at 110° C. with shaking for 16 h. LCMS analysis indicated consumption of the starting material. The solvent was removed with a Speedvac concentrator and the residue was purified by preparative TLC. To the isolated intermediate in a vial was added NH$_3$ in MeOH (7.0 M, 2.0 mL). The vial was capped and the mixture was maintained at 80° C. with shaking for 48 h with an additional aliquot of NH$_3$ in MeOH (7.0 M, 2.0 mL) added each at 16 and 32 h. LCMS analysis indicated consumption of the intermediate. The solvent was removed with a Speedvac concentrator. To the vial containing the residue was added 4:1 DCM/TFA (1.0 mL). The vial was capped and the mixture was maintained at 30° C. with shaking for 16 h. LCMS analysis indicated consumption of the intermediate. The solvent was removed with a Speedvac concentrator. The residue was purified by preparative HPLC with a YMC-Actus Triart C18 column (150×30 mm, 5 μm particle size), which was eluted with 13-53% MeCN/H$_2$O (+0.225% formic acid) with a flow rate of 35 mL/min to provide 4-[3-(1-ethyl-3-methyl-1H-pyrazol-5-yl)-1H-1,2,4-triazol-5-yl]-1-[3-(morpholin-4-yl)propyl]-1H-indazole-6-carboxamide formic acid salt (Example D01) and 4-[3-(1-ethyl-3-methyl-1H-pyrazol-5-yl)-1H-1,2,4-triazol-5-yl]-2-[3-(morpholin-4-yl)propyl]-2H-indazole-6-carboxamide formic acid salt (Example D01') (8.4 mg, 12% yield) as a 2.5:1 mixture of regioisomers (regioisomers not assigned). m/z (ESI+) for (C$_{23}$H$_{29}$N$_9$O$_2$), 474 (M+H)$^+$.

Examples D02-D05, D02'-D05' and D06 were prepared according to the methods used for the synthesis of Example D01, with non-critical changes or substitutions to the exemplified procedures that one skilled in the art would be able to realize.

| Compound Number | Structure/IUPAC Name | Analytical Data |
|---|---|---|
| D02 and D02' | 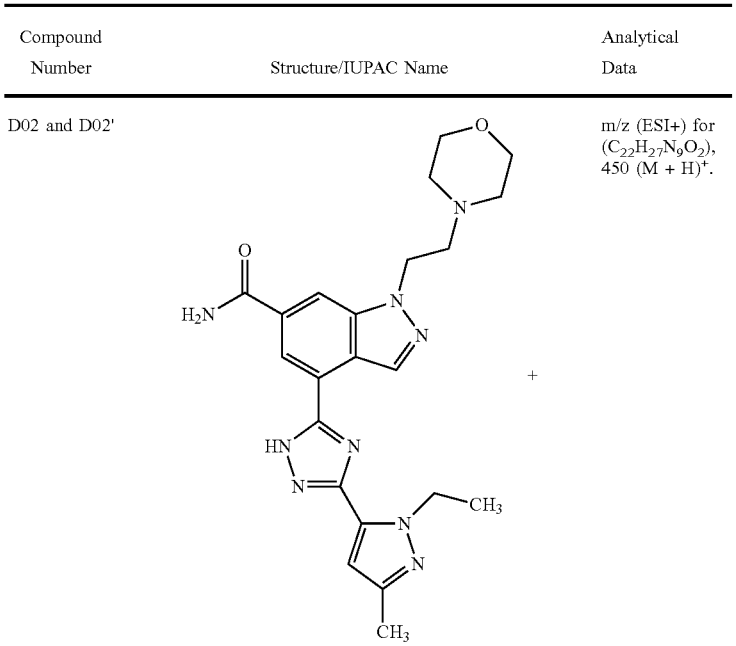 | m/z (ESI+) for (C$_{22}$H$_{27}$N$_9$O$_2$), 450 (M + H)$^+$. |

| Compound Number | Structure/IUPAC Name | Analytical Data |
|---|---|---|
| | 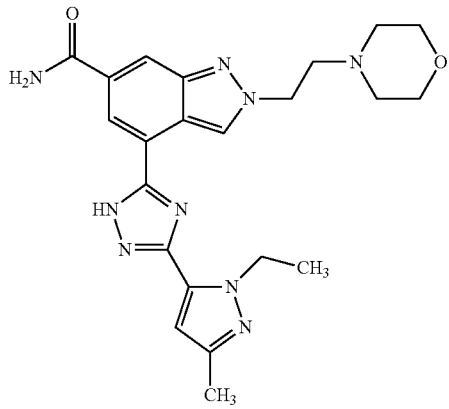<br>1.3:1 mixture<br>(regioisomers not assigned)<br><br>4-[3-(1-ethyl-3-methyl-1H-pyrazol-5-yl)-1H-1,2,4-triazol-5-yl]-1-[2-(morpholin-4-yl)ethyl]-1H-indazole-6-carboxamide formic acid salt and 4-[3-(1-ethyl-3-methyl-1H-pyrazol-5-yl)-1H-1,2,4-triazol-5-yl]-2-[2-(morpholin-4-yl)ethyl]-2H-indazole-6-carboxamide formic acid salt | |
| D03 and D03' | 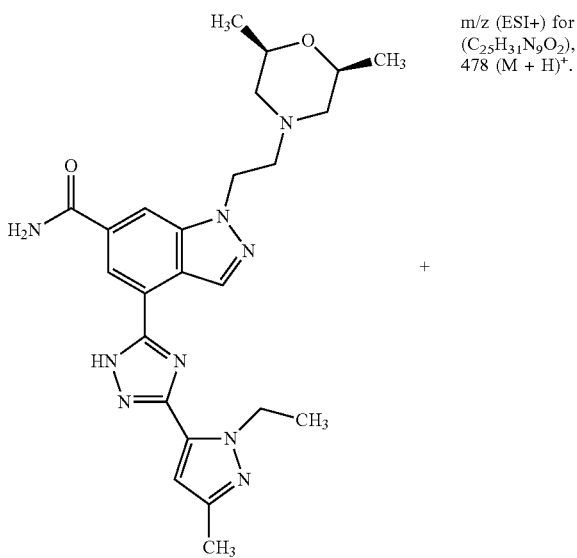 + | m/z (ESI+) for $(C_{25}H_{31}N_9O_2)$, 478 $(M + H)^+$. |

| Compound Number | Structure/IUPAC Name | Analytical Data |
|---|---|---|
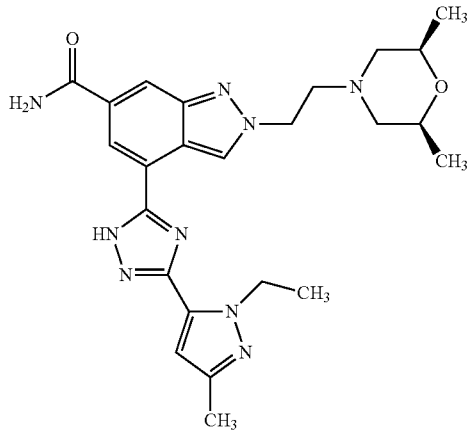
1.1:1 mixture
(regioisomers not assigned)
1-{2-[(2R,6S)-2,6-dimethylmorpholin-4-yl]ethyl}-4-[3-(1-ethyl-3-methyl-1H-pyrazol-5-yl)-1H-1,2,4-triazol-5-yl]-1H-indazole-6-carboxamide formic acid salt and 2-{2-[(2R,6S)-2,6-dimethylmorpholin-4-yl]ethyl}-4-[3-(1-ethyl-3-methyl-1H-pyrazol-5-yl)-1H-1,2,4-triazol-5-yl]-2H-indazole-6-carboxamide formic acid salt
| D04 and D04' | 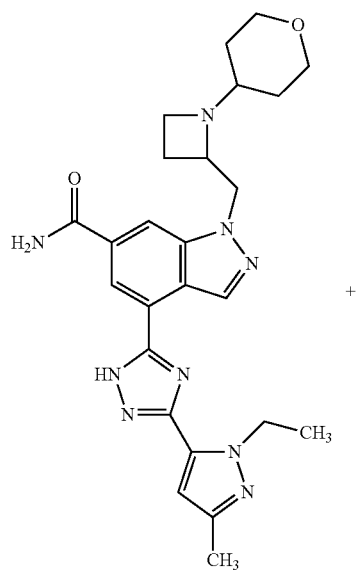 [SMILES: CCn1nc(C)cc1-c1n[nH]c(-c2cc(C(N)=O)cc3c2cnn3CC2CCN2C2CCOCC2)n1] + | m/z (ESI+) for (C$_{24}$H$_{31}$N$_9$O$_2$), 490 (M + H)$^+$. |

| Compound Number | Structure/IUPAC Name | Analytical Data |
|---|---|---|
| | 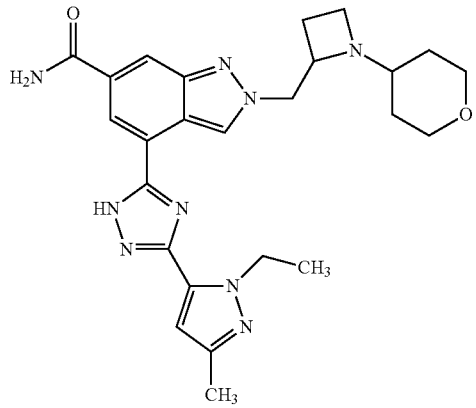 1.2:1 mixture (regioisomers not assigned) 4-[3-(1-ethyl-3-methyl-1H-pyrazol-5-yl)-1H-1,2,4-triazol-5-yl]-1-{[1-(oxan-4-yl)azetidin-2-yl]methyl}-1H-indazole-6-carboxamide formic acid salt and 4-[3-(1-ethyl-3-methyl-1H-pyrazol-5-yl)-1H-1,2,4-triazol-5-yl]-2-{[1-(oxan-4-yl)azetidin-2-yl]methyl}-2H-indazole-6-carboxamide formic acid salt | |
| D05 and D05' | 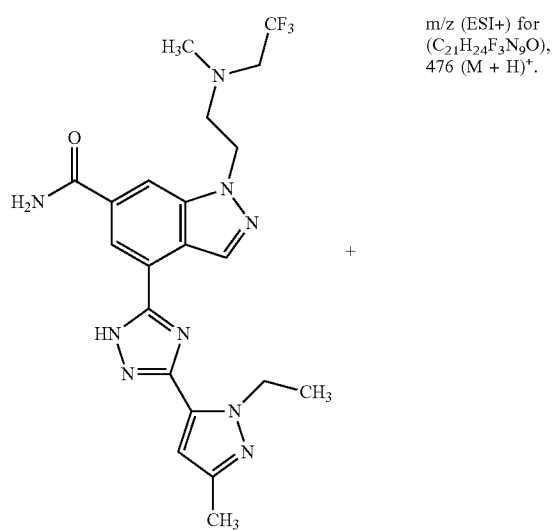 + | m/z (ESI+) for ($C_{21}H_{24}F_3N_9O$), 476 (M + H)$^+$. |

| Compound Number | Structure/IUPAC Name | Analytical Data |
|---|---|---|
| | 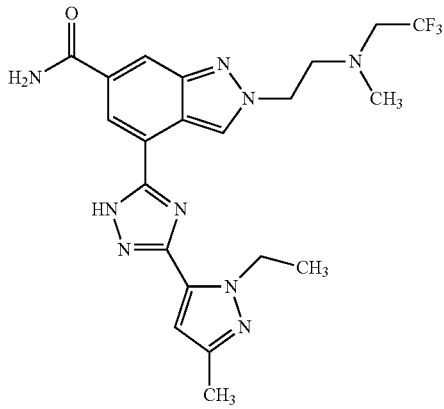<br>1.2:1 mixture<br>(regioisomers not assigned)<br><br>4-[3-(1-ethyl-3-methyl-1H-pyrazol-5-yl)-1H-1,2,4-triazol-5-yl]-1-{2-[methyl(2,2,2-trifluoroethyl)amino]ethyl}-1H-indazole-6-carboxamide formic acid salt and 4-[3-(1-ethyl-3-methyl-1H-pyrazol-5-yl)-1H-1,2,4-triazol-5-yl]-2-{2-[methyl(2,2,2-trifluoroethyl)amino]ethyl}-2H-indazole-6-carboxamide formic acid salt | |
| D06 | 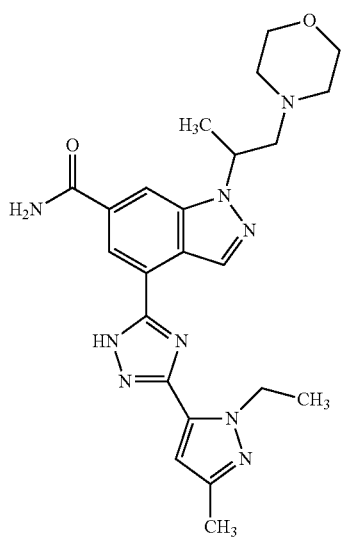 [SMILES: CCn1nc(C)cc1-c1n[nH]c(-c2cc(C(N)=O)cc3c2cnn3C(C)CN2CCOCC2)n1]<br>4-[5-(1-ethyl-3-methyl-1H-pyrazol-5-yl)-4H-1,2,4-triazol-3-yl]-1-[1-(morpholin-4-yl)propan-2-yl]-1H-indazole-6-carboxamide | m/z (ESI+) for $(C_{23}H_{29}N_9O_2)$, 464 $(M + H)^+$. |

Preparation of 4-[3-(1-ethyl-3-methyl-1H-pyrazol-5-yl)-1H-1,2,4-triazol-5-yl]-5-fluoro-1-methyl-1H-indazole-6-carboxamide (Example E01) According to Scheme E

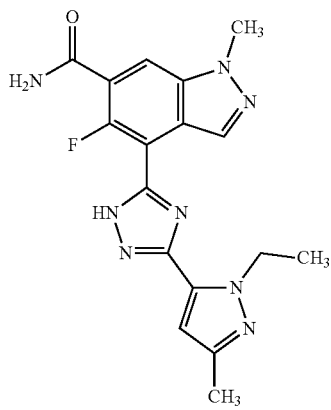 [SMILES: CCn1nc(C)cc1-c1n[nH]c(-c2c(F)c(C(N)=O)cc3c2cnn3C)n1]

Scheme E

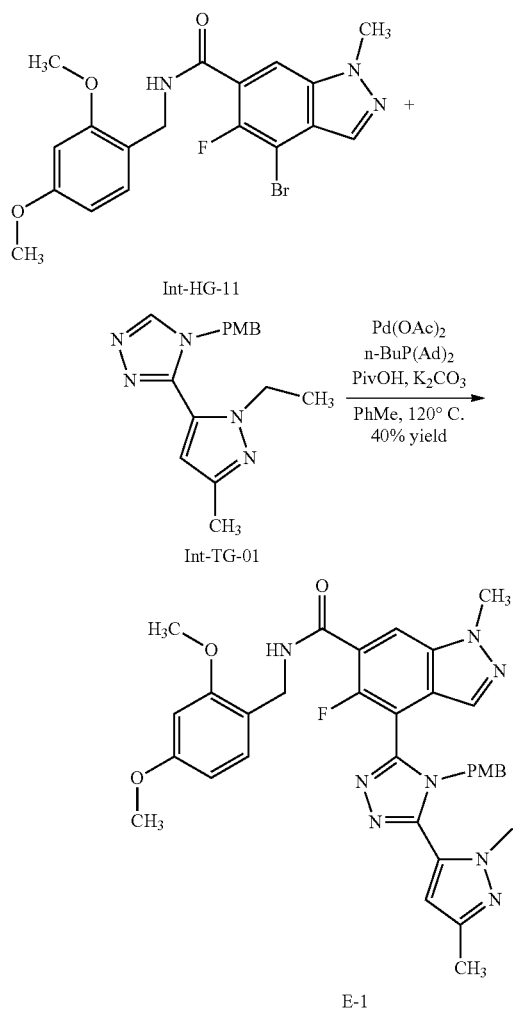

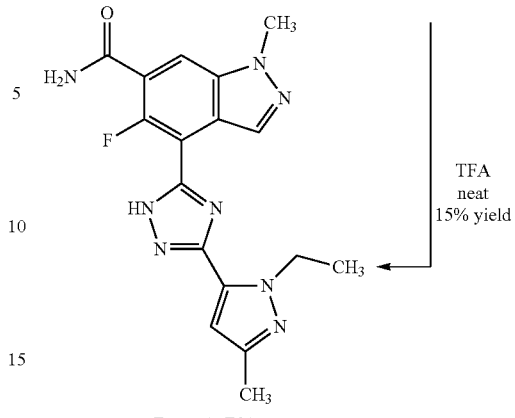

Example E01

Step 1: Synthesis of N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-5-fluoro-1-methyl-1H-indazole-6-carboxamide (E-1)

A mixture of 4-bromo-N-[(2,4-dimethoxyphenyl)methyl]-5-fluoro-1-methyl-1H-indazole-6-carboxamide (Int-HG-11) (49.0 mg, 0.120 mmol), 3-(1-ethyl-3-methyl-1H-pyrazol-5-yl)-4-[(4-methoxyphenyl)methyl]-4H-1,2,4-triazole (Int-TG-01) (52.6 mg, 0.174 mmol), PivOH (3.56 mg, 0.0348 mmol), $K_2CO_3$ (48.1 mg, 0.348 mmol), cataCXium A (8.32 mg, 0.232 mmol), and Pd(OAc)$_2$ (2.61 mg, 0.0116 mmol) in PhMe (2.3 mL) was sparged with $N_2$ and then stirred at 120° C. for 16 h. Additional Pd(OAc)$_2$ (2.61 mg, 0.0116 mmol) and cataCXium A (8.32 mg, 0.232 mmol) were added. The mixture was sparged with $N_2$ and then stirred at 120° C. for 24 h. LCMS analysis showed consumption of the starting material with formation of the desired product mass. The reaction was concentrated to dryness. The residue was purified by flash chromatography (4 g SiO$_2$, 5-10% MeOH/EtOAc) to provide N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-5-fluoro-1-methyl-1H-indazole-6-carboxamide (E-1) (30 mg, 40% yield) as a yellow solid. $^1$H NMR (400 MHz, CDCl$_3$) δ 8.34 (d, J=5.14 Hz, 1H), 7.88 (d, J=0.61 Hz, 1H), 7.25-7.29 (m, 1H), 6.52-6.57 (m, 2H), 6.43-6.50 (m, 4H), 6.25 (s, 1H), 5.08 (s, 2H), 4.62 (d, J=5.38 Hz, 2H), 4.24-4.33 (m, 2H), 4.14 (s, 3H), 3.84 (s, 3H), 3.80 (s, 3H), 3.64 (s, 3H), 2.33 (s, 3H), 1.37 (q, J=7.13 Hz, 3H); m/z (ESI+) for ($C_{34}H_{35}FN_8O_4$), 639.3 (M+H)$^+$.

Step 2: Synthesis of 4-[3-(1-ethyl-3-methyl-1H-pyrazol-5-yl)-1H-1,2,4-triazol-5-yl]-5-fluoro-1-methyl-1H-indazole-6-carboxamide (Example E01)

A solution of N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-5-fluoro-1-methyl-1H-indazole-6-carboxamide (E-1) (30 mg, 0.047 mmol) in TFA (3.0 mL) was stirred for 16 h. LCMS analysis showed consumption of the starting material with formation of the desired product mass. The reaction was concentrated to dryness. The residue was purified by preparative HPLC with a Phenemonex Gemini NX C18 column (150×21.2 mmol, 5 μmol particle size), which was eluted with 25-35% MeCN/H$_2$O (+10 mM NH$_4$OAc) with a flow rate of 40 mL/min to provide 4-[3-(1-ethyl-3-methyl-1H-pyrazol-5-yl)-1H-1,2,4-triazol-5-yl]-5-fluoro-1-methyl-1H-indazole-6-carboxamide (Example E01) (2.61 mg, 15% yield) as a solid. $^1$H NMR (600 MHz, DMSO-d$_6$) δ 8.70 (s, 1H), 7.80 (br s, 1H), 7.70 (d, J=4.6 Hz, 1H), 7.59 (br s, 1H), 6.87 (br s, 1H), 6.34 (s, 1H), 4.71 (q, J=7.1 Hz, 2H), 4.08 (s, 3H), 2.17 (s, 3H), 1.37 (t, J=7.2 Hz, 3H); $^{19}$F NMR (565 MHz, DMSO-d$_6$) δ −125.44; m/z (ESI+) for (C$_{17}$H$_{17}$FN$_8$O), 369.0 (M+H)$^+$.

Preparation of 8-[5-(1-ethyl-4-fluoro-3-methyl-1H-pyrazol-5-yl)-1H-1,2,4-triazol-3-yl]-3-methylimidazo[1,5-a]pyridine-6-carboxamide (Example F01) According to Scheme F

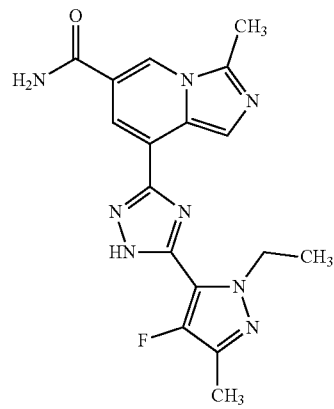 [SMILES: CCn1nc(C)c(F)c1-c1nc(-c2cc(C(N)=O)cn3c(C)ncc23)n[nH]1]

Scheme F

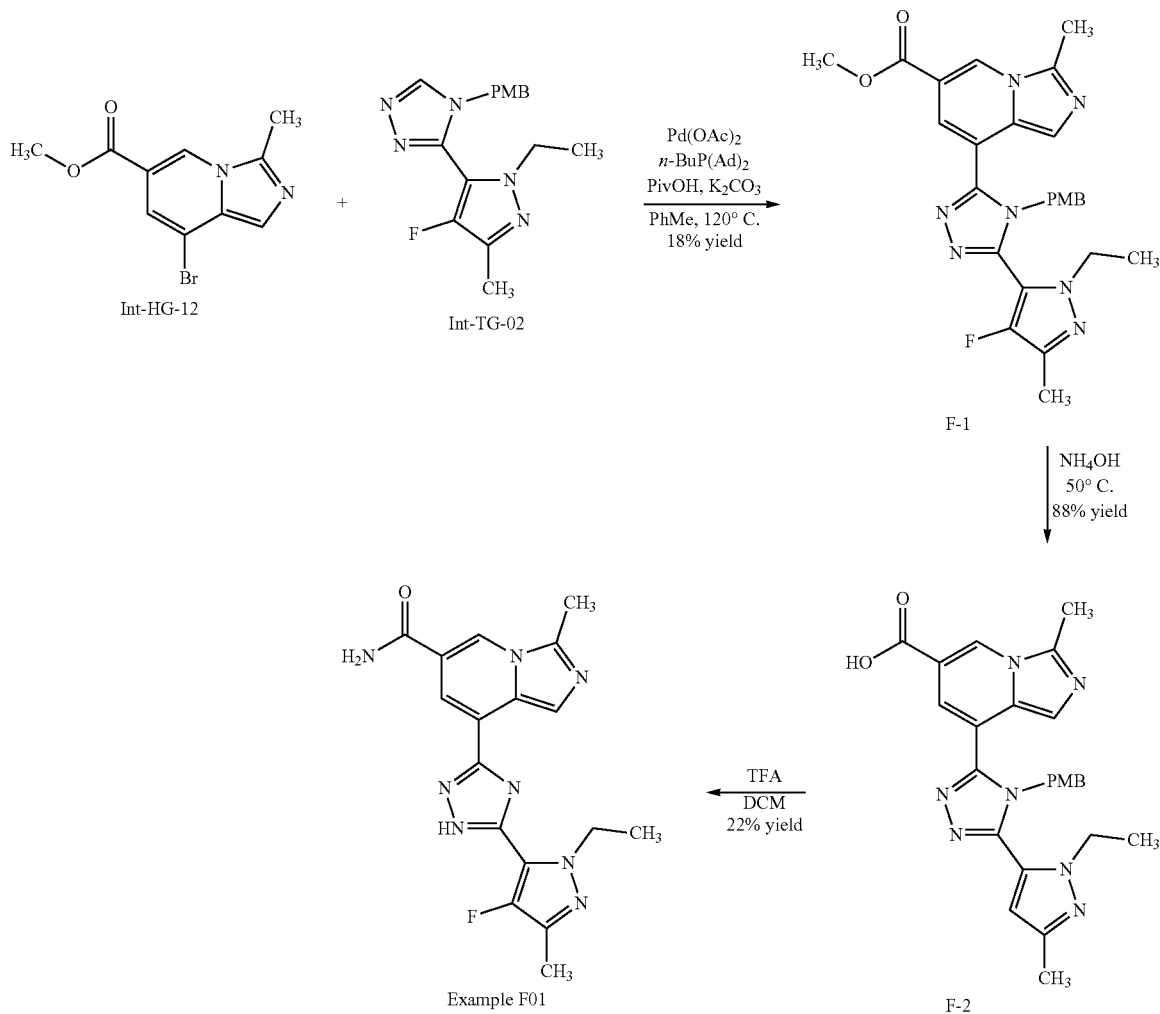

Step 1: Synthesis of methyl 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxylate (F-1)

A vial equipped with a magnetic stir bar was charged with methyl 8-bromo-3-methylimidazo[1,5-a]pyridine-6-carboxylate (Int-HG-12), $K_2CO_3$ (281 mg, 2.04 mml), Pd(OAc)$_2$ (15.2 mg, 0.0679 mmol), cataCXium A (48.7 mg, 0.136 mmol), and PivOH (20.8 mg, 0.204 mmol). The vial was purged with Ar and then a solution of 3-(1-ethyl-4-fluoro-3-methyl-1H-pyrazol-5-yl)-4-[(4-methoxyphenyl)methyl]-4H-1,2,4-triazole (Int-TG-02) (214 mg, 0.679 mmol) in PhMe (3.4 mL) was added. The mixture was stirred at 110° C. for 16 h. LCMS showed remaining staring material. The reaction was cooled to room temperature and Pd(OAc)$_2$ (15.2 mg, 0.678), cataCXium A (48.7, 0.136 mmol), and CsOPiv (47.6 mg, 0.204 mmol) were added. The mixture was purged with Ar and then stirred at 110° C. for 24 h. The mixture was cooled to room temperature and filtered through celite. The filter cake was washed successively with DCM, MeOH, and EtOAc. The combined filtrate was concentrated to dryness. The residue as purified by preparative HPLC with a Phenomenex Luna Omega Polar C18 column (250×30 mm, 5 μm particle size), which was eluted with 25-65% MeCN/H$_2$O (+0.1% AcOH) with a flow rate of 35 mL/min to provide methyl 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxylate (F-1) (61.6 mg, 18% yield) as a yellow solid. $^1$H NMR (400 MHz, CDCl$_3$) δ 8.63 (s, 1H), 7.64 (br s, 1H), 7.46 (s, 1H), 6.66 (d, J=8.8 Hz, 2H), 6.60 (d, J=8.8 Hz, 2H), 5.24 (d, J=2.9 Hz, 2H), 4.11 (q, J=7.2 Hz, 2H), 3.99 (s, 3H), 3.71 (s, 3H), 2.80 (s, 3H), 2.34 (s, 3H), 1.22 (t, J=7.2 Hz, 3H); m/z (ESI+) for ($C_{26}H_{26}FN_7O_3$), 504.2 (M+H)$^+$.

Step 2: Synthesis of 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxamide (F-2)

A solution of methyl 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxylate (F-1) (59.9 mg, 0.119 mmol) in saturated aqueous NH$_4$OH (~28%, 3.0 mL) was stirred at 50° C. for 7 h. LCMS analysis showed consumption of the starting material with formation of the desired product mass. The reaction was diluted with MeOH and then concentrated to dryness. The solid was dried by lyophilization from a mixture of MeOH (2 mL) and H$_2$O (5 mL) to provide 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxamide (F-2) (51.3 mg, 88% yield) as a yellow solid. $^1$H NMR (400 MHz, CD$_3$OD) δ 8.81 (s, 1H), 7.64 (s, 1H), 7.51 (d, J=1.2 Hz, 1H), 7.37 (s, 1H), 7.32 (s, 1H), 6.65 (s, 4H), 5.27 (s, 2H), 3.98 (q, J=7.5 Hz, 2H), 3.66 (s, 3H), 2.76 (s, 3H), 2.29 (s, 3H), 1.24-1.20 (m, 3H); $^{19}$F NMR (376 MHz, CD$_3$OD) δ −173.38; m/z (ESI+) for ($C_{25}H_{25}FN_8O_2$), 490.2 (M+H)$^+$.

Step 3: Synthesis of 8-[5-(1-ethyl-4-fluoro-3-methyl-1H-pyrazol-5-yl)-1H-1,2,4-triazol-3-yl]-3-methylimidazo[1,5-a]pyridine-6-carboxamide (Example F01)

To a solution of 8-{5-(1-ethyl-4-fluoro-3-methyl-1H-pyrazol-5-yl)-4-[(4-methoxyphenyl)methyl]-4H-1,2,4-triazol-3-yl}-3-methylimidazo[1,5-a]pyridine-6-carboxamide (F-2) (50.4 mg, 0.103 mmol) in DCM (2.0 mL) was added TFA (1.0 mL). The mixture was stirred for 16 h. LCMS analysis showed consumption of the starting material with formation of the desired product mass. The reaction was diluted with MeOH and concentrated to dryness. The residue was purified by preparative HPLC with a Phenemonex Gemini NX C18 column (21.2×150 mm, 5 μm particle size), which was eluted with 18-60% MeCN/H$_2$O (+10 mM NH$_4$OAc) with a flow rate of 40 mL/min to provide 8-[5-(1-ethyl-4-fluoro-3-methyl-1H-pyrazol-5-yl)-1H-1,2,4-triazol-3-yl]-3-methylimidazo[1,5-a]pyridine-6-carboxamide (Example F01) (3.97 mg, 10% yield) as a solid. $^1$H NMR (600 MHz, DMSO-d$_6$) δ 8.70 (s, 1H), 8.10 (br s, 1H), 8.03 (s, 1H), 7.93 (s, 1H), 7.44 (br s, 1H), 6.52 (br s, 1H), 4.54 (q, J=7.2 Hz, 2H), 2.69 (s, 3H), 2.20 (s, 3H), 1.36 (t, J=7.1 Hz, 3H); m/z (ESI+) for ($C_{17}H_{17}FN_8O$), 369.0 (M+H)$^+$.

Example G01: Preparation of 4-[4-(1-ethyl-3-methyl-1H-pyrazol-5-yl)-1H-imidazol-2-yl]-1-methyl-1H-indazole-6-carboxamide According to Scheme G

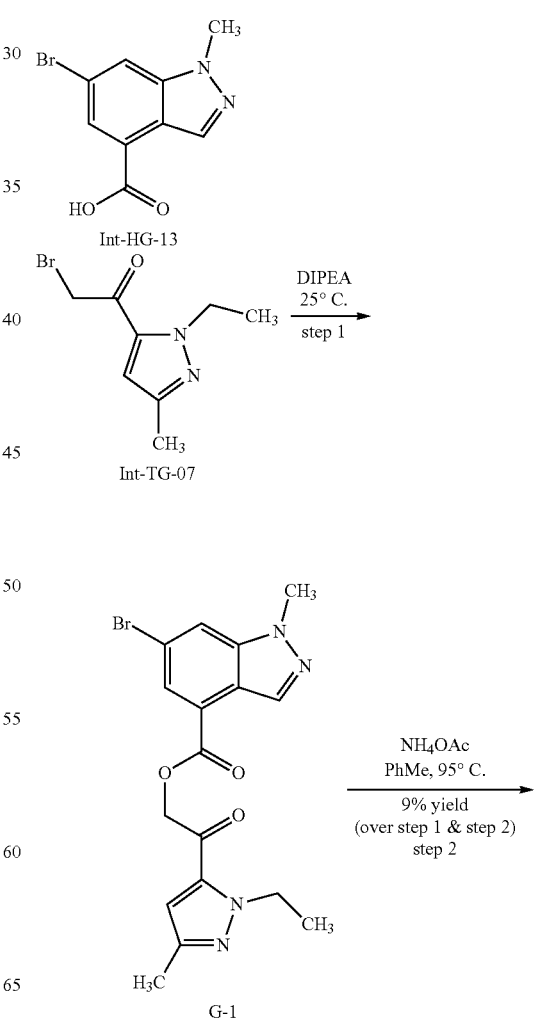

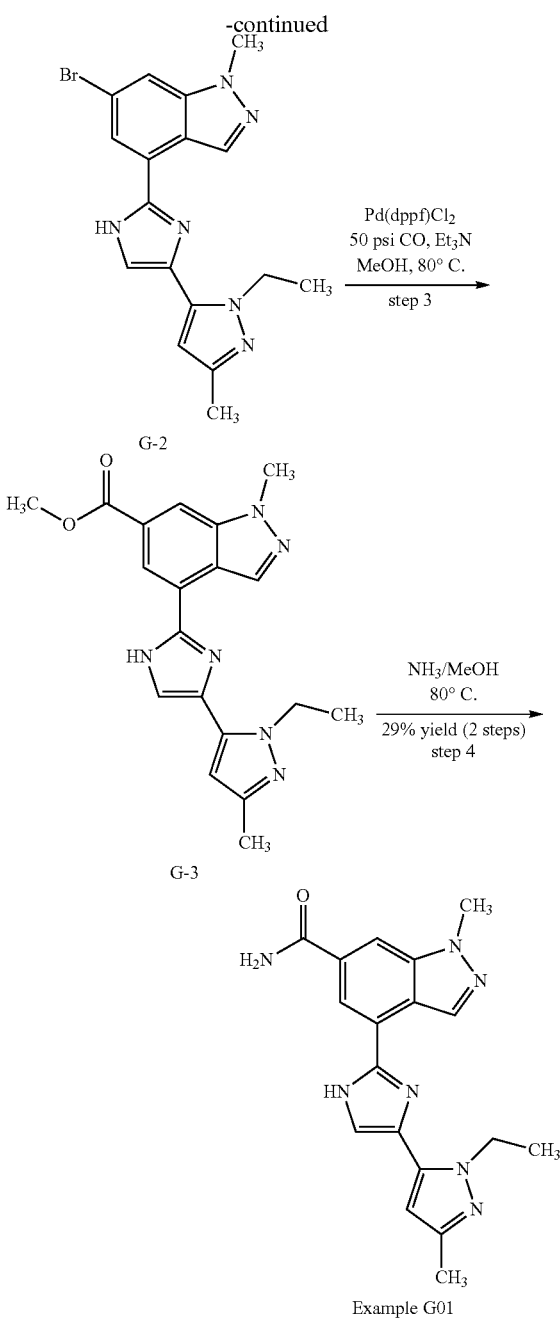

G-2

G-3

Example G01

Step 1: Synthesis of 2-(1-ethyl-3-methyl-1H-pyrazol-5-yl)-2-oxoethyl 6-bromo-1-methyl-1H-indazole-4-carboxylate (G-1)

To a suspension of 6-bromo-1-methyl-1H-indazole-4-carboxylic acid (Int-HG-13) (280 mg, 1.10 mmol) and 2-bromo-1-(1-ethyl-3-methyl-1H-pyrazol-5-yl)ethan-1-one (Int-TG-07) (279 mg, 1.21 mmol) under nitrogen, was added DIPEA (0.50 mL, 3.00 mmol). The yellow solution was stirred at 25° C. for 17 hours. LCMS analysis showed complete consumption of starting material. The solution was concentrated under vacuum to afford the title compound (G-1) which was used in the next step without further purification. $^1$H NMR (400 MHz, METHANOL-d$_4$) δ=8.48 (s, 1H), 8.18 (s, 1H), 8.05 (d, J=1.5 Hz, 1H), 6.98 (s, 1H), 5.57 (s, 2H), 4.50 (q, J=6.9 Hz, 2H), 4.11 (s, 3H), 2.31 (s, 3H), 1.35-1.33 (m, 3H).

Step 2: Synthesis of 6-bromo-4-[4-(1-ethyl-3-methyl-1H-pyrazol-5-yl)-1H-imidazol-2-yl]-1-methyl-1H-indazole (G-2)

To a yellow suspension of 2-(1-ethyl-3-methyl-1H-pyrazol-5-yl)-2-oxoethyl 6-bromo-1-methyl-1H-indazole-4-carboxylate (G-1) was added toluene (10 mL) and ammonium acetate (1.69 g, 22.0 mmol). The reaction was heated to reflux and stirred at 95° C. for 16 h. LCMS analysis of the dark green solution showed complete consumption of starting material. The reaction was quenched with water and transferred to a separatory funnel with EtOAc. The phases were separated, and the aqueous phase was extracted with EtOAc (3×15 mL). The combined organic extracts were concentrated under vacuum. The crude residue was purified via preparative thin-layer chromatography (DCM/MeOH 15:1) to give the title compound (G-2) (130 mg, 30% yield) as a green gum. LCMS analysis of this material showed significant impurities were still present. The isolated material was further purified by preparative thin-layer chromatography (DCM/MeOH 17:1) four times to afford the title compound (G-2) (41 mg, 9% yield) as a green solid which was used in the next step without further purification. m/z (ESI+) for (C$_{17}$H$_{17}$BrN$_6$), 385.1 (M+H)$^+$ observed.

Step 3: Synthesis of methyl 4-[4-(1-ethyl-3-methyl-1H-pyrazol-5-yl)-1H-imidazol-2-yl]-1-methyl-1H-indazole-6-carboxylate (G-3)

To a solution of 6-bromo-4-[4-(1-ethyl-3-methyl-1H-pyrazol-5-yl)-1H-imidazol-2-yl]-1-methyl-1H-indazole (G-2) (41 mg, 0.11 mmol) in MeOH (6.0 mL) was added PdCl$_2$(dppf)$_2$ (23.4 mg, 0.032 mmol) and Et$_3$N (0.1 mL, 0.700 mmol). The orange solution was stirred at 80° C. in an autoclave under a carbon monoxide atmosphere (50 psi) for 30 h. The brown heterogeneous mixture was filtered and the filtrate concentrated under vacuum to afford the title compound (G-3) (110 mg) as an orange gum. The crude material was used in the next step without further purification. m/z (ESI+) for (C$_{19}$H$_{20}$N$_6$O$_2$), 364.8 (M+H)$^+$ observed.

Step 4: Synthesis of 4-[4-(1-ethyl-3-methyl-1H-pyrazol-5-yl)-1H-imidazol-2-yl]-1-methyl-1H-indazole-6-carboxamide (Example G01)

To a flask containing methyl 4-[4-(1-ethyl-3-methyl-1H-pyrazol-5-yl)-1H-imidazol-2-yl]-1-methyl-1H-indazole-6-carboxylate (G-3) (110 mg, 0.210 mmol) was added ammonia (0.14M in MeOH, 1.5 mL). The reaction was stirred at 80° C. for 16 h. LCMS analysis showed the reaction had reached completion. The reaction was concentrated under vacuum, diluted in DMF (2.5 mL), and purified by preparatory HPLC with a Boston Prime C18 column (150×30 mm, 5 μm particle size). Elution with 25-50% MeCN/H$_2$O (0.05% NH$_4$OH) with a flow rate of 25 mL/min afforded the title compound (Example G01) (16.5 mg, 29% yield) as a light yellow solid. $^1$H NMR (400 MHz, DMSO-d$_6$) δ=13.10 (br s, 1H), 8.71 (s, 1H), 8.22 (d, J=2.4 Hz, 2H), 8.05 (br s, 1H), 7.67 (d, J=1.8 Hz, 1H), 7.57 (br s, 1H), 6.31 (s, 1H), 4.59 (q, J=7.1 Hz, 2H), 4.14 (s, 3H), 2.17 (s, 3H), 1.41 (t, J=7.1 Hz, 3H); m/z (ESI+) for (C$_{18}$H$_{19}$N$_7$O), 350.1 (M+H)$^+$ observed.

Example G02 was synthesized according to the methods used for the synthesis of 4-[4-(1-ethyl-3-methyl-1H-pyrazol-5-yl)-1H-imidazol-2-yl]-1-methyl-1H-indazole-6-carboxamide (Example G01) (Scheme G) with non-critical changes or substitutions to the exemplified procedures that someone who skilled in the art would be able to realize.

| Example Number | Intermediates | Structure/Name | Analytical Data |
|---|---|---|---|
| G02 | Int-HG-13 & Int-TG-08 were used in step 1 | 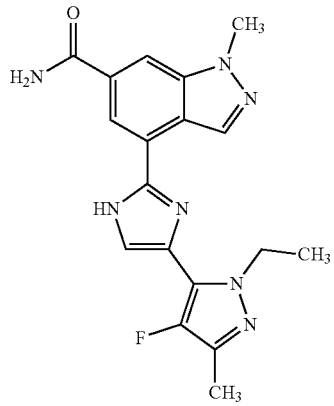<br>4-[4-(1-ethyl-4-fluoro-3-methyl-1H-pyrazol-5-yl)-1H-imidazol-2-yl]-1-methyl-1H-indazole-6-carboxamide | $^1$H NMR (400 MHz, DMSO-$d_6$) δ = 13.30 (br s, 1H), 8.68 (s, 1H), 8.26 (s, 1H), 8.24 (s, 1H), 8.07 (br s, 1H), 7.61 (br s, 1H), 7.59 (br s, 1H), 4.58 (q, J = 6.9 Hz, 2H), 4.14 (s, 3H), 2.18 (s, 3H), 1.41 (br t, J = 6.9 Hz, 3H); m/z (ESI+) for $C_{18}H_{18}FN_7O$, 368.1 (M + H)$^+$ observed. |

Example H01: Preparation of 4-[4-(1-ethyl-3-methyl-1H-pyrazol-5-yl)-1,3-thiazo-2-yl]-1-methyl-1H-indazole-6-carboxamide According to Scheme H

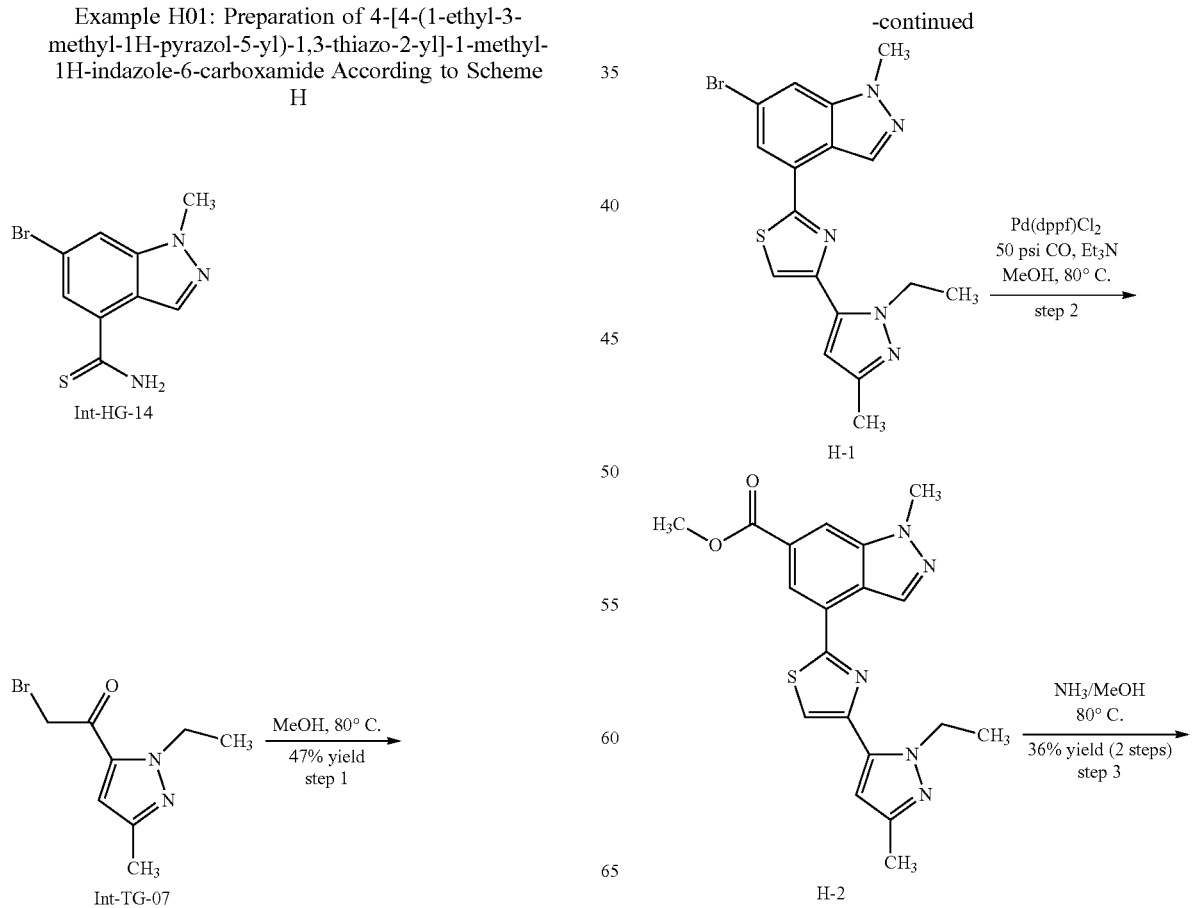

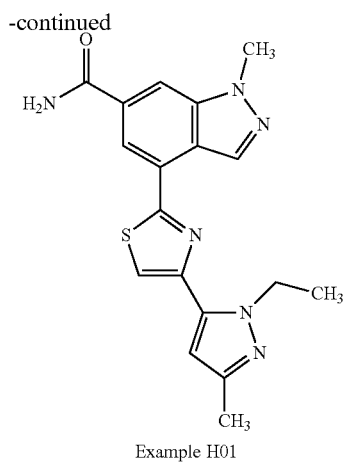

Example H01

Step 1: Synthesis of 6-bromo-4-[4-(1-ethyl-3-methyl-1H-pyrazol-5-yl)-1,3-thiazo-2-yl]-1-methyl-1H-indazole (H-1)

To a suspension of 6-bromo-1-methyl-1H-indazole-4-carbothioamide (Int-HG-14) (93.5 mg, 0.346 mmol) in MeOH (3.0 mL) was added 2-bromo-1-(1-ethyl-3-methyl-1H-pyrazol-5-yl)ethan-1-one (Int-TG-07) (105 mg, 0.454 mmol). The reaction was heated at 80° C. for 14 h. LCMS analysis showed consumption of starting material and formation of the product mass. The reaction was concentrated under vacuum to afford a white solid. The solid was triturated with DCM (5.0 mL) followed by drying under vacuum to afford the title compound (H-1) (65 mg, 47% yield) as a white solid. $^1$H NMR (400 MHz, DMSO-$d_6$) δ=8.57 (s, 1H), 8.22 (s, 1H), 8.19 (s, 1H), 7.87 (d, J=1.3 Hz, 1H), 6.55 (s, 1H), 4.53 (q, J=7.1 Hz, 2H), 4.12 (s, 3H), 2.21 (s, 3H), 1.39 (t, J=7.2 Hz, 3H); m/z (ESI+) for ($C_{17}H_{16}BrN_5S$), 401.7 (M+H)$^+$ observed.

Step 2: Synthesis of methyl 4-[4-(1-ethyl-3-methyl-1H-pyrazol-5-yl)-1,3-thiazo-2-yl]-1-methyl-1H-indazole-6-carboxylate (H-2)

To suspension of 6-bromo-4-[4-(1-ethyl-3-methyl-1H-pyrazol-5-yl)-1,3-thiazol-2-yl]-1-methyl-1H-indazole (H-1) (65 mg, 0.160 mmol) in MeOH (6.0 mL) was added Pd(dppf)Cl$_2$ and Et$_3$N (0.10 mL, 0.700 mmol). The orange solution was stirred at 80° C. in an autoclave under a carbon monoxide atmosphere (50 psi) for 16 h. LMCS analysis showed that the starting material was consumed. The solution was concentrated under vacuum to afford the title compound (H-2) as a crude orange gum which was used in the next step without further purification. m/z (ESI+) for ($C_{19}H_{19}N_5O_2S$), 381.7 (M+H)$^+$ observed.

Step 3: Synthesis of 4-[4-(1-ethyl-3-methyl-1H-pyrazol-5-yl)-1,3-thiazol-2-yl]-1-methyl-1H-indazole-6-carboxamide (Example H01)

To a flask containing methyl 4-[4-(1-ethyl-3-methyl-1H-pyrazol-5-yl)-1,3-thiazol-2-yl]-1-methyl-1H-indazole-6-carboxylate (H-2) (135 mg, 0.119 mmol) was added ammonia (0.08M in MeOH, 1.5 mL). The reaction was stirred at 80° C. for 36 h. The reaction was concentrated under vacuum and purified by preparatory HPLC with a YMC-Triart Prep C18 column (250×50 mm, 10 μm particle size). Elution with 31-61% MeCN/H$_2$O (0.05% NH$_4$OH) with a flow rate of 30 mL/min afforded the title compound 4-[4-(1-ethyl-3-methyl-1H-pyrazol-5-yl)-1,3-thiazol-2-yl]-1-methyl-1H-indazole-6-carboxamide (Example H01) (21.5 mg, 36% yield) as a white solid. $^1$H NMR (400 MHz, DMSO-$d_6$) δ=8.62 (s, 1H), 8.40 (s, 1H), 8.31 (s, 1H), 8.23 (d, J=1.0 Hz, 1H), 8.14 (s, 1H), 7.65 (s, 1H), 6.55 (s, 1H), 4.55 (q, J=7.2 Hz, 2H), 4.17 (s, 3H), 2.21 (s, 3H), 1.40 (t, J=7.2 Hz, 3H); m/z (ESI+) for ($C_{18}H_{18}N_6OS$), 367.0 (M+H)$^+$ observed.

Example J01: 4-[3-(1-ethyl-3-methyl-1H-pyrazol-5-yl)-1-methyl-1H-1,2,4-triazol-5-yl]-1-methyl-1H-pyrazolo[4,3-c]pyridine-6-carboxamide According to Scheme J Scheme J

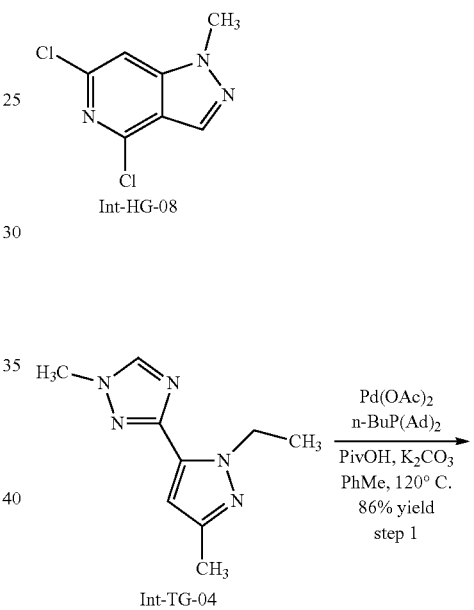

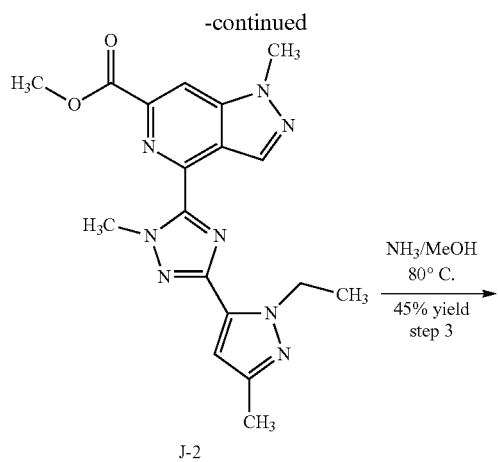

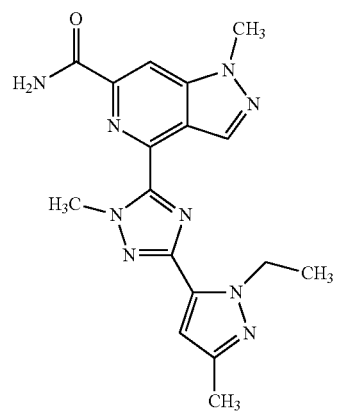

Example J01

Step 1: Synthesis of 6-choro-4-[3-(1-ethyl-3-methyl-1H-pyrazol-5-yl)-1-methyl-1H-1,2,4-triazol-5-yl]-1-methyl-1H-pyrazolo[4,3-c]pyridine (J-1)

To a suspension of 3-(1-ethyl-3-methyl-1H-pyrazol-5-yl)-1-methyl-1H-1,2,4-triazole (Int-TG-04) (55.6 mg, 0.291 mmol) in toluene (1.5 mL) was added 4,6-dichloro-1-methyl-1H-pyrazolo[4,3-c]pyridine (Int-HG-08) (88.7 mg, 0.439 mmol), Pd(OAc)$_2$ (6.5 mg, 0.029 mmol), P(n-Bu)Ad$_2$ (21.8 mg, 0.061 mmol), PivOH (8.9 mg, 0.087 mmol), and K$_2$CO$_3$ (129.8 mg, 0.939 mmol). The solution was sparged with nitrogen gas for 2 minutes and then sealed. The reaction was heated at 120° C. for 16 h. LCMS analysis showed that most of the starting material triazole had been consumed and formation of the desired mass could be detected. The solution was filtered through a pad of celite and the filtrate concentrated under vacuum. The crude residue was purified via preparatory thin-layer chromatography (DCM/MeOH 20:1) to afford the title compound (J-1) (89.5 mg, 86%) as a yellow oil. m/z (ESI+) for (C$_{16}$H$_{17}$ClN$_8$), 356.7 (M+H)$^+$ observed.

Step 2: Synthesis of methyl 4-[3-(1-ethyl-3-methyl-1H-pyrazol-5-yl)-1-methyl-1H-1,2,4-triazol-5-yl]-1-methyl-1H-pyrazolo[4,3-c]pyridine-6-carboxylate (J-2)

To a suspension of 6-chloro-4-[3-(1-ethyl-3-methyl-1H-pyrazol-5-yl)-1-methyl-1H-1,2,4-triazol-5-yl]-1-methyl-1H-pyrazolo[4,3-c]pyridine (J-1) (89.5 mg, 86% yield) in MeOH (10 mL) was added Pd(dppf)Cl$_2$ (64.8 mg, 0.089 mmol) and Et$_3$N (0.20 mL, 1.40 mmol). The reaction was stirred at 80° C. in an autoclave under a carbon monoxide atmosphere (50 psi) for 47 h. The solution was filtered and concentrated under vacuum. The crude residue was purified via preparatory thin-layer chromatography (EtOAc) to afford the title compound (J-2) (23.2 mg, 35% yield) as a light brown solid. $^1$H NMR (400 MHz, DMSO-d$_6$) δ=8.78 (s, 1H), 8.58 (s, 1H), 6.66 (s, 1H), 4.62 (q, J=7.0 Hz, 2H), 4.53 (s, 3H), 4.22 (s, 3H), 3.98 (s, 3H), 2.22 (s, 3H), 1.42 (br t, J=7.0 Hz, 3H); m/z (ESI+) for (C$_{18}$H$_{20}$N$_8$O$_2$), 381.0 (M+H)$^+$ observed. Step 3: Synthesis of 4-[3-(1-ethyl-3-methyl-1H-pyrazol-5-yl)-1-methyl-1H-1,2,4-triazol-5-yl]-1-methyl-1H-pyrazolo[4,3-c]pyridine-6-carboxamide (Example J01)

To a flask containing methyl 4-[3-(1-ethyl-3-methyl-1H-pyrazol-5-yl)-1-methyl-H-1,2,4-triazol-5-yl]-1-methyl-1H-pyrazolo[4,3-c]pyridine-6-carboxylate (J-2) (23.2 mg, 0.061 mmol) was added ammonia (solution in MeOH, 3.0 mL). The reaction was stirred at 80° C. for 15 h. LCMS analysis showed consumption of starting material. The solution was concentrated under vacuum then dissolved in DMF (2 mL) and DMSO (0.5 mL). The suspension was filtered and the filtrate was purified via preparatory HPLC with a Boston Prime C18 column (150×30 mm, 5 μm particle size). Elution with 35-55% MeCN/H$_2$O (0.225% HCO$_2$H) with a flow rate of 25 mL/min afforded the title compound (Example J01) (10.1 mg, 45% yield) as a white solid. $^1$H NMR (400 MHz, DMSO-d$_6$) δ=8.75 (s, 1H), 8.51 (s, 1H), 8.04 (br s, 1H), 7.94 (br s, 1H), 6.67 (s, 1H), 4.62 (q, J=7.1 Hz, 2H), 4.46 (s, 3H), 4.23 (s, 3H), 2.23 (s, 3H), 1.41 (t, J=7.1 Hz, 3H); m/z (ESI+) for (C$_{17}$H$_{19}$N$_9$O), 366.1 (M+H)$^+$ observed.

Examples J02 and J03 were synthesized according to the methods used for the synthesis of 4-[3-(1-ethyl-3-methyl-1H-pyrazol-5-yl)-1-methyl-1H-1,2,4-triazol-5-yl]-1-methyl-1H-pyrazolo[4,3-c]pyridine-6-carboxamide (Example J01) (Scheme J) with non-critical changes or substitutions to the exemplified procedures that someone who skilled in the art would be able to realize.

| Example Number | Intermediates | Structure/Name | Analytical Data |
|---|---|---|---|
| J02 | Int-HG-09 & Int-TG-05 were used in step 1 | 1-[2-(4-cyanopiperidin-1-yl)ethyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carboxamide | $^1$H NMR (400 MHz, DMSO-d$_6$) δ = 8.72 (s, 1H), 8.57 (s, 1H), 8.04 (br s, 1H), 7.94 (br s, 1H), 4.72 (br t, J = 5.9 Hz, 2H), 4.55 (q, J = 6.9 Hz, 2H), 4.49 (s, 3H), 2.85-2.73 (m, 3H), 2.65-2.59 (m, 2H), 2.36-2.28 (m, 2H), 2.22 (s, 3H), 1.81-1.67 (m, 2H), 1.63-1.49 (m, 2H), 1.40 (t, J = 7.1 Hz, 3H); m/z (ESI+) for (C$_{24}$H$_{28}$FN$_{11}$O), 506.1 (M + H)$^+$ observed. |
| J03 | Int-HG-01 & Int-TG-05 were used in step 1. Step 2 not required. | 4-[3-(1-ethyl-4-fluoro-3-methyl-1H-pyrazol-5-yl)-1-methyl-1H-1,2,4-triazol-5-yl]-1-methyl-1H-pyrazolo[4,3-c]-pyridine-6-carboxamide | $^1$H NMR (400 MHz, DMSO-d$_6$) δ 8.68 (s, 1H), 8.51 (s, 1H), 7.99 (d, J = 34.7 Hz, 2H), 4.53 (q, J = 7.1 Hz, 2H), 4.47 (s, 3H), 4.22 (s, 3H), 2.22 (s, 3H), 1.39 (t, J = 7.1 Hz, 3H). m/z (ESI+) for (C$_{17}$H$_{19}$FN$_9$O), 384.1 (M + H)$^+$ observed. |

Example K01: 4-[3-(1-ethyl-3-methyl-1H-pyrazol-5-yl)-1H-1,2,4-triazol-5-yl]-1-methyl-1H-pyrazolo[4,3-c]pyridine-6-carboxamide According to Scheme K Scheme K

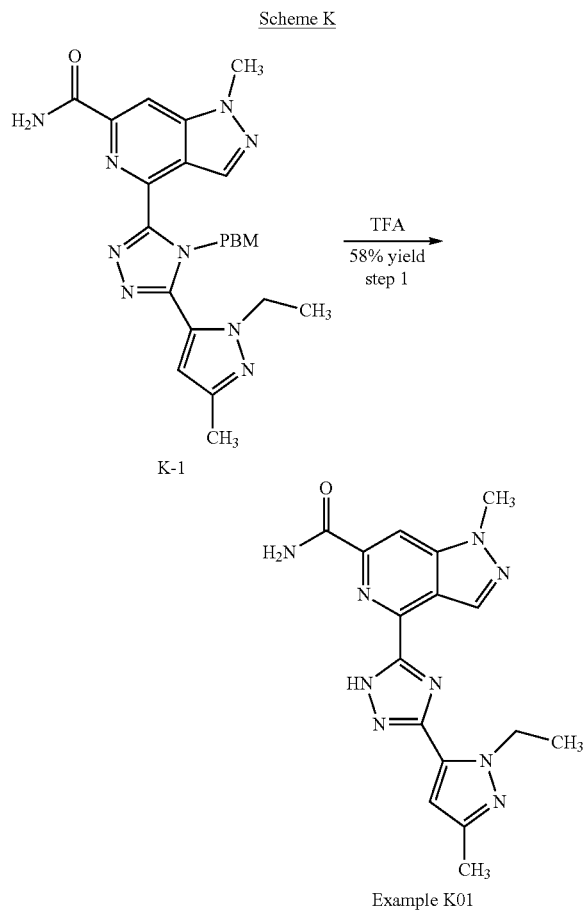

Step 1: Synthesis of 4-[3-(1-ethyl-3-methyl-1H-pyrazol-5-yl)-1H-1,2,4-triazol-5-yl]-1-methyl-1H-pyrazolo[4,3-c]pyridine-6-carboxamide (Example K01)

To a flask containing 4-{5-(1-ethyl-3-methyl-1H-pyrazol-5-yl)-4-[(4-methoxyphenyl)methyl]-4H-1,2,4-triazol-3-yl}-1-methyl-1H-pyrazolo[4,3-c]pyridine-6-carboxamide (K-1) (58 mg, 0.120 mmol), which was prepared by analogy to Example J01 according to the exemplified procedures for steps 1-3 in Scheme J starting with Int-HG-08 and Int-TG-01, was added TFA (1.0 mL). The reaction was stirred at room temperature for 4 h. LCMS analysis showed consumption of starting material and the desired product mass. The solution was concentrated and the crude residue purified via preparatory HPLC with a YMC-Actus Triart C18 column (150×30, 5 μm particle size). Elution with 17-57% MeCN/H$_2$O (0.1% TFA) with a flow rate of 30 mL/min afforded the title compound (Example K01) (25 mg, 58%) as a white solid. $^1$H NMR (400 MHz, DMSO-d$_6$) δ=15.34 (br s, 1H), 8.84 (br s, 1H), 8.80 (s, 1H), 8.47 (s, 1H), 7.88 (br s, 1H), 6.71 (s, 1H), 4.65 (q, J=7.1 Hz, 2H), 4.22 (s, 3H), 2.23 (s, 3H), 1.43 (t, J=7.1 Hz, 3H); m/z (ESI+) for (C$_{16}$H$_{17}$N$_9$O), 351.8 (M+H)$^+$ observed.

Example K02 was synthesized according to procedures exemplified in steps 1-3 used for the synthesis of (Example J01) (Scheme J) followed by the procedure in step 1 for the synthesis of (Example K01) (Scheme K) with non-critical changes or substitutions to the exemplified procedures that someone who skilled in the art would be able to realize.

| Example Number | Intermediates | Structure/Name | Analytical Data |
|---|---|---|---|
| K02 | Int-HG-08 & Int-TG-10 were used | ![structure] <br> 3-{5-[5-(6-carbamoyl-1-methyl-1H-pyrazolo[4,3-c]pyridin-4-yl)-1H-1,2,4-triazol-3-yl]-3-methyl-1H-pyrazol-1-yl}propanoic acid | $^1$H NMR (400 MHz, DMSO-d$_6$) δ = 15.37 (s, 1H), 12.39 (br s, 1H), 8.85 (br s, 1H), 8.84 (s, 1H), 8.46 (s, 1H), 7.88 (br d, J = 2.3 Hz, 1H), 6.72 (s, 1H), 4.87 (t, J = 7.5 Hz, 2H), 4.22 (s, 3H), 2.87 (t, J = 7.5 Hz, 2H), 2.23 (s, 3H); m/z (ESI+) for (C$_{17}$H$_{17}$N$_9$O$_3$), 396.1 (M + H)$^+$ observed. |

Example L01: Preparation of 7-[3-(1-ethyl-3-methyl-1H-pyrazol-5-yl)-1H-1,2,4-triazol-5-yl]-3-methyl-1H-indazole-5-carboxamide According to Scheme L

Scheme L

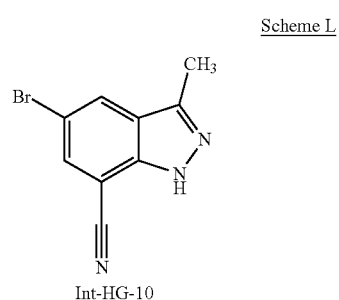
Int-HG-10

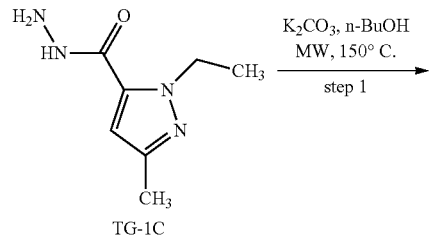
TG-1C

K₂CO₃, n-BuOH
MW, 150° C.
step 1

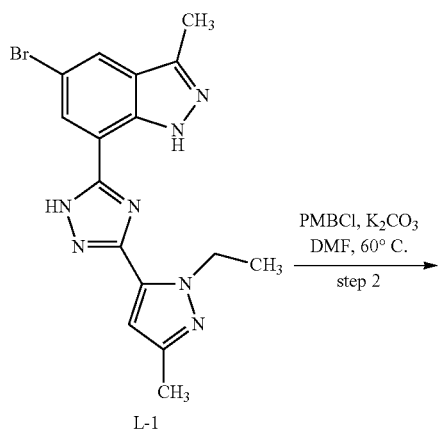
L-1

PMBCl, K₂CO₃
DMF, 60° C.
step 2

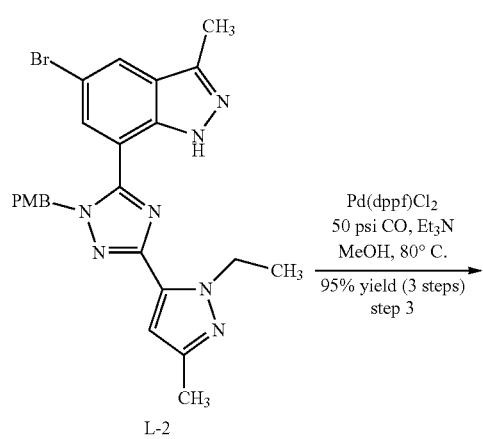
L-2

Pd(dppf)Cl₂
50 psi CO, Et₃N
MeOH, 80° C.
95% yield (3 steps)
step 3

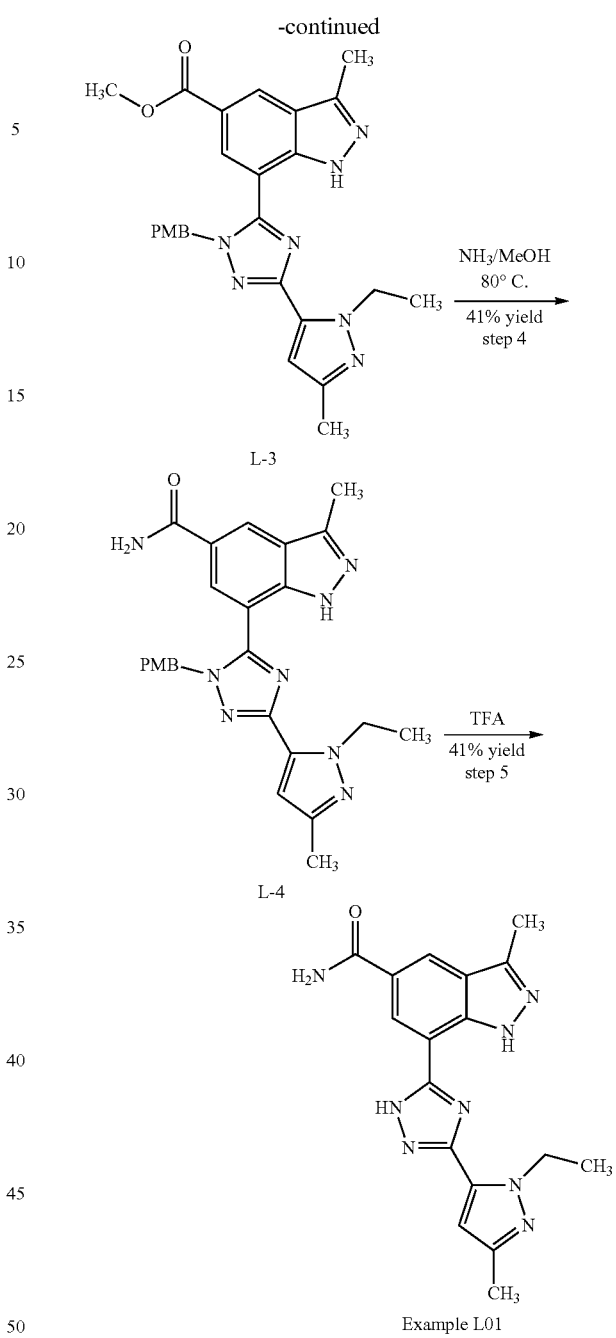

L-3

NH₃/MeOH
80° C.
41% yield
step 4

L-4

TFA
41% yield
step 5

Example L01

Step 1: Synthesis of 5-bromo-7-[3-(1-ethyl-3-methyl-1H-pyrazol-5-yl)-1H-1,2,4-triazol-5-yl]-3-methyl-1H-indazole (L-1)

To a microwave vial was added 5-bromo-3-methyl-1H-indazole-7-carbonitrile (Int-HG-10) (260 mg, 1.10 mmol), 1-ethyl-3-methyl-1H-pyrazole-5-carbohydrazide (TG-1c) (185 mg, 1.10 mmol), K₂CO₃ (457 mg, 3.30 mmol), and n-BuOH (5.0 mL). The reaction was heated in a microwave reactor at 150° C. for 1.5 h. LCMS analysis showed the mass of the desired product as the main component. The solution was concentrated under vacuum to afford the title compound (L-1) (900 mg) as a crude yellow solid which was used in the next step without further purification. m/z (ESI+) for ($C_{16}H_{16}BrN_7$), 386.1 (M+H)⁺ observed.

Step 2: Synthesis of (L-2)

To a flask containing 5-bromo-7-[3-(1-ethyl-3-methyl-1H-pyrazol-5-yl)-1H-1,2,4-triazol-5-yl]-3-methyl-1H-indazole (L-1) was added $K_2CO_3$ (227 mg, 1.64 mmol), DMF (5.0 mL), and 4-methoxybenzyl chloride (206 mg, 1.31 mmol). The reaction was heated at 60° C. for 1 h. LCMS analysis showed the desired product mass as the main component. The solution was concentrated under vacuum to afford the title compound (L-2) (550 mg) as a crude residue which was used in the next step without further purification. m/z (ESI+) for ($C_{24}H_{24}BrN_7O$), 505.9 (M+H)$^+$ observed.

Step 3: Synthesis of (L-3)

To a flask containing (L-2) (550 mg, 1.09 mmol) was added MeOH (10.0 mL), Pd(dppf)Cl$_2$ (238 mg, 0.326 mmol), and Et$_3$N (0.45 mL, 3.26 mmol). The reaction was stirred at 80° C. in an autoclave under a carbon monoxide atmosphere (50 psi) for 16 h. LCMS analysis showed a peak with the desired product mass as the main component. The solution was filtered through Celite and the filtrated concentrated under vacuum. The crude residue was purified via flash column chromatography (12 g SiO$_2$ column, 0-2% MeOH/DCM) to afford the title compound (500 mg, 94% yield) as a brown solid. $^1$H NMR (400 MHz, CHLOROFORM-d) δ=11.33 (s, 1H), 8.88 (s, 1H), 8.54 (s, 1H), 7.14 (br d, J=8.4 Hz, 2H), 6.88 (br d, J=8.4 Hz, 2H), 6.28 (s, 1H), 5.46 (s, 2H), 4.36 (q, J=7.1 Hz, 2H), 3.99 (s, 3H), 3.79 (s, 3H), 2.67 (s, 3H), 2.35 (s, 3H), 1.40 (t, J=7.2 Hz, 3H); m/z (ESI+) for ($C_{26}H_{27}N_7O_3$), 486.2 (M+H)$^+$ observed.

Step 4: Synthesis of (L-4)

To a flask containing (L-3) (250 mg, 0.410 mmol) was added a solution of ammonia in MeOH (10 mL). The reaction was heated at 80° C. for 16 h. LCMS analysis showed the desired product mass and significant starting material remaining. The solution was concentrated under vacuum and the crude residue dissolved in a solution of ammonia in MeOH (10 mL). The reaction was heated at 80° C. for 16 h. LCMS analysis showed increased conversion to the desired product mass. The heterogeneous mixture was filtered to afford the title compound (L-4) (80 mg, 41% yield) as a white solid. $^1$H NMR (400 MHz, DMSO-d$_6$) δ=8.61 (d, J=1.4 Hz, 1H), 8.47 (d, J=1.4 Hz, 1H), 8.12 (br s, 1H), 7.35 (br s, 1H), 7.19 (d, J=8.6 Hz, 2H), 6.90 (d, J=8.6 Hz, 2H), 6.57 (s, 1H), 6.03 (br s, 1H), 5.57 (s, 2H), 4.31 (q, J=7.2 Hz, 2H), 3.71 (s, 3H), 2.60 (s, 3H), 2.26 (s, 3H), 1.18 (t, J=7.1 Hz, 3H); m/z (ESI+) for ($C_{25}H_{26}N_8O_2$), 471.2 (M+H)$^+$ observed.

Step 5: Synthesis of 7-[3-(1-ethyl-3-methyl-1H-pyrazol-5-yl)-1H-1,2,4-triazol-5-yl]-3-methyl-1H-indazole-5-carboxamide (Example L01)

To a flask containing (L-4) (80 mg, 0.170 mmol) was added TFA (2.0 mL). The reaction was stirred at 15° C. for 16 h. LCMS analysis showed significant starting material remained. The reaction was heated at 60° C. for 16 h. LCMS analysis showed a peak with the desired product mass as the main component. The solution was concentrated under vacuum. The crude residue was purified via preparatory HPLC with a YMC-Actus Triart C18 column (150×30, 7 μm particle size). Elution with 15-35% MeCN/H$_2$O (0.05% NH$_4$OH) with a flow rate of 35 mL/min afforded the title compound (Example L01) (24 mg, 41% yield) as a white solid. $^1$H NMR (400 MHz, DMSO-d$_6$) δ=14.65 (br s, 1H), 12.29 (br s, 1H), 8.63 (s, 1H), 8.46 (br s, 1H), 7.49 (br s, 1H), 6.82 (br s, 1H), 4.79-4.54 (m, 2H), 2.61 (s, 3H), 2.26 (s, 3H), 1.41 (t, J=7.2 Hz, 3H); m/z (ESI+) for ($C_{17}H_{18}N_8O$), 351.1 (M+H)$^+$ observed.

Example M01: Preparation of 4-[3-(1-ethyl-3-methyl-1H-pyrazol-5-yl)-1H-1,2,4-triazol-5-yl]-1-[2-(3-fluoroazetidin-1-yl)ethyl]-1H-indazole-6-carboxamide trifluoroacetic acid salt According to Scheme M

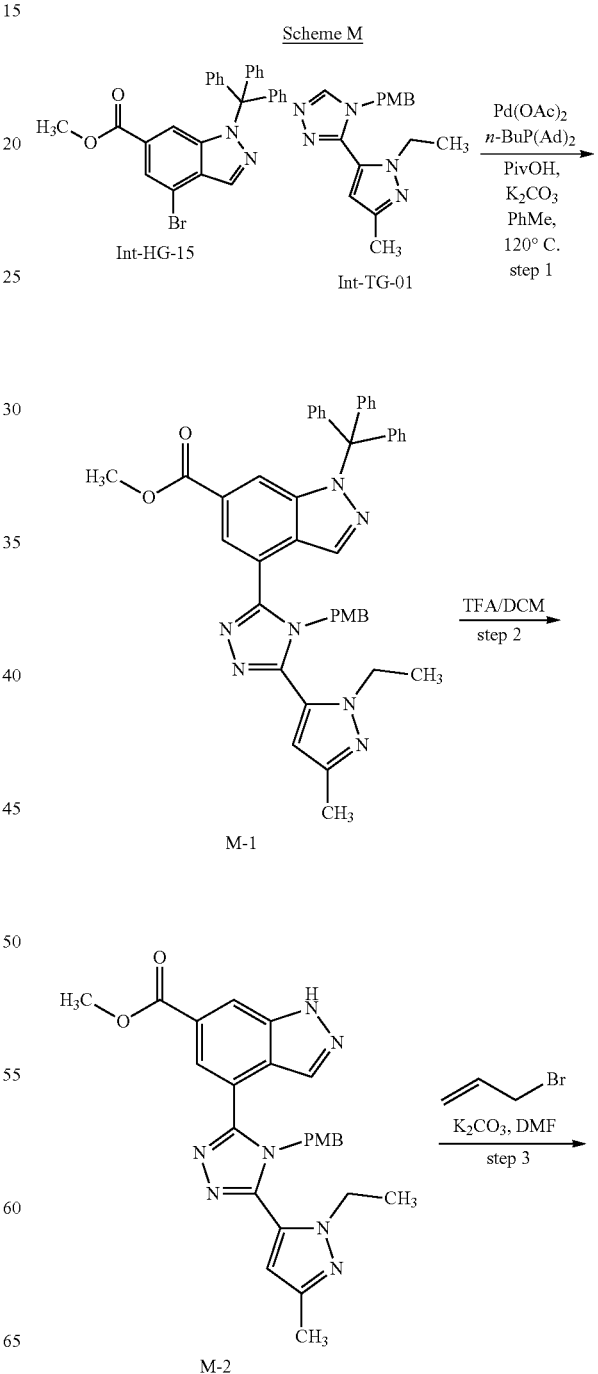

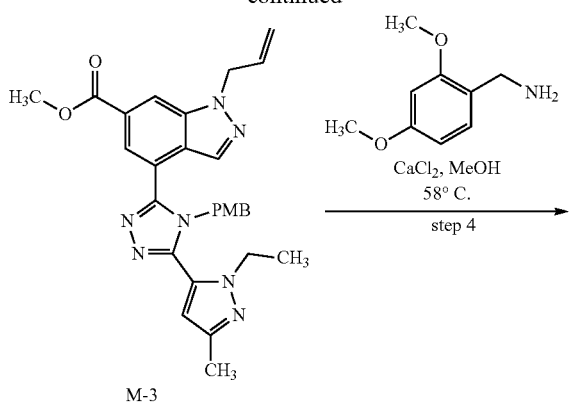

M-3

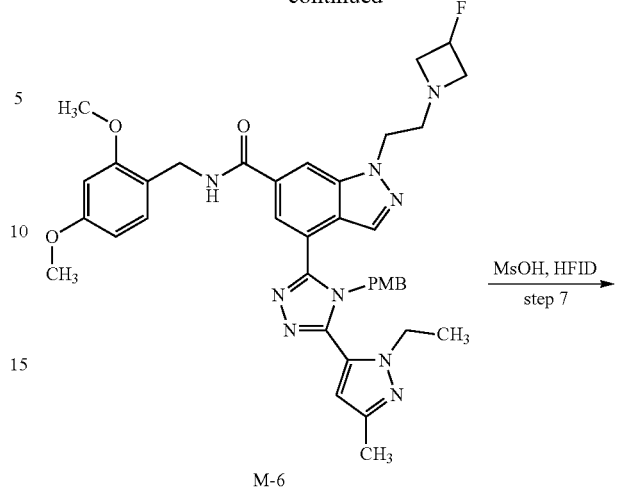

M-6

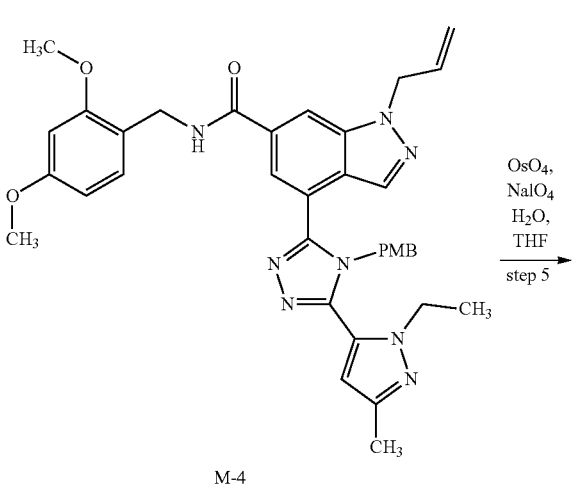

M-4

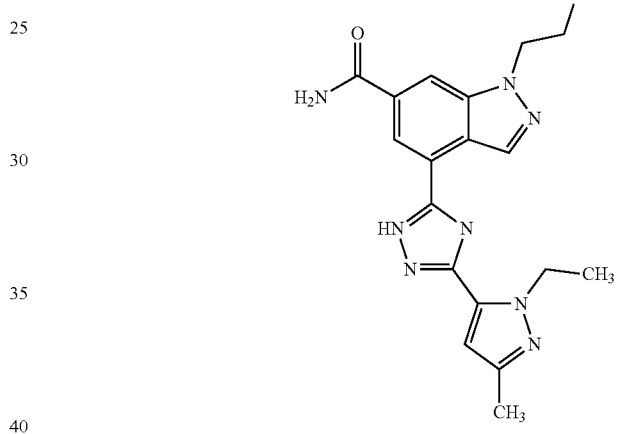

Example M01

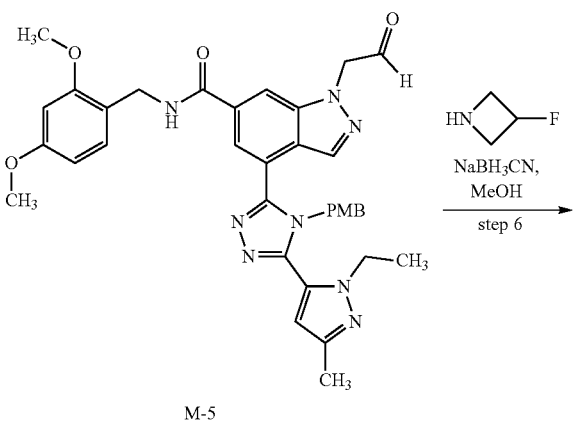

M-5

Step 1: Synthesis of methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (M-1)

To a 250 mL round bottom flask, equipped with a magnetic stirbar, was added methyl 4-bromo-1-(triphenylmethyl)-1H-indazole-6-carboxylate (Int-HG-15) (4.0 g, 8.00 mmol), 3-(1-ethyl-3-methyl-1H-pyrazol-5-yl)-4-[(4-methoxyphenyl)methyl]-4H-1,2,4-triazole (Int-TG-01) (2.63 g, 8.85 mmol), Pd(OAc)$_2$ (361 mg, 1.61 mmol), CataXCium A (1.15 g, 3.22 mmol), pivalic acid (246 mg, 2.41 mmol), and K$_2$CO$_3$ (3.33 g, 24.1 mmol). The flask was evacuated under vacuum and backfilled with N$_2$ gas. The flask was charged with anhydrous toluene (sparged with N$_2$ prior to use) and the reaction was refluxed under N$_2$ atmosphere for 18 h. The solution was allowed to cool to rt gradually, diluted with acetonitrile, and filtered over a pad of Celite. The filtrate was concentrated under vacuum. The crude residue was purified via flash chromatography (SiO$_2$ plug, 30-100% EtOAc/Hept., 500 mL fractions). The combined fractions containing desired product were concentrated under vacuum to afford the title compound methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (M-1) (4.65 g, 81% yield, mixture of N-1 and N-2 regioisomers) as a brown solid. m/z (ESI+) for ($C_{44}H_{39}N_7O_3$), 714.5 (M+H)$^+$ observed.

Step 2: Synthesis of methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (M-2)

To a flask containing methyl 4-{5-(1-ethyl-3-methyl-1H-pyrazol-5-yl)-4-[(4-methoxyphenyl)methyl]-4H-1,2,4-triazol-3-yl}-1-(triphenylmethyl)-1H-indazole-6-carboxylate (M-1) (4.65 g, 6.51 mmol) was added DCM (465 mL) and TFA (4.65 mL). The reaction was stirred for 1 h then quenched with sat. NaHCO$_3$ aq. and transferred to a separatory funnel with DCM. The phases were separated, and the aqueous phase was extracted with 1 portion DCM. The combined organic extracts were dried (MgSO$_4$), filtered, and concentrated under vacuum. The crude residue was purified via flash chromatography (80 g SiO$_2$, Isco, 100% EtOAc to 5% MeOH/EtOAc) to afford the title compound methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (M-2) (1.5 g, 49% yield) as a solid. $^1$H NMR (400 MHz, CHLOROFORM-d) δ=8.42 (s, 1H), 8.31 (s, 1H), 7.85 (s, 1H), 6.79-6.64 (m, 4H), 6.22 (s, 1H), 5.31 (s, 2H), 4.33 (q, J=7.0 Hz, 2H), 3.79 (s, 3H), 3.69 (s, 3H), 2.28 (s, 3H), 1.37 (t, J=7.2 Hz, 3H); m/z (ESI+) for ($C_{25}H_{25}N_7O_3$), 472.4 (M+H)$^+$ observed.

Step 3: Synthesis of methyl 4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxylate (M-3)

To a 100 mL round bottom flask was added methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (M-2) (870 mg, 1.85 mmol), K$_2$CO$_3$ (382 mg, 2.77 mmol), and anhydrous DMF (18.5 mL). To the solution was added allyl bromide (239 µL, 2.77 mmol) and the reaction was stirred at rt for 3 h. LCMS analysis showed complete consumption of the starting material and new peaks with the desired product mass. The solution was quenched with H$_2$O and further diluted with DCM. The phases were separated, and the organic phase was washed with 1 portion sat. brine aq., dried (MgSO$_4$), filtered, and concentrated under vacuum. The crude residue was purified via chromatography (OZ column) to afford the title compound methyl 4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxylate (M-3) (478 mg, 50% yield) as a viscous oil. $^1$H NMR (400 MHz, CHLOROFORM-d) δ=8.41 (d, J=0.8 Hz, 1H), 8.23-8.20 (m, 1H), 7.84 (d, J=1.2 Hz, 1H), 6.78-6.73 (m, 2H), 6.73-6.68 (m, 2H), 6.16 (s, 1H), 6.08-5.95 (m, 1H), 5.29 (s, 2H), 5.25-5.18 (m, 1H), 5.14-5.04 (m, 3H), 4.33 (q, J=7.3 Hz, 2H), 3.83 (s, 3H), 3.71 (s, 3H), 2.25 (s, 3H), 1.39 (t, J=7.2 Hz, 3H); $^{13}$C NMR (101 MHz, CHLOROFORM-d) δ=166.30, 159.39, 153.19, 147.93, 147.91, 139.43, 133.95, 132.17, 128.27, 127.91, 127.24, 127.13, 125.56, 121.18, 119.81, 118.29, 114.48, 113.63, 106.69, 55.27, 52.44, 52.06, 48.36, 45.69, 15.94, 13.50; m/z (API+) for ($C_{28}H_{29}N_7O_3$), 512.3 (M+H)$^+$ observed.

Step 4: Synthesis of N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxamide (M-4)

To round bottom flask was added methyl 4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxylate (M-3) (390 mg, 0.762 mmol), 1-(2,4-dimethoxyphenyl)methanamine (1.15 mL, 7.62 mmol), CaCl$_2$ (84.6 mg, 0.762 mmol) and MeOH (7.6 mL). The reaction was heated at 58° C. overnight then the reaction was allowed to cool gradually to rt. The solution was diluted with EtOAc (200 mL) and washed with 1 portion dilute NaHCO$_3$, dried (MgSO$_4$), filtered, and concentrated under vacuum. The crude residue was purified via flash chromatography (50 g SiO$_2$, Biotage, 100% EtOAc) to afford the title compound N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxamide (M-4) (258 mg, 52% yield) as a gum which solidified overtime. $^1$H NMR (400 MHz, CHLOROFORM-d) δ=8.31 (s, 1H), 8.12 (s, 1H), 7.70 (s, 1H), 7.46 (t, J=5.7 Hz, 1H), 6.73-6.68 (m, 2H), 6.68-6.63 (m, 2H), 6.48-6.38 (m, 3H), 6.20 (s, 1H), 6.05-5.92 (m, 1H), 5.32 (s, 2H), 5.19 (dd, J=0.8, 10.1 Hz, 1H), 5.06 (dd, J=1.2, 17.2 Hz, 1H), 5.01 (br d, J=5.5 Hz, 2H), 4.52 (d, J=5.9 Hz, 2H), 4.31 (q, J=7.3 Hz, 2H), 3.78 (s, 3H), 3.77 (s, 3H), 3.68 (s, 3H), 2.31 (s, 3H), 1.39 (t, J=7.0 Hz, 3H); m/z (ESI+) for ($C_{36}H_{38}N_8O_4$), 647.5 (M+H)$^+$ observed.

Step 5: Synthesis of N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(2-oxoethyl)-1H-indazole-6-carboxamide (M-5)

To a flask containing N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(prop-2-en-1-yl)-1H-indazole-6-carboxamide (M-4) (258 mg, 0.399 mmol) was added NaIO$_4$ (259 mg, 1.21 mmol), OsO$_4$ (250 µL, as a 2.5 wt % solution in t-BuOH, 0.02 mmol), THF (1.4 mL), and H$_2$O (270 µL). The reaction was stirred at rt for 3 h. The solution was quenched with H$_2$O and further diluted with DCM. The phases were separated, and the organic extract was dried (MgSO$_4$), filtered, and concentrated under vacuum. The crude residue was purified via flash chromatography (40 g SiO$_2$, Isco, 5-10% MeOH/EtOAc) to afford a colorless gum. This material was dissolved in 60% MeCN/H$_2$O (10 mL) followed by the addition of NaIO$_4$ (47 mg, 0.220 mmol). The reaction was stirred at rt for 5 h. The reaction was quenched with dilute NaS$_2$O$_3$ aq. and further diluted with EtOAc. The phases were separated and the organic extract was dried (MgSO$_4$), filtered, and concentrated under vacuum to afford the title compound N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(2-oxoethyl)-1H-indazole-6-carboxamide (M-5) (136 mg, 52% yield) as a tan solid. m/z (ESI+) for $C_{35}H_{38}N_8O_6$), 667.5 (M+H+H$_2$O)$^+$ observed.

Step 6: Synthesis of N-[(2,4-dimethoxyphenyl) methyl]-4-{5-(1-ethyl-3-methyl-1H-pyrazol-5-yl)-4-[(4-methoxyphenyl)methyl]-4H-1,2,4-triazol-3-yl}-1-[2-(3-fluoroazetidin-1-yl)ethyl]-1H-indazole-6-carboxamide (M-6)

To a vial containing N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-(2-oxoethyl)-1H-indazole-6-carboxamide (M-5) (25 mg, 0.039 mmol) was added anhydrous MeOH (1.0 mL) and 3-fluoroazetidine (19.1 mg, 0.077 mmol). The solution was stirred for 5 min. followed by the addition of sodium cyanoborohydride NaBH$_3$CN (4.84 mg, 0.077 mmol). The reaction was stirred at rt overnight. LCMS analysis showed a new peak with the desired product mass. The reaction was quenched with dilute NaHCO$_3$ aq. (0.5 mL) and further diluted with DCM. The phases were separated, and the aqueous phase extracted with 1 portion of DCM. The combined organic extracts were dried (MgSO$_4$), filtered, and concentrated under vacuum to afford the title compound N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-[2-(3-fluoroazetidin-1-yl)ethyl]-1H-indazole-6-carboxamide (M-6) (28 mg, >95% yield) as a crude gum which was used in the next step without further purification. m/z (ESI+) for (C$_{38}$H$_{42}$FN$_9$O$_4$), 708.7 (M+H)$^+$ observed.

Step 7: Synthesis of 4-[3-(1-ethyl-3-methyl-1H-pyrazol-5-yl)-1H-1,2,4-triazol-5-yl]-1-[2-(3-fluoroazetidin-1-yl)ethyl]-1H-indazole-6-carboxamide trifluoroacetic acid salt (Example M01)

To a vial containing N-[(2,4-dimethoxyphenyl)methyl]-4-{5-(1-ethyl-3-methyl-1H-pyrazol-5-yl)-4-[(4-methoxyphenyl)methyl]-4H-1,2,4-triazol-3-yl}-1-[2-(3-fluoroazetidin-1-yl)ethyl]-1H-indazole-6-carboxamide (M-6) (27 mg, 0.038 mmol) was added HFIP (20 mL) and MsOH (12.4 µL, 0.191 mmol). The reaction was stirred at rt for 2 h. The reaction was quenched with a few drops of sat. NaHCO$_3$ aq. and further diluted with H$_2$O (1.0 mL) and DCM (10 mL). The phases were separated by pipette and the organic extract was dried (MgSO$_4$), filtered, and concentrated under vacuum. The crude residue was purified via chromatography to afford the title compound 4-[3-(1-ethyl-3-methyl-1H-pyrazol-5-yl)-1H-1,2,4-triazol-5-yl]-1-[2-(3-fluoroazetidin-1-yl)ethyl]-1H-indazole-6-carboxamide trifluoroacetic acid salt (Example M1)(8.1 mg, 47% yield) as a white solid. m/z (ESI+) for (C$_{21}$H$_{24}$FN$_9$O), 438.4 (M+H)$^+$ observed.

Examples M02, M03 and M04 were synthesized according to procedures exemplified in steps 1-7 for the synthesis of (Example M01)(Scheme M) by substituting the appropriate amine intermediate for step 6 (Scheme M) with non-critical changes or substitutions to the exemplified procedures that someone who skilled in the art would be able to realize.

| Example Number | Intermediate | Structure/Name | Analytical Data |
|---|---|---|---|
| M02 | 4,4-difluoropiperidine was used | 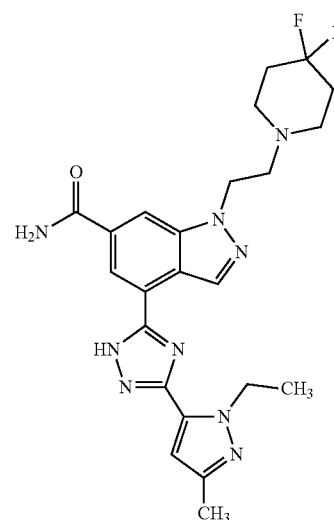<br>1-[2-(4,4-difluoropiperidin-1-yl)ethyl]-4-[3-(1-ethyl-3-methyl-1H-pyrazol-5-yl)-1H-1,2,4-triazol-5-yl]-1H-indazole-6-carboxamide | m/z (ESI+) for (C$_{23}$H$_{27}$F$_2$N$_9$O), 484.6 (M + H)$^+$ observed. |

-continued

| Example Number | Intermediate | Structure/Name | Analytical Data |
|---|---|---|---|
| M03 | 8-oxa-3-azabicyclo[3.2.1]octane was used | 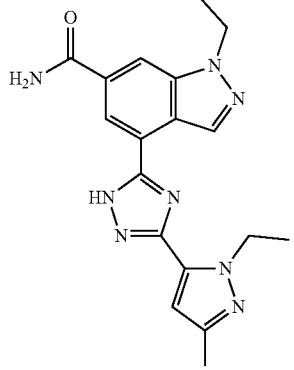<br>4-[3-(1-ethyl-3-methyl-1H-pyrazol-5-yl)-1H-1,2,4-triazol-5-yl]-1-[2-(8-oxa-3-azabicyclo[3.2.1]octan-3-yl)ethyl]-1H-indazole-6-carboxamide | m/z (ESI+) for ($C_{24}H_{30}N_9O_2$), 476.4 $(M + H)^+$ observed. |
| M04 | (2S,5S)-2,5-dimethylmorpholine was used | 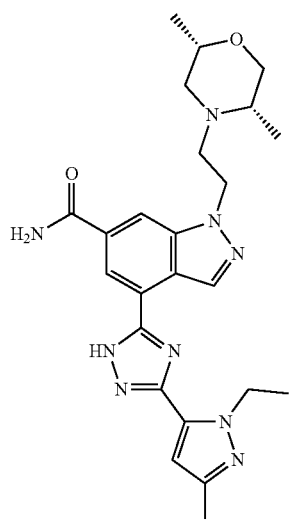<br>1-{2-[(2S,5S)-2,5-dimethyl-morpholin-4-yl]ethyl}-4-[3-(1-ethyl-3-methyl-1H-pyrazol-5-yl)-1H-1,2,4-triazol-5-yl]-1H-indazole-6-carboxamide | m/z (ESI+) for ($C_{24}H_{32}N_9O_2$), 478.5 $(M + H)^+$ observed. |

213

Example N01: Preparation of [3-(6-carbamoyl-1-methyl-1H-indazol-4-yl)-5-(1-ethyl-3-methyl-1H-pyrazol-5-yl)-1H-1,2,4-triazol-1-yl]methyl dihydrogenphosphate According to Scheme N

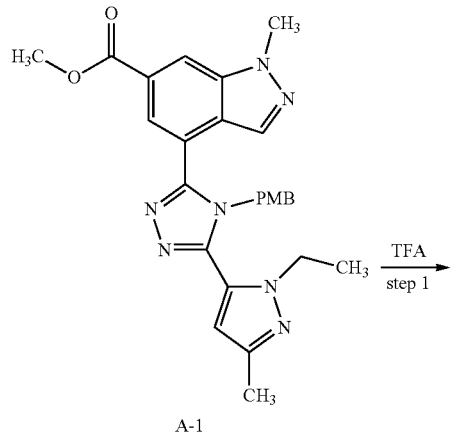

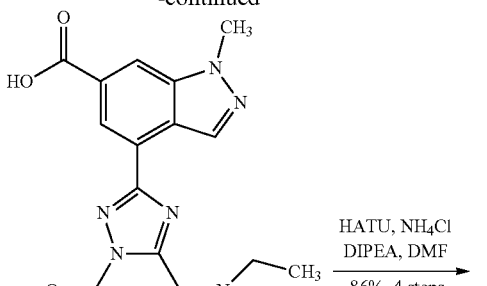

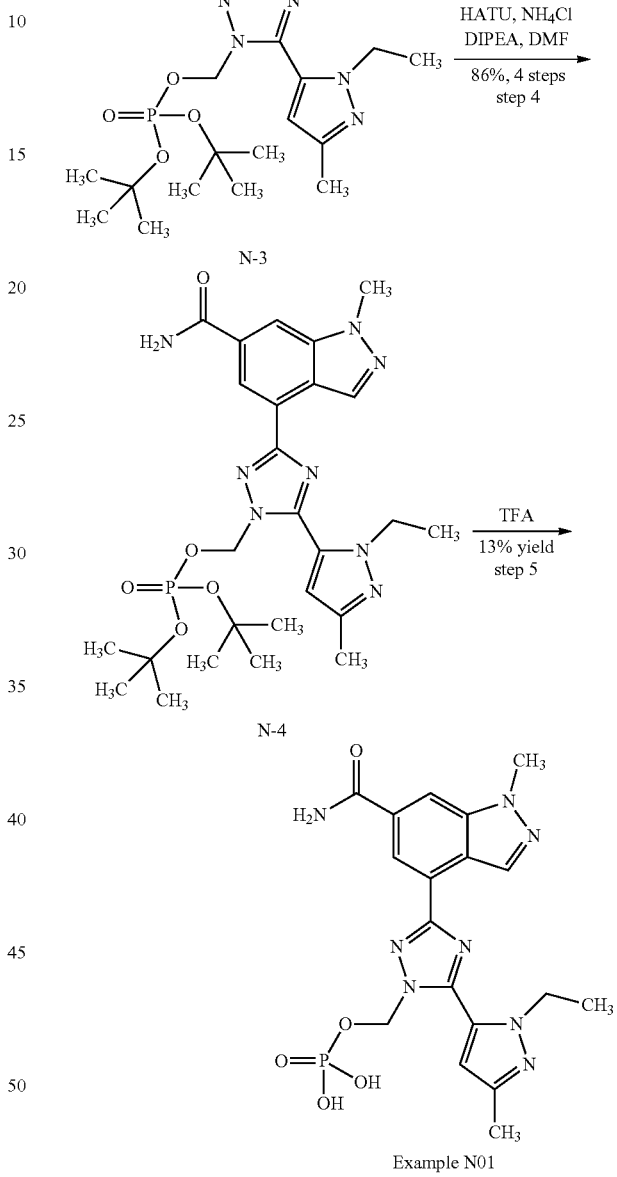

Step 1: Synthesis of methyl 4-[3-(1-ethyl-3-methyl-1H-pyrazol-5-yl)-1H-1,2,4-triazol-5-yl]-1-methyl-1H-indazole-6-carboxylate (N-1)

To a flask containing methyl 4-{5-(1-ethyl-3-methyl-1H-pyrazol-5-yl)-4-[(4-methoxyphenyl)methyl]-4H-1,2,4-triazol-3-yl}-1-methyl-1H-indazole-6-carboxylate (A-1) (540 mg, 1.11 mmol) was added TFA (4.0 mL). The reaction was stirred at 28° C. for 1 h. LCMS analysis showed consumption of starting material and a new peak with the desired product mass. The solution was concentrated under vacuum followed by lyophilization to afford the title compound 4-[3-(1-ethyl-3-methyl-1H-pyrazol-5-yl)-1H-1,2,4-triazol-5-yl]-1-methyl-1H-indazole-6-carboxylate (N-1) (690 mg) as a crude yellow solid. The material was used in the next step without further purification. $^1$H NMR (400 MHz, DMSO-d$_6$) δ=8.70 (s, 1H), 8.47 (s, 1H), 8.40 (s, 1H), 6.70 (s, 1H), 4.67 (q, J=7.0 Hz, 2H), 4.19 (s, 3H), 3.96 (s, 3H), 2.24 (s, 3H), 1.43 (t, J=7.1 Hz, 3H); m/z (ESI+) for (C$_{18}$H$_{19}$N$_7$O$_2$), 366.2 (M+H)$^+$ observed.

Step 2: Synthesis of methyl 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylate (N-2)

To a flask containing 4-[3-(1-ethyl-3-methyl-1H-pyrazol-5-yl)-1H-1,2,4-triazol-5-yl]-1-methyl-1H-indazole-6-carboxylate (N-1) (690 mg, 1.10 mmol) was added NMP (5.0 mL), di-tert-butyl-(chloromethyl)-phosphate (586 mg, 2.27 mmol), Cs$_2$CO$_3$ (1.48 g, 4.53 mmol), and potassium iodide (376 mg, 2.27 mmol). The reaction was stirred at rt for 20 h. The solution was quenched with water (25 mL) and transferred to a separatory funnel with EtOAc. The phases were separated, and the aqueous phase extracted with EtOAc (3×25 mL). The combined organic extracts were washed with brine (50 mL), dried (Na$_2$SO$_4$), filtered, and concentrated under vacuum. The crude residue was purified via flash chromatography (SiO$_2$, 0%-75%-100% Pet. Ether/EtOAc) to afford the title compound methyl 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylate (N-2) (1000 mg) with significant residue NMP solvent. This material was used in the next step without further purification. $^1$H NMR (400 MHz, CHLOROFORM-d) δ=8.80 (s, 1H), 8.69 (s, 1H), 8.26 (s, 1H), 6.71 (s, 1H), 6.08-6.01 (m, 2H), 4.60 (q, J=7.1 Hz, 2H), 4.20 (s, 3H), 4.01 (s, 3H), 1.56-1.50 (m, 21H); m/z (ESI+) for (C$_{27}$H$_{38}$N$_7$O$_6$P), 588.2 (M+H)$^+$ observed.

Step 3: Synthesis of 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylic acid (N-3)

To a flask containing methyl 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylate (N-2) (1000 mg, 1.10 mmol) was added THF (10 mL), H$_2$O (5.0 mL), and LiOH (71.8 mg, 1.71 mmol). The reaction was stirred at rt for 2 h. LCMS analysis showed consumption of starting material. The solution was concentrated under vacuum and lyophilized to afford the title compound 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylic acid (N-3) (1100 mg) as a crude yellow solid which was used in the next step without further purification. m/z (ESI+) for (C$_{26}$H$_{36}$N$_7$O$_6$P), 574.2 (M+H)$^+$ observed.

Step 4: Synthesis of di-tert-butyl [3-(6-carbamoyl-1-methyl-1H-indazol-4-yl)-5-(1-ethyl-3-methyl-1H-pyrazol-5-yl)-1H-1,2,4-triazol-1-yl]methyl phosphate (N-4)

To a flask containing 4-[1-{[(di-tert-butoxyphosphoryl)oxy]methyl}-5-(1-ethyl-3-methyl-1H-pyrazol-5-yl)-1H-1,2,4-triazol-3-yl]-1-methyl-1H-indazole-6-carboxylic acid (N-3) (1100 mg, 1.10 mmol) was added DMF (5.0 mL), HATU (508 mg, 1.33 mmol), NH$_4$Cl (178 mg, 3.34 mmol), and DIPEA (863 mg, 6.67 mmol). The reaction was stirred at rt for 2 h. LCMS analysis showed a new peak with the desired product mass. The reaction was quenched with water (25 mL) and transferred to a separatory funnel with EtOAc. The phases were separated and the aqueous phase was extracted with EtOAc (2×25 mL). The combined organic extracts were dried (Na$_2$SO$_4$), filtered, and concentrated under vacuum to afford the title compound di-tert-butyl [3-(6-carbamoyl-1-methyl-1H-indazol-4-yl)-5-(1-ethyl-3-methyl-1H-pyrazol-5-yl)-1H-1,2,4-triazol-1-yl]methyl phosphate (N-4) (550 mg, 86% yield) as a yellow oil which was used in the next step without further purification. m/z (ESI+) for (C$_{26}$H$_{37}$N$_8$O$_5$P), 461.1 (M+H-2xt-Bu)$^+$ observed.

Step 5: Synthesis of [3-(6-carbamoyl-1-methyl-1H-indazol-4-yl)-5-(1-ethyl-3-methyl-1H-pyrazol-5-yl)-1H-1,2,4-triazol-1-yl]methyl dihydrogen phosphate (Example N01)

To a flask containing di-tert-butyl [3-(6-carbamoyl-1-methyl-1H-indazol-4-yl)-5-(1-ethyl-3-methyl-1H-pyrazol-5-yl)-1H-1,2,4-triazol-1-yl]methyl phosphate (N-4) (550 mg, 0.961 mmol) was added TFA (5.0 mL). The reaction was stirred at rt for 16 h. LCMS analysis showed a new peak with the desired product mass. The solution was concentrated under vacuum and the crude residue was purified via preparatory HPLC with a YMC-Actus Triart C18 column (150×30, 5 μm particle size). Elution with 10-25% MeCN/H$_2$O (0.05% NH$_4$OH) with a flow rate of 35 mL/min afforded the title compound [3-(6-carbamoyl-1-methyl-1H-indazol-4-yl)-5-(1-ethyl-3-methyl-1H-pyrazol-5-yl)-1H-1,2,4-triazol-1-yl]methyl dihydrogen phosphate (Example N01) (61 mg, 13% yield) as a white solid. $^1$H NMR (400 MHz, DMSO-d$_6$) δ=8.60 (s, 1H), 8.38 (d, J=1.0 Hz, 1H), 8.29 (s, 1H), 8.23 (s, 1H), 7.53 (s, 1H), 7.23 (br s, 2H), 5.88-5.77 (m, 2H), 4.49 (q, J=7.2 Hz, 2H), 4.13 (s, 3H), 2.24 (s, 3H), 1.41 (t, J=7.0 Hz, 3H); m/z (ESI+) for C$_{18}$H$_{21}$N$_8$O$_5$P), 461.1 (M+H)$^+$ observed.

Example P01: Preparation of {6-carbamoyl-4-[3-(1-ethyl-3-methyl-1H-pyrazol-5-yl)-1H-1,2,4-triazol-5-yl]-1H-indazol-1-yl}acetic acid According to Scheme P

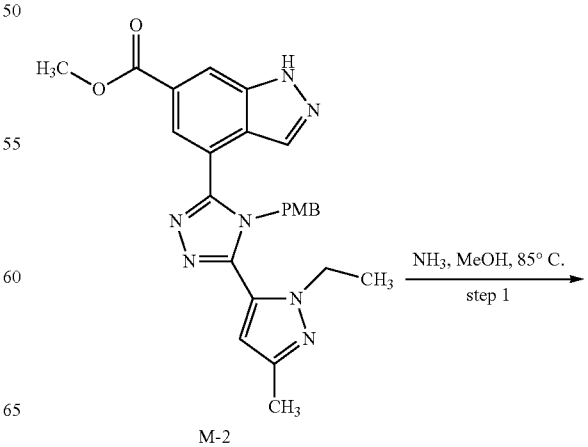

Scheme P

M-2

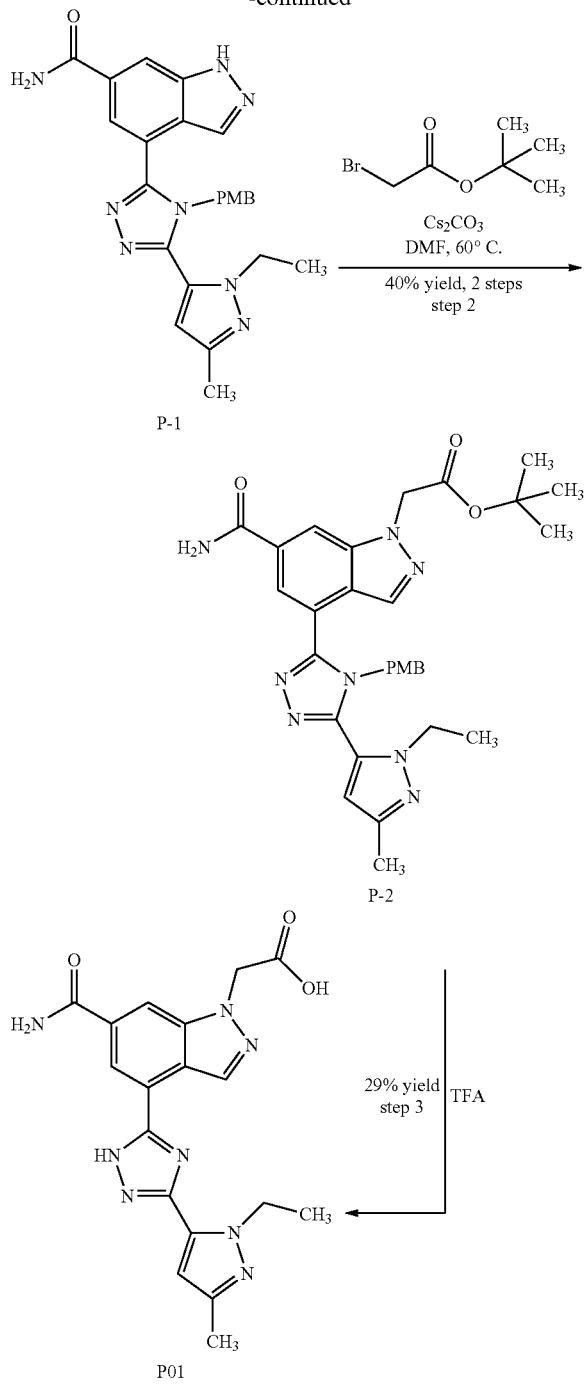

Step 1: Synthesis of 4-{5-(1-ethyl-3-methyl-1H-pyrazol-5-yl)-4-[(4-methoxyphenyl)methyl]-4H-1,2,4-triazol-3-yl}-1H-indazole-6-carboxamide (P-1)

A yellow solution of methyl 4-{5-(1-ethyl-3-methyl-1H-pyrazol-5-yl)-4-[(4-methoxyphenyl)methyl]-4H-1,2,4-triazol-3-yl}-1H-indazole-6-carboxylate (M-2) (301.0 mg, 0.638 mmol) in saturated NH/MeOH (15 mL) was stirred at 85° C. (oil bath) for 16 h. LCMS analysis showed that significant starting material remained. The reaction was concentrated under vacuum and saturated NH3/MeOH (15 mL) was added. The reaction was heated at 85° C. for another 4 h. The reaction was concentrated under vacuum at this stage to afford the title compound 4-{5-(1-ethyl-3-methyl-1H-pyrazol-5-yl)-4-[(4-methoxyphenyl)methyl]-4H-1,2,4-triazol-3-yl}-1H-indazole-6-carboxamide (P-1) (350 mg, >100%) as a crude yellow gum which was used in the next step without further purification. m/z (ESI+) for ($C_{24}H_{24}N_8O_2$), 456.9 (M+H)$^+$ observed.

Step 2: Synthesis of tert-butyl (6-carbamoyl-4-{5-(1-ethyl-3-methyl-1H-pyrazol-5-yl)-4-[(4-methoxyphenyl)methyl]-4H-1,2,4-triazol-3-yl}-1H-indazol-1-yl)acetate (P-2)

To a solution of 4-{5-(1-ethyl-3-methyl-1H-pyrazol-5-yl)-4-[(4-methoxyphenyl)methyl]-4H-1,2,4-triazol-3-yl}-1H-indazole-6-carboxamide (P-1) (175 mg, 0.383 mmol) and $Cs_2CO_3$ (250 mg, 0.767 mmol) in DMF (3.0 mL) was added tert-butyl bromoacetate (82.3 mg, 0.422 mmol). The reaction was stirred at 60° C. for 14 h. LCMS analysis showed complete consumption of starting material. The reaction was diluted with EtOAc (10 mL) and water (3 mL). The phases were separated, and the organic extract was concentrated under vacuum. This crude residue was purified by Prep-TLC (DCM:MeOH=15:1) twice to afford the title compound tert-butyl (6-carbamoyl-4-{5-(1-ethyl-3-methyl-1H-pyrazol-5-yl)-4-[(4-methoxyphenyl)methyl]-4H-1,2,4-triazol-3-yl}-1H-indazol-1-yl)acetate (P-2) (88 mg, 50% yield) as colorless gum. $^1$H NMR (400 MHz, METHANOL-d4) δ=8.33 (s, 1H), 8.24 (d, J=0.8 Hz, 1H), 7.94 (d, J=1.3 Hz, 1H), 6.72-6.64 (m, 2H), 6.58 (d, J=8.8 Hz, 2H), 6.54 (s, 1H), 5.49 (s, 2H), 5.38-5.28 (m, 4H), 4.11 (q, J=7.3 Hz, 2H), 3.67 (s, 3H), 2.32 (s, 3H), 1.45 (s, 9H), 1.28 (t, J=7.2 Hz, 3H); m/z (ESI+) for ($C_{30}H_{34}N_8O_4$), 571.0 (M+H)$^+$ observed.

Step 3: Synthesis of {6-carbamoyl-4-[3-(1-ethyl-3-methyl-1H-pyrazol-5-yl)-1H-1,2,4-triazol-5-yl]-1H-indazol-1-yl}acetic acid (Example P01)

A yellow solution of tert-butyl (6-carbamoyl-4-{5-(1-ethyl-3-methyl-1H-pyrazol-5-yl)-4-[(4-methoxyphenyl)methyl]-4H-1,2,4-triazol-3-yl}-1H-indazol-1-yl)acetate (P-2) (88 mg, 0.15 mmol) in TFA (2.0 mL) was stirred at rt for 1.5 h. LCMS analysis showed complete consumption of starting material. The reaction was concentrated under vacuum. The crude residue was dissolved in DMF (2 mL) and purified via preparatory HPLC with a YMC-Triart C18 column (150×40, 7 μm particle size). Elution with 15-55% MeCN/H$_2$O (0.1% TFA) with a flow rate of 30 mL/min afforded the title compound {6-carbamoyl-4-[3-(1-ethyl-3-methyl-1H-pyrazol-5-yl)-1H-1,2,4-triazol-5-yl]-1H-indazol-1-yl}acetic acid (Example P01) (22.87 mg, 29% yield, 1 eq. mol TFA salt) as a white solid. $^1$H NMR (400 MHz, DMSO-d6) δ=14.62 (br s, 1H), 8.70 (d, J=0.8 Hz, 1H), 8.41 (s, 1H), 8.31 (br s, 1H), 7.60 (br s, 2H), 6.68 (br s, 1H), 5.32 (s, 2H), 4.68 (q, J=6.8 Hz, 2H), 2.25 (s, 3H), 1.45 (t, J=7.2 Hz, 3H); m/z (ESI+) for ($C_{18}H_{18}N_8O_3$), 395.1 (M+H)$^+$ observed.

Example Q01: Preparation of 4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide According to Scheme Q
Scheme Q
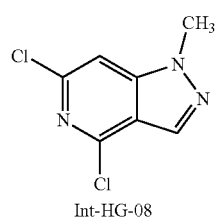
Int-HG-08
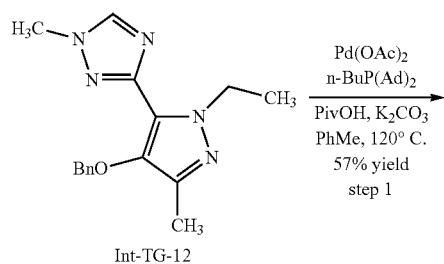
Int-TG-12
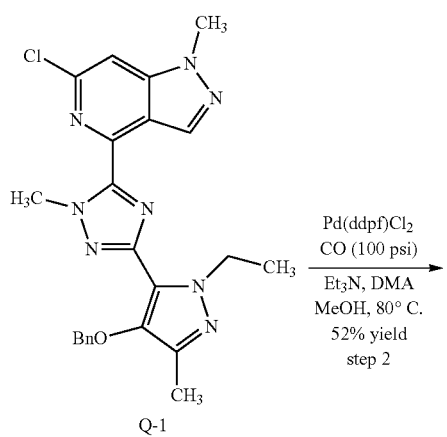
Q-1
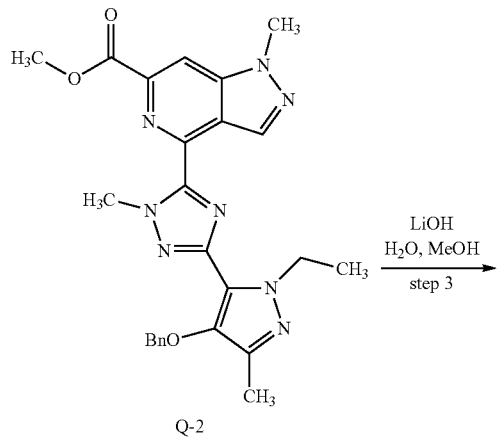
Q-2
-continued
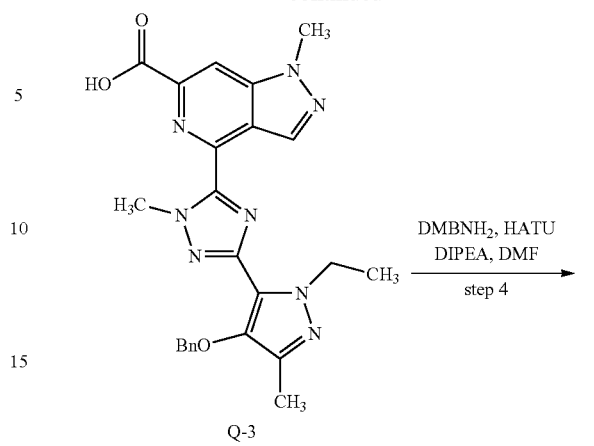
Q-3
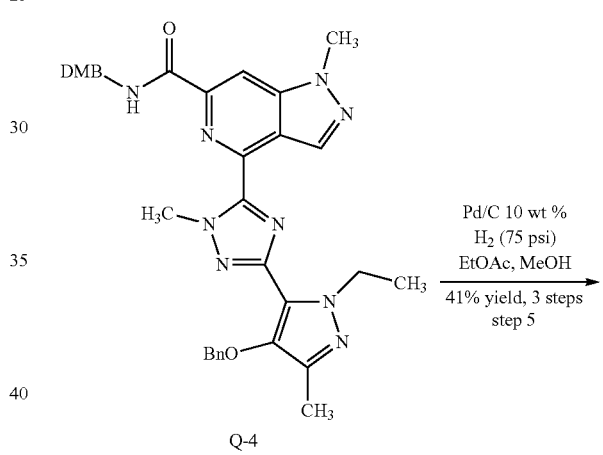
Q-4
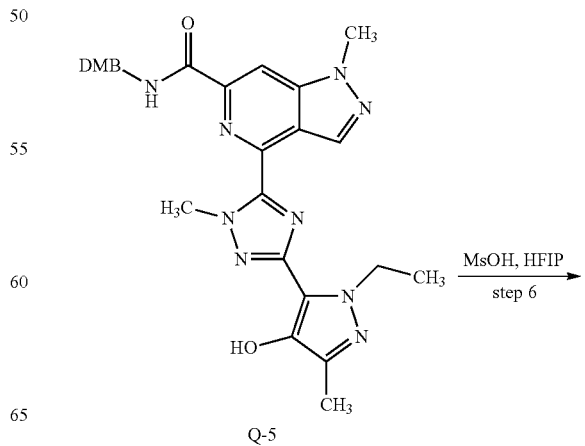
Q-5

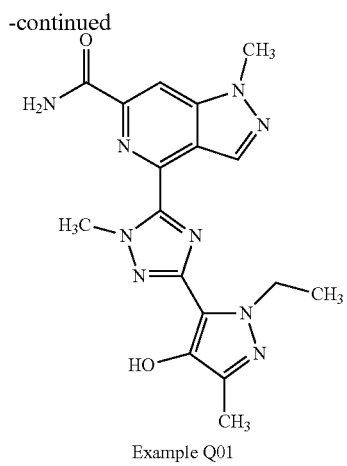

Example Q01

Step 1: Synthesis of 4-{3-[4-(benzyloxy)-1-ethyl-3-methyl-1H-pyrazol-5-yl]-1-methyl-1H-1,2,4-triazol-5-yl}-6-chloro-1-methyl-1H-pyrazolo[4,3-c]pyridine (Q-1)

A vial was charged with 3-[4-(benzyloxy)-1-ethyl-3-methyl-1H-pyrazol-5-yl]-1-methyl-1H-1,2,4-triazole (Int-TG-12) (187 mg, 0.629 mmol), 4,6-dichloro-1-methyl-1H-pyrazolo[4,3-c]pyridine (Int-HG-08) (191 mg, 0.943 mmol), Pd(OAc)$_2$ (28.2 mg, 0.126 mmol), cataCXium A (90.2 mg, 0.252 mmol), pivalic acid (19.3 mg, 0.189 mmol) and potassium carbonate (261 mg, 1.89 mmol) in toluene (1 mL), degassed at rt for 5 min., then heated at 120° C. overnight. The reaction mixture was filtered through a pad of celite and concentrated in vacuo. The crude material was purified by flash chromatography (12 g SiO$_2$, Isco, 0-100% EtOAc in Hept.) to afford the title compound 4-{3-[4-(benzyloxy)-1-ethyl-3-methyl-1H-pyrazol-5-yl]-1-methyl-1H-1,2,4-triazol-5-yl}-6-chloro-1-methyl-1H-pyrazolo[4,3-c]pyridine (Q-1) (63 mg, 22% yield) as a yellow oil. m/z (ESI+) for ($C_{23}H_{23}ClN_8O$), 463.3 (M+H)$^+$ observed.

Step 2: Synthesis of methyl 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylate (Q-2)

To a solution of 4-{3-[4-(benzyloxy)-1-ethyl-3-methyl-1H-pyrazol-5-yl]-1-methyl-1H-1,2,4-triazol-5-yl}-6-chloro-1-methyl-1H-pyrazolo[4,3-c]pyridine (Q-1) (63 mg, 0.099 mmol) in MeOH (20 mL) and DMA (3 mL) was added Pd(dppf)Cl$_2$ (29.9 mg, 0.0408 mmol) and TEA (142 µL, 1.02 mmol) at rt. The reaction mixture was heated at 80° C. under CO (100 psi) for 22 h. LCMS analysis showed a peak with the desired product mass. The reaction was allowed to cool gradually to rt and the mixture was filtered through a pad of celite followed by concentration of the filtrate in vacuo. The crude material was transferred to a separatory funnel with DCM and washed with 3 portions of water. The organic phase was concentrated in vacuo and the crude product was purified by flash chromatography (40 g SiO$_2$, Isco, 0-100% EtOAc in hept) to afford the title compound as an impure mixture. This material was purified again via flash chromatography (12 g SiO$_2$, Isco, 0-100% EtOAc in hept.) to afford the title compound 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylate (Q-2) (34.1 mg, 52% yield) as an off-white solid. m/z (ESI+) for ($C_{25}H_{26}N_8O_3$), 487.6 (M+H)$^+$ observed.

Step 3: Synthesis of 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylic acid (Q-3)

To a solution of 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylate (Q-2) (34.1 mg, 0.0701 mmol) in MeOH (4 mL) was added LiOH·H$_2$O (10.1 mg, 0.421 mmol) as a solution in water (1 mL). The reaction was stirred at rt for 1 h. LCMS analysis showed significant starting material remained. An additional aliquot of LiOH·H$_2$O (9.99 mg, 0.417 mmol) was added and the reaction was stirred at rt for 2 h. The reaction mixture was neutralized to ~pH 6 by addition of 1N HCl aq. The solution was concentrated in vacuo and further azeotroped with 4 portions PhMe to remove residual water to afford the title compound 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylic acid (Q-3) which was used in the next step without further purification. m/z (ESI+) for ($C_{24}H_{24}N_8O_3$), 473.4 (M+H)$^+$ observed.

Step 4: Synthesis of 4-{3-[4-(benzyloxy)-1-ethyl-3-methyl-1H-pyrazol-5-yl]-1-methyl-1H-1,2,4-triazol-5-yl}-N-[(3,4-dimethylphenyl)methyl]-1-methyl-1H-pyrazolo[4,3-c]pyridine-6-carboxamide (Q-4)

To a solution of 4-{3-[4-(benzyloxy)-1-ethyl-3-methyl-1H-pyrazol-5-yl]-1-methyl-1H-1,2,4-triazol-5-yl}-1-methyl-1H-pyrazolo[4,3-c]pyridine-6-carboxylic acid (Q-3) (33 mg, 0.070 mmol) in DMF (1 mL) was added HATU (37.2 mg, 0.0978 mmol), DIPEA (31.1 µL, 0.175 mmol) and 2,4-dimethoxybenzylamine (21.0 µL, 0.140 mmol) as a solution in DMF. The reaction was stirred at rt for 3 h. The reaction mixture was poured into water and extracted with 3 portions DCM. The combined organic extracts were washed with 3 portions of water followed by concentration in vacuo. The crude material was purified by flash chromatography (4 g SiO$_2$, Isco, 0-100% EtOAc in Hept.) to afford the title compound 4-{3-[4-(benzyloxy)-1-ethyl-3-methyl-1H-pyrazol-5-yl]-1-methyl-1H-1,2,4-triazol-5-yl}-N-[(3,4-dimethylphenyl)methyl]-1-methyl-1H-pyrazolo[4,3-c]pyridine-6-carboxamide (Q-4) (60.4 mg) as a yellow oil which was used in the next step without further purification. m/z (ESI+) for ($C_{33}H_{35}N_9O_4$), 622.5 (M+H)$^+$ observed.

Step 5: Synthesis of N-[(3,4-dimethylphenyl)methyl]-4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide (Q-5)

A suspension of 4-{3-[4-(benzyloxy)-1-ethyl-3-methyl-1H-pyrazol-5-yl]-1-methyl-1H-1,2,4-triazol-5-yl}-N-[(3,4-dimethylphenyl)methyl]-1-methyl-1H-pyrazolo[4,3-c]pyridine-6-carboxamide (Q-4) (43 mg, 0.069 mmol), Pd—C 10 wt % (15 mg) as a solution in EtOAc (8 mL), and MeOH (2 mL) was hydrogenated under hydrogen gas (75 psi) at rt for 2.5 h. The reaction mixture was filtered through a pad of celite and filtrate was concentrated in vacuo. The crude material was purified by flash chromatography (4 g SiO$_2$, Isco, 0-100% EtOAc in Hept) to afford the title compound N-[(3,4-dimethylphenyl)methyl]-4-[3-(1-ethyl-4-hydroxy-3-methyl-1H-pyrazol-5-yl)-1-methyl-1H-1,2,4-triazol-5- yl]-1-methyl-1H-pyrazolo[4,3-c]pyridine-6-carboxamide (Q-5) (15 mg, 41% yield, 3 steps) as a white solid. m/z (ESI+) for ($C_{26}H_{29}N_9O_4$), 532.3 (M+H)$^+$ observed.

Step 6: Synthesis of 4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide (Example Q01)

To a solution of N-[(3,4-dimethylphenyl)methyl]-4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide (Q-5) (15 mg, 0.028 mmol) in HFIP (3 mL) was added MsOH (9.16 μL, 0.141 mmol). The reaction was stirred at rt for 2 h. The solution was concentrated in vacuo and the crude residue was purified via chromatography to afford the title compound 4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide (Example Q01) (10 mg, 93% yield) as a solid. $^1$H NMR (600 MHz, DMSO-d6) δ=8.76 (d, J=0.9 Hz, 1H), 8.53 (d, J=0.9 Hz, 1H), 8.08 (br s, 1H), 8.04 (br s, 1H), 7.97 (br s, 1H), 4.47 (s, 3H), 4.44 (q, J=7.0 Hz, 2H), 4.23 (s, 3H), 2.14 (s, 3H), 1.34 (t, J=7.2 Hz, 3H); m/z (ESI+) for ($C_{17}H_{19}N_9O_2$), 382.5 (M+H)$^+$ observed.

Example R01: Preparation of 4-[5-(aminomethyl)-2-(1-ethyl-3-methyl-1H-pyrazol-5-yl)-1,3-thiazol-4-yl]-1-methyl-1H-pyrazolo[4,3-c]pyridine-6-carboxamide According to Scheme R

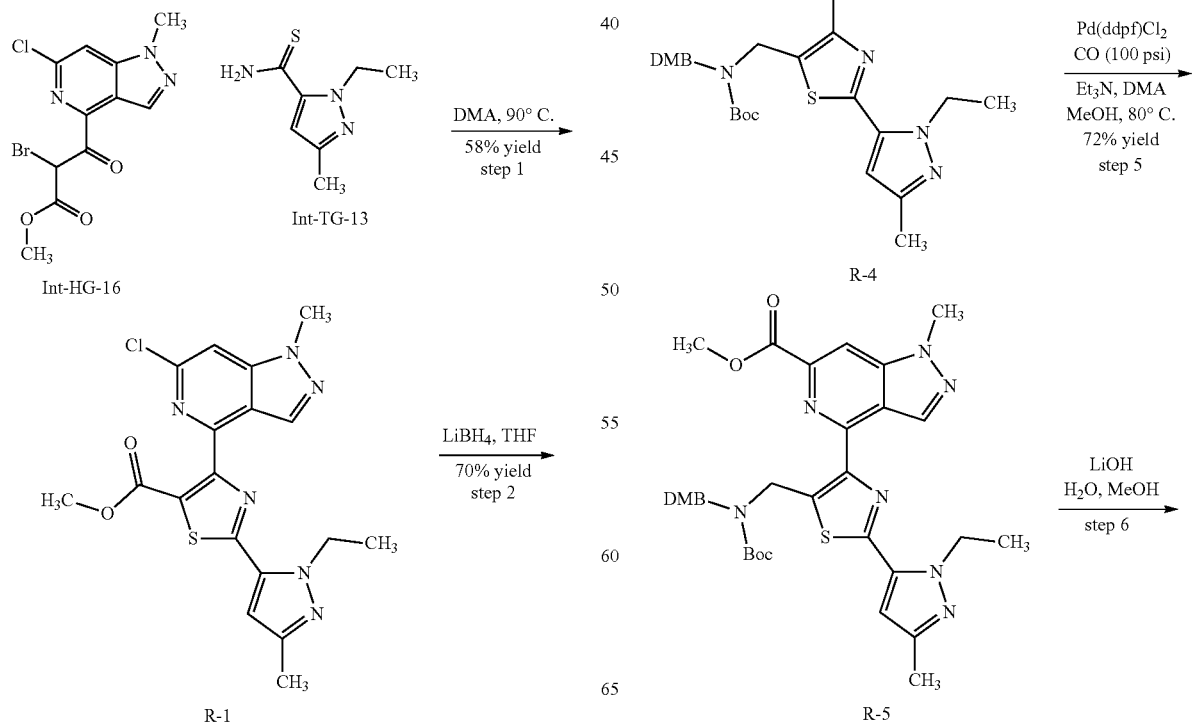

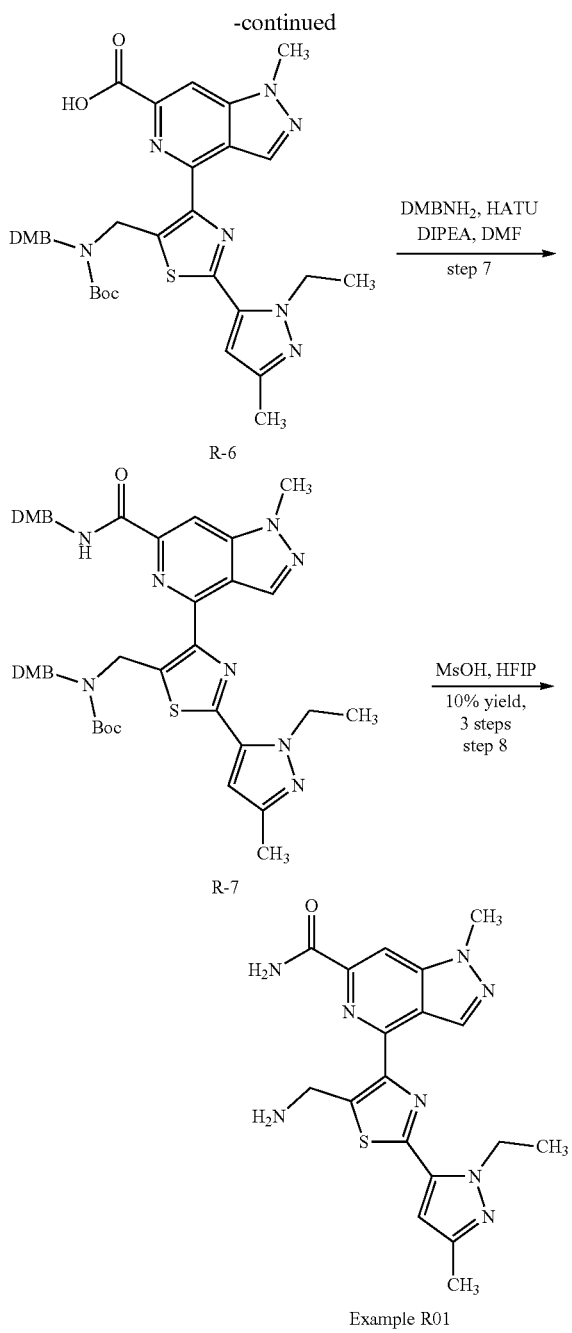

Step 1: Synthesis of methyl-4-(6-chloro-1-methyl-1H-pyrazolo[4,3-c]pyridin-4-yl)-2-(1-ethyl-3-methyl-1H-pyrazol-5-yl)-1,3-thiazole-5-carboxylate (R-1)

This step was performed in duplicate and the batches combined prior to final purification. To a flask containing methyl 2-bromo-3-(6-chloro-1-methyl-1H-pyrazolo[4,3-c]pyridin-4-yl)-3-oxopropanoate (Int-HG-16) (238 mg, 0.340 mmol) and 1-ethyl-3-methyl-1H-pyrazole-5-carbothioamide (Int-TG-13) (44.7 mg, 0.264 mmol) was added DMA (4 mL). The reaction was heated at 90° C. for 3 h. The reaction solution was concentrated in vacuo. The crude reaction mixture was purified by preparatory-HPLC with a Phenomenex C18 column (100×30 mm, 5 μm particle size). Elution with 2-90% MeCN/H$_2$O (0.1% TFA) with a flow rate of 20 mL/min afforded the title compound methyl-4-(6-chloro-1-methyl-1H-pyrazolo[4,3-c]pyridin-4-yl)-2-(1-ethyl-3-methyl-1H-pyrazol-5-yl)-1,3-thiazole-5-carboxylate (R-1) (237 mg, 58% yield) as a light yellow foam. $^1$H NMR (400 MHz, DMSO-d6) δ=8.40 (d, J=0.8 Hz, 1H), 8.02 (d, J=0.8 Hz, 1H), 6.87 (s, 1H), 4.59 (q, J=7.0 Hz, 2H), 4.11 (s, 3H), 3.81 (s, 3H), 2.23 (s, 3H), 1.37 (t, J=7.2 Hz, 3H).

Step 2: Synthesis of [4-(6-chloro-1-methyl-1H-pyrazolo[4,3-c]pyridin-4-yl)-2-(1-ethyl-3-methyl-1H-pyrazol-5-yl)-1,3-thiazol-5-yl]methanol (R-2)

A vial was charged with methyl-4-(6-chloro-1-methyl-1H-pyrazolo[4,3-c]pyridin-4-yl)-2-(1-ethyl-3-methyl-1H-pyrazol-5-yl)-1,3-thiazole-5-carboxylate (R-1) (165 mg, 0.379 mmol), THF (10 mL), and lithium borohydride (16.5 mg, 0.759 mmol). The reaction was stirred at rt overnight. LCMS analysis showed that significant starting material remained. The reaction was cooled to 0° C. and the flask was charged with an additional aliquot of lithium borohydride (33 mg, 1.52 mmol). The flask was removed from the ice bath and allowed to warm gradually to rt. The reaction was stirred at rt overnight. The solution was quenched with sat. NH$_4$Cl aq. (2 mL), diluted with H$_2$O (10 mL), and transferred to a separatory funnel with DCM. The phases were separated, and the aqueous phase extracted with 3 portions of DCM followed by 2 portions EtOAc. The combined organic extracts were concentrated in vacuo and MeOH was added resulting in precipitation of solids that were collected by filtration to afford the title compound [4-(6-chloro-1-methyl-1H-pyrazolo[4,3-c]pyridin-4-yl)-2-(1-ethyl-3-methyl-1H-pyrazol-5-yl)-1,3-thiazol-5-yl]methanol (R-2) (108 mg, 70% yield) as a white solid. $^1$H NMR (400 MHz, DMSO-d6) δ=8.64 (d, J=1.2 Hz, 1H), 7.89 (d, J=0.8 Hz, 1H), 6.70 (s, 1H), 6.24 (t, J=5.3 Hz, 1H), 5.23 (d, J=5.5 Hz, 2H), 4.66 (q, J=7.0 Hz, 2H), 4.09 (s, 3H), 2.23 (s, 3H), 1.43 (t, J=7.0 Hz, 3H); m/z (ESI+) for (C$_{17}$H$_{17}$ClN$_6$OS), 389.3 (M+H)$^+$ observed.

Step 3: Synthesis of 4-(6-chloro-1-methyl-1H-pyrazolo[4,3-c]pyridin-4-yl)-2-(1-ethyl-3-methyl-1H-pyrazol-5-yl)-1,3-thiazole-5-carbaldehyde (R-3)

To a suspension of [4-(6-chloro-1-methyl-1H-pyrazolo[4,3-c]pyridin-4-yl)-2-(1-ethyl-3-methyl-1H-pyrazol-5-yl)-1,3-thiazol-5-yl]methanol (R-2) (117 mg, 0.301 mmol) in DCM (10 mL) was added Dess-Martin periodinane (255 mg, 0.602 mmol). The reaction was stirred at rt for 6 h. The solution was diluted with DCM (50 mL), poured into sat. NaHCO$_3$, and transferred to a separatory funnel.

The phases were separated and the aqueous phase was extracted with 3 portions DCM. The combined organic extracts were concentrated in vacuo. The crude residue was purified via flash chromatography (12 g SiO$_2$, Isco, 0-100% EtOAc in Hept.) to afford the title compound 4-(6-chloro-1-methyl-1H-pyrazolo[4,3-c]pyridin-4-yl)-2-(1-ethyl-3-methyl-1H-pyrazol-5-yl)-1,3-thiazole-5-carbaldehyde (R-3) (125 mg, >95% yield) as a yellow solid. $^1$H NMR (400 MHz, DMSO-d6) δ=10.81 (s, 1H), 8.63 (d, J=0.8 Hz, 1H), 8.12 (d, J=0.8 Hz, 1H), 6.96 (s, 1H), 4.69 (q, J=7.2 Hz, 2H), 4.13 (s, 3H), 2.25 (s, 3H), 1.43 (t, J=7.0 Hz, 3H).

Step 4: Synthesis of tert-butyl {[4-(6-chloro-1-methyl-1H-pyrazolo[4,3-c]pyridin-4-yl)-2-(1-ethyl-3-methyl-1H-pyrazol-5-yl)-1,3-thiazol-5-yl]methyl}[(2,4-dimethoxyphenyl)methyl]carbamate (R-4)

To a solution of 4-(6-chloro-1-methyl-1H-pyrazolo[4,3-c]pyridin-4-yl)-2-(1-ethyl-3-methyl-1H-pyrazol-5-yl)-1,3- thiazole-5-carbaldehyde (R-3) (80 mg, 0.21 mmol) in DCE was added 2,4-dimethoxybenzylamine (77.7 µL, 0.517 mmol) and AcOH (35.5 µL, 0.620 mmol). The reaction was stirred at 60° C. for 25 min at which point the color of reaction mixture changed to light brown. The flask was removed from heating and allowed to cool gradually to rt with stirring overnight. The solution was concentrated in vacuo and the crude mixture dissolved in MeOH (5 mL). The solution was cooled in an ice water bath to 0° C. and sodium borohydride (23.5 mg, 0.620 mmol) was added. The reaction was stirred at 0° C. for 5 min., then the ice bath was removed allowing the reaction to gradually warm to rt, and it was stirred for 30 min at rt. Precipitation occurred and the solids were collected by filtration. The solids were suspended in MeCN (5 mL) followed by the addition of Di-tert-butyl dicarbonate (113 mg, 0.517 mmol) and triethylamine (86.5 µL, 0.620 mmol). The suspension was stirred for 10 min at rt followed by the addition of DCM (5 mL). The reaction was stirred at rt for an additional 20 min. LCMS analysis showed that the starting material had been consumed. The solution was concentrated in vacuo and the crude residue purified via flash chromatography (12 g $SiO_2$, Isco, 0-100% EtOAc in Hept) to afford the title compound tert-butyl {[4-(6-chloro-1-methyl-1H-pyrazolo[4,3-c]pyridin-4-yl)-2-(1-ethyl-3-methyl-1H-pyrazol-5-yl)-1,3-thiazol-5-yl]methyl}[(2,4-dimethoxyphenyl)methyl]carbamate (R-4) (112 mg, >95%) as a light orange solid. $^1$H NMR (400 MHz, DMSO-d6) δ=8.51 (s, 1H), 7.89 (d, J=0.8 Hz, 1H), 6.87 (d, J=8.2 Hz, 1H), 6.67 (br d, J=4.7 Hz, 1H), 6.36-6.14 (m, 2H), 5.18 (br s, 2H), 4.61 (q, J=7.0 Hz, 2H), 4.33 (br d, J=10.5 Hz, 2H), 4.09 (s, 3H), 3.60 (s, 3H), 3.53-3.39 (m, 3H), 2.22 (s, 3H), 1.60-1.29 (m, 12H).

Step 5: Synthesis of methyl 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylate (R-5)

To a solution of tert-butyl {[4-(6-chloro-1-methyl-1H-pyrazolo[4,3-c]pyridin-4-yl)-2-(1-ethyl-3-methyl-1H-pyrazol-5-yl)-1,3-thiazol-5-yl]methyl}[(2,4-dimethoxyphenyl)methyl]carbamate (R-4) (122 mg, 0.191 mmol) in MeOH (20 mL) and DMA (5 mL) was added Pd(dppf)Cl$_2$ (42.0 mg, 0.0573 mmol) and triethylamine (200 µL, 1.43 mmol). The reaction mixture was heated at 80° C. under CO gas (100 psi) for 22 h. The reaction mixture was filtered through a pad of celite and the filtrate concentrated in vacuo. The crude residue was redissolved in DCM, transferred to a separatory funnel, and washed with 3 portions water. The organic phase was concentrated in vacuo. The crude residue was purified via flash chromatography (40 g $SiO_2$, Isco, 0-100% EtOAc in Hept.) to afford the desired product as a mixture with significant impurities present. The isolated material was resubmitted to purification by flash chromatography (40 g $SiO_2$, Isco, 0-10% MeOH in DCM) to afford the title compound methyl 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylate (R-5) (92 mg, 72% yield) as a light brown oil. m/z (ESI+) for ($C_{33}H_{39}N_7O_6S$), 662.9 (M+H)$^+$ observed.

Step 6: Synthesis of 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylic acid (R-6)

To a solution of methyl 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylate (R-5) (92.0 mg, 0.14 mmol) in MeOH (5 mL) was added LiOH·H$_2$O (9.99 mg, 0.417 mmol) as a solution in water. The reaction was stirred at rt for 2 h. At this stage an additional aliquot of LiOH·H$_2$O (9.99 mg, 0.417 mmol) was added. The reaction was stirred at rt overnight. The solution was neutralized to ~pH 6 with 1N HCl aq. The solution was concentrated in vacuo and further azeotroped with 4 portions PhMe to remove residual water to afford the title compound 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylic acid (R-6) which was used in the next step without further purification. m/z (APCI+) for ($C_{32}H_{37}N_7O_6S$), 648.5 (M+H)$^+$ observed.

Step 7: Synthesis of tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-thiazol-5-yl]methyl}carbamate (R-7)

To a solution of 4-[5-({(tert-butoxycarbonyl)[(2,4-dimethoxyphenyl)methyl]amino}methyl)-2-(1-ethyl-3-methyl-1H-pyrazol-5-yl)-1,3-thiazol-4-yl]-1-methyl-1H-pyrazolo[4,3-c]pyridine-6-carboxylic acid (R-6) (90 mg, 0.14 mmol) in DMF was added HATU (74.0 mg, 0.195 mmol), DIPEA (61.8 µL, 0.347 mmol) and 2,4-dimethoxybenzylamine (41.7 µL, 0.278 mmol). The reaction was stirred at rt for 4.5 h. The solution was poured into H$_2$O, transferred to a separatory funnel, and extracted with 3 portions DCM. The combined organic extracts were washed with 3 portions H$_2$O followed by concentration in vacuo. The crude residue was purified via flash chromatography (40 g $SiO_2$, Isco, 0-10% MeOH in DCM) to afford the title compound tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-thiazol-5-yl]methyl}carbamate (R-7) which was used in the next step without further purification. m/z (ESI+) for ($C_{41}H_{48}N_8O_7S$), 797.6 (M+H)$^+$ observed.

Step 8: Synthesis of 4-[5-(aminomethyl)-2-(1-ethyl-3-methyl-1H-pyrazol-5-yl)-1,3-thiazol-4-yl]-1-methyl-1H-pyrazolo[4,3-c]pyridine-6-carboxamide (Example R01)

To a solution of tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-thiazol-5-yl]methyl}carbamate (R-7) (150 mg, 0.188 mmol) in HFIP (3 mL) was added MsOH (611 µL, 9.41 mmol). The reaction was stirred at rt for 3 h. At this stage, an addition aliquot of MsOH (611 µL, 9.41 mmol) was added and the reaction was heated at 50° C. until LCMS analysis showed reaction showed that reaction progress had stalled. The solution was then concentrated in vacuo, transferred to a separatory funnel with DCM, and diluted with sat. Na$_2$CO$_3$ aq. to ~pH 9. The phases were separated, and LCMS analysis showed that all of the desired product resided in the aqueous phase. The aqueous phase was lyophilized overnight to afford a white powder. The organic phase contained product with one remaining DMB protecting group as determined by LCMS. Thus, the organic phase was dried (Na$_2$SO$_4$), filtered, and concentrated in vacuo. The crude mixture was taken up in PhMe (~3 mL) and concentrated in vacuo to remove residual water. The crude residue was dissolved in DCM (0.7 mL) followed by the addition of TFA (0.7 mL). The reaction was heated at 35° C. until completion as monitored by LCMS. The solution was concentrated in vacuo and the combined crude product was submitted to purification via preparatory-HPLC to afford the title compound 4-[5-(aminomethyl)-2-(1-ethyl-3-methyl-1H-pyrazol-5-yl)-1,3-thiazol-4-yl]-1-methyl-1H-pyrazolo[4,3-c]pyridine-6-carboxamide (Example R01) (10 mg, 10% yield, 3 steps) as a TFA salt. m/z (ESI+) for ($C_{18}H_{20}N_8OS$), 397.4 $(M+H)^+$ observed; $^1$H NMR (400 MHz, METHANOL-$d_4$) δ=8.73 (s, 1H), 8.33 (s, 1H), 6.65 (s, 1H), 4.75 (q, J=7.0 Hz, 2H), 4.58 (br s, 2H), 4.21 (s, 3H), 2.31 (s, 3H), 1.51 (t, J=7.2 Hz, 3H)

Example S01: Preparation of 4-[5-(aminomethyl)-2-(1-ethyl-4-fluoro-3-methyl-1H-pyrazol-5-yl)-1,3-thiazol-4-yl]-1-methyl-1H-pyrazolo[4,3-c]pyridine-6-carboxamide According to Scheme S Scheme S

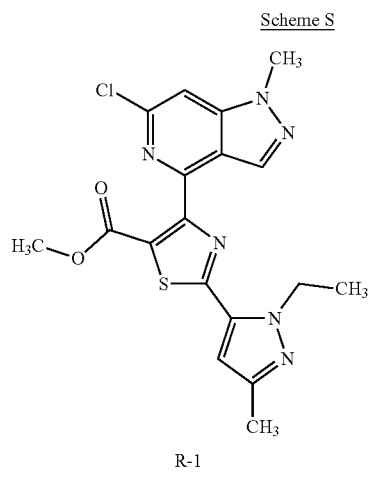

R-1

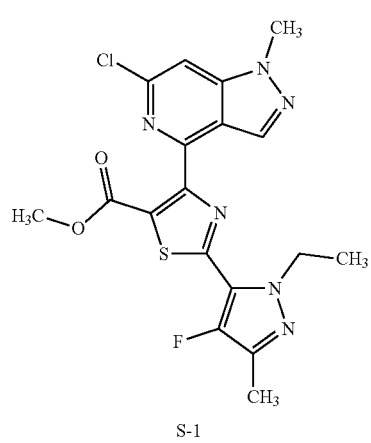

S-1

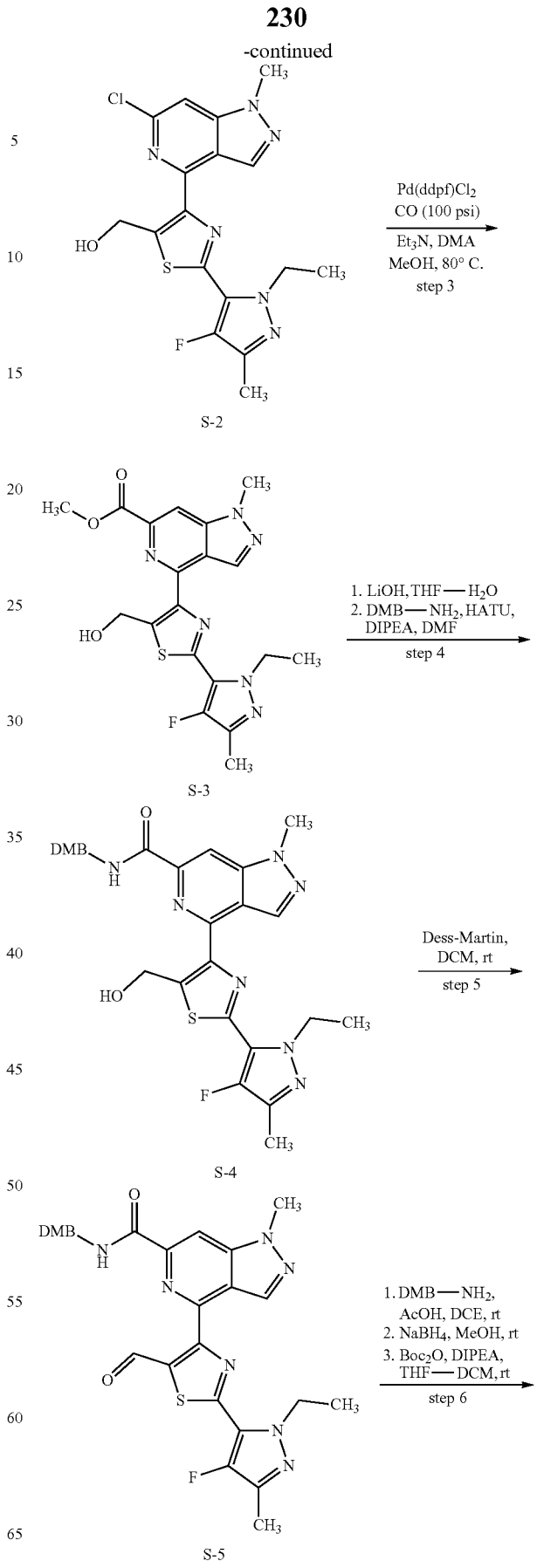

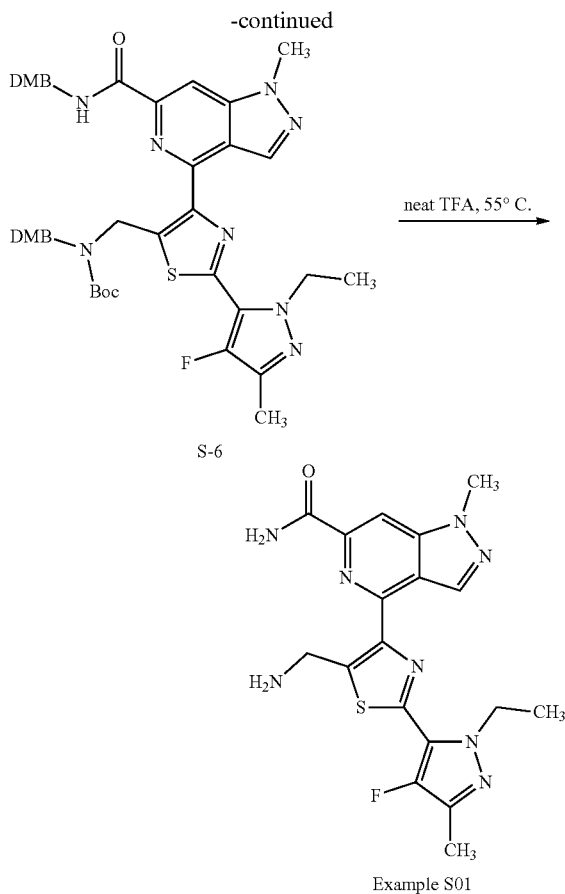

S-6

Example S01

Step 1: Synthesis of methyl 4-(6-chloro-1-methyl-1H-pyrazolo[4,3-c]pyridin-4-yl)-2-(1-ethyl-4-fluoro-3-methyl-1H-pyrazol-5-yl)-1,3-thiazole-5-carboxylate (S-1)

To a solution of methyl-4-(6-chloro-1-methyl-1H-pyrazolo[4,3-c]pyridin-4-yl)-2-(1-ethyl-3-methyl-1H-pyrazol-5-yl)-1,3-thiazole-5-carboxylate (R-1) (358.0 mg, 0.859 mmol) in 2 mL of anhydrous acetonitrile was added select fluoro (26.2 mg, 0.0732 mmol) at room temperature. The cloudy reaction turned to clear after 5 min and was stirred for 20 hours at 45° C. Removed solvent the crude product was purified by ISCO (silica, 40 g, 0-100% EtOAc in Heptane) to afford methyl 4-(6-chloro-1-methyl-1H-pyrazolo[4,3-c]pyridin-4-yl)-2-(1-ethyl-4-fluoro-3-methyl-1H-pyrazol-5-yl)-1,3-thiazole-5-carboxylate (S-1) (225 mg, 60% yield) as a white solid. m/z (ESI+) for ($C_{17}H_{16}ClFN_6S$), 435.3 (M+H)+ observed.

Step 2: Synthesis of [4-(6-chloro-1-methyl-1H-pyrazolo[4,3-c]pyridin-4-yl)-2-(1-ethyl-4-fluoro-3-methyl-1H-pyrazol-5-yl)-1,3-thiazol-5-yl]methanol (S-2)

To a solution of methyl 4-(6-chloro-1-methyl-1H-pyrazolo[4,3-c]pyridin-4-yl)-2-(1-ethyl-4-fluoro-3-methyl-1H-pyrazol-5-yl)-1,3-thiazole-5-carboxylate (S-1) (285 mg, 0.655 mmol) in THF (5 mL) was added lithium borohydride (28.6 mg, 1.31 mmol), the reaction mixture was allowed to stir at 40-45° C. for 7 hours. The solid was collected by filtration and washed with EtOAc, dried under vacuum overnight to afford [4-(6-chloro-1-methyl-1H-pyrazolo[4,3-c]pyridin-4-yl)-2-(1-ethyl-4-fluoro-3-methyl-1H-pyrazol-5-yl)-1,3-thiazol-5-yl]methanol (S-2) (271 mg, >95% yield) as a white solid. $^1$H NMR (400 MHz, DMSO-$d_6$) δ 8.65 (d, J=1.0 Hz, 1H), 7.91 (d, J=1.0 Hz, 1H), 6.30 (t, J=5.3 Hz, 1H), 5.27 (d, J=5.2 Hz, 2H), 4.66 (p, J=8.3, 7.7 Hz, 2H), 4.10 (s, 3H), 2.25 (s, 3H), 1.43 (t, J=7.1 Hz, 3H).

Step 3: Synthesis of methyl 4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxylate (S-3)

To a suspension of [4-(6-chloro-1-methyl-1H-pyrazolo[4,3-c]pyridin-4-yl)-2-(1-ethyl-4-fluoro-3-methyl-1H-pyrazol-5-yl)-1,3-thiazol-5-yl]methanol (S-2) (120 mg, 0.295 mmol) in 20 mL MeOH and 2 mL DMA was added Pd(dppf)Cl$_2$ (42.0 mg, 0.0573 mmol) and TEA (200 μL, 1.43 mmol) at rt. The reaction mixture was heated at 80° C. under CO (100 psi) for 5 days. The reaction was allowed to cool down to 35° C., filtered through a pad of celite and the filtrate was concentrated in vacuo. The crude product was purified by ISCO (silica 12 g, 0-10% MeOH in $CH_2C_{12}$) to afford methyl 4-[2-(1-ethyl-4-fluoro-3-methyl-1H-pyrazol-5-yl)-5-(hydroxymethyl)-1,3-thiazo-4-yl]-1-methyl-1H-pyrazolo[4,3-c]pyridine-6-carboxylate (S-3) (81 mg, 64% yield) as a white solid. $^1$H NMR (400 MHz, DMSO-$d_6$) δ 8.73 (d, J=1.0 Hz, 1H), 8.46 (d, J=1.0 Hz, 1H), 6.32 (t, J=5.7 Hz, 1H), 5.33 (d, J=5.7 Hz, 2H), 4.69 (d, J=7.2 Hz, 2H), 4.23 (s, 3H), 3.99 (s, 3H), 2.26 (s, 3H), 1.44 (t, J=7.1 Hz, 3H).

Step 4: Synthesis of N-[(2,4-dimethoxyphenyl)methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-4)

To a suspension of methyl 4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxylate (S-3) (75 mg, 0.17 mmol) in 10 mL THF was added lithium hydroxide monohydrate (22.9 mg, 0.958 mmol) dissolved in 1.5 mL water, stirred at room temperature for 2 h. The reaction mixture was neutralized to pH 5 by adding 1N HCl. The reaction mixture was concentrated in vacuo and treated with toluene×3 to remove trace of water. The crude acid 4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxylic acid was dried in a vacuum oven overnight and used directly in next step. To a solution of 4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxylic acid (73.0 mg, 0.18 mmol) in DMF (8 mL) was added HATU (133 mg, 0.351 mmol), N-ethyldisopropylamine (93.6 uL, 0.526 mmol) and 2,4-dimethoxybenzylamine (39.5 μL, 0.263 mmol) at room temperature, stirred at room temperature for 5 h. Solvent was removed in vacuo and the crude product was purified by ISCO (silica, 12 g, 0-100% EtOAc in Heptane) to afford N-[(2,4-dimethoxyphenyl)methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-4) (75 mg, 76% yield) as a white solid. m/z (ESI+) for ($C_{27}H_{28}FN_7O_4S$), 566.3 (M+H)+ observed.

Step 5: Synthesis of N-[(2,4-dimethoxyphenyl) methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-5)

To a suspension of N-[(2,4-dimethoxyphenyl)methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-4) (78 mg, 0.14 mmol) in dichloromethane (10 mL) was added Dess-Martin periodinane (119 mg, 0.276 mmol) at room temperature. The reaction was stirred at rt for 6 h. The reaction mixture was diluted with dichloromethane and poured in sat NaHCO$_3$, extracted with dichloromethane×3, EtOAc×2, The solution was concentrated in vacuo and the crude N-[(2,4-dimethoxyphenyl)methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-5) was used directly in next step without further purification. m/z (ESI+) for (C$_{27}$H$_{26}$FN$_7$O$_4$S), 564.3 (M+H)$^+$ observed.

Step 6: Synthesis of tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-4-fluoro-3-methyl-1H-pyrazol-5-yl)-1,3-thiazol-5-yl]methyl}carbamate (S-6)

To a solution of N-[(2,4-dimethoxyphenyl)methyl]-4-[2-(1-ethyl-4-fluoro-3-methyl-1H-pyrazol-5-yl)-5-(hydroxymethyl)-1,3-thiazol-4-yl]-1-methyl-1H-pyrazolo[4,3-c]pyridine-6-carboxamide (S-5) (72.0 mg, 0.13 mmol) in 1,2-dichloroethane (5 mL) was added 2,4-dimethoxybenzylamine (38.4 uL, 0.255 mmol) and acetic acid (7.31 μL, 0.128 mmol) at room temperature. The reaction was heated at 55° C. for 20 min then to cool gradually to room temperature with stirring overnight. The solution was concentrated in vacuo and the crude mixture dissolved in MeOH (5 mL). The solution was cooled in an ice water bath to 0° C. and sodium borohydride (9.67 mg, 0.255 mmol) was added. The reaction was stirred at 0° C. for 5 min., then the ice bath was removed allowing the reaction to gradually warm to room temperature, and it was stirred for 30 min at room temperature. All volatiles were removed in vacuo. The crude solids were suspended in DCM/THF (1:1, 6 mL) followed by the addition of di-tert-butyl dicarbonate (83.6 mg, 0.383 mmol) and N-ethyldiisopropylamine (0.0668 mL, 0.383 mmol). The suspension was stirred for 10 min at rt followed by the addition of dichloromethane (5 mL). The reaction was stirred at room temperature for an additional 1 h. The solution was concentrated in vacuo and the crude residue was purified via flash chromatography (12 g SiO$_2$, Isco, 0-100% EtOAc in Heptane) to afford the title compound tert-butyl [(2,4-dimethoxyphenyl)methyl]{[4-(6-{[(2,4-dimethoxyphenyl)methyl]-carbamoyl}-1-methyl-1H-pyrazolo[4,3-c]pyridin-4-yl)-2-(1-ethyl-4-fluoro-3-methyl-1H-pyrazol-5-yl)-1,3-thiazol-5-yl]methyl}carbamate (S-6) (45 mg, 45% yield, 3 steps). m/z (ESI+) for (C$_{41}$H$_{47}$FN$_8$O$_7$S), 815.6 (M+H)$^+$ observed.

Step 7: Synthesis of 4-[5-(aminomethyl)-2-(1-ethyl-4-fluoro-3-methyl-1H-pyrazol-5-yl)-1,3-thiazol-4-yl]-1-methyl-1H-pyrazolo[4,3-c]pyridine-6-carboxamide, trifluoroacetic acid salt (Example S01)

tert-b=Butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-4-fluoro-3-methyl-1H-pyrazol-5-yl)-1,3-thiazol-5-yl]methyl}carbamate (S-6) (45 mg, 0.055 mmol) was split equally into two vials. The material in the first vial was treated with TFA (1 mL). The reaction was heated at 55° C. for 5 days. The material in the second vial was treated with TFA (1 mL) and mercaptan C12 (112 mg, 0.552 mmol, 0.132 mL). The reaction was heated at 55° C. for 5 days. Two crude reaction mixtures were combined and concentrated in vacuo. The crude product was submitted to purification via preparatory-HPLC to afford the title compound 4-[3-(1-ethyl-4-hydroxy-3-methyl-1H-pyrazol-5-yl)-1-methyl-1H-1,2,4-triazol-5-yl]-1-methyl-1H-pyrazolo[4,3-c]pyridine-6-carboxamide (Example S01) (10 mg, 83% yield) as a TFA salt. m/z (ESI+) for (C$_{18}$H$_{19}$FN$_8$O S), 415.4 (M+H)$^+$ observed.

Example T01: Preparation of 4-[5-(aminomethyl)-2-(1-ethyl-3-methyl-1H-pyrazol-5-yl)-1,3-oxazol-4-yl]-1-methyl-1H-pyrazolo[4,3-c]pyridine-6-carboxamide According to Scheme T Scheme T

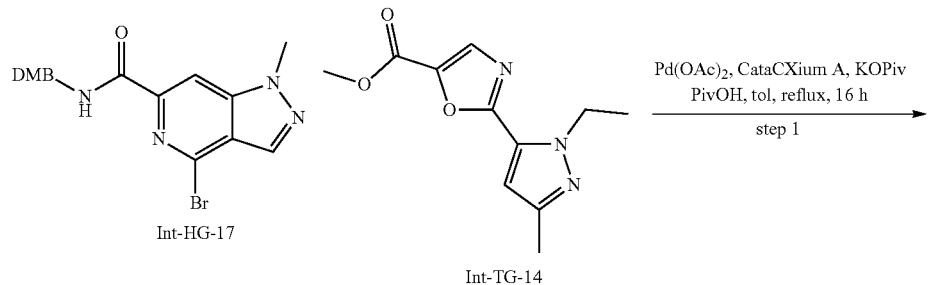

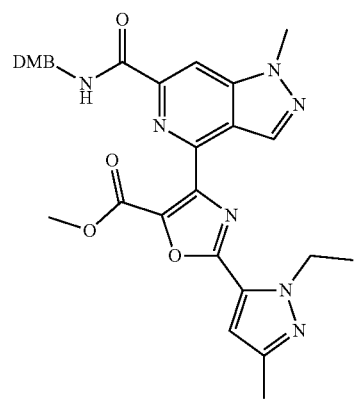

T-1

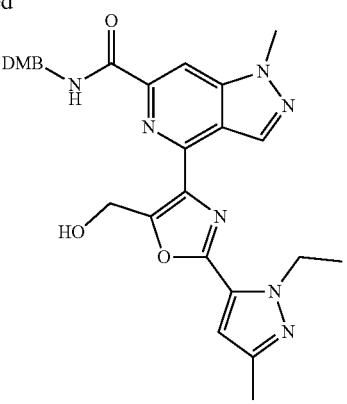

T-2

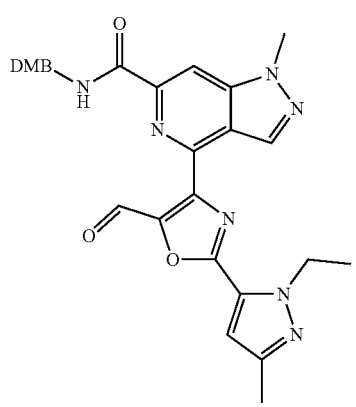

T-3

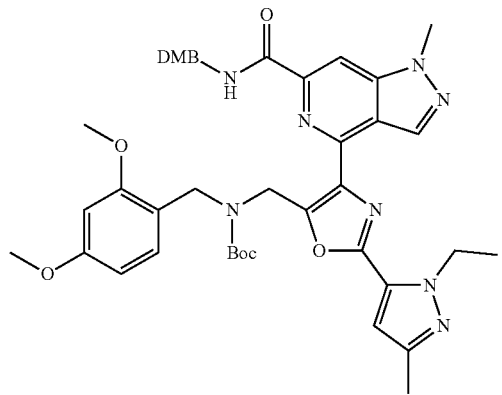

T-4

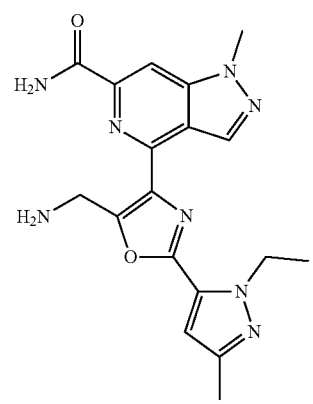

Example T01

Step 1: Synthesis of methyl 4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-oxazole-5-carboxylate (T-1)

A vial was charged with methyl 2-(1-ethyl-3-methyl-1H-pyrazol-5-yl)-1,3-oxazole-5-carboxylate (int-TG-14) (87.7 mg, 0.216 mmol), 4-bromo-N-[(2,4-dimethoxyphenyl)methyl]-1-methyl-1H-pyrazolo[4,3-c]pyridine-6-carboxamide (Int-HG-17) (50.8 mg, 0.216 mmol), Pd(OAc)$_2$ (9.69 mg, 0.0432 mmol), cataCXium A (31.0 mg, 0.0864 mmol), potassium pivalate (45.4 mg, 0.324 mmol) and pivalic acid (11.0 mg, 0.108 mmol) in toluene (10 mL), degassed at room temperature for 5 min, then heated at reflux overnight. The reaction mixture was combined with a previous run at the same scale, filtered through a pad of celite and concentrated in vacuo. The crude mixture was purified by ISCO (silica, 24 g, 0-100% EtOAc in Heptane) to afford the title compound (68.2 mg, 28% yield) methyl 4-(6-{[(2,4-dimethoxyphenyl)methyl-carbamoyl}-1-methyl-1H-pyrazolo[4,3-c]pyridin-4-yl)-2-(1-ethyl-3-methyl-1H-pyrazol-5-yl)-1,3-oxazole-5-carboxylate (T-1) as a white solid. $^1$H NMR (400 MHz, DMSO-d$_6$) δ 9.04 (s, 1H), 8.64 (d, J=1.0 Hz, 1H), 8.47 (d, J=1.0 Hz, 1H), 7.23 (d, J=8.4 Hz, 1H), 6.92 (s, 1H), 6.60 (d, J=2.3 Hz, 1H), 6.54-6.46 (m, 1H), 4.69 (d, J=7.2 Hz, 2H), 4.52 (d, J=5.9 Hz, 2H), 4.23 (s, 3H), 3.82 (s, 3H), 3.78 (d, J=3.8 Hz, 3H), 3.75 (s, 3H), 2.28 (s, 3H), 1.46 (t, J=7.2 Hz, 3H). m/z (ESI+) for ($C_{28}H_{29}N_7O_6$), 560.4 (M+H)$^+$ observed.

Step 2: Synthesis of N-[(2,4-dimethoxyphenyl)methyl]-4-[2-(1-ethyl-3-methyl-1H-pyrazol-5-yl)-5-(hydroxymethyl)-1,3-oxazol-4-yl]-1-methyl-1H-pyrazolo[4,3-c]pyridine-6-carboxamide (T-2)

A flask was charged with methyl 4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-oxazole-5-carboxylate (T-1) (68 mg, 0.11 mmol) and lithium borohydride (5.98 mg, 0.274 mmol) in 10 mL THF. The reaction was stirred at 0° C. to rt overnight. The reaction was concentrated in vacuo, the crude mixture was purified by ISCO (silica, 12 g, 0-100% EtOAc in Heptane) to afford N-[(2,4-dimethoxyphenyl)methyl]-4-[2-(1-ethyl-3-methyl-1H-pyrazol-5-yl)-5-(hydroxymethyl)-1,3-oxazol-4-yl]-1-methyl-1H-pyrazolo[4,3-c]pyridine-6-carboxamide (T-2) (77.4 mg) as a white solid, which contained impurities. m/z (ESI+) for ($C_{27}H_{29}N_7O_5$), 532.3 (M+H)$^+$ observed.

Step 3: Synthesis of N-[(2,4-dimethoxyphenyl)methyl]-4-[2-(1-ethyl-3-methyl-1H-pyrazol-5-yl)-5-formyl-1,3-oxazol-4-yl]-1-methyl-1H-pyrazolo[4,3-c]pyridine-6-carboxamide (T-3)

To a suspension of N-[(2,4-dimethoxyphenyl)methyl]-4-[2-(1-ethyl-3-methyl-1H-pyrazol-5-yl)-5-(hydroxymethyl)-1,3-oxazol-4-yl]-1-methyl-1H-pyrazolo[4,3-c]pyridine-6-carboxamide (T-2) (77.4 mg, 0.146 mmol) in dichloromethane (10 mL) was added Dess-Martin periodinane (126 mg, 0.291 mmol) at room temperature, stirred at room temperature for 3 h. The reaction mixture was diluted with 20 mL dichloromethane and washed with sat NaHCO$_3$ (aq), concentrated in vacuo to afford the crude N-[(2,4-dimethoxyphenyl)methyl]-4-[2-(1-ethyl-3-methyl-1H-pyrazol-5-yl)-5-formyl-1,3-oxazol-4-yl]-1-methyl-1H-pyrazolo[4,3-c]pyridine-6-carboxamide (T-3), which was used directly without further purification. m/z (ESI+) for ($C_{27}H_{27}N_7O_5$), 530.3 (M+H)$^+$ observed.

Step 4: Synthesis of tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-oxazol-5-yl]methyl}carbamate (T-4)

To a solution of N-[(2,4-dimethoxyphenyl)methyl]-4-[2-(1-ethyl-3-methyl-1H-pyrazol-5-yl)-5-formyl-1,3-oxazol-4-yl]-1-methyl-1H-pyrazolo[4,3-c]pyridine-6-carboxamide (T-3) (43 mg, 0.81 mmol) in 1,2-dichloroethane (8 mL) was added 2,4-dimethoxybenzylamine (20.4 mg, 0.122 mmol, 18.3 μL) and acetic acid (4.88 mg, 0.0812 mmol, 4.64 μL) at room temperature. The reaction was stirred at room temperature for 2 h then heated at 56° C. overnight. The solution was concentrated in vacuo and the crude mixture was dissolved in MeOH (5 mL). The solution was cooled in an ice water bath at 0° C. and sodium borohydride (23.5 mg, 0.62 mmol) was added. The reaction was stirred at 0° C. for 5 min., then the ice bath was removed allowing the reaction to gradually warm to room temperature, and it was stirred for 30 min at room temperature. All volatiles were removed in vacuo. The crude solids were suspended in CH$_2$C$_{12}$-MeCN (5 mL) followed by the addition of di-tert-butyl dicarbonate (53.2 mg, 0.244 mmol) and N-ethyldiisopropylamine (0.042 mL, 0.244 mmol). The suspension was stirred at room temperature for 2 h. The solution was concentrated in vacuo and the crude residue was purified via flash chromatography ISCO (silica, 12 g, 0-100% EtOAc in Hept) to afford the title compound tert-butyl [(2,4-dimethoxyphenyl)methyl]{[4-(6-{[(2,4-dimethoxyphenyl)methyl]-carbamoyl}-1-methyl-1H-pyrazolo[4,3-c]pyridin-4-yl)-2-(1-ethyl-3-methyl-1H-pyrazol-5-yl)-1,3-oxazol-5-yl]methyl}carbamate (T-4) (25.0 mg, 29% yield, 5 steps) as a yellow solid. m/z (ESI+) for ($C_{41}H_{48}N_8O_8$), 781.7 (M+H)$^+$ observed.

Step 5: 4-[5-(aminomethyl)-2-(1-ethyl-3-methyl-1H-pyrazol-5-yl)-1,3-oxazol-4-yl]-1-methyl-1H-pyrazolo[4,3-c]pyridine-6-carboxamide (Example T01)

To a solution of tert-butyl [(2,4-dimethoxyphenyl)methyl]{[4-(6-{[(2,4-dimethoxyphenyl)methyl]-carbamoyl}-1-methyl-1H-pyrazolo[4,3-c]pyridin-4-yl)-2-(1-ethyl-3-methyl-1H-pyrazol-5-yl)-1,3-oxazol-5-yl]methyl}carbamate (T-4) (25 mg, 0.032 mmol) in HFIP (0.1 mL) was added MsOH (0.4 mL) and TFA (1.5 mL). The reaction was stirred at 50° C. for 4 h. The solution was then concentrated in vacuo. The crude product was submitted to purification via preparatory-HPLC to afford the title compound 4-[5-(aminomethyl)-2-(1-ethyl-3-methyl-1H-pyrazol-5-yl)-1,3-oxazol-4-yl]-1-methyl-1H-pyrazolo[4,3-c]pyridine-6-carboxamide (Example T01) (3.1 mg, 26% yield) as a TFA salt. m/z (ESI+) for ($C_{18}H_{20}N_8O_2$), 381.3 (M+H)$^+$ observed; $^1$H NMR (400 MHz, DMSO-d$_6$) δ=8.77 (d, J=0.9 Hz, 1H), 8.58-8.22 (m, 3H), 8.09 (s, 1H), 8.01 (br s, 1H), 6.82 (s, 1H), 4.79 (s, 2H), 4.72 (q, J=7.1 Hz, 2H), 4.20 (s, 3H), 2.28 (s, 3H), 1.48 (t, J=7.2 Hz, 3H).

Example U01: Preparation of 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide According to Scheme U Scheme U

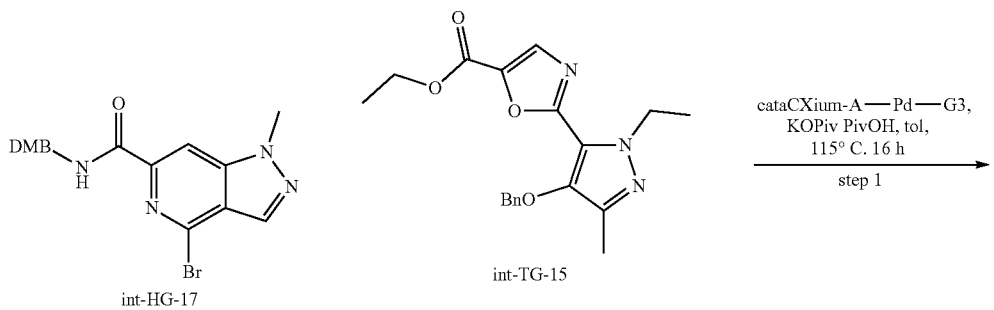

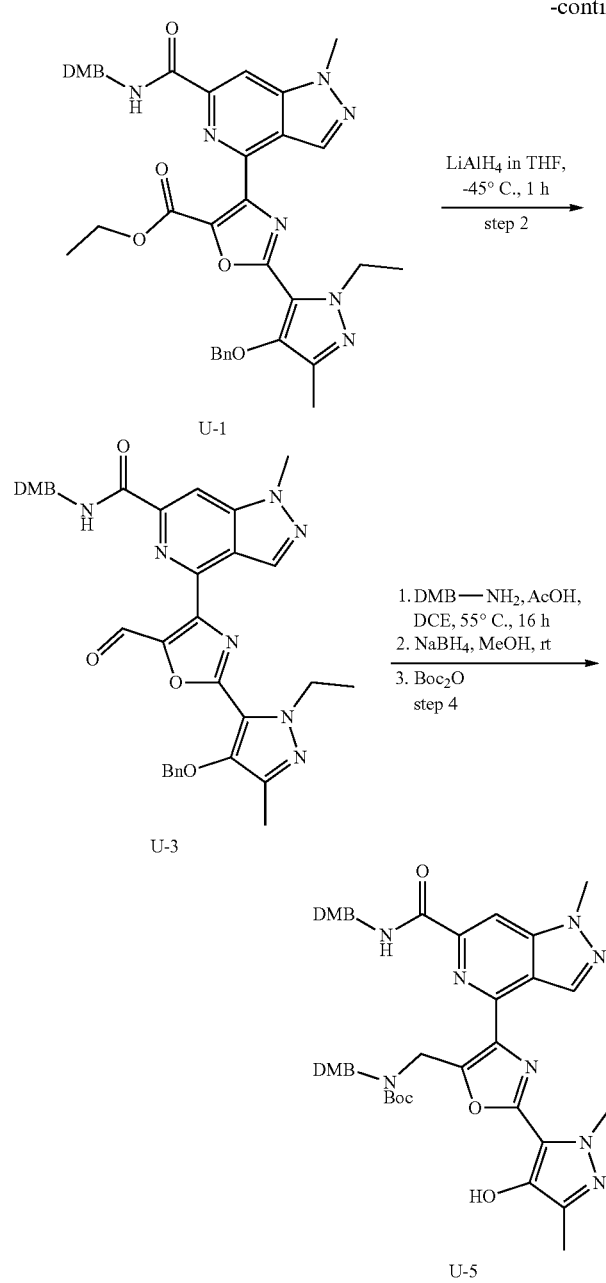
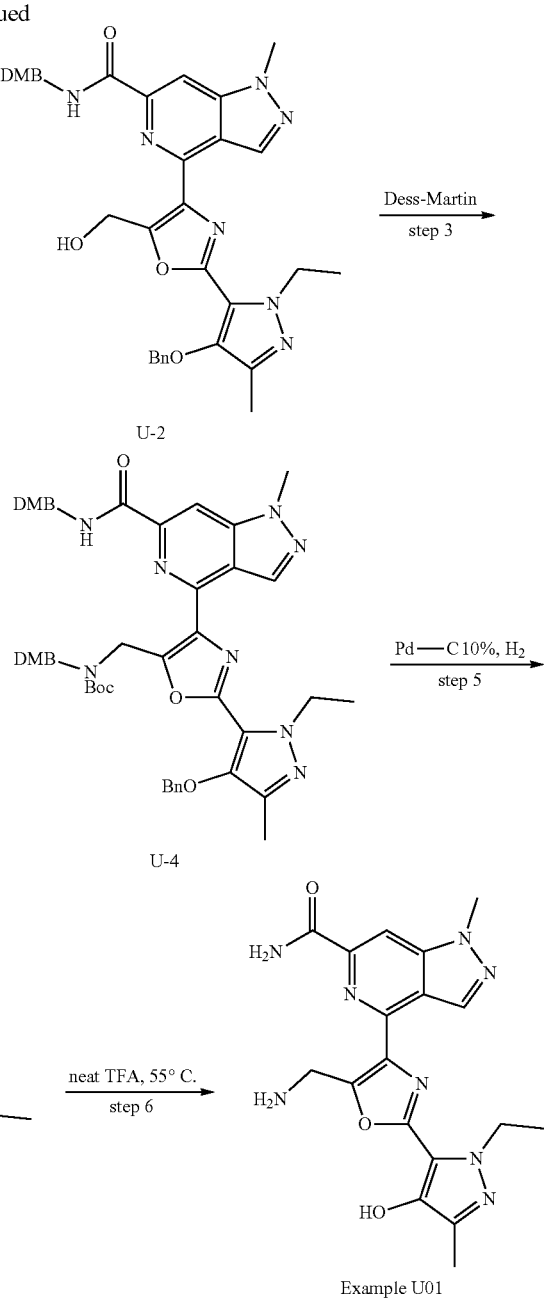

Step 1: Synthesis of ethyl 2-[4-(benzyloxy)-1-ethyl-3-methyl-1H-pyrazol-5-yl]-4-(6-{[(2,4-dimethoxyphenyl)methyl]carbamoyl}-1-methyl-1H-pyrazolo[4,3-c]pyridin-4-yl)-1,3-oxazole-5-carboxylate (U-1)

A vial was charged with ethyl 2-[4-(benzyloxy)-1-ethyl-3-methyl-1H-pyrazol-5-yl]-1,3-oxazole-5-carboxylate (Int-TG-15) (128 mg, 0.360 mmol), cataCXium-A-Pd-G3 (105 mg, 0.144 mmol), 4-bromo-N-[(2,4-dimethoxyphenyl)methyl]-1-methyl-1H-pyrazolo[4,3-c]pyridine-6-carboxamide (Int-HG-17) (146 mg, 0.360 mmol), potassium pivalate (75.8 mg, 0.540 mmol) and pivalic acid (18.4 mg, 0.180 mmol) in toluene (1 mL), degassed at room temperature for 5 min, then heated at 115° C. overnight. The reaction mixture was filtered through a pad of celite and concentrated in vacuo, the crude product was purified by ISCO (silica, 40 g, 0-100% EtOAc in heptane) to afford 45 mg (13% yield) of the title ethyl 2-[4-(benzyloxy)-1-ethyl-3-methyl-1H-pyrazol-5-yl]-4-(6-{[(2,4-dimethoxyphenyl)methyl]carbamoyl}-1-methyl-1H-pyrazolo[4,3-c]pyridin-4-yl)-1,3-oxazole-5-carboxylate (U-1) as a light brown oil. Another batch of 113 mg less pure product ethyl 2-[4-(benzyloxy)-1-ethyl-3-methyl-1H-pyrazol-5-yl]-1,3-oxazole-5-carboxylate was also recovered. $^1$H NMR (400 MHz, DMSO-$d_6$) δ ppm 1.08-1.15 (m, 3H), 1.42 (t, J=7.22 Hz, 3H), 2.14 (s, 3H), 3.73-3.77 (m, 4H), 3.82 (s, 3H), 4.16-4.27 (m, 6H) 4.51 (d, J=5.85 Hz, 2H), 4.59 (d, J=7.02 Hz, 2H), 5.07 (s, 2H), 6.50 (dd, J=8.39, 2.54 Hz, 1H), 6.61 (d, J=2.34 Hz, 1H) 7.23

(d, J=8.59 Hz, 1H), 7.30-7.42 (m, 3H), 7.50 (dd, J=7.61, 1.37 Hz, 2H), 8.47 (s, 1H), 8.59 (d, J=0.78 Hz, 1H), 9.03 (t, J=5.88 Hz, 1H).

Step 2: Synthesis of 4-{2-[4-(benzyloxy)-1-ethyl-3-methyl-1H-pyrazol-5-yl]-5-(hydroxymethyl)-1,3-oxazol-4-yl}-N-[(2,4-dimethoxyphenyl)methyl]-1-methyl-1H-pyrazolo[4,3-c]pyridine-6-carboxamide (U-2)

A vial was charged with 2-[4-(benzyloxy)-1-ethyl-3-methyl-1H-pyrazol-5-yl]-4-(6-{[(2,4-dimethoxyphenyl)methyl]carbamoyl}-1-methyl-1H-pyrazolo[4,3-c]pyridin-4-yl)-1,3-oxazole-5-carboxylate (U-1) (13.8 mg, 0.0203 mmol) in 1.8 mL anhydrous THF at −45° C. Then lithium aluminum hydride (1.54 mg, 0.0406 mmol, 40.6 uL, 1.0 M) was introduced at −45° C., the color of the reaction was immediately changed from light yellow to blue, then gradually changed back to yellow. The reaction was stirred at −45° C. for 1 h, then quenched by adding water. The reaction mixture was diluted with dichloromethane, filtered through a pad of celite, the filtrate was concentrated in vacuo to afford the crude product. The above reaction was repeated at scales between 13.5 mg to 19 mg for a total of 5 times. The crude products from each run were combined and purified by ISCO (silica 24 g, 0-100% EtOAc in heptane) to afford 58.9 mg (73% yield) of a mixture of 4-{2-[4-(benzyloxy)-1-ethyl-3-methyl-1H-pyrazol-5-yl]-5-(hydroxymethyl)-1,3-oxazol-4-yl}-N-[(2,4-dimethoxyphenyl)methyl]-1-methyl-1H-pyrazolo[4,3-c]pyridine-6-carboxamide (U-2) and 4-{2-[4-(benzyloxy)-1-ethyl-3-methyl-1H-pyrazol-5-yl]-5-formyl-1,3-oxazol-4-yl}-N-[(2,4-dimethoxy-phenyl)methyl]-1-methyl-1H-pyrazolo[4,3-c]pyridine-6-carboxamide (U-3) in 1:1 ratio as a light yellow solid. m/z (ESI+) for ($C_{34}H_{35}N_7O_6$), 638.5 (M+H)+ observed and m/z (ESI+) for ($C_{34}H_{33}N_7O_6$), 636.5 (M+H)+ observed.

Step 3: Synthesis of 4-{2-[4-(benzyloxy)-1-ethyl-3-methyl-1H-pyrazol-5-yl]-5-formyl-1,3-oxazol-4-yl}-N-[(2,4-dimethoxyphenyl)methyl]-1-methyl-1H-pyrazolo[4,3-c]pyridine-6-carboxamide (U-3)

To a suspension of a mixture of 4-{2-[4-(benzyloxy)-1-ethyl-3-methyl-1H-pyrazol-5-yl]-5-(hydroxymethyl)-1,3-oxazol-4-yl}-N-[(2,4-dimethoxyphenyl)methyl]-1-methyl-1H-pyrazolo[4,3-c]pyridine-6-carboxamide (U-2) and 4-{2-[4-(benzyloxy)-1-ethyl-3-methyl-1H-pyrazol-5-yl]-5-formyl-1,3-oxazol-4-yl}-N-[(2,4-dimethoxy-phenyl)methyl]-1-methyl-1H-pyrazolo[4,3-c]pyridine-6-carboxamide (U-3) (58.0 mg, 0.091 mmol) in dichloromethane (3 mL) was added Dess-Martin periodinane (126 mg, 0.291 mmol) at room temperature, and the reaction mixture was stirred at room temperature for 4 h. The reaction mixture was diluted with 20 mL dichloromethane and washed with sat NaHCO$_3$ (aq), concentrated in vacuo to afford 58 mg of crude 4-{2-[4-(benzyloxy)-1-ethyl-3-methyl-1H-pyrazol-5-yl]-5-formyl-1,3-oxazol-4-yl}-N-[(2,4-dimethoxy-phenyl)methyl]-1-methyl-1H-pyrazolo[4,3-c]pyridine-6-carboxamide (U-3) which was used directly without further purification. m/z (ESI+) for ($C_{34}H_{33}N_7O_6$), 636.4 (M+H)+ observed.

Step 4: Synthesis of tert-butyl ({2-[4-(benzyloxy)-1-ethyl-3-methyl-1H-pyrazol-5-yl]-4-(6-{[(2,4-dimethoxyphenyl)methyl]carbamoyl}-1-methyl-1H-pyrazolo[4,3-c]pyridin-4-yl)-1,3-oxazol-5-yl}methyl)[(2,4-dimethoxyphenyl)methyl]carbamate (U-4)

To a suspension of 4-{2-[4-(benzyloxy)-1-ethyl-3-methyl-1H-pyrazol-5-yl]-5-formyl-1,3-oxazol-4-yl}-N-[(2,4-dimethoxy-phenyl)methyl]-1-methyl-1H-pyrazolo[4,3-c]pyridine-6-carboxamide (U-3) (58 mg, 0.091 mmol) in 3 mL 1,2-dichloroethane was added 2,4-dimethoxybenzylamine (22.9 mg, 0.137 mmol, 20.6 μL) and acetic acid (5.48 mg, 0.0912 mmol, 5.22 μL) at room temperature, and the reaction mixture was stirred at 56° C. for 90 min. 1,2-Dichloroethane was removed in vacuo and the crude material was cooled to 0° C., 5 mL methanol was added followed by sodium borohydride (8.63 mg, 0.228 mmol), the reaction was stirred at 0° C. for 5 min, then at room temperature for 30 min. The solvent was removed and the crude product was redissolved in dichloromethane, and Boc$_2$O (59.7 mg, 0.274 mmol) and N-ethyldiisopropylamine (35.4 mg, 0.274 mmol, 47.7 uL) were introduced at room temperature, the reaction was stirred at room temperature for 1 h. removed solvent and the crude material was purified by ISCO (silica, 12 g, 0-100% EtOAc in heptane) to afford the title compound tert-butyl ({2-[4-(benzyloxy)-1-ethyl-3-methyl-1H-pyrazol-5-yl]-4-(6-{[(2,4-dimethoxyphenyl)methyl]-carbamoyl}-1-methyl-1H-pyrazolo[4,3-c]pyridin-4-yl)-1,3-oxazol-5-yl}methyl)[(2,4-dimethoxy-phenyl)methyl]carbamate (U-4) (81 mg) which contained impurities. m/z (ESI+) for ($C_{48}H_{54}N_8O_9$), 887.8 (M+H)+ observed.

Step 5: Synthesis of tert-butyl [(2,4-dimethoxyphenyl)methyl]{[4-(6-{[(2,4-dimethoxyphenyl)methyl]carbamoyl}-1-methyl-1H-pyrazolo[4,3-c]pyridin-4-yl)-2-(1-ethyl-4-hydroxy-3-methyl-1H-pyrazol-5-yl)-1,3-oxazol-5-yl]methyl}carbamate (U-5)

A suspension of tert-butyl ({2-[4-(benzyloxy)-1-ethyl-3-methyl-1H-pyrazol-5-yl]-4-(6-{[(2,4-dimethoxyphenyl)methyl]carbamoyl}-1-methyl-1H-pyrazolo[4,3-c]pyridin-4-yl)-1,3-oxazol-5-yl}methyl)[(2,4-dimethoxyphenyl)methyl]carbamate (U-4) (81.0 mg, 0.10 mmol) and Pd-C10% (120 mg 0.11 mmol) in 8 mL EtOAc and 2 mL methanol was hydrogenated under H$_2$ (75 Psi) for 90 min. The reaction mixture was filtered through a pad of celite and concentrated in vacuo, the crude product was purified by ISCO (silica, 12 g, 0-100% EtOAc in Hept) to afford the title compound tert-butyl [(2,4-dimethoxyphenyl)methyl]{[4-(6-{[(2,4-dimethoxyphenyl)methyl]-carbamoyl}-1-methyl-1H-pyrazolo[4,3-c]pyridin-4-yl)-2-(1-ethyl-4-hydroxy-3-methyl-1H-pyrazol-5-yl)-1,3-oxazol-5-yl]methyl}carbamate (U-5) (30 mg, 41%, over 5-steps) as a white solid m/z (ESI+) for ($C_{41}H_{48}N_8O_9$), 797.5 (M+H)+ observed.

Step 6: Synthesis of 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example U01)

A mixture of tert-butyl [(2,4-dimethoxyphenyl)methyl]{[4-(6-{[(2,4-dimethoxyphenyl)methyl]-carbamoyl}-1-methyl-1H-pyrazolo[4,3-c]pyridin-4-yl)-2-(1-ethyl-4-hydroxy-3-methyl-1H-pyrazol-5-yl)-1,3-oxazol-5-yl]methyl}carbamate (U-5) (30.0 mg, 0.038 mmol) in neat TFA (1.5 mL) was heated at 55° C. for 2 days. Excess TFA was removed and the crude product was purified via preparatory-HPLC to afford the title compound 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example U01) (10.2 mg, 53% yield) as a TFA salt. m/z (ESI+) for ($C_{18}H_{20}N_8O_3$), 397.4 (M+H)+ observed.

Example U01: Alternative preparation of 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide According to Scheme U′
Scheme U′
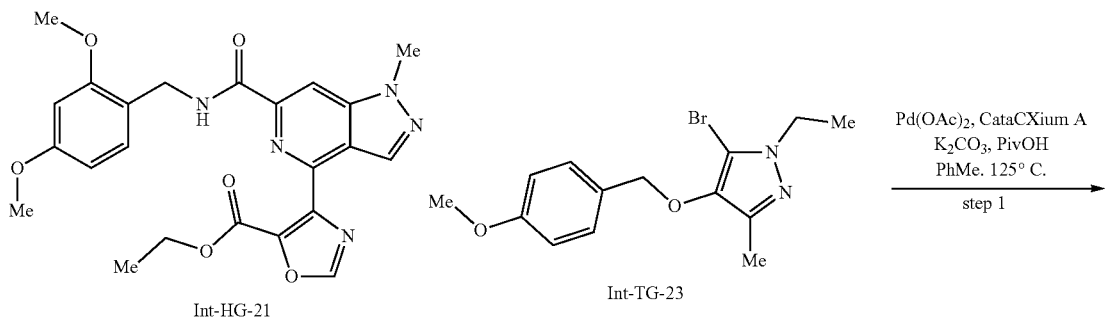
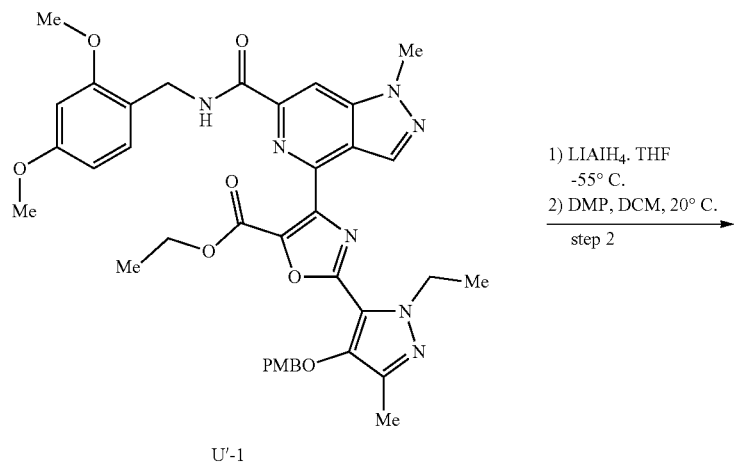
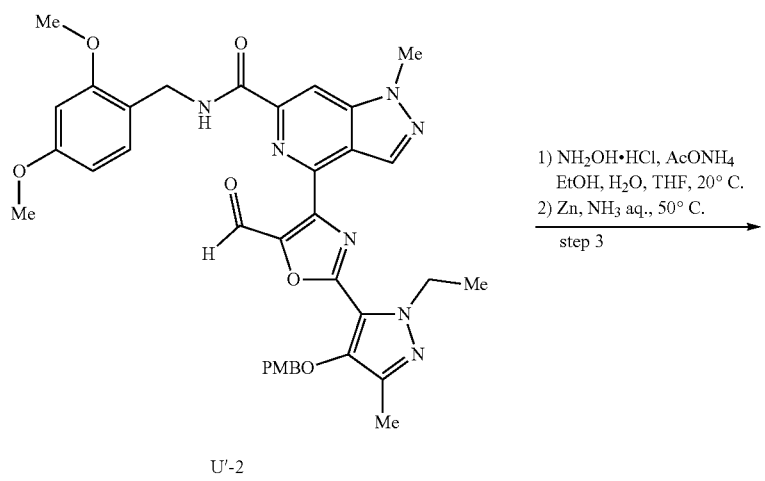

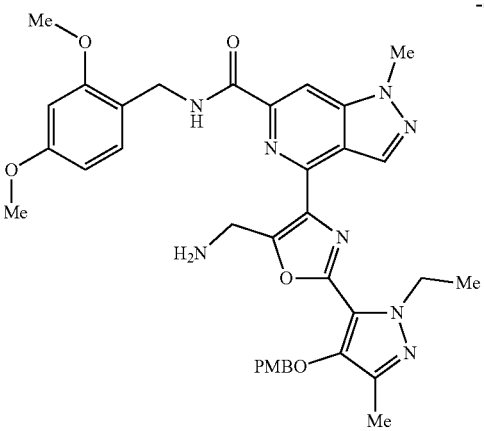

U'-3

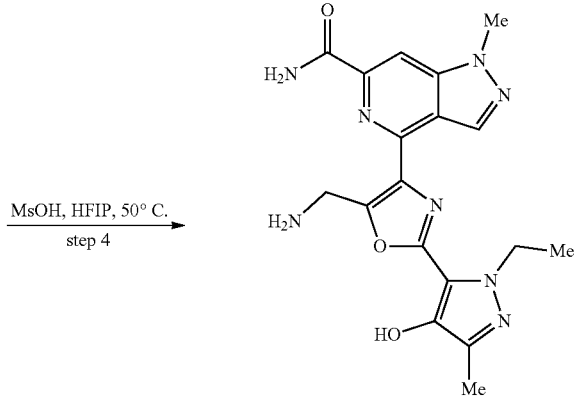

MsOH, HFIP, 50° C.
step 4

Example U01

Step 1: Synthesis of ethyl 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylate (U'-1)

To a stirred solution of ethyl 4-(6-{[(2,4-dimethoxyphenyl)methyl]carbamoyl}-1-methyl-1H-pyrazolo[4,3-c]pyridin-4-yl)-1,3-oxazole-5-carboxylate (Int-HG-21) (7.8 g, 16.76 mmol, 1 eq) in toluene (160 mL) was added 5-bromo-1-ethyl-4-[(4-methoxyphenyl)methoxy]-3-methyl-1H-pyrazole (Int-TG-23) (7.4 g, 22.76 mmol, 1.36 eq), CataXiumA (2.40 g, 6.70 mmol, 0.4 eq), PivOH (684.60 mg, 6.70 mmol, 770.08 µL, 0.4 eq) and $K_2CO_3$ (6.95 g, 50.27 mmol, 3 eq) at 20° C. The mixture was degassed under vacuum and purged with $N_2$ three times. $Pd(OAc)_2$ (752.45 mg, 3.35 mmol, 0.2 eq) was added at 20° C. The mixture was again degassed under vacuum and purged with $N_2$ an additional three times. The reaction mixture was heated to 106° C. (internal temperature, 125° C. external oil bath) and stirred for 16 hrs. LCMS analysis showed consumption of starting material and a new peak with the desired product mass. The reaction was removed from the oil bath and allowed to cool to 20° C. The reaction was concentrated under vacuum to give crude product. The crude product was purified by column chromatography on silica gel (eluted with 0-100% EtOAc/Pet. Ether) to afford the title compound ethyl 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylate (U'-1) (5.6 g, 7.89 mmol, 47% yield) as a brown solid. $^1H$ NMR (400 MHz, DMSO-$d_6$) δ=9.16-8.94 (m, 1H), 8.53 (br s, 1H), 8.41 (br s, 1H), 7.48-7.28 (m, 2H), 7.27-7.15 (m, 1H), 6.97-6.77 (m, 2H), 6.68-6.54 (m, 1H), 6.52-6.40 (m, 1H), 4.95 (br s, 2H), 4.68-4.40 (m, 4H), 4.33-4.06 (m, 5H), 3.81 (br s, 3H), 3.74 (br s, 3H), 3.67 (br s, 3H), 2.08 (br s, 3H), 1.48-1.26 (m, 3H), 1.21-1.08 (m, 3H).

Step 2: Synthesis of N-[(2,4-dimethoxyphenyl)methyl]-4-(2-{1-ethyl-4-[(4-methoxyphenyl)methoxy]-3-methyl-1H-pyrazol-5-yl}-5-formyl-1,3-oxazol-4-yl)-1-methyl-1H-pyrazolo[4,3-c]pyridine-6-carboxamide (U'-2)

A 1 L three necked round bottom flask was charged with ethyl 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylate (U'-1) (5.6 g, 7.89 mmol, 1 eq) in THF (560 mL) at 20° C. The reaction was degassed and purged with $N_2$ for three times. The reaction was cooled to −55° C. (acetone dry-ice bath). $LiAlH_4$ (1 M in THF, 37.33 mL, 4.73 eq) was added dropwise at −55° C. (acetone dry-ice bath). A brown solution was formed. This reaction was stirred at a temperature between −55° C. and −50° C. (acetone dry-ice bath) for 2 hours. LCMS analysis showed consumption of the starting material, a new peak with the desired aldehyde product mass, and a peak for the mass of the over reduced alcohol product. The reaction was quenched with $Na_2SO_4 \cdot 10H_2O$ (25 g) and MeOH/$H_2O$ (50 mL, 1:1) below −50° C. and stirred at −50° C. for 1 hr. The reaction was diluted with DCM (300 mL). The mixture was filtered through a pad of Celite. The filter cake was rinsed with DCM (6×50 mL). The organic phase of combined filtrate was separated. The organic layer was dried over $MgSO_4$, filtered and the filtrate concentrated under vacuum to give miscible crude mixture of aldehyde and alcohol products as a light yellow solid. This mixture was used in the next step without further purification. To a suspension of miscible crude aldehyde/alcohol products (5.5 g, 8.24 mmol, 1 eq) in DCM (220 mL) was added Dess-Martin periodinane (5.24 g, 12.36 mmol, 3.83 mL, 1.5 eq) at 20° C. The reaction mixture was stirred at 20° C. for 2 hrs. The reaction was diluted with $H_2O$ (100 mL). The suspension turned to a solution. The organic phase was separated. The aqueous phase was extracted with DCM (3×50 mL). The combined organic extracts were dried over $MgSO_4$ and filtered. The filtrate was concentrated under vacuum to afford the title compound N-[(2,4-dimethoxyphenyl)methyl]-4-(2-{1-ethyl-4-[(4-methoxyphenyl)methoxy]-3-methyl-1H-pyrazol-5-yl}-5-formyl-1,3-oxazol-4-yl)-1-methyl-1H-pyrazolo[4,3-c]pyridine-6-carboxamide (U'-2) (6 g, crude) as a light-yellow solid. This material was used in the next step without further purification. m/z (ESI+) for ($C_{35}H_{36}N_7O_7$), 666.1 (M+H)$^+$ observed.

Step 3: Synthesis of 4-[5-(aminomethyl)-2-{1-ethyl-4-[(4-methoxyphenyl)methoxy]-3-methyl-1H-pyrazol-5-yl}-1,3-oxazol-4-yl]-N-[(2,4-dimethoxyphenyl)methyl]-1-methyl-1H-pyrazolo[4,3-c]pyridine-6-carboxamide (U'-3)

To a suspension of N-[(2,4-dimethoxyphenyl)methyl]-4-(2-{1-ethyl-4-[(4-methoxyphenyl)methoxy]-3-methyl-1H- pyrazol-5-yl}-5-formyl-1,3-oxazol-4-yl)-1-methyl-1H-pyrazolo[4,3-c]pyridine-6-carboxamide (U'-2) (5.9 g, 8.86 mmol, 1 eq) in EtOH (50 mL) and H$_2$O (20 mL) was added NH$_2$OH·HCl (1.85 g, 26.59 mmol, 3 eq) and AcONH$_4$ (3.42 g, 44.31 mmol, 5 eq) at 20° C. Then, THF (200 mL) was added to the reaction mixture. A light-yellow suspension was formed. The mixture was stirred at 20° C. for 2 hrs. The light-yellow suspension turn to a light-yellow solution. LCMS analysis showed a new peak with the desired product mass. At this stage, NH$_3$ (28% solution in H$_2$O) (22.19 g, 177.26 mmol, 24.38 mL, 28% purity, 20 eq) and Zn (13.91 g, 212.71 mmol, 24 eq) were added to the reaction mixture. The reaction was heated to 50° C. and stirred for 2 hrs. LCMS analysis showed consumption of starting material and a new peak with the desired product mass. The reaction was removed from heating and allowed to cool to 20° C. The mixture was filtered through a pad of Celite. The filter cake was rinsed with DCM (3×100 mL). The combined filtrate was diluted with H$_2$O (20 mL). The organic layer was separated, dried over MgSO$_4$ and filtered. The filtrate was concentrated under vacuum to afford the title compound 4-[5-(aminomethyl)-2-{1-ethyl-4-[(4-methoxyphenyl)methoxy]-3-methyl-1H-pyrazol-5-yl}-1,3-oxazol-4-yl]-N-[(2,4-dimethoxyphenyl)methyl]-1-methyl-1H-pyrazolo[4,3-c]pyridine-6-carboxamide (U'-3) (6 g, crude) as a light-yellow solid. This material was used in the next step without further purification. m/z (ESI+) for (C$_{35}$H$_{39}$N$_8$O$_6$), 667.1 (M+H)$^+$ observed.

Step 4: Synthesis of 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example U01)

To a solution of 4-[5-(aminomethyl)-2-{1-ethyl-4-[(4-methoxyphenyl)methoxy]-3-methyl-1H-pyrazol-5-yl}-1,3-oxazol-4-yl]-N-[(2,4-dimethoxyphenyl)methyl]-1-methyl-1H-pyrazolo[4,3-c]pyridine-6-carboxamide (U'-3) (6 g, crude) in HFIP (50 mL) was added methanesulfonic acid (3.19 g, 33.24 mmol, 2.37 mL, 11 eq). The resulting red solution was heated to 50° C. and stirred for 2 hours. LCMS analysis showed a new peak with the desired product mass. This reaction was quenched by the addition of saturated NaHCO$_3$ aq. until neutral pH-7 was achieved. The solution was transferred to a separatory funnel and the phased separated. The organic phase was concentrated under vacuum at 50° C. The crude residue was combined with the crude material from another batch and purified by prep-HPLC (Phenomenex Gemini-NX 150×30 mm×5 µm column, 5-45% MeCN/H$_2$O (containing 0.05% HCl), 25 mL/min flowrate, 54 injections) to afford a crude yellow solid (440 mg). The solid was suspended in MeOH (5 mL) and DCM (15 mL). The suspension was stirred at 20° C. for 30 min. The mixture was filtered and the filter cake was washed with DCM (10 mL). The solids were isolated and dried under vacuum to afford the title compound 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example U01) (365.19 mg, 30%) as a solid yellow hydrochloride salt. m/z (ESI+) for (C$_{18}$H$_{20}$N$_8$O$_3$), 397.1 (M+H)$^+$ observed; $^1$H NMR (400 MHz, DMSO-d$_6$) δ=8.90 (br s, 1H), 8.77 (d, J=0.9 Hz, 1H), 8.73 (br s, 2H), 8.41 (d, J=0.8 Hz, 1H), 8.13 (br s, 1H), 7.98 (s, 1H), 4.79 (q, J=5.3 Hz, 2H), 4.56 (q, J=7.1 Hz, 2H), 4.20 (s, 3H), 2.17 (s, 3H), 1.40 (t, J=7.1 Hz, 3H)

Examples U02, U03, and U04 were synthesized according to the methods used for the synthesis of 4-[5-(aminomethyl)-2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example U01) (Scheme U') with non-critical changes or substitutions to the exemplified procedures that someone who skilled in the art would be able to realize.

| Example Number | Intermediates | Structure/Name | Analytical Data |
|---|---|---|---|
| U02 | Int-HG-21 & Int-TG-25 were used in step 1 | 4-[5-(aminomethyl)-2-(1-ethyl-4-hydroxy-1H-pyrazol-5-yl)-1,3-oxazol-4-yl]-1-methyl-1H-pyrazolo[4,3-c]pyridine-6-carboxamide | $^1$H NMR (400 MHz, DMSO-d$_6$) δ = 8.75 (s, 1H), 8.29 (s, 1H), 7.93 (br s, 1H), 7.90 (br s, 1H), 7.25 (s, 1H), 4.61 (q, J = 7.1 Hz, 2H), 4.31 (s, 2H), 4.18 (s, 3H), 1.42 (t, J = 7.0 Hz, 3H); m/z (ESI+) for C$_{17}$H$_{18}$N$_8$O$_3$, 383.1 (M + H)$^+$ observed. |

| Example Number | Intermediates | Structure/Name | Analytical Data |
|---|---|---|---|
| U03 | Int-HG-21 & Int-TG-29 were used in step 1 | 4-{5-(aminomethyl)-2-[4-hydroxy-1-(3-hydroxypropyl)-3-methyl-1H-pyrazol-5-yl]-1,3-oxazol-4-yl}-1-methyl-1H-pyrazolo[4,3-c]pyridine-6-carboxamide | $^1$H NMR (400 MHz, DMSO-d$_6$) δ 9.13-8.91 (m, 3H), 8.76 (s, 1H), 8.36 (s, 1H), 8.18 (br s, 1H), 7.86 (br s, 1H), 4.78-4.64 (m, 2H), 4.62-4.49 (m, 2H), 4.13 (br s, 3H), 3.48-3.34 (m, 2H), 2.11 (s, 3H), 1.96-1.84 (m, 2H); m/z (ESI+) for $C_{19}H_{22}N_8O_4$, 427.0 (M + H)$^+$ observed. |
| U04 | Int-HG-21 & Int-TG-30 were used in step 1 | 4-{5-(aminomethyl)-2-[1-(3-hydroxypropyl)-3-methyl-1H-pyrazol-5-yl]-1,3-oxazol-4-yl}-1-methyl-1H-pyrazolo[4,3-c]pyridine-6-carboxamide | m/z (ESI+) for $C_{19}H_{22}N_8O_3$, 411.1 (M + H)$^+$ observed. |

Example V01: Preparation of 4-5-[4-hydroxy-1-(2-hydroxyethyl)-3-methyl-1H-pyrazol-5-yl]-4H-1,2,4-triazol-3-yl)-1-methyl-1H-pyrazolo[4,3-c]pyridine-6-carboxamide According to Scheme V

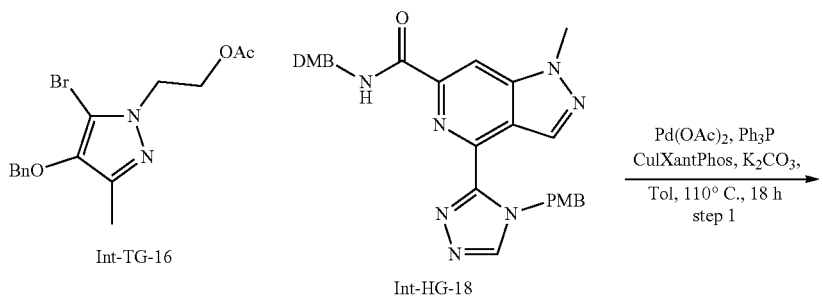

Scheme V

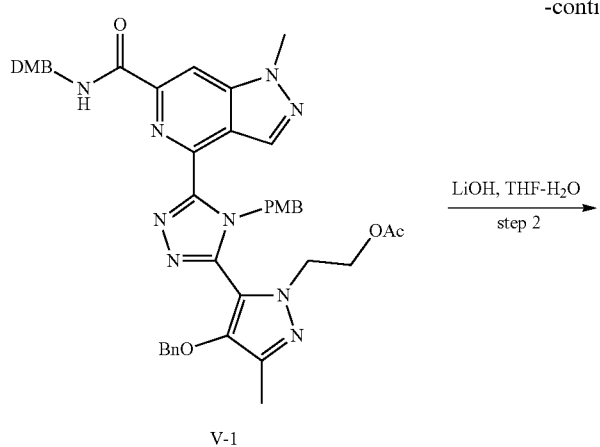

V-1

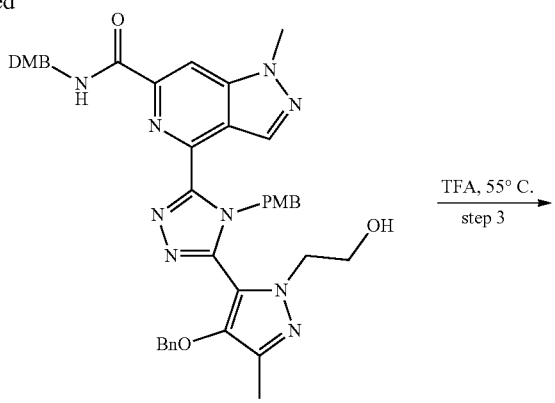

V-2

LiOH, THF-H₂O
step 2

TFA, 55° C.
step 3

Example V01

Step 1: Synthesis of 2-[4-(benzyloxy)-5-{5-(6-{[(3,5-dimethoxyphenyl)methyl]carbamoyl}-1-methyl-1H-pyrazolo[4,3-c]pyridin-4-yl)-4-[(4-methoxyphenyl)methyl]-4H-1,2,4-triazol-3-yl}-3-methyl-1H-pyrazol-1-yl]ethyl acetate (V-1)

A vial was charged with 2-[4-(benzyloxy)-5-bromo-3-methyl-1H-pyrazol-1-yl]ethyl acetate (Int-TG-16) (73 mg, 0.21 mmol) and N-[(2,4-dimethoxyphenyl)methyl]-4-{4-[(4-methoxyphenyl)-methyl]-4H-1,2,4-triazol-3-yl}-1-methyl-1H-pyrazolo[4,3-c]pyridine-6-carboxamide (Int-HG-18) (106 mg, 0.207 mmol), Pd(OAc)2 (4.64 mg, 0.0207 mmol), Ph₃P (10.8 mg, 0.0413 mmol), potassium carbonate (85.7 mg, 0.620 mmol) and iodo[4,5-bis(diphenylphosphino)-9,9-dimethylxanthene]copper(I) (63.6 mg, 0.0827 mmol) in toluene (3 mL), degassed at room temperature for 5 min, then heated at 110° C. overnight. The reaction mixture was filtered through a pad of celite and the filtrate was concentrated in vacuo. The crude product was purified by ISCO (silica, 12 g, 0-100% EtOAc in heptane) to afford the title compound 2-[4-(benzyloxy)-5-{5-(6-{[(3,5-dimethoxyphenyl)methyl]carbamoyl}-1-methyl-1H-pyrazolo[4,3-c]pyridin-4-yl)-4-[(4-methoxy-phenyl)methyl]-4H-1,2,4-triazol-3-yl}-3-methyl-1H-pyrazol-1-yl]ethyl acetate (V-1) (126 mg, 78% yield) as a white foam ¹H NMR (400 MHz, DMSO-d₆) δ=8.82 (d, J=1.2 Hz, 1H), 8.48 (d, J=1.2 Hz, 1H), 8.13 (t, J=6.2 Hz, 1H), 7.23-7.15 (m, 5H), 6.95 (d, J=8.2 Hz, 1H), 6.72-6.65 (m, J=9.0 Hz, 2H), 6.59-6.54 (m, 2H), 6.52 (d, J=2.3 Hz, 1H), 6.36 (dd, J=2.3, 8.2 Hz, 1H), 5.81 (s, 2H), 4.76 (s, 2H), 4.38 (d, J=5.9 Hz, 2H), 4.23 (s, 3H), 4.18-4.12 (m, 2H), 4.11-4.06 (m, 2H), 3.76 (s, 3H), 3.74-3.70 (m, 3H), 3.52 (s, 3H), 2.14 (s, 3H), 1.89 (s, 3H). m/z (ESI+) for (C₄₂H₄₃N₉O₇), 786.5 (M+H)⁺ observed.

Step 2: Synthesis of 4-{5-[4-(benzyloxy)-1-(2-hydroxyethyl)-3-methyl-1H-pyrazol-5-yl]-4-[(4-methoxyphenyl)methyl]-4H-1,2,4-triazol-3-yl}-N-[(3,5-dimethoxyphenyl)methyl]-1-methyl-1H-pyrazolo[4,3-c]pyridine-6-carboxamide (V-2)

A vial was charged with 2-[4-(benzyloxy)-5-{5-(6-{[(3,5-dimethoxyphenyl)methyl]carbamoyl}-1-methyl-1H-pyrazolo[4,3-c]pyridin-4-yl)-4-[(4-methoxy-phenyl)methyl]-4H-1,2,4-triazol-3-yl}-3-methyl-1H-pyrazol-1-yl]ethyl acetate (V-1) (132 mg, 0.168 mmol), lithium hydroxide (8.04 mg, 0.336 mmol, 0.336 mL, 1.0 M), water (3.03 mg, 0.168 mmol) and THF (9 mL) at room temperature. The reaction was stirred at room temperature for 2 h. Then additional 1M LiOH (0.1 mL) was added at room temperature, the reaction was stirred at room temperature for 3 h. The reaction mixture was concentrated in vacuo, the crude product was treated with methanol and toluene×3 to remove trace amount of water, concentrated in vacuo to afford the title compound 4-{5-[4-(benzyloxy)-1-(2-hydroxyethyl)-3-methyl-1H-pyrazol-5-yl]-4-[(4-methoxyphenyl)methyl]-4H-1,2,4-triazol-3-yl}-N-[(3,5-dimethoxyphenyl)methyl]-1-methyl-1H-pyrazolo[4,3-c]pyridine-6-carboxamide (V-2) 105 mg as crude product, which was used without purification. m/z (ESI+) for (C₄₀H₄₁N₉O₆), 744.3 (M+H)⁺ observed.

Step 3: Synthesis of 4-{5-[4-hydroxy-1-(2-hydroxyethyl)-3-methyl-1H-pyrazol-5-yl]-4H-1,2,4-triazol-3-yl}-1-methyl-1H-pyrazolo[4,3-c]pyridine-6-carboxamide (Example V01)

A vial was charged with 4-{5-[4-(benzyloxy)-1-(2-hydroxyethyl)-3-methyl-1H-pyrazol-5-yl]-4-[(4-methoxyphenyl)methyl]-4H-1,2,4-triazol-3-yl}-N-[(3,5-dimethoxyphenyl)methyl]-1-methyl-1H-pyrazolo[4,3-c]pyridine-6-carboxamide (V-2) (100 mg, 0.134 mmol) in TFA (1.5 mL) stirred at 55° C. overnight. Excess TFA was removed in vacuo, the crude reaction mixture was treated with methanol×3 and toluene×3 and concentrated in vacuo to afford a crude 2-{5-[5-(6-carbamoyl-1-methyl-1H-pyrazolo[4,3-c]pyridin-4-yl)-4H-1,2,4-triazol-3-yl]-4-hydroxy-3-methyl-1H-pyrazol-1-yl}ethyl trifluoroacetate which was then treated with potassium carbonate (37.2 mg, 0.269 mmol) in methanol (1 mL) with a few drops of dichloromethane to increase solubility at room temperature for 30 min. The solid was filtered out and the filtrated was concentrated, the crude product was purified via preparatory-HPLC to afford the title compound 4-{5-[4-hydroxy-1-(2-hydroxyethyl)-3-methyl-1H-pyrazol-5-yl]-4H-1,2,4-triazol-3-yl}-1-methyl-1H-pyrazolo[4,3-c]pyridine-6-carboxamide (Example V01) (32 mg, 68% yield) as a white solid. m/z (ESI+) for ($C_{16}H_{17}N_9O_3$), 384.2 $(M+H)^+$ observed.

Example W01: Preparation of 4-[5-(1-aminoethyl)-2-(1-ethyl-3-methyl-1H-pyrazol-5-yl)-1,3-thiazol-4-yl]-1-methyl-1H-pyrazolo[4,3-c]pyridine-6-carboxamide According to Scheme W Scheme W

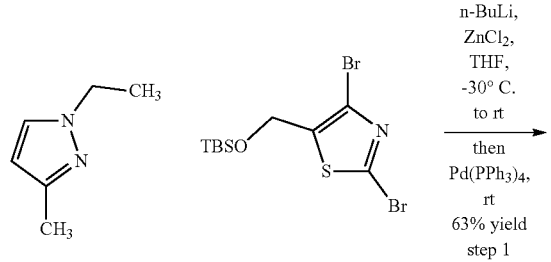

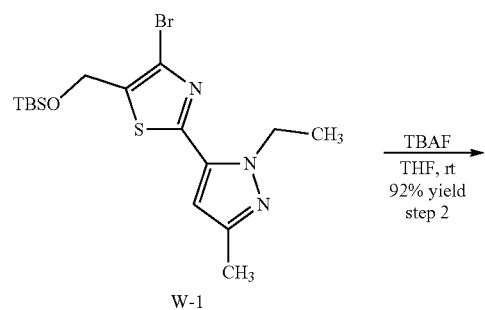

W-1

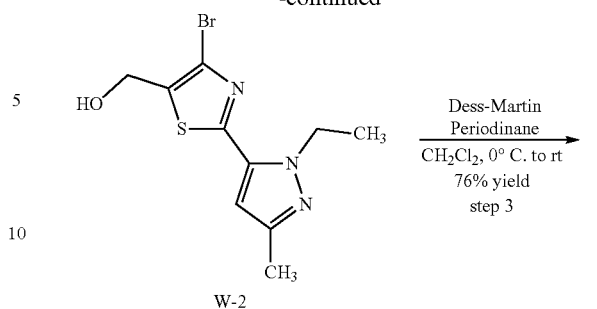

W-2

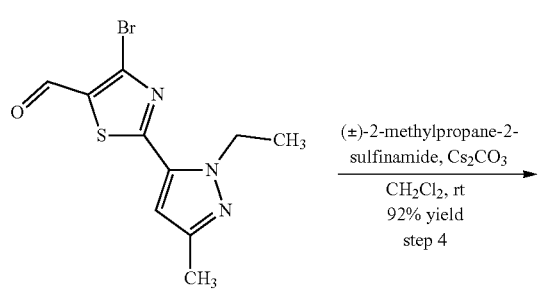

W-3

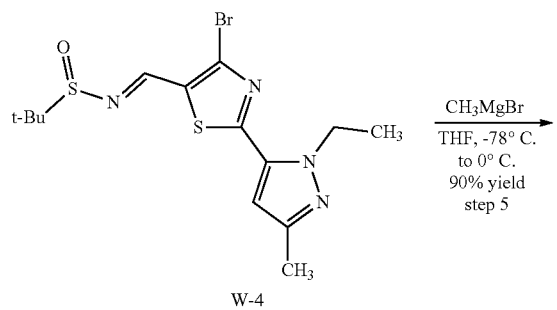

W-4

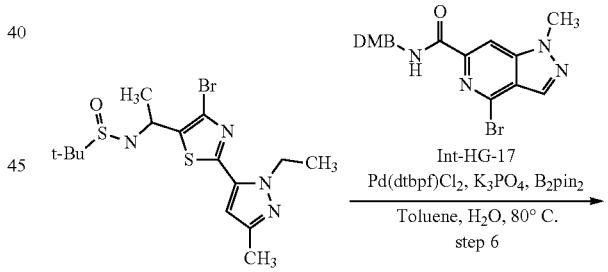

W-5

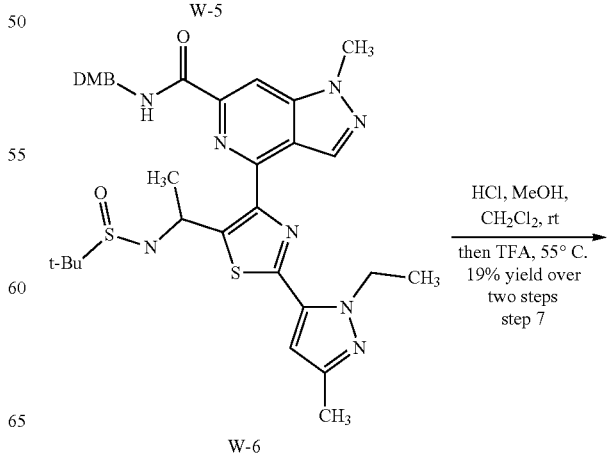

W-6

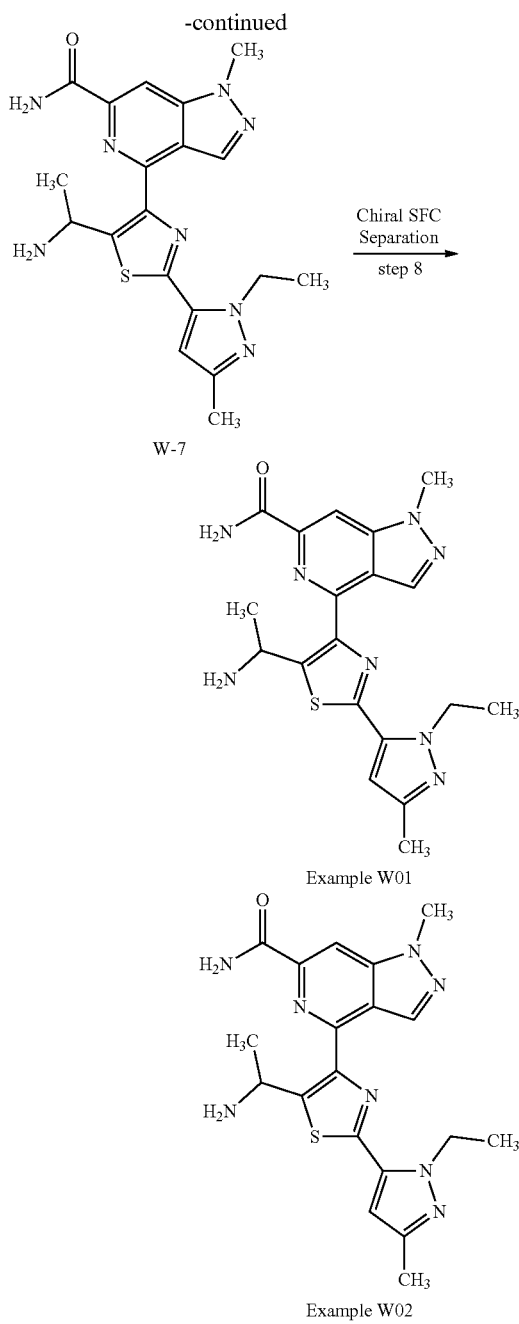

W-7

Chiral SFC Separation
step 8

Example W01

Example W02

Step 1: Synthesis of 4-bromo-5-(((tert-butyldimethylsilyl)oxy)methyl)-2-(1-ethyl-3-methyl-1H-pyrazol-5-yl)thiazole (W-1)

To a solution of 1-ethyl-3-methyl-1H-pyrazole (776 mg, 7.04 mmol) in THF (30 mL) at −30° C. was added n-BuLi (2.5 M in hexane, 3.10 mL, 7.75 mmol) dropwise, and the mixture was stirred for 20 minutes. A solution of $ZnCl_2$ (1.9 M in 2-MeTHF, 4.45 mL, 8.45 mmol) was then added dropwise, and the reaction was warmed to room temperature. After 2 hours, LCMS analysis showed consumption of the starting material. A solution of 2,4-dibromo-5-(((tert-butyldimethylsilyl)oxy)methyl)thiazole (prepared in 3 steps according to International Patent Application PCT/CA2010/000779 which published on 25 Nov. 2010 as WO 2010/132999 A1) (3.00 g, 7.75 mmol) in THF (9 mL) was then added, followed by addition of $Pd(PPh_3)_4$ (814 mg, 0.704 mmol). The reaction was stirred at room temperature for 2.5 hours. LCMS analysis showed consumption of the starting material, and the reaction was then quenched with saturated aqueous $NH_4Cl$ (10 mL). The layers were separated, and the aqueous phase was extracted three times with EtOAc. The combined organic extract was dried over $MgSO_4$, filtered, and concentrated in vacuo. The residue was purified by flash chromatography (80 g $SiO_2$, 0-10% EtOAc/heptanes) to provide 4-bromo-5-(((tert-butyldimethylsilyl)oxy)methyl)-2-(1-ethyl-3-methyl-1H-pyrazol-5-yl)thiazole (W-1) (2.03 g, 63%) as a colorless oil. $^1$H NMR (400 MHz, $CDCl_3$) δ 6.42 (s, 1H), 4.83 (s, 2H), 4.58 (q, J=7.0 Hz, 2H), 2.29 (s, 3H), 1.44 (t, J=7.4 Hz, 3H) 0.94 (s, 9H), 0.15 (s, 6H); m/z (ESI+) for ($C_{16}H_{27}BrN_3OSSi$), 416.0 (M+H)$^+$ observed.

Step 2: Synthesis of (4-bromo-2-(1-ethyl-3-methyl-1H-pyrazol-5-yl)thiazol-5-yl)methanol (W-2)

To a solution of 4-bromo-5-(((tert-butyldimethylsilyl)oxy)methyl)-2-(1-ethyl-3-methyl-1H-pyrazol-5-yl)thiazole (W-1) (1.34 g, 3.22 mmol) in THF (6.44 mL) was added TBAF (1.0 M in THF, 6.44 mL, 6.44 mmol) and stirred at room temperature for 30 minutes. TLC analysis (4:1 heptanes:EtOAc) showed consumption of the starting material. The mixture was then diluted with $H_2O$ and extracted three times with EtOAc. The combined organic extract was dried over $MgSO_4$, filtered, and concentrated in vacuo. The residue was purified by flash chromatography (40 g $SiO_2$, 40-80% EtOAc/heptanes) to provide (4-bromo-2-(1-ethyl-3-methyl-1H-pyrazol-5-yl)thiazol-5-yl)methanol (W-2) (896 mg, 92%) as a white solid. $^1$H NMR (400 MHz, $CDCl_3$) δ 6.42 (s, 1H), 4.86 (s, 2H), 4.58 (q, J=7.0 Hz, 2H), 2.29 (s, 3H), 1.44 (t, J=7.4 Hz, 3H); m/z (ESI+) for ($C_{10}H_{13}BrN_3S$), 302.0 (M+H)$^+$ observed.

Step 3: Synthesis of 4-bromo-2-(1-ethyl-3-methyl-1H-pyrazol-5-yl)thiazole-5-carbaldehyde (W-3)

To a solution of (4-bromo-2-(1-ethyl-3-methyl-1H-pyrazol-5-yl)thiazol-5-yl)methanol (W-2) (896 mg, 2.96 mmol) in $CH_2Cl_2$ (14.8 mL) at 0° C. was added Dess-Martin periodinane (1.92 g, 4.45 mmol). The mixture was then warmed to room temperature, stirred for 1 hour, and LCMS analysis showed consumption of the starting material. The reaction was quenched with $H_2O$ and extracted three times with EtOAc. The combined organic extract was dried over $MgSO_4$, filtered, and concentrated in vacuo. The residue was purified by flash chromatography (24 g $SiO_2$, 10-60% EtOAc/heptanes) to provide 4-bromo-2-(1-ethyl-3-methyl-1H-pyrazol-5-yl)thiazole-5-carbaldehyde (W-3) (678 mg, 76%) as a yellow solid. $^1$H NMR (400 MHz, $CDCl_3$) δ 10.01 (s, 1H), 6.58 (s, 1H), 4.64 (q, J=7.0 Hz, 2H), 2.30 (s, 3H), 1.46 (t, J=7.2 Hz, 3H); m/z (ESI+) for ($C_{10}HBrN_3S$), 300.0 (M+H)$^+$ observed.

Step 4: Synthesis of (E)-N-((4-bromo-2-(1-ethyl-3-methyl-1H-pyrazol-5-yl)thiazol-5-yl)methylene)-2-methylpropane-2-sulfinamide (W-4)

A mixture of 4-bromo-2-(1-ethyl-3-methyl-1H-pyrazol-5-yl)thiazole-5-carbaldehyde (W-3) (678 mg, 2.26 mmol), $Cs_2CO_3$ (1.47 g, 4.51 mmol), 2-methylpropane-2-sulfinamide (547 mg, 4.51 mmol), and $CH_2Cl_2$ (7.5 mL) was stirred at room temperature for 3 hours. LCMS analysis showed consumption of the starting material. The mixture was then filtered through a Celite pad with EtOAc and concentrated in vacuo. The residue was purified by flash chromatography (24 g SiO$_2$, 10-40% EtOAc/heptanes) to provide (E)-N-((4-bromo-2-(1-ethyl-3-methyl-1H-pyrazol-5-yl)thiazol-5-yl)methylene)-2-methylpropane-2-sulfinamide (W-4) (836 mg, 92%) as a yellow solid. $^1$H NMR (400 MHz, CDCl$_3$) δ 8.72 (s, 1H), 6.54 (s, 1H), 4.64 (q, J=7.0 Hz, 2H), 2.31 (s, 3H), 1.46 (t, J=7.2 Hz, 3H), 1.27 (s, 9H); m/z (ESI+) for (C$_{14}$H$_{20}$BrN$_4$OS$_2$), 403.0 (M+H)$^+$ observed.

Step 5: Synthesis of N-(1-(4-bromo-2-(1-ethyl-3-methyl-1H-pyrazol-5-yl)thiazol-5-yl)ethyl)-2-methylpropane-2-sulfinamide (W-5)

To a solution of (E)-N-((4-bromo-2-(1-ethyl-3-methyl-1H-pyrazol-5-yl)thiazol-5-yl)methylene)-2-methylpropane-2-sulfinamide (W-4) (835 mg, 2.07 mmol) in CH$_2$Cl$_2$ (21 mL) at −78° C. was added a solution of methylmagnesium bromide (1.4 M in THF:toluene 1:3, 4.44 mL, 6.21 mmol). After stirring for 5 minutes, the reaction was warmed to 0° C. and stirred for 1 hour. LCMS analysis showed consumption of the starting material. The reaction was then quenched with H$_2$O and extracted three times with EtOAc. The combined organic extract was dried over MgSO$_4$, filtered, and concentrated in vacuo. The residue was purified by flash chromatography (24 g SiO$_2$, 50-100% EtOAc/heptanes) to provide N-(1-(4-bromo-2-(1-ethyl-3-methyl-1H-pyrazol-5-yl)thiazol-5-yl)ethyl)-2-methylpropane-2-sulfinamide (W-5) (785 mg, 90%). $^1$H NMR (400 MHz, CDCl$_3$) δ 6.38 (s, 1H), 4.97 (m, 1H), 4.57 (q, J=7.0 Hz, 2H), 3.47 (s, 1H), 2.27 (s, 3H), 1.62 (d, J=6.6 Hz, 3H), 1.44 (t, J=7.0 Hz, 3H), 1.23 (s, 9H); m/z (ESI+) for (C$_{15}$H$_{24}$BrN$_4$OS$_2$), 419.1 (M+H)$^+$ observed.

Step 6: Synthesis of 4-(5-(1-(((tert-butylsulfinyl)amino)ethyl)-2-(1-ethyl-3-methyl-1H-pyrazol-5-yl)thiazol-4-yl)-N-(3,4-dimethylbenzyl)-1-methyl-1H-pyrazolo[4,3-c]pyridine-6-carboxamide (W-6)

A mixture of N-(1-(4-bromo-2-(1-ethyl-3-methyl-1H-pyrazol-5-yl)thiazol-5-yl)ethyl)-2-methylpropane-2-sulfinamide (W-5) (785 mg, 1.87 mmol), 4-bromo-N-(2,4-dimethoxybenzyl)-1-methyl-1H-pyrazolo[4,3-c]pyridine-6-carboxamide (Int-HG-17) (758 mg, 1.87 mmol), K$_3$PO$_4$ (1.19 g, 5.61 mmol), 4,4,4',4',5,5,5',5'-octamethyl-2,2'-bi(1,3,2-dioxaborolane) (951 mg, 3.74 mmol), Pd(dtbpf) C12 (122 mg, 0.187 mmol), H$_2$O (3.70 mL, sparged with N$_2$), and toluene (18.7 mL) was stirred at 80° C. for 17 hours. LCMS analysis showed consumption of the starting material. The mixture was cooled to room temperature, filtered through a Celite pad with EtOAc, and added to a separatory funnel. The mixture was then diluted with H$_2$O, extracted three times with EtOAc, and combined organic extract was dried over MgSO$_4$. The solution was then filtered, concentrated in vacuo, and the residue purified by flash chromatography (40 g SiO$_2$, EtOAc) to provide a mixture of 4-(5-(1-(((tert-butylsulfinyl)amino)ethyl)-2-(1-ethyl-3-methyl-1H-pyrazol-5-yl)thiazol-4-yl)-N-(3,4-dimethylbenzyl)-1-methyl-1H-pyrazolo[4,3-c]pyridine-6-carboxamide (W-6) with other unknown impurities (597 mg). This material was used in the next step without further purification. m/z (ESI+) for (C$_{32}$H$_{41}$N$_8$O$_4$S$_2$), 665.3 (M+H)$^+$ observed.

Step 7: Synthesis of 1-(4-(6-carbamoyl-1-methyl-1H-pyrazolo[4,3-c]pyridin-4-yl)-2-(1-ethyl-3-methyl-1H-pyrazol-5-yl)thiazol-5-yl)ethan-1-aminium trifluoroacetate (W-7)

To a solution of 4-(5-(1-(((tert-butylsulfinyl)amino)ethyl)-2-(1-ethyl-3-methyl-1H-pyrazol-5-yl)thiazol-4-yl)-N-(3,4- dimethylbenzyl)-1-methyl-1H-pyrazolo[4,3-c]pyridine-6-carboxamide (W-6) (597 mg, 0.898 mmol) in MeOH (4.59 mL) and CH$_2$Cl$_2$ (4.59 mL) was added HCl (4 M in dioxane, 2.29 mL, 9.17 mmol) and stirred at room temperature. After 30 minutes, LCMS analysis showed reaction progression, the reaction mixture was concentrated in vacuo, dissolved in TFA (7.00 mL, 91.7 mmol), and heated at 55° C. for 70 minutes. The mixture was then allowed to cool to room temperature, concentrated in vacuo, and the residue was slurried in EtOAc and stirred for 16 hours. The solid was filtered under N$_2$ to provide 1-(4-(6-carbamoyl-1-methyl-1H-pyrazolo[4,3-c]pyridin-4-yl)-2-(1-ethyl-3-methyl-1H-pyrazol-5-yl)thiazol-5-yl)ethan-1-aminium trifluoracetate (W-7) (228 mg, 19% over two steps) as a pink solid. $^1$H NMR (400 MHz, DMSO-d$_6$) b 8.63 (s, 1H), 8.36 (s, 1H), 7.97 (br s, 1H), 7.82 (br s, 1H), 6.68 (s, 1H), 5.28 (m, 1H), 4.65 (q, J=7.1 Hz, 2H), 4.20 (s, 3H), 2.23 (s, 3H), 1.49 (d, J=6.2 Hz, 3H), 1.42 (t, J=7.0 Hz, 3H); m/z (ESI+) for (C$_{19}$H$_{23}$N$_8$OS), 411.2 (M+H)$^+$ observed.

Step 8: Purification of (R)-4-(5-(1-aminoethyl)-2-(1-ethyl-3-methyl-1H-pyrazol-5-yl)thiazol-4-yl)-1-methyl-1H-pyrazolo[4,3-c]pyridine-6-carboxamide and (S)-4-(5-(1-aminoethyl)-2-(1-ethyl-3-methyl-1H-pyrazol-5-yl)thiazol-4-yl)-1-methyl-1H-pyrazolo[4,3-c]pyridine-6-carboxamide (Examples W01 and W02)

1-(4-(6-Carbamoyl-1-methyl-1H-pyrazolo[4,3-c]pyridin-4-yl)-2-(1-ethyl-3-methyl-1H-pyrazol-5-yl)thiazol-5-yl)ethan-1-aminium trifluoracetate (W-7) was purified by preparative HPLC with a Chiral Tech OX-H column (250×30.0 mm, 5 μm partial size), which was eluted with 20-70% Methanol (2% ammonia):CO$_2$ with a flow rate of 80 mL/min to provide enantiomers (R)-4-(5-(1-aminoethyl)-2-(1-ethyl-3-methyl-1H-pyrazol-5-yl)thiazol-4-yl)-1-methyl-1H-pyrazolo[4,3-c]pyridine-6-carboxamide and (S)-4-(5-(1-aminoethyl)-2-(1-ethyl-3-methyl-1H-pyrazol-5-yl)thiazol-4-yl)-1-methyl-1H-pyrazolo[4,3-c]pyridine-6-carboxamide as brown solids (Example W01, 39 mg, 11% and Example W02, 48 mg, 13%—enantiomers not assigned). W01—LCMS [M+H]=411.4 observed; W02—LCMS [M+H]= 411.3 observed; $^1$H NMR (400 MHz, DMSO-d$_6$) δ=8.62 (d, J=0.8 Hz, 1H), 8.35 (d, J=0.8 Hz, 1H), 7.97 (br d, J=2.3 Hz, 1H), 7.81 (br d, J=2.3 Hz, 1H), 6.67 (s, 1H), 5.38-5.17 (m, 1H), 4.65 (q, J=7.2 Hz, 2H), 4.19 (s, 3H), 2.23 (s, 3H), 1.48 (d, J=6.2 Hz, 3H), 1.41 (t, J=7.0 Hz, 3H).

Example X01: Preparation of (4-(6-carbamoyl-1-methyl-1H-pyrazolo[4,3-c]pyridin-4-yl)-2-(1-ethyl-4-hydroxy-3-methyl-1H-pyrazol-5-yl)thiazol-5-yl)methanaminium formate According to Scheme X

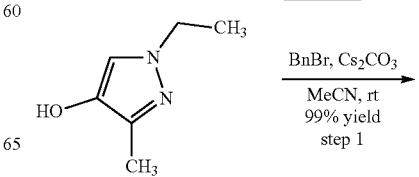

-continued
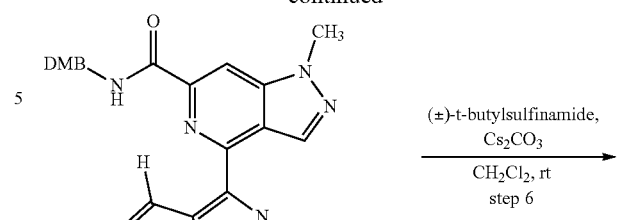
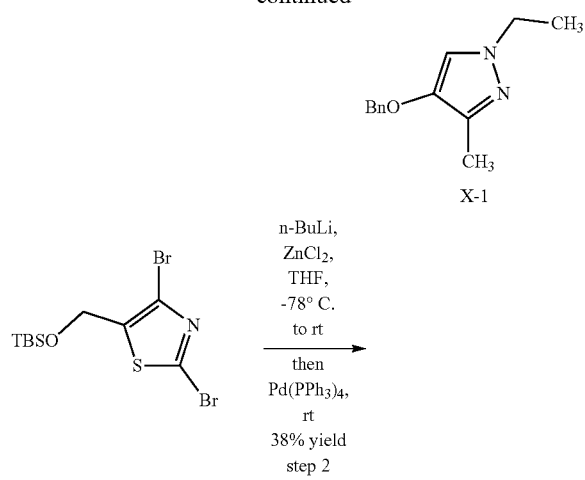
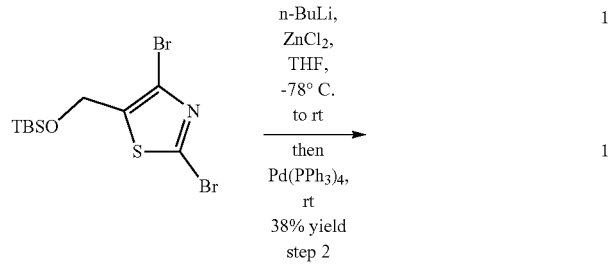
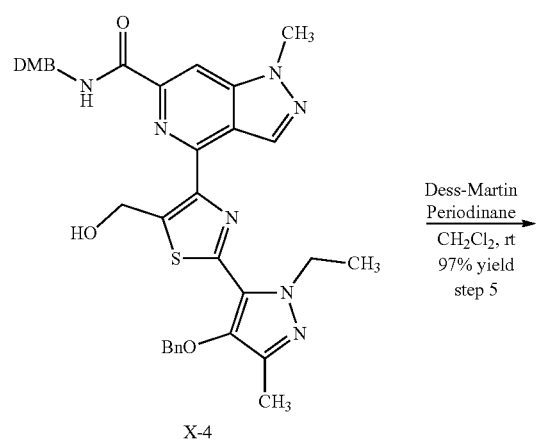
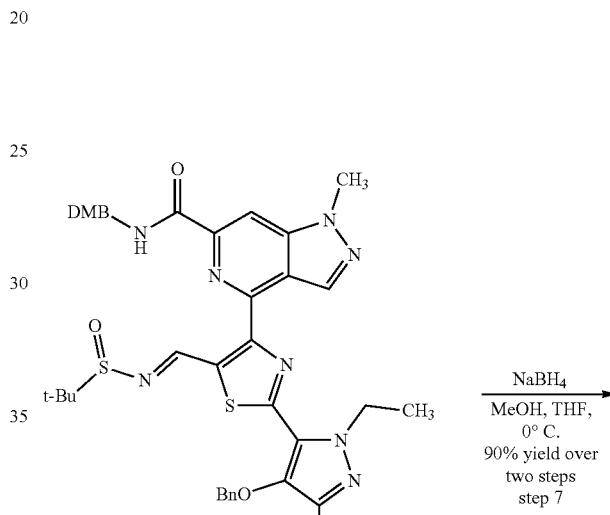
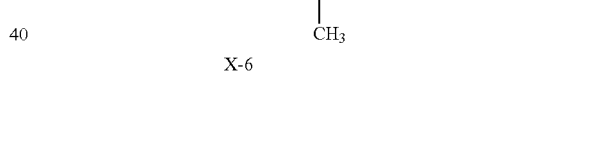
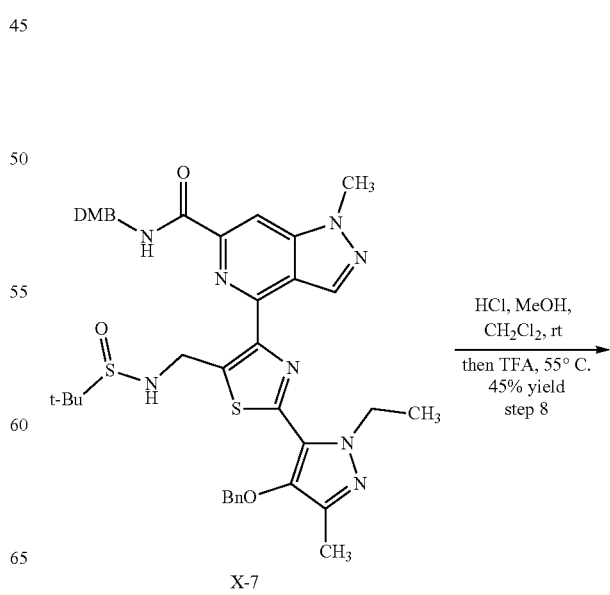

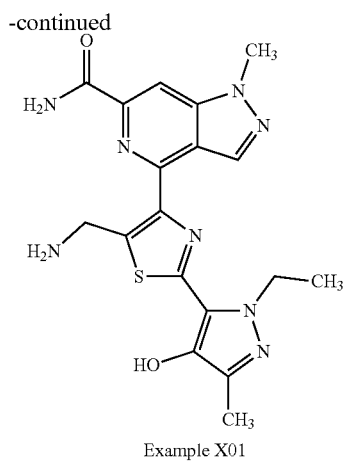

Example X01

Step 1: Synthesis of 4-(benzyloxy)-1-ethyl-3-methyl-1H-pyrazole (X-1)

A mixture of 1-ethyl-3-methyl-1H-pyrazol-4-ol (15.0 g, 119 mmol), benzyl bromide (30.5 g, 178 mmol), Cs$_2$CO$_3$ (46.5 g, 143 mmol), and MeCN (1.19 L) was stirred at room temperature for 19 hours. LCMS analysis showed consumption of the starting material. The reaction was then concentrated in vacuo, H$_2$O was added, and the mixture was extracted with EtOAc three times. The combined organic extract was dried over MgSO$_4$, filtered, and concentrated in vacuo. The crude residue was purified by flash chromatography (SiO$_2$ plug, CH$_2$Cl$_2$ [1.5 L] then EtOAc [3.0 L], 500 mL fractions) to provide 4-(benzyloxy)-1-ethyl-3-methyl-1H-pyrazole (X-1) (25.4 g, 99%) as a yellow oil. $^1$H NMR (400 MHz, CDCl$_3$) δ 7.44-7.30 (m, 5H), 6.96 (s, 1H), 4.89 (s, 2H), 4.00 (q, J=7.2 Hz, 2H), 2.22 (s, 3H), 1.41 (t, J=7.2 Hz, 3H); m/z (ESI+) for (C$_{13}$H$_{17}$N$_2$O), 217.1 (M+H)$^+$ observed.

Step 2: Synthesis of 2-(4-(benzyloxy)-1-ethyl-3-methyl-1H-pyrazol-5-yl)-4-bromo-5-(((tert-butyldimethylsilyl)oxy)methyl)thiazole (X-2)

To a solution of 4-(benzyloxy)-1-ethyl-3-methyl-1H-pyrazole (X-1) (1.03 g, 4.76 mmol) in THF (20 mL) at −78° C. was added n-BuLi (2.5 M in hexane, 1.90 mL, 4.76 mmol) dropwise, and the mixture was stirred for 10 minutes. A solution of ZnCl$_2$ (1.9 M in 2-MeTHF, 3.01 mL, 5.71 mmol) was then added dropwise, and the reaction was warmed to room temperature. After 1.5 hours, a solution of 2,4-dibromo-5-(((tert-butyldimethylsilyl)oxy)methyl)thiazole (prepared in 3 steps according to WO 2010132999 A1) (2.03 g, 5.24 mmol) in THF (3.8 mL mL) was added, followed by addition of Pd(PPh$_3$)$_4$ (550 mg, 0.476 mmol). The reaction was stirred at room temperature for 3 hours, and LCMS analysis showed consumption of starting material. The reaction was then quenched with saturated aqueous NH$_4$Cl, the layers were separated, and the aqueous phase was extracted three times with EtOAc. The combined organic extract was dried over MgSO$_4$, filtered, and concentrated in vacuo. The residue was purified by flash chromatography (40 g SiO$_2$, 0-20% EtOAc/heptanes) to provide 2-(4-(benzyloxy)-1-ethyl-3-methyl-1H-pyrazol-5-yl)-4-bromo-5-(((tert-butyldimethylsilyl)oxy)methyl)thiazole (X-2) (951 mg, 38%) as a white solid. $^1$H NMR (400 MHz, CDCl$_3$) δ 7.36-7.22 (m, 5H), 4.84 (s, 2H), 4.73 (s, 2H), 4.50 (q, J=7.3 Hz, 2H), 2.11 (s, 3H), 1.31 (t, J=7.2 Hz, 3H), 0.82 (s, 9H), 0.02 (s, 6H); m/z (ESI+) for (C$_{23}$H$_{33}$BrN$_3$O$_2$SSi), 522.1 (M+H)$^+$ observed.

Step 3: Synthesis of 4-(2-(4-(benzyloxy)-1-ethyl-3-methyl-1H-pyrazol-5-yl)-5-(((tert-butyldimethylsilyl)oxy)methyl)thiazol-4-yl)-N-(2,4-dimethoxybenzyl)-1-methyl-1H-pyrazolo[4,3-c]pyridine-6-carboxamide (X-3)

A mixture of 2-(4-(benzyloxy)-1-ethyl-3-methyl-1H-pyrazol-5-yl)-4-bromo-5-(((tert-butyldimethylsilyl)oxy)methyl)thiazole (X-2) (944 mg, 1.81 mmol), 4-bromo-N-(2,4-dimethoxybenzyl)-1-methyl-1H-pyrazolo[4,3-c]pyridine-6-carboxamide (Int-HG-17) (732 mg, 1.81 mmol), K$_3$PO$_4$ (1.15 g, 5.42 mmol), 4,4,4',4',5,5,5',5'-octamethyl-2,2'-bi(1,3,2-dioxaborolane) (917 mg, 3.61 mmol), (t-Bu)$_3$P—Pd-G3 (103 mg, 0.181 mmol), H$_2$O (3.62 mL, sparged with N$_2$), and toluene (18.1 mL, sparged with N$_2$) was stirred at 80° C. for 23 hours. TLC analysis (4:1 heptanes:EtOAc) showed consumption of the starting material. The mixture was then cooled to room temperature, filtered through a Celite pad with EtOAc, dried over MgSO$_4$, filtered, and concentrated in vacuo. The residue was purified by flash chromatography (40 g SiO$_2$, 60-80% EtOAc:heptanes) to provide a mixture of the desired product 4-(2-(4-(benzyloxy)-1-ethyl-3-methyl-1H-pyrazol-5-yl)-5-(((tert-butyldimethylsilyl)oxy)methyl)thiazol-4-yl)-N-(2,4-dimethoxybenzyl)-1-methyl-1H-pyrazolo[4,3-c]pyridine-6-carboxamide (X-3) (825 mg) and byproduct N-(2,4-dimethoxybenzyl)-1-methyl-1H-pyrazolo[4,3-c]pyridine-6-carboxamide (1:1.4 by $^1$H NMR analysis). This mixture was used in the next step without further purification. m/z (ESI+) for (C$_{40}$H$_{50}$N$_7$O$_5$SSi), 768.4 (M+H)$^+$ observed.

Step 4: Synthesis of 4-(2-(4-(benzyloxy)-1-ethyl-3-methyl-1H-pyrazol-5-yl)-5-(hydroxymethyl)thiazol-4-yl)-N-(2,4-dimethoxybenzyl)-1-methyl-1H-pyrazolo[4,3-c]pyridine-6-carboxamide (X-4)

To a solution of a 1:1.4 mixture of 4-(2-(4-(benzyloxy)-1-ethyl-3-methyl-1H-pyrazol-5-yl)-5-(((tert-butyldimethylsilyl)oxy)methyl)thiazol-4-yl)-N-(2,4-dimethoxybenzyl)-1-methyl-1H-pyrazolo[4,3-c]pyridine-6-carboxamide (X-3) and byproduct N-(2,4-dimethoxybenzyl)-1-methyl-1H-pyrazolo[4,3-c]pyridine-6-carboxamide (825 mg) in THF (2.15 mL) was added TBAF (1 M in THF, 3.22 mL, 3.22 mmol) and stirred at room temperature. After 2 hours, an aliquot was analyzed by $^1$H NMR in CDCl$_3$ and showed consumption of the starting material. The reaction was then diluted in CH$_2$Cl$_2$ and concentrated in vacuo. The residue was purified by flash chromatography (24 g SiO$_2$, 40-100% EtOAc/heptanes) to provide 4-(2-(4-(benzyloxy)-1-ethyl-3-methyl-1H-pyrazol-5-yl)-5-(hydroxymethyl)thiazol-4-yl)-N-(2,4-dimethoxybenzyl)-1-methyl-1H-pyrazolo[4,3-c]pyridine-6-carboxamide (X-4) (363 mg, 31% over two steps) as a white solid. $^1$H NMR (400 MHz, CDCl$_3$) b 8.75 (s, 1H), 8.74 (m, 1H), 8.25 (s, 1H), 7.49-7.29 (m, 6H), 6.50-6.41 (m, 2H), 5.17 (s, 2H), 5.00 (s, 2H), 4.74 (q, J=7.0 Hz, 2H), 4.65 (m, 2H), 4.17-4.11 (m, 4H), 3.90 (s, 3H), 3.78 (s, 3H), 2.23 (s, 3H), 1.50 (t, J=7.0 Hz, 3H); m/z (ESI+) for (C$_{34}$H$_{36}$N$_7$O$_5$S), 654.3 (M+H)$^+$ observed.

Step 5: Synthesis of 4-(2-(4-(benzyloxy)-1-ethyl-3-methyl-1H-pyrazol-5-yl)-5-formylthiazol-4-yl)-N-(2,4-dimethoxybenzyl)-1-methyl-1H-pyrazolo[4,3-c]pyridine-6-carboxamide (X-5)

To a solution of 4-(2-(4-(benzyloxy)-1-ethyl-3-methyl-1H-pyrazol-5-yl)-5-(hydroxymethyl)thiazol-4-yl)-N-(2,4-dimethoxybenzyl)-1-methyl-1H-pyrazolo[4,3-c]pyridine-6-carboxamide (X-4) (313 mg, 0.479 mmol) in CH$_2$Cl$_2$ (2.39 mL) at 0° C. was added Dess-Martin periodinane (305 mg, 0.718 mmol). The mixture was then warmed to room temperature and stirred for 1 hour. LCMS analysis showed consumption of the starting material. The reaction was then diluted with $CH_2Cl_2$ and concentrated in vacuo. The residue was purified by flash chromatography (12 g $SiO_2$, 50-100% EtOAc/heptanes) to provide 4-(2-(4-(benzyloxy)-1-ethyl-3-methyl-1H-pyrazol-5-yl)-5-formylthiazol-4-yl)-N-(2,4-dimethoxybenzyl)-1-methyl-1H-pyrazolo[4,3-c]pyridine-6-carboxamide (X-5) (302 mg, 84% between two combined batches) as a yellow solid. $^1$H NMR (400 MHz, $CDCl_3$) 10.78 (s, 1H), 8.63 (s, 1H), 8.43 (s, 1H), 7.50-7.25 (m, 6H), 6.52 (d, J=2.3 Hz, 1H), 6.45 (dd, J=8.2, 2.3 Hz, 1H), 5.09 (s, 2H), 4.77 (q, J=7.3 Hz, 2H), 4.66 (d, J=5.9 Hz, 2H), 4.21 (s, 3H), 3.91 (s, 3H), 3.80 (s, 3H), 2.26 (s, 3H), 1.48 (t, J=7.4 Hz, 3H); m/z (ESI+) for ($C_{34}H_{34}N_7O_5S$), 652.3 (M+H)$^+$ observed.

Step 6: Synthesis of (E)-4-(2-(4-(benzyloxy)-1-ethyl-3-methyl-1H-pyrazol-5-yl)-5-(((tert-butylsulfinyl)imino)methyl)thiazol-4-yl)-N-(2,4-dimethoxybenzyl)-1-methyl-1H-pyrazolo[4,3-c]pyridine-6-carboxamide (X-6)

A mixture of 4-(2-(4-(benzyloxy)-1-ethyl-3-methyl-1H-pyrazol-5-yl)-5-formylthiazol-4-yl)-N-(2,4-dimethoxybenzyl)-1-methyl-1H-pyrazolo[4,3-c]pyridine-6-carboxamide (X-5) (302 mg, 0.463 mmol), $Cs_2CO_3$ (302 mg, 0.927 mmol), 2-methylpropane-2-sulfinamide (168 mg, 1.39 mmol), and $CH_2Cl_2$ (2.32 mL) was stirred at room temperature for 19 hours. LCMS analysis showed consumption of the starting material. The mixture was then filtered through a Celite pad with EtOAc and concentrated in vacuo to provide (E)-4-(2-(4-(benzyloxy)-1-ethyl-3-methyl-1H-pyrazol-5-yl)-5-(((tert-butylsulfinyl)imino)methyl)thiazol-4-yl)-N-(2,4-dimethoxybenzyl)-1-methyl-1H-pyrazolo[4,3-c]pyridine-6-carboxamide (X-6) (558 mg) as a yellow solid. This material was used in the next step without further purification. m/z (ESI+) for ($C_{38}H_{43}N_8O_5S_2$), 755.3 (M+H)$^+$ observed.

Step 7: Synthesis of 4-(2-(4-(benzyloxy)-1-ethyl-3-methyl-1H-pyrazol-5-yl)-5-(((tert-butylsulfinyl) amino)methyl)thiazol-4-yl)-N-(2,4-dimethoxybenzyl)-1-methyl-1H-pyrazolo[4,3-c]pyridine-6-carboxamide (X-7)

To a solution of (E)-4-(2-(4-(benzyloxy)-1-ethyl-3-methyl-1H-pyrazol-5-yl)-5-(((tert-butylsulfinyl)imino)methyl)thiazol-4-yl)-N-(2,4-dimethoxybenzyl)-1-methyl-1H-pyrazolo[4,3-c]pyridine-6-carboxamide (X-6) (208 mg, 0.276 mmol) in methanol (1.38 mL) and THF (1.38 mL) at 0° C. was added $NaBH_4$ (31.3 mg, 0.827 mmol). After 3 hours, LCMS analysis showed consumption of the starting material. The reaction was quenched with saturated aqueous $NH_4Cl$ and extracted three times with EtOAc. The combined organic extract was then dried over $MgSO_4$, filtered, and concentrated in vacuo. The residue was purified by flash chromatography (24 g $SiO_2$, 50-100% EtOAc/heptanes) to provide 4-(2-(4-(benzyloxy)-1-ethyl-3-methyl-1H-pyrazol-5-yl)-5-(((tert-butylsulfinyl)amino)methyl)thiazol-4-yl)-N-(2,4-dimethoxybenzyl)-1-methyl-1H-pyrazolo[4,3-c]pyridine-6-carboxamide (X-7) (193 mg, 92%) as a yellow oil. $^1$H NMR (400 MHz, $CDCl_3$) δ 8.68 (s, 1H), 8.44 (t, J=5.8 Hz, 1H), 8.30 (s, 1H), 7.49-7.25 (m, 6H), 6.48-6.42 (m, 2H), 5.05-4.95 (m, 4H), 4.74 (q, J=7.3 Hz, 2H), 4.68 (d, J=6.2 Hz, 2H), 4.21 (t, J=5.6 Hz, 1H), 4.15 (s, 3H), 3.87 (s, 3H), 3.77 (s, 3H), 2.24 (s, 3H), 1.49 (t, J=7.2 Hz, 3H), 1.13 (s, 9H); m/z (ESI+) for ($C_{38}H_{45}N_8O_5S_2$), 757.3 (M+H)$^+$ observed.

Step 8: Synthesis of (4-(6-carbamoyl-1-methyl-1H-pyrazolo[4,3-c]pyridin-4-yl)-2-(1-ethyl-4-hydroxy-3-methyl-1H-pyrazol-5-yl)thiazol-5-yl)methanaminium formate (Example X01)

To a solution of 4-(2-(4-(benzyloxy)-1-ethyl-3-methyl-1H-pyrazol-5-yl)-5-(((tert-butylsulfinyl)amino)methyl)thiazol-4-yl)-N-(2,4-dimethoxybenzyl)-1-methyl-1H-pyrazolo[4,3-c]pyridine-6-carboxamide (X-7) (315 mg, 0.416 mmol) in MeOH (2.08 mL) and $CH_2Cl_2$ (2.08 mL) was added HCl (4 M in dioxane, 1.04 mL, 4.16 mmol) and stirred at room temperature. After 45 minutes, the reaction mixture was concentrated in vacuo, dissolved in TFA (3.20 mL, 41.6 mmol), and heated at 55° C. for 27 hours. LCMS analysis showed consumption of the starting material. The mixture was then allowed to cool to room temperature, concentrated in vacuo, and the residue was slurried in EtOAc for 16 hours. The solid was then filtered under $N_2$. The solid was purified by preparative HPLC with Princeton STX C18 column (250×21.2 mm, 5 μm partial size), which was eluted with 5-100% Acetonitrile:$H_2O$ (1% formic acid) with a flow rate of 27 mL/min to provide (4-(6-carbamoyl-1-methyl-1H-pyrazolo[4,3-c]pyridin-4-yl)-2-(1-ethyl-4-hydroxy-3-methyl-1H-pyrazol-5-yl)thiazol-5-yl)methanaminium formate (Example X01) (86 mg, 45%) as a white solid. $^1$H NMR (400 MHz, DMSO-$d_6$) δ 8.63 (s, 1H), 8.37 (s, 1H), 8.22 (s, 1H), 8.12 (s, 1H), 7.93 (s, 1H), 4.68 (q, J=7.4 Hz, 2H), 4.56 (s, 2H), 4.19 (s, 3H), 2.17 (s, 3H), 1.36 (t, J=7.0 Hz, 3H); m/z (ESI+) for ($C_{18}H_{21}N_8O_2S$), 413.2 (M+H)$^+$ observed.

Example Y01: Preparation of 4-[3-(1-ethyl-4-fluoro-3-methyl-1H-pyrazol-5-yl)-1-methyl-1H-1,2,4-triazol-5-yl]-1-[3-hydroxy-2-(hydroxymethyl)propyl]-1H-pyrazolo[4,3-c]pyridine-6-carboxamide According to Scheme Y Scheme Y

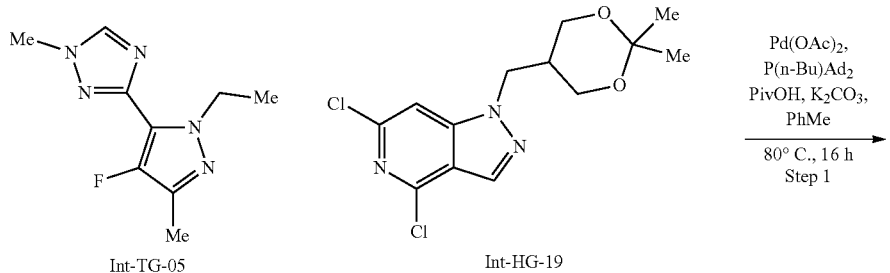

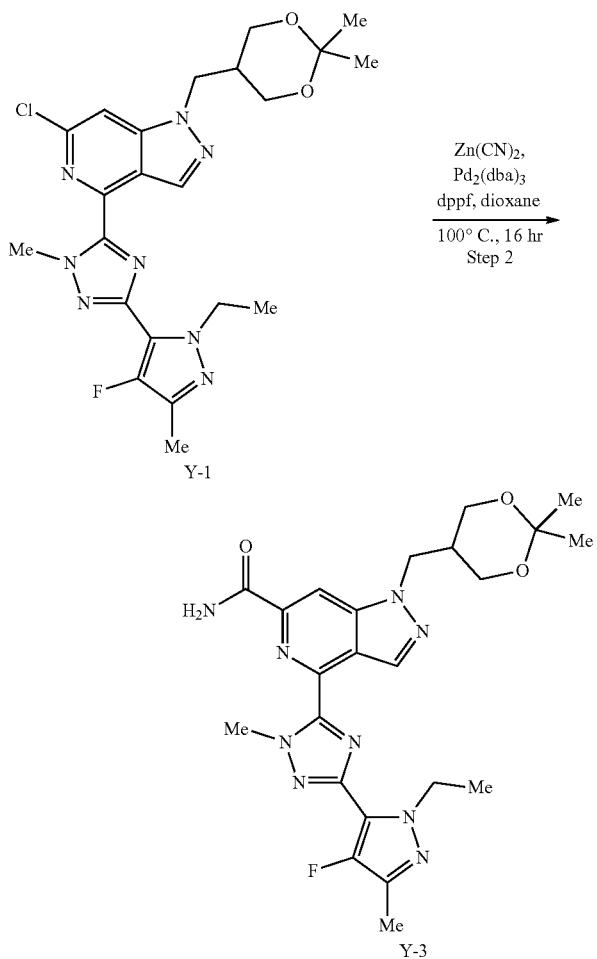

Y-1

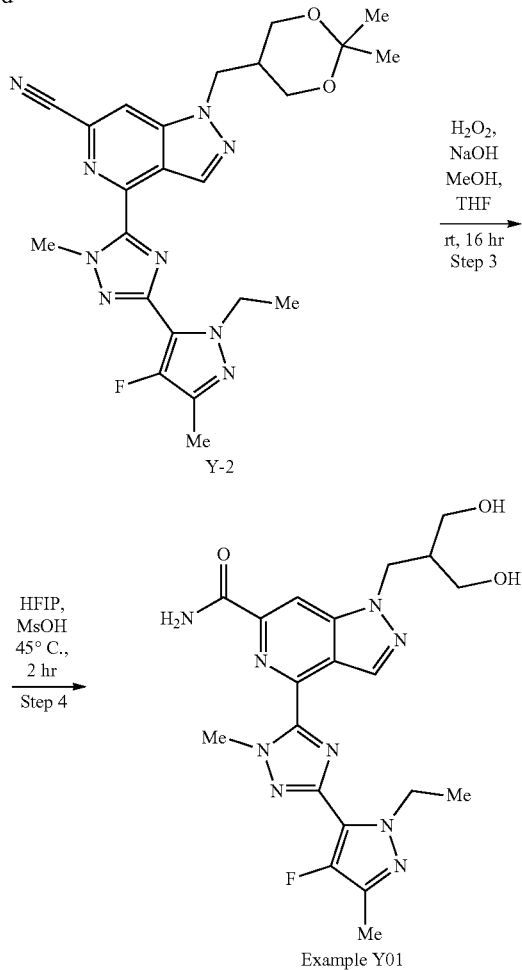

Y-2

Y-3

Example Y01

Step 1: Synthesis of 6-chloro-1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine (Y-1)

To a solution of 3-(1-ethyl-4-fluoro-3-methyl-1H-pyrazol-5-yl)-1-methyl-1H-1,2,4-triazole (Int-TG-05) (430 mg 2.06 mmol, 1 eq) and 4,6-dichloro-1-[(2,2-dimethyl-1,3-dioxan-5-yl)methyl]-1H-pyrazolo[4,3-c]pyridine (Int-HG-19) (650 mg 2.06 mmol, 1 eq) in anhydrous toluene (10 mL, 0.2 M) was added $K_2CO_3$ (852 mg, 6.17 mmol, 3 eq), PivOH (126 mg, 1.23 mmol, 0.6 eq), P(n-Bu)Ad$_2$ (295 mg, 0.822 mmol, 0.4 eq) and Pd(OAc)$_2$ (92.3 mg, 0.411 mmol, 0.2 eq) at room temperature. The mixture was stirred at 80° C. under $N_2$ for 60 hr. TLC at this time (petroleum ether:EtOAc=1:2) showed that starting material was consumed, and 2 new spots were detected, the less polar of the two proving to be the desired product. The brown mixture was cooled to room temperature and filtered, then the filtrate was concentrated in vacuo. The resulting black residue was purified by Prep-TLC (Petroleum ether:EtOAc 1:2) to afford the title compound 6-chloro-1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine (Y-1) (200 mg, 19.9%) as a yellow solid. $^1$H NMR (400 MHz, Chloroform-d) δ 8.88 (d, J=1.0 Hz, 1H), 7.52 (d, J=1.0 Hz, 1H), 4.66 (d, J=7.7 Hz, 2H), 4.61 (t, J=7.2 Hz, 1H), 4.54 (s, 3H), 4.09 (q, 2H, J=7.1 Hz), 3.53 (dd, J=12.6, 2.5 Hz, 2H), 2.31 (d, J=0.7 Hz, 3H), 2.25 (dq, J=6.6, 3.3 Hz, 1H), 1.58 (s, 3H), 1.52 (s, 3H), 1.50 (t, J=7.1 Hz, 1H).

Step 2: Synthesis of 1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carbonitrile (Y-2)

To a yellow solution of 6-chloro-1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine (Y-1) (70 mg, 0.14 mmol) in dioxane (5.0 mL, 0.03 M) were added Zn(CN)$_2$ (87.4 mg, 0.744 mmol, 5 eq), dppf (139 mg, 0.251 mmol, 1.7 eq) and Pd$_2$(dba) (50.1 mg, 0.055 mmol, 0.4 eq) at room temperature. The resulting yellow reaction mixture was stirred at 100° C. under $N_2$ for 16 h. LCMS at this time showed that the starting material was almost consumed, and the desired product was present. The light brown solution was then diluted with 20 mL water, then extracted thrice with 50 mL EtOAc. The combined organics were dried over $Na_2SO_4$, filtered, and concentrated under reduced pressure. The resultant yellow oil was purified via preparative TLC (15:1 DCM/MeOH) to afford the title compound 1-[(2,2-dimethyl-1,3-dioxan-5-yl)methyl]-4-[3-(1-ethyl-4-fluoro-3-methyl-1H-pyrazol-5-yl)-1-methyl- 1H-1,2,4-triazol-5-yl]-1H-pyrazolo[4,3-c]pyridine-6-carbonitrile (Y-2) (45 mg, 92%) as a light-yellow solid.

Step 3: Synthesis of 1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carboxamide (Y-3)

To a yellow solution of 1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carbonitrile (Y-2) (90 mg, 0.12 mmol) in MeOH (2 mL) and THF (1 mL, 0.04 M in substrate overall) were added $H_2O_2$ (136 mg, 1.20 mmol, 10 eq) and NaOH (24.0 mg, 0.6 mmol, 5 eq), and the resulting yellow suspension was stirred at room temperature for 16 h. LCMS analysis at this point showed the starting material was consumed, in addition to detecting the desired product. TLC (DCM:MeOH=10:1) also showed that the starting material was consumed, and 2 new spots, one more polar than starting material and one less so, were noted. The white suspension was then quenched with saturated aq. $Na_2SO_3$ (2 mL) and extracted four times with 20 mL EtOAc. The combined organic phase was dried over anhydrous $Na_2SO_4$, filtered, and this filtrate was concentrated in vacuo to give the desired crude 1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carboxamide (Y-3) as a white solid, which was used directly in the next step.

Step 4: Synthesis of 4-[3-(1-ethyl-4-fluoro-3-methyl-1H-pyrazol-5-yl)-1-methyl-1H-1,2,4-triazol-5-yl]-1-[3-hydroxy-2-(hydroxymethyl)propyl]-1H-pyrazolo[4,3-c]pyridine-6-carboxamide (Example Y01)

To a solution of the 1-[(2,2-dimethyl-1,3-dioxan-5-yl)methyl]-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carboxamide (Y-3) acetal (60 mg, 0.12 mmol) in HFIP (1 mL, 0.12 M) was added MsOH (58 mg, 0.6 mmol, 5 eq).

The mixture was heated at 45° C. for 2 hours. LCMS at this time showed consumption of starting material in conjunction with product formation. The mixture was thus concentrated to give a brown oil, which was purified via preparative HPLC to give the desired product 4-[3-(1-ethyl-4-fluoro-3-methyl-1H-pyrazol-5-yl)-1-methyl-1H-1,2,4-triazol-5-yl]-1-[3-hydroxy-2-(hydroxymethyl)propyl]-1H-pyrazolo[4,3-c]pyridine-6-carboxamide (Example Y01) (9.7 mg, 18%) as a solid. $^1$H NMR (400 MHz, DMSO-d6) δ 8.72 (d, J=1.0 Hz, 1H), 8.48 (d, J=1.0 Hz, 1H), 8.00 (d, J=47.6 Hz, 2H), 4.69 (t, J=5.0 Hz, 2H), 4.58 (d, J=7.0 Hz, 2H), 4.53 (q, J=7.1 Hz, 2H), 4.47 (s, 3H), 3.38 (m, 6H), 2.21 (s, 3H), 1.39 (t, J=7.1 Hz, 3H).

Example Z01: Preparation of 4-{3-[1-(3-hydroxypropyl)-3-methyl-1H-pyrazol-5-yl]-1H-1,2,4-triazol-5-yl}-1-methyl-1H-pyrazolo[4,3-c]pyridine-6-carboxamide According to Scheme Z Scheme Z

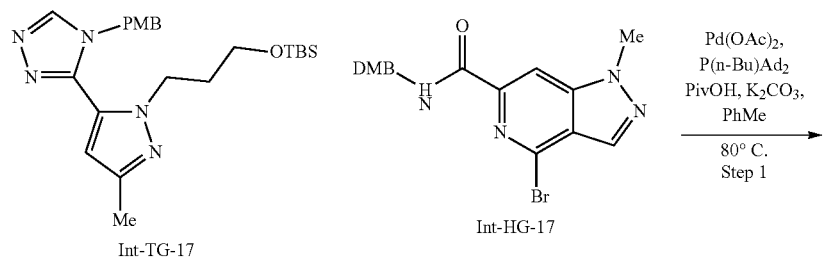

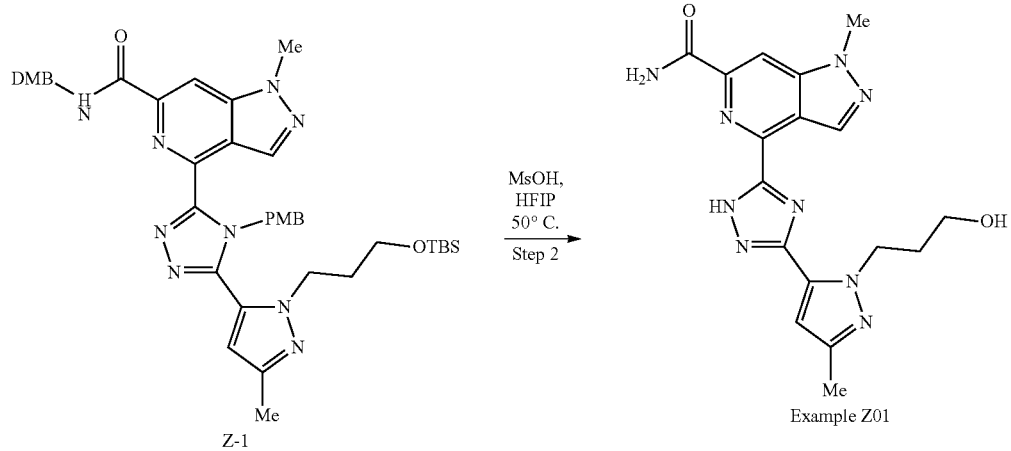

Step 1: Synthesis of 4-{5-[1-(3-{[tert-butyl(dimethyl)silyl]oxy}propyl)-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (Z-1)

To a solution of 3-[1-(3-{[tert-butyl(dimethyl)silyl]oxy}propyl)-3-methyl-1H-pyrazol-5-yl]-4-[(4-methoxyphenyl)methyl]-4H-1,2,4-triazole (Int-TG-17) (275.0 mg, 0.623 mmol) and 4-bromo-N-[(2,4-dimethoxyphenyl)methyl]-1-methyl-1H-pyrazolo[4,3-c]pyridine-6-carboxamide (Int-HG-17) (303 mg, 0.747 mmol) in anhydrous toluene (4.0 mL) was added $K_2CO_3$ (258 mg, 1.87 mmol), PivOH (38.2 mg, 0.374 mmol), $P(n-Bu)Ad_2$ (89.3 mg, 0.249 mmol) and $Pd(OAc)_2$ (28.0 mg, 0.125 mmol) at 20° C. The mixture was stirred at 80° C. in $N_2$ for 16 h. Stirring was continued at 80° C. for an additional 48 h. LCMS analysis showed the starting material was still not consumed, however the desired product was detected. This reaction was combined with another batch performed on the same scale under similar conditions and these were further processed together. The combined reactions were quenched with $H_2O$ (50 mL) giving a light yellow solution. The solution was transferred to a separatory funnel and extracted with EtOAc (50 mL*3). The combined organic extracts were washed with brine (50 mL), dried ($Na_2SO_4$), and concentrated under vacuum to furnish a light yellow solid. The crude solid was further purified by flash chromatography (EtOAc in petroleum ether from 0 to 80% on 40 g silica gel) to afford the title compound 4-{5-[1-(3-{[tert-butyl(dimethyl)silyl]oxy}propyl)-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (Z-1) (250 mg, 52%) as a light yellow solid. m/z (ESI+) for ($C_{40}H_{52}N_9O_5Si$), 766.2 (M+H)$^+$ observed.

Step 2: Synthesis of 4-{3-[1-(3-hydroxypropyl)-3-methyl-1H-pyrazol-5-yl]-1H-1,2,4-triazol-5-yl}-1-methyl-1H-pyrazolo[4,3-c]pyridine-6-carboxamide (Example Z01)

To a yellow solution of 4-{5-[1-(3-{[tert-butyl(dimethyl)silyl]oxy}propyl)-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (Z-1) (250 mg, 0.326 mmol) in HFIP (4.0 mL) was added $MeSO_3H$ (314 mg, 3.26 mmol). After the addition, the resulting light red reaction solution was stirred at 50° C. for 16 h. The reaction was concentrated to give a red oil which was purified via Prep-HPLC (Boston Prime C18 150*25 mm*5 um, water (0.05% ammonia hydroxide v/v)-MeCN (11%-35% gradient), 25 mL/min). Product containing fractions were collected to afford the title compound 4-{3-[1-(3-hydroxypropyl)-3-methyl-1H-pyrazol-5-yl]-1H-1,2,4-triazol-5-yl}-1-methyl-1H-pyrazolo[4,3-c]pyridine-6-carboxamide (Example Z01) (86.4 mg, 69%) as a white solid. m/z (ESI+) for ($C_{17}H_{20}N_9O_2$), 382.0 (M+H)$^+$ observed. $^1$H NMR (400 MHz, DMSO-d6) δ=15.33 (s, 1H), 8.86 (s, 1H), 8.84 (br s, 1H), 8.45 (s, 1H), 7.85 (br s, 1H), 6.70 (s, 1H), 4.70 (br t, J=7.3 Hz, 2H), 4.58 (br t, J=4.9 Hz, 1H), 4.22 (s, 3H), 3.53-3.45 (m, 2H), 2.23 (s, 3H), 2.05-1.95 (m, 2H).

Example AA01: Preparation of 4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide According to Scheme AA Scheme AA

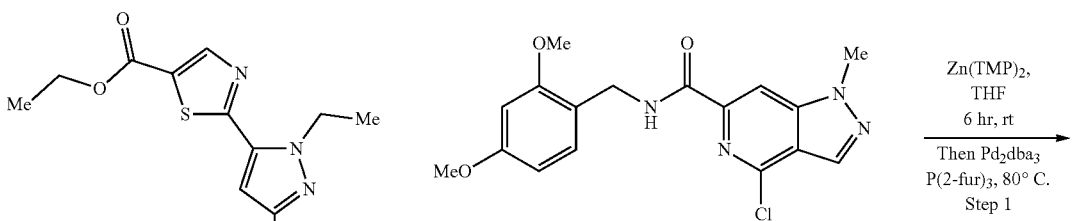

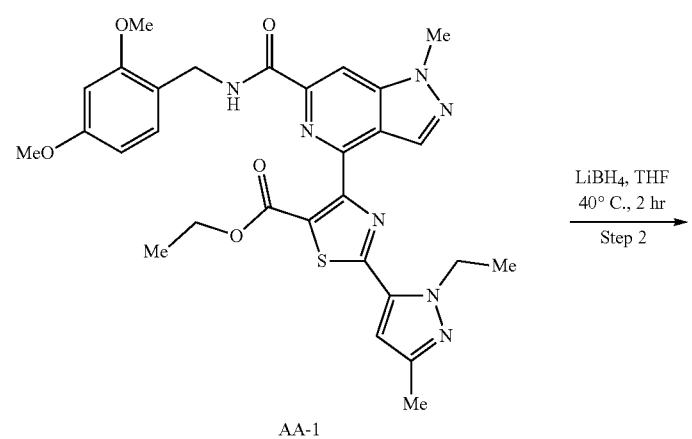

AA-1

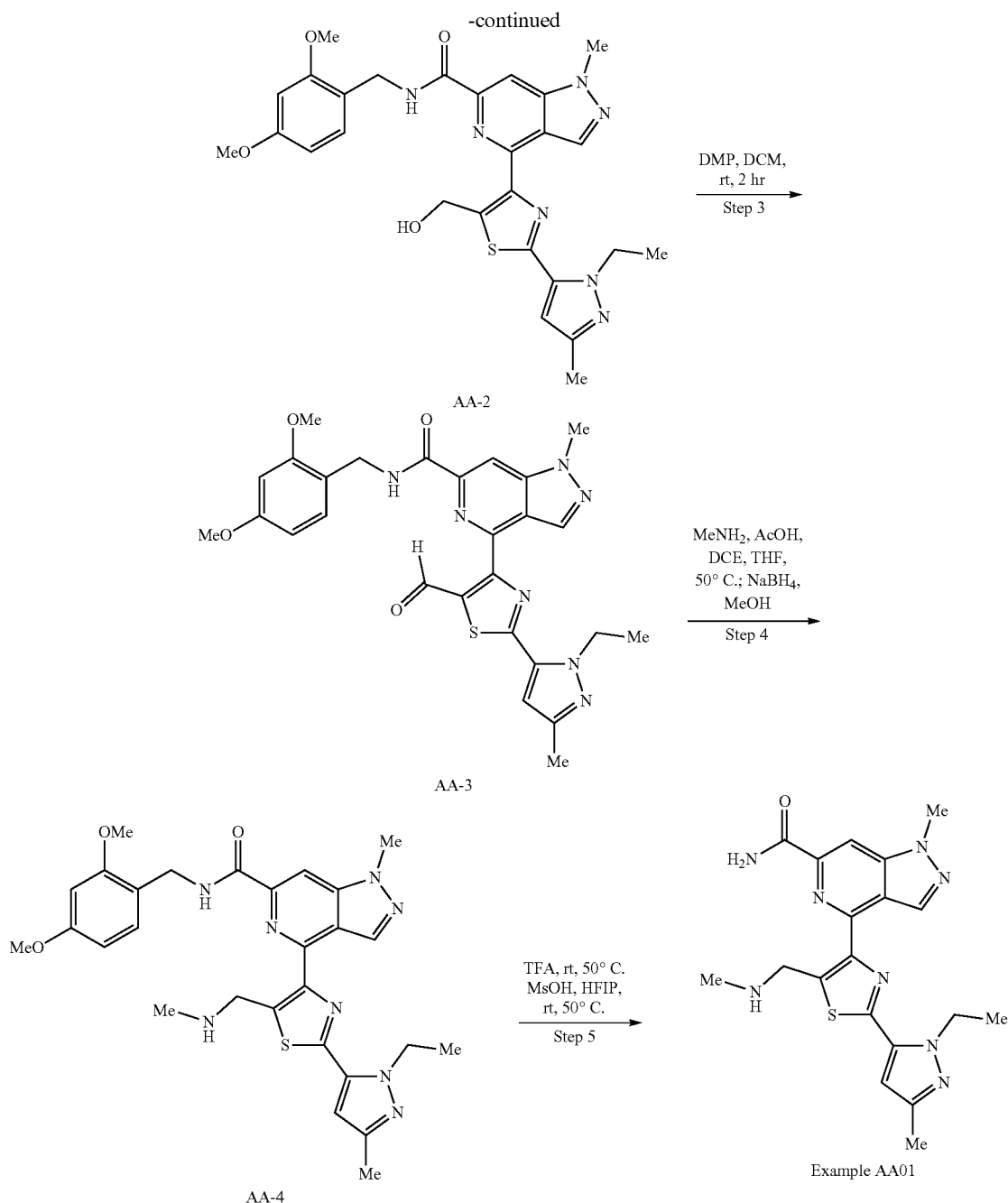

Step 1: Synthesis of Ethyl 4-(6-[(2,4-dimeth oxy-phenyl)methyl]carbamoyl-1-methyl-1H-pyrazolo[4,3-c]pyridin-4-yl)-2-(1-ethyl-3-methyl-11H-pyrazol-5-yl)-1,3-thiazole-5-carboxylate (AA-1)

A dried 25-mL flask was charged first with a solution of ethyl 2-(1-ethyl-3-methyl-1H-pyrazol-5-yl)-1,3-thiazole-5-carboxylate (nt-TG-19) (250 mg, 0.942 mmol) in THF (0.94 mL, 0.1 M), and to this was added Zn(TMP)$_2$ (0.35 Min THF, 3.23 mL, 1.13 mmol, 1.2 eq), producing a red solution. After 6 hr at room temperature, 4-chloro-N-[(2,4-dimethoxyphenyl)methyl]-1-methyl-1H-pyrazolo[4,3-c]pyridine-6-carboxamide (Int-HG-20) (340 mg, 0.942 mmol, 1 eq) was added, followed by Pd$_2$(dba)$_3$ (43 mg, 0.05 mmol, 0.05 eq) and P(2-fur)$_3$ (22 mg, 0.094 mmol, 0.1 eq). The solution was heated to 70° C., after 20 min, LCMS analysis showed only starting material present. This reaction was then heated instead to 80° C. and allowed to stir at this temperature overnight. After 18 hr, LCMS analysis showed a new peak with the desired product mass had formed and solvent had largely evaporated leaving a tar-like residue. This residue was dissolved in EtOAc and stirred with sat. aqueous NH$_4$Cl until all solids had been dissolved. The biphasic mixture was then transferred to a separatory funnel and the phases separated. The organic phase was washed with 1 portion brine, dried (Na$_2$SO$_4$), filtered, and concentrated under vacuum. Purification via column chromatography (SiO$_2$, 95% EtOAc/heptane) afforded the title compound ethyl 4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-thiazole-5-carboxylate (AA-1) (120 mg, 0.204 mmol, 22%) as an orange solid. $^1$H NMR (400 MHz, Chloroform-d) δ 8.47 (t, J=6.0 Hz, 1H), 8.42 (d, J=1.0 Hz, 1H), 8.34 (d, J=1.0 Hz, 1H), 7.28 (d, J=8.2 Hz, 1H), 6.55 (s, 1H), 6.47 (d, J=2.3 Hz, 1H), 6.43 (dd, J=8.2, 2.4 Hz, 1H), 4.68 (q, J=7.2 Hz, 2H), 4.64 (d, J=6.1 Hz, 2H), 4.17 (s, 3H), 4.00 (q, J=7.1 Hz, 2H), 3.84 (s, 3H), 3.78 (s, 3H), 2.31 (s, 3H), 1.46 (t, J=7.2 Hz, 3H), 1.03 (t, J=7.1 Hz, 3H).

Step 2: Synthesis of N-[(2,4-dimethoxyphenyl)methyl]-4-[2-(1-ethyl-3-methyl-1H-pyrazol-5-yl)-5-(hydroxymethyl)-1,3-thiazol-4-yl]-1-methyl-1H-pyrazolo[4,3-c]pyridine-6-carboxamide (AA-2)

To a 2-dram vial containing ethyl 4-(6-{[(2,4-dimethoxyphenyl)methyl]carbamoyl}-1-methyl-1H-pyrazolo[4,3-c]pyridin-4-yl)-2-(1-ethyl-3-methyl-1H-pyrazol-5-yl)-1,3-thiazole-5-carboxylate (AA-1) (100 mg, 0.17 mmol) in THF (0.85 mL, 0.2 M) was added LiBH$_4$ (7.4 mg, 0.34 mmol, 2 eq). The resulting white suspension was heated to 40° C. which led to formation of a dark homogeneous solution. After 2 hr, LCMS analysis showed disappearance of starting material and a new peak with the desired product mass. The reaction was removed from heating and allowed to cool gradually to room temperature. The reaction was quenched with MeOH (1 mL). The reaction mixture then turned a light yellow, then orange, followed by precipitate formation. After stirring for 4 hr, the white solid was filtered off and dried to afford the title compound N-[(2,4-dimethoxyphenyl)methyl]-4-[2-(1-ethyl-3-methyl-1H-pyrazol-5-yl)-5-(hydroxymethyl)-1,3-thiazol-4-yl]-1-methyl-1H-pyrazolo[4,3-c]pyridine-6-carboxamide (AA-2) (60 mg, 0.11 mmol, 65%). $^1$H NMR (400 MHz, DMSO-d6) δ 8.69 (t, J=6.2 Hz, 1H), 8.68 (d, J=1.0 Hz, 1H), 8.32 (d, J=1.0 Hz, 1H), 7.19 (d, J=8.3 Hz, 1H), 6.71 (s, 1H), 6.60 (d, J=2.4 Hz, 1H), 6.49 (dd, J=8.3, 2.4 Hz, 1H), 6.28 (t, J=5.8 Hz, 1H), 5.28 (d, J=5.7 Hz, 2H), 4.67 (q, J=7.1 Hz, 2H), 4.52 (d, J=6.2 Hz, 2H), 4.19 (s, 3H), 3.89 (s, 3H), 3.74 (s, 3H), 2.23 (s, 3H), 1.42 (t, J=7.1 Hz, 3H).

Step 3: Synthesis of N-[(2,4-dimethoxyphenyl)methyl]-4-[2-(1-ethyl-3-methyl-1H-pyrazol-5-yl)-5-formyl-1,3-thiazol-4-yl]-1-methyl-1H-pyrazolo[4,3-c]pyridine-6-carboxamide (AA-3)

To a 2-dram vial containing the N-[(2,4-dimethoxyphenyl)methyl]-4-[2-(1-ethyl-3-methyl-1H-pyrazol-5-yl)-5-(hydroxymethyl)-1,3-thiazol-4-yl]-1-methyl-1H-pyrazolo[4,3-c]pyridine-6-carboxamide (AA-2) (30 mg, 0.055 mmol) was added DCM (0.274 mL, 0.2 M) followed by Dess-Martin periodinane (47 mg, 0.11 mmol, 2 eq). The reaction was stirred at rt for 2 hr. LCMS analysis showed full conversion to a new peak with the desired product mass. The reaction mixture was then diluted with DCM and transferred to a separatory funnel. The organic phase was washed with 1 portion sat. aqueous NaHCO$_3$, dried (Na$_2$SO$_4$), filtered, and concentrated under vacuum to afford the title compound N-[(2,4-dimethoxyphenyl)methyl]-4-[2-(1-ethyl-3-methyl-1H-pyrazol-5-yl)-5-formyl-1,3-thiazol-4-yl]-1-methyl-1H-pyrazolo[4,3-c]pyridine-6-carboxamide (AA-3) as a white solid which was used in the next step without further purification.

Step 4: Synthesis of N-[(2,4-dimethoxyphenyl)methyl]-4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide (AA-4)

To a 2-dram vial containing the N-[(2,4-dimethoxyphenyl)methyl]-4-[2-(1-ethyl-3-methyl-1H-pyrazol-5-yl)-5-formyl-1,3-thiazol-4-yl]-1-methyl-1H-pyrazolo[4,3-c]pyridine-6-carboxamide (AA-3) (30 mg, 0.055 mmol) dissolved in DCE (0.275 mL, 0.2 M) was added MeNH$_2$ (17 mg, 0.55 mmol, 10 eq) and AcOH (9.91 mg, 0.165 mmol, 3 eq) as a combined solution in THF (0.275 mL). This reaction was heated at 40° C. for 20 min during which time a white precipitate formed. The vial was charged with 300 μL DCE heated to 50° C. and stirred for 1.5 h. LCMS analysis showed formation of a new peak with the desired mass of the imine. At this stage, the reaction was concentrated under vacuum and the residue suspended in MeOH (0.275 mL, 0.2 mL). To the solution was added NaBH$_4$ (3.12 mg, 0.0825 mmol, 1.5 eq). The reaction was stirred at rt for 1.5 h. The solution was then concentrated to afford the title compound N-[(2,4-dimethoxyphenyl)methyl]-4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide (AA-4) which was used in the next step without further purification.

Step 5: Synthesis of 4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide (Example AA01)

To a 2-dram vial containing N-[(2,4-dimethoxyphenyl)methyl]-4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide (AA-4) was added TFA (0.55 mL, 0.1 M) which produced a light yellow homogeneous solution. The reaction was stirred for 30 min at which point LCMS analysis did not reveal peaks with the desired product mass. The reaction was then heated to 50° C. and stirred overnight. LCMS analysis did not show peaks with the desired product mass and significant starting material remained. The reaction mixture was concentrated under vacuum to afford a white solid. The solid was dissolved in HFIP (200 μL) and MsOH (20 μL) was added. The reaction was heated at 50° C. for 4 h. LCMS analysis showed consumption of starting material and formation of a new peak with the desired product mass. The reaction was concentrated under vacuum and the crude residue purified via preparative HPLC to afford the title compound 4-{2-(1-ethyl-3-methyl-1H-pyrazol-5-yl)-5-[(methylamino)methyl]-1,3-thiazol-4-yl}-1-methyl-1H-pyrazolo[4,3-c]pyridine-6-carboxamide (Example AA01) (4.4 mg, 19%). LCMS [M+H]=411.4 observed.

Example AB01: Preparation of 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxamide According to Scheme AB

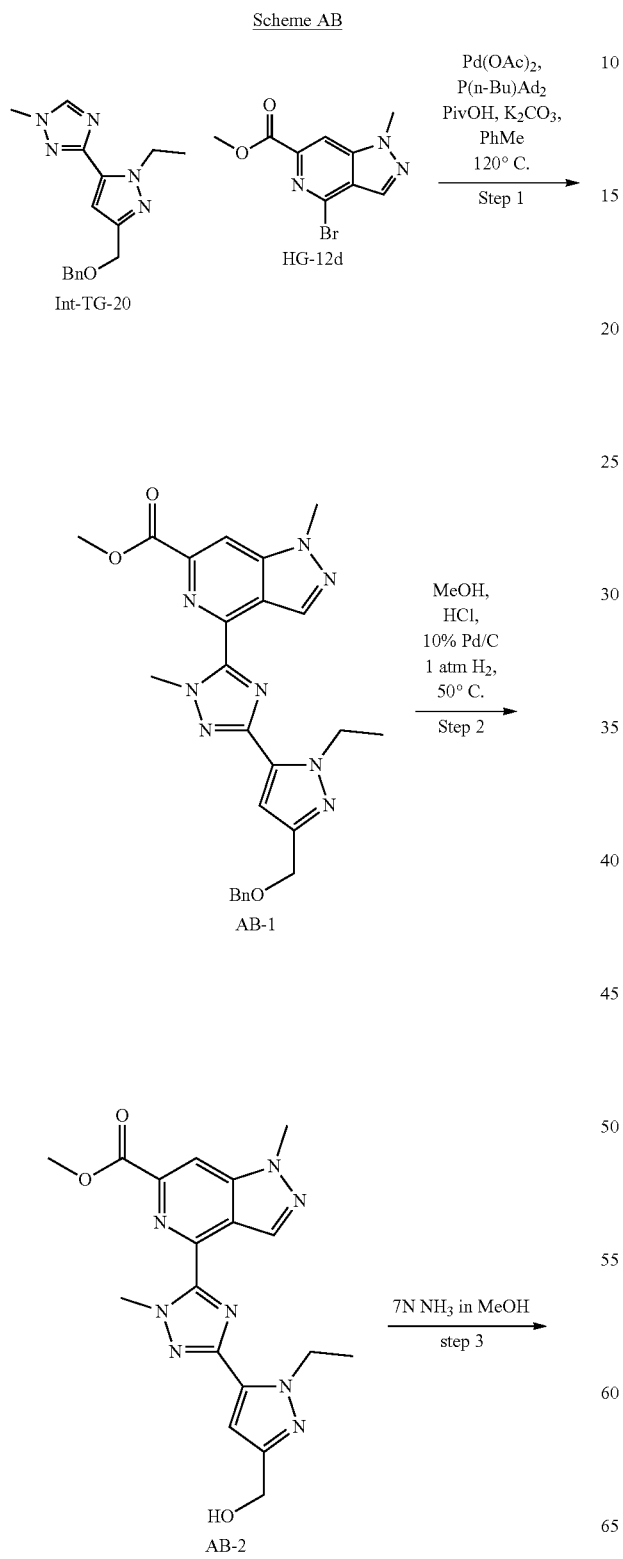

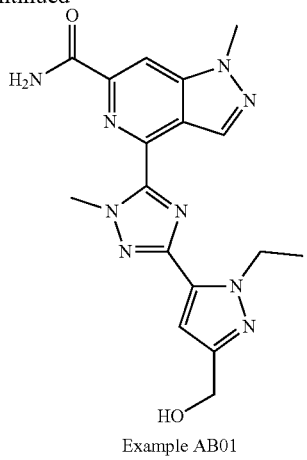

Step 1: Synthesis of methyl 4-(3-{3-[(benzyloxy)methyl]-1-ethyl-1H-pyrazol-5-yl}-1-methyl-1H-1,2,4-triazol-5-yl)-1-methyl-1H-pyrazolo[4,3-c]pyridine-6-carboxylate (AB-1)

A sealed vial containing 3-{3-[(benzyloxy)methyl]-1-ethyl-1H-pyrazol-5-yl}-1-methyl-1H-1,2,4-triazole (Int-TG-20) (55 mg, 0.19 mmol), methyl 4-bromo-1-methyl-1H-pyrazolo[4,3-c]pyridine-6-carboxylate (HG-12d) (50 mg, 0.19 mmol), Pd(OAc)$_2$ (4.2 mg, 0.019 mmol), di(1-adamantyl)-n-butylphosphine (13 mg, 0.037 mmol), pivalic acid (5.7 mg, 0.056 mmol) and potassium carbonate (77 mg, 0.56 mmol) was purged with N$_2$. Toluene (1.9 mL) was added and the mixture was bubbled with N$_2$. The reaction was heated at 120° C. and stirred overnight. The reaction was cooled to room temperature and filtered through celite. The filtrate was concentrated under vacuum and purified via flash chromatography (12 g SiO$_2$, Isco, 0-10% MeOH/DCM) to afford the title compound methyl 4-(3-{3-[(benzyloxy)methyl]-1-ethyl-1H-pyrazol-5-yl}-1-methyl-1H-1,2,4-triazol-5-yl)-1-methyl-1H-pyrazolo[4,3-c]pyridine-6-carboxylate (AB-1) (60 mg, 66%). LCMS [M+H]=487 observed; $^1$H NMR (400 MHz, DMSO-d6) δ ppm 8.83 (d, J=0.98 Hz, 1H) 8.61 (d, J=0.86 Hz, 1H) 7.37 (d, J=4.52 Hz, 4H) 7.26-7.33 (m, 1H) 6.91 (s, 1H) 4.69 (q, J=7.17 Hz, 2H) 4.56-4.58 (m, 5H) 4.53 (s, 2H) 4.25 (s, 3H) 3.99 (s, 3H) 1.45 (t, J=7.15 Hz, 3H).

Step 2: Synthesis of methyl 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxylate (AB-2)

To a solution of methyl 4-(3-{3-[(benzyloxy)methyl]-1-ethyl-1H-pyrazol-5-yl}-1-methyl-1H-1,2,4-triazol-5-yl)-1-methyl-1H-pyrazolo[4,3-c]pyridine-6-carboxylate (AB-1) (60 mg, 0.12 mmol) in methanol (3 mL) and HCl (4 N in dioxane, 300 μL, 1.2 mmol) was added 10% Pd/C (15 mg). The flask was evacuated and back filled with N$_2$ gas (3×) then H$_2$ gas (3×). The reaction was heated at 50° C. under 1 atm H$_2$ gas and stirred overnight. The solution was filtered through a glass fiber filter. The filtrate was concentrated under vacuum to afford the title compound methyl 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxylate (AB-2) which was used in the next step without further purification. LCMS [M+H]=397 observed.

Step 3: Synthesis of methyl 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxylate (Example AB01)

To a vial containing methyl 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxylate (AB-2) (24 mg, 0.06 mmol) was added 7 N NH₃ in methanol (1 mL). The reaction mixture was heated at 80° C. for 0.5 h. The vial was removed from heating and allowed to cool gradually to rt. The solution was concentrated under vacuum. The residue was slurried in MeOH and the solids were collected by filtration to afford the title compound methyl 4-{3-[1-ethyl-3-(hydroxymethyl)-1H-pyrazol-5-yl]-1-methyl-1H-1,2,4-triazol-5-yl}-1-methyl-1H-pyrazolo[4,3-c]pyridine-6-carboxylate (Example AB01) (10 mg, 43%) as a white solid. LCMS [M+H]=382 observed; ¹H NMR (400 MHz, DMSO-d6) δ ppm 8.75 (s, 1H) 8.51 (s, 1H) 8.03 (br s, 1H) 7.91 (br s, 1H) 6.82 (s, 1H) 5.07 (t, J=5.87 Hz, 1H) 4.66 (q, J=7.09 Hz, 2H) 4.43-4.52 (m, 5H) 4.23 (s, 3H) 1.44 (t, J=7.09 Hz, 3H).

Example AC01: Preparation of 4-[3-(1-ethyl-4-hydroxy-3-methyl-1H-pyrazol-5-yl)-1H-1,2,4-triazol-5-yl]-1-methyl-1H-pyrazolo[4,3-c]pyridine-6-carboxamide According to Scheme AC methyl-1H-pyrazolo[4,3-c]pyridine-6-carboxamide (Int-HG-17) (5.79 g, 14.3 mmol), K₂CO₃ (4.93 g, 35.7 mmol), Pd(OAc)₂ (801 mg, 3.57 mmol), cataCXium A (2.56 g, 7.14 mmol), CuI (906 mg, 4.76 mmol), PivOH (729 mg, 7.14 mmol) and toluene (80 mL). The resulting dark red mixture was degassed with N₂ for 5 times and heated to 120° C. The mixture was stirred at 120° C. for 18 h. LCMS analysis showed consumption of starting material and formation of a new peak with the desired product mass. The resulting yellow suspension was filtered through celite and the filtrate concentrated under vacuum. The crude residue was slurried with EtOAc (50 mL) for 30 minutes and the solids were filtered off. The filtrate was concentrated under vacuum. The crude residue was purified via column chromatography (120 g SiO₂, 15% EtOAc/Petroleum ether to 100% EtOAc) to afford the title compound 4-{5-[4-(benzyloxy)-1-ethyl-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (AC-1) (4.47 g, 51%) as a yellow solid. ¹H NMR (400 MHz, CHLOROFORM-d) δ=9.04 (s, 1H), 8.40 (s, 1H), 7.83 (br t, J=5.9 Hz, 1H), 7.19-7.12 (m, 5H), 7.09 (d, J=8.3 Hz, 1H), 6.65 (d, J=8.7 Hz, 2H), 6.53-6.45 (m, 2H), 6.37 (dd, J=2.4, 8.4 Hz, 1H), 6.40-6.33 (m, 1H), 6.30 (d, J=2.3 Hz, 1H), 5.80 (s, 2H), 4.78 (s, 2H), 4.50 (d, J=6.0 Hz, 2H), 4.22 (s, 3H),

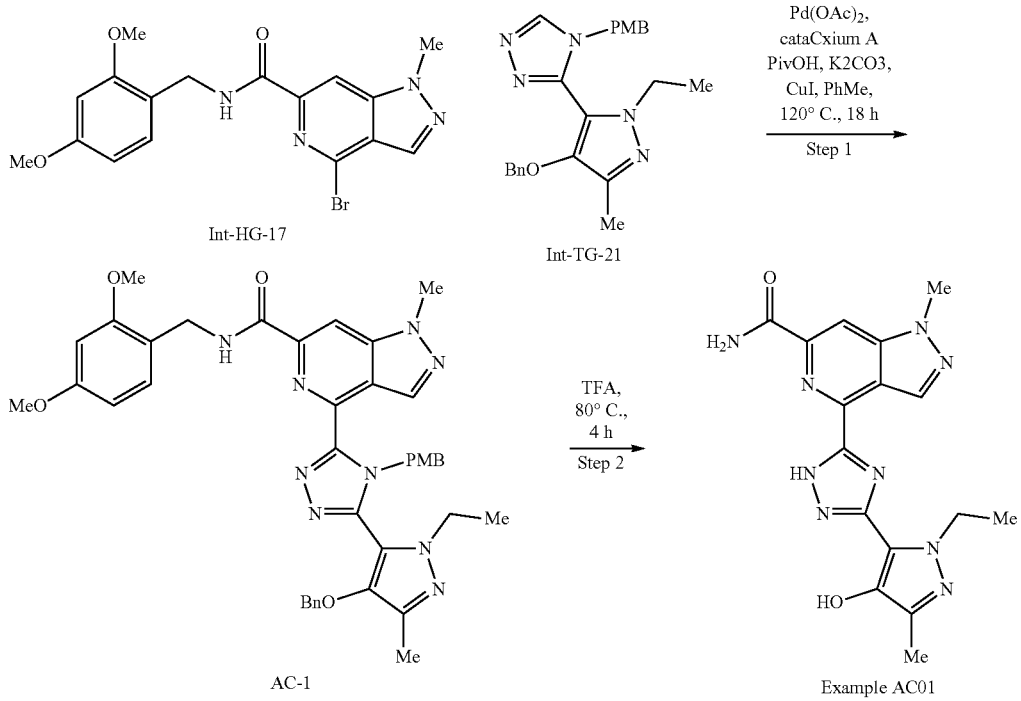

Step 1: Synthesis of 4-{5-[4-(benzyloxy)-1-ethyl-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (AC-1)

A pressure flask was charged with 3-[4-(benzyloxy)-1-ethyl-3-methyl-1H-pyrazol-5-yl]-4-[(4-methoxyphenyl)methyl]-4H-1,2,4-triazole (Int-TG-21) (4.80 g, 11.90 mmol), 4-bromo-N-[(2,4-dimethoxyphenyl)methyl]-1-

3.92 (q, J=7.1 Hz, 2H), 3.77 (s, 3H), 3.64 (s, 3H), 3.60 (s, 3H), 2.27 (s, 3H), 1.08 (t, J=7.2 Hz, 3H).

Step 2: Synthesis of 4-[3-(1-ethyl-4-hydroxy-3-methyl-1H-pyrazol-5-yl)-1H-1,2,4-triazol-5-yl]-1-methyl-1H-pyrazolo[4,3-c]pyridine-6-carboxamide (Example AC01)

A solution of 4-{5-[4-(benzyloxy)-1-ethyl-3-methyl-1H-pyrazol-5-yl]-4-[(4-methoxyphenyl)methyl]-4H-1,2,4-triazol-3-yl}-N-[(2,4-dimethoxyphenyl)methyl]-1-methyl-1H-pyrazolo[4,3-c]pyridine-6-carboxamide (AC-1) (4.51 g, 6.197 mmol) in TFA (84 mL) was heated to 80° C. and stirred for 4 h.

LCMS analysis showed consumption of starting material and formation of new peak with the desired product mass. The purple solution was concentrated under vacuum. The crude residue was slurried in EtOAc (100 mL) for 1.5 h and filtered. The solids were washed with EtOAc (20 mL×5). The filter cake was collected and slurried with MeOH (50 mL) for 0.5 h. The suspension was filtered and the solids collected followed by drying under high vacuum to afford a white solid (1.72 g). NMR analysis indicated impurities were still present. The white solid was slurried in DCM/MeOH (1:5, 50 mL) for 0.5 h and filtered. The filter cake was collected and dried under high vacuum to afford the title compound 4-[3-(1-ethyl-4-hydroxy-3-methyl-1H-pyrazol-5-yl)-1H-1,2,4-triazol-5-yl]-1-methyl-1H-pyrazolo[4,3-c]pyridine-6-carboxamide (Example AC01) (1.59 g) as a white solid. m/z (ESI+) for ($C_{16}H_{18}N_9O_2$), 368.0 (M+H)$^+$ observed; $^1$H NMR (400 MHz, DMSO-$d_6$) δ=15.35 (s, 1H), 8.87 (br s, 1H), 8.81 (s, 1H), 8.47 (s, 1H), 7.99 (s, 1H), 7.90 (br s, 1H), 4.46 (q, J=6.8 Hz, 2H), 4.23 (s, 3H), 2.15 (s, 3H), 1.36 (t, J=7.0 Hz, 3H).

Example AC02 was synthesized according to the methods used for the synthesis of 4-[3-(1-ethyl-4-hydroxy-3-methyl-1H-pyrazol-5-yl)-1H-1,2,4-triazol-5-yl]-1-methyl-1H-pyrazolo[4,3-c]pyridine-6-carboxamide (Example AC01) (Scheme AC-1) with non-critical changes or substitutions to the exemplified procedures that someone who skilled in the art would be able to realize.

| Example Number | Intermediates | Structure/Name | Analytical Data |
|---|---|---|---|
| AC02 | Int-HG-17 & Int-TG-26 were used in step 1 | 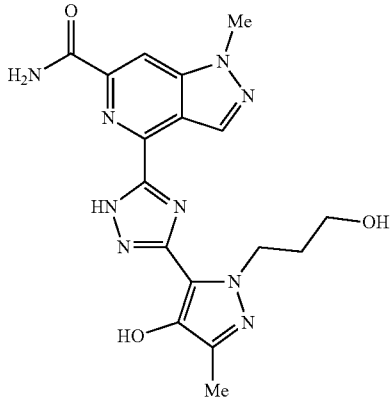<br>4-{3-[4-hydroxy-1-(3-hydroxypropyl)-3-methyl-1H-pyrazol-5-yl]-1H-1,2,4-triazol-5-yl}-1-methyl-1H-pyrazolo[4,3-c]pyridine-6-carboxamide | $^1$H NMR (400 MHz, DMSO-$d_6$) δ = 8.83 (s, 1H), 8.37 (s, 1H), 8.33-8.20 (m, 1H), 4.46 (br t, J = 6.3 Hz, 2H), 4.18 (s, 3H), 3.41 (br t, J = 5.8 Hz, 2H), 2.13 (s, 3H), 1.96-1.86 (m, 2H); m/z (ESI+) for $C_{17}H_{18}N_8O_3$, 398.2 (M + H)$^+$ observed. |

Example AD01: Preparation of 4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide According to Scheme AD Scheme AD

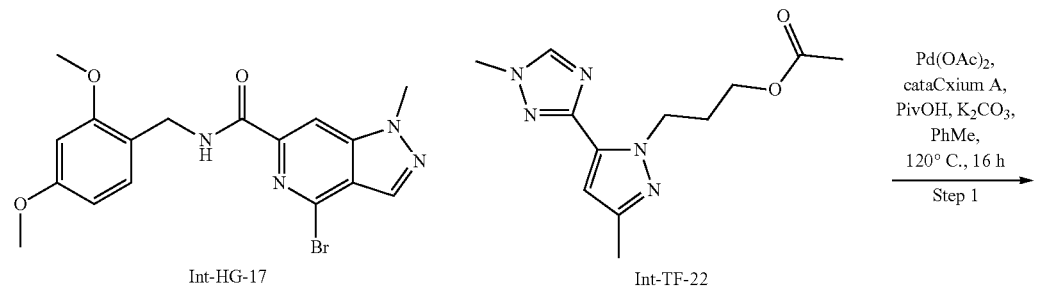

281

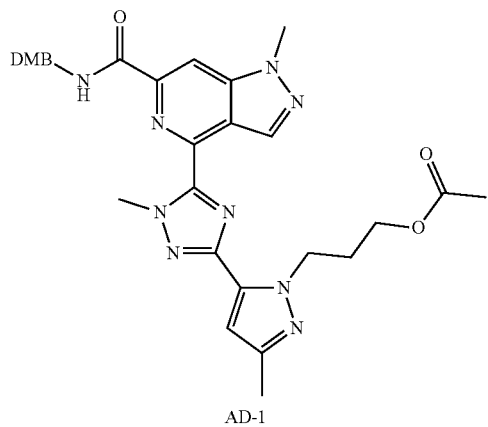

AD-1

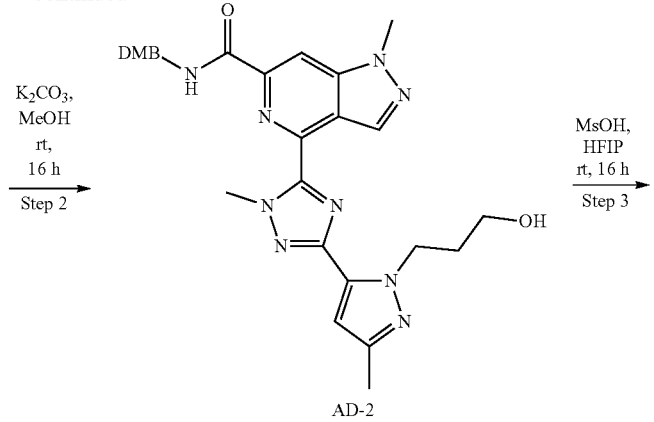

AD-2

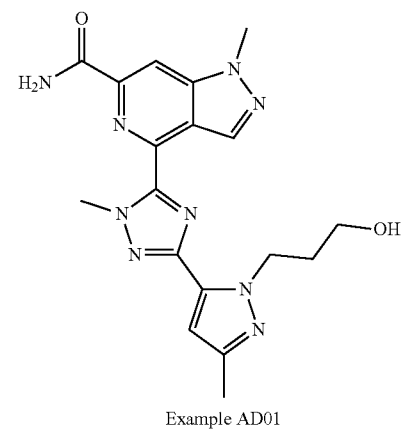

Example AD01

Step 1: Synthesis of 3-{5-[5-(6-{[(2,4-dimethoxyphenyl)methyl]carbamoyl}-1-methyl-1H-pyrazolo[4,3-c]pyridin-4-yl)-1-methyl-1H-1,2,4-triazol-3-yl]-3-methyl-1H-pyrazol-1-yl}propyl acetate (AD-1)

A dark red suspension of 3-[3-methyl-5-(1-methyl-1H-1,2,4-triazol-3-yl)-1H-pyrazol-1-yl]propyl acetate (Int-TG-22) (666 mg, 1.64 mmol, 1.1 eq), 4-bromo-N-[(2,4-dimethoxyphenyl)methyl]-1-methyl-1H-pyrazolo[4,3-c]pyridine-6-carboxamide (Int-HG-17) (404.5 mg, 1.536 mmol), $K_2CO_3$ (667 mg, 4.82 mmol, 3 eq), Pd(OAc)$_2$ (69.0 mg, 0.307 mmol, 0.2 eq), PivOH (62.8 mg, 0.615 mmol, 0.3 eq), and P(n-Bu)Ad$_2$ (165 mg, 0.461 mmol, 0.4 eq) in toluene (10 mL, 0.15 M) was sparged with $N_2$ for 2 min and then sealed before stirring at 120° C. for 16 hr. The reaction mixture was combined with another batch of crude material and the solids filtered off. The filter cake was washed with 10:1 DCM/MeOH (10 mL). The filtrate was concentrated in vacuo and the crude residue purified by flash column chromatography (ISCO, silica gel: 20 g, MeOH, 0% to 5% in ethyl acetate) to afford the title compound 3-{5-[5-(6-{[(2,4-dimethoxyphenyl)methyl]carbamoyl}-1-methyl-1H-pyrazolo[4,3-c]pyridin-4-yl)-1-methyl-1H-1,2,4-triazol-3-yl]-3-methyl-1H-pyrazol-1-yl}propyl acetate (AD-1) (538 mg, 55%) as a yellow solid. m/z (ESI+) for ($C_{29}H_{34}N_9O_5$), 588.1 (M+H)$^+$ observed.

Step 2: Synthesis of N-[(2,4-dimethoxyphenyl)methyl]-4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (AD-2)

To a solution of 3-{5-[5-(6-{[(2,4-dimethoxyphenyl)methyl]carbamoyl}-1-methyl-1H-pyrazolo[4,3-c]pyridin-4-yl)-1-methyl-1H-1,2,4-triazol-3-yl]-3-methyl-1H-pyrazol-1-yl}propyl acetate (AD-1) (538.7 mg, 0.92 mmol) in MeOH (15 mL, 0.06 M) was added $K_2CO_3$ (380 mg, 2.75 mmol) at room temperature and the mixture was stirred for 16 hrs. The reaction mixture was neutralized with 4.0 N HCl in MeOH. The mixture was concentrated in vacuo and the crude residue purified by flash column chromatography (ISCO, silica gel: 25 g, MeOH in DCM from 0% to 5%) to afford the title compound N-[(2,4-dimethoxyphenyl)

methyl]-4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (AD-2) (397.7 mg, 79%) as a yellow solid. m/z (ESI+) for ($C_{27}H_{32}N_9O_4$), 546.1 (M+H)+ observed.

Step 3: Synthesis of 4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (Example AD01)

To a light yellow solution of N-[(2,4-dimethoxyphenyl)methyl]-4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (AD-2) (97.7 mg, 0.11 mmol) in HFIP (1 mL, 0.1 M) was added MsOH (155 mg, 1.61 mmol, 1.5 eq). The reaction mixture was stirred at room temperature for 16 hrs. The reaction mixture was neutralized with aq. NH$_4$OH and the mixture concentrated in vacuo. The crude residue was purified by preparative HPLC (Boston Prime C18 150×25 mm×5 μM column, 25 mL/min, 20%-43% MeCN/H$_2$O containing 0.225% formic acid, 5 injections) to provide the title compound. This material was subjected to further purification by SFC to afford the title compound 4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (Example AD01) (14 mg, 34%) as a white solid. m/z (ESI+) for ($C_{18}H_{22}N_9O_2$), 396.1 (M+H)+ observed; $^1$H NMR (400 MHz, DMSO-d$_6$) δ=8.80 (s, 1H), 8.52 (s, 1H), 8.05 (br s, 1H), 7.94 (br s, 1H), 6.66 (s, 1H), 4.67 (t, J=7.3 Hz, 2H), 4.56 (t, J=5.1 Hz, 1H), 4.45 (s, 3H), 4.23 (s, 3H), 3.50-3.43 (m, 2H), 2.22 (s, 3H), 1.98 (quin, J=6.7 Hz, 2H).

Example AD02 was synthesized according to the methods used for the synthesis of 4-{3-[1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide (Example AD01) (Scheme AD) with non-critical changes or substitutions to the exemplified procedures that someone who skilled in the art would be able to realize.

Example AE01: Preparation of 4-[2-(1-ethyl-4-hydroxy-3-methyl-1H-pyrazol-5-yl)-1,3-oxazol-4-yl]-1-methyl-1H-pyrazolo[4,3-c]pyridine-6-carboxamide According to Scheme AE Scheme AE

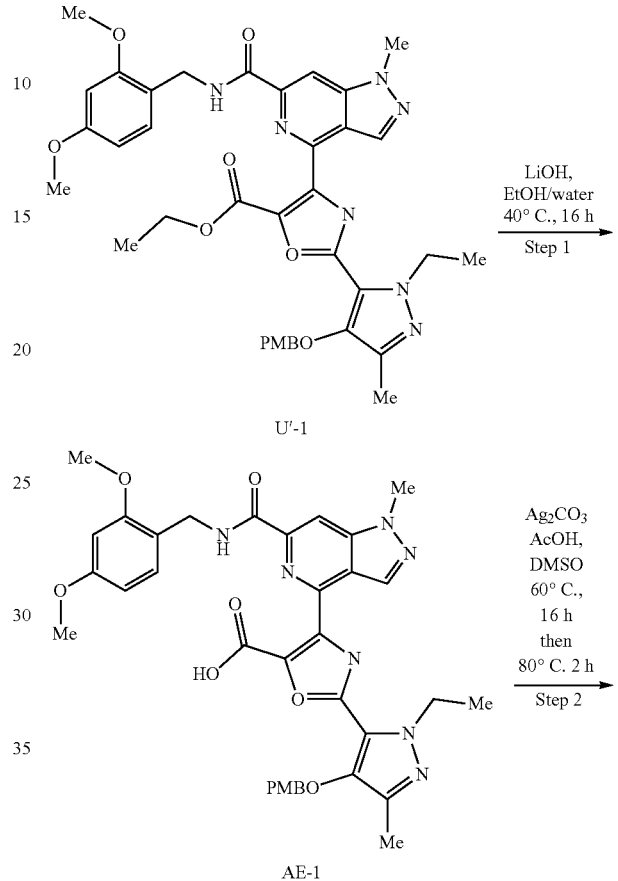

| Example Number | Intermediates | Structure/Name | Analytical Data |
|---|---|---|---|
| AD02 | Int-HG-17 & Int-HG-27 were used in step 1 | 4-{3-[4-hydroxy-1-(3-hydroxypropyl)-3-methyl-1H-pyrazol-5-yl]-1-methyl-1H-1,2,4-triazol-5-yl}-1-methyl-1H-pyrazolo[4,3-c]pyridine-6-carboxamide | $^1$H NMR (400 MHz, DMSO-d$_6$) δ = 8.75 (s, 1H), 8.29 (s, 1H), 7.93 (br s, 1H), 7.90 (br s, 1H), 7.25 (s, 1H), 4.61 (q, J = 7.1 Hz, 2H), 4.31 (s, 2H), 4.18 (s, 3H), 1.42 (t, J = 7.0 Hz, 3H); m/z (ESI+) for $C_{17}H_{18}N_8O_3$, 383.1 (M + H)+ observed. |

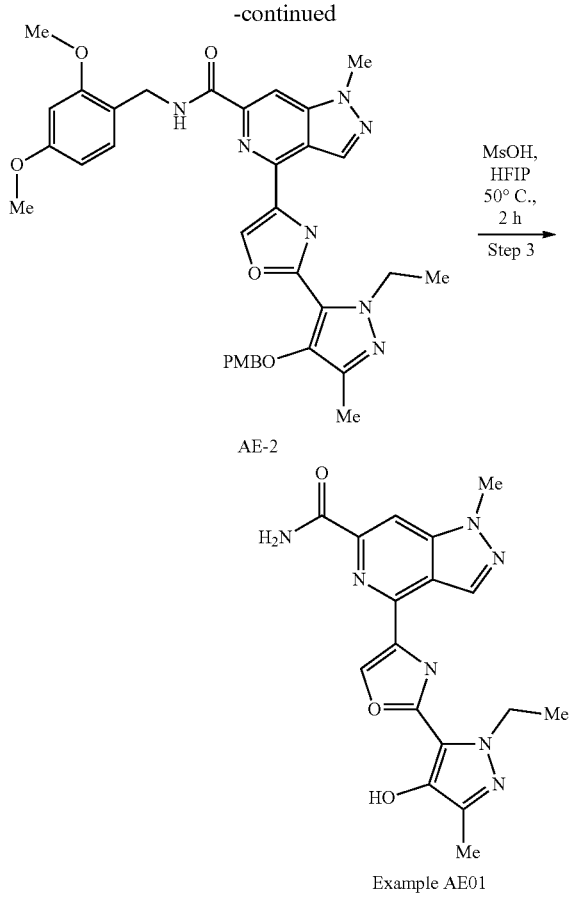

Step 1: Synthesis of 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylic acid (AE-1)

To a yellow suspension of ethyl 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylate (U'-1) (190 mg, 0.268 mmol) in EtOH (5 mL) and H$_2$O (0.5 mL) was added LiOH·H$_2$O (22.5 mg, 0.535 mmol). The resulting light-yellow suspension was heated to 40° C. and stirred for 16 hrs. The resulting light-yellow suspension was concentrated to dryness. The crude residue was dissolved in water (10 mL) and transferred to a separatory funnel with EtOAc. The phases were separated, and the aqueous phase extracted with EtOAc (3×10 mL). The aqueous layer was acidified with 12N HCl to achieve pH 5-6 which resulted in formation of a yellow precipitate. The suspension was filtered, the solids isolated, and further dried under vacuum to afford the title compound 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylic acid (AE-1) (120 mg, 65%) as a yellow solid. m/z (ESI+) for (C$_{35}$H$_{35}$N$_7$O$_8$), 682.1 (M+H)$^+$ observed.

Step 2: Synthesis of N-[(2,4-dimethoxyphenyl)methyl]-4-(2-{1-ethyl-4-[(4-methoxyphenyl)methoxy]-3-methyl-1H-pyrazol-5-yl}-1,3-oxazol-4-yl)-1-methyl-1H-pyrazolo[4,3-c]pyridine-6-carboxamide (AE-2)

To a yellow suspension of 4-(6-{[(2,4-dimethoxyphenyl)methyl]carbamoyl}-1-methyl-1H-pyrazolo[4,3-c]pyridin-4-yl)-2-{1-ethyl-4-[(4-methoxyphenyl)methoxy]-3-methyl-1H-pyrazol-5-yl}-1,3-oxazole-5-carboxylic acid (AE-1) (115.3 mg, 0.1691 mmol) in DMSO (1.00 mL) was added Ag$_2$CO$_3$ (5.2 mg, 0.019 mmol) and AcOH (1.8 mg, 0.030 mmol). The resulting mixture was heated to 60° C. and stirred for 16 hrs. LCMS analysis indicated starting material had not been completely consumed, however, a new peak with the desired product was observed. At this stage, additional aliquots of Ag$_2$CO$_3$ (22.3 mg, 0.0809 mmol) and AcOH (7.6 mg, 0.13 mmol) were added. The resulting mixture was stirred at 80° C. for 2 hrs. The reaction was removed from heating and allowed to cool to rt. The solution was diluted with DCM (5 mL) and filtered through celite. The filtrate was transferred to a separatory funnel and washed with sat. NaHCO$_3$ (5 mL) and water (3×5 mL). The combined aqueous washes were back extracted with DCM (2×10 mL). The combined organic extracts were dried over anhydrous Na$_2$SO$_4$, filtered and concentrated under vacuum to afford the title compound N-[(2,4-dimethoxyphenyl)methyl]-4-(2-{1-ethyl-4-[(4-methoxyphenyl)methoxy]-3-methyl-1H-pyrazol-5-yl}-1,3-oxazol-4-yl)-1-methyl-1H-pyrazolo[4,3-c]pyridine-6-carboxamide (AE-2) (85 mg) as a yellow solid. This material was used in the next step without further purification. m/z (ESI+) for (C$_{34}$H$_{35}$N$_7$O$_6$), 638.2 (M+H)$^+$ observed.

Step 3: Synthesis of 4-[2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example AE01)

To a yellow suspension of N-[(2,4-dimethoxyphenyl)methyl]-4-(2-{1-ethyl-4-[(4-methoxyphenyl)methoxy]-3-methyl-1H-pyrazol-5-yl}-1,3-oxazol-4-yl)-1-methyl-1H-pyrazolo[4,3-c]pyridine-6-carboxamide (AE-2) (85 mg, 0.13 mmol) in HFIP (1.50 mL) was added MsOH (128 mg, 1.33 mmol). The resulting mixture was heated to 50° C. and stirred at the temperature for 2 hrs. A purple solution formed and LCMS analysis showed that starting material had been consumed. The resulting mixture was concentrated to dryness to give a crude residue. The residue was dissolved in DCM (10 mL), basified with NH$_3$/MeOH to achieve pH 7-8, and concentrated under vacuum. The crude residue was purified by flash column chromatography (12 g SiO$_2$, Combi-Flash, 0-5% MeOH/EtOAc) to afford the product (39 mg) with minor impurities still present. The material was further subjected to purification via prep-TLC (DCM/MeOH=10:1) to afford the title compound 4-[2-(1-ethyl-4-hydroxy-3-methyl-1H-pyrazol-5-yl)-1,3-oxazol-4-yl]-1-methyl-1H-pyrazolo[4,3-c]pyridine-6-carboxamide (Example AE01) (22 mg, 22% over 3 steps) as a white solid. m/z (ESI+) for (C$_{17}$H$_{17}$N$_7$O$_3$), 368.3 (M+H)$^+$ observed; $^1$H NMR (400 MHz, DMSO-d$_6$) δ=9.34 (s, 1H), 8.84 (s, 1H), 8.75 (d, J=0.8 Hz, 1H), 8.54 (br d, J=2.5 Hz, 1H), 8.29 (s, 1H), 7.83 (br d, J=2.3 Hz, 1H), 4.56 (q, J=7.0 Hz, 2H), 4.18 (s, 3H), 2.15 (s, 3H), 1.41 (t, J=7.2 Hz, 3H).

Example AF01: Preparation of 4-{5-(aminomethyl)-2-[1-(3-hydroxypropyl)-3-methyl-1H-pyrazol-5-yl]-1,3-thiazol-4-yl}-1-methyl-1H-pyrazolo[4,3-c]pyridine-6-carboxamide According to Scheme AF-1

Scheme AF-1

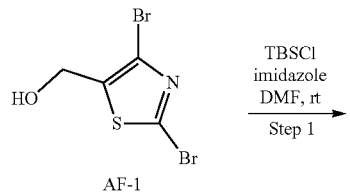

AF-1

TBSCl
imidazole
DMF, rt
Step 1

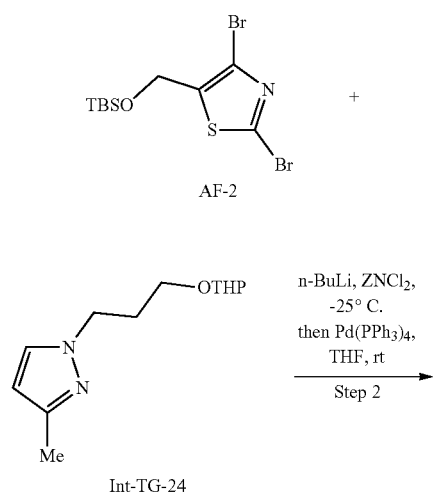

AF-2

Int-TG-24 n-BuLi, ZnCl$_2$,
-25° C.
then Pd(PPh$_3$)$_4$,
THF, rt
Step 2

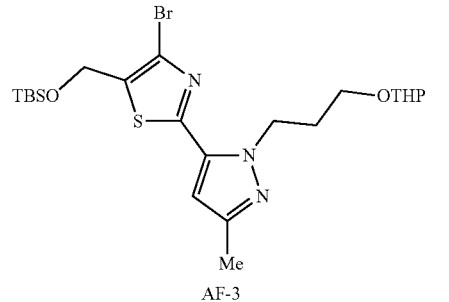

AF-3

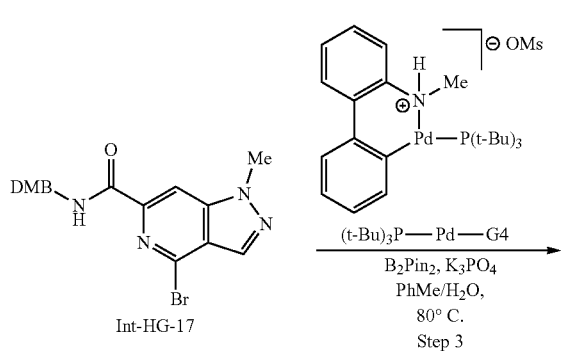

Int-HG-17

(t-Bu)$_3$P—Pd—G4
B$_2$Pin$_2$, K$_3$PO$_4$
PhMe/H$_2$O,
80° C.
Step 3

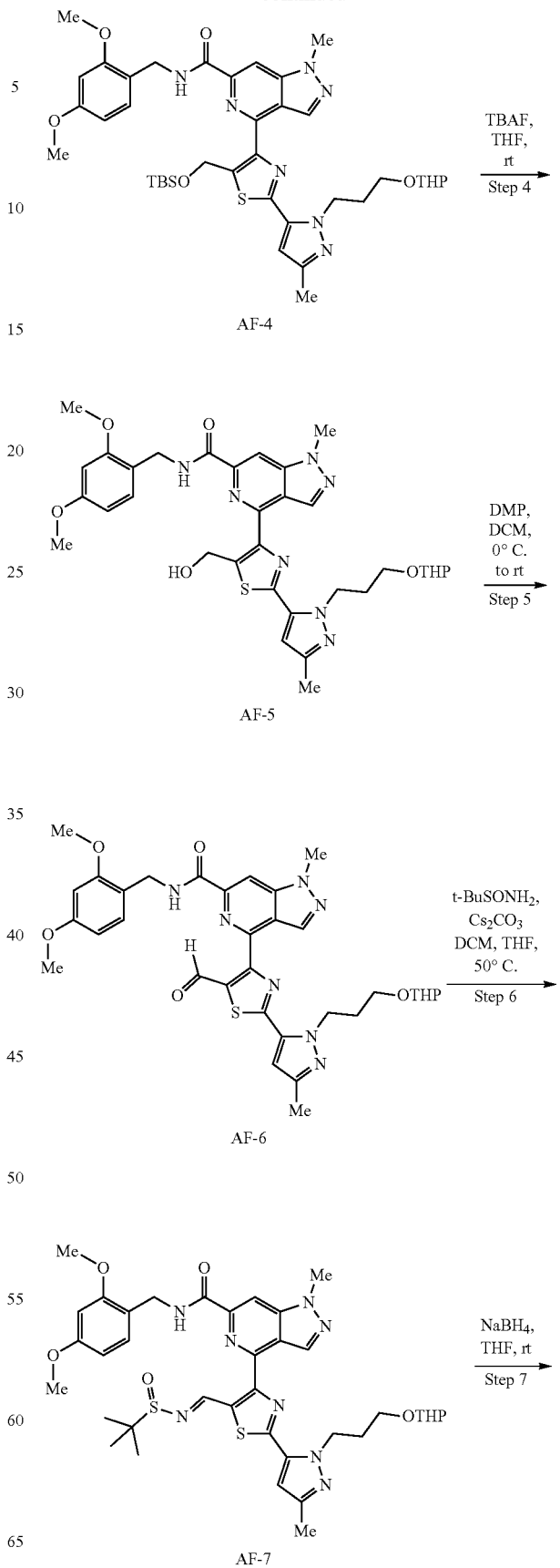

AF-4

TBAF,
THF,
rt
Step 4

AF-5

DMP,
DCM,
0° C.
to rt
Step 5

AF-6 t-BuSONH$_2$,
Cs$_2$CO$_3$
DCM, THF,
50° C.
Step 6

AF-7

NaBH$_4$,
THF, rt
Step 7

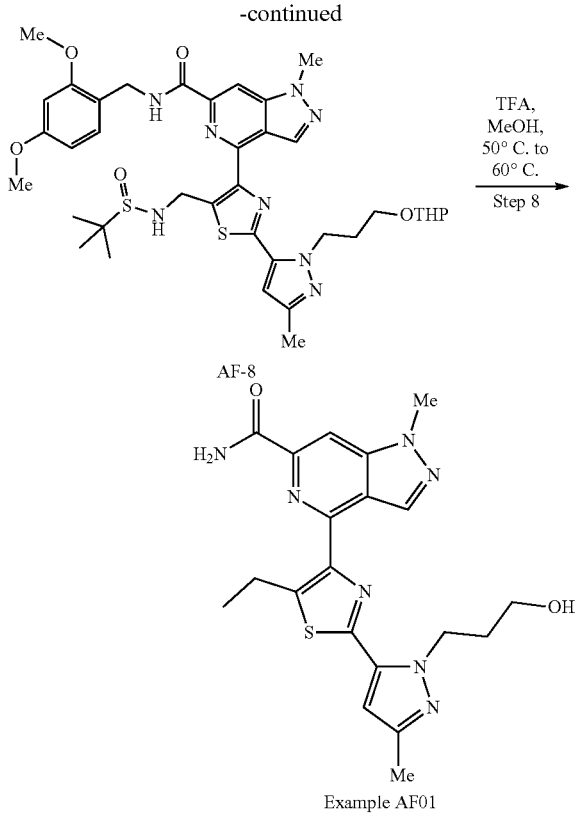

Step 1: Synthesis of 2,4-dibromo-5-({[tert-butyl(dimethyl)silyl]oxy}methyl)-1,3-thiazole (AF-2)

To a round bottom flask was added (2,4-dibromo-1,3-thiazol-5-yl)methanol (AF-1) (1.3 g, 4.8 mmol), tert-butyldimethylsilyl chloride (1.1 g, 7.3 mmol), imidazole (660 mg, 7.3 mmol), and DMF (16 mL). The reaction was stirred at room temperature for 2 hours. At this stage, the reaction was concentrated and the crude residue purified via flash column chromatography (40 g SiO$_2$, Isco, 0-10% EtOAc/heptanes) to afford the title compound 2,4-dibromo-5-({[tert-butyl(dimethyl)silyl]oxy}methyl)-1,3-thiazole (AF-2) (1.7 g, 90%) as a faint yellow oil. m/z (ESI+) for (C$_{10}$H$_{17}$Br$_2$NOSSi), 230 (M-2Br+H)$^+$ observed; $^1$H NMR (400 MHz, DMSO-d$_6$) δ ppm 4.78 (s, 2H) 0.88 (s, 9H) 0.10 (s, 6H).

Step 2: Synthesis of 4-bromo-5-({[tert-butyl(dimethyl)silyl]oxy}methyl)-2-(3-methyl-1-{3-[(oxan-2-yl)oxy]propyl}-1H-pyrazol-5-yl)-1,3-thiazole (AF-3)

To a cooled (~25 to –30° C. acetone/enough dry ice to control the temp) solution of 3-methyl-1-{3-[(oxan-2-yl)oxy]propyl}-1H-pyrazole (Int-TG-24) (100 mg, 0.45 mmol) in THF (3.0 mL) was added n-butyl lithium (2.3 M in hexanes, 210 μL, 0.49 mmol) drop-wise. After 20 min, zinc chloride (1.9 M in MeTHF, 280 μL, 0.54 mmol) was added and the ice bath was removed. After 30 min, a solution of 2,4-dibromo-5-({[tert-butyl(dimethyl)silyl]oxy}methyl)-1,3-thiazole (AF-2) (190 mg, 0.49 mmol) in THF (0.50 mL) was added followed by tetrakis(triphenylphosphine)palladium(0) (52 mg, 0.045 mmol). The reaction was stirred at room temperature overnight then concentrated under vacuum. The crude residue was purified via flash column chromatography (12 g SiO$_2$, Isco, 0-15% EtOAc/heptanes) to afford the title compound 4-bromo-5-({[tert-butyl(dimethyl)silyl]oxy}methyl)-2-(3-methyl-1-{3-[(oxan-2-yl)oxy]propyl}-1H-pyrazol-5-yl)-1,3-thiazole (AF-3) (69 mg, 29%). m/z (ESI+) for (C$_{22}$H6BrN$_3$O$_3$SSi), 530 (M+H)$^+$ observed; $^1$H NMR (400 MHz, DMSO-d$_6$) δ ppm 6.64 (s, 1H) 4.84 (s, 2H) 4.48-4.61 (m, 2H) 4.42-4.48 (m, 1H) 3.49-3.67 (m, 2H) 3.32-3.40 (m, 1H) 3.21-3.27 (m, 1H) 2.18 (s, 3H) 2.00 (quin, J=6.60 Hz, 2H) 1.62-1.73 (m, 1H) 1.48-1.58 (m, 1H) 1.34-1.47 (m, 4H) 0.90 (s, 9H) 0.12 (s, 6H).

Step 3: Synthesis of 4-[5-({[tert-butyl(dimethyl)silyl]oxy}methyl)-2-(3-methyl-1-{3-[(oxan-2-yl)oxy]propyl}-1H-pyrazol-5-yl)-1,3-thiazol-4-yl]-N-[(2,4-dimethoxyphenyl)methyl]-1-methyl-1H-pyrazolo[4,3-c]pyridine-6-carboxamide (AF-4)

A round bottom flask was charged with 4-bromo-N-[(2,4-dimethoxyphenyl)methyl]-1-methyl-1H-pyrazolo[4,3-c]pyridine-6-carboxamide (Int-HG-17) (56 mg, 0.14 mmol), B$_2$Pin$_2$ (67 mg, 0.27 mmol), potassium carbonate (84 mg, 0.40 mmol) and (t-Bu$_3$P)—Pd-G4 (6.8 mg, 0.013 mmol) and purged with nitrogen. To the flask was added 4-bromo-5-({[tert-butyl(dimethyl)silyl]oxy}methyl)-2-(3-methyl-1-{3-[(oxan-2-yl)oxy]propyl}-1H-pyrazol-5-yl)-1,3-thiazole (AF-3) (70 mg, 0.13 mmol) as a solution in toluene (1.3 mL) followed by water (0.26 mL). The reaction mixture was sparged with nitrogen and heated at 80° C. overnight. The flask was removed from heating and allowed to cool to rt. The solution was diluted with EtOAc and washed with water and brine. The organic phase was dried over Na$_2$SO$_4$, filtered and concentrated under vacuum. The crude residue was purified by via flash column chromatography (4 g SiO$_2$, Isco, 0-50% EtOAc/heptanes) to afford the title compound 4-[5-({[tert-butyl(dimethyl)silyl]oxy}methyl)-2-(3-methyl-1-{3-[(oxan-2-yl)oxy]propyl}-1H-pyrazol-5-yl)-1,3-thiazol-4-yl]-N-[(2,4-dimethoxyphenyl)methyl]-1-methyl-1H-pyrazolo[4,3-c]pyridine-6-carboxamide (AF-4) (28 mg, 27%). m/z (ESI+) for (C$_{39}$H$_{53}$N$_7$O$_6$SSi), 776 (M+H)$^+$ observed; $^1$H NMR (400 MHz, DMSO-d$_6$) δ ppm 8.72 (d, J=0.98 Hz, 1H) 8.61 (t, J=6.24 Hz, 1H) 8.34 (d, J=0.86 Hz, 1H) 7.15 (d, J=8.44 Hz, 1H) 6.71 (s, 1H) 6.59 (d, J=2.32 Hz, 1H) 6.46 (dd, J=8.38, 2.38 Hz, 1H) 5.51 (s, 2H) 4.77 (t, J=6.97 Hz, 2H) 4.52 (d, J=6.24 Hz, 2H) 4.19 (s, 3H) 3.84 (s, 4H) 3.73 (s, 3H) 3.54-3.60 (m, 2H) 3.21-3.26 (m, 2H) 2.23 (s, 3H) 2.04-2.12 (m, 2H) 1.29-1.44 (m, 4H) 1.14-1.20 (m, 2H) 0.88 (s, 9H) 0.02 (s, 6H).

Step 4: Synthesis of N-[(2,4-dimethoxyphenyl)methyl]-4-[5-(hydroxymethyl)-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-5)

To a solution of 4-[5-({[tert-butyl(dimethyl)silyl]oxy}methyl)-2-(3-methyl-1-{3-[(oxan-2-yl)oxy]propyl}-1H-pyrazol-5-yl)-1,3-thiazol-4-yl]-N-[(3,4-dimethylphenyl)methyl]-1-methyl-1H-pyrazolo[4,3-c]pyridine-6-carboxamide (AF-4) (50 mg, 0.64 mmol in THF (650 μL) was added tetrabutylammonium fluoride (1 N in THF, 97 μL, 0.097 mmol). The reaction was stirred at rt for 1 hour. The reaction was concentrated under vacuum and the crude residue purified via flash column chromatography (4 g SiO$_2$, Isco, 0-200% EtOAc/heptanes) to afford the title compound N-[(2,4-dimethoxyphenyl)methyl]-4-[5-(hydroxymethyl)-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-5) (31 mg, 73%). m/z (ESI+) for ($C_{33}H_{39}N_7O_6S$), 662 (M+H)$^+$ observed.

Step 5: Synthesis of N-[(2,4-dimethoxyphenyl)methyl]-4-[5-formyl-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-6)

To a cooled (ice-water bath) solution of N-[(3,4-dimethylphenyl)methyl]-4-[5-(hydroxymethyl)-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-5) (31 mg, 0.047) in dichloromethane (1.0 mL) was added Des-Martin periodinane (30 mg, 0.070 mmol) and the ice-bath was removed. The reaction was stirred at room temperature for 2 hours. At this stage, the reaction was diluted with EtOAc and washed with water and brine. The organic phase was dried over $Na_2SO_4$, filtered, and concentrated under vacuum to afford the title compound N-[(2,4-dimethoxyphenyl)methyl]-4-[5-formyl-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-6). This material was use in the next step without further purification. m/z (ESI+) for ($C_{33}H_{37}N_7O_6S$), 660 (M+H)$^+$ observed.

Step 6: Synthesis of N-[(2,4-dimethoxyphenyl)methyl]-1-methyl-4-[2-(3-methyl-1-{3-[(oxan-2-yl)oxy]propyl}-1H-pyrazol-5-yl)-5-{(E)-[(2-methylpropane-2-sulfinyl)imino]methyl}-1,3-thiazol-4-yl]-1H-pyrazolo[4,3-c]pyridine-6-carboxamide (AF-7)

To a flask containing crude N-[(2,4-dimethoxyphenyl)methyl]-4-[5-formyl-2-(3-methyl-1-{3-[(oxan-2-yl)oxy]propyl}-1H-pyrazol-5-yl)-1,3-thiazol-4-yl]-1-methyl-1H-pyrazolo[4,3-c]pyridine-6-carboxamide (AF-6) was added tert-butylsulfinamide (11 mg, 0.094 mmol), cesium carbonate (301 mg, 0.094 mmol), and dichloromethane (1.0 mL). The reaction was stirred for 6 hours at rt. LCMS analysis showed a trace amount of peak with the desired product mass had formed. At this stage, THF (1.0 mL) was added and the reaction was heated to 50° C. overnight. At this stage, an additional 2 equivalents of tert-butylsulfinamide and cesium carbonate were added. After 3 hours, the reaction was filtered through celite and concentrated under vacuum to afford the title compound N-[(2,4-dimethoxyphenyl)methyl]-1-methyl-4-[2-(3-methyl-1-{3-[(oxan-2-yl)oxy]propyl}-1H-pyrazol-5-yl)-5-{(E)-[(2-methylpropane-2-sulfinyl)imino]methyl}-1,3-thiazol-4-yl]-1H-pyrazolo[4,3-c]pyridine-6-carboxamide (AF-7). This material was used in the next step without further purification. m/z (ESI+) for ($C_{37}H_{46}N_8O_6S_2$), 763 (M+H)$^+$ observed.

Step 7: Synthesis of N-[(2,4-dimethoxyphenyl)methyl]-1-methyl-4-[2-(3-methyl-1-{3-[(oxan-2-yl)oxy]propyl}-1H-pyrazol-5-yl)-5-{[(2-methylpropane-2-sulfinyl)amino]methyl}-1,3-thiazol-4-yl]-1H-pyrazolo[4,3-c]pyridine-6-carboxamide (AF-8)

To a flask containing crude N-[(2,4-dimethoxyphenyl)methyl]-1-methyl-4-[2-(3-methyl-1-{3-[(oxan-2-yl)oxy]propyl}-1H-pyrazol-5-yl)-5-{(E)-[(2-methylpropane-2-sulfinyl)imino]methyl}-1,3-thiazol-4-yl]-1H-pyrazolo[4,3-c]pyridine-6-carboxamide (AF-7) was added THF (1.0 mL) and sodium borohydride (5.3 mg, 0.14 mmol). The reaction was stirred at room temperature for 30 minutes. At this stage, the reaction was quenched with methanol and concentrated under vacuum to afford the title compound N-[(2,4-dimethoxyphenyl)methyl]-1-methyl-4-[2-(3-methyl-1-{3-[(oxan-2-yl)oxy]propyl}-1H-pyrazol-5-yl)-5-{[(2-methylpropane-2-sulfinyl)amino]methyl}-1,3-thiazol-4-yl]-1H-pyrazolo[4,3-c]pyridine-6-carboxamide (AF-8). This material was used in the next step without further purification. m/z (ESI+) for ($C_{37}H_{48}N_8O_6S_2$), 765 (M+H)$^+$ observed.

Step 8: Synthesis of 4-{5-(aminomethyl)-2-[1-(3-hydroxypropyl)-3-methyl-1H-pyrazol-5-yl]-1,3-thiazol-4-yl}-1-methyl-1H-pyrazolo[4,3-c]pyridine-6-carboxamide (Example AF01)

To a flask containing crude N-[(2,4-dimethoxyphenyl)methyl]-1-methyl-4-[2-(3-methyl-1-{3-[(oxan-2-yl)oxy]propyl}-1H-pyrazol-5-yl)-5-{[(2-methylpropane-2-sulfinyl)amino]methyl}-1,3-thiazol-4-yl]-1H-pyrazolo[4,3-c]pyridine-6-carboxamide (AF-8) was added MeOH (0.5 mL) and TFA (0.5 mL). The reaction was heated at 50° C. and stirred overnight. At this stage, the reaction was concentrated under vacuum and the crude residue dissolved in neat trifluoroacetic acid and heated to 60° C. for 20 min. The solution was then concentrated under vacuum. The crude residue was dissolved in MeOH and 1 N NaOH (100 μL) was added. The mixture was stirred at room temperature for 15 minutes then concentrated under vacuum. The crude residue was purified via prep HPLC (Phenomenex Gemini C18 5 μm×150×21.2 mm column, at ambient temperature, 10-100% MeCN/Water with 0.1% ammonium hydroxide, 40 mL/min flowrate) to afford the title compound 4-{5-(aminomethyl)-2-[1-(3-hydroxypropyl)-3-methyl-1H-pyrazol-5-yl]-1,3-thiazol-4-yl}-1-methyl-1H-pyrazolo[4,3-c]pyridine-6-carboxamide (Example AF01) (6 mg, 30% over 4 steps). m/z (ESI+) for ($C_{19}H_{22}N_8O_2S$), 427 (M+H)$^+$ observed; $^1$H NMR (400 MHz, DMSO-$d_6$) δ ppm $^1$H NMR (600 MHz, Solvent) δ ppm 8.70 (s, 1H) 8.32 (s, 1H) 6.66 (s, 1H) 4.68-4.73 (m, 2H) 4.46-4.55 (m, 2H) 4.19 (s, 3H) 3.40-3.43 (m, 2H) 2.23 (s, 3H) 1.91-2.07 (m, 2H).

Example AF02 was synthesized according to the methods used for the synthesis of 4-{5-(aminomethyl)-2-[1-(3-hydroxypropyl)-3-methyl-1H-pyrazol-5-yl]-1,3-thiazol-4-yl}-1-methyl-1H-pyrazolo[4,3-c]pyridine-6-carboxamide (Example AF01) (Scheme AF-1) with non-critical changes or substitutions to the exemplified procedures that someone who skilled in the art would be able to realize.

| Example Number | Intermediates | Structure/Name | Analytical Data |
|---|---|---|---|
| AF02 | AF-2 & Int-TG-28 were used in step 2 | 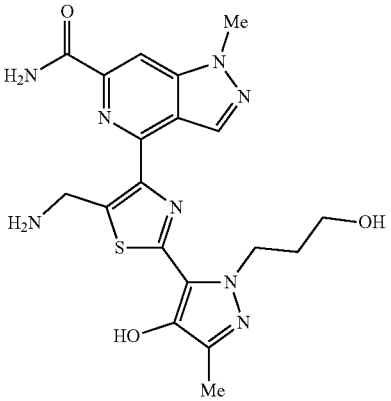<br>4-{5-(aminomethyl)-2-[4-hydroxy-1-(3-hydroxypropyl)-3-methyl-1H-pyrazol-5-yl]-1,3-thiazol-4-yl}-1-methyl-1H-pyrazolo[4,3-c]pyridine-6-carboxamide | $^1$H NMR (400 MHz, DMSO-$d_6$) δ = 8.68 (s, 1H), 8.34 (d, J = 0.9 Hz, 1H), 8.28-8.20 (m, 1H), 8.06 (br s, 1H), 7.91 (br s, 1H), 4.71 (t, J = 7.1 Hz, 2H), 4.50 (s, 2H), 4.19 (s, 3H), 3.38 (t, J = 6.4 Hz, 2H), 2.17 (s, 3H), 1.92 (quin, J = 6.7 Hz, 2H); m/z (ESI+) for $C_{19}H_{22}N_8O_3S$, 443.3 (M + H)$^+$ observed. |

Example AG01: Preparation of 4-[2-(1-ethyl-3-hydroxy-4-methyl-1H-pyrrol-2-yl)-1,3-thiazol-4-yl]-1-methyl-1H-pyrazolo[4,3-c]pyridine-6-carboxamide According to Scheme AG

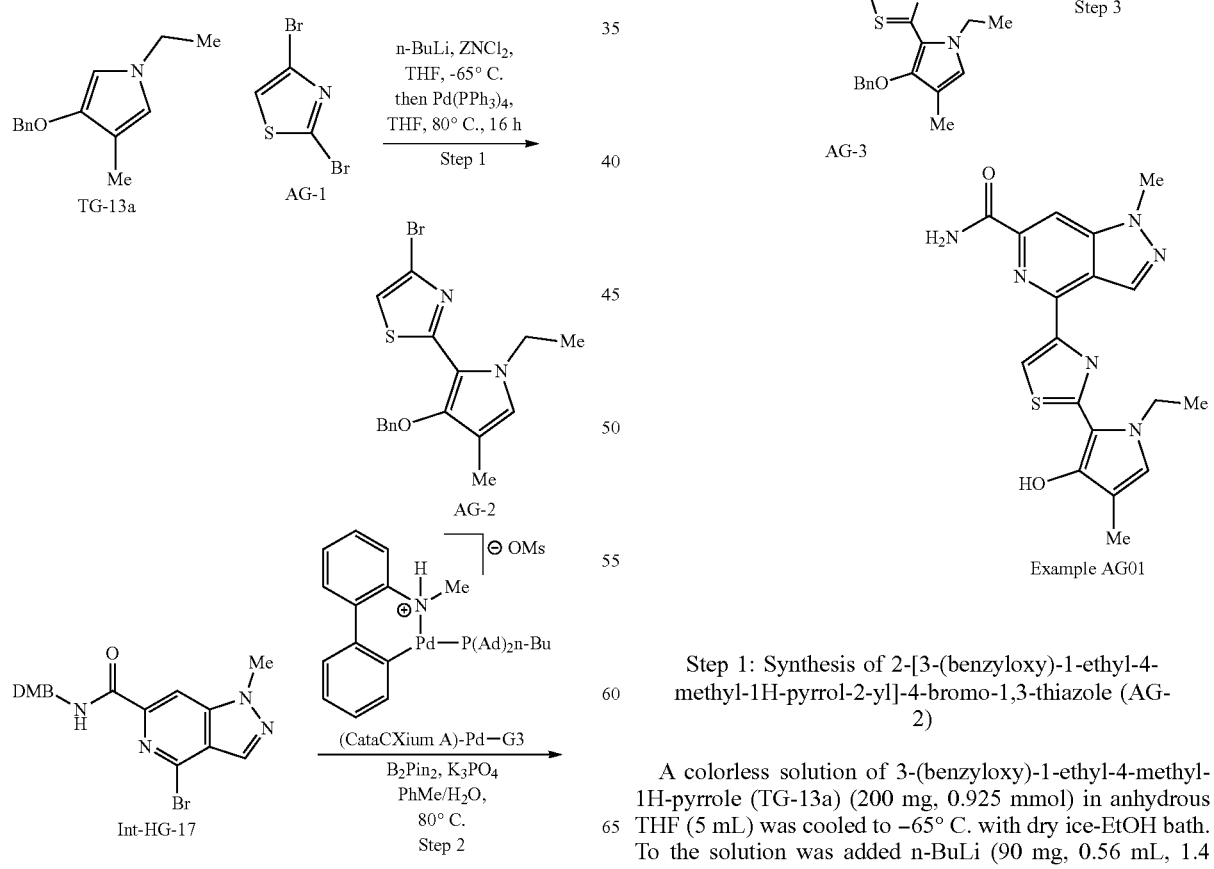

Step 1: Synthesis of 2-[3-(benzyloxy)-1-ethyl-4-methyl-1H-pyrrol-2-yl]-4-bromo-1,3-thiazole (AG-2)

A colorless solution of 3-(benzyloxy)-1-ethyl-4-methyl-1H-pyrrole (TG-13a) (200 mg, 0.925 mmol) in anhydrous THF (5 mL) was cooled to −65° C. with dry ice-EtOH bath. To the solution was added n-BuLi (90 mg, 0.56 mL, 1.4 mmol) drop-wise to maintain the inner temperature below −60° C. The resulting yellow solution was stirred for 30 min. Then ZnCl$_2$ (190 mg, 0.70 mL, 1.4 mmol, 2.5 M in 2-MeTHF) was added drop-wise to maintain the inner temperature below −60° C. A light-yellow slurry was formed. The reaction was stirred at the temperature for 10 min then the ice bath was removed and the reaction allowed to warm gradually to room temperature with stirring for 30 minutes. A colorless solution was formed. Then 2,4-dibromo-1,3-thiazole (AG-1) (247 mg, 1.02 mmol) and Pd(PPh$_3$)$_4$ (107 mg, 0.0925 mmol) were added. The resulting mixture was flushed with N$_2$ for 2 min, sealed, and heated at 80° C. for 16 hrs. The resulting yellow solution was concentrated under vacuum and the crude residue purified via flash column chromatography (12 g SiO$_2$, Combi-Flash, 5%-20% EtOAc/Pet. Ether) to afford the title compound 2-[3-(benzyloxy)-1-ethyl-4-methyl-1H-pyrrol-2-yl]-4-bromo-1,3-thiazole (AG-2) (174 mg, 49%) as a yellow solid. $^1$H NMR (400 MHz, CHLOROFORM-d) δ=7.50-7.33 (m, 5H), 7.23 (s, 1H), 4.97 (s, 2H), 4.63 (q, J=7.1 Hz, 2H), 2.23 (s, 3H), 1.43 (t, J=7.2 Hz, 3H).

Step 2: Synthesis of 4-{2-[3-(benzyloxy)-1-ethyl-4-methyl-1H-pyrrol-2-yl]-1,3-thiazol-4-yl}-N-[(2,4-dimethoxyphenyl)methyl]-1-methyl-1H-pyrazolo[4,3-c]pyridine-6-carboxamide (AG-3)

A flask was charged with 2-[3-(benzyloxy)-1-ethyl-4-methyl-1H-pyrrol-2-yl]-4-bromo-1,3-thiazole (AG-2) (170 mg, 0.449 mmol), 4-bromo-N-[(3,4-dimethylphenyl)methyl]-1-methyl-1H-pyrazolo[4,3-c]pyridine-6-carboxamide (Int-HG-17) (182 mg, 0.449 mmol), K$_3$PO$_4$ (286 mg, 1.35 mmol), B$_2$Pin$_2$ (228 mg, 0.899 mmol), (CataCXium A)-Pd-G3 (32.7 mg, 0.0449 mmol) and toluene (2.50 mL), H$_2$O (0.50 mL). The resulting mixture was flushed with N$_2$ for 2 min, sealed, and heated at 80° C. for 16 hrs. The resulting mixture was diluted with EtOAc (10 mL), dried over anhydrous Na$_2$SO$_4$, filtered through Celite, and concentrated under vacuum. The crude residue was purified via flash column chromatography (20 g SiO$_2$, Combi-Flash, 15%-100% EtOAc/Pet. Ether) to afford the title compound 4-{2-[3-(benzyloxy)-1-ethyl-4-methyl-1H-pyrrol-2-yl]-1,3-thiazol-4-yl}-N-[(2,4-dimethoxyphenyl)methyl]-1-methyl-1H-pyrazolo[4,3-c]pyridine-6-carboxamide (AG-3) (126 mg, 45%) as a yellow gum. m/z (ESI+) for (C$_{34}$H$_{34}$N6O$_4$S), 624.1 (M+H)$^+$ observed.

Step 3: Synthesis of 4-[2-(1-ethyl-3-hydroxy-4-methyl-1H-pyrrol-2-yl)-1,3-thiazol-4-yl]-1-methyl-1H-pyrazolo[4,3-c]pyridine-6-carboxamide (Example AG01)

To a mixture of 4-{2-[3-(benzyloxy)-1-ethyl-4-methyl-1H-pyrrol-2-yl]-1,3-thiazol-4-yl}-N-[(2,4-dimethoxyphenyl)methyl]-1-methyl-1H-pyrazolo[4,3-c]pyridine-6-carboxamide (AG-3) (126 mg, 0.202 mmol) in HFIP (2.00 mL) was added MsOH (194 mg, 2.02 mmol). The resulting mixture was heated at 50° C. for 2.5 hrs. The resulting mixture was concentrated under vacuum. The crude residue was diluted with DMF (2 mL), neutralized with NH$_4$OH (28% solution in H$_2$O), and purified via prep-HPLC (YMC Triart C18 250×50 mm×7 µm column, 8%-48% MeCN/H$_2$O with 0.05% NH$_4$OH, 60 mL/min flowrate, 2 injections). The product containing fractions were lyophilized to afford the title compound (18.46 mg, 23%) as a white solid. m/z (ESI+) for (C$_{18}$H$_{18}$N6O$_2$S), 384.1 (M+H)$^+$ observed; $^1$H NMR (400 MHz, DMSO-d$_6$) δ=9.24 (s, 1H), 8.74 (d, J=1.0 Hz, 1H), 8.63 (br s, 1H), 8.32 (d, J=0.8 Hz, 1H), 7.79 (br d, J=2.0 Hz, 1H), 4.75 (q, J=7.0 Hz, 2H), 4.19 (s, 3H), 2.18 (s, 3H), 1.42 (t, J=7.2 Hz, 3H).

Example AH01: Preparation of 4-{3-[1-(3-aminopropyl)-4-hydroxy-3-methyl-1H-pyrazol-5-yl]-1H-1,2,4-triazol-5-yl}-1-methyl-1H-pyrazolo[4,3-c]pyridine-6-carboxamide According to Scheme AH

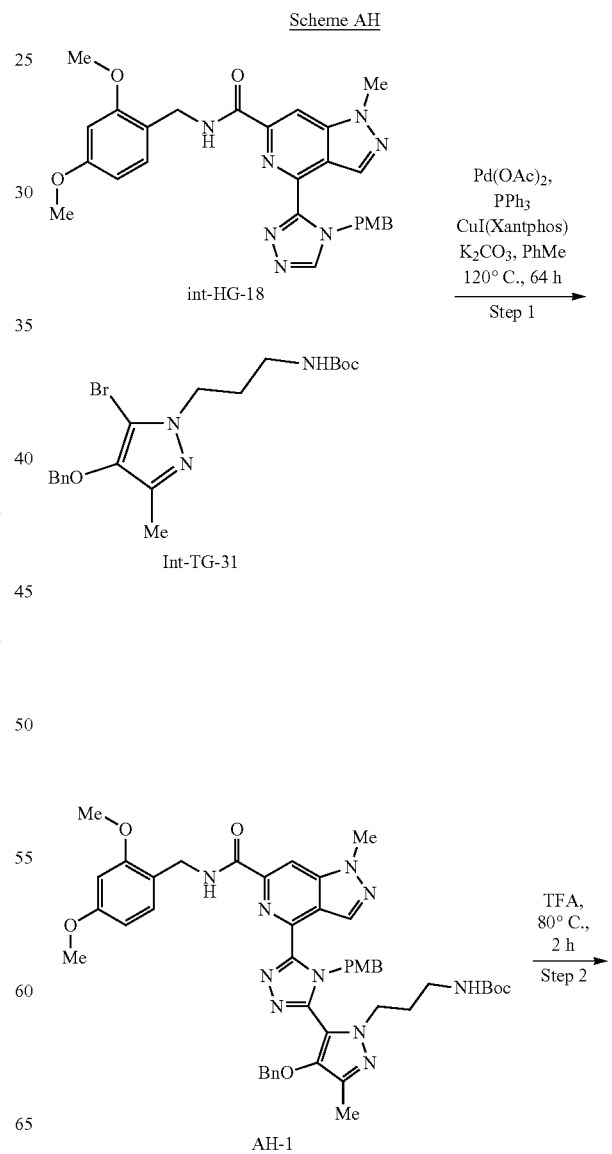

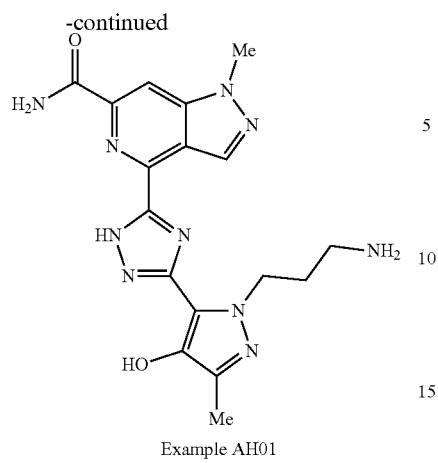

Example AH01

Step 1: Synthesis of tert-butyl {3-[4-(benzyloxy)-5-{5-(6-{[(2,4-dimethoxyphenyl)methyl]carbamoyl}-1-methyl-1H-pyrazolo[4,3-c]pyridin-4-yl)-4-[(4-methoxyphenyl)methyl]-4H-1,2,4-triazol-3-yl}-3-methyl-1H-pyrazol-1-yl]propyl}carbamate (AH-1)

A vial was charged with tert-butyl {3-[4-(benzyloxy)-5-bromo-3-methyl-1H-pyrazol-1-yl]propyl}carbamate (Int-TG-31)(121 mg, 0.285 mmol), N-[(2,4-dimethoxyphenyl)methyl]-4-{4-[(4-methoxyphenyl)methyl]-4H-1,2,4-triazol-3-yl}-1-methyl-1H-pyrazolo[4,3-c]pyridine-6-carboxamide (Int-HG-17) (176 mg, 0.342 mmol), Pd(OAc)$_2$ (7.1 mg, 0.032 mmol), PPh$_3$ (15.0 mg, 0.0570 mmol), K$_2$CO$_3$ (117.0 mg, 0.847 mmol), CuI (Xantphos) (67 mg, 0.0.087 mmol) and toluene (5 mL). The reaction mixture was degassed at room temperature for ~1 minute, then heated at 120° C. for 16 hours. LCMS analysis showed that starting material still remained thus the reaction was stirred at 120° C. for an additional 48 hours under nitrogen atmosphere. At this stage, the reaction was filtered and concentrated in vacuo. The crude residue was purified via prep-TLC (100% EtOAc) to afford the title compound tert-butyl {3-[4-(benzyloxy)-5-{5-(6-{[(2,4-dimethoxyphenyl)methyl]carbamoyl}-1-methyl-1H-pyrazolo[4,3-c]pyridin-4-yl)-4-[(4-methoxyphenyl)methyl]-4H-1,2,4-triazol-3-yl}-3-methyl-1H-pyrazol-1-yl]propyl}carbamate (AH-1) (85 mg, 35%) as a colorless gum. This material was used in the next step without further purification. m/z (ESI+) for (C$_{46}$H$_{52}$N$_{10}$O$_7$), 857.4 (M+H)$^+$ observed.

Step 2: Synthesis of 4-{3-[1-(3-aminopropyl)-4-hydroxy-3-methyl-1H-pyrazol-5-yl]-1H-1,2,4-triazol-5-yl}-1-methyl-1H-pyrazolo[4,3-c]pyridine-6-carboxamide (Example AH01)

A light yellow solution of tert-butyl {3-[4-(benzyloxy)-5-{5-(6-{[(2,4-dimethoxyphenyl)methyl]carbamoyl}-1-methyl-1H-pyrazolo[4,3-c]pyridin-4-yl)-4-[(4-methoxyphenyl)methyl]-4H-1,2,4-triazol-3-yl}-3-methyl-1H-pyrazol-1-yl]propyl}carbamate (AH-1) (85 mg, 0.099 mmol) in TFA (2 mL) was stirred at 80° C. for 2 hours. LCMS analysis showed consumption of starting material. The reaction was concentrated in vacuo and the crude residue was purified by Prep-HPLC (Waters Xbridge BEH C18 100×30 mm×10 µm column, 0%-37% MeCN/H$_2$O with 0.05% NH$_4$OH, 25 mL/min, 4 injections). Product containing fractions were collected and lyophilized to afford the title compound 4-{3-[1-(3-aminopropyl)-4-hydroxy-3-methyl-1H-pyrazol-5-yl]-1H-1,2,4-triazol-5-yl}-1-methyl-1H-pyrazolo[4,3-c]pyridine-6-carboxamide (Example AH01) (22.34 mg, 57%) as a white TFA salt. m/z (ESI+) for (C$_{17}$H$_{20}$N$_{10}$O$_2$), 397.3 (M+H)$^+$ observed; $^1$H NMR (400 MHz, DMSO-d$_6$) δ=15.38 (s, 1H), 8.86 (br d, J=1.7 Hz, 1H), 8.83 (s, 1H), 8.49 (s, 1H), 8.11 (s, 1H), 7.89 (br s, 1H), 7.65 (br s, 3H), 4.53 (br t, J=6.4 Hz, 2H), 4.23 (s, 3H), 2.86-2.71 (m, 2H), 2.15 (s, 3H), 2.12-2.03 (m, 2H); $^{19}$F NMR (377 MHz, DMSO-d$_6$) δ=−73.45 (s, 1F).

Examples YY01-YY35 were prepared according to synthetic routes and synthetic methods analogous to those described herein, with non-critical changes or substitutions to the exemplified procedures that one skilled in the art would be able to realize.

| Example Number | Structure | Name | Analytical Data |
|---|---|---|---|
| YY01 | ![structure] | 4-[5-(1-ethyl-3-methyl-1H-pyrazol-5-yl)-4H-1,2,4-triazol-3-yl]-1-methyl-1H-benzimidazole-6-carboxamide | LCMS [M + H] = 351.1 observed; $^1$H NMR (400 MHz, DMSO-d$_6$) ä = 14.23 (br d, J = 4.5 Hz, 1H), 8.60 (s, 1H), 8.52 (d, J = 1.5 Hz, 1H), 8.35 (d, J = 1.3 Hz, 1H), 8.25-8.13 (m, 1H), 7.49 (br s, 1H), 6.61 (s, 1H), 4.64 (q, J = 7.3 Hz, 2H), 3.99 (s, 3H), 2.23 (s, 3H), 1.39 (t, J = 7.2 Hz, 3H) |

| Example Number | Structure | Name | Analytical Data |
|---|---|---|---|
| YY02 | 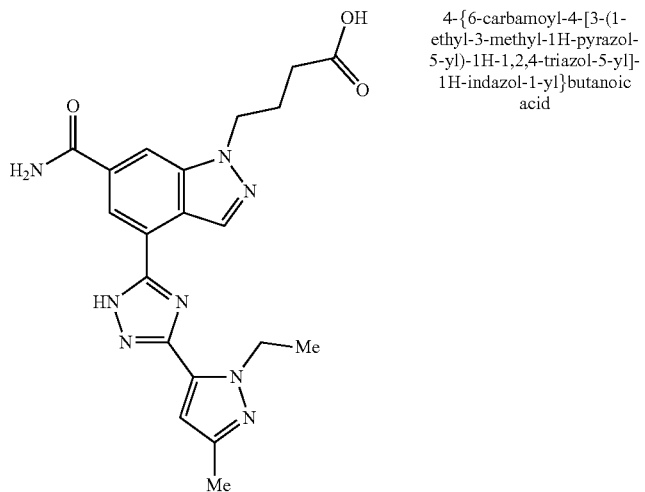 | 4-{6-carbamoyl-4-[3-(1-ethyl-3-methyl-1H-pyrazol-5-yl)-1H-1,2,4-triazol-5-yl]-1H-indazol-1-yl}butanoic acid | LCMS [M + H] = 422.8 observed |
| YY03 | 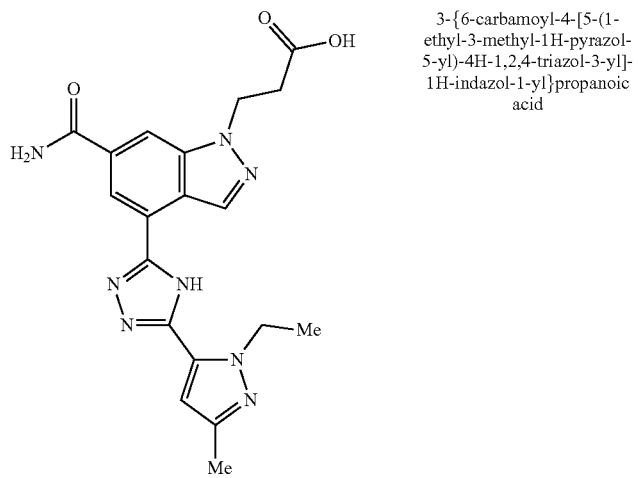 | 3-{6-carbamoyl-4-[5-(1-ethyl-3-methyl-1H-pyrazol-5-yl)-4H-1,2,4-triazol-3-yl]-1H-indazol-1-yl}propanoic acid | LCMS [M + H] = 409.2 observed |
| YY04 | 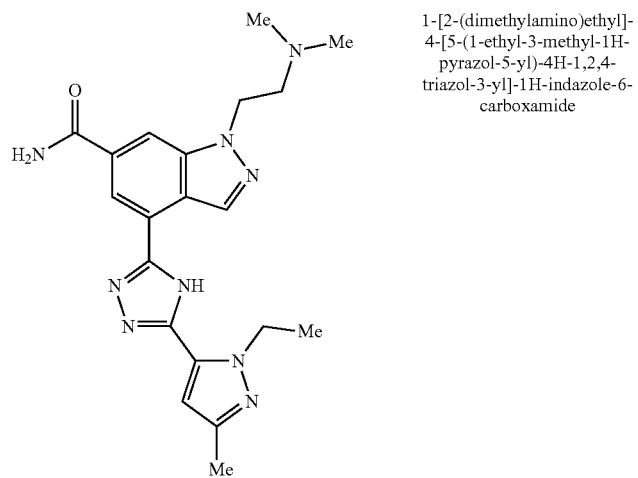 | 1-[2-(dimethylamino)ethyl]-4-[5-(1-ethyl-3-methyl-1H-pyrazol-5-yl)-4H-1,2,4-triazol-3-yl]-1H-indazole-6-carboxamide | LCMS [M + H] = 407.9 observed |

| Example Number | Structure | Name | Analytical Data |
|---|---|---|---|
| YY05 | 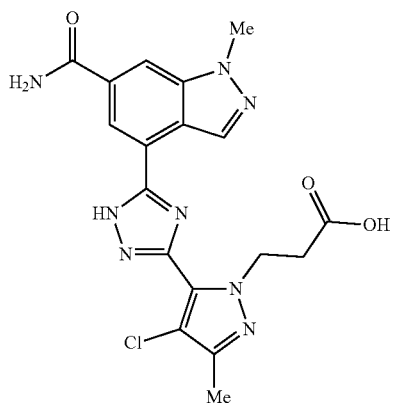 | 3-{5-[5-(6-carbamoyl-1-methyl-1H-indazol-4-yl)-1H-1,2,4-triazol-3-yl]-4-chloro-3-methyl-1H-pyrazol-1-yl}propanoic acid | LCMS [M + H] = 429.1 observed |
| YY06 | 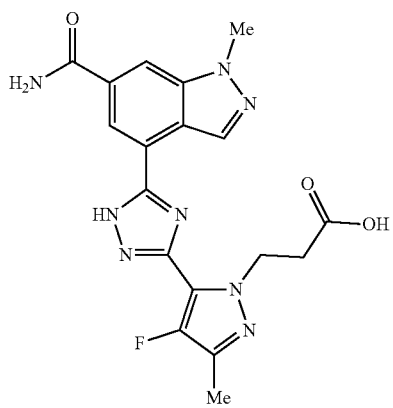 [SMILES: Cc1nn(CCC(=O)O)c(-c2n[nH]c(-c3cc(C(N)=O)cc4c3cnn4C)n2)c1Cl] | 3-{5-[5-(6-carbamoyl-1-methyl-1H-indazol-4-yl)-1H-1,2,4-triazol-3-yl]-4-fluoro-3-methyl-1H-pyrazol-1-yl}propanoic acid | LCMS [M + H] = 412.8 observed |
| YY07 | 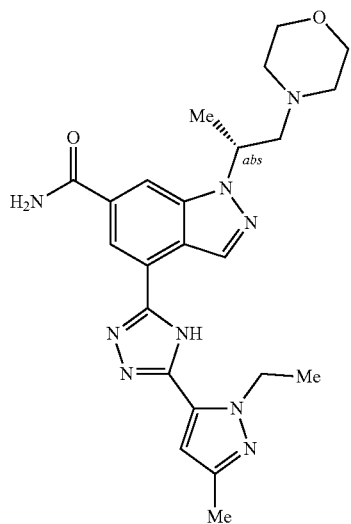 [SMILES: CCn1nc(C)cc1-c1nnc(-c2cc(C(N)=O)cc3c2cnn3[C@H](C)CN2CCOCC2)[nH]1] | 4-[5-(1-ethyl-3-methyl-1H-pyrazol-5-yl)-4H-1,2,4-triazol-3-yl]-1-[(2R)-1-(morpholin-4-yl)propan-2-yl]-1H-indazole-6-carboxamide | LCMS [M + H] = 464 observed |

| Example Number | Structure | Name | Analytical Data |
|---|---|---|---|
| YY08 | 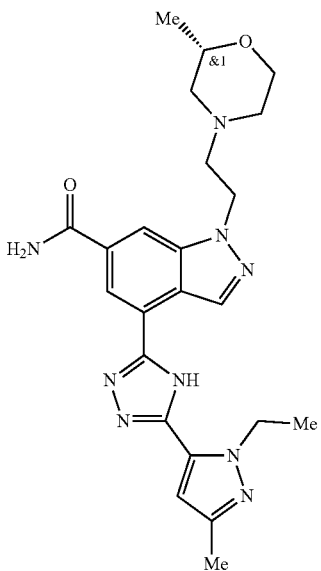 [SMILES: CCn1nc(C)cc1-c1nnc(-c2cc(C(N)=O)cc3c2cnn3CCN2CCO[C@@H](C)C2)[nH]1] | 4-[5-(1-ethyl-3-methyl-1H-pyrazol-5-yl)-4H-1,2,4-triazol-3-yl]-1-{2-[(2S)-2-methylmorpholin-4-yl]ethyl}-1H-indazole-6-carboxamide | LCMS [M + H] = 464 observed |
| YY09 | 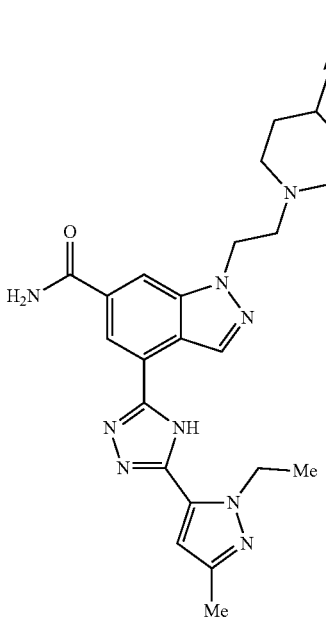 | 1-[2-(4-cyanopiperidin-1-yl)ethyl]-4-[5-(1-ethyl-3-methyl-1H-pyrazol-5-yl)-4H-1,2,4-triazol-3-yl]-1H-indazole-6-carboxamide | LCMS [M + H] = 473 observed |

| Example Number | Structure | Name | Analytical Data |
|---|---|---|---|
| YY10 | 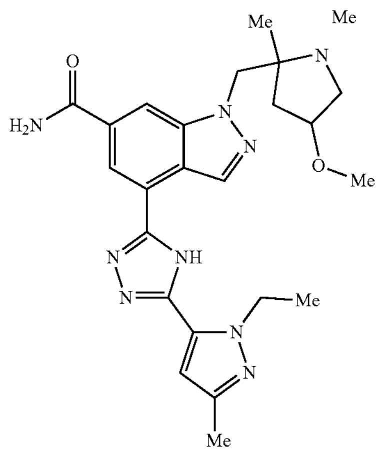 [SMILES: CCn1nc(C)cc1-c1nnc(-c2cc(C(N)=O)cc3c2cnn3CC2(C)CC(OC)CN2)[nH]1 ; "Me"] | 4-[5-(1-ethyl-3-methyl-1H-pyrazol-5-yl)-4H-1,2,4-triazol-3-yl]-1-[(4-methoxy-1,2-dimethylpyrrolidin-2-yl)methyl]-1H-indazole-6-carboxamide | LCMS [M + H] = 478 observed |
| YY11 | 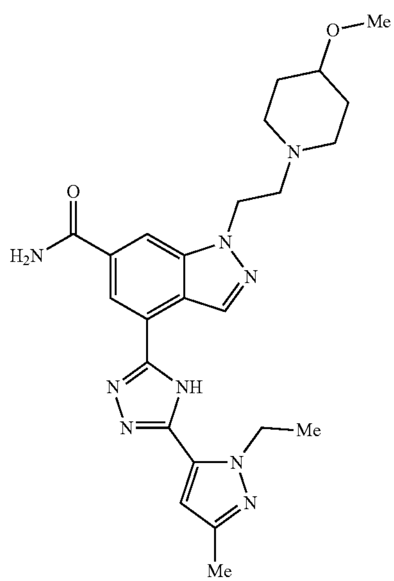 [SMILES: CCn1nc(C)cc1-c1nnc(-c2cc(C(N)=O)cc3c2cnn3CCN2CCC(OC)CC2)[nH]1] | 4-[5-(1-ethyl-3-methyl-1H-pyrazol-5-yl)-4H-1,2,4-triazol-3-yl]-1-[2-(4-methoxypiperidin-1-yl)ethyl]-1H-indazole-6-carboxamide | LCMS [M + H] = 478 observed |
| YY12 | 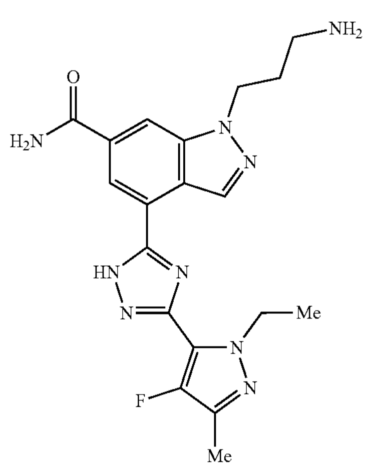 [SMILES: CCn1nc(C)c(F)c1-c1n[nH]c(-c2cc(C(N)=O)cc3c2cnn3CCCN)n1] | 1-(3-aminopropyl)-4-[3-(1-ethyl-4-fluoro-3-methyl-1H-pyrazol-5-yl)-1H-1,2,4-triazol-5-yl]-1H-indazole-6-carboxamide | LCMS [M + H] = 412.2 observed |

| Example Number | Structure | Name | Analytical Data |
|---|---|---|---|
| YY13 | 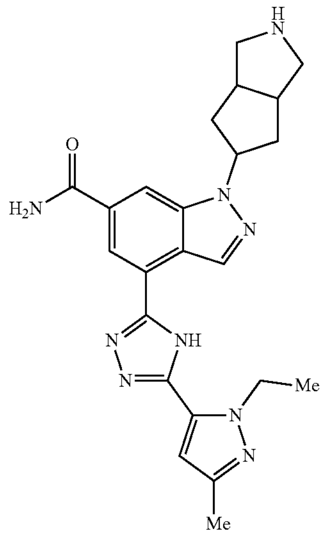 [SMILES: CCn1nc(C)cc1-c1nnc(-c2cc(C(N)=O)cc3c2cnn3C2CC3CNCC3C2)[nH]1] | 4-[5-(1-ethyl-3-methyl-1H-pyrazol-5-yl)-4H-1,2,4-triazol-3-yl]-1-(octahydrocyclopenta[c]pyrrol-5-yl)-1H-indazole-6-carboxamide | LCMS [M + H] = 446 observed |
| YY14 | 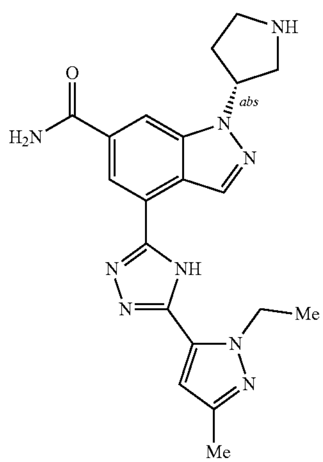 [SMILES: CCn1nc(C)cc1-c1nnc(-c2cc(C(N)=O)cc3c2cnn3[C@@H]2CCNC2)[nH]1] | 4-[5-(1-ethyl-3-methyl-1H-pyrazol-5-yl)-4H-1,2,4-triazol-3-yl]-1-[(3R)-pyrrolidin-3-yl]-1H-indazole-6-carboxamide | LCMS [M + H] = 406 observed |
| YY15 | 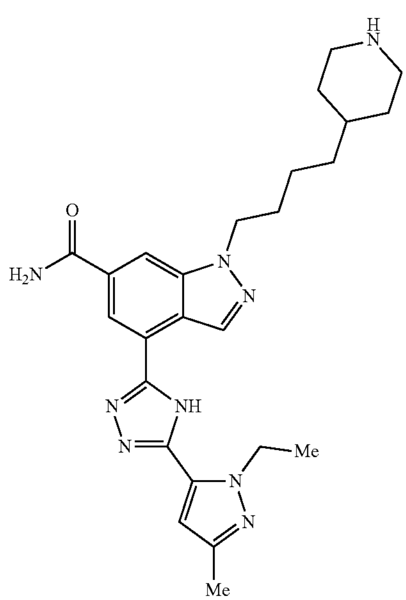 [SMILES: CCn1nc(C)cc1-c1nnc(-c2cc(C(N)=O)cc3c2cnn3CCCCC2CCNCC2)[nH]1] | 4-[5-(1-ethyl-3-methyl-1H-pyrazol-5-yl)-4H-1,2,4-triazol-3-yl]-1-[4-(piperidin-4-yl)butyl]-1H-indazole-6-carboxamide | LCMS [M + H] = 476 observed |

-continued

| Example Number | Structure | Name | Analytical Data |
|---|---|---|---|
| YY16 | 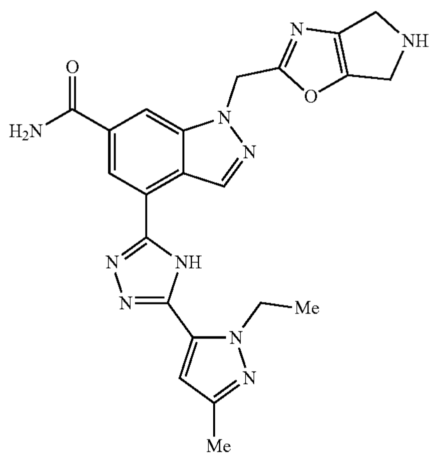 [SMILES: CCn1nc(C)cc1-c1nnc(-c2cc(C(N)=O)cc3c2cnn3Cc2nc3c(o2)CNC3)[nH]1] | 1-[(5,6-dihydro-4H-pyrrolo[3,4-d][1,3]oxazol-2-yl)methyl]-4-[5-(1-ethyl-3-methyl-1H-pyrazol-5-yl)-4H-1,2,4-triazol-3-yl]-1H-indazole-6-carboxamide | LCMS [M + H] = 459 observed |
| YY17 | 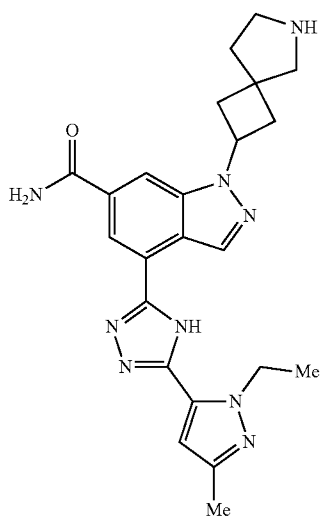 [SMILES: CCn1nc(C)cc1-c1nnc(-c2cc(C(N)=O)cc3c2cnn3C2CC3(CCNC3)C2)[nH]1] | 1-(6-azaspiro[3.4]octan-2-yl)-4-[5-(1-ethyl-3-methyl-1H-pyrazol-5-yl)-4H-1,2,4-triazol-3-yl]-1H-indazole-6-carboxamide | LCMS [M + H] = 446 observed |
| YY18 | 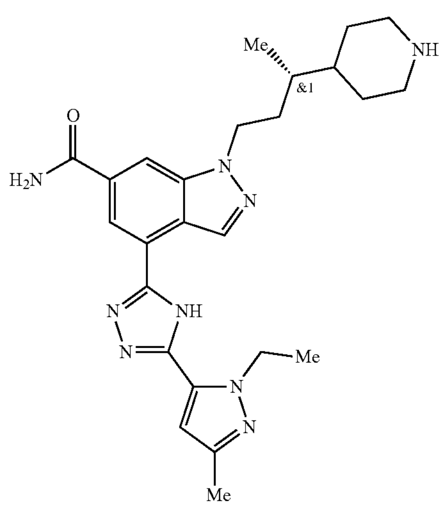 [SMILES: CCn1nc(C)cc1-c1nnc(-c2cc(C(N)=O)cc3c2cnn3CC[C@H](C)C2CCNCC2)[nH]1] | 4-[5-(1-ethyl-3-methyl-1H-pyrazol-5-yl)-4H-1,2,4-triazol-3-yl]-1-[(3S)-3-(piperidin-4-yl)butyl]-1H-indazole-6-carboxamide | LCMS [M + H] = 476 observed |

| Example Number | Structure | Name | Analytical Data |
|---|---|---|---|
| YY19 | 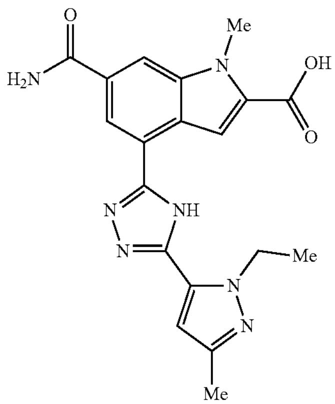 [SMILES: CCn1nc(C)cc1-c1nnc(-c2cc(C(N)=O)cc3c2cc(C(=O)O)n3C)[nH]1] | 6-carbamoyl-4-[5-(1-ethyl-3-methyl-1H-pyrazol-5-yl)-4H-1,2,4-triazol-3-yl]-1-methyl-1H-indole-2-carboxylic acid | $^1$H NMR (600 MHz, DMSO-d$_6$) δ ppm 8.38 (br s, 1 H) 8.21 (br s, 1 H) 8.08 (br s, 1 H) 7.74 (br s, 1 H) 7.33 (br s, 1 H) 6.65 (br s, 1 H) 4.67 (br d, J = 6.60 Hz, 2H) 4.17 (br s, 3 H) 2.23 (s, 3 H) 1.43 (br t, J = 6.79 Hz, 3 H) |
| YY20 | 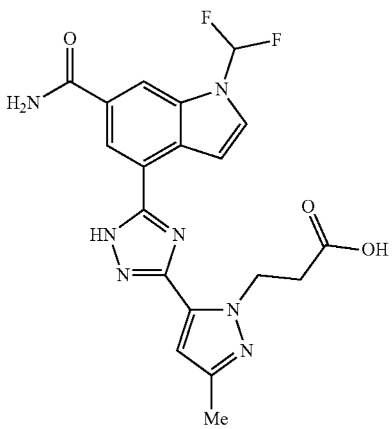 [SMILES: Cc1cc(-c2n[nH]c(-c3cc(C(N)=O)cc4c3ccn4C(F)F)n2)n(CCC(=O)O)n1] | 3-(5-{5-[6-carbamoyl-1-(difluoromethyl)-1H-indazol-4-yl]-1H-1,2,4-triazol-3-yl}-3-methyl-1H-pyrazol-1-yl)propanoic acid | LCMS [M + H] = 431.1 observed |
| YY21 | 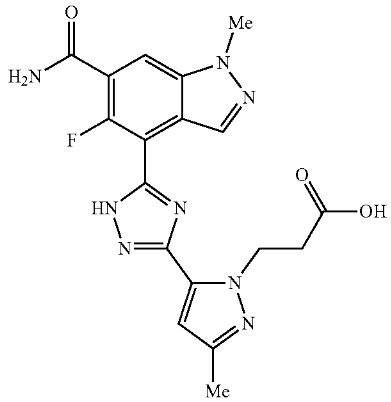 [SMILES: Cc1cc(-c2n[nH]c(-c3c(F)c(C(N)=O)cc4c3cnn4C)n2)n(CCC(=O)O)n1] | 3-{5-[5-(6-carbamoyl-5-fluoro-1-methyl-1H-indazol-4-yl)-1H-1,2,4-triazol-3-yl]-3-methyl-1H-pyrazol-1-yl}propanoic acid | LCMS [M + H] = 413.1 observed |

-continued

| Example Number | Structure | Name | Analytical Data |
|---|---|---|---|
| YY22 | 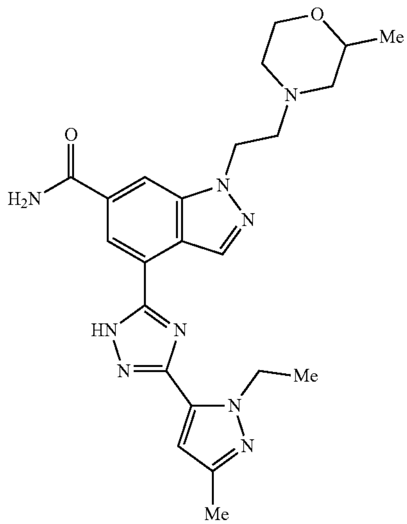 [SMILES: CCn1nc(C)cc1-c1n[nH]c(-c2cc(C(N)=O)cc3c2cnn3CCN2CCOC(C)C2)n1] | 4-[3-(1-ethyl-3-methyl-1H-pyrazol-5-yl)-1H-1,2,4-triazol-5-yl]-1-[2-(2-methylmorpholin-4-yl)ethyl]-1H-indazole-6-carboxamide | LCMS [M + H] = 464.4 observed |
| YY23 | 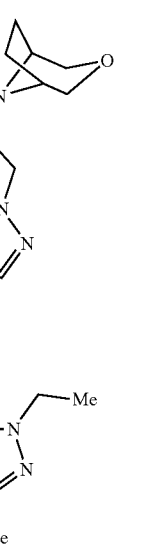 | 4-[3-(1-ethyl-3-methyl-1H-pyrazol-5-yl)-1H-1,2,4-triazol-5-yl]-1-[2-(3-oxa-8-azabicyclo[3.2.1]octan-8-yl)ethyl]-1H-indazole-6-carboxamide | LCMS [M + H] = 476.4 observed |
| YY24 | 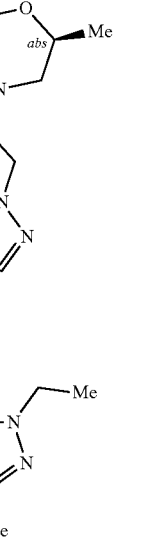 | 4-[3-(1-ethyl-3-methyl-1H-pyrazol-5-yl)-1H-1,2,4-triazol-5-yl]-1-{2-[(2S)-2-methylmorpholin-4-yl]ethyl}-1H-indazole-6-carboxamide | LCMS [M + H] = 464.4 observed |

| Example Number | Structure | Name | Analytical Data |
|---|---|---|---|
| YY25 | 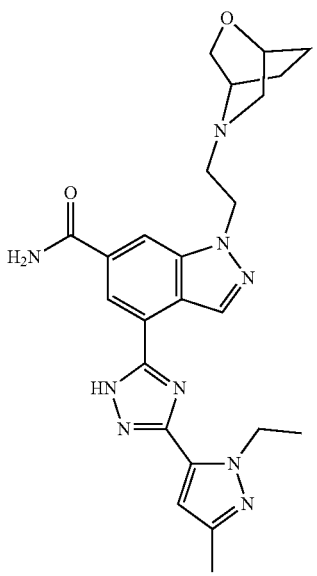 [SMILES: CCn1nc(C)cc1-c1n[nH]c(-c2cc(C(N)=O)cc3c2cnn3CCN2CC3CCC2CO3)n1] | 4-[3-(1-ethyl-3-methyl-1H-pyrazol-5-yl)-1H-1,2,4-triazol-5-yl]-1-[2-(2-oxa-5-azabicyclo[2.2.2]octan-5-yl)ethyl]-1H-indazole-6-carboxamide | LCMS [M + H] = 476.4 observed |
| YY26 | 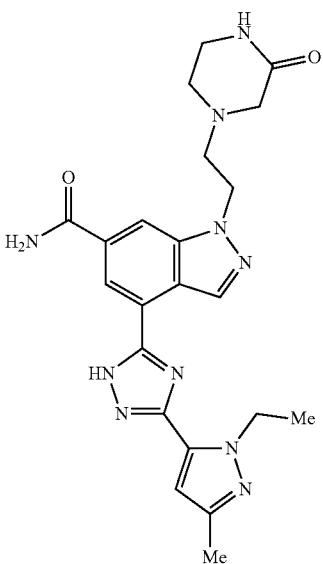 [SMILES: CCn1nc(C)cc1-c1n[nH]c(-c2cc(C(N)=O)cc3c2cnn3CCN2CCNC(=O)C2)n1] | 4-[3-(1-ethyl-3-methyl-1H-pyrazol-5-yl)-1H-1,2,4-triazol-5-yl]-1-[2-(3-oxopiperazin-1-yl)ethyl]-1H-indazole-6-carboxamide | LCMS [M + H] = 463.4 observed |

-continued

| Example Number | Structure | Name | Analytical Data |
|---|---|---|---|
| YY27 | 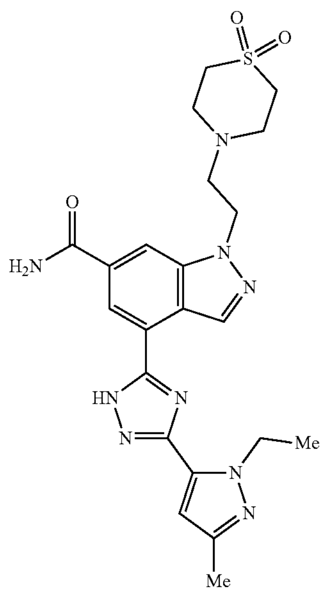 [SMILES: CCn1nc(C)cc1-c1n[nH]c(-c2cc(C(N)=O)cc3c2cnn3CCN2CCS(=O)(=O)CC2)n1] | 1-[2-(1,1-dioxo-1lambda~6~-thiomorpholin-4-yl)ethyl]-4-[3-(1-ethyl-3-methyl-1H-pyrazol-5-yl)-1H-1,2,4-triazol-5-yl]-1H-indazole-6-carboxamide | LCMS [M + H] = 498.4 observed |
| YY28 | 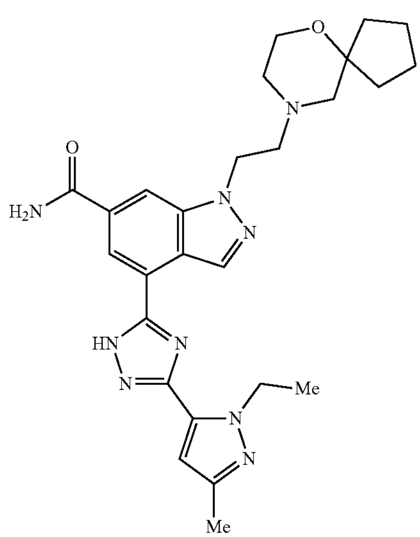 [SMILES: CCn1nc(C)cc1-c1n[nH]c(-c2cc(C(N)=O)cc3c2cnn3CCN2CCOC3(CCCC3)C2)n1] | 4-[3-(1-ethyl-3-methyl-1H-pyrazol-5-yl)-1H-1,2,4-triazol-5-yl]-1-[2-(6-oxa-9-azaspiro[4.5]decan-9-yl)ethyl]-1H-indazole-6-carboxamide | LCMS [M + H] = 504.5 observed |
| YY29 | 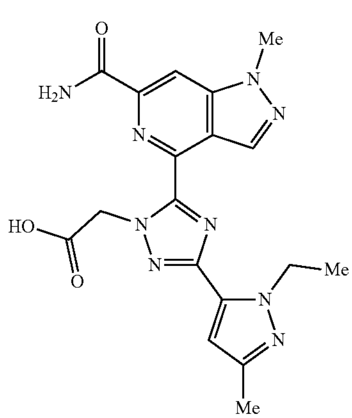 [SMILES: CCn1nc(C)cc1-c1nc(-c2nc(C(N)=O)cc3c2cnn3C)n(CC(=O)O)n1] | [5-(6-carbamoyl-1-methyl-1H-pyrazolo[4,3-c]pyridin-4-yl)-3-(1-ethyl-3-methyl-1H-pyrazol-5-yl)-1H-1,2,4-triazol-1-yl]acetic acid | LCMS [M + H] = 410.1 observed |

| Example Number | Structure | Name | Analytical Data |
|---|---|---|---|
| YY30 | 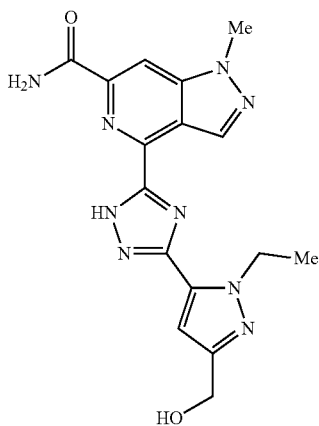 [SMILES: CCn1nc(CO)cc1-c1n[nH]c(-c2nc(C(N)=O)cc3c2cnn3C)n1] | 4-{3-[1-ethyl-3-(hydroxymethyl)-1H-pyrazol-5-yl]-1H-1,2,4-triazol-5-yl}-1-methyl-1H-pyrazolo[4,3-c]pyridine-6-carboxamide | LCMS [M + H] = 368.2 observed |
| YY31 | 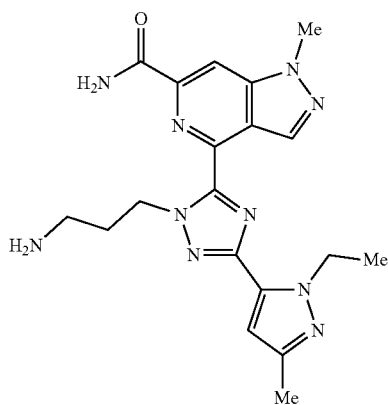 [SMILES: CCn1nc(C)cc1-c1nc(-c2nc(C(N)=O)cc3c2cnn3C)n(CCCN)n1] | 4-[1-(3-aminopropyl)-3-(1-ethyl-3-methyl-1H-pyrazol-5-yl)-1H-1,2,4-triazol-5-yl]-1-methyl-1H-pyrazolo[4,3-c]pyridine-6-carboxamide | LCMS [M + H] = 409.2 observed |
| YY32 | 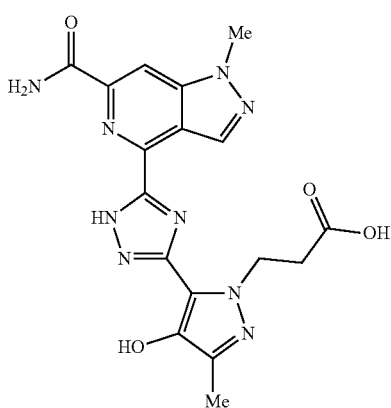 [SMILES: Cc1nn(CCC(=O)O)c(-c2n[nH]c(-c3nc(C(N)=O)cc4c3cnn4C)n2)c1O] | 3-{5-[5-(6-carbamoyl-1-methyl-1H-pyrazolo[4,3-c]pyridin-4-yl)-1H-1,2,4-triazol-3-yl]-4-hydroxy-3-methyl-1H-pyrazol-1-yl}propanoic acid | LCMS [M + H] = 412.2 observed |

| Example Number | Structure | Name | Analytical Data |
|---|---|---|---|
| YY33 | 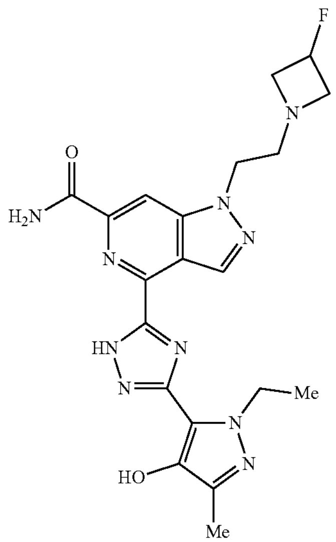 [SMILES: CCn1nc(C)c(O)c1-c1n[nH]c(-c2nc(C(N)=O)cc3c2cnn3CCN2CC(F)C2)n1] | 4-[3-(1-ethyl-4-hydroxy-3-methyl-1H-pyrazol-5-yl)-1H-1,2,4-triazol-5-yl]-1-[2-(3-fluoroazetidin-1-yl)ethyl]-1H-pyrazolo[4,3-c]pyridine-6-carboxamide | LCMS [M + H] = 455.3 observed |
| YY34 | 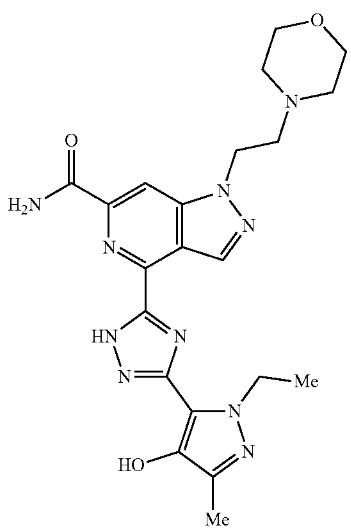 [SMILES: CCn1nc(C)c(O)c1-c1n[nH]c(-c2nc(C(N)=O)cc3c2cnn3CCN2CCOCC2)n1] | 4-[3-(1-ethyl-4-hydroxy-3-methyl-1H-pyrazol-5-yl)-1H-1,2,4-triazol-5-yl]-1-[2-(morpholin-4-yl)ethyl]-1H-pyrazolo[4,3-c]pyridine-6-carboxamide | LCMS [M + H] = 467.2 observed |
| YY35 | 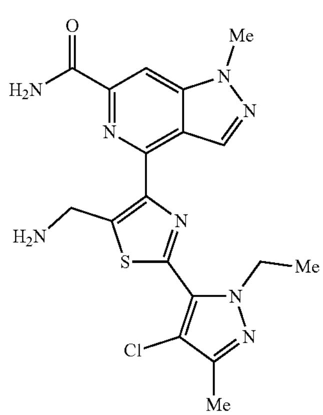 [SMILES: CCn1nc(C)c(Cl)c1-c1nc(-c2nc(C(N)=O)cc3c2cnn3C)c(CN)s1] | 4-[5-(aminomethyl)-2-(4-chloro-1-ethyl-3-methyl-1H-pyrazol-5-yl)-1,3-thiazol-4-yl]-1-methyl-1H-pyrazolo[4,3-c]pyridine-6-carboxamide | LCMS [M + H] = 432.1 observed |

Examples ZZZ01-ZZZ132 were prepared according to synthetic routes and synthetic methods methods analogous to those described herein, with non-critical changes or substitutions to the exemplified procedures that one skilled in the art would be able to realize.

| Example Number | Structure | Name | Analytical Data |
|---|---|---|---|
| ZZZ001 | 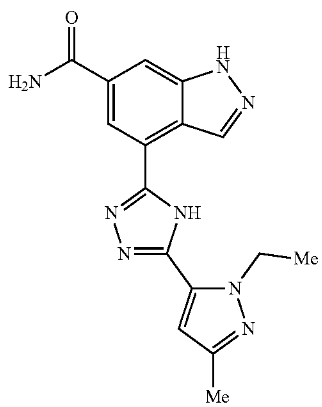 [SMILES: CCn1nc(C)cc1-c1nnc(-c2cc(C(N)=O)cc3[nH]ncc23)[nH]1] | 4-[5-(1-ethyl-3-methyl-1H-pyrazol-5-yl)-4H-1,2,4-triazol-3-yl]-1H-indazole-6-carboxamide | LCMS [M + H] = 337.2 observed |
| ZZZ002 | 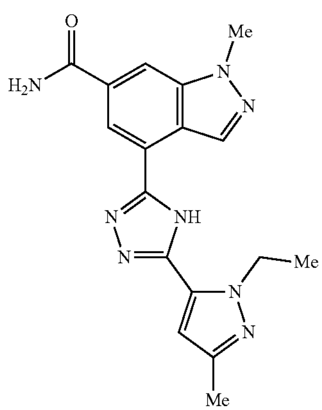 [SMILES: CCn1nc(C)cc1-c1nnc(-c2cc(C(N)=O)cc3c2cnn3C)[nH]1] | 4-[5-(1-ethyl-3-methyl-1H-pyrazol-5-yl)-4H-1,2,4-triazol-3-yl]-1-methyl-1H-benzotriazole-6-carboxamide | LCMS [M + H] = 352.2 observed |
| ZZZ003 | 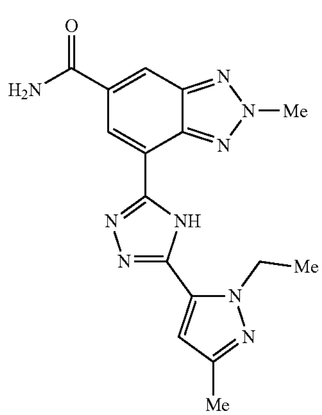 [SMILES: CCn1nc(C)cc1-c1nnc(-c2cc(C(N)=O)cc3nn(C)nc23)[nH]1] | 7-[5-(1-ethyl-3-methyl-1H-pyrazol-5-yl)-4H-1,2,4-triazol-3-yl]-2-methyl-2H-benzotriazole-5-carboxamide | LCMS [M + H] = 352.2 observed |

| Example Number | Structure | Name | Analytical Data |
|---|---|---|---|
| ZZZ004 | 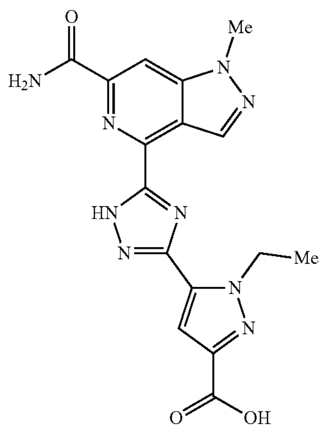 [SMILES: CCn1nc(C(=O)O)cc1-c1n[nH]c(-c2nc(C(N)=O)cc3c2cnn3C)n1] | 5-[5-(6-carbamoyl-1-methyl-1H-pyrazolo[4,3-c]pyridin-4-yl)-1H-1,2,4-triazol-3-yl]-1-ethyl-1H-pyrazole-3-carboxylic acid | LCMS [M + H] = 382 observed |
| ZZZ005 | 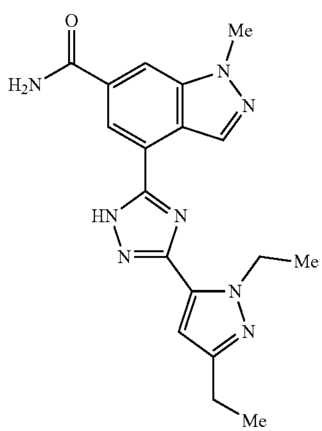 [SMILES: CCc1cc(-c2n[nH]c(-c3cc(C(N)=O)cc4c3cnn4C)n2)n(CC)n1] | 4-[3-(1,3-diethyl-1H-pyrazol-5-yl)-1H-1,2,4-triazol-5-yl]-1-methyl-1H-indazole-6-carboxamide | LCMS [M + H] = 365.1 observed |
| ZZZ006 | 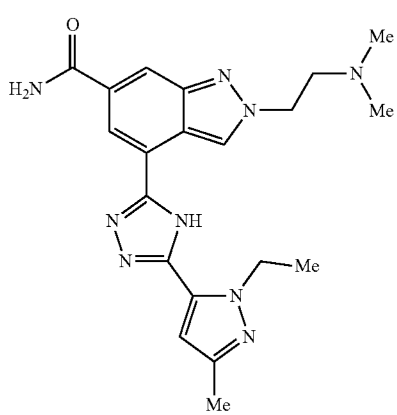 [SMILES: CCn1nc(C)cc1-c1nnc(-c2cc(C(N)=O)cc3nn(CCN(C)C)cc23)[nH]1] | 2-[2-(dimethylamino)ethyl]-4-[5-(1-ethyl-3-methyl-1H-pyrazol-5-yl)-4H-1,2,4-triazol-3-yl]-2H-indazole-6-carboxamide | LCMS [M + H] = 408.1 observed |

-continued

| Example Number | Structure | Name | Analytical Data |
|---|---|---|---|
| ZZZ007 | 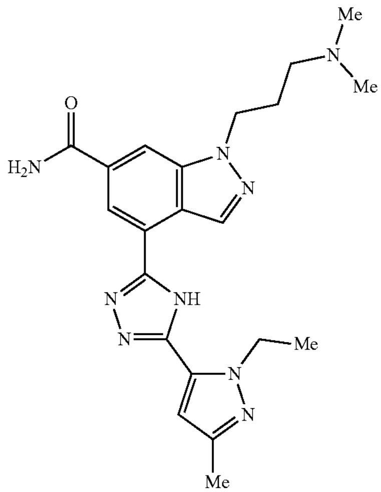 [SMILES: CCn1nc(C)cc1-c1nnc(-c2cc(C(N)=O)cc3c2cnn3CCCN(C)C)[nH]1] | 1-[3-(dimethylamino)propyl]-4-[5-(1-ethyl-3-methyl-1H-pyrazol-5-yl)-4H-1,2,4-triazol-3-yl]-1H-indazole-6-carboxamide | LCMS [M + H] = 421.9 observed |
| ZZZ008 | 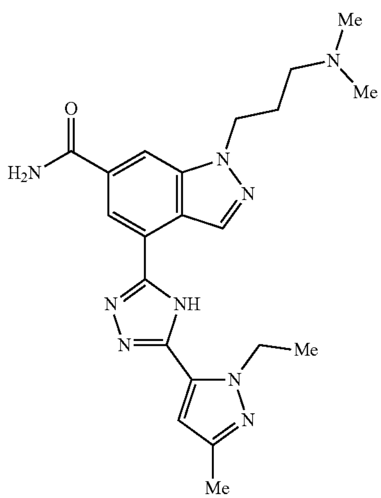 [SMILES: CCn1nc(C)cc1-c1nnc(-c2cc(C(N)=O)cc3c2cnn3CCCN(C)C)[nH]1] | 2-[3-(dimethylamino)propyl]-4-[5-(1-ethyl-3-methyl-1H-pyrazol-5-yl)-4H-1,2,4-triazol-3-yl]-2H-indazole-6-carboxamide | LCMS [M + H] = 422.3 observed |
| ZZZ009 | 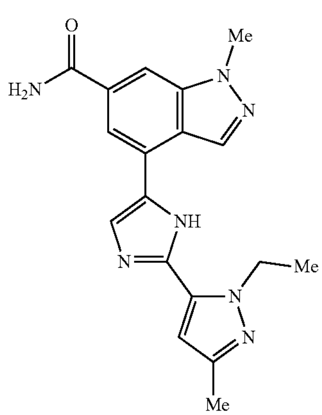 [SMILES: CCn1nc(C)cc1-c1ncc(-c2cc(C(N)=O)cc3c2cnn3C)[nH]1] | 4-[2-(1-ethyl-3-methyl-1H-pyrazol-5-yl)-1H-imidazol-5-yl]-1-methyl-1H-indazole-6-carboxamide | LCMS [M + H] = 350.1 observed |

-continued

| Example Number | Structure | Name | Analytical Data |
|---|---|---|---|
| ZZZ010 | 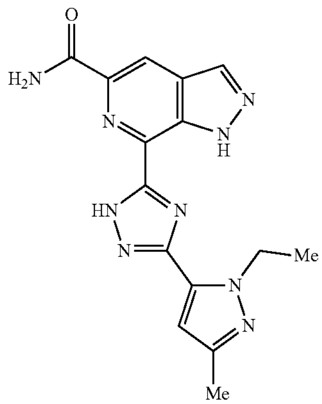 [SMILES: CCn1nc(C)cc1-c1n[nH]c(-c2nc(C(N)=O)cc3cn[nH]c23)n1] | 7-[3-(1-ethyl-3-methyl-1H-pyrazol-5-yl)-1H-1,2,4-triazol-5-yl]-1H-pyrazolo[3,4-c]pyridine-5-carboxamide | LCMS [M + H] = 338.1 observed |
| ZZZ011 | 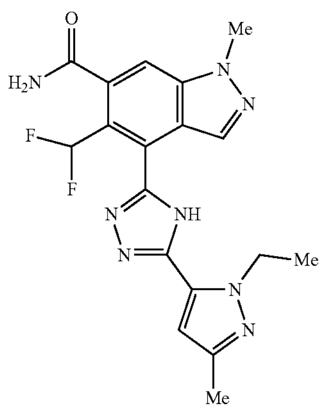 [SMILES: CCn1nc(C)cc1-c1nnc(-c2c(C(F)F)c(C(N)=O)cc3c2cnn3C)[nH]1] | 5-(difluoromethyl)-4-[5-(1-ethyl-3-methyl-1H-pyrazol-5-yl)-4H-1,2,4-triazol-3-yl]-1-methyl-1H-indazole-6-carboxamide | LCMS [M + H] = 401.2 observed |
| ZZZ012 | 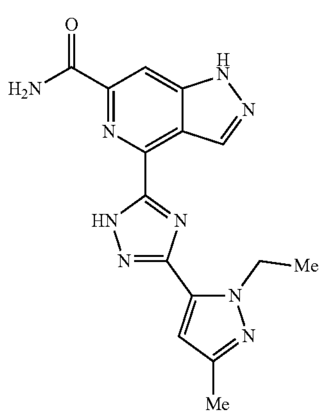 [SMILES: CCn1nc(C)cc1-c1n[nH]c(-c2nc(C(N)=O)cc3[nH]ncc23)n1] | 4-[3-(1-ethyl-3-methyl-1H-pyrazol-5-yl)-1H-1,2,4-triazol-5-yl]-1H-pyrazolo[4,3-c]pyridine-6-carboxamide | LCMS [M + H] = 338 observed |

-continued

| Example Number | Structure | Name | Analytical Data |
|---|---|---|---|
| ZZZ013 | 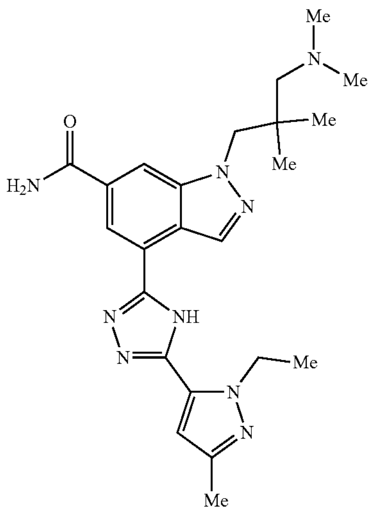 [SMILES: CCn1nc(C)cc1-c1nnc(-c2cc(C(N)=O)cc3c2cnn3CC(C)(C)CN(C)C)[nH]1] | 1-[3-(dimethylamino)-2,2-dimethylpropyl]-4-[5-(1-ethyl-3-methyl-1H-pyrazol-5-yl)-4H-1,2,4-triazol-3-yl]-1H-indazole-6-carboxamide | LCMS [M + H] = 450 observed |
| ZZZ014 | 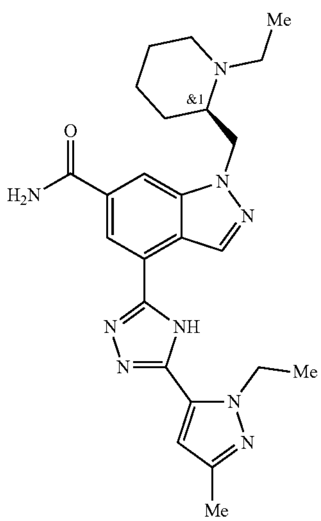 [SMILES: CCN1CCCC[C@@H]1Cn1ncc2c(-c3nnc(-c4cc(C)nn4CC)[nH]3)cc(C(N)=O)cc21] | 4-[5-(1-ethyl-3-methyl-1H-pyrazol-5-yl)-4H-1,2,4-triazol-3-yl]-1-{[(2R)-1-ethylpiperidin-2-yl]methyl}-1H-indazole-6-carboxamide | LCMS [M + H] = 462 observed |
| ZZZ015 | 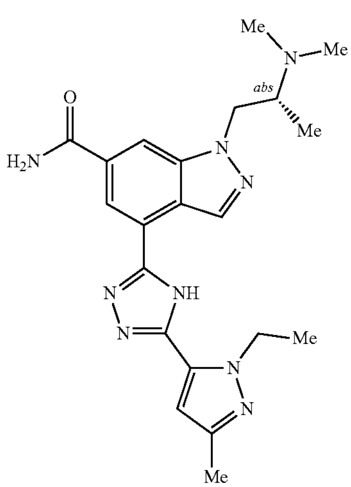 [SMILES: CCn1nc(C)cc1-c1nnc(-c2cc(C(N)=O)cc3c2cnn3C[C@@H](C)N(C)C)[nH]1] | 1-[(2R)-2-(dimethylamino)propyl]-4-[5-(1-ethyl-3-methyl-1H-pyrazol-5-yl)-4H-1,2,4-triazol-3-yl]-1H-indazole-6-carboxamide | LCMS [M + H] = 422 observed |

-continued

| Example Number | Structure | Name | Analytical Data |
|---|---|---|---|
| ZZZ016 | 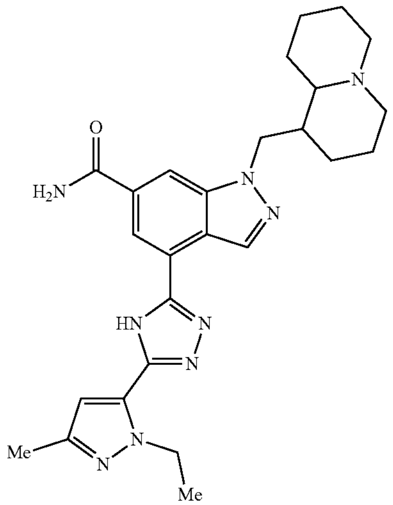 [SMILES: CCn1nc(C)cc1-c1nnc(-c2cc(C(N)=O)cc3c2cnn3CC2CCCN3CCCCC23)[nH]1] | 4-[5-(1-ethyl-3-methyl-1H-pyrazol-5-yl)-4H-1,2,4-triazol-3-yl]-1-[(octahydro-2H-quinolizin-1-yl)methyl]-1H-indazole-6-carboxamide | LCMS [M + H] = 488 observed |
| ZZZ017 | 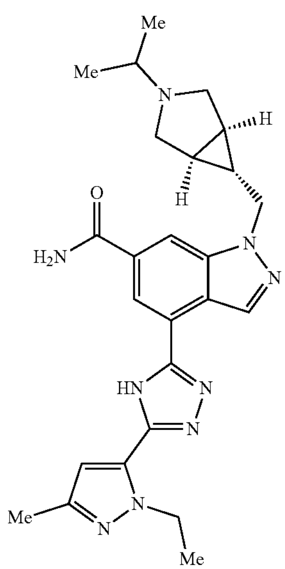 [SMILES: CCn1nc(C)cc1-c1nnc(-c2cc(C(N)=O)cc3c2cnn3C[C@H]2[C@@H]3CN(C(C)C)C[C@@H]32)[nH]1] | 4-[5-(1-ethyl-3-methyl-1H-pyrazol-5-yl)-4H-1,2,4-triazol-3-yl]-1-{[(1R,5S,6r)-3-(propan-2-yl)-3-azabicyclo[3.1.0]hexan-6-yl]methyl}-1H-indazole-6-carboxamide | LCMS [M + H] = 474 observed |

-continued

| Example Number | Structure | Name | Analytical Data |
|---|---|---|---|
| ZZZ018 | 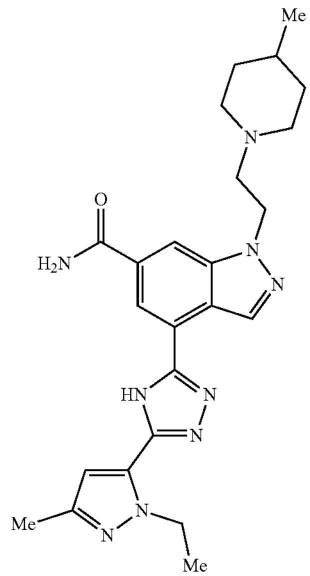 [SMILES: CCn1nc(C)cc1-c1nnc(-c2cc(C(N)=O)cc3c2cnn3CCN2CCC(C)CC2)[nH]1] | 4-[5-(1-ethyl-3-methyl-1H-pyrazol-5-yl)-4H-1,2,4-triazol-3-yl]-1-[2-(4-methylpiperidin-1-yl)ethyl]-1H-indazole-6-carboxamide | LCMS [M + H] = 462 observed |
| ZZZ019 | 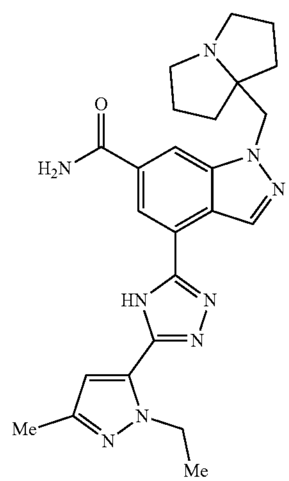 [SMILES: CCn1nc(C)cc1-c1nnc(-c2cc(C(N)=O)cc3c2cnn3CC23CCCN2CCC3)[nH]1] | 4-[5-(1-ethyl-3-methyl-1H-pyrazol-5-yl)-4H-1,2,4-triazol-3-yl]-1-[(tetrahydro-1H-pyrrolizin-7a(5H)-yl)methyl]-1H-indazole-6-carboxamide | LCMS [M + H] = 460 observed |
| ZZZ020 | 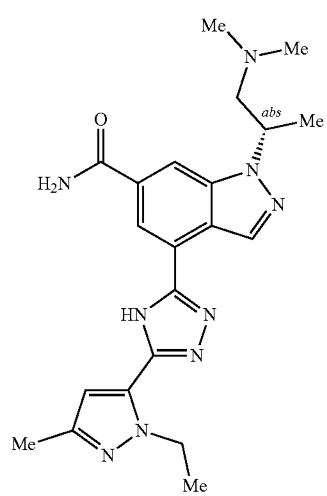 [SMILES: CCn1nc(C)cc1-c1nnc(-c2cc(C(N)=O)cc3c2cnn3[C@@H](C)CN(C)C)[nH]1] | 1-[(2S)-1-(dimethylamino)propan-2-yl]-4-[5-(1-ethyl-3-methyl-1H-pyrazol-5-yl)-4H-1,2,4-triazol-3-yl]-1H-indazole-6-carboxamide | LCMS [M + H] = 422 observed |

| Example Number | Structure | Name | Analytical Data |
|---|---|---|---|
| ZZZ021 | 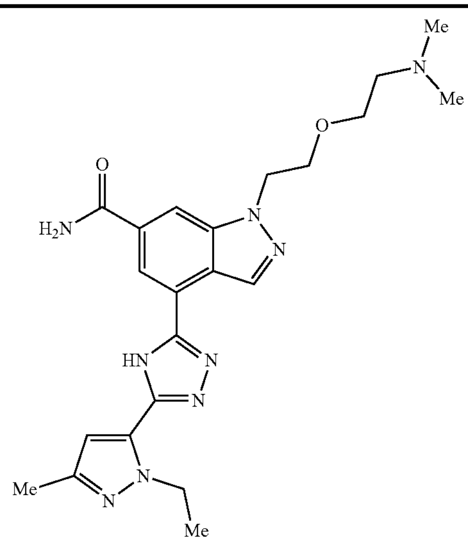 | 1-{2-[2-(dimethylamino)ethoxy]ethyl}-4-[5-(1-ethyl-3-methyl-1H-pyrazol-5-yl)-4H-1,2,4-triazol-3-yl]-1H-indazole-6-carboxamide | LCMS [M + H] = 452 observed |
| ZZZ022 | 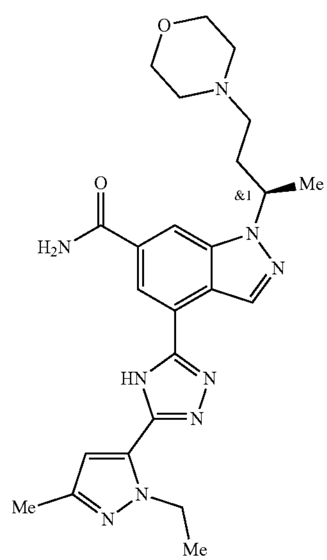 [SMILES: CCn1nc(C)cc1-c1nnc(-c2cc(C(N)=O)cc3c2cnn3[C@H](C)CCN2CCOCC2)[nH]1] | 4-[5-(1-ethyl-3-methyl-1H-pyrazol-5-yl)-4H-1,2,4-triazol-3-yl]-1-[(2R)-4-(morpholin-4-yl)butan-2-yl]-1H-indazole-6-carboxamide | LCMS [M + H] = 478 observed |
| ZZZ023 | 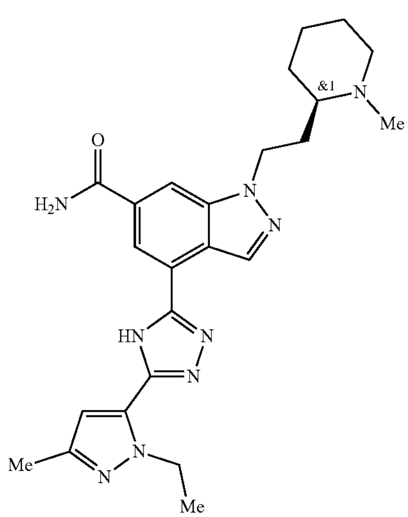 [SMILES: CCn1nc(C)cc1-c1nnc(-c2cc(C(N)=O)cc3c2cnn3CC[C@H]2CCCCN2C)[nH]1] | 4-[5-(1-ethyl-3-methyl-1H-pyrazol-5-yl)-4H-1,2,4-triazol-3-yl]-1-{2-[(2R)-1-methylpiperidin-2-yl]ethyl}-1H-indazole-6-carboxamide | LCMS [M + H] = 462 observed |

-continued

| Example Number | Structure | Name | Analytical Data |
|---|---|---|---|
| ZZZ024 | 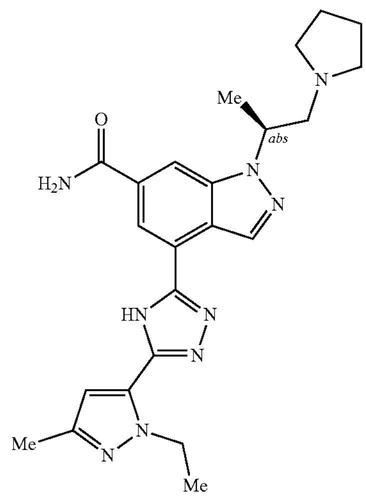 [SMILES: CCn1nc(C)cc1-c1nnc(-c2cc(C(N)=O)cc3c2cnn3[C@@H](C)CN2CCCC2)[nH]1] | 4-[5-(1-ethyl-3-methyl-1H-pyrazol-5-yl)-4H-1,2,4-triazol-3-yl]-1-[(2S)-1-(pyrrolidin-1-yl)propan-2-yl]-1H-indazole-6-carboxamide | LCMS [M + H] = 448 observed |
| ZZZ025 | 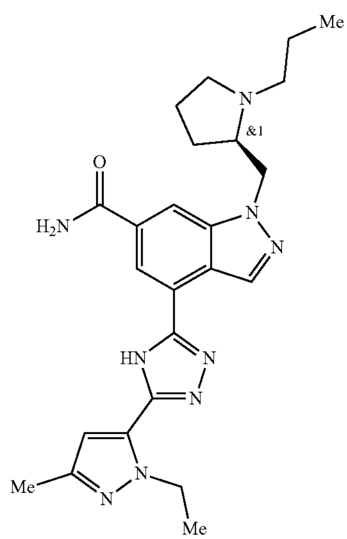 [SMILES: CCCN1CCC[C@@H]1Cn1ncc2c(-c3nnc(-c4cc(C)nn4CC)[nH]3)cc(C(N)=O)cc21] | 4-[5-(1-ethyl-3-methyl-1H-pyrazol-5-yl)-4H-1,2,4-triazol-3-yl]-1-{[(2R)-1-propylpyrrolidin-2-yl]methyl}-1H-indazole-6-carboxamide | LCMS [M + H] = 462 observed |
| ZZZ026 | 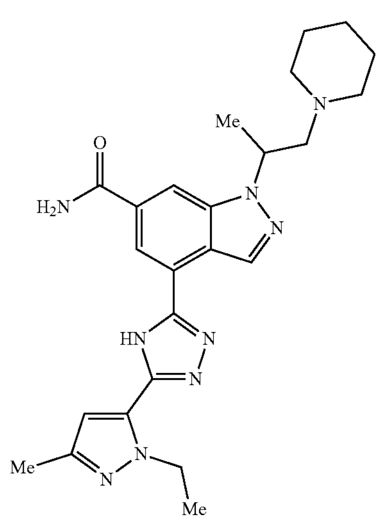 [SMILES: CCn1nc(C)cc1-c1nnc(-c2cc(C(N)=O)cc3c2cnn3C(C)CN2CCCCC2)[nH]1] | 4-[5-(1-ethyl-3-methyl-1H-pyrazol-5-yl)-4H-1,2,4-triazol-3-yl]-1-[1-(piperidin-1-yl)propan-2-yl]-1H-indazole-6-carboxamide | LCMS [M + H] = 462 observed |

-continued

| Example Number | Structure | Name | Analytical Data |
|---|---|---|---|
| ZZZ027 | 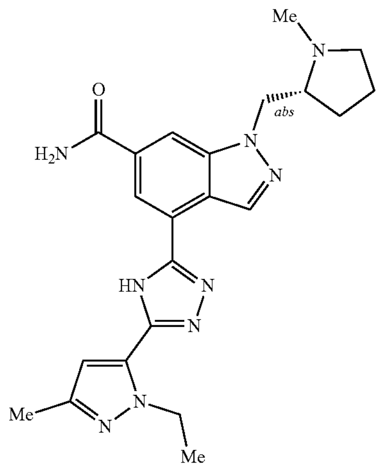 [SMILES: CCn1nc(C)cc1-c1nnc(-c2cc(C(N)=O)cc3c2cnn3C[C@H]2CCCN2C)[nH]1] | 4-[5-(1-ethyl-3-methyl-1H-pyrazol-5-yl)-4H-1,2,4-triazol-3-yl]-1-{[(2R)-1-methylpyrrolidin-2-yl]methyl}-1H-indazole-6-carboxamide | LCMS [M + H] = 434 observed |
| ZZZ028 | 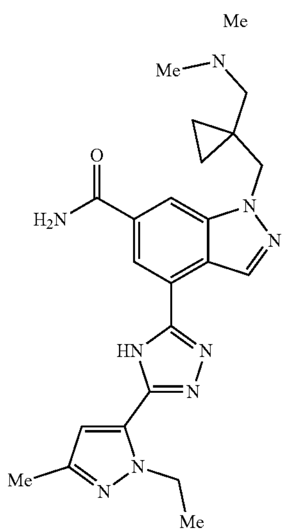 [SMILES: CCn1nc(C)cc1-c1nnc(-c2cc(C(N)=O)cc3c2cnn3CC2(CNC)CC2)[nH]1 ; "Me"] | 1-({1-[(dimethylamino)methyl]cyclopropyl}methyl)-4-[5-(1-ethyl-3-methyl-1H-pyrazol-5-yl)-4H-1,2,4-triazol-3-yl]-1H-indazole-6-carboxamide | LCMS [M + H] = 448 observed |
| ZZZ029 | 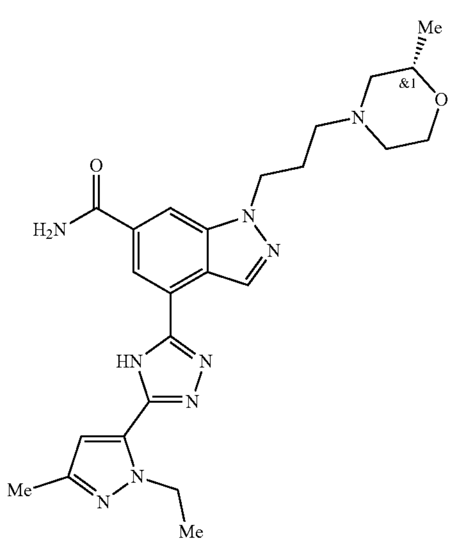 [SMILES: CCn1nc(C)cc1-c1nnc(-c2cc(C(N)=O)cc3c2cnn3CCCN2CCO[C@@H](C)C2)[nH]1] | 4-[5-(1-ethyl-3-methyl-1H-pyrazol-5-yl)-4H-1,2,4-triazol-3-yl]-1-{3-[(2S)-2-methylmorpholin-4-yl]propyl}-1H-indazole-6-carboxamide | LCMS [M + H] = 478 observed |

-continued

| Example Number | Structure | Name | Analytical Data |
|---|---|---|---|
| ZZZ030 | 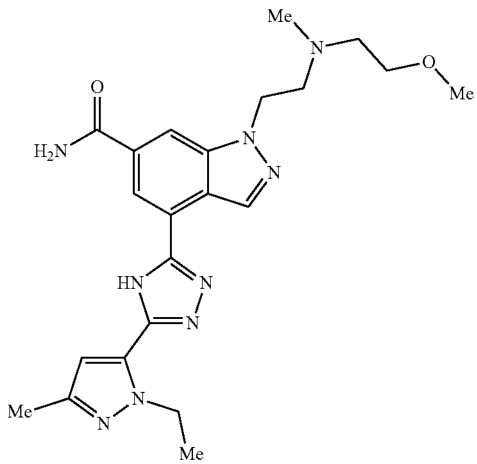 [SMILES: CCn1nc(C)cc1-c1nnc(-c2cc(C(N)=O)cc3c2cnn3CCN(C)CCOC)[nH]1] | 4-[5-(1-ethyl-3-methyl-1H-pyrazol-5-yl)-4H-1,2,4-triazol-3-yl]-1-{2-[(2-methoxyethyl)(methyl)amino]ethyl}-1H-indazole-6-carboxamide | LCMS [M + H] = 452 observed |
| ZZZ031 | 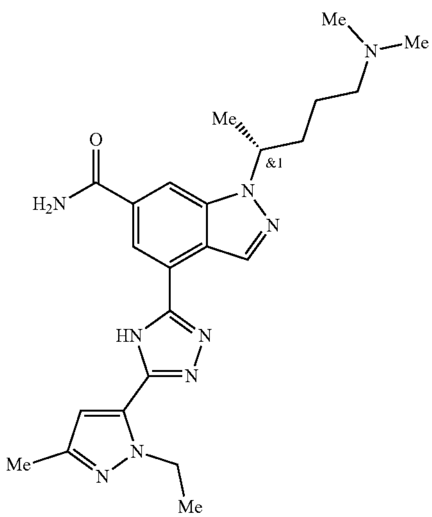 [SMILES: CCn1nc(C)cc1-c1nnc(-c2cc(C(N)=O)cc3c2cnn3[C@H](C)CCCN(C)C)[nH]1] | 1-[(2R)-5-(dimethylamino)pentan-2-yl]-4-[5-(1-ethyl-3-methyl-1H-pyrazol-5-yl)-4H-1,2,4-triazol-3-yl]-1H-indazole-6-carboxamide | LCMS [M + H] = 450 observed |
| ZZZ032 | 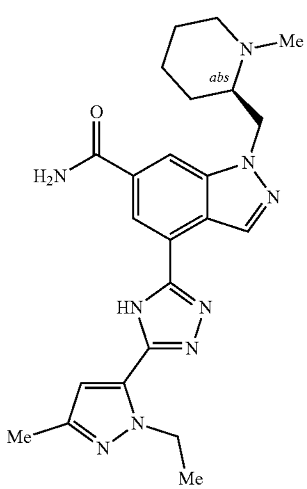 [SMILES: CCn1nc(C)cc1-c1nnc(-c2cc(C(N)=O)cc3c2cnn3C[C@H]2CCCCN2C)[nH]1] | 4-[5-(1-ethyl-3-methyl-1H-pyrazol-5-yl)-4H-1,2,4-triazol-3-yl]-1-{[(2R)-1-methylpiperidin-2-yl]methyl}-1H-indazole-6-carboxamide | LCMS [M + H] = 448 observed |

| Example Number | Structure | Name | Analytical Data |
|---|---|---|---|
| ZZZ033 | 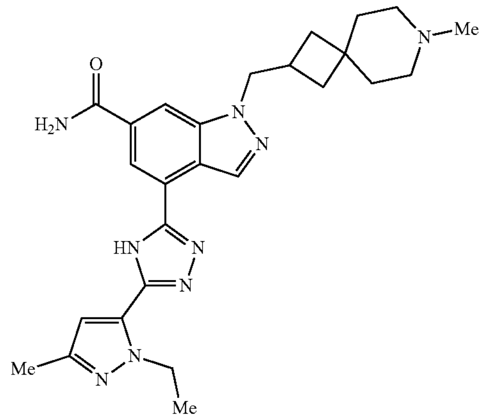 [SMILES: CCn1nc(C)cc1-c1nnc(-c2cc(C(N)=O)cc3c2cnn3CC2CC3(CCN(C)CC3)C2)[nH]1] | 4-[5-(1-ethyl-3-methyl-1H-pyrazol-5-yl)-4H-1,2,4-triazol-3-yl]-1-[(7-methyl-7-azaspiro[3.5]nonan-2-yl)methyl]-1H-indazole-6-carboxamide | LCMS [M + H] = 488 observed |
| ZZZ034 | 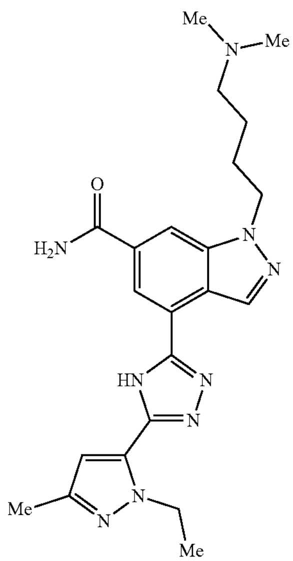 [SMILES: CCn1nc(C)cc1-c1nnc(-c2cc(C(N)=O)cc3c2cnn3CCCCN(C)C)[nH]1] | 1-[4-(dimethylamino)butyl]-4-[5-(1-ethyl-3-methyl-1H-pyrazol-5-yl)-4H-1,2,4-triazol-3-yl]-1H-indazole-6-carboxamide | LCMS [M + H] = 436 observed |
| ZZZ035 | 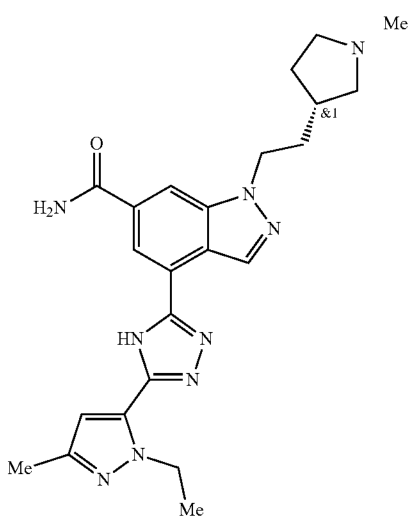 [SMILES: CCn1nc(C)cc1-c1nnc(-c2cc(C(N)=O)cc3c2cnn3CC[C@@H]2CCNC2)[nH]1 ; "Me"] | 4-[5-(1-ethyl-3-methyl-1H-pyrazol-5-yl)-4H-1,2,4-triazol-3-yl]-1-{2-[(3S)-1-methylpyrrolidin-3-yl]ethyl}-1H-indazole-6-carboxamide | LCMS [M + H] = 448 observed |

-continued

| Example Number | Structure | Name | Analytical Data |
|---|---|---|---|
| ZZZ036 | 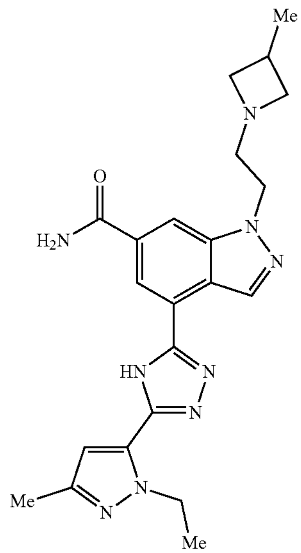 [SMILES: CCn1nc(C)cc1-c1nnc(-c2cc(C(N)=O)cc3c2cnn3CCN2CC(C)C2)[nH]1] | 4-[5-(1-ethyl-3-methyl-1H-pyrazol-5-yl)-4H-1,2,4-triazol-3-yl]-1-[2-(3-methylazetidin-1-yl)ethyl]-1H-indazole-6-carboxamide | LCMS [M + H] = 434 observed |
| ZZZ037 | 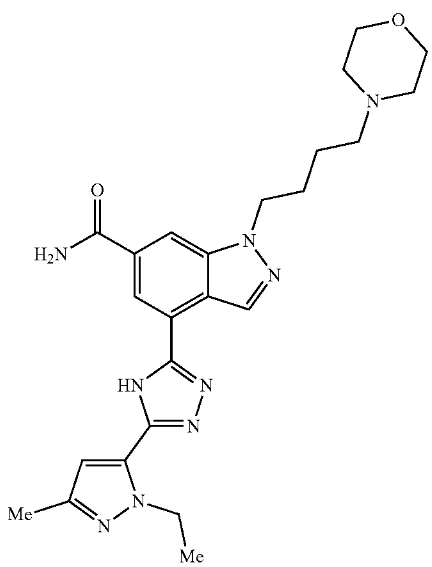 [SMILES: CCn1nc(C)cc1-c1nnc(-c2cc(C(N)=O)cc3c2cnn3CCCCN2CCOCC2)[nH]1] | 4-[5-(1-ethyl-3-methyl-1H-pyrazol-5-yl)-4H-1,2,4-triazol-3-yl]-1-[4-(morpholin-4-yl)butyl]-1H-indazole-6-carboxamide | LCMS [M + H] = 478 observed |
| ZZZ038 | 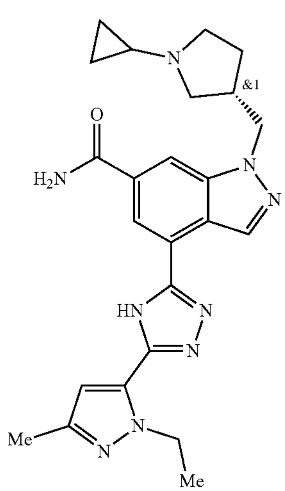 [SMILES: CCn1nc(C)cc1-c1nnc(-c2cc(C(N)=O)cc3c2cnn3C[C@H]2CCN(C3CC3)C2)[nH]1] | 1-{[(3S)-1-cyclopropylpyrrolidin-3-yl]methyl}-4-[5-(1-ethyl-3-methyl-1H-pyrazol-5-yl)-4H-1,2,4-triazol-3-yl]-1H-indazole-6-carboxamide | LCMS [M + H] = 460 observed |

| Example Number | Structure | Name | Analytical Data |
|---|---|---|---|
| ZZZ039 | 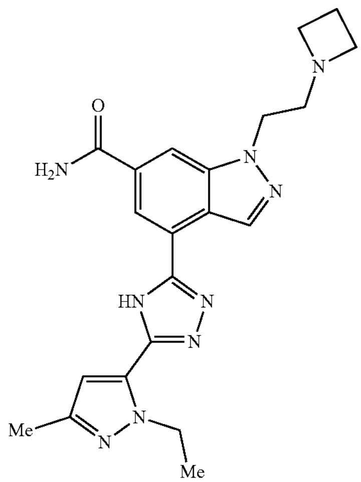 [SMILES: CCn1nc(C)cc1-c1nnc(-c2cc(C(N)=O)cc3c2cnn3CCN2CCC2)[nH]1] | 1-[2-(azetidin-1-yl)ethyl]-4-[5-(1-ethyl-3-methyl-1H-pyrazol-5-yl)-4H-1,2,4-triazol-3-yl]-1H-indazole-6-carboxamide | LCMS [M + H] = 420 observed |
| ZZZ040 | 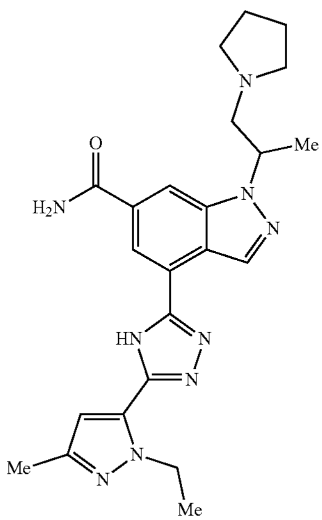 [SMILES: CCn1nc(C)cc1-c1nnc(-c2cc(C(N)=O)cc3c2cnn3C(C)CN2CCCC2)[nH]1] | 4-[5-(1-ethyl-3-methyl-1H-pyrazol-5-yl)-4H-1,2,4-triazol-3-yl]-1-[1-(pyrrolidin-1-yl)propan-2-yl]-1H-indazole-6-carboxamide | LCMS [M + H] = 448 observed |
| ZZZ041 | 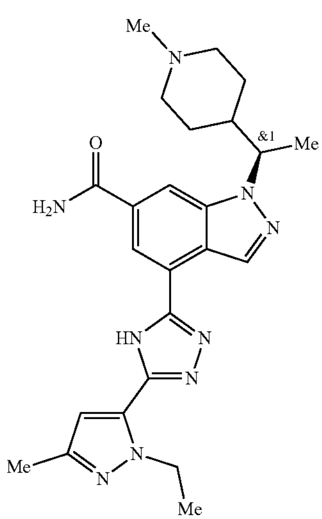 [SMILES: CCn1nc(C)cc1-c1nnc(-c2cc(C(N)=O)cc3c2cnn3[C@H](C)C2CCN(C)CC2)[nH]1] | 4-[5-(1-ethyl-3-methyl-1H-pyrazol-5-yl)-4H-1,2,4-triazol-3-yl]-1-[(1R)-1-(1-methylpiperidin-4-yl)ethyl]-1H-indazole-6-carboxamide | LCMS [M + H] = 462 observed |

| Example Number | Structure | Name | Analytical Data |
|---|---|---|---|
| ZZZ042 | 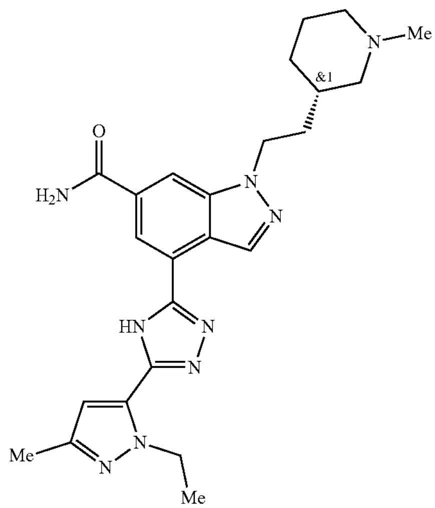 [SMILES: CCn1nc(C)cc1-c1nnc(-c2cc(C(N)=O)cc3c2cnn3CC[C@@H]2CCCN(C)C2)[nH]1] | 4-[5-(1-ethyl-3-methyl-1H-pyrazol-5-yl)-4H-1,2,4-triazol-3-yl]-1-{2-[(3S)-1-methylpiperidin-3-yl]ethyl}-1H-indazole-6-carboxamide | LCMS [M + H] = 462 observed |
| ZZZ043 | 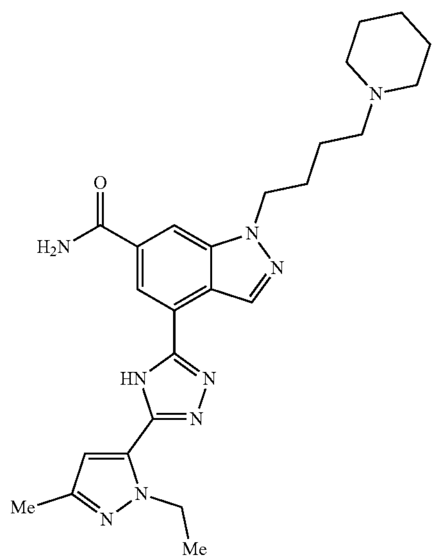 [SMILES: CCn1nc(C)cc1-c1nnc(-c2cc(C(N)=O)cc3c2cnn3CCCCN2CCCCC2)[nH]1] | 4-[5-(1-ethyl-3-methyl-1H-pyrazol-5-yl)-4H-1,2,4-triazol-3-yl]-1-[4-(piperidin-1-yl)butyl]-1H-indazole-6-carboxamide | LCMS [M + H] = 476 observed |
| ZZZ044 | 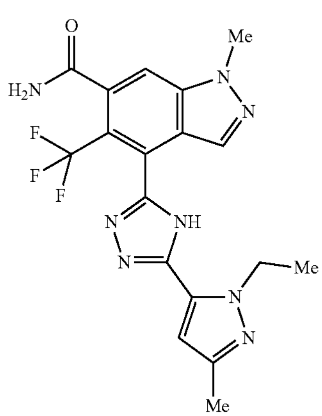 [SMILES: CCn1nc(C)cc1-c1nnc(-c2c(C(F)(F)F)c(C(N)=O)cc3c2cnn3C)[nH]1] | 4-[5-(1-ethyl-3-methyl-1H-pyrazol-5-yl)-4H-1,2,4-triazol-3-yl]-1-methyl-5-(trifluoromethyl)-1H-indazole-6-carboxamide | LCMS [M + H] = 419 observed |

| Example Number | Structure | Name | Analytical Data |
|---|---|---|---|
| ZZZ045 | 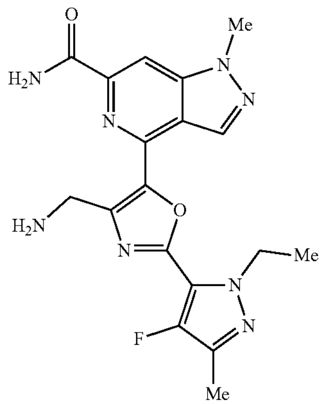 [SMILES: CCn1nc(C)c(F)c1-c1nc(CN)c(-c2nc(C(N)=O)cc3c2cnn3C)o1] | 4-[4-(aminomethyl)-2-(1-ethyl-4-fluoro-3-methyl-1H-pyrazol-5-yl)-1,3-oxazol-5-yl]-1-methyl-1H-pyrazolo[4,3-c]pyridine-6-carboxamide | LCMS [M + H] = 399.3 observed |
| ZZZ046 | 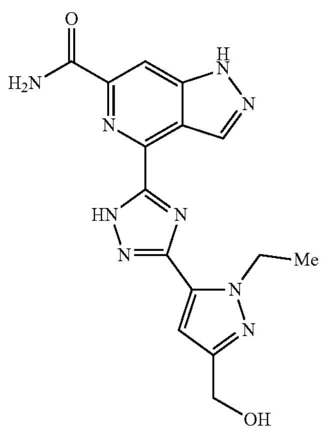 [SMILES: CCn1nc(CO)cc1-c1n[nH]c(-c2nc(C(N)=O)cc3[nH]ncc23)n1] | 4-{3-[1-ethyl-3-(hydroxymethyl)-1H-pyrazol-5-yl]-1H-1,2,4-triazol-5-yl}-1H-pyrazolo[4,3-c]pyridine-6-carboxamide | LCMS [M + H] = 354 observed |
| ZZZ047 | 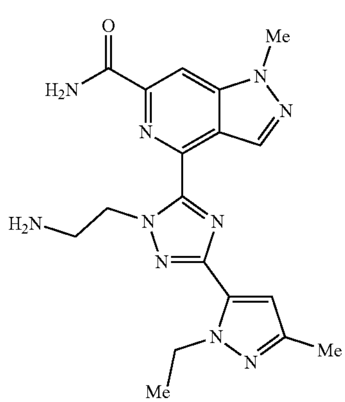 [SMILES: CCn1nc(C)cc1-c1nc(-c2nc(C(N)=O)cc3c2cnn3C)n(CCN)n1] | 4-[1-(2-aminoethyl)-3-(1-ethyl-3-methyl-1H-pyrazol-5-yl)-1H-1,2,4-triazol-5-yl]-1-methyl-1H-pyrazolo[4,3-c]pyridine-6-carboxamide | LCMS [M + H] = 395 observed |

-continued

| Example Number | Structure | Name | Analytical Data |
|---|---|---|---|
| ZZZ048 | 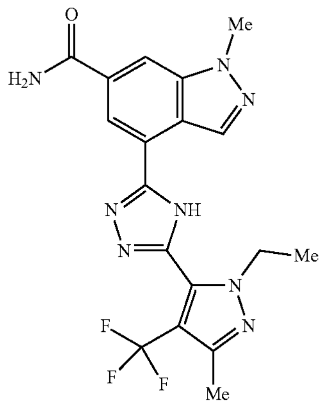 [SMILES: CCn1nc(C)c(C(F)(F)F)c1-c1nnc(-c2cc(C(N)=O)cc3c2cnn3C)[nH]1] | 4-{5-[1-ethyl-3-methyl-4-(trifluoromethyl)-1H-pyrazol-5-yl]-4H-1,2,4-triazol-3-yl}-1-methyl-1H-indazole-6-carboxamide | LCMS [M + H] = 419 observed |
| ZZZ049 | 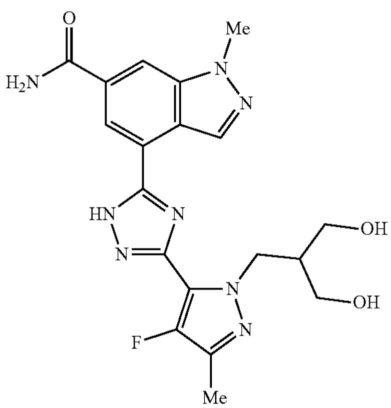 [SMILES: Cc1nn(CC(CO)CO)c(-c2n[nH]c(-c3cc(C(N)=O)cc4c3cnn4C)n2)c1F] | 4-(3-{4-fluoro-1-[3-hydroxy-2-(hydroxymethyl)propyl]-3-methyl-1H-pyrazol-5-yl}-1H-1,2,4-triazol-5-yl)-1-methyl-1H-indazole-6-carboxamide | $^1$H NMR (400 MHz, DMSO-$d_6$) δ = 15.04 (s, 1H), 8.68 (s, 1H), 8.40 (s, 1H), 8.37 (br s, 1H), 8.16 (br s, 1H), 7.60 (br s, 1H), 4.54 (br d, J = 6.8 Hz, 4H), 4.16 (s, 3H), 3.46-3.36 (m, 4H), 2.23 (s, 3H), 2.17-2.10 (m, 1H) |
| ZZZ050 | 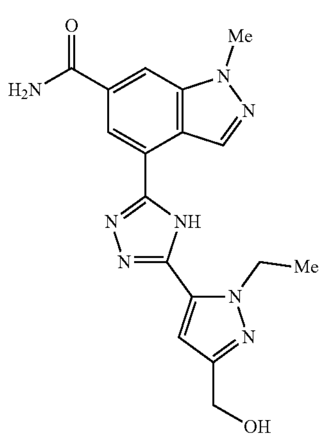 [SMILES: CCn1nc(CO)cc1-c1nnc(-c2cc(C(N)=O)cc3c2cnn3C)[nH]1] | 4-{5-[1-ethyl-3-(hydroxymethyl)-1H-pyrazol-5-yl]-4H-1,2,4-triazol-3-yl}-1-methyl-1H-indazole-6-carboxamide | LCMS [M + H] = 367 observed |

-continued

| Example Number | Structure | Name | Analytical Data |
|---|---|---|---|
| ZZZ051 | 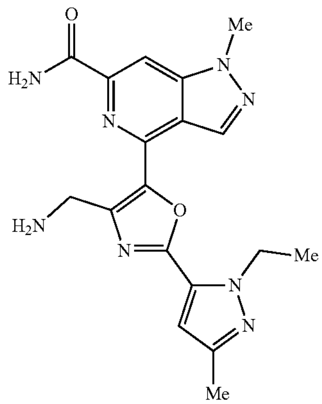 [SMILES: CCn1nc(C)cc1-c1nc(CN)c(-c2nc(C(N)=O)cc3c2cnn3C)o1] | 4-[4-(aminomethyl)-2-(1-ethyl-3-methyl-1H-pyrazol-5-yl)-1,3-oxazol-5-yl]-1-methyl-1H-pyrazolo[4,3-c]pyridine-6-carboxamide | LCMS [M + H] = 381.2 observed |
| ZZZ052 | 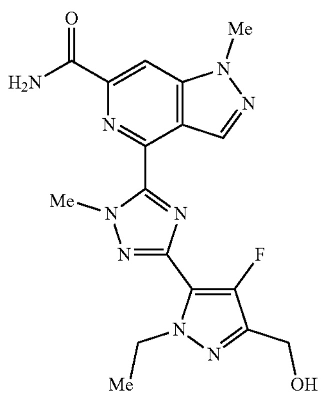 [SMILES: CCn1nc(CO)c(F)c1-c1nc(-c2nc(C(N)=O)cc3c2cnn3C)n(C)n1] | 4-{3-[1-ethyl-4-fluoro-3-(hydroxymethyl)-1H-pyrazol-5-yl]-1-methyl-1H-1,2,4-triazol-5-yl}-1-methyl-1H-pyrazolo[4,3-c]pyridine-6-carboxamide | $^1$H NMR (400 MHz, DMSO-d$_6$) δ ppm 8.71 (d, J = 0.86 Hz, 1 H) 8.53 (d, J = 0.73 Hz, 1 H) 8.04 (br s, 1 H) 7.92 (br s, 1 H) 5.20 (t, J = 5.69 Hz, 1 H) 4.58 (q, J = 7.17 Hz, 2 H) 4.47-4.51 (m, 5 H) 4.23 (s, 3 H) 1.42 (t, J = 7.15 Hz, 3 H) |
| ZZZ053 | 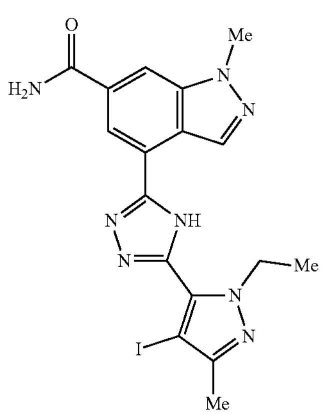 [SMILES: CCn1nc(C)c(I)c1-c1nnc(-c2cc(C(N)=O)cc3c2cnn3C)[nH]1] | 4-[5-(1-ethyl-4-iodo-3-methyl-1H-pyrazol-5-yl)-4H-1,2,4-triazol-3-yl]-1-methyl-1H-indazole-6-carboxamide | LCMS [M + H] = 477 observed |

-continued

| Example Number | Structure | Name | Analytical Data |
|---|---|---|---|
| ZZZ054 | 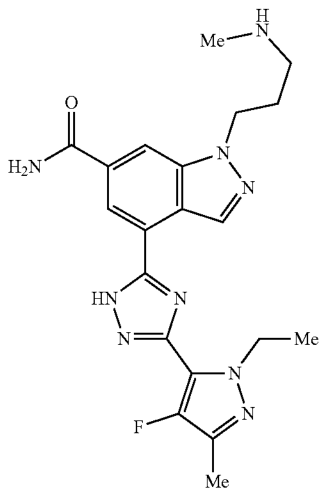 [SMILES: CCn1nc(C)c(F)c1-c1n[nH]c(-c2cc(C(N)=O)cc3c2cnn3CCCNC)n1] | 4-[3-(1-ethyl-4-fluoro-3-methyl-1H-pyrazol-5-yl)-1H-1,2,4-triazol-5-yl]-1-[3-(methylamino)propyl]-1H-indazole-6-carboxamide | LCMS [M + H] = 426.1 observed |
| ZZZ055 | 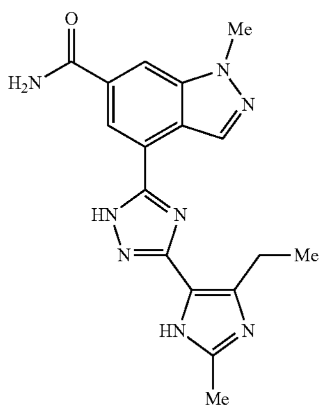 [SMILES: CCc1nc(C)[nH]c1-c1n[nH]c(-c2cc(C(N)=O)cc3c2cnn3C)n1] | 4-[3-(4-ethyl-2-methyl-1H-imidazol-5-yl)-1H-1,2,4-triazol-5-yl]-1-methyl-1H-indazole-6-carboxamide | $^1$H NMR (600 MHz, DMSO-$d_6$) δ ppm 8.67 (s, 1 H) 8.37 (s, 1 H) 8.22 (s, 1 H) 8.13-8.19 (m, 1 H) 7.47 (br s, 1 H) 4.13 (s, 3 H) 3.05-3.17 (m, 3 H) 2.33 (s, 3.000 H) 1.28 (t, J = 7.52 Hz, 3 H) |
| ZZZ056 | 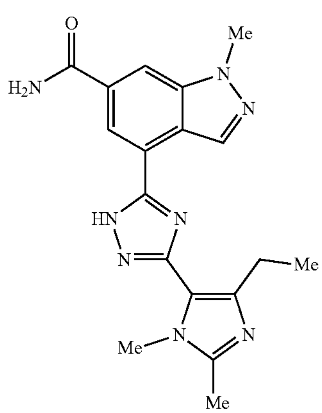 [SMILES: CCc1nc(C)n(C)c1-c1n[nH]c(-c2cc(C(N)=O)cc3c2cnn3C)n1] | 4-[3-(4-ethyl-1,2-dimethyl-1H-imidazol-5-yl)-1H-1,2,4-triazol-5-yl]-1-methyl-1H-indazole-6-carboxamide | $^1$H NMR (600 MHz, DMSO-$d_6$) δ ppm 8.67 (s, 1 H) 8.41 (s, 1 H) 8.29 (s, 1 H) 8.19 (br s, 1 H) 7.52 (br s, 1 H) 4.15 (s, 3 H) 3.79 (d, J = 0.73 Hz, 4 H) 2.77 (q, J = 7.34 Hz, 2 H) 2.35 (s, 3 H) 1.17 (t, J = 7.43 Hz, 3 H) |

| Example Number | Structure | Name | Analytical Data |
|---|---|---|---|
| ZZZ057 | 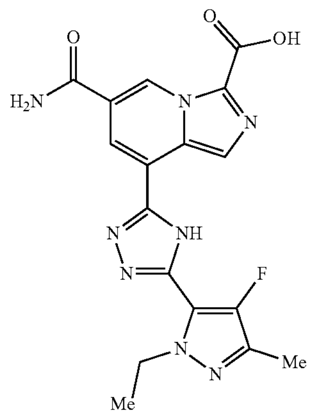 [SMILES: CCn1nc(C)c(F)c1-c1nnc(-c2cc(C(N)=O)cn3c(C(=O)O)ncc23)[nH]1] | 6-carbamoyl-8-[5-(1-ethyl-4-fluoro-3-methyl-1H-pyrazol-5-yl)-4H-1,2,4-triazol-3-yl]imidazo[1,5-a]pyridine-3-carboxylic acid | $^1$H NMR (700 MHz, DMSO-$d_6$) δ ppm 10.07 (br s, 1 H) 8.30 (br s, 1 H) 8.11 (br s, 1 H) 7.91 (br s, 1 H) 7.35 (br s, 1 H) 4.46-4.61 (m, 3 H) 1.30-1.33 (m, 3H) |
| ZZZ058 | 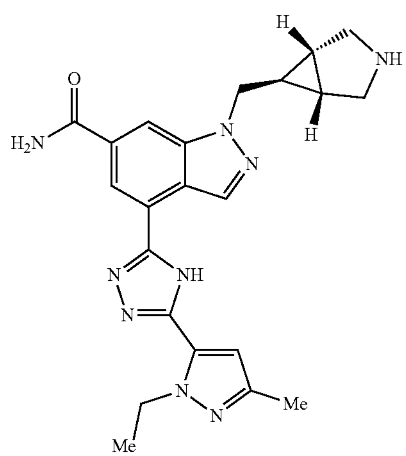 [SMILES: CCn1nc(C)cc1-c1nnc(-c2cc(C(N)=O)cc3c2cnn3C[C@H]2[C@@H]3CNC[C@@H]32)[nH]1] | 1-{[(1R,5S,6r)-3-azabicyclo[3.1.0]hexan-6-yl]methyl}-4-[5-(1-ethyl-3-methyl-1H-pyrazol-5-yl)-4H-1,2,4-triazol-3-yl]-1H-indazole-6-carboxamide | LCMS [M + H] = 432 observed |
| ZZZ059 | 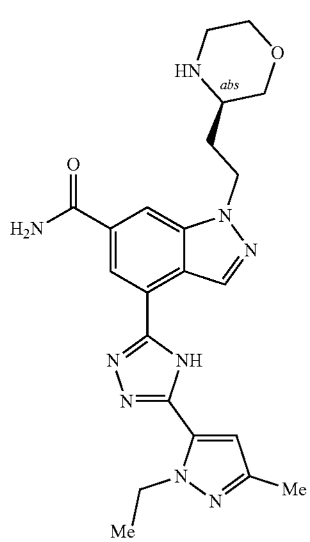 [SMILES: CCn1nc(C)cc1-c1nnc(-c2cc(C(N)=O)cc3c2cnn3CC[C@@H]2COCCN2)[nH]1] | 4-[5-(1-ethyl-3-methyl-1H-pyrazol-5-yl)-4H-1,2,4-triazol-3-yl]-1-{2-[(3R)-morpholin-3-yl]ethyl}-1H-indazole-6-carboxamide | LCMS [M + H] = 450 observed |

| Example Number | Structure | Name | Analytical Data |
|---|---|---|---|
| ZZZ060 | 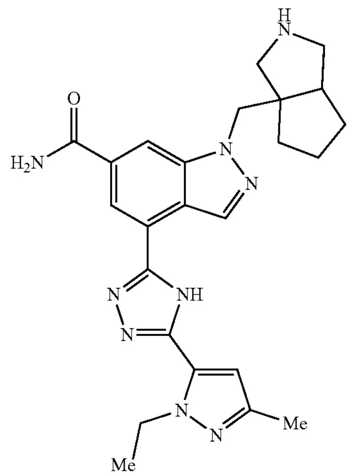 [SMILES: CCn1nc(C)cc1-c1nnc(-c2cc(C(N)=O)cc3c2cnn3CC23CCCC2CNC3)[nH]1] | 4-[5-(1-ethyl-3-methyl-1H-pyrazol-5-yl)-4H-1,2,4-triazol-3-yl]-1-[(hexahydrocyclopenta[c]pyrrol-3a(1H)-yl)methyl]-1H-indazole-6-carboxamide | LCMS [M + H] = 460 observed |
| ZZZ061 | 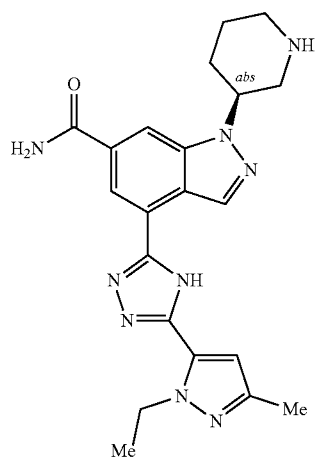 [SMILES: CCn1nc(C)cc1-c1nnc(-c2cc(C(N)=O)cc3c2cnn3[C@H]2CCCNC2)[nH]1] | 4-[5-(1-ethyl-3-methyl-1H-pyrazol-5-yl)-4H-1,2,4-triazol-3-yl]-1-[(3S)-piperidin-3-yl]-1H-indazole-6-carboxamide | LCMS [M + H] = 420 observed |
| ZZZ062 | 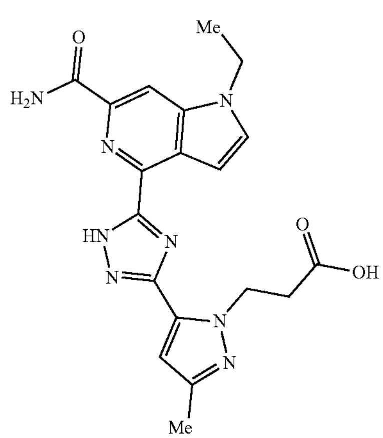 [SMILES: CCn1ccc2c(-c3nc(-c4cc(C)nn4CCC(=O)O)n[nH]3)nc(C(N)=O)cc21] | 3-{5-[5-(6-carbamoyl-1-ethyl-1H-pyrrolo[3,2-c]pyridin-4-yl)-1H-1,2,4-triazol-3-yl]-3-methyl-1H-pyrazol-1-yl}propanoic acid | LCMS [M + H] = 409.2 observed |

-continued

| Example Number | Structure | Name | Analytical Data |
|---|---|---|---|
| ZZZ063 | 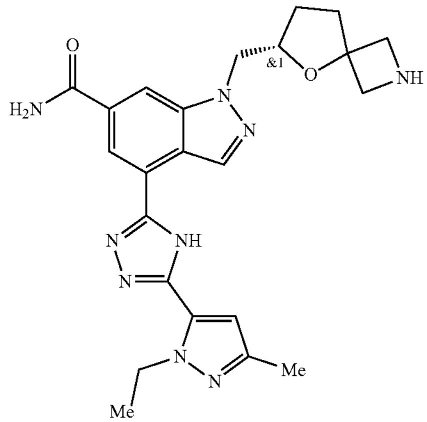 [SMILES: CCn1nc(C)cc1-c1nnc(-c2cc(C(N)=O)cc3c2cnn3C[C@@H]2CCC3(CNC3)O2)[nH]1] | 4-[5-(1-ethyl-3-methyl-1H-pyrazol-5-yl)-4H-1,2,4-triazol-3-yl]-1-{[(6S)-5-oxa-2-azaspiro[3.4]octan-6-yl]methyl}-1H-indazole-6-carboxamide | LCMS [M + H] = 462 observed |
| ZZZ064 | 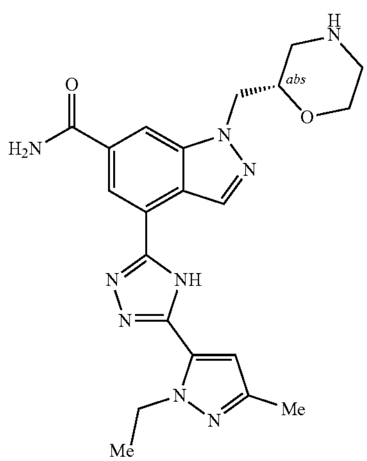 [SMILES: CCn1nc(C)cc1-c1nnc(-c2cc(C(N)=O)cc3c2cnn3C[C@@H]2CNCCO2)[nH]1] | 4-[5-(1-ethyl-3-methyl-1H-pyrazol-5-yl)-4H-1,2,4-triazol-3-yl]-1-{[(2S)-morpholin-2-yl]methyl}-1H-indazole-6-carboxamide | LCMS [M + H] = 436 observed |
| ZZZ065 | 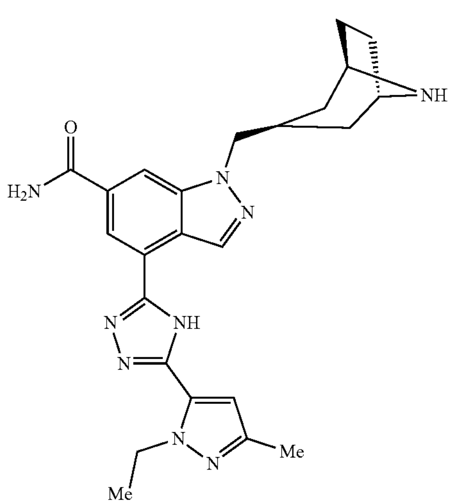 [SMILES: CCn1nc(C)cc1-c1nnc(-c2cc(C(N)=O)cc3c2cnn3C[C@H]2C[C@H]3CC[C@@H](C2)N3)[nH]1] | 1-{[(1R,3r,5S)-8-azabicyclo[3.2.1]octan-3-yl]methyl}-4-[5-(1-ethyl-3-methyl-1H-pyrazol-5-yl)-4H-1,2,4-triazol-3-yl]-1H-indazole-6-carboxamide | LCMS [M + H] = 460 observed |

-continued

| Example Number | Structure | Name | Analytical Data |
|---|---|---|---|
| ZZZ066 | 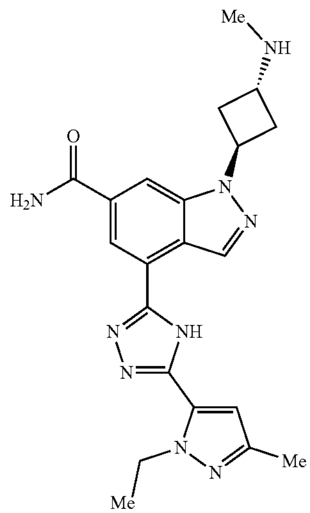 [SMILES: CCn1nc(C)cc1-c1nnc(-c2cc(C(N)=O)cc3c2cnn3[C@H]2C[C@H](NC)C2)[nH]1] | 4-[5-(1-ethyl-3-methyl-1H-pyrazol-5-yl)-4H-1,2,4-triazol-3-yl]-1-[(1r,3r)-3-(methylamino)cyclobutyl]-1H-indazole-6-carboxamide | LCMS [M + H] = 420 observed |
| ZZZ067 | 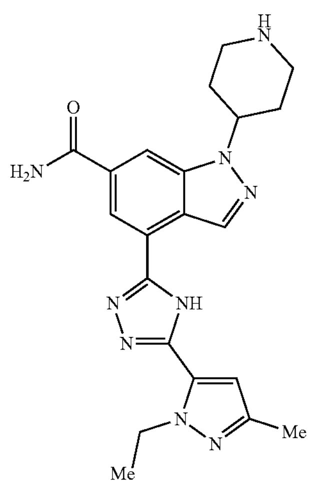 [SMILES: CCn1nc(C)cc1-c1nnc(-c2cc(C(N)=O)cc3c2cnn3C2CCNCC2)[nH]1] | 4-[5-(1-ethyl-3-methyl-1H-pyrazol-5-yl)-4H-1,2,4-triazol-3-yl]-1-(piperidin-4-yl)-1H-indazole-6-carboxamide | LCMS [M + H] = 420 observed |
| ZZZ068 | 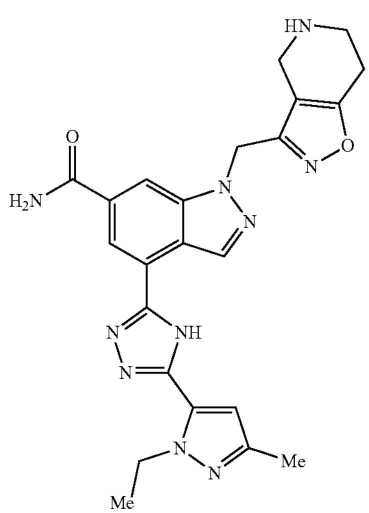 [SMILES: CCn1nc(C)cc1-c1nnc(-c2cc(C(N)=O)cc3c2cnn3Cc2noc3c2CNCC3)[nH]1] | 4-[5-(1-ethyl-3-methyl-1H-pyrazol-5-yl)-4H-1,2,4-triazol-3-yl]-1-[(4,5,6,7-tetrahydro[1,2]oxazolo[4,5-c]pyridin-3-yl)methyl]-1H-indazole-6-carboxamide | LCMS [M + H] = 473 observed |

-continued

| Example Number | Structure | Name | Analytical Data |
|---|---|---|---|
| ZZZ069 | 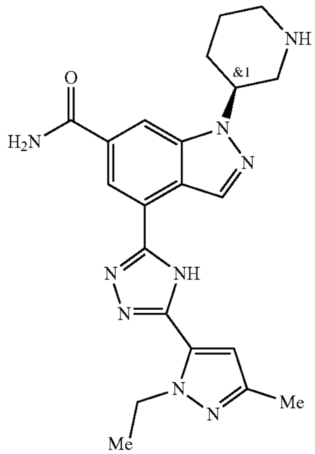 [SMILES: CCn1nc(C)cc1-c1nnc(-c2cc(C(N)=O)cc3c2cnn3[C@H]2CCCNC2)[nH]1] | 4-[5-(1-ethyl-3-methyl-1H-pyrazol-5-yl)-4H-1,2,4-triazol-3-yl]-1-[(3S)-piperidin-3-yl]-1H-indazole-6-carboxamide | LCMS [M + H] = 420 observed |
| ZZZ070 | 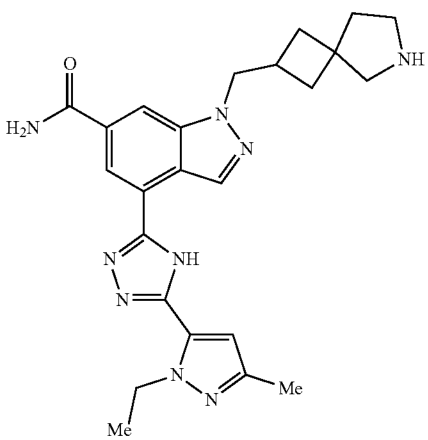 [SMILES: CCn1nc(C)cc1-c1nnc(-c2cc(C(N)=O)cc3c2cnn3CC2CC3(CCNC3)C2)[nH]1] | 1-[(6-azaspiro[3.4]octan-2-yl)methyl]-4-[5-(1-ethyl-3-methyl-1H-pyrazol-5-yl)-4H-1,2,4-triazol-3-yl]-1H-indazole-6-carboxamide | LCMS [M + H] = 460 observed |
| ZZZ071 | 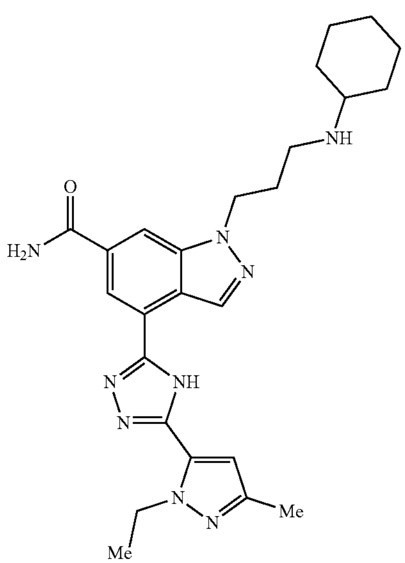 [SMILES: CCn1nc(C)cc1-c1nnc(-c2cc(C(N)=O)cc3c2cnn3CCCNC2CCCCC2)[nH]1] | 1-[3-(cyclohexylamino)propyl]-4-[5-(1-ethyl-3-methyl-1H-pyrazol-5-yl)-4H-1,2,4-triazol-3-yl]-1H-indazole-6-carboxamide | LCMS [M + H] = 476 observed |

| Example Number | Structure | Name | Analytical Data |
|---|---|---|---|
| ZZZ072 | 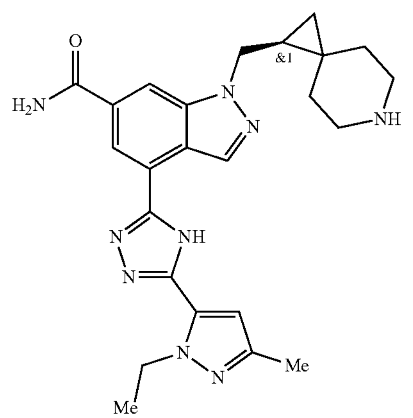 [SMILES: CCn1nc(C)cc1-c1nnc(-c2cc(C(N)=O)cc3c2cnn3C[C@H]2CC23CCNCC3)[nH]1] | 1-{[(1S)-6-azaspiro[2.5]octan-1-yl]methyl}-4-[5-(1-ethyl-3-methyl-1H-pyrazolo-5-yl)-4H-1,2,4-triazol-3-yl]-1H-indazole-6-carboxamide | LCMS [M + H] = 460 observed |
| ZZZ073 | 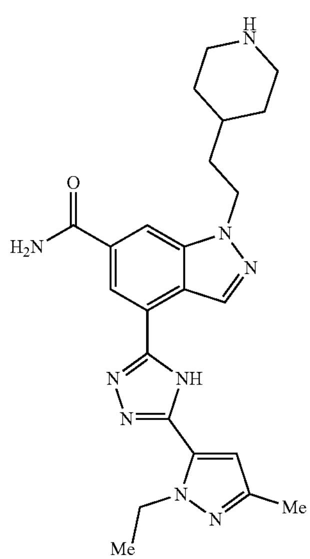 [SMILES: CCn1nc(C)cc1-c1nnc(-c2cc(C(N)=O)cc3c2cnn3CCC2CCNCC2)[nH]1] | 4-[5-(1-ethyl-3-methyl-1H-pyrazol-5-yl)-4H-1,2,4-triazol-3-yl]-1-[2-(piperidin-4-yl)ethyl]-1H-indazole-6-carboxamide | LCMS [M + H] = 448 observed |
| ZZZ074 | 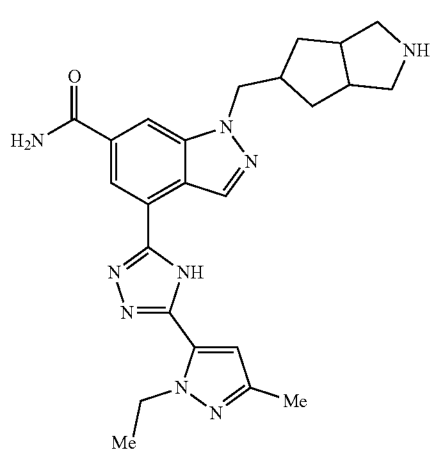 [SMILES: CCn1nc(C)cc1-c1nnc(-c2cc(C(N)=O)cc3c2cnn3CC2CC3CNCC3C2)[nH]1] | 4-[5-(1-ethyl-3-methyl-1H-pyrazol-5-yl)-4H-1,2,4-triazol-3-yl]-1-[(octahydrocyclopenta[c]pyrrol-5-yl)methyl]-1H-indazole-6-carboxamide | LCMS [M + H] = 460 observed |

| Example Number | Structure | Name | Analytical Data |
|---|---|---|---|
| ZZZ075 | 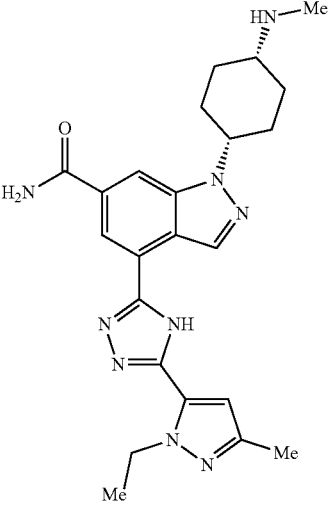 [SMILES: CCn1nc(C)cc1-c1nnc(-c2cc(C(N)=O)cc3c2cnn3[C@H]2CC[C@@H](NC)CC2)[nH]1] | 4-[5-(1-ethyl-3-methyl-1H-pyrazol-5-yl)-4H-1,2,4-triazol-3-yl]-1-[(1s,4s)-4-(methylamino)cyclohexyl]-1H-indazole-6-carboxamide | LCMS [M + H] = 448 observed |
| ZZZ076 | 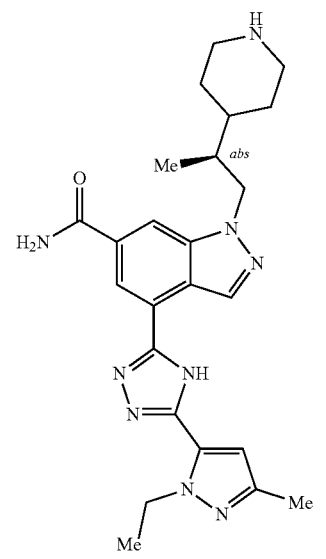 [SMILES: CCn1nc(C)cc1-c1nnc(-c2cc(C(N)=O)cc3c2cnn3C[C@@H](C)C2CCNCC2)[nH]1] | 4-[5-(1-ethyl-3-methyl-1H-pyrazol-5-yl)-4H-1,2,4-triazol-3-yl]-1-[(2S)-2-(piperidin-4-yl)propyl]-1H-indazole-6-carboxamide | LCMS [M + H] = 462 observed |
| ZZZ077 | 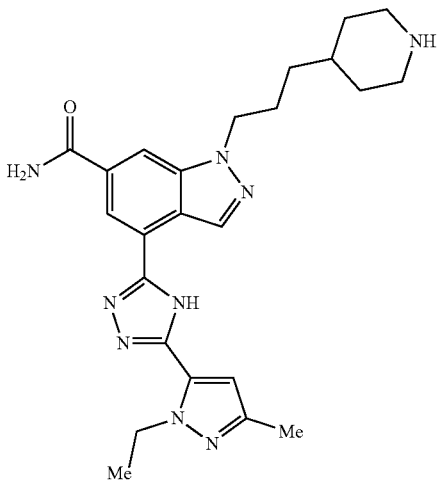 [SMILES: CCn1nc(C)cc1-c1nnc(-c2cc(C(N)=O)cc3c2cnn3CCCC2CCNCC2)[nH]1] | 4-[5-(1-ethyl-3-methyl-1H-pyrazol-5-yl)-4H-1,2,4-triazol-3-yl]-1-[3-(piperidin-4-yl)propyl]-1H-indazole-6-carboxamide | LCMS [M + H] = 462 observed |

-continued

| Example Number | Structure | Name | Analytical Data |
|---|---|---|---|
| ZZZ078 | 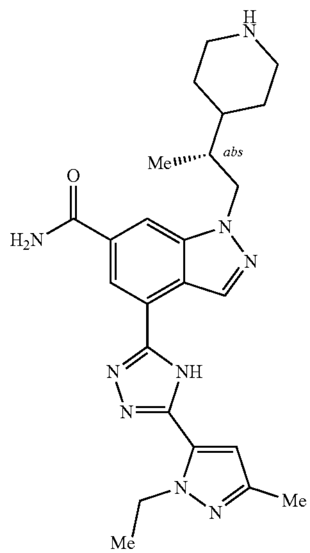 [SMILES: CCn1nc(C)cc1-c1nnc(-c2cc(C(N)=O)cc3c2cnn3C[C@H](C)C2CCNCC2)[nH]1] | 4-[5-(1-ethyl-3-methyl-1H-pyrazol-5-yl)-4H-1,2,4-triazol-3-yl]-1-[(2R)-2-(piperidin-4-yl)propyl]-1H-indazole-6-carboxamide | LCMS [M + H] = 462 observed |
| ZZZ079 | 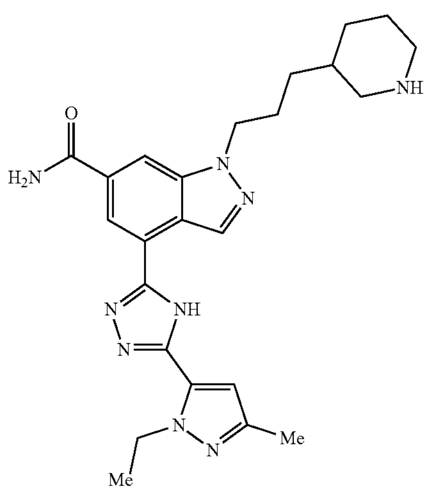 [SMILES: CCn1nc(C)cc1-c1nnc(-c2cc(C(N)=O)cc3c2cnn3CCCC2CCCNC2)[nH]1] | 4-[5-(1-ethyl-3-methyl-1H-pyrazol-5-yl)-4H-1,2,4-triazol-3-yl]-1-[3-(piperidin-3-yl)propyl]-1H-indazole-6-carboxamide | LCMS [M + H] = 462 observed |
| ZZZ080 | 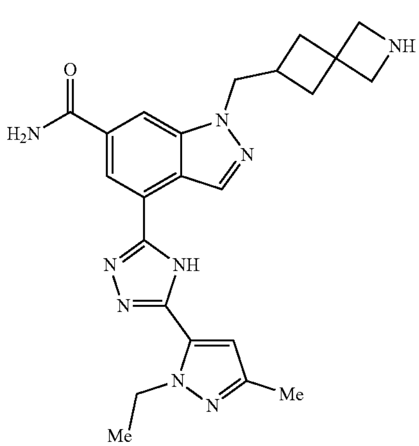 [SMILES: CCn1nc(C)cc1-c1nnc(-c2cc(C(N)=O)cc3c2cnn3CC2CC3(CNC3)C2)[nH]1] | 1-[(2-azaspiro[3.3]heptan-6-yl)methyl]-4-[5-(1-ethyl-3-methyl-1H-pyrazol-5-yl)-4H-1,2,4-triazol-3-yl]-1H-indazole-6-carboxamide | LCMS [M + H] = 446 observed |

-continued

| Example Number | Structure | Name | Analytical Data |
|---|---|---|---|
| ZZZ081 | 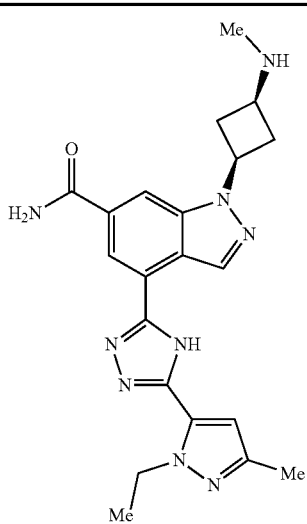 | 4-[5-(1-ethyl-3-methyl-1H-pyrazol-5-yl)-4H-1,2,4-triazol-3-yl]-1-[(1s,3s)-3-(methylamino)cyclobutyl]-1H-indazole-6-carboxamide | LCMS [M + H] = 420 observed |
| ZZZ082 | 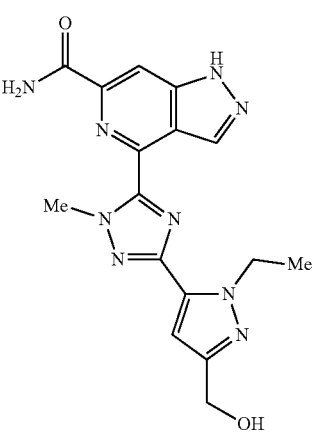 [SMILES: CCn1nc(CO)cc1-c1nc(-c2nc(C(N)=O)cc3[nH]ncc23)n(C)n1] | 4-{3-[1-ethyl-3-(hydroxymethyl)-1H-pyrazol-5-yl]-1-methyl-1H-1,2,4-triazol-5-yl}-1H-pyrazolo[4,3-c]pyridine-6-carboxamide | LCMS [M + H] = 368 observed |
| ZZZ083 | 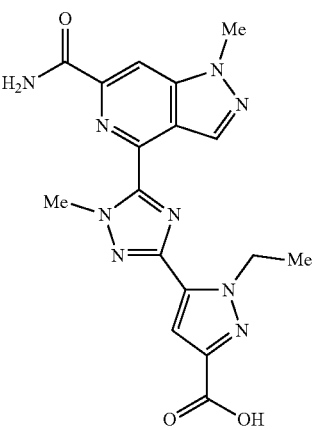 [SMILES: CCn1nc(C(=O)O)cc1-c1nc(-c2nc(C(N)=O)cc3c2cnn3C)n(C)n1] | 5-[5-(6-carbamoyl-1-methyl-1H-pyrazolo[4,3-c]pyridin-4-yl)-1-methyl-1H-1,2,4-triazol-3-yl]-1-ethyl-1H-pyrazole-3-carboxylic acid | LCMS [M + H] = 396 observed |

| Example Number | Structure | Name | Analytical Data |
|---|---|---|---|
| ZZZ084 | 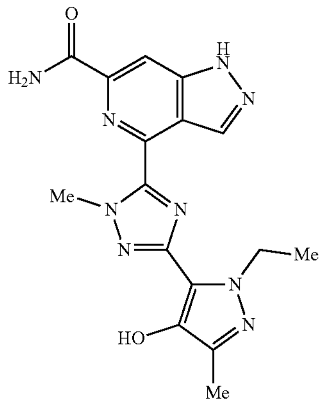 [SMILES: CCn1nc(C)c(O)c1-c1nc(-c2nc(C(N)=O)cc3[nH]ncc23)n(C)n1] | 4-[3-(1-ethyl-4-hydroxy-3-methyl-1H-pyrazol-5-yl)-1-methyl-1H-1,2,4-triazol-5-yl]-1H-pyrazolo[4,3-c]pyridine-6-carboxamide | LCMS [M + H] = 368 observed |
| ZZZ085 | 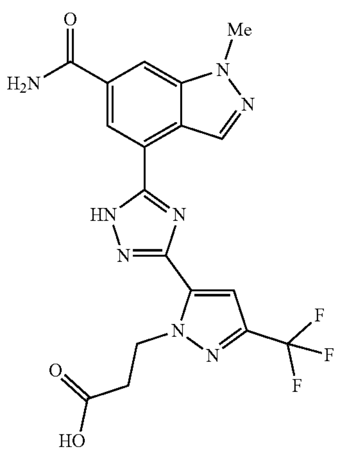 [SMILES: Cn1ncc2c(-c3nc(-c4cc(C(F)(F)F)nn4CCC(=O)O)n[nH]3)cc(C(N)=O)cc21] | 3-{5-[5-(6-carbamoyl-1-methyl-1H-indazol-4-yl)-1H-1,2,4-triazol-3-yl]-3-(trifluoromethyl)-1H-pyrazol-1-yl}propanoic acid | LCMS [M + H] = 449.1 observed |
| ZZZ086 | 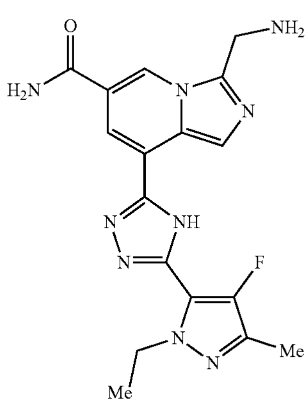 [SMILES: CCn1nc(C)c(F)c1-c1nnc(-c2cc(C(N)=O)cn3c(CN)ncc23)[nH]1] | 3-(aminomethyl)-8-[5-(1-ethyl-4-fluoro-3-methyl-1H-pyrazol-5-yl)-4H-1,2,4-triazol-3-yl]imidazo[1,5-c]pyridine-6-carboxamide | LCMS [M + H] = 384.0 observed |

| Example Number | Structure | Name | Analytical Data |
|---|---|---|---|
| ZZZ087 | 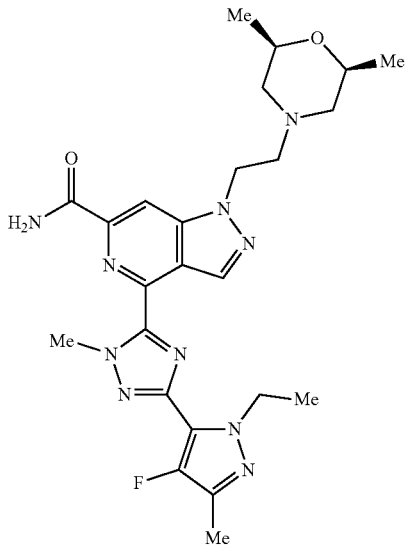 [SMILES: CCn1nc(C)c(F)c1-c1nc(-c2nc(C(N)=O)cc3c2cnn3CCN2C[C@@H](C)O[C@@H](C)C2)n(C)n1] | 1-{2-[(2R,6S)-2,6-dimethylmorpholin-4-yl]ethyl}-4-[3-(1-ethyl-4-fluoro-3-methyl-1H-pyrazol-5-yl)-1-methyl-1H-1,2,4-triazol-5-yl]-1H-pyrazolo[4,3-c]pyridine-6-carboxamide | LCMS [M + H] = 511.2 observed |
| ZZZ088 | 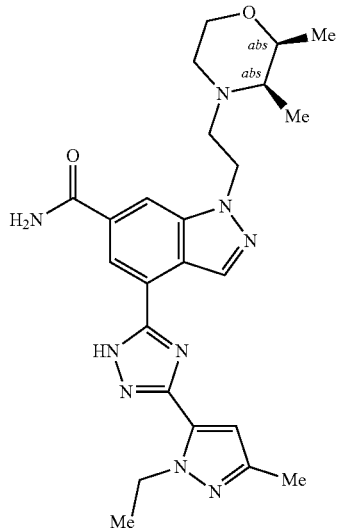 [SMILES: CCn1nc(C)cc1-c1n[nH]c(-c2cc(C(N)=O)cc3c2cnn3CCN2CCO[C@@H](C)[C@H]2C)n1] | 1-{2-[(2S,3R)-2,3-dimethylmorpholin-4-yl]ethyl}-4-[3-(1-ethyl-3-methyl-1H-pyrazol-5-yl)-1H-1,2,4-triazol-5-yl]-1H-indazole-6-carboxamide | LCMS [M + H] = 478.5 observed |

| Example Number | Structure | Name | Analytical Data |
|---|---|---|---|
| ZZZ089 | 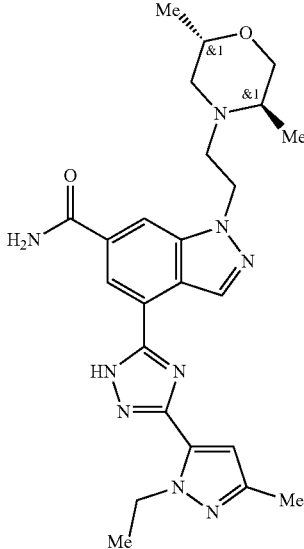 [SMILES: CCn1nc(C)cc1-c1n[nH]c(-c2cc(C(N)=O)cc3c2cnn3CCN2C[C@H](C)OC[C@H]2C)n1] | 1-{2-[(2S,5R)-2,5-dimethylmorpholin-4-yl]ethyl}-4-[3-(1-ethyl-3-methyl-1H-pyrazol-5-yl)-1H-1,2,4-triazol-5-yl]-1H-indazole-6-carboxamide | LCMS [M + H] = 478.5 observed |
| ZZZ090 | 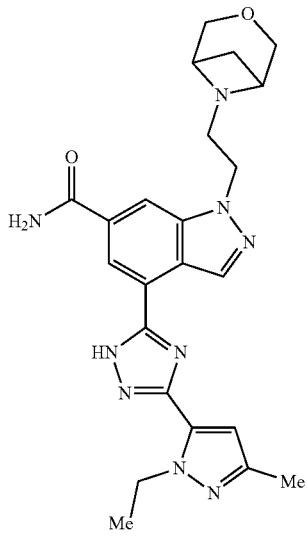 [SMILES: CCn1nc(C)cc1-c1n[nH]c(-c2cc(C(N)=O)cc3c2cnn3CCN2C3COCC2C3)n1] | 4-[3-(1-ethyl-3-methyl-1H-pyrazol-5-yl)-1H-1,2,4-triazol-5-yl]-1-[2-(3-oxa-6-azabicyclo[3.1.1]heptan-6-yl)ethyl]-1H-indazole-6-carboxamide | LCMS [M + H] = 462.4 observed |

| Example Number | Structure | Name | Analytical Data |
|---|---|---|---|
| ZZZ091 | 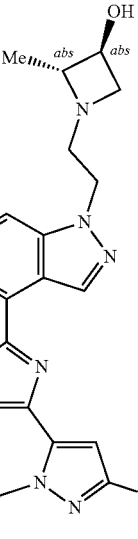 | 4-[3-(1-ethyl-3-methyl-1H-pyrazol-5-yl)-1H-1,2,4-triazol-5-yl]-1-{2-[(2R,3S)-3-hydroxy-2-methylazetidin-1-yl]ethyl}-1H-indazole-6-carboxamide | LCMS [M + H] = 450.4 observed |
| ZZZ092 | 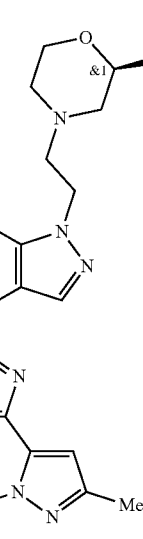 | 4-[3-(1-ethyl-3-methyl-1H-pyrazol-5-yl)-1H-1,2,4-triazol-5-yl]-1-{2-[(2R)-2-(hydroxymethyl)morpholin-4-yl]ethyl}-1H-indazole-6-carboxamide | LCMS [M + H] = 480.4 observed |
| ZZZ093 | 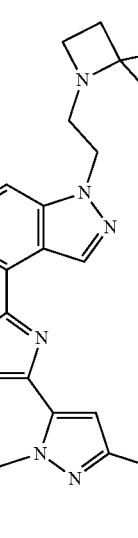 | 1-[2-(4-azaspiro[2.3]hexan-4-yl)ethyl]-4-[3-(1-ethyl-3-methyl-1H-pyrazol-5-yl)-1H-1,2,4-triazol-5-yl]-1H-indazole-6-carboxamide | LCMS [M + H] = 446.4 observed |

-continued
| Example Number | Structure | Name | Analytical Data |
|---|---|---|---|
| ZZZ094 | 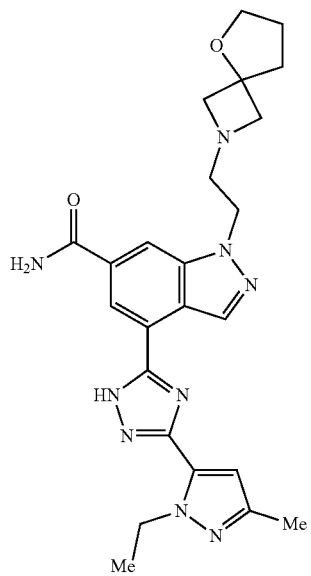 [SMILES: CCn1nc(C)cc1-c1n[nH]c(-c2cc(C(N)=O)cc3c2cnn3CCN2CC3(CCCO3)C2)n1] | 4-[3-(1-ethyl-3-methyl-1H-pyrazol-5-yl)-1H-1,2,4-triazol-5-yl]-1-[2-(5-oxa-2-azaspiro[3.4]octan-2-yl)ethyl]-1H-indazole-6-carboxamide | LCMS [M + H] = 476.4 observed |
| ZZZ095 | 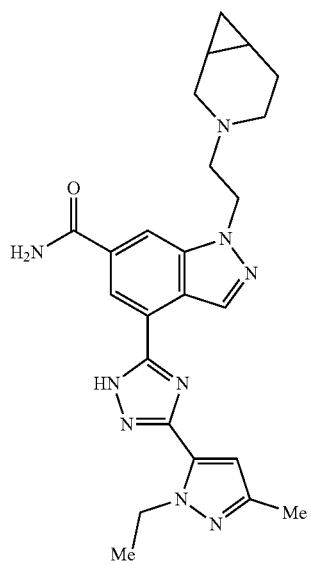 [SMILES: CCn1nc(C)cc1-c1n[nH]c(-c2cc(C(N)=O)cc3c2cnn3CCN2CCC3CC3C2)n1] | 1-[2-(3-azabicyclo[4.1.0]heptan-3-yl)ethyl]-4-[3-(1-ethyl-3-methyl-1H-pyrazol-5-yl)-1H-1,2,4-triazol-5-yl]-1H-indazole-6-carboxamide | LCMS [M + H] = 460.4 observed |

| Example Number | Structure | Name | Analytical Data |
|---|---|---|---|
| ZZZ096 | 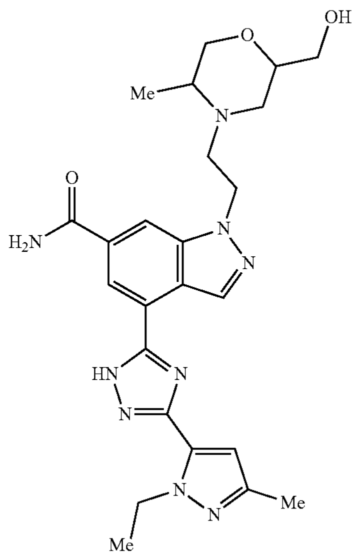 [SMILES: CCn1nc(C)cc1-c1n[nH]c(-c2cc(C(N)=O)cc3c2cnn3CCN2CC(CO)OCC2C)n1] | 4-[3-(1-ethyl-3-methyl-1H-pyrazol-5-yl)-1H-1,2,4-triazol-5-yl]-1-{2-[2-(hydroxymethyl)-5-methylmorpholin-4-yl]ethyl}-1H-indazole-6-carboxamide | LCMS [M + H] = 494.5 observed |
| ZZZ097 | 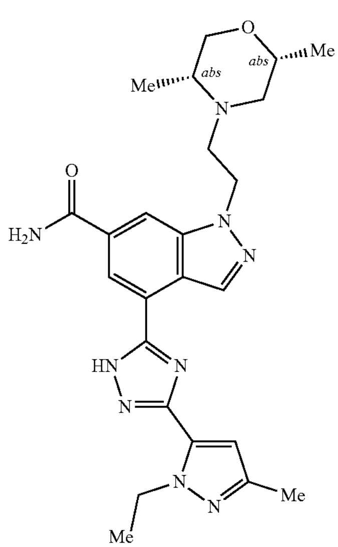 [SMILES: CCn1nc(C)cc1-c1n[nH]c(-c2cc(C(N)=O)cc3c2cnn3CCN2C[C@@H](C)OC[C@H]2C)n1] | 1-{2-[(2R,5R)-2,5-dimethylmorpholin-4-yl]ethyl}-4-[3-(1-ethyl-3-methyl-1H-pyrazol-5-yl)-1H-1,2,4-triazol-5-yl]-1H-indazole-6-carboxamide | LCMS [M + H] = 478.5 observed |

| Example Number | Structure | Name | Analytical Data |
|---|---|---|---|
| ZZZ098 | 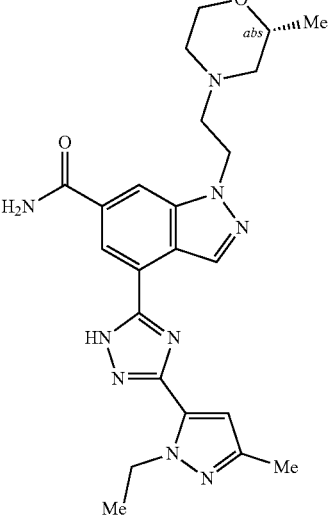 | 4-[3-(1-ethyl-3-methyl-1H-pyrazol-5-yl)-1H-1,2,4-triazol-5-yl]-1-{2-[(2R)-2-methylmorpholin-4-yl]ethyl}-1H-indazole-6-carboxamide | LCMS [M + H] = 464.4 observed |
| ZZZ099 | 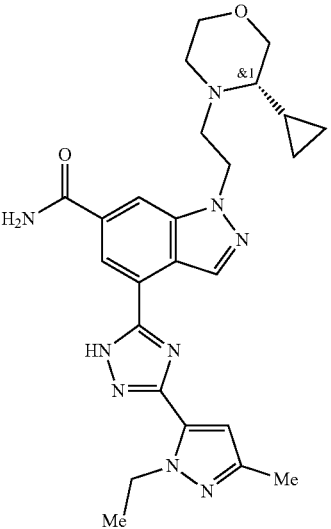 [SMILES: CCn1nc(C)cc1-c1n[nH]c(-c2cc(C(N)=O)cc3c2cnn3CCN2CCOC[C@@H]2C2CC2)n1] | 1-{2-[(3S)-3-cyclopropylmorpholin-4-yl]ethyl}-4-[3-(1-ethyl-3-methyl-1H-pyrazol-5-yl)-1H-1,2,4-triazol-5-yl]-1H-indazole-6-carboxamide | LCMS [M + H] = 490.5 observed |

-continued
| Example Number | Structure | Name | Analytical Data |
|---|---|---|---|
| ZZZ100 | 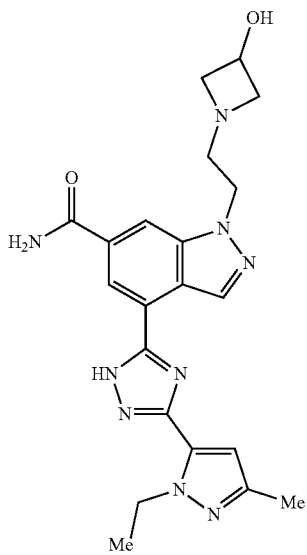 [SMILES: CCn1nc(C)cc1-c1n[nH]c(-c2cc(C(N)=O)cc3c2cnn3CCN2CC(O)C2)n1] | 4-[3-(1-ethyl-3-methyl-1H-pyrazol-5-yl)-1H-1,2,4-triazol-5-yl]-1-[2-(3-hydroxyazetidin-1-yl)ethyl]-1H-indazole-6-carboxamide | LCMS [M + H] = 436.4 observed |
| ZZZ101 | 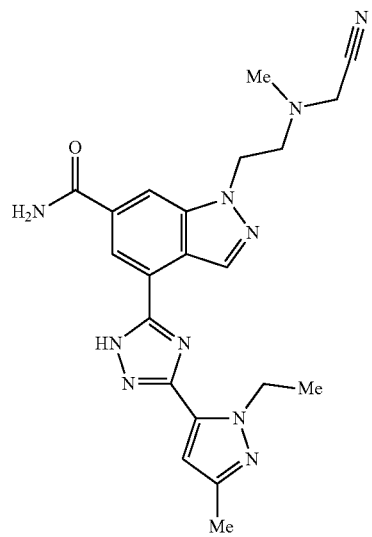 [SMILES: CCn1nc(C)cc1-c1n[nH]c(-c2cc(C(N)=O)cc3c2cnn3CCN(C)CC#N)n1] | 1-{2-[(cyanomethyl)(methyl)amino]ethyl}-4-[3-(1-ethyl-3-methyl-1H-pyrazol-5-yl)-1H-1,2,4-triazol-5-yl]-1H-indazole-6-carboxamide | LCMS [M + H] = 433.4 observed |

| Example Number | Structure | Name | Analytical Data |
|---|---|---|---|
| ZZZ102 | 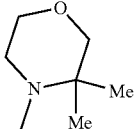 | 1-[2-(3,3-dimethylmorpholin-4-yl)ethyl]-4-[3-(1-ethyl-3-methyl-1H-pyrazol-5-yl)-1H-1,2,4-triazol-5-yl]-1H-indazole-6-carboxamide | LCMS [M + H] = 478.5 observed |
| ZZZ103 | 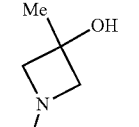 | 4-[3-(1-ethyl-3-methyl-1H-pyrazol-5-yl)-1H-1,2,4-triazol-5-yl]-1-[2-(3-hydroxy-3-methylazetidin-1-yl)ethyl]-1H-indazole-6-carboxamide | LCMS [M + H] = 450.4 observed |
| ZZZ104 | 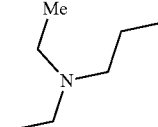 | 1-{2-[(2-cyanoethyl)(ethyl)amino]ethyl}-4-[3-(1-ethyl-3-methyl-1H-pyrazol-5-yl)-1H-1,2,4-triazol-5-yl]-1H-indazole-6-carboxamide | LCMS [M + H] = 461.4 observed |

| Example Number | Structure | Name | Analytical Data |
|---|---|---|---|
| ZZZ105 | 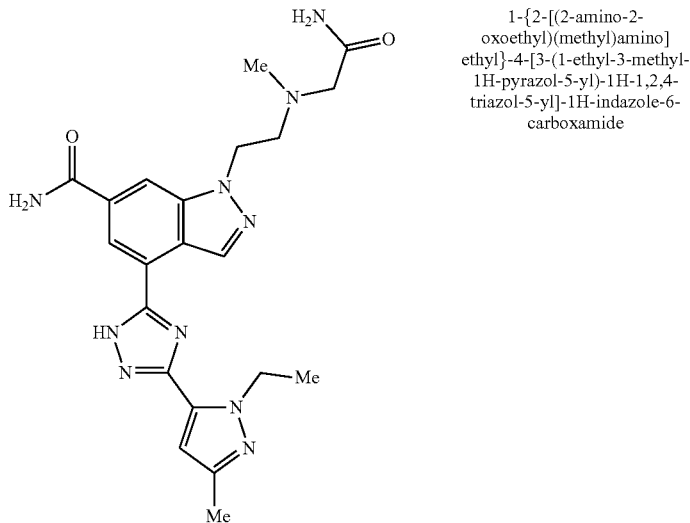 | 1-{2-[(2-amino-2-oxoethyl)(methyl)amino]ethyl}-4-[3-(1-ethyl-3-methyl-1H-pyrazol-5-yl)-1H-1,2,4-triazol-5-yl]-1H-indazole-6-carboxamide | LCMS [M + H] = 451.4 observed |
| ZZZ106 | 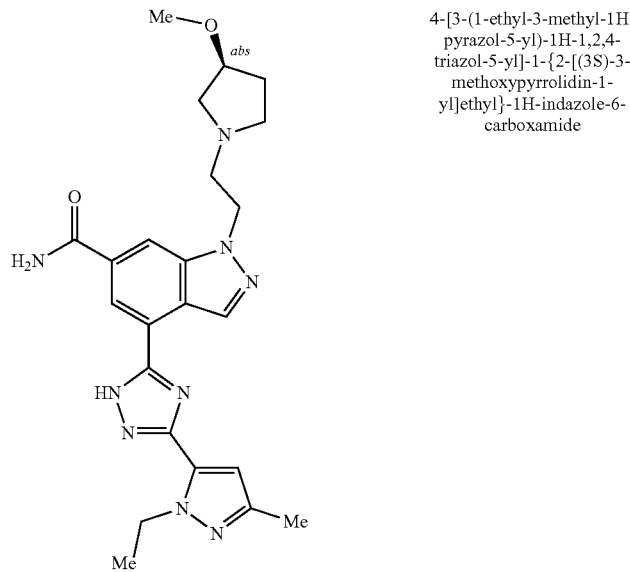 | 4-[3-(1-ethyl-3-methyl-1H-pyrazol-5-yl)-1H-1,2,4-triazol-5-yl]-1-{2-[(3S)-3-methoxypyrrolidin-1-yl]ethyl}-1H-indazole-6-carboxamide | LCMS [M + H] = 464.4 observed |

-continued

| Example Number | Structure | Name | Analytical Data |
|---|---|---|---|
| ZZZ107 | 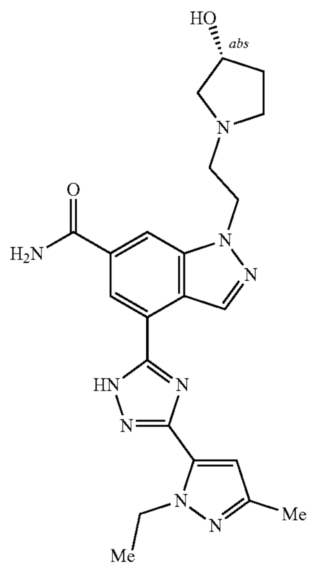 [SMILES: CCn1nc(C)cc1-c1n[nH]c(-c2cc(C(N)=O)cc3c2cnn3CCN2CC[C@@H](O)C2)n1] | 4-[3-(1-ethyl-3-methyl-1H-pyrazol-5-yl)-1H-1,2,4-triazol-5-yl]-1-{2-[(3R)-3-hydroxypyrrolidin-1-yl]ethyl}-1H-indazole-6-carboxamide | LCMS [M + H] = 450.4 observed |
| ZZZ108 | 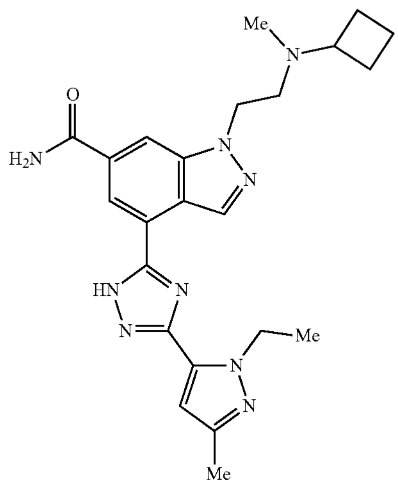 [SMILES: CCn1nc(C)cc1-c1n[nH]c(-c2cc(C(N)=O)cc3c2cnn3CCN(C)C2CCC2)n1] | 1-{2-[cyclobutyl(methyl)amino]ethyl}-4-[3-(1-ethyl-3-methyl-1H-pyrazol-5-yl)-1H-1,2,4-triazol-5-yl]-1H-indazole-6-carboxamide | LCMS [M + H] = 448.4 observed |
| ZZZ109 | 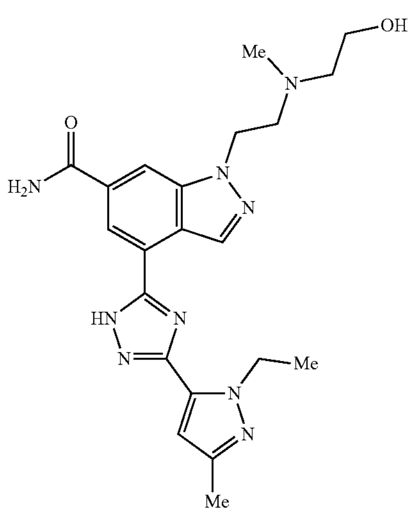 [SMILES: CCn1nc(C)cc1-c1n[nH]c(-c2cc(C(N)=O)cc3c2cnn3CCN(C)CCO)n1] | 4-[3-(1-ethyl-3-methyl-1H-pyrazol-5-yl)-1H-1,2,4-triazol-5-yl]-1-{2-[(2-hydroxyethyl)(methyl)amino]ethyl}-1H-indazole-6-carboxamide | LCMS [M + H] = 438.4 observed |

| Example Number | Structure | Name | Analytical Data |
|---|---|---|---|
| ZZZ110 | 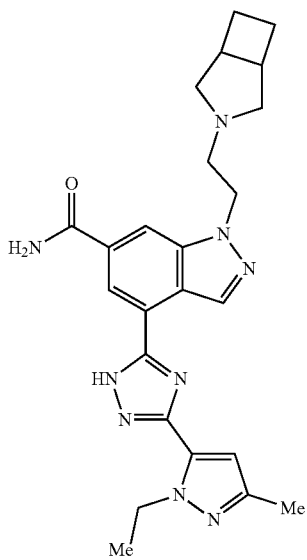 [SMILES: CCn1nc(C)cc1-c1n[nH]c(-c2cc(C(N)=O)cc3c2cnn3CCN2CC3CCC3C2)n1] | 1-[2-(3-azabicyclo[3.2.0]heptan-3-yl)ethyl]-4-[3-(1-ethyl-3-methyl-1H-pyrazol-5-yl)-1H-1,2,4-triazol-5-yl]-1H-indazole-6-carboxamide | LCMS [M + H] = 460.4 observed |
| ZZZ111 | 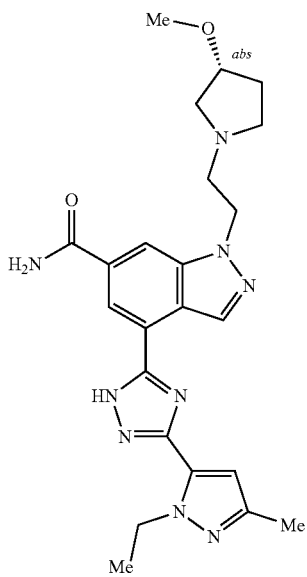 [SMILES: CCn1nc(C)cc1-c1n[nH]c(-c2cc(C(N)=O)cc3c2cnn3CCN2CC[C@@H](OC)C2)n1] | 4-[3-(1-ethyl-3-methyl-1H-pyrazol-5-yl)-1H-1,2,4-triazol-5-yl]-1-{2-[(3R)-3-methoxypyrrolidin-1-yl]ethyl}-1H-indazole-6-carboxamide | LCMS [M + H] = 464.4 observed |
| ZZZ112 | 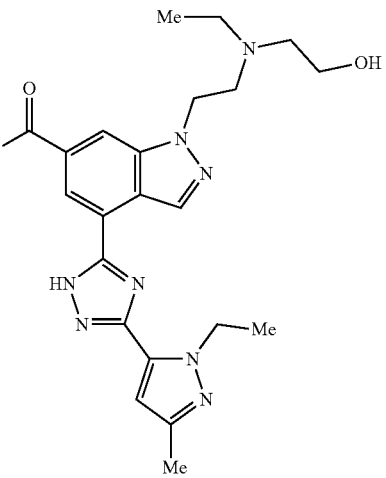 | 1-{2-[ethyl(2-hydroxyethyl)amino]ethyl}-4-[3-(1-ethyl-3-methyl-1H-pyrazol-5-yl)-1H-1,2,4-triazol-5-yl]-1H-indazole-6-carboxamide | LCMS [M + H] = 452.4 observed |

| Example Number | Structure | Name | Analytical Data |
|---|---|---|---|
| ZZZ113 | 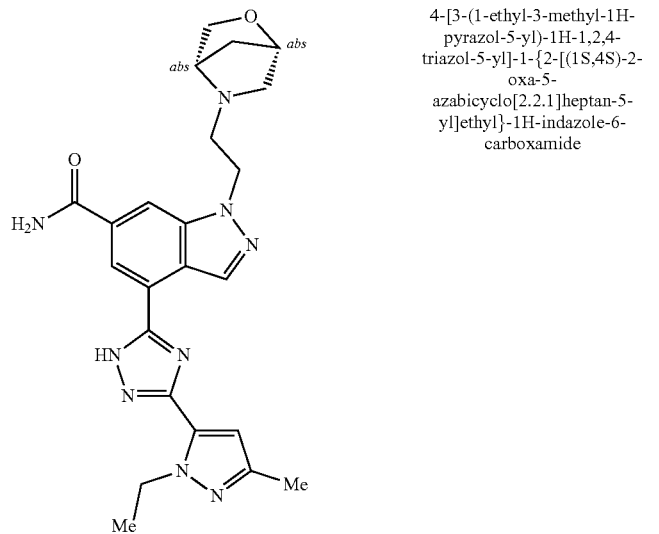 | 4-[3-(1-ethyl-3-methyl-1H-pyrazol-5-yl)-1H-1,2,4-triazol-5-yl]-1-{2-[(1S,4S)-2-oxa-5-azabicyclo[2.2.1]heptan-5-yl]ethyl}-1H-indazole-6-carboxamide | LCMS [M + H] = 462.4 observed |
| ZZZ114 | 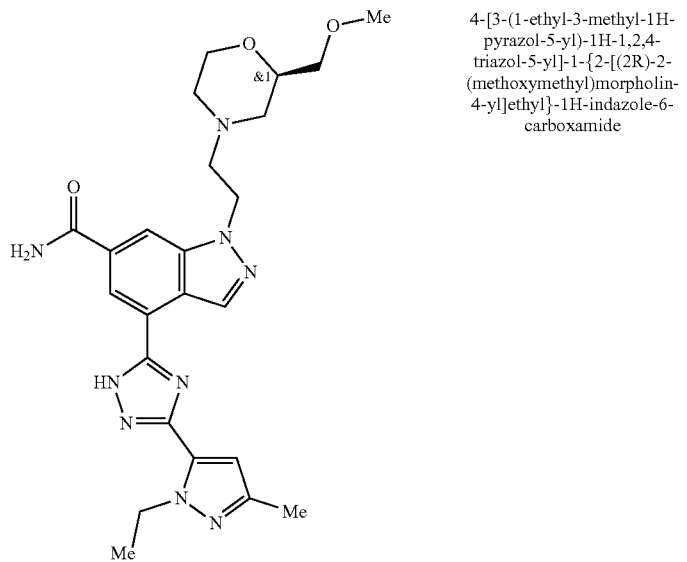 | 4-[3-(1-ethyl-3-methyl-1H-pyrazol-5-yl)-1H-1,2,4-triazol-5-yl]-1-{2-[(2R)-2-(methoxymethyl)morpholin-4-yl]ethyl}-1H-indazole-6-carboxamide | LCMS [M + H] = 494.5 observed |

-continued
| Example Number | Structure | Name | Analytical Data |
|---|---|---|---|
| ZZZ115 | 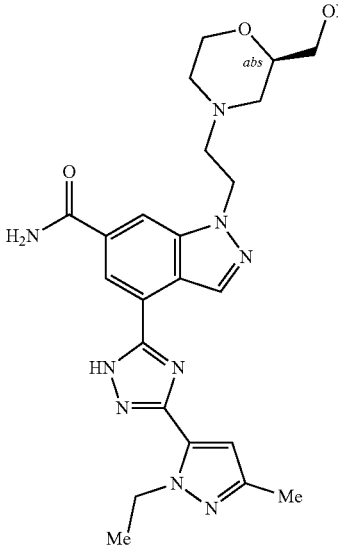 | 4-[3-(1-ethyl-3-methyl-1H-pyrazol-5-yl)-1H-1,2,4-triazol-5-yl]-1-{2-[(2R)-2-(hydroxymethyl)morpholin-4-yl]ethyl}-1H-indazole-6-carboxamide | LCMS [M + H] = 480.4 observed |
| ZZZ116 | 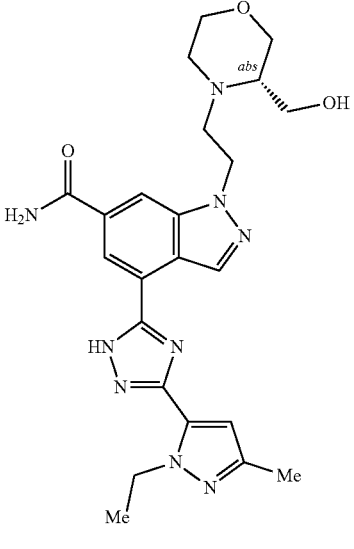 [SMILES: CCn1nc(C)cc1-c1n[nH]c(-c2cc(C(N)=O)cc3c2cnn3CCN2CCOC[C@@H]2CO)n1] | 4-[3-(1-ethyl-3-methyl-1H-pyrazol-5-yl)-1H-1,2,4-triazol-5-yl]-1-{2-[(3S)-3-(hydroxymethyl)morpholin-4-yl]ethyl}-1H-indazole-6-carboxamide | LCMS [M + H] = 480.4 observed |

| Example Number | Structure | Name | Analytical Data |
|---|---|---|---|
| ZZZ117 | 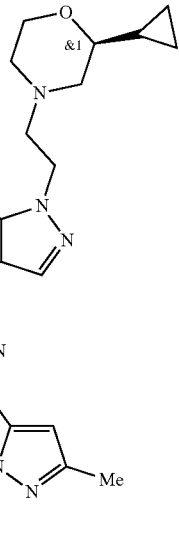 | 1-{2-[(2S)-2-cyclopropylmorpholin-4-yl]ethyl}-4-[3-(1-ethyl-3-methyl-1H-pyrazol-5-yl)-1H-1,2,4-triazol-5-yl]-1H-indazole-6-carboxamide | LCMS [M + H] = 490.5 observed |
| ZZZ118 | 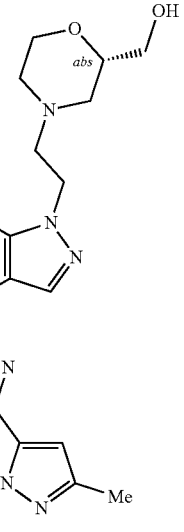 | 4-[3-(1-ethyl-3-methyl-1H-pyrazol-5-yl)-1H-1,2,4-triazol-5-yl]-1-{2-[(2S)-2-(hydroxymethyl)morpholin-4-yl]ethyl}-1H-indazole-6-carboxamide | LCMS [M + H] = 480.4 observed |

-continued

| Example Number | Structure | Name | Analytical Data |
|---|---|---|---|
| ZZZ119 | 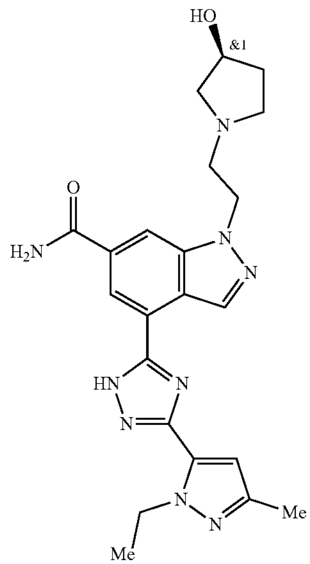 [SMILES: CCn1nc(C)cc1-c1n[nH]c(-c2cc(C(N)=O)cc3c2cnn3CCN2CC[C@H](O)C2)n1] | 4-[3-(1-ethyl-3-methyl-1H-pyrazol-5-yl)-1H-1,2,4-triazol-5-yl]-1-{2-[(3S)-3-hydroxypyrrolidin-1-yl]ethyl}-1H-indazole-6-carboxamide | LCMS [M + H] = 450.4 observed |
| ZZZ120 | 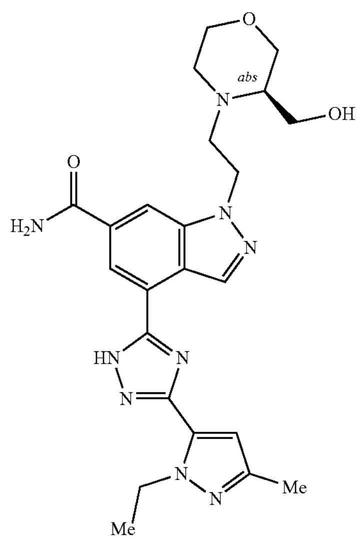 [SMILES: CCn1nc(C)cc1-c1n[nH]c(-c2cc(C(N)=O)cc3c2cnn3CCN2CCOC[C@H]2CO)n1] | 4-[3-(1-ethyl-3-methyl-1H-pyrazol-5-yl)-1H-1,2,4-triazol-5-yl]-1-{2-[(3R)-3-(hydroxymethyl)morpholin-4-yl]ethyl}-1H-indazole-6-carboxamide | LCMS [M + H] = 480.4 observed |
| ZZZ121 | 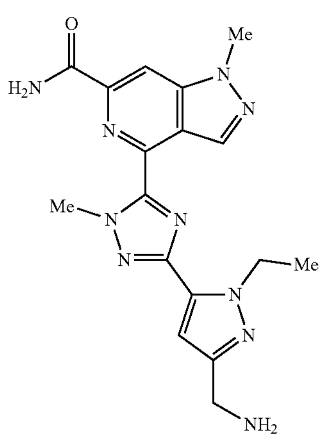 [SMILES: CCn1nc(CN)cc1-c1nc(-c2nc(C(N)=O)cc3c2cnn3C)n(C)n1] | 4-{3-[3-(aminomethyl)-1-ethyl-1H-pyrazol-5-yl]-1-methyl-1H-1,2,4-triazol-5-yl}-1-methyl-1H-pyrazolo[4,3-c]pyridine-6-carboxamide | $^1$H NMR (400 MHz, DMSO-d$_6$) δ ppm 8.74 (d, J = 0.86 Hz, 1 H) 8.54 (d, J = 0.73 Hz, 1 H) 7.91-8.06 (m, 4 H) 7.03 (s, 1 H) 4.72 (q, J = 7.25 Hz, 2 H) 4.48 (s, 3H) 4.23 (s, 3 H) 4.06 (s, 2 H) 1.47 (t, J = 7.15 Hz, 3 H) |

| Example Number | Structure | Name | Analytical Data |
|---|---|---|---|
| ZZZ122 | 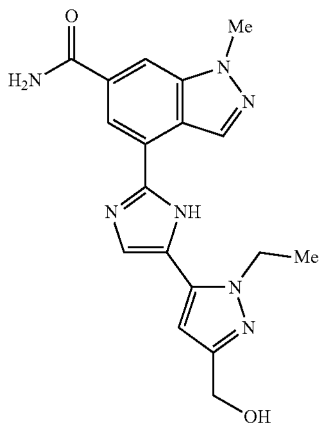 [SMILES: CCn1nc(CO)cc1-c1cnc(-c2cc(C(N)=O)cc3c2cnn3C)[nH]1] | 4-{5-[1-ethyl-3-(hydroxymethyl)-1H-pyrazol-5-yl]-1H-imidazol-2-yl}-1-methyl-1H-indazole-6-carboxamide | LCMS [M + H] = 366 observed |
| ZZZ123 | 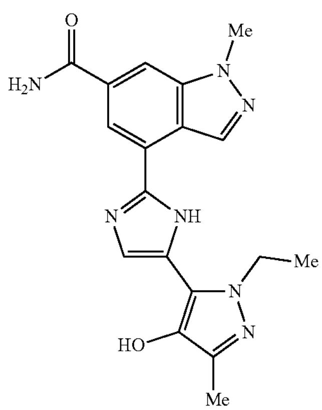 [SMILES: CCn1nc(C)c(O)c1-c1cnc(-c2cc(C(N)=O)cc3c2cnn3C)[nH]1] | 4-[5-(1-ethyl-4-hydroxy-3-methyl-1H-pyrazol-5-yl)-1H-imidazol-2-yl]-1-methyl-1H-indazole-6-carboxamide | LCMS [M + H] = 366 observed |
| ZZZ124 | 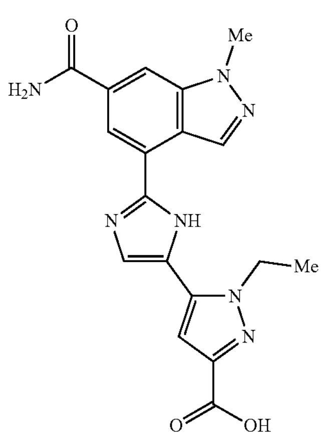 [SMILES: CCn1nc(C(=O)O)cc1-c1cnc(-c2cc(C(N)=O)cc3c2cnn3C)[nH]1] | 5-[2-(6-carbamoyl-1-methyl-1H-indazol-4-yl)-1H-imidazol-5-yl]-1-ethyl-1H-pyrazole-3-carboxylic acid | LCMS [M + H] = 380 observed |

-continued

| Example Number | Structure | Name | Analytical Data |
|---|---|---|---|
| ZZZ125 | 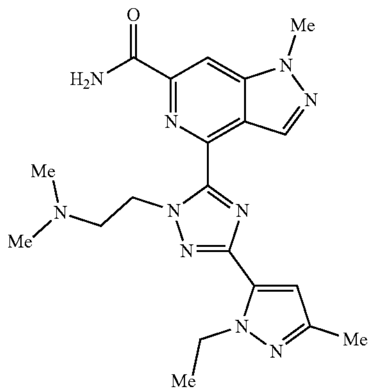 [SMILES: CCn1nc(C)cc1-c1nc(-c2nc(C(N)=O)cc3c2cnn3C)n(CCN(C)C)n1] | 4-{1-[2-(dimethylamino)ethyl]-3-(1-ethyl-3-methyl-1H-pyrazol-5-yl)-1H-1,2,4-triazol-5-yl}-1-methyl-1H-pyrazolo[4,3-c]pyridine-6-carboxamide | $^1$H NMR (400 MHz, METHANOL-$d_4$) δ ppm 1.39 (t, J = 7.22 Hz, 3 H), 2.17 (s, 6 H) 2.21 (s, 3 H) 2.78-2.85 (br t, J = 6.63 Hz, 2 H), 4.11 (s, 3 H) 4.56-4.68 (m, 2 H) 4.96 (t, J = 6.83 Hz, 2 H) 6.69 (s, 1 H) 8.32 (s, 1 H) 8.68 (s, 1 H) |
| ZZZ126 | 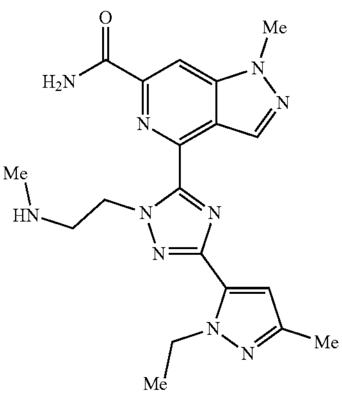 [SMILES: CCn1nc(C)cc1-c1nc(-c2nc(C(N)=O)cc3c2cnn3C)n(CCNC)n1] | 4-{3-(1-ethyl-3-methyl-1H-pyrazol-5-yl)-1-[2-(methylamino)ethyl]-1H-1,2,4-triazol-5-yl}-1-methyl-1H-pyrazolo[4,3-c]pyridine-6-carboxamide | $^1$H NMR (400 MHz, METHANOL-$d_4$) δ ppm 1.47-1.53 (m, 3 H), 2.31 (s, 3 H), 2.43 (s, 3 H), 3.44-3.69 (m, 2 H) 4.23 (s, 3 H) 4.69-4.75 (m, 2 H) 5.04-5.16 (m, 2 H), 6.63 (s, 1 H) 8.46 (s, 1 H) 8.79-8.84 (s, 1 H) |
| ZZZ127 | 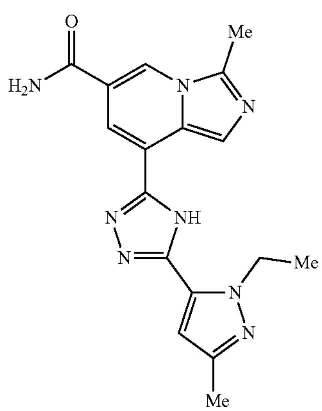 [SMILES: CCn1nc(C)cc1-c1nnc(-c2cc(C(N)=O)cn3c(C)ncc23)[nH]1] | 3-amino-8-[5-(1-ethyl-3-methyl-1H-pyrazol-5-yl)-4H-1,2,4-triazol-3-yl]imidazo[1,5-a]pyridine-6-carboxamide | $^1$H NMR (600 MHz, DMSO-$d_6$) δ ppm 8.52 (br s, 1 H) 8.42 (br s, 1 H) 7.93 (br s, 1 H) 7.63 (s, 1 H) 7.58 (s, 1 H) 7.26-7.39 (m, 1 H) 6.56 (s, 1 H) 6.05 (br s, 2 H) 4.66 (q, J = 7.09 Hz, 2 H) 2.20 (s, 3 H) 1.38 (t, J = 7.06 Hz, 3 H) |
| ZZZ128 | 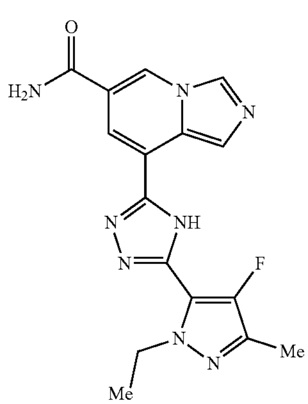 [SMILES: CCn1nc(C)c(F)c1-c1nnc(-c2cc(C(N)=O)cn3cncc23)[nH]1] | 8-[5-(1-ethyl-4-fluoro-3-methyl-1H-pyrazol-5-yl)-4H-1,2,4-triazol-3-yl]imidazo[1,5-a]pyridine-6-carboxamide | $^1$H NMR (700 MHz, DMSO-$d_6$) δ ppm 8.85 (br s, 1 H) 8.49 (br s, 1 H) 8.16 (br s, 1 H) 8.08 (br s, 1 H) 7.90 (br s, 1 H) 7.42 (br s, 1 H) 4.53 (br s, 2 H) 2.17 (br s, 3 H) 1.32 (br s, 3 H) |

| Example Number | Structure | Name | Analytical Data |
|---|---|---|---|
| ZZZ129 | 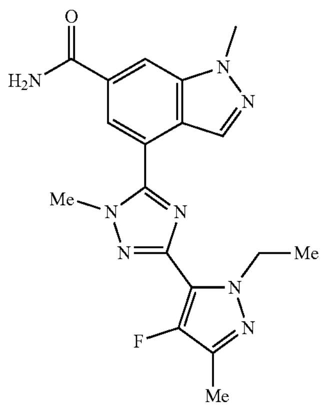 [SMILES: CCn1nc(C)c(F)c1-c1nc(-c2cc(C(N)=O)cc3c2cnn3C)n(C)n1] | 4-[3-(1-ethyl-4-fluoro-3-methyl-1H-pyrazol-5-yl)-1-methyl-1H-1,2,4-triazol-5-yl]-1-methyl-1H-indazole-6-carboxamide | LCMS [M + H] = 383.1 observed |
| ZZZ130 | 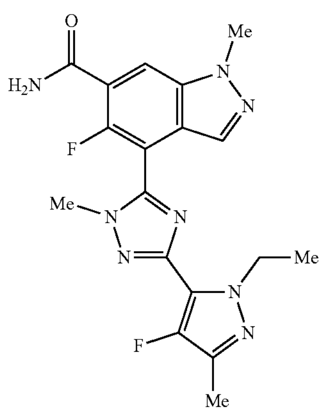 [SMILES: CCn1nc(C)c(F)c1-c1nc(-c2c(F)c(C(N)=O)cc3c2cnn3C)n(C)n1] | 4-[3-(1-ethyl-4-fluoro-3-methyl-1H-pyrazol-5-yl)-1-methyl-1H-1,2,4-triazol-5-yl]-5-fluoro-1-methyl-1H-indazole-6-carboxamide | LCMS [M + H] = 401.3 observed |
| ZZZ131 | 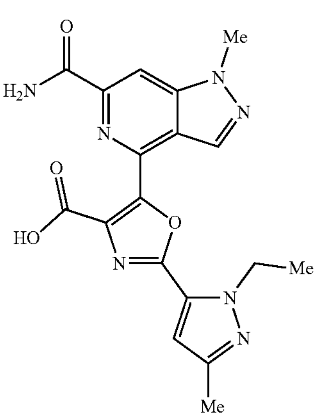 [SMILES: CCn1nc(C)cc1-c1nc(C(=O)O)c(-c2nc(C(N)=O)cc3c2cnn3C)o1] | 5-(6-carbamoyl-1-methyl-1H-pyrazolo[4,3-c]pyridin-4-yl)-2-(1-ethyl-3-methyl-1H-pyrazol-5-yl)-1,3-oxazole-4-carboxylic acid | LCMS [M + H] = 396.4 observed |

| Example Number | Structure | Name | Analytical Data |
|---|---|---|---|
| ZZZ132 | 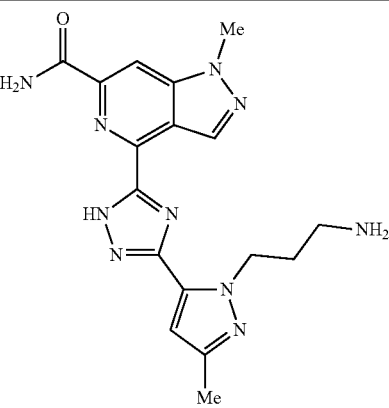 | 4-{3-[1-(3-aminopropyl)-3-methyl-1H-pyrazol-5-yl]-1H-1,2,4-triazol-5-yl}-1-methyl-1H-pyrazolo[4,3-c]pyridine-6-carboxamide | LCMS [M + H] = 381.1 observed |

BIOLOGICAL EXAMPLES

Biochemical Assay Methods
Scintillation Proximity Assay (SPA) Competitive Binding A radioligand binding assay was developed to determine whether compound interactions were competitive with a tritium-labeled version of the native STING ligand, $^3$H-cyclic guanine (2',5') monophosphate adenine (3',5') monophosphate ($^3$H-cGAMP). The STING constructs (WT and H232R) were comprised of residues 155-341 with both N- and C-terminal truncations; the N-terminal transmembrane domains were removed (1-154), as well as the C-terminal tail (342-379). A highly specific N-terminal biotinylation was achieved enzymatically with the E. coli biotin ligase (BirA) and inclusion of the high-affinity biotinylation peptide AviTag™. 100 nM STING protein was immobilized on 20 µg streptavidin polyvinyl toluene (SA-PVT) beads in 150 mM NaCl, 25 mM Hepes (pH 7.5), 0.1 mM EDTA, 1 mM DTT, 0.005% (v/v) Tween-20, 1% (v/v) DMSO. 100 nM $^3$H-cGAMP and compounds were added and allowed to come to equilibrium at room temperature (20 min). Compounds were tested in three-fold dilution series from a 100 µM starting concentration and normalized to a positive control compound that completely blocked $^3$H-cGAMP binding and the negative control DMSO. The $K_i$ for competitive binding was determined from the IC$_{50}$ with the Cheng-Prusoff equation (Cheng & Prusoff, Biochemical Pharmacology, 22 (1973), pp. 3099-3108). The $K_D$ values for $^3$H-cGAMP used in the Cheng-Prusoff equation were determined empirically to be 1 nM for WT STING, and 750 nM for R232H STING. SPA competitive binding data is provided in Table 1, Table 1A and Table 1B.

TABLE 1

| Example Number | R232-STING SPA-IC50 Ki (µM) |
|---|---|
| A01 | 0.0251 |
| A02 | 0.0294 |
| B01 | 0.4296 |
| B02 | 0.0460 |
| C01 | 0.2296 |
| C02 | 0.0089 |
| C03 | 0.0081 |

TABLE 1-continued

| Example Number | R232-STING SPA-IC50 Ki (µM) |
|---|---|
| C04 | 0.0133 |
| C05 | 0.1652 |
| C06 | 0.2769 |
| C07 | 0.0036 |
| C08 | 0.0047 |
| C09 | 0.0014 |
| *D01 + D01' | 0.3228 |
| *D02 + D02' | 0.1753 |
| *D03 + D03' | 0.3137 |
| *D04 + D04' | 0.3307 |
| D05 | 0.2316 |
| D06 | 0.3012 |
| E01 | 0.0287 |
| F01 | 0.0927 |
| G01 | 0.0658 |
| G02 | 0.0304 |
| H01 | 0.0876 |
| J01 | 0.0142 |
| J02 | 0.0324 |
| J03 | 0.0068 |
| K01 | 0.0160 |
| K02 | 0.0081 |
| L01 | 0.0662 |
| M01 | 0.5006 |
| M02 | 0.2776 |
| M03 | 0.1587 |
| M04 | 0.3061 |
| N01 | 0.9901 |
| P01 | 0.2408 |
| Q01 | 0.0032 |
| R01 | 0.0328 |
| S01 | 0.0115 |
| T01 | 0.0277 |
| U01 | 0.0044 |
| U02 | 0.0516 |
| U03 | 0.0298 |
| A01 | 0.0251 |
| A02 | 0.0294 |
| B01 | 0.4296 |
| B02 | 0.0460 |
| C01 | 0.2296 |
| C02 | 0.0089 |
| U04 | 0.0344 |
| V01 | 0.0069 |
| Compound W-7 | 0.0334 |
| W01 | 0.1724 |
| W02 | 0.0675 |
| X01 | 0.0006 |

TABLE 1-continued

| Example Number | R232-STING SPA-IC50 Ki (μM) |
|---|---|
| Y01 | 0.0272 |
| Z01 | 0.0002 |
| AA01 | 0.1342 |
| AB01 | 0.0236 |
| AC01 | 0.0002 |
| AC02 | 0.0004 |
| AD01 | 0.0022 |
| AD02 | 0.0040 |
| AE01 | 0.0026 |
| AF01 | 0.1378 |
| AF02 | 0.0115 |
| AG01 | 0.0083 |
| AH01 | 0.1841 |

*Compounds so indicated were prepared as a mixture of regioisomers as indicated in the Examples section above, and tested in the in vitro biological assays as such.

TABLE 1A

| Example Number | R232-STING SPA-IC50 Ki (μM) |
|---|---|
| YY01 | >0.9901 |
| YY02 | 0.0848 |
| YY03 | 0.1090 |
| YY04 | >0.6384 |
| YY05 | 0.3962 |
| YY06 | 0.0471 |
| YY07 | 0.3371 |
| YY08 | 0.3732 |
| YY09 | 0.1415 |
| YY10 | 0.2371 |
| YY11 | 0.5295 |
| YY12 | 0.7216 |
| YY13 | 0.4309 |
| YY14 | 0.4839 |
| YY15 | 0.3287 |
| YY16 | 0.3687 |
| YY17 | 0.3756 |
| YY18 | 0.4365 |
| YY19 | 0.1753 |
| YY20 | 0.1712 |
| YY21 | >0.8914 |
| YY22 | 0.4909 |
| YY23 | 0.4568 |
| YY24 | 0.3540 |
| YY25 | 0.2118 |
| YY26 | 0.1950 |
| YY27 | 0.4896 |
| YY28 | 0.1416 |
| YY29 | 0.0202 |
| YY30 | 0.0416 |
| YY31 | 0.1571 |
| YY32 | 0.0072 |
| YY33 | 0.1641 |
| YY34 | 0.0842 |
| YY35 | 0.1080 |

TABLE 1B

| Example Number | R232-STING SPA-IC50 Ki (μM) |
|---|---|
| ZZZ001 | >0.9901 |
| ZZZ002 | >0.9901 |
| ZZZ003 | >0.9901 |
| ZZZ004 | >0.0900 |
| ZZZ005 | >0.9901 |
| ZZZ006 | >0.9901 |
| ZZZ007 | 0.8501 |
| ZZZ008 | >0.9901 |

TABLE 1B-continued

| Example Number | R232-STING SPA-IC50 Ki (μM) |
|---|---|
| ZZZ009 | 0.9466 |
| ZZZ010 | >0.9901 |
| ZZZ011 | >0.2703 |
| ZZZ012 | 0.1896 |
| ZZZ013 | >0.9901 |
| ZZZ014 | >0.9901 |
| ZZZ015 | >0.9901 |
| ZZZ016 | 0.8261 |
| ZZZ017 | >0.9901 |
| ZZZ018 | 0.7482 |
| ZZZ019 | 0.7259 |
| ZZZ020 | >0.9901 |
| ZZZ021 | >0.9901 |
| ZZZ022 | 0.4470 |
| ZZZ023 | >0.9901 |
| ZZZ024 | >0.9901 |
| ZZZ025 | 0.7137 |
| ZZZ026 | >0.9901 |
| ZZZ027 | >0.9901 |
| ZZZ028 | >0.9901 |
| ZZZ029 | 0.5611 |
| ZZZ030 | 0.8613 |
| ZZZ031 | >0.9901 |
| ZZZ032 | 0.9665 |
| ZZZ033 | 0.5715 |
| ZZZ034 | >0.9901 |
| ZZZ035 | >0.9901 |
| ZZZ036 | >0.9901 |
| ZZZ037 | 0.7270 |
| ZZZ038 | 0.9278 |
| ZZZ039 | >0.9901 |
| ZZZ040 | >0.9901 |
| ZZZ041 | >0.9901 |
| ZZZ042 | >0.9901 |
| ZZZ043 | >0.9901 |
| ZZZ044 | >0.9000 |
| ZZZ045 | >0.9000 |
| ZZZ046 | >0.9901 |
| ZZZ047 | >0.0900 |
| ZZZ048 | 0.9122 |
| ZZZ049 | >0.9000 |
| ZZZ050 | >0.9901 |
| ZZZ051 | 0.1912 |
| ZZZ052 | >0.9901 |
| ZZZ053 | >0.9901 |
| ZZZ054 | >1.8861 |
| ZZZ055 | >0.9901 |
| ZZZ056 | >0.9901 |
| ZZZ057 | >0.9901 |
| ZZZ058 | >0.9901 |
| ZZZ059 | 0.9482 |
| ZZZ060 | 0.5408 |
| ZZZ061 | 0.8822 |
| ZZZ062 | 0.5427 |
| ZZZ063 | >0.9901 |
| ZZZ064 | >0.9901 |
| ZZZ065 | 0.9640 |
| ZZZ066 | >0.9901 |
| ZZZ067 | 0.5365 |
| ZZZ068 | >0.9901 |
| ZZZ069 | >0.9901 |
| ZZZ070 | >0.9901 |
| ZZZ071 | >0.9901 |
| ZZZ072 | 0.8349 |
| ZZZ073 | 0.6504 |
| ZZZ074 | >0.9901 |
| ZZZ075 | 0.9612 |
| ZZZ076 | 0.9760 |
| ZZZ077 | >0.9901 |
| ZZZ078 | 0.6413 |
| ZZZ079 | 0.7853 |
| ZZZ080 | >0.9901 |
| ZZZ081 | >0.9901 |
| ZZZ082 | 0.5012 |
| ZZZ083 | >0.2703 |
| ZZZ084 | >0.0901 |

TABLE 1B-continued

| Example Number | R232-STING SPA-IC50 Ki (μM) |
|---|---|
| ZZZ085 | 0.0442 |
| ZZZ086 | >0.9901 |
| ZZZ087 | >0.9901 |
| ZZZ088 | >0.9901 |
| ZZZ089 | 0.9166 |
| ZZZ090 | >0.9901 |
| ZZZ091 | 0.8306 |
| ZZZ092 | 0.9685 |
| ZZZ093 | >0.9901 |
| ZZZ094 | 0.5500 |
| ZZZ095 | 0.7734 |
| ZZZ096 | 0.8609 |
| ZZZ097 | 0.6614 |
| ZZZ098 | 0.5412 |
| ZZZ099 | 0.7235 |
| ZZZ100 | 0.8418 |
| ZZZ101 | 0.5093 |
| ZZZ102 | 0.9002 |
| ZZZ103 | >0.9901 |
| ZZZ104 | 0.8063 |
| ZZZ105 | 0.8791 |
| ZZZ106 | 0.9438 |
| ZZZ107 | >0.9901 |
| ZZZ108 | 0.8504 |
| ZZZ109 | 0.9535 |
| ZZZ110 | 0.6226 |
| ZZZ111 | 0.8424 |
| ZZZ112 | >0.9901 |
| ZZZ113 | 0.7307 |
| ZZZ114 | 0.9429 |
| ZZZ115 | 0.8458 |
| ZZZ116 | >0.9901 |
| ZZZ117 | 0.8479 |
| ZZZ118 | 0.5381 |
| ZZZ119 | >0.9901 |
| ZZZ120 | 0.9053 |
| ZZZ121 | >0.9901 |
| ZZZ122 | >0.9000 |
| ZZZ123 | 0.0633 |
| ZZZ124 | >0.0900 |
| ZZZ125 | 0.5118 |
| ZZZ126 | >0.9901 |
| ZZZ127 | 0.4989 |
| ZZZ128 | 0.5562 |
| ZZZ129 | 0.9521 |
| ZZZ130 | >0.9901 |
| ZZZ131 | >0.9901 |
| ZZZ132 | >0.9901 |

Phosphorylation of IRF3: THP-1 Cell ELISA

STING activation results in recruitment of TBK1 and phosphorylation of IRF3 transcription factor before induction of type I interferons. THP-1 cells (InvivoGen) were grown in RPMI media plus 2 mM L-glutamine, 10% fetal bovine serum, and 0.5% Pen-Strep. $10^4$ cells were seeded in 96-well plates and incubated overnight 37° C., 5% $CO_2$. Compounds serial diluted compounds in media (final 0.5% DMSO) were added to the cells and incubated for an additional 3 hours. After incubation, the plates were centrifuged at 2000 rpm for 5 min. The cells were then lysed in 100 μl RIPA buffer and vortexed for 30 minutes at room temperature. 25 μl of lysate was then transferred to clear polystyrene High Bind plates that had been previously coated with mouse anti-human IRF-3 capture antibody (BD Pharmigen), and allowed to incubate at 4° C. for 16 hours. The plates were then washed and incubated with rabbit anti-phospho-IRF3 detection antibody (Cell Signaling Technologies) for 1.5 hours at room temperature. Finally, an HRP-linked secondary antibody (Cell Signaling Technologies) was added for 30 min before the Glo Substrate Reagent (R&D Systems) was used generate the luminescent signal. The signal was measured using a Perkin-Elmer Envision microplate reader. Data were normalized to "% effect" with a positive control STING agonist that was known to maximize the phosphorylated IRF3 signal and the negative control was DMSO. IRF3 Phosphorylation data is provided in Table 2 and Table 2A.

TABLE 2

| Example Number | THP-1 CELL P-IRF3 EC50 (μM) |
|---|---|
| A01 | 0.92 |
| A02 | 6.68 |
| B01 | 25.07 |
| B02 | 8.00 |
| C01 | 100.0 |
| C02 | 0.16 |
| C03 | 10.89 |
| C04 | 0.25 |
| C05 | 31.65 |
| C06 | 96.68 |
| C07 | 0.11 |
| C08 | 0.14 |
| C09 | 15.06 |
| *D01 + D01' | 89.60 |
| *D02 + D02' | 79.88 |
| *D03 + D03' | 43.88 |
| *D04 + D04' | 96.61 |
| D05 | 20.23 |
| D06 | 82.94 |
| A01 | 0.92 |
| A02 | 6.68 |
| E01 | 0.64 |
| F01 | 0.77 |
| G01 | 6.52 |
| G02 | 1.16 |
| H01 | 10.84 |
| J01 | 0.53 |
| J02 | 3.60 |
| J03 | 0.63 |
| K01 | 0.17 |
| K02 | 6.54 |
| L01 | 3.09 |
| M01 | 77.29 |
| M02 | 16.58 |
| M03 | 32.13 |
| M04 | 27.97 |
| N01 | 100.00 |
| P01 | 75.62 |
| Q01 | 0.12 |
| R01 | 1.71 |
| S01 | 1.30 |
| T01 | 0.98 |
| U01 | 0.40 |
| U02 | 6.50 |
| U03 | 2.82 |
| U04 | 1.99 |
| V01 | 0.89 |
| Compound W-7 | 1.50 |
| W01 | 9.17 |
| W02 | 2.32 |
| X01 | 0.34 |
| Y01 | 7.10 |
| Z01 | 0.06 |
| AA01 | 11.82 |
| AB01 | 3.75 |
| AC01 | 0.02 |
| AC02 | 0.34 |
| AD01 | 0.08 |
| AD02 | 0.06 |
| AE01 | 0.20 |
| AF01 | 5.95 |
| AF02 | 2.26 |

TABLE 2-continued

| Example Number | THP-1 CELL P-IRF3 EC50 (µM) |
|---|---|
| A01 | 0.92 |
| A02 | 6.68 |
| AG01 | 0.24 |
| AH01 | >11.11 |

*Compounds so indicated were prepared as a mixture of regioisomers as indicated in the Examples section above, and tested in the in vitro biological assays as such.

TABLE 2A

| Example Number | THP-1 CELL P-IRF3 EC50 (µM) |
|---|---|
| YY01 | >100.00 |
| YY02 | >100.00 |
| YY03 | >100.00 |
| YY04 | >100.00 |
| YY05 | >100.00 |
| YY06 | >100.00 |
| YY07 | >100.00 |
| YY08 | >100.00 |
| YY09 | >100.00 |
| YY10 | >100.00 |
| YY11 | >100.00 |
| YY12 | >100.00 |
| YY13 | >100.00 |
| YY14 | >100.00 |
| YY15 | >100.00 |
| YY16 | >100.00 |
| YY17 | >100.00 |
| YY18 | >100.00 |
| YY19 | >100.00 |
| YY20 | >100.00 |
| YY21 | >100.00 |
| YY22 | >33.33 |
| YY23 | >33.33 |
| YY24 | >33.33 |
| YY25 | >33.33 |
| YY26 | >33.33 |
| YY27 | >33.33 |
| YY28 | >33.33 |
| YY29 | >33.33 |
| YY30 | >13.30 |
| YY31 | >10.00 |
| YY32 | >11.11 |
| YY33 | >10.00 |
| YY34 | >10.00 |
| YY35 | >10.00 |

Interferon-β Induction: THP-1 ISG Reporter Cell Line

THP-1 Lucia™ ISG cells (InvivoGen) express the secreted luciferase "Lucia" reporter gene under the control of an IRF-inducible composite promotor comprised of five interferon response elements. THP-1 Lucia™ ISG cells were grown in RPMI media plus 2 mM L-glutamine, 10% fetal bovine serum, and 0.5% Pen-Strep. Hygromycin B and Zeocin were present to maintain stable transfection. $10^4$ cells were seeded in 96-well plates and incubated overnight 37° C., 5% $CO_2$. 50 µL of serial diluted compounds in media (final 0.5% DMSO) was and incubated for an additional 24 hours. After incubation, the plates were centrifuged at 2000 rpm for 10 min. 50 µl of cell culture supernatant of each well was transferred to a white, opaque 96-well plate. One pouch of QUANTI-Luc™ (InvivoGen) powder was prepared in 25 mL of endotoxin-free water and 100 µL of prepared warm QUANTI-Luc solution were added to each well containing the supernatant. The luminescence signal was measured using a Perkin-Elmer Envision microplate reader. Data were normalized to "% effect" with a positive control STING agonist that was known to maximize the luciferase signal and the negative control DMSO. Interferon-β induction data is provided in Table 3 and Table 3A.

TABLE 3

| Example Number | THP-1 Lucia ISG Cells IFN-β EC50 (µM) |
|---|---|
| A01 | 1.02 |
| A02 | 7.48 |
| B01 | 23.15 |
| B02 | 6.33 |
| C01 | 45.35 |
| C02 | 0.18 |
| C03 | 8.93 |
| C04 | 0.24 |
| C05 | 27.39 |
| C06 | 92.75 |
| C07 | 0.11 |
| C08 | 0.13 |
| C09 | 12.30 |
| *D01 + D01' | 95.59 |
| *D02 + D02' | 82.94 |
| *D03 + D03' | 40.88 |
| *D04 + D04' | 99.78 |
| D05 | 19.85 |
| D06 | 100.00 |
| E01 | 0.65 |
| F01 | 0.68 |
| G01 | 6.43 |
| G02 | 1.18 |
| H01 | 7.17 |
| J01 | 0.51 |
| J02 | 2.76 |
| J03 | 0.76 |
| K01 | 0.18 |
| K02 | 5.24 |
| L01 | 3.25 |
| M01 | 81.85 |
| M02 | 22.55 |
| M03 | 28.50 |
| M04 | 28.64 |
| N01 | 76.90 |
| P01 | 100.00 |
| Q01 | 0.14 |
| R01 | 2.10 |
| S01 | 2.30 |
| T01 | 1.46 |
| A01 | 1.02 |
| A02 | 7.48 |
| B01 | 23.15 |
| U01 | 0.49 |
| U02 | 6.20 |
| U03 | 2.52 |
| U04 | 1.85 |
| V01 | 0.59 |
| Compound W-7 | 1.87 |
| W01 | 11.61 |
| W02 | 2.46 |
| X01 | 0.38 |
| Y01 | 7.34 |
| Z01 | 0.05 |
| AA01 | 13.17 |
| AB01 | 5.01 |
| AC01 | 0.01 |
| AC02 | 0.18 |
| AD01 | 0.08 |
| AD02 | 0.06 |
| AE01 | 0.16 |
| AF01 | 5.22 |
| AF02 | 1.95 |
| AG01 | 0.34 |
| AH01 | 6.25 |

*Compounds so indicated were prepared as a mixture of regioisomers as indicated in the Examples section above, and tested in the in vitro biological assays as such.

TABLE 3A

| Example Number | THP-1 Lucia ISG Cells IFN-β EC50 (μM) |
|---|---|
| YY01 | >100.00 |
| YY02 | >100.00 |
| YY03 | >100.00 |
| YY04 | >100.00 |
| YY05 | >100.00 |
| YY06 | >100.00 |
| YY07 | >100.00 |
| YY08 | >100.00 |
| YY09 | >100.00 |
| YY10 | >100.00 |
| YY11 | >100.00 |
| YY12 | >100.00 |
| YY13 | >100.00 |
| YY14 | >100.00 |
| YY15 | >100.00 |
| YY16 | >100.00 |
| YY17 | >100.00 |
| YY18 | >100.00 |
| YY19 | >100.00 |
| YY20 | >100.00 |
| YY21 | >100.00 |
| YY22 | >33.33 |
| YY23 | >33.33 |
| YY24 | >100.00 |
| YY25 | >33.33 |
| YY26 | >33.33 |
| YY27 | >33.33 |
| YY28 | >33.33 |
| YY29 | >33.33 |
| YY30 | >33.33 |
| YY31 | >13.30 |
| YY32 | >10.00 |
| YY33 | >11.11 |
| YY34 | >10.00 |
| YY35 | >10.00 |

PBMC Phospho-IRF3 and IFNβ Assay

Peripheral blood mononuclear cells (PBMCs) were isolated from a leukopak preparation of fresh human whole blood (StemCell Technologies, Cambridge, MA, USA). Blood was mixed with equal volumes of phosphate buffered saline (PBS) with 2% fetal bovine serum (FBS) (PBS+2% FBS), layered on top of Lymphoprep™ density gradient medium, and centrifuged to separate the PBMCs. PBMCs were frozen in standard cell cryopreserveration medium and thawed before being used as needed in the experiments. A single human donor, verified to be wild-type for STING, was used for all the studies described herein.

For the homogeneous time resolved fluorescence (HTRF) IFNβ assay, 400 k PBMCs/well were seeded in RPMI media and incubated overnight at 37° C., 5% $CO_2$. Compounds were serial diluted in media (final 0.5% DMSO) and incubated with the PMBCs for an additional 4 hours. After incubation, the plates were centrifuged at 1500×g for 5 min and the media was collected for the IFNβ HTRF assay (Product Reference 62HIFNBPEG, Cisbio US, Bedford, MA, USA). 14 μL of media was mixed with 6 μL of antibody-reaction reagent (Cisbio US, Bedford, MA, USA) and then combined with the assay's antibodies at a 2:1 ratio. The antibodies were incubated with the media overnight at 4° C., and the FRET signal was measured on a BMG Pherastar microplate reader (ratio 665 nm/620 nm). Data were normalized to "% effect" with a positive control STING agonist known to maximize the IFNβ signal and a negative control of DMSO. The results are shown in Table 4 below.

For the phospho-IRF3 assay, 400 k PBMCs/well were seeded in RPMI media and incubated overnight at 37° C., 5% $CO_2$. Compounds were serial diluted in media (final 0.5% DMSO) and incubated with the PMBCs for an additional 4 hours. The cells were then lysed in 50 μl RIPA buffer and vortexed for 30 minutes at 4° C. 25 μl of lysate was then transferred to clear polystyrene High Bind plates that had been previously coated with mouse anti-human IRF-3 capture antibody (BD Pharmigen), and allowed to incubate at 4° C. for 16 hours. The plates were then washed and incubated with rabbit anti-phospho-IRF3 detection antibody (Cell Signaling Technologies) for 1.5 hours at room temperature. Finally, an HRP-linked secondary antibody (Cell Signaling Technologies) was added for 30 min before the Glo Substrate Reagent (R&D Systems) was used generate the luminescent signal. The signal was measured using a Perkin-Elmer Envision microplate reader. Data were normalized to "% effect" with a positive control STING agonist known to maximize the phosphorylated IRF3 signal and a negative control of DMSO. The results are shown in Table 4 below.

TABLE 4

| Example Number | PBMC STING:PBMC Donor# 110040898 Phospho-IRF3 GMean EC50 (μM) | PBMC STING:PBMC Donor# 110040898 IFNB HTRF GMean EC50 (μM) |
|---|---|---|
| C02 | 0.051 | 0.076 |
| C07 | 0.031 | 0.053 |
| G01 | 0.673 | 0.890 |
| K02 | 11.466 | 1.769 |
| R01 | 0.404 | 0.431 |
| U01 | 0.025 | 0.029 |
| W01 | 0.358 | — |
| Z01 | 0.022 | 0.032 |
| AC01 | 0.008 | 0.016 |
| AC02 | — | 0.111 |

What is claimed is:

1. A compound of formula (I):

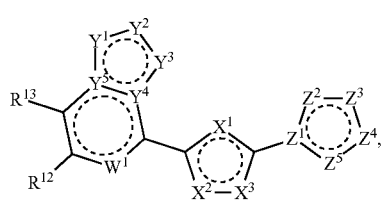

or a pharmaceutically acceptable salt thereof, wherein each

in a ring independently represents two conjugated double bonds in a five-membered heteroaromatic ring and three conjugated double bonds in a six-membered aromatic or heteroaromatic ring;

$W^1$ is selected from $CR^{11}$ and N;
$X^1$ is selected from $CR^1$, N, $NR^1$, O and S;
$X^2$ is selected from $CR^2$, N, $NR^2$, O and S;
$X^3$ is selected from $CR^3$, N, $NR^3$, O and S;
where two or three of $X^1$, $X^2$ and $X^3$ are independently selected from N, $NR^1$, $NR^2$, $NR^3$, O and S; and where at least one of $X^1$, $X^2$ and $X^3$ is selected from N, $NR^1$, $NR^2$ and $NR^3$;
$Y^1$ is selected from N, $NR^4$, O, S, and $CR^4$;
$Y^2$ is selected from N, $NR^5$, O, S, and $CR^5$;
$Y^3$ is selected from N, $NR^6$, O, S, and $CR^6$;
$Y^4$ is selected from C and N;
$Y^5$ is selected from C and N;
where at least one and not more than two of $Y^1$, $Y^2$ and $Y^3$ are independently selected from N, $NR^4$, $NR^5$ and $NR^6$;
where when one of $Y^4$ or $Y^5$ is N, the other one of $Y^4$ or $Y^5$ is C;
$Z^1$ is selected from C and N;
$Z^2$ is selected from N, $NR^8$ and $CR^8$;
$Z^3$ is selected from N, $NR^9$ and $CR^9$;
$Z^4$ is selected from N, $NR^{10}$ and $CR^{10}$;
$Z^5$ is selected from N, $NR^7$ and $CR^7$;
where two or three of $Z^1$, $Z^2$, $Z^3$, $Z^4$ and $Z^5$ are independently selected from N, $NR^7$, $NR^8$, $NR^9$, and $NR^{10}$;
each $R^1$ is independently selected from the group consisting of H, $C_1$-$C_8$ alkyl, $C_1$-$C_8$ alkylene-NRR and $C_1$-$C_8$ alkylene-C(O) OR;
each $R^2$ is independently selected from the group consisting of H, $C_1$-$C_8$ alkyl, $C_1$-$C_8$ alkylene-NRR, $C_1$-$C_8$ alkylene-C(O) OR, $C_1$-$C_8$ alkylene-OR and $C_1$-$C_8$ alkylene-O—P(O)(OH)$_2$;
each $R^3$ is independently selected from the group consisting of H, $C_1$-$C_8$ alkyl, $C_1$-$C_8$ alkylene-NRR, $C_1$-$C_8$ alkylene-C(O) OR and $C_1$-$C_8$ alkylene-O—P(O)(OH)$_2$;
each $R^4$ is independently selected from the group consisting of H, —OR, —NRR, $C_1$-$C_8$ alkyl optionally substituted with one or two —OR, $C_1$-$C_8$ alkylene-NRR, —C(O) OR, $C_1$-$C_8$ alkylene-C(O) OR, 3-10 membered heterocycle, $C_1$-$C_8$ alkylene-3-10 membered heterocycle optionally substituted with one 3-10 membered heterocycle, ($C_3$-$C_{10}$)-cycloalkyl, and $C_1$-$C_8$ alkylene-($C_3$-$C_{10}$)-cycloalkyl;
each $R^5$ is independently selected from the group consisting of H, —OR, $C_1$-$C_8$ alkyl, —NRR, $C_1$-$C_8$ alkylene-NRR, —C(O) OR, $C_1$-$C_8$ alkylene-C(O) OR, 3-10 membered heterocycle, $C_1$-$C_8$ alkylene-3-10 membered heterocycle optionally substituted with one 3-10 membered heterocycle, and $C_1$-$C_8$ alkylene-OR;
each $R^6$ is H;
$R^7$ is selected from the group consisting of H, halo, hydroxy and $NH_2$;
$R^8$ is selected from the group consisting of H, $C_1$-$C_8$ alkyl optionally substituted with one or two —NRR or —OR, $C_1$-$C_8$ alkylene-C(O) OR and $C_1$-$C_8$ alkylene-$SO_2R$;
$R^9$ is H;
$R^{10}$ is selected from the group consisting of H, $C_1$-$C_8$ alkyl optionally substituted with one or two —OR, and halo;
$R^{11}$ is selected from the group consisting of H, $C_1$-$C_8$ alkyl, —OR and halo;
$R^{12}$ is —C(O)N(R)$_2$;
$R^{13}$ is H;
each R is independently selected from the group consisting of H, $C_1$-$C_8$ alkyl, and $C_1$-$C_8$ haloalkyl, or two R join to form, together with the N atom to which they are bound, a 3-10 membered heterocycle, where said 3-10 member heterocycle contains one N and optionally one or two additional heteroatoms each independently selected from N, O and S; and
where, when two R join to form, together with the atom or atoms to which they are bound, a 3-10 membered heterocycle, said 3-10 membered heterocycle is optionally substituted with one or more substituents each independently selected from $C_1$-$C_8$ alkyl, hydroxy, $C_1$-$C_8$ alkoxy, —($C_3$-$C_{10}$) cycloalkyl, 3-10 membered heterocycle, halo and cyano.

2. A compound, or a pharmaceutically acceptable salt thereof, according to claim 1, wherein each $R^1$ is independently H.

3. A compound, or a pharmaceutically acceptable salt thereof, according to claim 1, wherein each $R^2$ is independently selected from the group consisting of H, $CH_3$, $CH_2NH_2$, $CH(NH_2)CH_3$ and $CH_2NH(CH_3)$.

4. A compound, or a pharmaceutically acceptable salt thereof, according to claim 1, wherein each $R^3$ is independently selected from the group consisting of H and $CH_2OPO(OH)_2$.

5. A compound, or a pharmaceutically acceptable salt thereof, according to claim 1, wherein each $R^4$ is independently selected from the group consisting of $CH_3$, $CH_2CH_3$, $(CH_2)_3OH$, $CH_2CH(CH_2OH)_2$, $(CH_2)_2N(CH_3)CH_2CF_3$, $(CH_2)_2$—(N-morpholinyl), $(CH_2)_3$—(N-morpholinyl), $CH(CH_3)CH_2$—(N-morpholinyl), $(CH_2)_2$—(N-2,6-dimethyl morpholinyl), $(CH_2)_2$—(N-2, 5-dimethyl-morpholinyl), $(CH_2)_2$—(N-8-oxa-3-azabicyclo[3.2.1]octan-3-yl), $(CH_2)_2$—(N-4-cyano piperidinyl), $(CH_2)_2$—(N-4,4-difluoro-piperidinyl), $(CH_2)_2$—(N-2-fluoro azetidinyl), $CH_2$-(2-azetidinyl-N-tetrahydropyranyl) and $CH_2C(O)OH$.

6. A compound, or a pharmaceutically acceptable salt thereof, according to claim 1, wherein each $R^5$ is independently selected from the group consisting of H, $CH_3$, $CH_2CH_3$, $(CH_2)_2N(CH_3)(CH_2CF_3)$, $(CH_2)_2$—(N-morpholinyl), $(CH_2)_3$—(N-morpholinyl), $(CH_2)_2$—(N-2,6-dimethyl morpholinyl) and $CH_2$-(2-azetidinyl-N-tetrahydropyranyl).

7. A compound, or a pharmaceutically acceptable salt thereof, according to claim 1, wherein $R^7$ is selected from the group consisting of H, fluoro, chloro, OH and $NH_2$.

8. A compound, or a pharmaceutically acceptable salt thereof, according to claim 1, wherein $R^8$ is selected from the group consisting of $CH_3$, $CH_2CH_3$, $(CH_2)_3NH_2$, $(CH_2)_2OH$, $(CH_2)_3OH$ and $(CH_2)_2COOH$.

9. A compound, or a pharmaceutically acceptable salt thereof, according to claim 1, wherein $R^{10}$ is selected from the group consisting of $CH_3$ and $CH_2OH$.

10. A compound, or a pharmaceutically acceptable salt thereof, according to claim 1, wherein $R^{11}$ is selected from the group consisting of H and fluoro.

11. A compound, or a pharmaceutically acceptable salt thereof, according to claim 1, wherein $R^{12}$ is —$CONH_2$.

12. A compound, or a pharmaceutically acceptable salt thereof, according to claim 1, wherein each R is independently selected from the group consisting of H, $CH_3$, and $CH_2CF_3$.

13. A compound, according to claim 1, of formula (II)

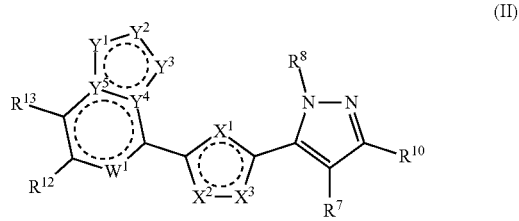

(II)

or a pharmaceutically acceptable salt thereof.

14. A compound, according to claim 1, of formula (VII)
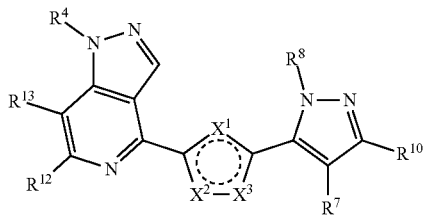
or a pharmaceutically acceptable salt thereof.
15. A compound, according to claim 1, of formula (VIID)
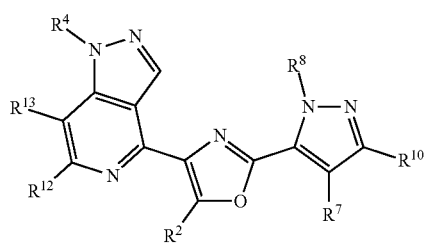
or a pharmaceutically acceptable salt thereof.
16. A compound selected from:
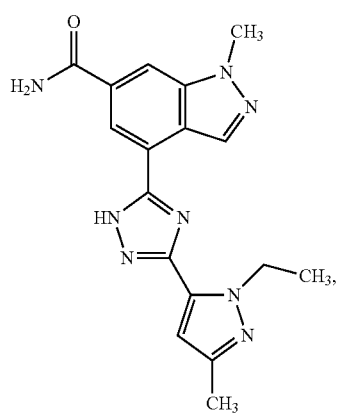
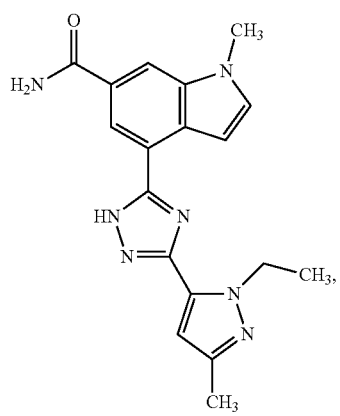
-continued
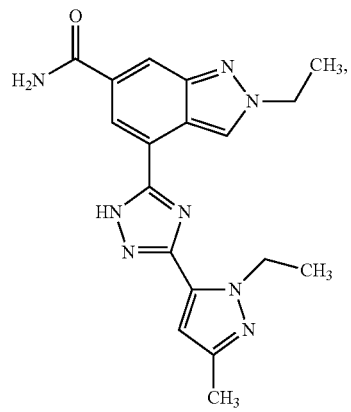
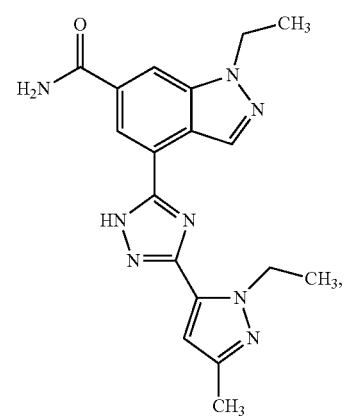
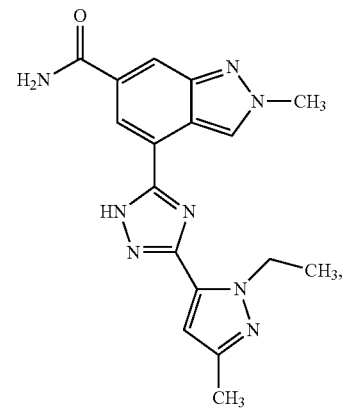
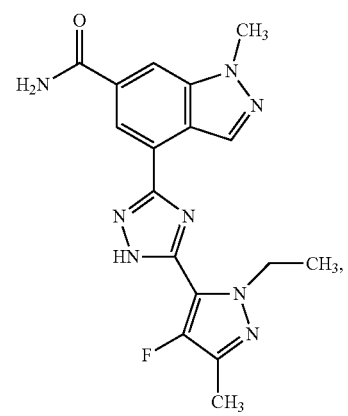

431
-continued
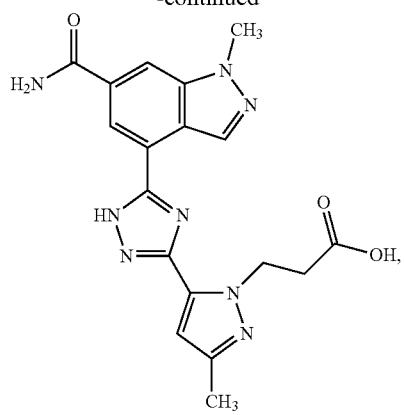
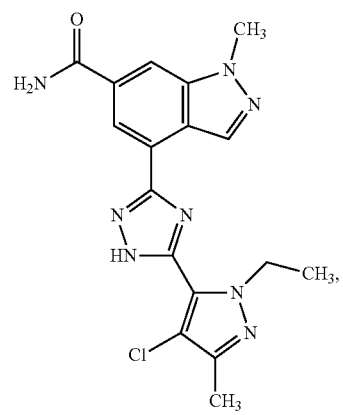
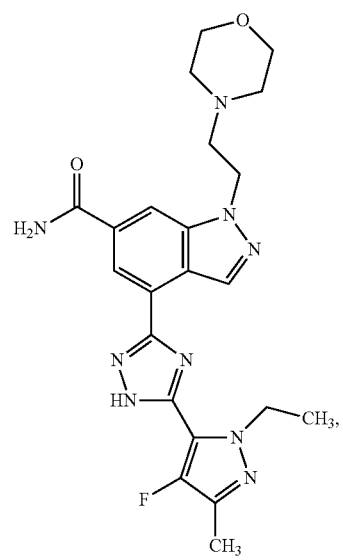
432
-continued
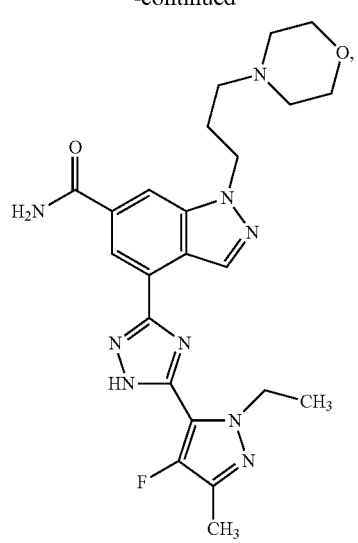
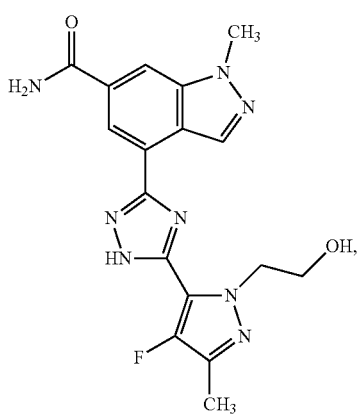
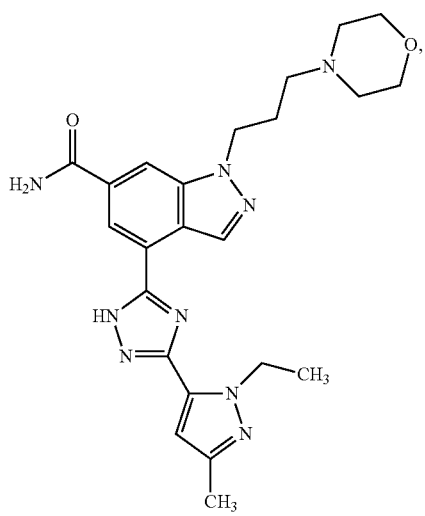

433
-continued
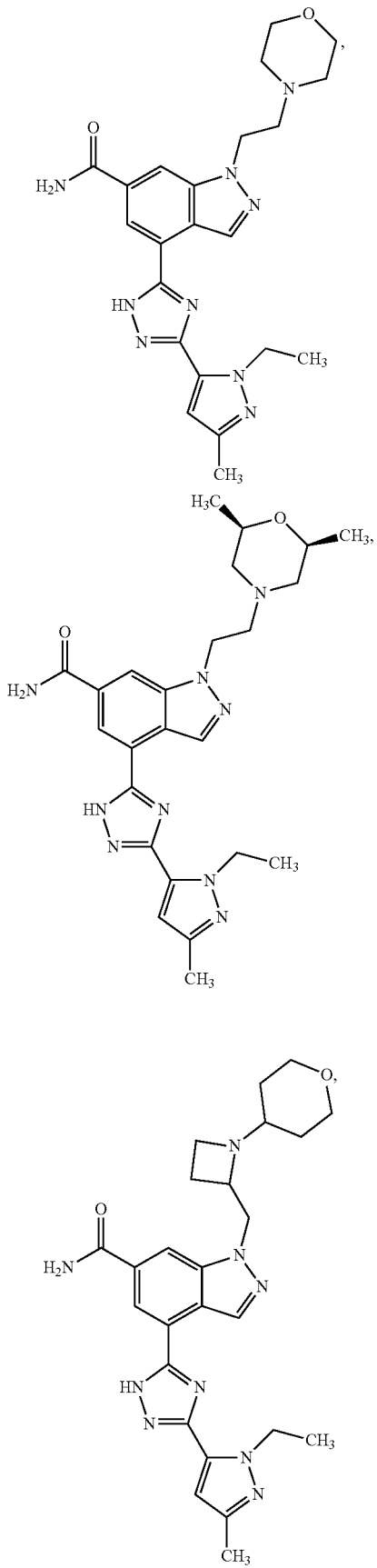
434
-continued
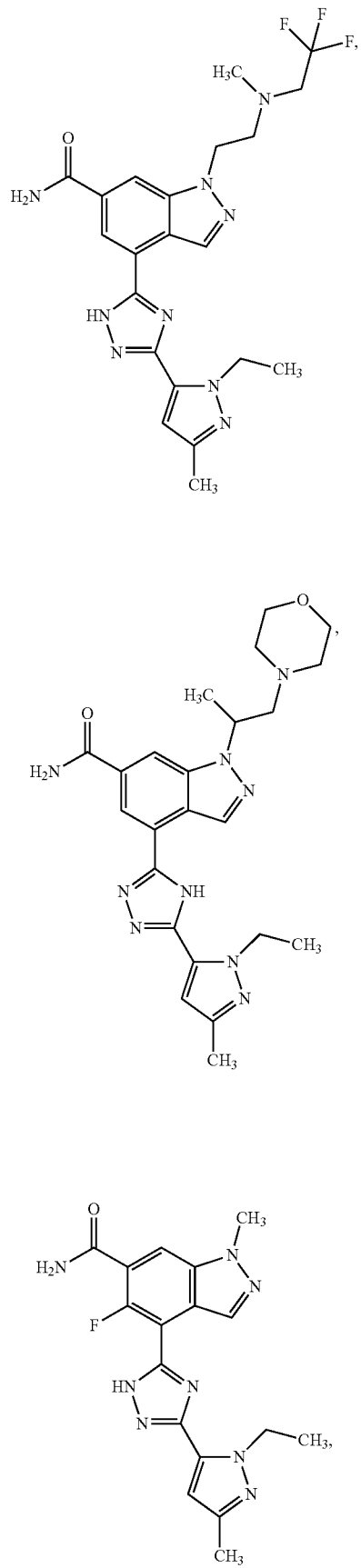

435
-continued
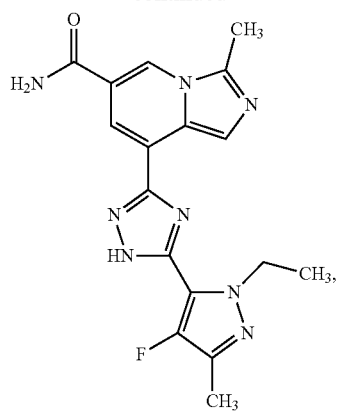
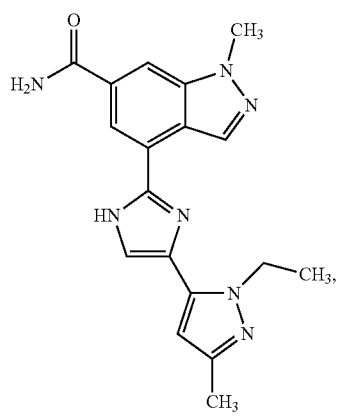
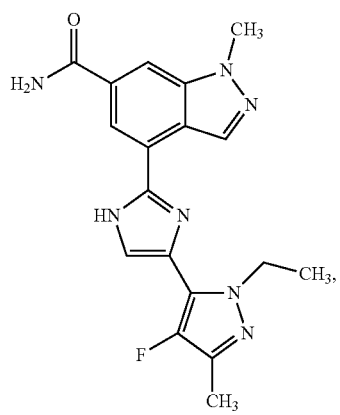
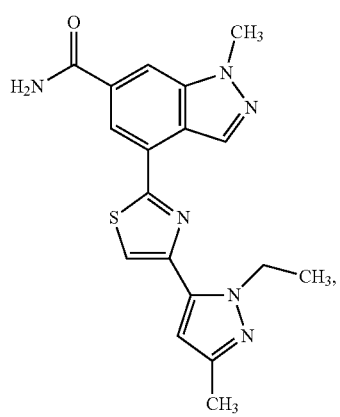
436
-continued
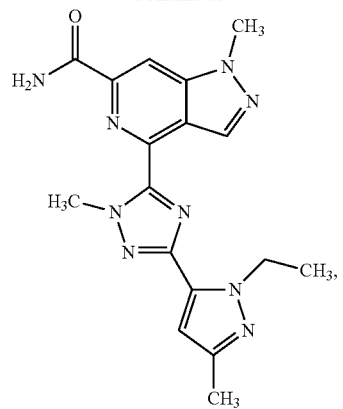
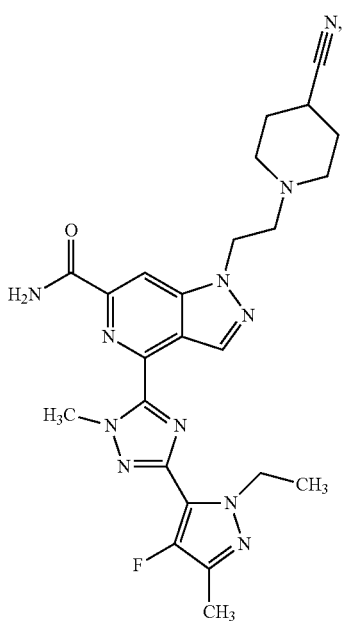
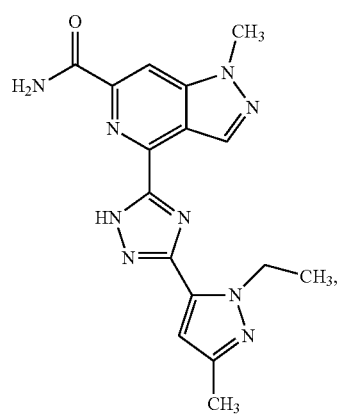

437
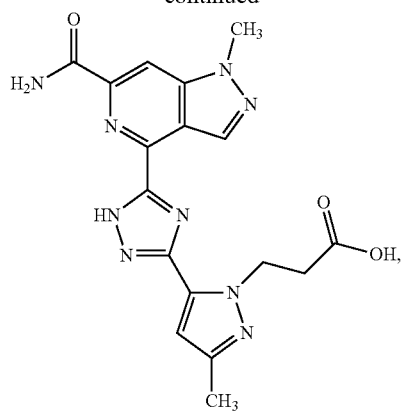
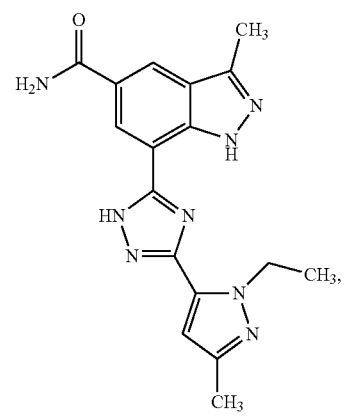
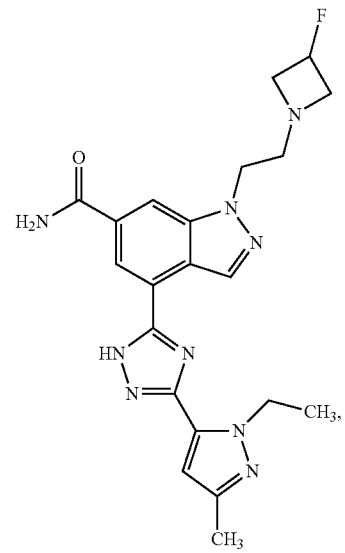
438
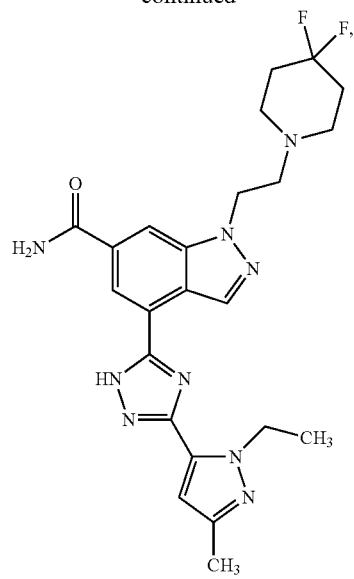
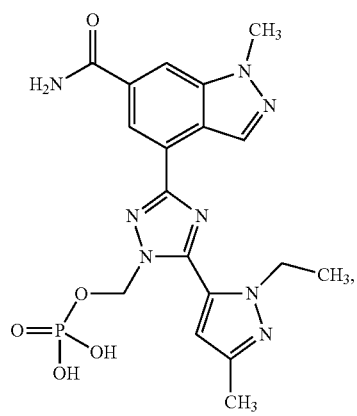
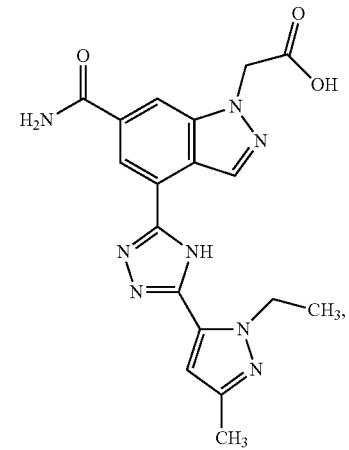

| 439 -continued | 440 -continued |
|---|---|
| 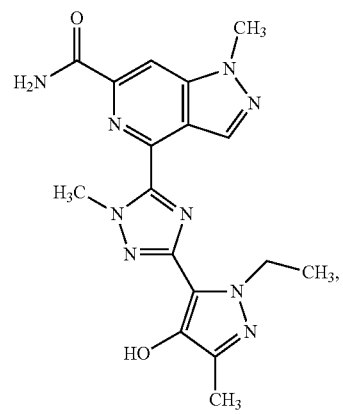 | 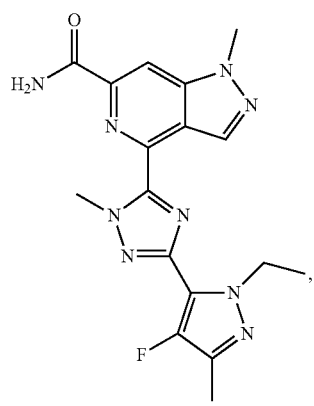 [SMILES: CCn1nc(C)c(F)c1-c1nc(-c2nc(C(N)=O)cc3c2cnn3C)n(C)n1] |
| 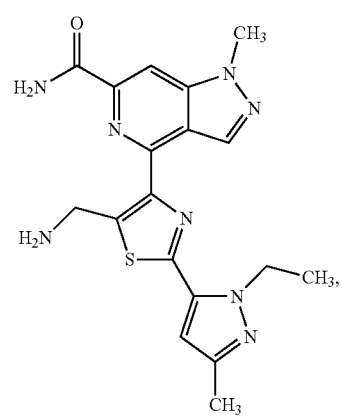 | 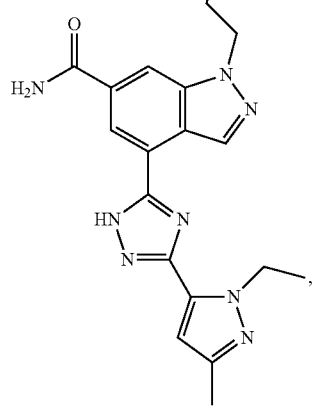 |
| 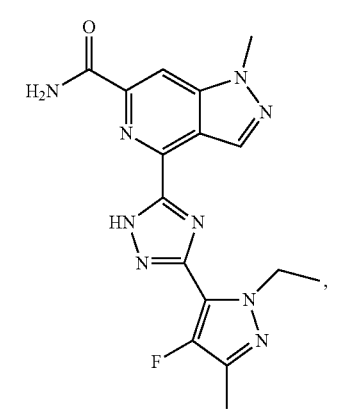 | |
| 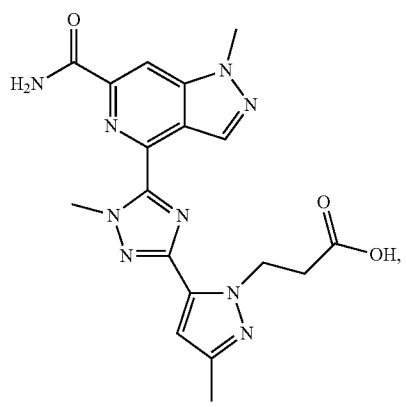 | 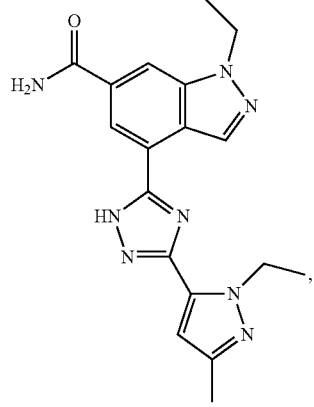 |

441
-continued
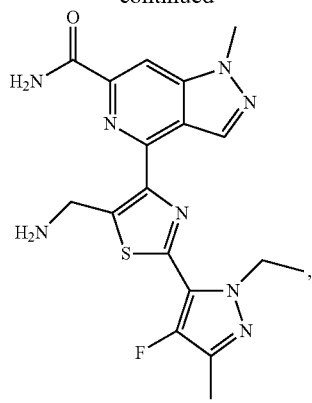
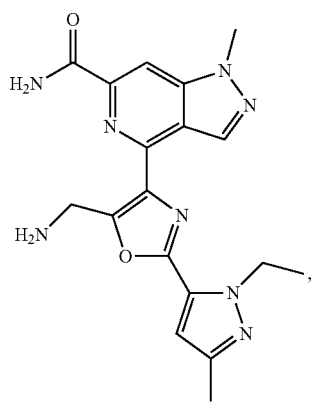
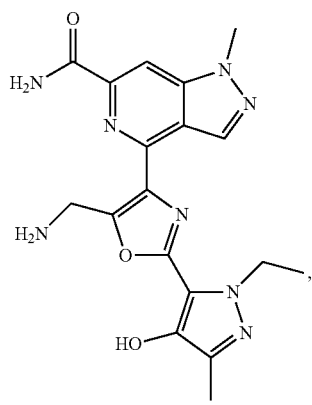
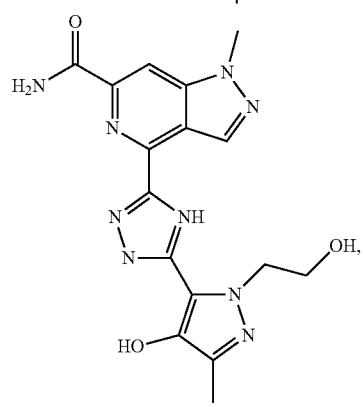
442
-continued
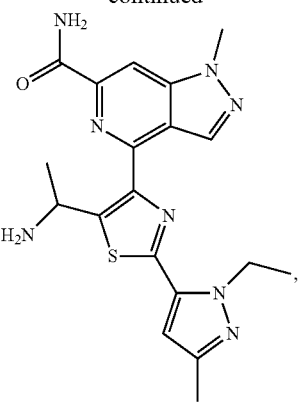
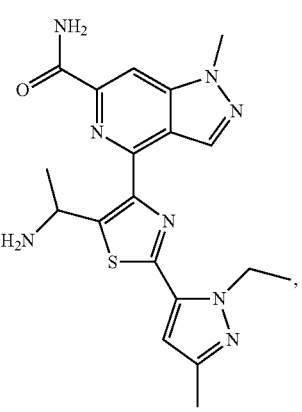
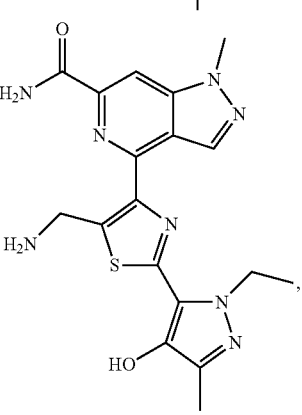
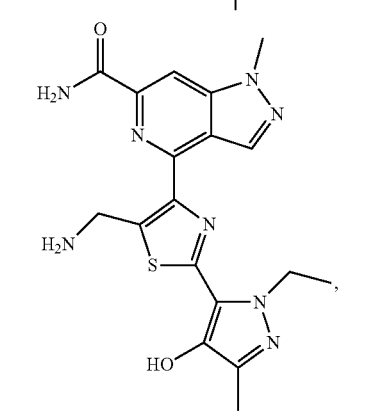

-continued
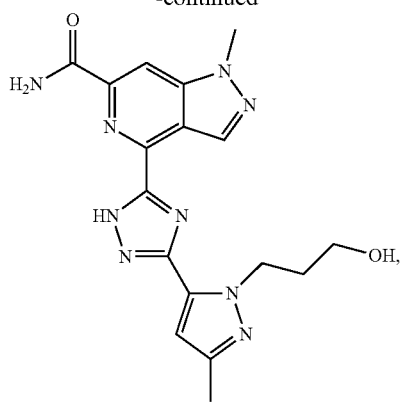
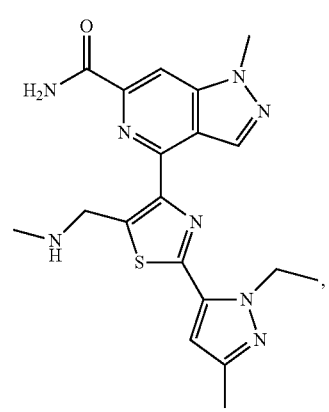
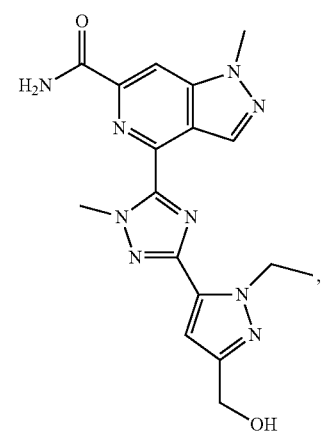
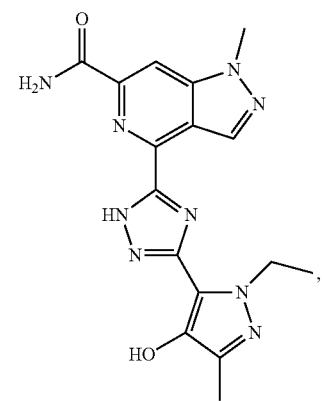
-continued
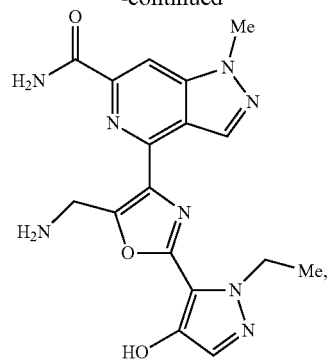
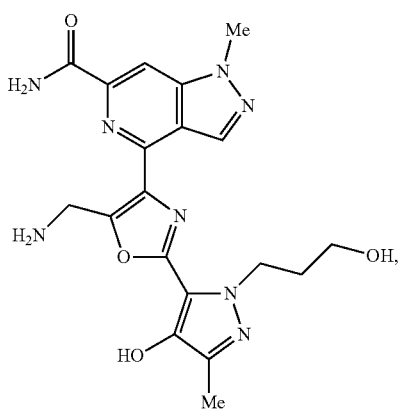
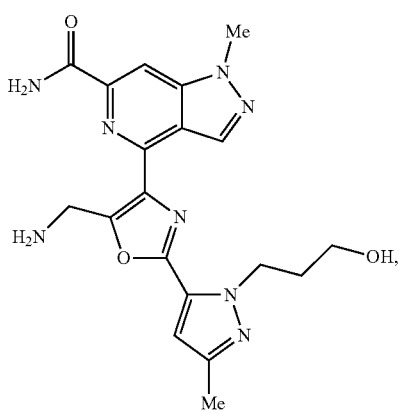
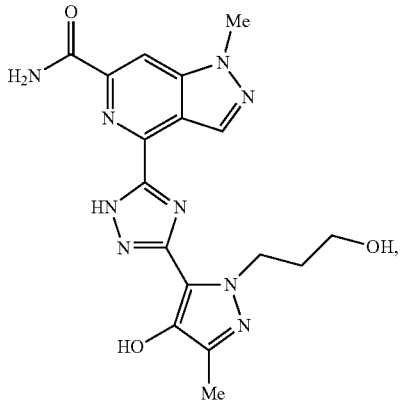

445

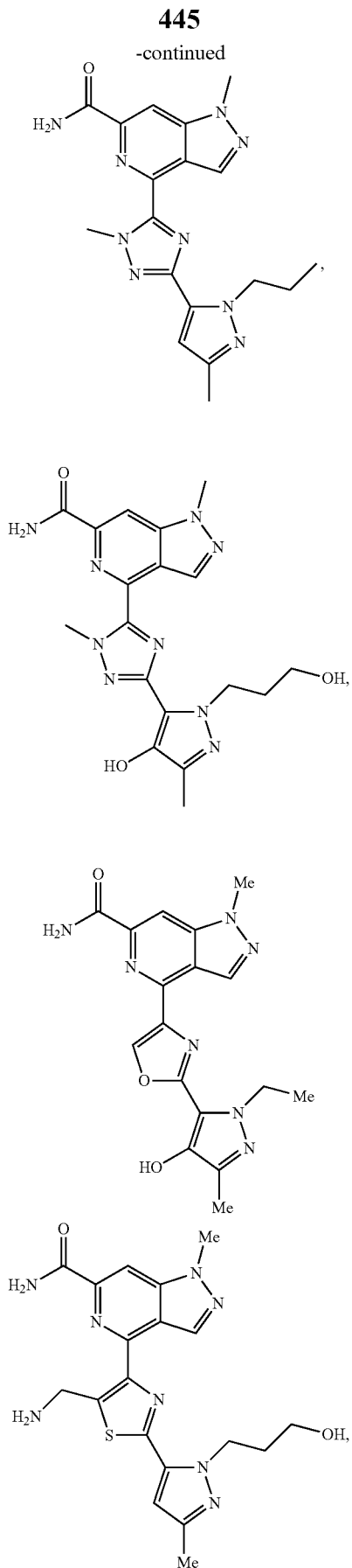

446

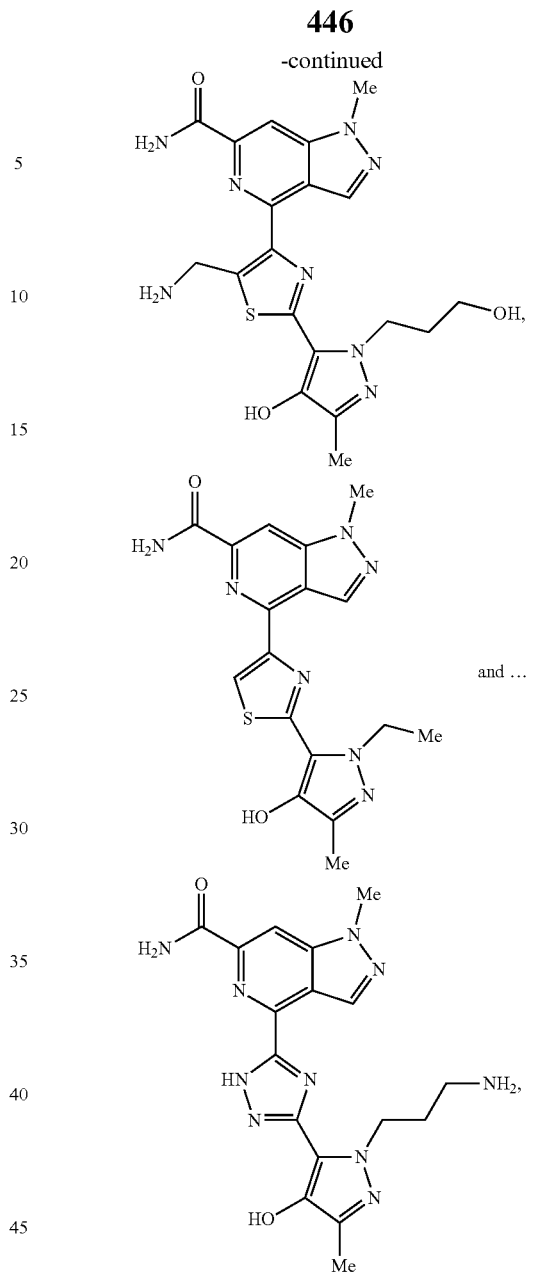

or a pharmaceutically acceptable salt thereof.

17. A pharmaceutical composition comprising a compound, or a pharmaceutically acceptable salt thereof, according to claim 1, and a pharmaceutically acceptable carrier.

18. A pharmaceutical composition comprising a compound, or a pharmaceutically acceptable salt thereof, according to claim 1, wherein said compound is a component of an antibody-drug conjugate.

19. A pharmaceutical composition comprising a compound, or a pharmaceutically acceptable salt thereof, according to claim 1, wherein said compound is a component of a particle-based delivery system.

20. A method of treating cancer in a mammal, the method comprising administering to the mammal a therapeutically effective amount of a compound, or a pharmaceutically acceptable salt thereof, according to claim 1, wherein the cancer is lung cancer, bone cancer, pancreatic cancer, skin cancer, cancer of the head or neck, cutaneous or intraocular melanoma, ovarian cancer, rectal cancer, cancer of the anal region, stomach cancer, colon cancer, breast cancer, carcinoma of the endometrium, carcinoma of the cervix, Hodgkin's Disease, cancer of the esophagus, cancer of the small intestine, sarcoma of soft tissue, prostate cancer, chronic or acute leukemia, lymphocytic lymphomas, cancer of the bladder, renal cell carcinoma, carcinoma of the renal pelvis, neoplasms of the central nervous system (CNS), spinal axis tumors, or brain stem glioma.

21. The method of claim 20, wherein the cancer is bladder cancer.

22. The method of claim 20, wherein the mammal is a human.

23. The method of claim 20 which comprises administering an additional therapeutic agent.

24. The method of claim 23, wherein the additional therapeutic agent is selected from the group consisting of an interferon, a CTLA-4 pathway antagonist, an anti-4-1BB antibody, an anti-PD-1 antibody, and an anti-PD-L1 antibody.

25. The method of claim 20, further comprising the step of increasing interferon-beta levels in a mammal, by comprising the step of administering to said mammal an effective amount of a compound, or a pharmaceutically acceptable salt thereof, according to claim 1.

26. A compound, according to claim 14, wherein
$X^1$ is N; $X^2$ is N or $NR^2$; $X^3$ is $CR^3$ or N;
$R^2$ is $C_1$-$C_8$ alkyl or $C_1$-$C_8$ alkylene-NRR;
$R^3$ is H or $C_1$-$C_8$ alkyl;
$R^4$ is $C_1$-$C_8$ alkyl;
$R^7$ is H or F;
$R^8$ is $C_1$-$C_8$ alkyl optionally substituted with one —NRR or —OR;
$R^{10}$ is $C_1$-$C_8$ alkyl;
$R^{12}$ is —C(O) $NH_2$;
$R^{13}$ is H; and
each R is independently selected from the group consisting of H, $C_1$-$C_8$ alkyl, and $C_1$-$C_8$ haloalkyl.

27. A method of treating cancer in a mammal, the method comprising administering to the mammal a therapeutically effective amount of a compound, or a pharmaceutically acceptable salt thereof, according to claim 1, wherein the cancer is urothelial carcinoma.

28. The method of claim 27, wherein the mammal is a human.

* * * * *